US011976071B2

(12) United States Patent
Palmer et al.

(10) Patent No.: US 11,976,071 B2
(45) Date of Patent: May 7, 2024

(54) SUBSTITUTED PYRROLO[1,2-B]PYRIDAZINES AS BIFUNCTIONAL DEGRADERS OF INTERLEUKIN-1 RECEPTOR-ASSOCIATED KINASES

(71) Applicants: Nurix Therapeutics, Inc., San Francisco, CA (US); Gilead Sciences, Inc., Foster City, CA (US)

(72) Inventors: Wylie Palmer, San Francisco, CA (US); Jeffrey Wu, San Francisco, CA (US); John Lee, San Francisco, CA (US); Kerem Ozboya, San Francisco, CA (US); Tim Kane, San Francisco, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 17/820,770

(22) Filed: Aug. 18, 2022

(65) Prior Publication Data

US 2023/0120619 A1    Apr. 20, 2023

Related U.S. Application Data

(60) Provisional application No. 63/234,606, filed on Aug. 18, 2021.

(51) Int. Cl.
    *A61K 31/5025*    (2006.01)
    *C07D 237/26*    (2006.01)
    *C07D 487/04*    (2006.01)
    *C07D 519/00*    (2006.01)

(52) U.S. Cl.
    CPC .......... *C07D 487/04* (2013.01); *C07D 519/00* (2013.01)

(58) Field of Classification Search
    CPC .................. A61K 31/5025; C07D 237/26
    USPC ........................................ 514/248; 544/235
    See application file for complete search history.

(56) References Cited

U.S. PATENT DOCUMENTS

| 6,306,663 | B1 | 10/2001 | Kenten et al. |
| 7,041,298 | B2 | 5/2006 | Deshaies et al. |
| 7,208,157 | B2 | 4/2007 | Dashaies et al. |
| 9,464,326 | B2 | 10/2016 | Davila |
| 10,202,390 | B2 | 2/2019 | Duncia et al. |
| 10,336,762 | B2 | 7/2019 | Bacon et al. |
| 10,849,982 | B2 | 12/2020 | Phillips et al. |
| 10,875,866 | B2 | 12/2020 | Ammann et al. |
| 11,046,686 | B2 | 6/2021 | Ammann et al. |
| 2018/0215731 | A1 | 8/2018 | Crew et al. |
| 2019/0192668 | A1 | 6/2019 | Mainolfi et al. |
| 2020/0048261 | A1 | 2/2020 | Ammann et al. |
| 2020/0079769 | A1 | 3/2020 | Ammann et al. |
| 2020/0358513 | A1 | 11/2020 | Ku et al. |
| 2023/0142629 | A1 | 5/2023 | Palmer et al. |

FOREIGN PATENT DOCUMENTS

| WO | 2005030144 A2 | 4/2005 |
| WO | 2008030579 A2 | 3/2008 |
| WO | 2015103453 A1 | 7/2015 |
| WO | 2015160845 A2 | 10/2015 |
| WO | 2016105518 A1 | 6/2016 |
| WO | 2016210034 A1 | 12/2016 |
| WO | 2016210037 A1 | 12/2016 |
| WO | 2017075054 A1 | 5/2017 |
| WO | 2017197046 A1 | 11/2017 |
| WO | 2018071606 A1 | 4/2018 |
| WO | 2018081738 A1 | 5/2018 |
| WO | 2018232288 A1 | 12/2018 |
| WO | 2019099926 A1 | 5/2019 |
| WO | 2019160915 A1 | 8/2019 |
| WO | 2021011868 A1 | 1/2021 |
| WO | 2021067606 A1 | 4/2021 |
| WO | 2021168197 A1 | 8/2021 |
| WO | 2021180103 A1 | 9/2021 |

(Continued)

OTHER PUBLICATIONS

International Search Report & Written Opinion for PCT/US2022/040765, dated Nov. 21, 2022, 10 Pages.

(Continued)

*Primary Examiner* — Douglas M Willis
(74) *Attorney, Agent, or Firm* — Mintz, Levin, Cohn, Ferris, Glovsky and Popeo, P.C.

(57) ABSTRACT

The present disclosure provides bifunctional compounds of Formula (I),

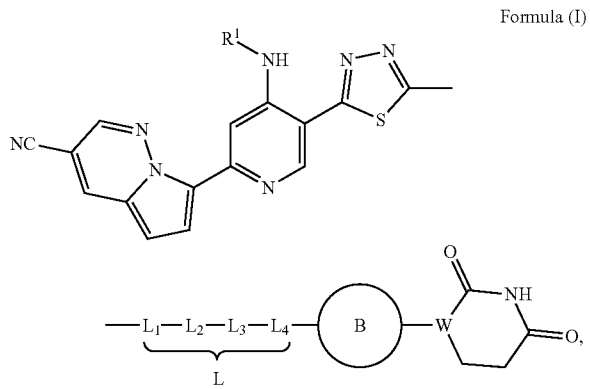

and pharmaceutically acceptable salts, isotopic forms, isolated stereoisomers, or mixtures of stereoisomers thereof, as IRAK4 degraders via ubiquitin proteasome pathway, and method for treating diseases modulated by IRAK4.

14 Claims, No Drawings

(56) References Cited

FOREIGN PATENT DOCUMENTS

| WO | 2021255212 A1 | 12/2021 |
| WO | 2021257914 A1 | 12/2021 |
| WO | 2022235698 A1 | 11/2022 |

OTHER PUBLICATIONS

International Search Report and Written Opinion received for PCT/US2021/018710, dated Mar. 31, 2021, 11 Pages.
Li et al. (2002) "IRAK-4: A Novel Member of the IRAK Family with the Properties of an IRAK-kinase", PNAS, 6 Pages.
Lu et al. (2015) "Hijacking the E3 Ubiquitin Ligase Cereblon to Efficiently Target BRD4", Chemistry & Biology, 10 Pages.
Wang et al. (2006) "Crystal Structures of IRAK-4 Kinase in Complex with Inhibitors: A Serine/threonine Kinase with Tyrosine as a Gatekeeper", Structure, 10 Pages.
Wietek et al. (2002) "Irak-4: A New Drug Target in Inflammation, Sepsis, and Autoimmunity", Molecular Interventions, 4 Pages.
Winter et al. (2015) "Phthalimide Conjugation as a Strategy for In Vivo Target Protein Degradation", Science, 7 Pages.
Chamberlain et al., "Evolution of Cereblon-Mediated Protein Degradation as a Therapeutic Modality" ACS Med Chem Lett 10(12)1592-1602, 2019.

SUBSTITUTED PYRROLO[1,2-B]PYRIDAZINES AS BIFUNCTIONAL DEGRADERS OF INTERLEUKIN-1 RECEPTOR-ASSOCIATED KINASES

CROSS-REFERENCE TO RELATED APPLICATIONS

This application claims the benefit of priority to U.S. Provisional Application No. 63/234,606, filed Aug. 18, 2021, which application is hereby incorporated by reference in its entirety.

BACKGROUND

Technical Field

The present invention provides novel bifunctional compounds for proteolytically degrading Interleukin-1 Receptor-Associated Kinase 4 (IRAK4) and methods for treating diseases modulated by IRAK4.

Description of the Related Art

Interleukin-1 receptor-associated kinase-4 (IRAK4) is a serine/threonine kinase that plays a key role in mediating toll-like receptor (TLR) and interleukin-1 receptor (IL1R) signaling in immune cells resulting in the production of pro-inflammatory cytokines. IRAK4 functions as part of the Myddosome, a large multi-protein complex that assembles at the plasma membrane upon ligand binding to TLR and IL1R receptors. The first step in Myddosome assembly is the recruitment of the scaffolding protein MyD88, followed by IRAK4 binding to Myd88 through homotypic death domain (DD) interactions. IRAK4 then undergoes auto-activation followed by phosphorylating downstream kinases IRAK1 and IRAK2. IRAK4 is considered the "master regulator" of Myddosome signaling due to it being the most upstream kinase in this complex. The importance of IRAK4 kinase function has been demonstrated in IRAK-4 kinase dead mice which are resistant to TLR-induced septic shock due to their inability to produce pro-inflammatory cytokines.

IRAK4 is also reportedly to have kinase-independent scaffolding functions. For instance, macrophages from IRAK4 kinase-dead mice are still capable of activating NF-Kb signaling through IL1, TLR2, TLR4 & TLR7 stimulation. Similar scaffolding functions have been shown in human fibroblast cells in which kinase-dead IRAK4 is capable of restoring IL-1 induced NF-κb signaling to comparable levels as WT IRAK4.

Thus, IRAK4 may be targeted for degradation, thereby providing therapeutic opportunities in treating autoimmune, inflammatory, and oncological diseases. Specific degradation of IRAK4 could be accomplished by using heterobifunctional small molecules to recruit IRAK4 to a ubiquitin ligase and thus promoting ubiquitylation and proteasomal degradation of IRAK4. For instance, thalidomide derivatives, such as lenalidomide or pomalidomide, have been reported to recruit potential protein substrates to cereblon (CRBN), a component of a ubiquitin ligase complex. See, e.g., WO 2019/099926, WO 2020/023851, PCT/US2021/018710, and U.S. Published Application No. 2019/0192668.

There is a need to further develop therapeutic agents that target IRAK4.

BRIEF SUMMARY

The present disclosure provides bifunctional compounds represented by Formula (I):

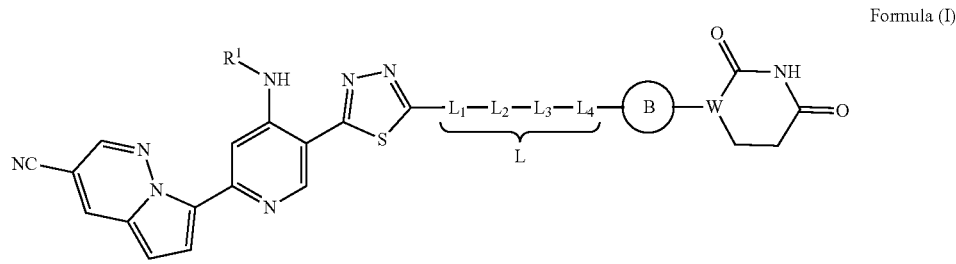

Formula (I)

or a pharmaceutically acceptable salt, isotopic form, isolated stereoisomer, or a mixture of stereoisomers thereof, wherein:

$R^1$ is $C_{1-10}$ alkyl optionally substituted with 1-3 $R^a$; $C_{3-10}$ cycloalkyl optionally substituted with 1-3 $R^a$; or 4-12 membered heterocyclyl optionally substituted with 1-3 $R^a$; or 5-12 membered heteroaryl optionally substituted with 1-3 $R^a$;

L is —$L_1$—$L_2$—$L_3$—$L_4$—, each $L_1$, $L_2$, $L_3$, and $L_4$ being independently:
 a) $C_{3-12}$ cycloalkyl optionally substituted with 1-3 $R^b$;
 b) $C_{6-12}$ aryl optionally substituted with 1-3 $R^b$;
 c) 4-12 membered heterocyclyl optionally substituted with 1-3 $R^b$;
 d) 5-12 membered heteroaryl optionally substituted with 1-3 $R^b$;
 e) direct bond;
 f) $C_{1-12}$ alkylene chain optionally substituted with 1-3 $R^d$;
 g) $C_{2-12}$ alkenylene chain optionally substituted with 1-3 $R^d$;
 h) $C_{2-12}$ alkynylene chain optionally substituted with 1 to 3 $R^d$;
 i) 1-6 ethylene glycol units;
 j) 1-6 propylene glycol units; or
 k) —C(O)—, —C(O)O—, —O—, —N($R^c$)—, —S—, —C(S)—, —C(S)—O—, —S(O)$_2$—, —S(O)=N—, —S(O)$_2$NH—, —C(O)—N($R^c$)—, —C=N—, —O—C(O)—N($R^c$)—, -or —O—C(O)—O—;

each $R^a$ is independently halo, —CN, $C_{1-3}$ alkyl optionally substituted with 1 to 3 $R^d$, $C_{3-6}$ cycloalkyl optionally substituted with 1 to 3 $R^d$, or —$OR^c$;

each $R^b$ is independently oxo, imino, sulfoximino, halo, nitro, —CN, $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, 4-12 membered heterocyclyl, —O—$R^c$, —C(O)—$R^c$, —C(O)O—$R^c$, —C(O)—N($R^c$)($R^c$), —N($R^c$)($R^c$), —N($R^c$)C(O)—R, —N($R^c$)C(O)O—$R^c$, —N($R^c$)C(O)N($R^c$)($R^c$), —N($R^c$)S(O)$_2$($R^c$), —N$R^c$S(O)$_2$N($R^c$)($R^c$), —N($R^c$)S(O)$_2$O($R^c$), —OC(O)$R^c$, —OC(O)—N($R^c$)($R^c$), —Si($R^c$)$_3$, —S—R, —S(O)$R^c$, —S(O)(NH)$R^c$, —S(O)$_2R^c$ or —S(O)$_2$N($R^c$)($R^c$), wherein each of $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, and 4-12 membered heterocyclyl may be optionally substituted with 1 to 3 $R^d$;

each $R^c$ is independently hydrogen or $C_{1-6}$ alkyl;

each $R^d$ is independently halo, oxo, —CN, —OH, $C_{1-6}$ alkyl optionally substituted with 1 to 3 fluoro, or $C_{3-8}$ cycloalkyl, or —O—$C_{1-6}$ alkyl optionally substituted with 1 to 3 fluoro;

W is —C($R^g$)— or —N—;

B ring is $C_{6-12}$ aryl, 5-12 membered heteroaryl, or 4-12 membered heterocyclyl, each being optionally substituted with 1 to 3 $R^j$;

each $R^j$ is independently hydrogen, oxo, imino, sulfoximino, halo, nitro, —CN, $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, 4-12 membered heterocyclyl, —O—$R^g$, —C(O)—$R^g$, —C(O)O—$R^g$, —C(O)—N($R^g$)($R^g$), —N($R^g$)($R^g$), —N($R^g$)C(O)—$R^g$, —N($R^g$)C(O)O—$R^g$, —N($R^g$)C(O)N($R^g$)($R^g$), —N($R^g$)S(O)$_2$($R^g$), —N$R^g$S(O)$_2$N($R^g$)($R^g$), —N($R^g$)S(O)$_2$O($R^g$), —OC(O)$R^g$, —OC(O)—N($R^g$)($R^g$), —Si($R^g$)$_3$, —S—$R^g$, —S(O)$R^g$, —S(O)(NH)$R^g$, —S(O)$_2R^g$ or —S(O)$_2$N($R^g$)($R^g$), wherein each of $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, and 4-12 membered heterocyclyl may be optionally substituted with 1 to 3 $R^k$;

$R^g$ is hydrogen or $C_{1-6}$ alkyl; and each $R^k$ is independently halo, oxo, —CN, —OH, $C_{1-6}$ alkyl optionally substituted with 1 to 3 fluoro, or $C_{3-8}$ cycloalkyl, or —O—$C_{1-6}$ alkyl optionally substituted with 1 to 3 fluoro.

Also provided herein are bifunctional compound represented by Formula (I):

or a pharmaceutically acceptable salt, isotopic form, isolated stereoisomer, or a mixture of stereoisomers thereof, wherein:

$R^1$ is $C_{1-10}$ alkyl optionally substituted with 1-3 $R^a$; $C_{3-10}$ cycloalkyl optionally substituted with 1-3 $R^a$; or 4-12 membered heterocyclyl optionally substituted with 1-3 $R^a$; L is —$L_1$—$L_2$—$L_3$—$L_4$—, each $L_1$, $L_2$, $L_3$, and $L_4$ being independently:

a) $C_{3-12}$ cycloalkyl optionally substituted with 1-3 $R^b$;
b) $C_{6-12}$ aryl optionally substituted with 1-3 $R^b$;
c) 4-12 membered heterocyclyl optionally substituted with 1-3 $R^b$;
d) 5-12 membered heteroaryl optionally substituted with 1-3 $R^b$;
e) direct bond;
f) $C_{1-12}$ alkylene chain optionally substituted with 1-3 $R^d$;
g) $C_{2-12}$ alkenylene chain optionally substituted with 1-3 $R^d$;
h) $C_{2-12}$ alkynylene chain optionally substituted with 1 to 3 $R^d$;
i) 1-6 ethylene glycol units;
j) 1-6 propylene glycol units; or
k) —C(O)—, —C(O)O—, —O—, —N($R^c$)—, —S—, —C(S)—, —C(S)—O—, —S(O)$_2$—, —S(O)=N—, —S(O)$_2$NH—, —C(O)—N($R^c$)—, —C=N—, —O—C(O)—N($R^c$)—, -or —O—C(O)—O—;

each $R^a$ is independently halo, —CN, $C_{1-3}$ alkyl optionally substituted with 1 to 3 $R^d$, $C_{3-6}$ cycloalkyl optionally substituted with 1 to 3 $R^d$, or —O$R^c$;

each $R^b$ is independently oxo, imino, sulfoximino, halo, nitro, —CN, $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, 4-12 membered heterocyclyl, —O—$R^c$, —C(O)—$R^c$, —C(O)O—$R^c$, —C(O)—N($R^c$)($R^c$), —N($R^c$)($R^c$), —N($R^c$)C(O)—R, —N($R^c$)C(O)O—$R^c$, —N($R^c$)C(O)N($R^c$)($R^c$), —N($R^c$)S(O)$_2$($R^c$), —N$R^c$S(O)$_2$N($R^c$)($R^c$), —N($R^c$)S(O)$_2$O($R^c$), —OC(O)$R^c$, —OC(O)—N($R^c$)($R^c$), —Si($R^c$)$_3$, —S—R, —S(O)$R^c$, —S(O)(NH)$R^c$, —S(O)$_2R^c$ or —S(O)$_2$N($R^c$)($R^c$), wherein each of $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, and 4-12 membered heterocyclyl may be optionally substituted with 1 to 3 $R^d$;

each $R^c$ is independently hydrogen or $C_{1-6}$ alkyl;

each $R^d$ is independently halo, oxo, —CN, —OH, $C_{1-6}$ alkyl optionally substituted with 1 to 3 fluoro, or $C_{3-8}$ cycloalkyl, or —O—$C_{1-6}$ alkyl optionally substituted with 1 to 3 fluoro;

W is —C($R^g$)— or —N—;

Formula (I)

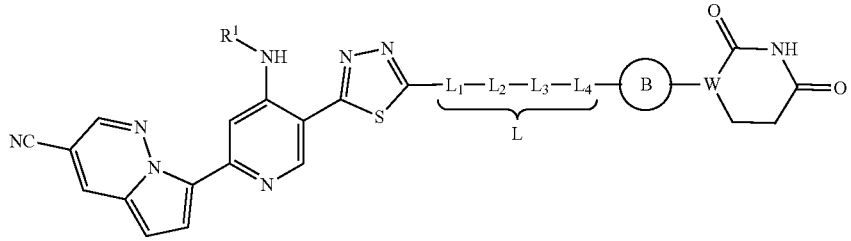

B ring is $C_{6-12}$ aryl, 5-12 membered heteroaryl, or 4-12 membered heterocyclyl, each being optionally substituted with 1 to 3 $R^j$;

each $R^j$ is independently hydrogen, oxo, imino, sulfoximino, halo, nitro, —CN, $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, 4-12 membered heterocyclyl, —O—$R^g$, —C(O)—$R^g$, —C(O)O—$R^g$, —C(O)—N(R$^g$)(R$^g$), —N(R$^g$)(R$^g$), —N(R$^g$)C(O)—R$^g$, —N(R$^g$)C(O)O—R, —N(R$^g$)C(O)N(R$^g$)(R$^g$), —N(R$^g$)S(O)$_2$(R$^g$), —NR$^g$S(O)$_2$N(R$^g$)(R$^g$), —N(R$^g$)S(O)$_2$O(R$^g$), —OC(O)R$^g$, —OC(O)—N(R$^g$)(R$^g$), —Si(R$^g$)$_3$, —S—R$^g$, —S(O)R$^g$, —S(O)(NH)R$^g$, —S(O)$_2$R$^g$ or —S(O)$_2$N(R$^g$)(R$^g$), wherein each of C$_{1-6}$ alkyl, C$_{2-6}$ alkenyl, C$_{2-6}$ alkynyl, C$_{3-15}$ cycloalkyl, C$_{1-8}$ haloalkyl, C$_{6-12}$ aryl, 5-12 membered heteroaryl, and 4-12 membered heterocyclyl may be optionally substituted with 1 to 3 R$^k$;

R$^g$ is hydrogen or C$_{1-6}$ alkyl; and each R$^k$ is independently halo, oxo, —CN, —OH, C$_{1-6}$ alkyl optionally substituted with 1 to 3 fluoro, or C$_{3-8}$ cycloalkyl, or —O—C$_{1-6}$ alkyl optionally substituted with 1 to 3 fluoro.

In particular, the

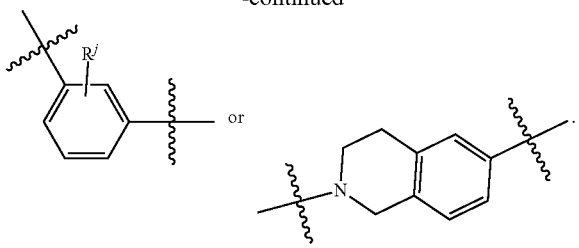

moiety is a ligase harness moiety (LHM) that specifically targets CRBN ligases, which are harnessed by the bifunctional compound to induce ubiquitination and subsequent proteasomal degradation of IRAK4.

In more specific embodiments, the B ring of the LHM has one of the following structures:

In more specific embodiments, the bifunctional compounds are Examples 1-147 described in the Examples.

A further embodiment provides a pharmaceutical composition comprising a compound of Formula (I) or any one of its substructures and a pharmaceutically acceptable carrier.

In some embodiment, the compounds of Formula (I) or pharmaceutical compositions thereof are useful as therapeutic agents for treating cancer, such as lymphomas, leukemia, acute myeloid leukemia (AML) and myelodysplastic syndrome (MDS).

In other embodiments, the compounds of Formula (I) or pharmaceutical compositions thereof are useful as therapeutic agents for treating metabolic disorders, such as diabetes (type I and type II diabetes), metabolic syndrome, dyslipidemia, obesity, glucose intolerance, hypertension, elevated serum cholesterol, and elevated triglycerides.

In other embodiments, the compounds of Formula (I) or pharmaceutical compositions thereof are useful as therapeutic agents for treating inflammatory disorders such as rheumatoid arthritis (RA), inflammatory bowel disease (IBD), Crohn's disease, ulcerative colitis, necrotizing enterocolitis, gout, Lyme disease, arthritis, psoriasis, pelvic inflammatory disease, systemic lupus erythematosus (SLE), Sjogren's syndrome, inflammation associated with gastrointestinal infections, including *C. difficile*, viral myocarditis, acute and chronic tissue injury, non-alcoholic steatohepatitis (NASH), alcoholic hepatitis and kidney disease, including chronic kidney disease and diabetic kidney disease.

DETAILED DESCRIPTION

Disclosed are bifunctional compounds capable of recruiting IRAK4 to E3 Ubiquitin Ligase for degradation, and methods of preparation and uses thereof. In particular, a bifunctional compound typically comprises an IRAK4 binder, which is covalently conjugated, via a linker, to a ligase harness moiety for targeting Ubiquitin Ligase. Advantageously, the targeted degradation of IRAK4 provides effective treatment or amelioration of disease conditions involving IRAK4 function.

Provided herein are thus bifunctional compounds represented by Formula (I)

Formula (I)

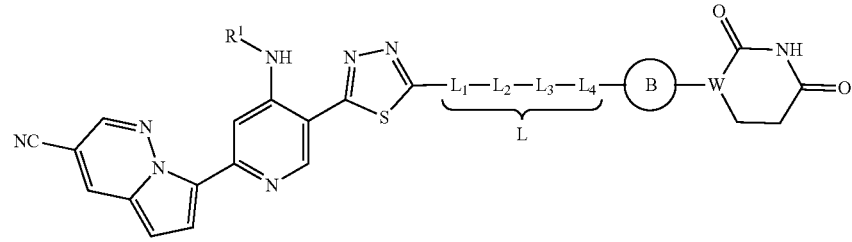

or a pharmaceutically acceptable salt, isotopic form, isolated stereoisomer, or a mixture of stereoisomers thereof, wherein:

$R^1$ is $C_{1-10}$ alkyl optionally substituted with 1-3 $R^a$; $C_{3-10}$ cycloalkyl optionally substituted with 1-3 $R^a$; or 4-12 membered heterocyclyl optionally substituted with 1-3 $R^a$; or 5-12 membered heteroaryl optionally substituted with 1-3 $R^a$;

L is $-L_1-L_2-L_3-L_4-$, each $L_1$, $L_2$, $L_3$, and $L_4$ being independently:
   a) $C_{3-12}$ cycloalkyl optionally substituted with 1-3 $R^b$;
   b) $C_{6-12}$ aryl optionally substituted with 1-3 $R^b$;
   c) 4-12 membered heterocyclyl optionally substituted with 1-3 $R^b$;
   d) 5-12 membered heteroaryl optionally substituted with 1-3 $R^b$;
   e) direct bond;
   f) $C_{1-12}$ alkylene chain optionally substituted with 1-3 $R^d$;
   g) $C_{2-12}$ alkenylene chain optionally substituted with 1-3 $R^d$;
   h) $C_{2-12}$ alkynylene chain optionally substituted with 1 to 3 $R^d$;
   i) 1-6 ethylene glycol units;
   j) 1-6 propylene glycol units; or
   k) $-C(O)-$, $-C(O)O-$, $-O-$, $-N(R^c)-$, $-S-$, $-C(S)-$, $-C(S)-O-$, $-S(O)_2-$, $-S(O)=N-$, $-S(O)_2NH-$, $-C(O)-N(R^c)-$, $-C=N-$, $-O-C(O)-N(R^c)-$, -or $-O-C(O)-O-$;

each $R^a$ is independently halo, $-CN$, $C_{1-3}$ alkyl optionally substituted with 1 to 3 $R^d$, $C_{3-6}$ cycloalkyl optionally substituted with 1 to 3 $R^d$, or $-OR^c$;

each $R^b$ is independently oxo, imino, sulfoximino, halo, nitro, $-CN$, $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, 4-12 membered heterocyclyl, $-O-R^c$, $-C(O)-R^c$, $-C(O)O-R^c$, $-C(O)-N(R^c)(R^c)$, $-N(R^c)(R^c)$, $-N(R^c)C(O)-R$, $-N(R^c)C(O)O-R^c$, $-N(R^c)C(O)N(R^c)(R^c)$, $-N(R^c)S(O)_2(R^c)$, $-NR^cS(O)_2N(R^c)(R^c)$, $-N(R^c)S(O)_2O(R^c)$, $-OC(O)R^c$, $-OC(O)-N(R^c)(R^c)$, $-Si(R^c)_3$, $-S-R$, $-S(O)R^c$, $-S(O)(NH)R^c$, $-S(O)_2R^c$ or $-S(O)_2N(R^c)(R^c)$, wherein each of $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, and 4-12 membered heterocyclyl may be optionally substituted with 1 to 3 $R^d$;

each $R^c$ is independently hydrogen or $C_{1-6}$ alkyl;

each $R^d$ is independently halo, oxo, $-CN$, $-OH$, $C_{1-6}$ alkyl optionally substituted with 1 to 3 fluoro, or $C_{3-8}$ cycloalkyl, or $-O-C_{1-6}$ alkyl optionally substituted with 1 to 3 fluoro;

W is $-C(R^g)-$ or $-N-$;

B ring is $C_{6-12}$ aryl, 5-12 membered heteroaryl, or 4-12 membered heterocyclyl, each being optionally substituted with 1 to 3 $R^j$;

each $R^j$ is independently hydrogen, oxo, imino, sulfoximino, halo, nitro, $-CN$, $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, 4-12 membered heterocyclyl, $-O-R^g$, $-C(O)-R^g$, $-C(O)O-R^g$, $-C(O)-N(R^g)(R^g)$, $-N(R^g)(R^g)$, $-N(R^g)C(O)-R^g$, $-N(R^g)C(O)O-R^g$, $-N(R^g)C(O)N(R^g)(R^g)$, $-N(R^g)S(O)_2(R^g)$, $-NR^gS(O)_2N(R^g)(R^g)$, $-N(R^g)S(O)_2O(R^g)$, $-OC(O)R^g$, $-OC(O)-N(R^g)(R^g)$, $-Si(R^g)_3$, $-S-R^g$, $-S(O)R^g$, $-S(O)(NH)R^g$, $-S(O)_2R^g$ or $-S(O)_2N(R^g)(R^g)$, wherein each of $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, and 4-12 membered heterocyclyl may be optionally substituted with 1 to 3 $R^k$;

$R^g$ is hydrogen or $C_{1-6}$ alkyl; and each $R^k$ is independently halo, oxo, $-CN$, $-OH$, $C_{1-6}$ alkyl optionally substituted with 1 to 3 fluoro, or $C_{3-8}$ cycloalkyl, or $-O-C_{1-6}$ alkyl optionally substituted with 1 to 3 fluoro.

One specific embodiment provides a bifunctional compound of Formula (I):

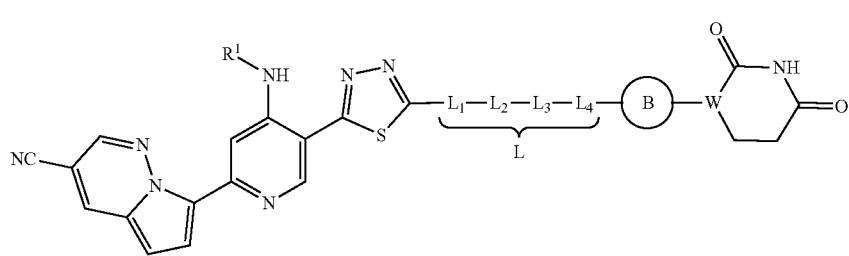

Formula (I)

or a pharmaceutically acceptable salt, isotopic form, isolated stereoisomer, or a mixture of stereoisomers thereof, wherein:

$R^1$ is $C_{1-10}$ alkyl optionally substituted with 1-3 $R^a$; $C_{3-10}$ cycloalkyl optionally substituted with 1-3 $R^a$; or 4-12 membered heterocyclyl optionally substituted with 1-3 $R^a$;

L is $-L_1-L_2-L_3-L_4-$, each $L_1$, $L_2$, $L_3$, and $L_4$ being independently:
   a) $C_{3-12}$ cycloalkyl optionally substituted with 1-3 $R^b$;
   b) $C_{6-12}$ aryl optionally substituted with 1-3 $R^b$;
   c) 4-12 membered heterocyclyl optionally substituted with 1-3 $R^b$;
   d) 5-12 membered heteroaryl optionally substituted with 1-3 $R^b$;
   e) direct bond;
   f) $C_{1-12}$ alkylene chain optionally substituted with 1-3 $R^d$;
   g) $C_{2-12}$ alkenylene chain optionally substituted with 1-3 $R^d$;
   h) $C_{2-12}$ alkynylene chain optionally substituted with 1 to 3 $R^d$;
   i) 1-6 ethylene glycol units;
   j) 1-6 propylene glycol units; or
   k) $-C(O)-$, $-C(O)O-$, $-O-$, $-N(R^c)-$, $-S-$, $-C(S)-$, $-C(S)-O-$, $-S(O)_2-$, $-S(O)=N-$, $-S(O)_2NH-$, $-C(O)-N(R^c)-$, $-C=N-$, $-O-C(O)-N(R^c)-$, -or $-O-C(O)-O-$;

each $R^a$ is independently halo, —CN, $C_{1-3}$ alkyl optionally substituted with 1 to 3 $R^d$, $C_{3-6}$ cycloalkyl optionally substituted with 1 to 3 $R^d$, or —$OR^c$;

each $R^b$ is independently oxo, imino, sulfoximino, halo, nitro, —CN, $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, 4-12 membered heterocyclyl, —O—$R^c$, —C(O)—$R^c$, —C(O)O—$R^c$, —C(O)—N($R^c$)($R^c$), —N($R^c$)($R^c$), —N($R^c$)C(O)—R, —N($R^c$)C(O)O—$R^c$, —N($R^c$)C(O)N($R^c$)($R^c$), —N($R^c$)S(O)$_2$($R^c$), —N$R^c$S(O)$_2$N($R^c$)($R^c$), —N($R^c$)S(O)$_2$O($R^c$), —OC(O)$R^c$, —OC(O)—N($R^c$)($R^c$), —Si($R^c$)$_3$, —S—R, —S(O)$R^c$, —S(O)(NH)$R^c$, —S(O)$_2R^c$ or —S(O)$_2$N($R^c$)($R^c$), wherein each of $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, and 4-12 membered heterocyclyl may be optionally substituted with 1 to 3 $R^d$;

each $R^c$ is independently hydrogen or $C_{1-6}$ alkyl;

each $R^d$ is independently halo, oxo, —CN, —OH, $C_{1-6}$ alkyl optionally substituted with 1 to 3 fluoro, or $C_{3-8}$ cycloalkyl, or —O—$C_{1-6}$ alkyl optionally substituted with 1 to 3 fluoro;

W is —C($R^g$)— or —N—;

B ring is $C_{6-12}$ aryl, 5-12 membered heteroaryl, or 4-12 membered heterocyclyl, each being optionally substituted with 1 to 3 $R^j$;

each $R^j$ is independently hydrogen, oxo, imino, sulfoximino, halo, nitro, —CN, $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, 4-12 membered heterocycyl, —O—$R^g$, —C(O)—$R^g$, —C(O)O—$R^g$, —C(O)—N($R^g$)($R^g$), —N($R^g$)($R^g$), —N($R^g$)C(O)—$R^g$, —N($R^g$)C(O)O—$R^g$, —N($R^g$)C(O)N($R^g$)($R^g$), —N($R^g$)S(O)$_2$($R^g$), —N$R^g$S(O)$_2$N($R^g$)($R^g$), —N($R^g$)S(O)$_2$O($R^g$), —OC(O)$R^g$, —OC(O)—N($R^g$)($R^g$), —Si($R^g$)$_3$, —S—$R^g$, —S(O)$R^g$, —S(O)(NH)$R^g$, —S(O)$_2R^g$ or —S(O)$_2$N($R^g$)($R^g$), wherein each of $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, and 4-12 membered heterocyclyl may be optionally substituted with 1 to 3 $R^k$;

$R^g$ is hydrogen or $C_{1-6}$ alkyl; and each $R^k$ is independently halo, oxo, —CN, —OH, $C_{1-6}$ alkyl optionally substituted with 1 to 3 fluoro, or $C_{3-8}$ cycloalkyl, or —O—$C_{1-6}$ alkyl optionally substituted with 1 to 3 fluoro.

IRAK4 Binders

The IRAK4 Binder moiety of the bifunctional compounds of Formula (I) has the following structure, in which the wavy line shows the bond attached to the remainder of the compound of Formula (I).

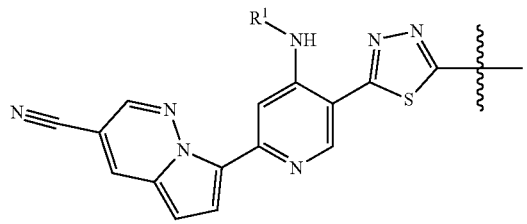

wherein $R^1$ is $C_{1-10}$ alkyl optionally substituted with 1-3 $R^a$; $C_{3-10}$ cycloalkyl optionally substituted with 1-3 $R^a$; 4-12 membered heterocyclyl optionally substituted with 1-3 $R^a$, or 5-12 membered heteroaryl optionally substituted with 1-3 R.

In more specific embodiments, $R^1$ is:

a) $C_{1-5}$ alkyl optionally substituted with one to three substituents independently selected from the group consisting of halo, —OH, —$OC_{1-4}$alkyl and —CN;

b) 4-8 membered heterocyclyl optionally substituted with one to three substituents independently selected from the group consisting of halo, $C_{1-5}$ alkyl, —OH, —$OC_{1-4}$alkyl and —CN;

c) $C_{3-10}$ cycloalkyl optionally substituted with one to three substituents independently selected from the group consisting of halo, $C_{1-5}$ alkyl, —OH, —$OC_{1-4}$alkyl and —CN;

d) 5-6 membered heteroaryl optionally substituted with one to three substituents independently selected from the group consisting of halo, $C_{1-5}$ alkyl, —OH, —$OC_{1-4}$alkyl and —CN.

In even more specific embodiments, $R^1$ is:

a) $C_{1-5}$ alkyl optionally substituted with halo, —OH, or —CN;

b) 4-8 membered heterocyclyl optionally substituted with halo, $C_{1-5}$ alkyl, —OH, or —CN; or c) $C_{3-10}$ cycloalkyl optionally substituted with halo, $C_{1-5}$ alkyl, —OH, or —CN.

In more specific embodiments, $R^1$ is oxetane, tetrahydrofuran or tetrahydropyran, each may be optionally substituted with F, $C_{1-3}$ alkyl, —OH, or —CN.

In some embodiments, $R^1$ is cyclobutyl, cyclohexyl, cyclopropyl, isoxazolyl or $C_{1-4}$alkyl, each being optionally substituted with one to three substituents independently selected from the group consisting of F, $C_{1-3}$ alkyl, —OH, —$OCH_3$ or —CN.

In other more specific embodiments, the

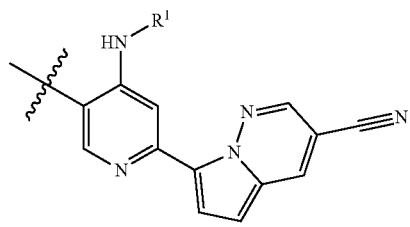

moiety has one of the following structures (the wavy line shows the bond attached to the thiadiazol moiety):

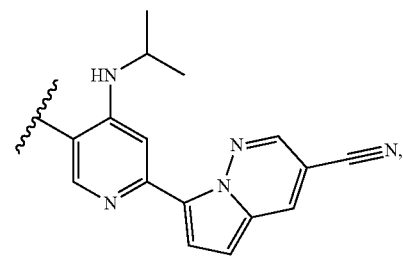

-continued
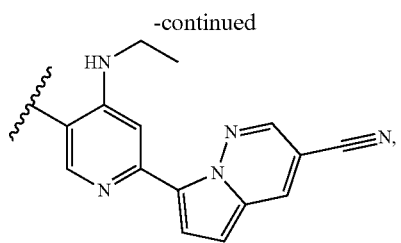
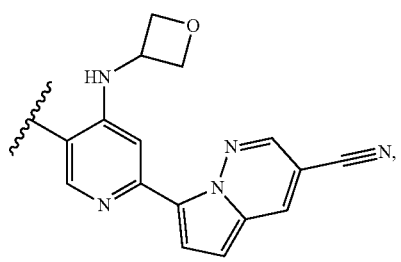
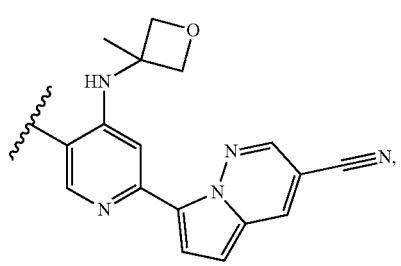
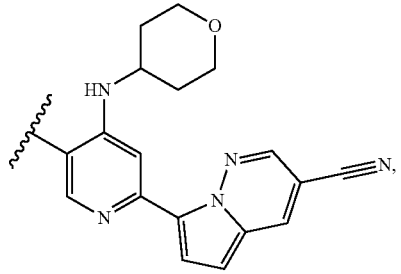
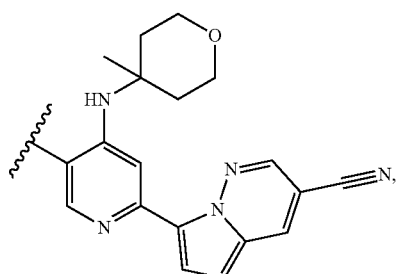
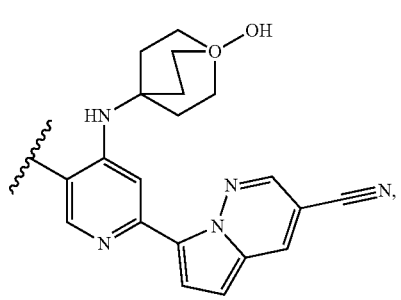
-continued
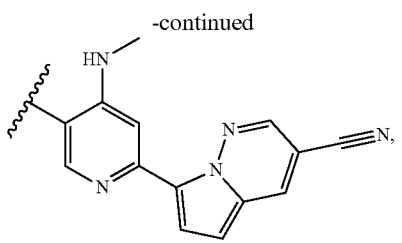
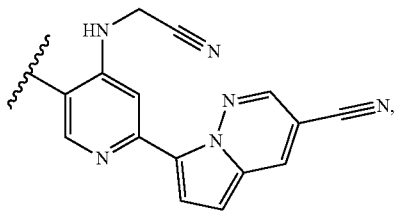
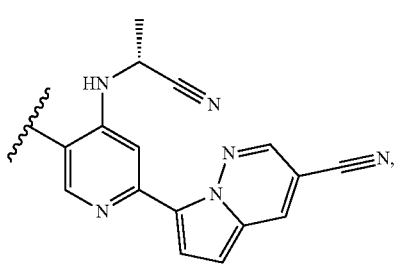
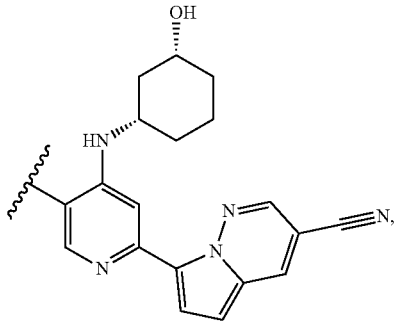
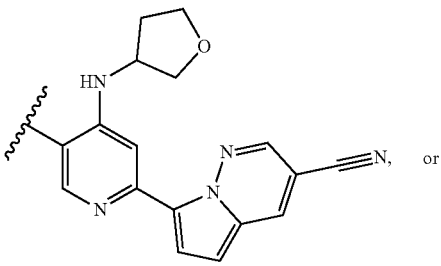, or
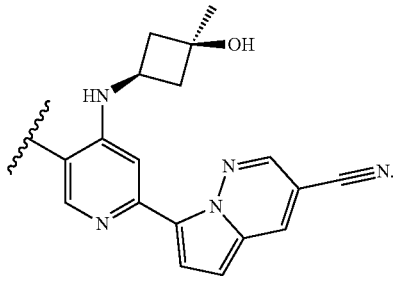 [SMILES: *c1cnc(-c2ccc3cc(C#N)cnn23)cc1N[C@H]1C[C@@](C)(O)C1]

In further embodiments, the

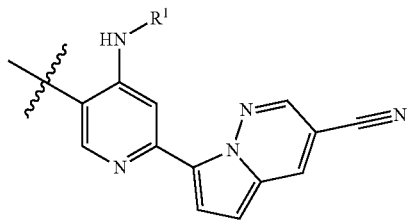

moiety has one of the following structures (the wavy line shows the bond attached to the thiadiazol moiety):

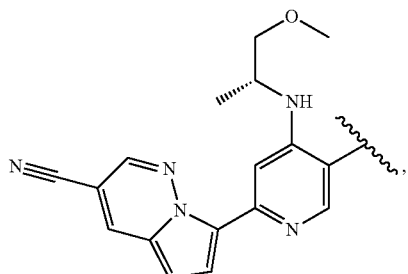

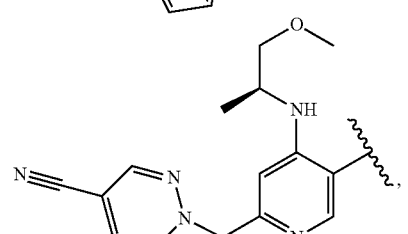

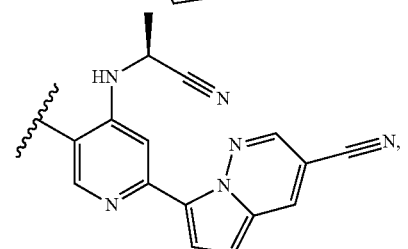

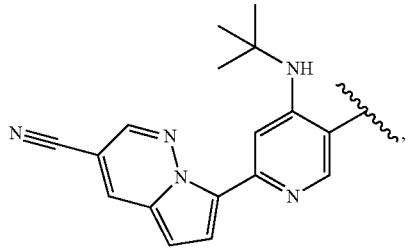

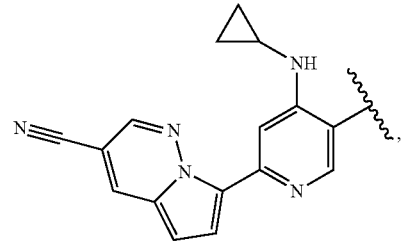

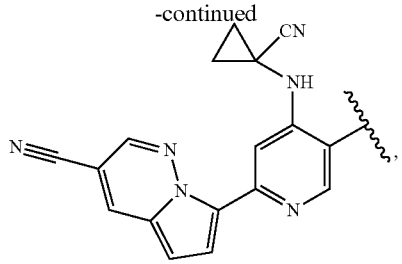

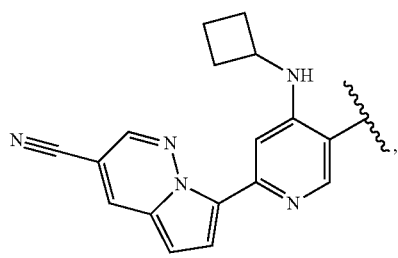

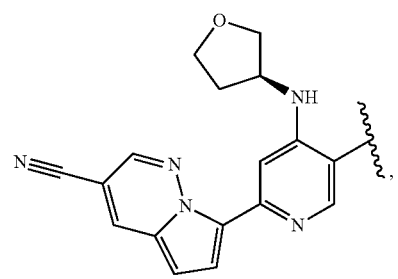

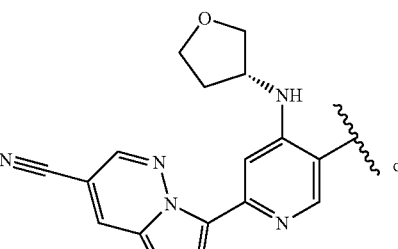

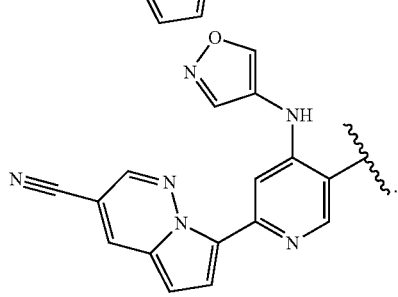 or

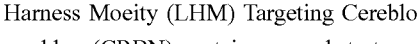
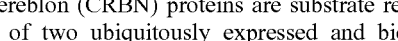

Ligase Harness Moeity (LHM) Targeting Cereblon

The cereblon (CRBN) proteins are substrate recognition subunits of two ubiquitously expressed and biologically important Cullin RING E3 ubiquitin ligase complexes. The LHM of compounds of Formula (I) targets CRBN of E3 ligases, which are harnessed by the bifunctional compound to induce ubiquitination and subsequent proteasomal degradation of IRAK4.

One embodiment provides a CRBN-targeting LHM having the following structure (the wavy line shows the bond attached to the remainder of the compound of Formula (I)):

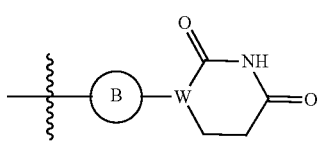

Formula (II)

wherein,
B ring is $C_{6-12}$ aryl, 5-12 membered heteroaryl, or 4-12 membered heterocyclyl, each being optionally substituted with 1 to 3 $R^j$;

each $R^j$ is independently hydrogen, oxo, imino, sulfoximino, halo, nitro, —CN, $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, 4-12 membered heterocyclyl, —O—$R^g$, —C(O)—$R^g$, —C(O)O—$R^g$, —C(O)—N($R^g$)($R^g$), —N($R^g$)($R^g$), —N($R^g$)C(O)—$R^g$, —N($R^g$)C(O)O—R, —N($R^g$)C(O)N($R^g$)($R^g$), —N($R^g$)S(O)$_2$($R^g$), —N$R^g$S(O)$_2$N($R^g$)($R^g$), —N($R^g$)S(O)$_2$O($R^g$), —OC(O)$R^g$, —OC(O)—N($R^g$)($R^g$), —Si($R^g$)$_3$, —S—$R^g$, —S(O)$R^g$, —S(O)(NH)$R^g$, —S(O)$_2$$R^g$ or —S(O)$_2$N($R^g$)($R^g$), wherein each of $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, and 4-12 membered heterocyclyl may be optionally substituted with 1 to 3 $R^k$;

$R^g$ is hydrogen or $C_{1-6}$ alkyl; and each $R^k$ is independently halo, oxo, —CN, —OH, $C_{1-6}$ alkyl optionally substituted with 1 to 3 fluoro, or $C_{3-8}$ cycloalkyl, or —O—$C_{1-6}$ alkyl optionally substituted with 1 to 3 fluoro.

In certain specific embodiments, the B ring has one of the following structures:

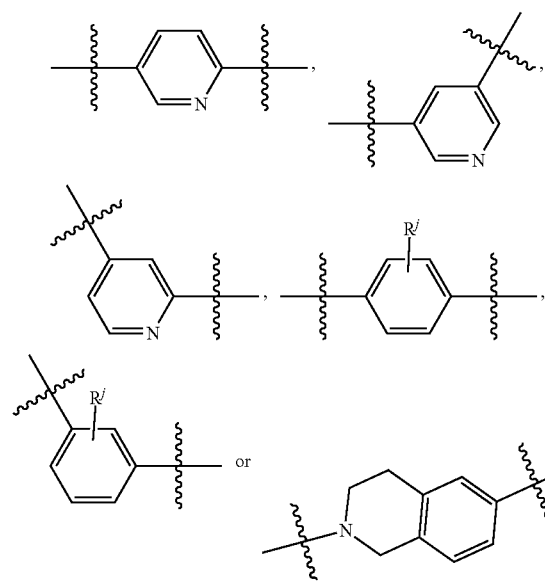

In preferred embodiments, W is —CH—.

In more specific embodiments, W is —CH— and the CRBN-targeting LHM has one of the following structures:

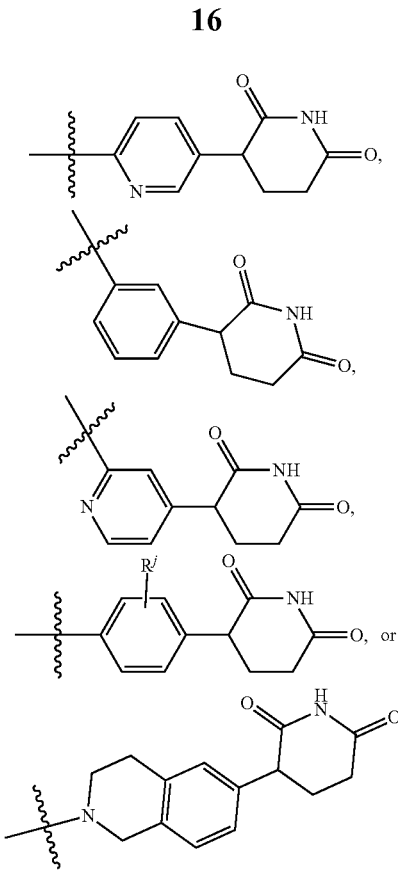

In more specific embodiments, $R^j$ is hydrogen or halo (e.g., fluoro).

In other embodiments, W is —N—.

In more specific embodiments, W is —N— and the CRBN-targeting LHM has the following structure:

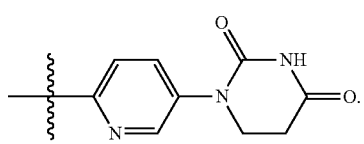 [SMILES: *c1ccc(N2CCC(=O)NC2=O)cn1]

In more specific embodiments, W is —N—, and the CRBN-targeting LHM has the following structure:

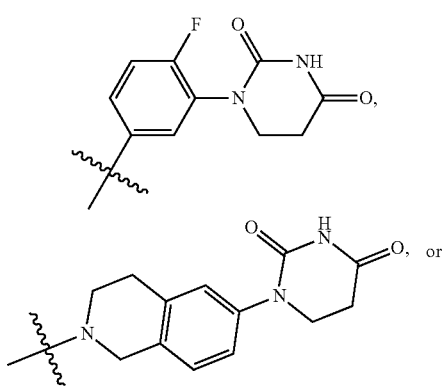

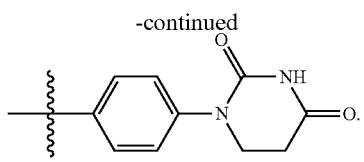

Linker

The bifunctional compounds of Formula (I) comprises a linker moiety that couples the IRAK4 Binder to the LHM. The structure (e.g., length or rigidity) of the linker moiety may impact the efficiency or selectivity of the degradation process. Typically, the linker moiety comprises multiple segments, which contribute to the overall length and rigidity of the linker, in addition to providing the respective attachment points to the IRAK4 binder and the LHM.

In certain embodiments, the linker moiety (L) of Formula (I) has up to 4 linker segments ($L_s$, s is 1, 2, 3 or 4) and each $L_1$, $L_2$, $L_3$, and $L_4$ is independently a bivalent moiety selected from:

a) $C_{3-12}$ cycloalkyl optionally substituted with 1-3 $R^b$;
b) aryl optionally substituted with 1-3 $R^b$;
c) 4-12 membered heterocyclyl optionally substituted with 1-3 $R^b$;
d) 5-12 membered heteroaryl optionally substituted with 1-3 $R^b$;
e) direct bond;
f) $C_{1-12}$ alkylene chain optionally substituted with 1-3 $R^d$;
g) $C_{2-12}$ alkenylene chain optionally substituted with 1-3 $R^d$;
h) $C_{2-12}$ alkynylene chain optionally substituted 1 to 3 with $R^d$;
i) 1-6 ethylene glycol units;
j) 1-6 propylene glycol units; and
k) —C(O)—, —C(O)O—, —O—, —N($R^c$)—, —C(S)—, —C(S)—O—, —S(O)$_2$—, —S(O)=N—, —S(O)$_2$NH—, —C(O)—N($R^c$)—, —C=N—, —O—C(O)—N($R^c$)—, -or —O—C(O)—O—;

wherein each $R^b$ is independently oxo, imino, sulfoximino, halo, nitro, —CN, $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, 4-12 membered heterocyclyl, —O—$R^c$, —C(O)—$R^c$, —C(O)O—$R^c$, —C(O)N($R^c$)($R^c$), —N($R^c$)($R^c$), —N($R^c$)C(O)—R, —N($R^c$)C(O)O—$R^c$, —N($R^c$)C(O)N($R^c$)($R^c$), —N($R^c$)S(O)$_2$($R^c$), —N$R^c$S(O)$_2$N($R^c$)($R^c$), —N($R^c$)S(O)$_2$O($R^c$), —OC(O)$R^c$, —OC(O)—N($R^c$)($R^c$), —Si($R^c$)$_3$, —S—R, —S(O)$R^c$, —S(O)(NH)$R^c$, —S(O)$_2R^c$ or —S(O)$_2$N($R^c$)($R^c$), wherein each of $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, and 4-12 membered heterocyclyl may be optionally substituted with 1 to 3 $R^d$;
each $R^c$ is independently hydrogen or $C_{1-6}$ alkyl; and
each $R^d$ is independently halo, oxo, —CN, —OH, $C_{1-6}$ alkyl optionally substituted with 1 to 3 fluoro, or $C_{3-8}$ cycloalkyl optionally substituted with 1 to 3 fluoro.

In more specific embodiments, each $L_1$, $L_2$, $L_3$, and $L_4$ being independently:

a) $C_{4-12}$ cycloalkyl optionally substituted with 1-3 $R^b$;
b) $C_{6-12}$ aryl optionally substituted with 1-3 $R^b$;
c) 4-12 membered heterocyclyl optionally substituted with 1-3 $R^b$;
d) 5-12 membered heteroaryl optionally substituted with 1-3 $R^b$;
e) direct bond;
f) $C_{1-12}$ alkylene chain optionally substituted with 1-3 $R^d$; or
g) —C(O)—, —O—, —N($R^c$)—, or —C(O)—N($R^c$)—.

It is to be understood that, unless otherwise specified and provided that the valence is satisfied, the bivalent moieties described herein (e.g., L or $L_s$) are not limited to the direction in which they are expressed. For instance, for a given linker segment, e.g., —C(O)—NH—, the manner in which it is connected to the remainder of the molecule may be either direction: i.e., —C(O)—NH— or —NH—C(O)—, provided that the connection does not violate valence rules.

On the other hand, when L is expressed by a series of $L_s$, directionality may be established by the location of the specific $L_s$ in a manner consistent with the structure of Formula (I). For instance, a linker segment $L_1$ is to be understood to couple directly to the IRAK4 Binder moiety; whereas a linker segment $L_4$ is to be understood to couple directly to the LHM.

One or more linker segments may be direct bonds. For instance, in —$L_2$—$L_3$—$L_4$—, when $L_3$ is a direct bond, it is effectively absent because $L_2$ and $L_4$ are attached directly to each other.

In various specific embodiments, $L_1$ is a ring selected from $C_{3-12}$ cycloalkyl; 6-15 membered aryl, 3-15 membered heterocyclyl, and 5-15 membered heteroaryl, each of which may be further substituted with up to 3 $R^d$ (as defined herein). In more specific embodiments, $L_1$ is a ring selected from $C_{4-12}$ cycloalkyl; 6-12 membered aryl, 4-12 membered heterocyclyl, and 5-12 membered heteroaryl, each of which may be further substituted with up to 3 $R^d$ (as defined herein).

In various specific embodiments, $L_1$ may be one of the following ring moities:

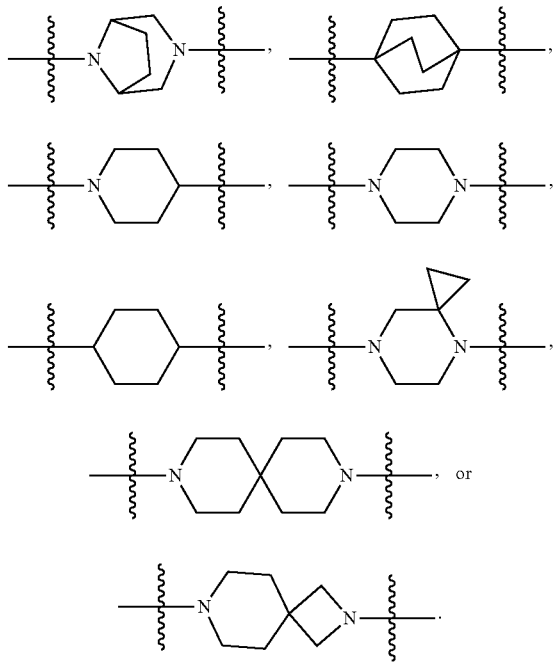

In other specific embodiments, $L_1$ may be
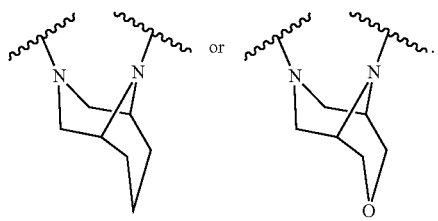 [SMILES: *N1CC2CCCC(C1)N2* ; *N1CC2COCC(C1)N2*] or 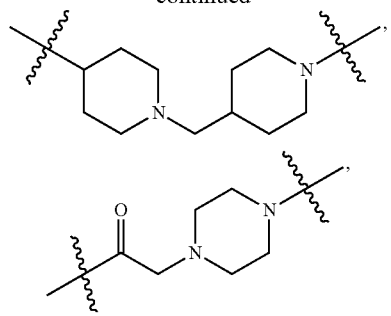
In specific embodiments, —$L_2$—$L_3$—$L_4$— has one of the following structures:
—C(O)—, —(CH$_2$)$_m$—, 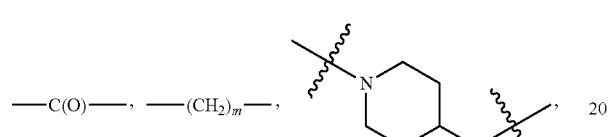
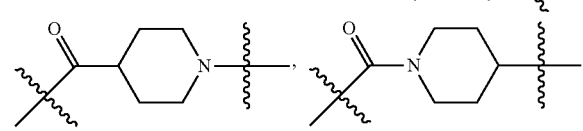
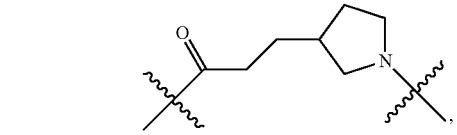
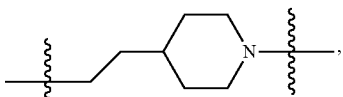
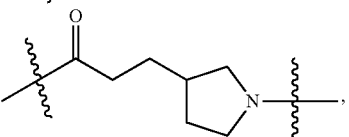
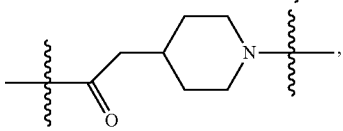
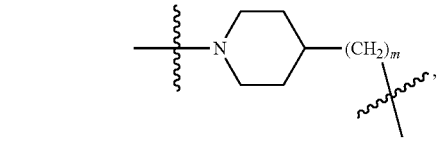
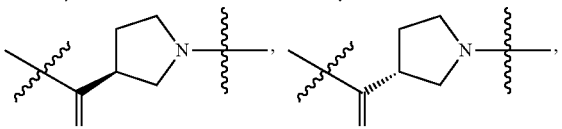
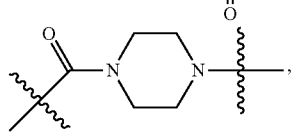
wherein, m is 1, 2 or 3, and $R^c$ is H or $C_{1-3}$ alkyl.
In further specific embodiments, —$L_2$—$L_3$—$L_4$— has one of the following structures:

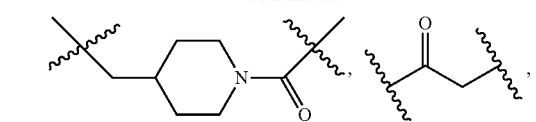
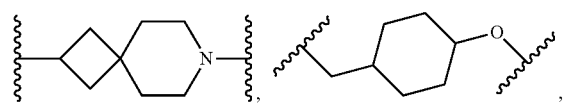
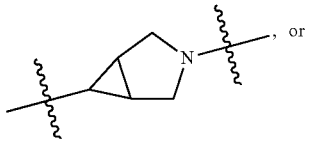
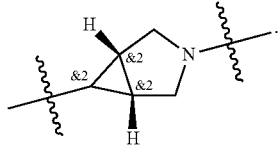
In more specific embodiments, L has one of the following structures:
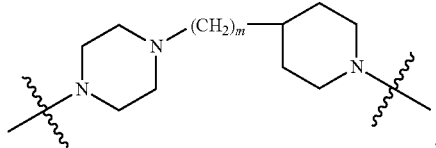
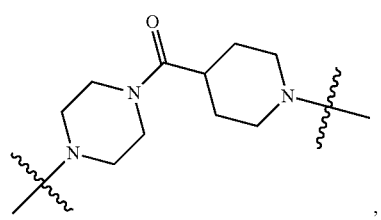
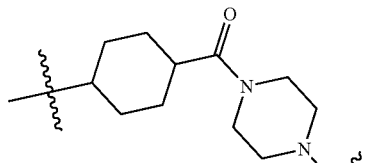
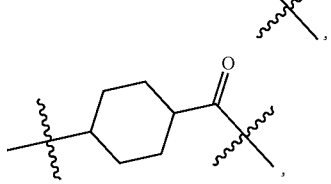
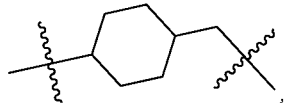
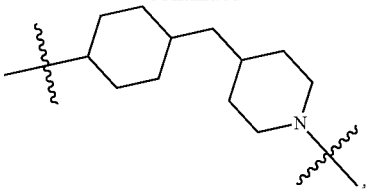
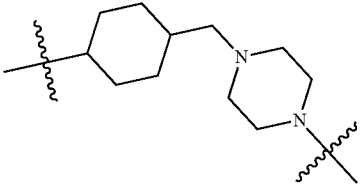
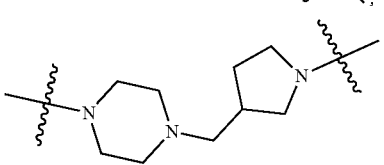
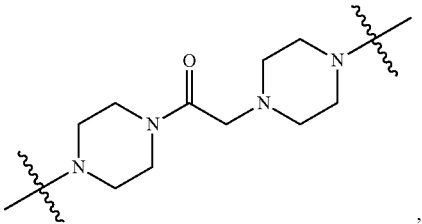
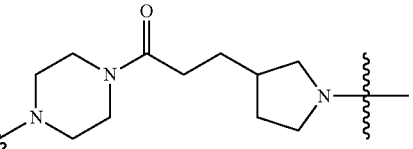
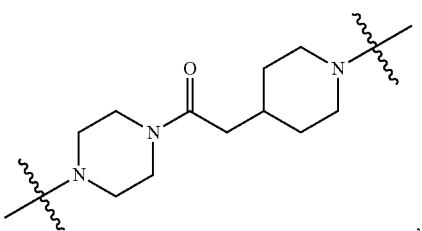
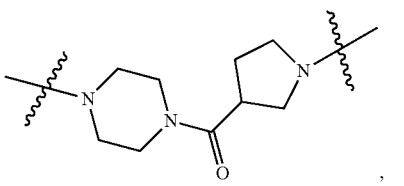
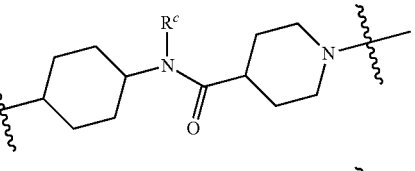
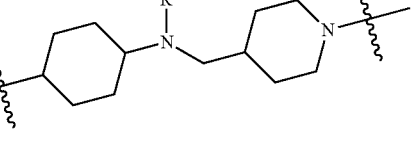

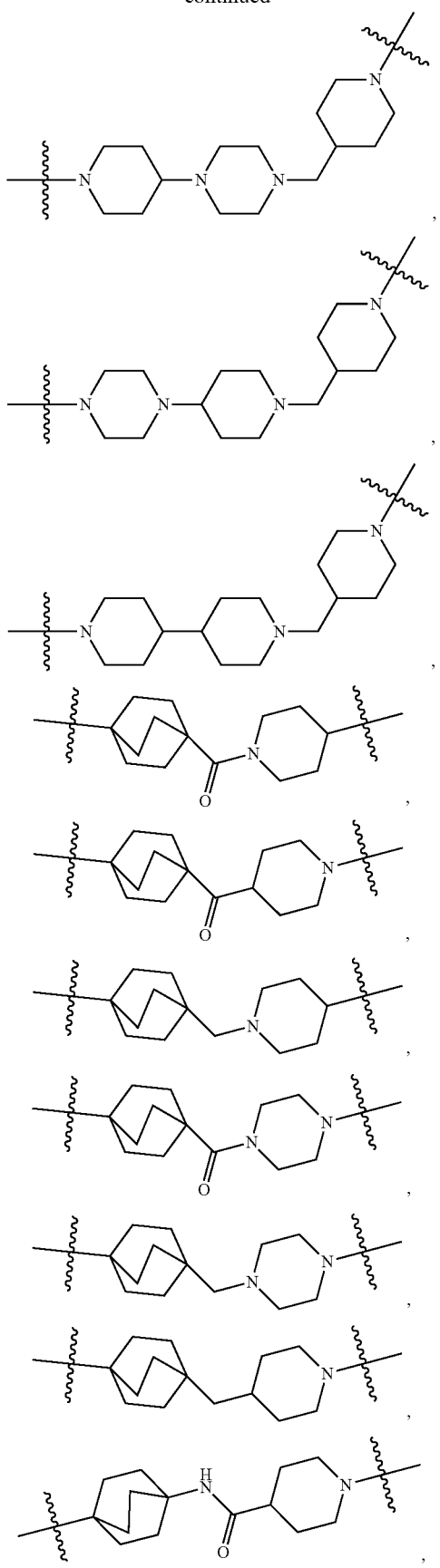
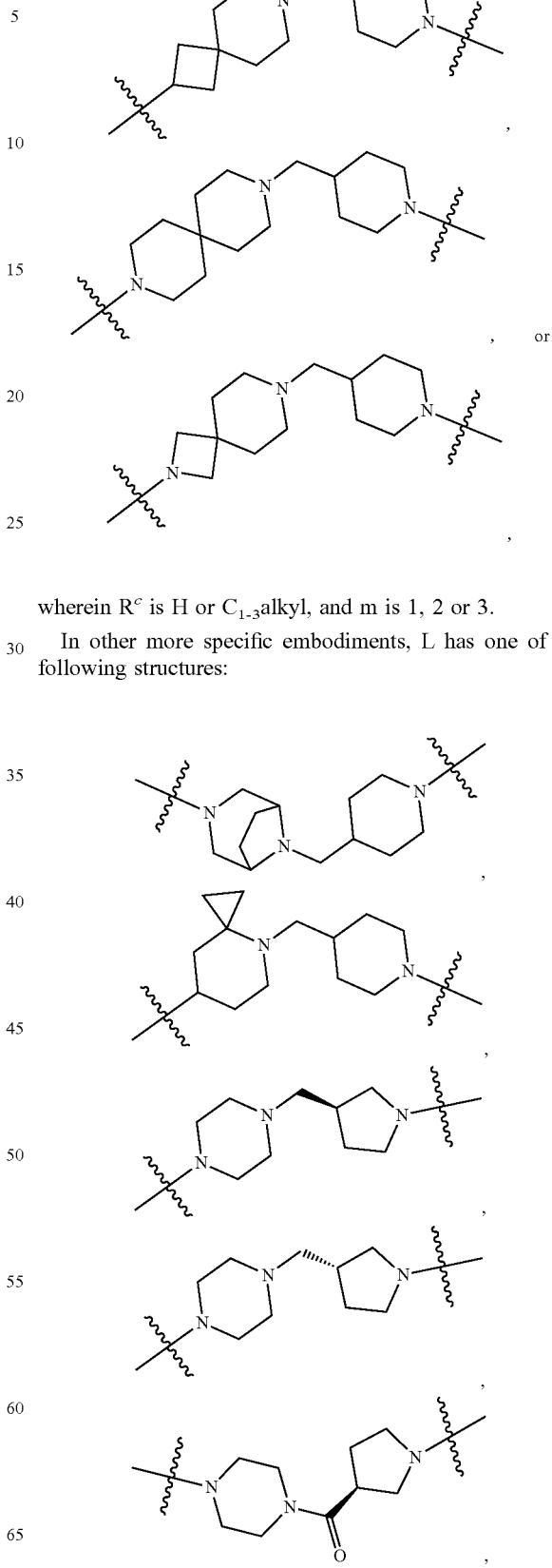
wherein $R^c$ is H or $C_{1-3}$alkyl, and m is 1, 2 or 3.
In other more specific embodiments, L has one of the following structures:

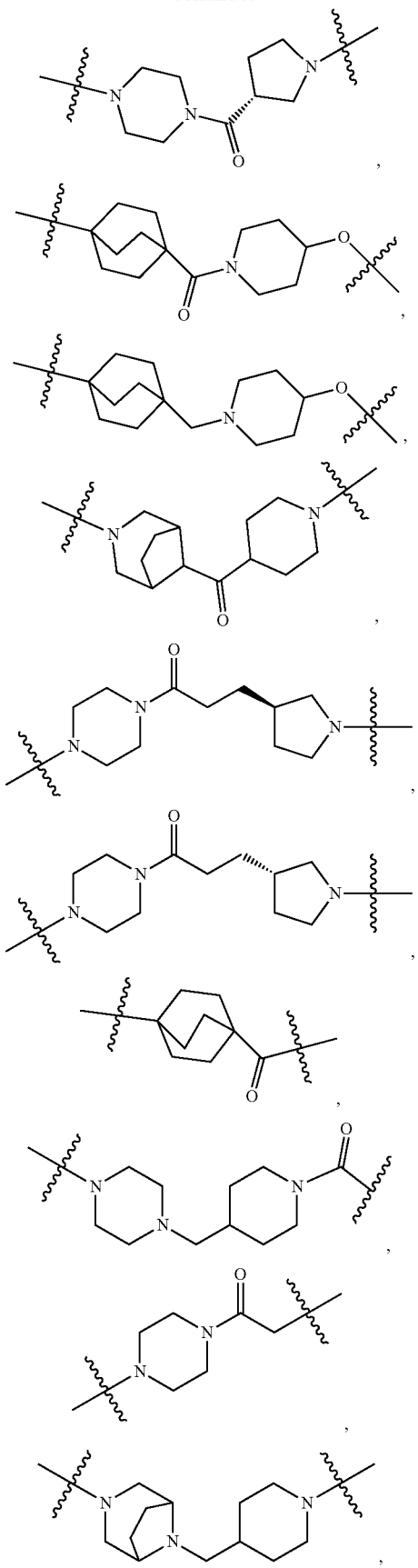
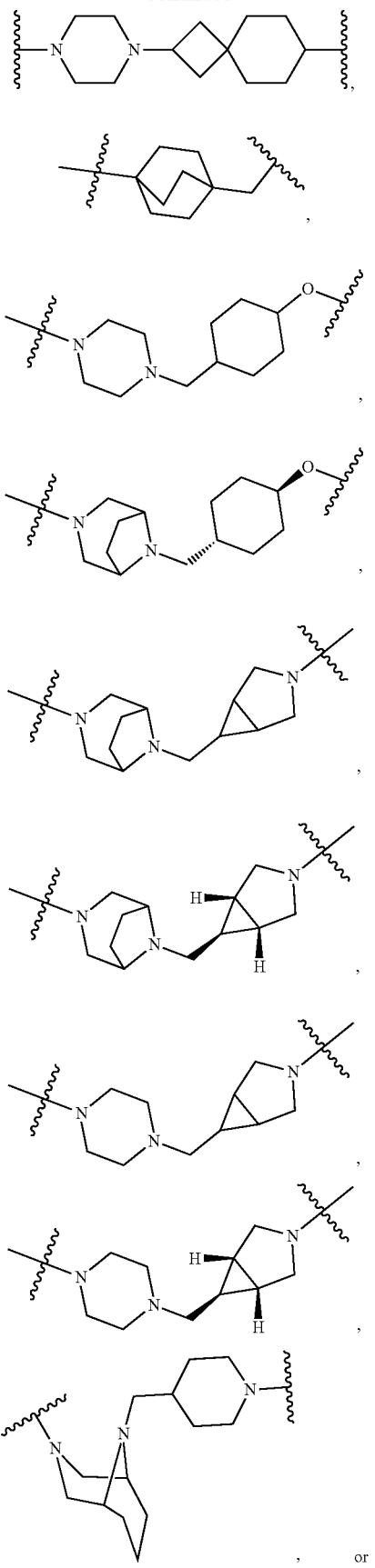

-continued

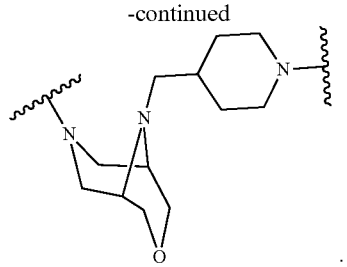

Construction of Compounds of Formula (I)

The synthesis or construction of the compounds of Formula (I) can be carried out in multiple steps, typically involving separately preparing building blocks of the IRAK4 binder and the LHM moiety, followed by joining the respective building blocks through covalent bond formation. Generally speaking, either or both building blocks may be prepared with one or more linker precursors ($L_x$). A linker precursor comprises one or more linker segments ($L_s$) and has a terminal reactive group for further coupling. The two building blocks can be finally coupled (via formation of an $L_s$ segment) to afford a compound of Formula (I).

The following schemes demonstrate the general approaches of preparing building blocks. Examples 1-147 are specific examples of Formula (I) that were synthesized and characterized by their respective physiochemical properties.

A. Preparing IRAK4 Binder Building Blocks

Described herein are a number of general schemes for preparing IRAK4 Binder building blocks.

SCHEME A1

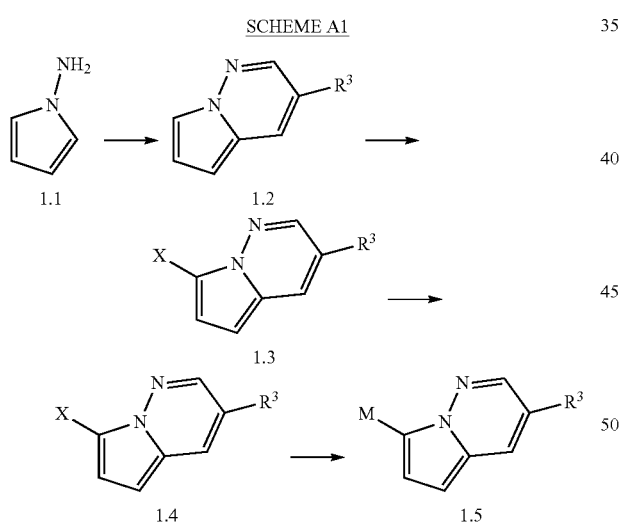

The compounds of formula 1.5 may be accessed according to the method outlined in Scheme 1.1-aminopyrrole 1.1 may be condensed with a suitable coupling partner to produce substituted pyrrolo[1,2-b]pyridazine 1.2 using a suitable catalyst (e.g., HCl, etc.) and suitable solvent (e.g., EtOH, etc.). Halogenation at the position shown using a known halogenating reagent (e.g., NBS, etc.) can form the intermediate 1.3, which can be further substituted either via C—H activation or electrophilic aromatic substitution with a suitable reagent (e.g., selectfluor, etc.) to produce intermediate 1.4. Halogen metal exchange of —X to —M can then be achieved using a suitable reagent (e.g., n-BuLi, etc.) or transition metal coupling using a palladium catalyst and metal source (e.g., $B_2Pin_2$, $Me_6Sn_2$, etc.) to give intermediate 1.5.

SCHEME A2

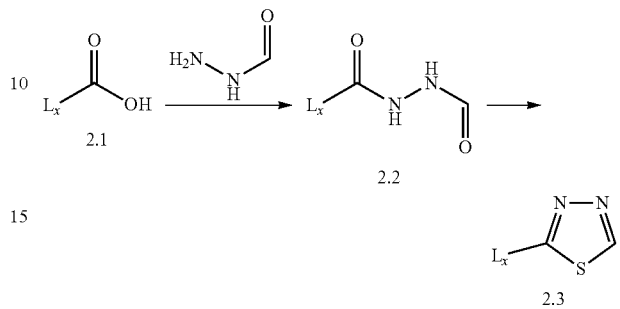

The compounds of the formula 2.3 may be accessed according to the method outlined in Scheme 2. The acid 2.1 can be converted to the corresponding acyl hydrazine using a coupling reagent (e.g., HATU, etc.) in the presence of a base (e.g., DIPEA, etc.). Cyclization of compound 2.2 can be accomplished by heating in the presence of a thionating reagent (e.g., Lawesson's reagent, etc.) to provide compound 2.3.

SCHEME A3

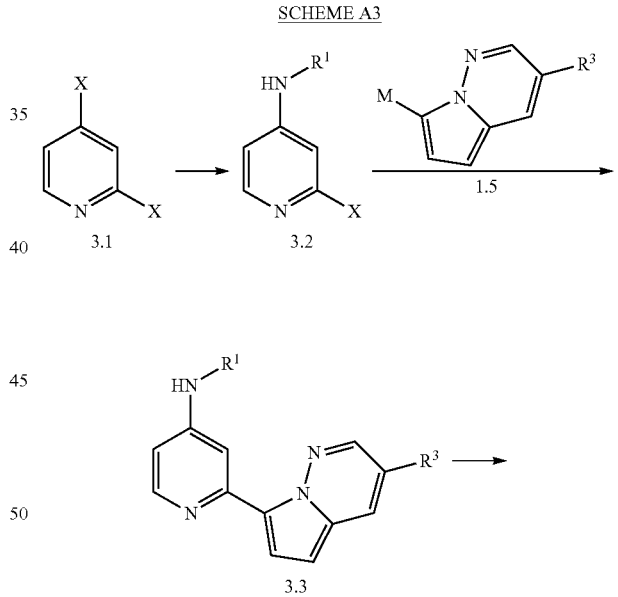

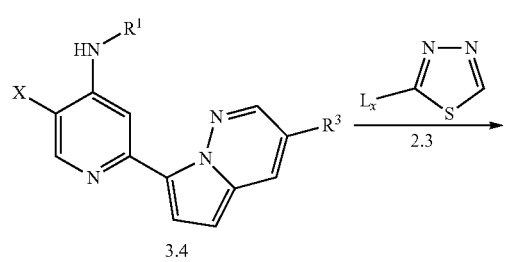

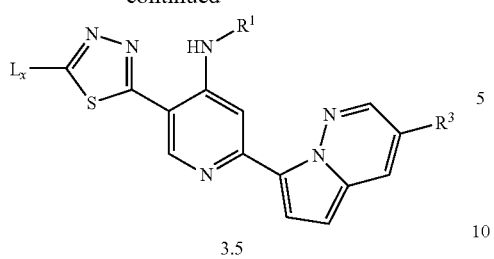

3.5

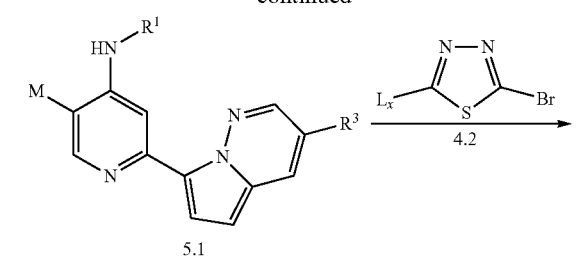

5.1

The compounds of formula 3.6 may be accessed according to the method outlined in Scheme 3. Dihalopyridine 3.1 may be converted to compound 3.2 via displacement of one of the halogen groups (e.g., nucleophilic aromatic substitution, etc.). Further functionalization of compound 3.2 using a metal-containing heterocyclic species (e.g., compound 1.5) with a suitable catalyst, such as a palladium catalyst, can afford compound 3.3. Halogenation at the position shown using a known halogenating reagent (e.g., NBS, etc.) can form the intermediate 3.4 which can be further substituted through a cross-coupling reaction using a suitable catalyst, such as a palladium catalyst, to provide compound 3.5.

SCHEME A4

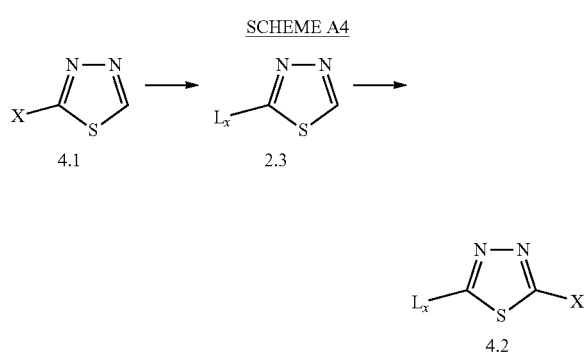

Compounds of formula 4.2 may be assembled following Scheme A4. Displacement of the halogen group (e.g., nucleophilic aromatic substitution, etc.) of a halothiadiazole 4.1 with a nucleophile (e.g., an amine, etc.) can provide compound 2.3. Halogenation at the position shown using a known halogenating reagent (e.g., NBS, etc.) can form the intermediate 4.2.

SCHEME A5

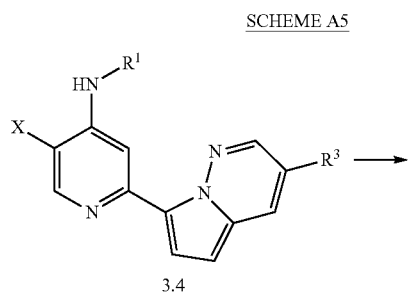

3.4

3.5

Compounds of formula 3.5 may also be assembled following Scheme A5. Halogen metal exchange of —X to -M can then be achieved using a suitable reagent (e.g., n-BuLi, etc.) or transition metal coupling using a palladium catalyst and metal source (e.g., $B_2Pin_2$, $Me_6Sn_2$, etc.) to give intermediate 5.1. Functionalization of compound 5.1 can be done utilizing a cross-coupling reaction with compound 4.2 using a suitable catalyst, such as a palladium catalyst, to provide compound 3.5.

Under Scheme A5, $L_x$ may be a ring having a reactive moiety, which could in turn be coupled to another linker segment. For instance, a BOC-protected $L_x$ may be:

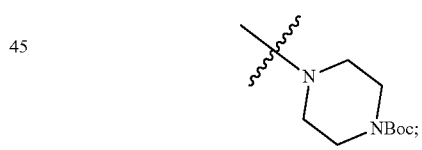

and compound 4.2 is

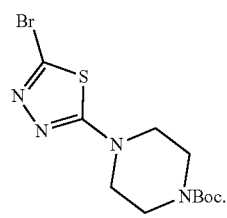 [SMILES: CC(C)(C)OC(=O)N1CCN(c2nnc(Br)s2)CC1]

The resulting compound 3.5 is an IRAK4 Binder building block having an $L_1$ precursor, i.e., a piperazine ring, which can be further coupled to another linker segment via the reactive secondary amine of piperazine.

SCHEME A6

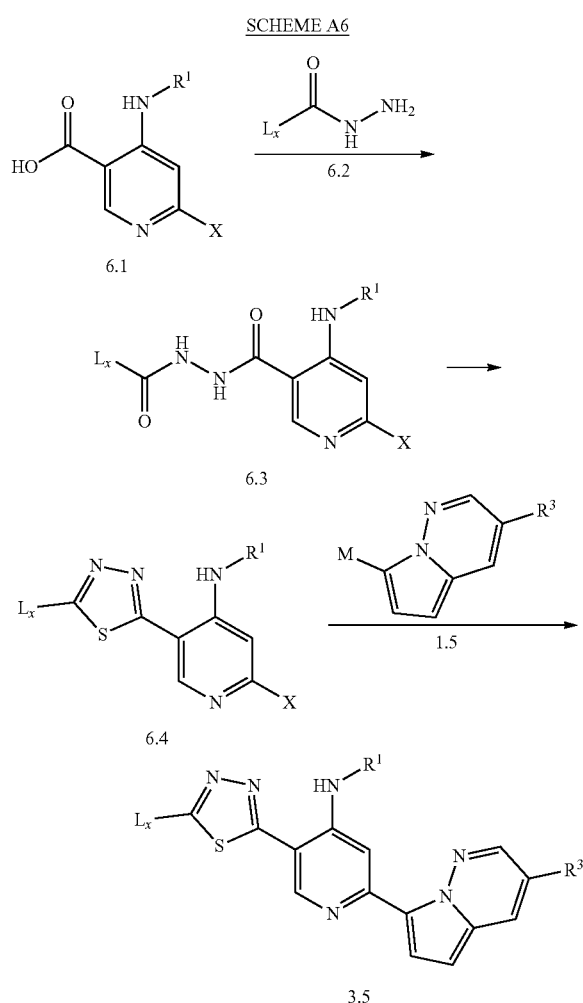

An alternative method of access compound 3.5 is shown in Scheme A6. Starting from the nicotinic acid 6.1, the corresponding acyl hydrazine can be prepared using a coupling reagent (e.g., HATU, etc.) in the presence of a base (e.g., DIPEA, etc.). Cyclization of compound 6.3 can be accomplished by heating in the presence of a thionating reagent (e.g., Lawesson's reagent, etc.) to provide compound 6.4. Further functionalization of compound 6.4 using a metal-containing heterocyclic species (e.g., compound 1.5) with a suitable catalyst, such as a palladium catalyst, can afford compound 3.5.

Under Scheme A6, $L_x$ may be a ring having a reactive moiety, which could in turn be coupled to another linker segment. For instance, $L_x$ may be:

(optionally in a BOC-protected form during synthesis) and the resulting compound 3.5 is another IRAK4 Binder building block having an $L_1$ precursor, i.e., a bicyclo[2.2.2]octane ring, which can be further coupled to another linker segment via the reactive primary amine.

Specific examples of preparing IRAK4 Binder building blocks, which are intermediates to be further coupled to LHM, are described in further detail below.

Intermediate A: 7-(5-(5-(piperazin-1-yl)-1,3,4-thiadiazol-2-yl)-4-((tetrahydro-2H-pyran-4-yl)amino)pyridin-2-yl)pyrrolo[1,2-b]pyridazine-3-carbonitrile

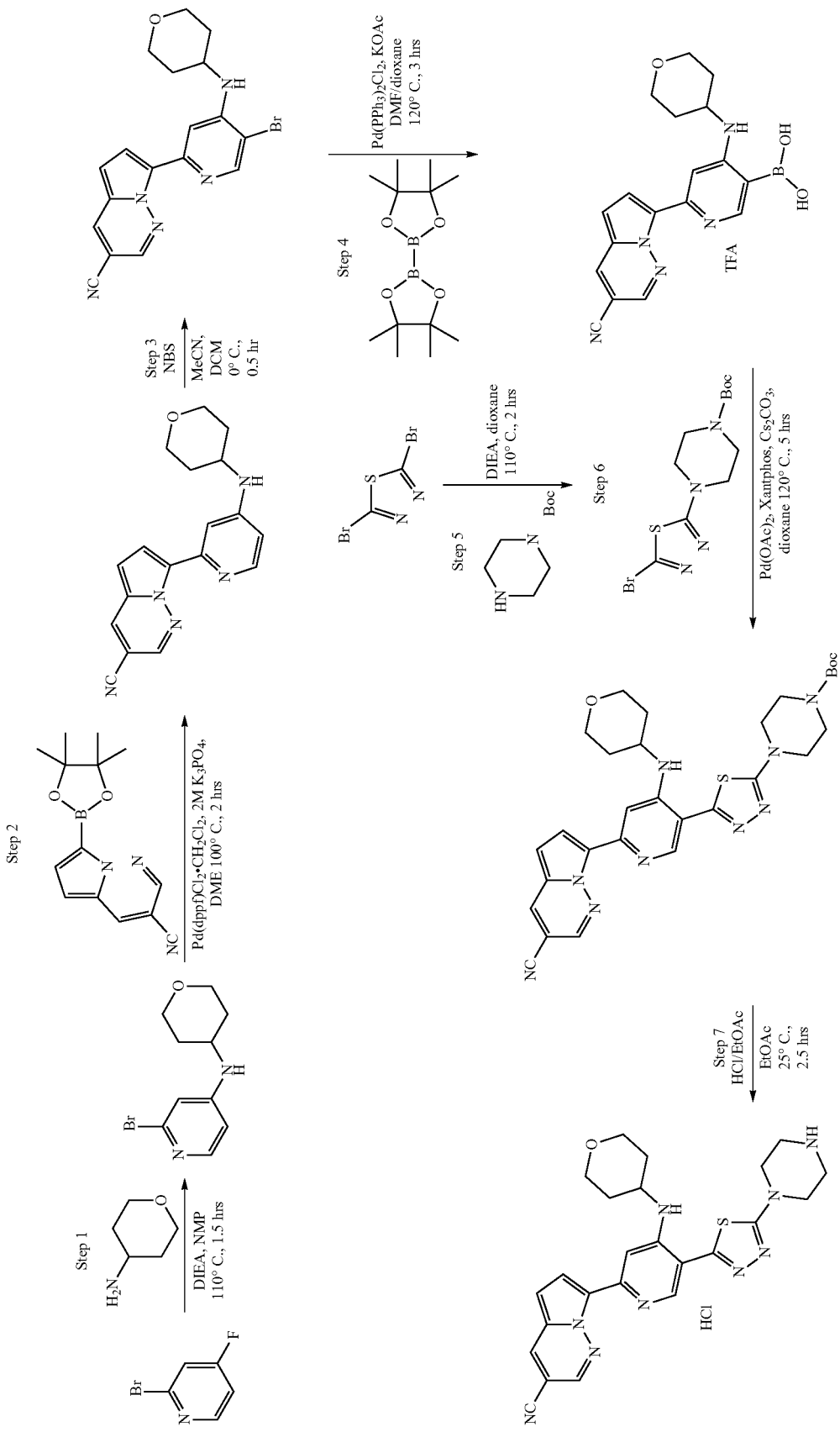

Step 1: To a solution of 2-bromo-4-fluoropyridine (30.0 g, 170 mmol, 1.00 eq) in NMP (300 mL) was added DIEA (33.1 g, 255 mmol, 44.5 mL, 1.50 eq) and tetrahydro-2H-pyran-4-amine (20.7 g, 204 mmol, 1.20 eq), then the mixture was stirred at 110° C. for 1.5 hrs. The reaction mixture was poured into $H_2O$ (500 mL), extracted with methyl tert-butyl ether (500 mL*4). The combined organic layer was washed with saturated brine (500 mL*6) and organic layer was dried over anhydrous $Na_2SO_4$, filtered and concentrated under vacuum to give 2-bromo-N-(tetrahydro-2H-pyran-4-yl)pyridin-4-amine. The residue was used to next step without further purification (46 g). LCMS: m/z=257.2 $(M+H)^+$ Step 2: The product from step 1 (30.0 g, 101 mmol, 1.00 eq) and 7-(4,4,5,5-tetramethyl-1,3,2-dioxaborolan-2-yl)pyrrolo[1,2-b]pyridazine-3-carbonitrile (35.5 g, 132 mmol, 1.30 eq) in DME (300 mL) was added $K_3PO_4$ (2.00 M, 102 mL, 2.00 eq) and $Pd(dppf)Cl_2 \cdot CH_2Cl_2$ (8.29 g, 10.2 mmol, 0.100 eq) under $N_2$, the mixture was stirred at 100° C. for 2 hrs under $N_2$. The reaction mixture was concentrated under reduced pressure to give a residue, which was purified by MPLC ($SiO_2$, petroleum ether/ethyl acetate=10/1 to 0/1, $R_f$=0.10). 7-(4-((tetrahydro-2H-pyran-4-yl)amino)pyridin-2-yl)pyrrolo[1,2-b]pyridazine-3-carbonitrile (30.0 g, 93.5 mmol, 92.1% yield) was obtained as a yellow solid. LCMS: m/z=320.2 $(M+H)^+$ Step 3: To a solution of 7-(4-((tetrahydro-2H-pyran-4-yl)amino)pyridin-2-yl)pyrrolo[1,2-b]pyridazine-3-carbonitrile (36.0 g, 106 mmol, 1.00 eq) in MeCN (758 mL) and DCM (758 mL) was added a solution of NBS (16.7 g, 93.6 mmol, 0.880 eq) in MeCN (127 mL) and DCM (127 mL) at 0° C., the mixture was stirred at 0° C. for 0.5 hr. The reaction mixture was filtered, the filter cake was collected, and the filtrate was concentrated under reduced pressure to give a residue. The residue was purified by MPLC ($SiO_2$, petroleum ether/ethyl acetate=10/1 to 1/1, $R_f$=0.60). 7-(5-bromo-4-((tetrahydro-2H-pyran-4-yl)amino)pyridin-2-yl)pyrrolo[1,2-b]pyridazine-3-carbonitrile (34.9 g, 85.8 mmol, 80.6% yield) was obtained with combined the filter cake and the residue of MPLC which was a yellow solid. LCMS: m/z=397.9 $(M+H)^+$ Step 4: To a solution of 7-(5-bromo-4-((tetrahydro-2H-pyran-4-yl)amino)pyridin-2-yl)pyrrolo[1,2-b]pyridazine-3-carbonitrile (34.9 g, 85.7 mmol, 1.00 eq) and 4,4,4',4',5,5,5',5'-octamethyl-2,2'-bi(1,3,2-dioxaborolane) (43.5 g, 171 mmol, 2.00 eq) in DMF (175 mL) and dioxane (350 mL) was added KOAc (25.2 g, 257 mmol, 3.00 eq) and $Pd(PPh_3)_2Cl_2$ (9.02 g, 12.9 mmol, 0.150 eq) under $N_2$, the mixture was stirred at 120° C. for 3 hrs under $N_2$. The reaction mixture was filtered with silica gel, the filtrate was concentrated under reduced pressure to give a residue. The crude product was purified by reverse-phase HPLC (TFA condition). Desired product (13.3 g, 25.5 mmol, 29.8% yield, TFA) was obtained as a yellow solid. LCMS: product: m/z=364.0 $(M+H)^+$ Step 5: To a solution of 2,5-dibromo-1,3,4-thiadiazole (20.0 g, 82.0 mmol, 1.00 eq) and tert-butyl piperazine-1-carboxylate (18.3 g, 98.4 mmol, 1.20 eq) in dioxane (200 mL) was added DIEA (21.2 g, 164 mmol, 28.5 mL, 2.00 eq), then the mixture was stirred at 110° C. for 2 h. The mixture was cooled to 25° C. and filtered, the filter cake was washed with ethyl acetate (50.0 mL*2), the filtrate was washed with brine (200 mL*2), dried over anhydrous $Na_2SO_4$, filtered and concentrated under reduced pressure to give a residue. The residue was used in the next step without further purification. tert-butyl 4-(5-bromo-1,3,4-thiadiazol-2-yl)piperazine-1-carboxylate (31.8 g, crude) was obtained as a red solid. LCMS: m/z=294.8 $(M+H)^+$ Step 6: To a solution of (6-(3-cyanopyrrolo[1,2-b]pyridazin-7-yl)-4-((tetrahydro-2H-pyran-4-yl)amino)pyridin-3-yl)boronic acid (6.00 g, 11.5 mmol, 1.00 eq, TFA) and tert-butyl 4-(5-bromo-1,3,4-thiadiazol-2-yl)piperazine-1-carboxylate (4.23 g, 12.1 mmol, 1.05 eq) in dioxane (315 mL) was added $Pd(OAc)_2$ (518 mg, 2.3 mmol, 0.200 eq), Xantphos (2.67 g, 4.6 mmol, 0.400 eq) and $Cs_2CO_3$ (9.39 g, 28.8 mmol, 2.50 eq) under $N_2$. The mixture was stirred at 120° C. for 5 hrs under $N_2$. The reaction mixture was filtered; the filter cake was washed with ethyl acetate (200 mL*3) and collected. The filtrate was filtered, the filter cake was collected, and the filtrate was washed with water (500 mL*2), dried over $Na_2SO_4$, filtered and concentrated under reduced pressure to give tert-butyl 4-(5-(6-(3-cyanopyrrolo[1,2-b]pyridazin-7-yl)-4-((tetrahydro-2H-pyran-4-yl)amino)pyridin-3-yl)-1,3,4-thiadiazol-2-yl)piperazine-1-carboxylate (6.00 g, 8.7 mmol, 75% yield) as a yellow solid, which was used in the next step without further purification. Desired Step 7: A mixture of tert-butyl 4-(5-(6-(3-cyanopyrrolo[1,2-b]pyridazin-7-yl)-4-((tetrahydro-2H-pyran-4-yl)amino)pyridin-3-yl)-1,3,4-thiadiazol-2-yl)piperazine-1-carboxylate (6.00 g, 8.7 mmol, 1.00 eq) in HCl/EtOAc (4.00 M, 52.4 mL, 24.2 eq) and EtOAc (20.0 mL) was stirred at 25° C. for 2.5 hrs. The reaction mixture was filtered and the resulting filter cake was collected and concentrated under reduced pressure to give the HCl salt of the titled product (4.06 g, 7.2 mmol, 82.6% yield) as a yellow solid. LCMS: m/z=488.4 (M+H)+. $^1$H NMR: (400 MHz, $D_2O$) δ 8.52 (s, 2H), 8.19 (s, 1H), 7.87 (d, J=4.8 Hz, 1H), 7.25 (s, 1H), 7.14 (d, J=5.2 Hz, 1H), 3.99-4.03 (m, 2H), 3.91-3.95 (m, 4H), 3.74 (t, J=20.0 Hz, 2H), 3.48-3.52 (m, 4H), 2.12 (d, J=11.2 Hz, 2H), 1.66-1.78 (m, 2H).

Intermediate B: 7-(4-(isopropylamino-5-(5-(piperazin-1-yl)-1,3,4-thiadiazol-2-yl)pyridin-2-yl)pyrrolo[1,2-b]pyridazine-3-carbonitrile Intermediate B

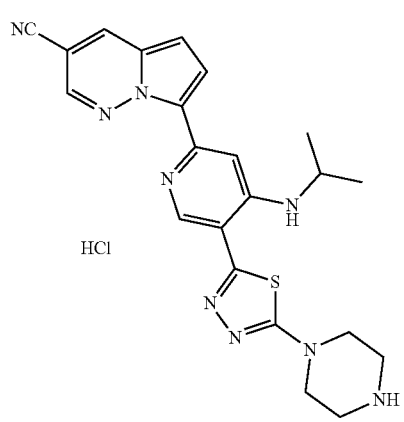

Intermediate B was prepared in a similar manner as Intermediate A, substituting tetrahydro-2H-pyran-4-amine for isopropyl-amine in Step 1 to give the HCL salt of the title product as a yellow solid. LCMS: m/z=446.2 (M+H)+. $^1$H NMR: (400 MHz, MeOD) δ 8.77 (d, J=2.0 Hz, 1H), 8.69 (d, J=2.4 Hz, 1H), 8.56 (s, 1H), 8.10 (d, J=5.2 Hz, 1H), 7.90 (s, 1H), 7.24 (d, J=4.8 Hz, 1H), 4.32-4.29 (m, 1H), 3.97-3.94 (d, J=10.4 Hz, 4H), 3.48-3.44 (d, J=14.4 Hz, 4H), 1.48 (d, J=6.4 Hz, 6H).

Intermediate B: Alternate Route:

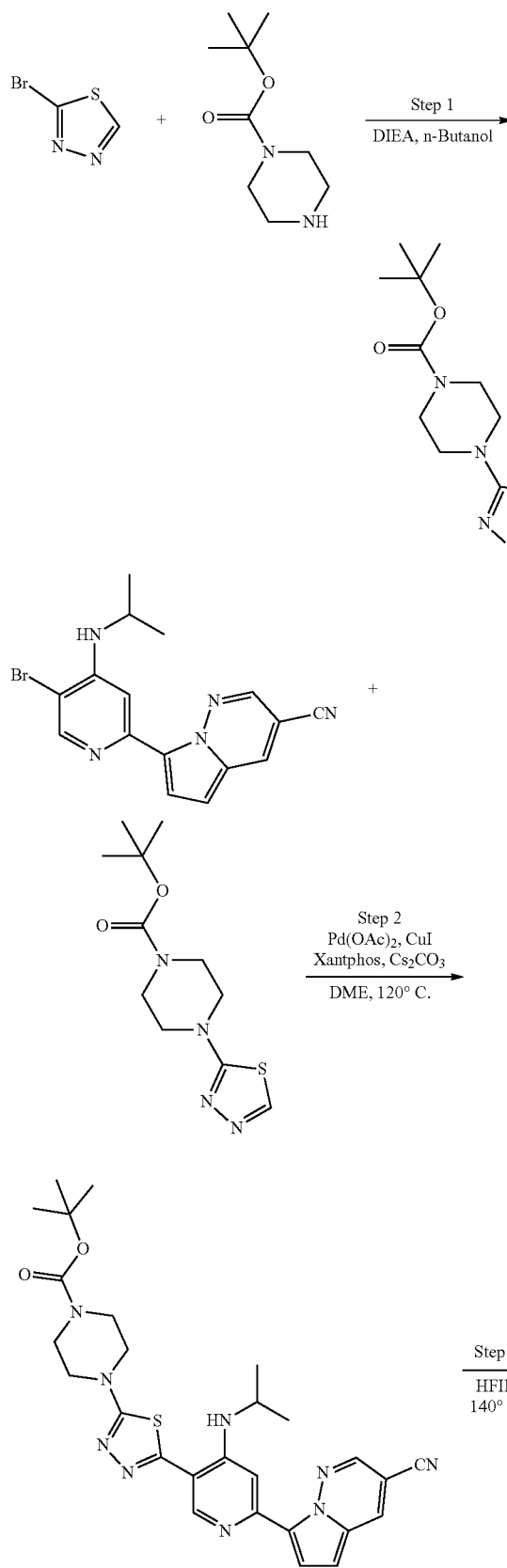

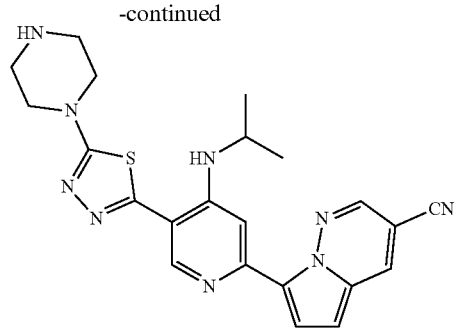

Step 1: To a solution of 2-bromo-1,3,4-thiadiazole (7.29 g, 42.4 mmol, 1.0 eq) and tert-butyl piperazine-1-carboxylate (19.75 g, 106 mmol, 2.5 eq) in n-butanol (83 mL, 0.51M) was added N,N-diisopropylethylamine (29.56 mL, 169.68 mmol, 4.0 eq). The reaction mixture was stirred at 120° C. for 1 hour. The reaction mixture was cooled, concentrated in vacuo. The resulting crude was purified by chromatography eluting with EtOAc in hexane (0 to 70% gradient) to get tert-butyl 4-(1,3,4-thiadiazol-2-yl)piperazine-1-carboxylate as a light-red solid (9.93 g, 86% yield). LCMS: ESI(+)[M−tBu]$^+$=215.26. $^1$H NMR (300 MHz, DMSO-d$_6$) δ 8.84 (s, 1H), 3.46 (m, 8H), 1.42 (s, 9H).

Step 2: 7-{5-Bromo-4-[(propan-2-yl)amino]pyridin-2-yl}pyrrolo[1,2-b]pyridazine-3-carbonitrile (5.50 g, 15.4 mmol, 1.0 eq), tert-butyl 4-(1,3,4-thiadiazol-2-yl)piperazine-1-carboxylate (3.95 g, 13.9 mmol, 0.9 eq), palladium (II) acetate (0.173 g, 0.8 mmol, 0.05 eq), CuI (0.294 g, 1.5 mmol, 0.10 eq), Xantphos (0.893 g, 1.54 mmol, 0.1 eq) and Cs$_2$CO$_3$ (10.06 g, 30.88 mmol, 2.0 eq) was placed in a pressure vessel equipped with a magnetic stirrer, followed by dimethoxyethane (250 mL, 0.061M) and degassed with vacuum and backfilling with argon (5×). The reaction mixture was stirred at 105° C. for 24 hr. After cooling down the reaction mixture was filtered through a pad of Celite and concentrated in vacuo. The crude was purified by FC eluting with DCM/EtOAc (gradient 0-30%) followed by recrystallization from 96% EtOH to tert-butyl 4-[5-(6-{3-cyanopyrrolo[1,2-b]pyridazin-7-yl}-4-[(propan-2-yl)amino]pyridin-3-yl)-1,3,4-thiadiazol-2-yl]piperazine-1-carboxylate as a yellow solid (2.271 g, 27% yield). LCMS: ESI(+)[M+H]$^+$= 546.70. $^1$H NMR (300 MHz, CDCl$_3$) δ 8.76 (s, 1H), 8.51 (s, 1H), 8.36 (s, 1H), 8.21 (d, J=2.1 Hz, 1H), 8.18 (s, 1H), 8.02 (s, 1H), 7.02 (d, J=4.8 Hz, 1H), 3.99 (h, J=6.4 Hz, 1H), 3.63 (s, 8H), 1.51 (s, 9H), 1.43 (d, J=6.4 Hz, 6H).

Step 3: Tert-butyl 4-[5-(6-{3-cyanopyrrolo[1,2-b]pyridazin-7-yl}-4-[(propan-2-yl)amino]pyridin-3-yl)-1,3,4-thiadiazol-2-yl]piperazine-1-carboxylate (2.27 g, 4.2 mmol, 1.0 eq) and 1,1,1,3,3,3-hexafluoro-2-propanol (6.57 mL, 62.4 mmol, 15 eq) was placed in microwave reactor and stirred at 140° C. for 3 hours. The solvent was then evaporated in vacuo. The resulting residue was purified by chromatography eluting with MeOH/DCM to get the titled compound as a yellow solid (1.615 g, 87% yield). LCMS: ESI(+)[M+H]$^+$=446.03. $^1$H NMR (300 MHz, DMSO-d$_6$) δ 8.83 (d, J=2.3 Hz, 1H), 8.72 (d, J=2.2 Hz, 1H), 8.55 (d, J=7.1 Hz, 1H), 8.47 (s, 1H), 8.19 (s, 1H), 7.83 (d, J=4.8 Hz, 1H), 7.11 (d, J=4.8 Hz, 1H), 3.92 (h, J=6.4 Hz, 1H), 3.51-3.41 (m, 4H), 2.88-2.79 (m, 4H), 1.35 (d, J=6.3 Hz, 6H).

Intermediate C: 7-(4-(methylamino)-5-(5-(piperazin-1-yl)-1,3,4-thiadiazol-2-yl)pyridin-2-yl)pyrrolo[1,2-b]pyridazine-3-carbonitrile

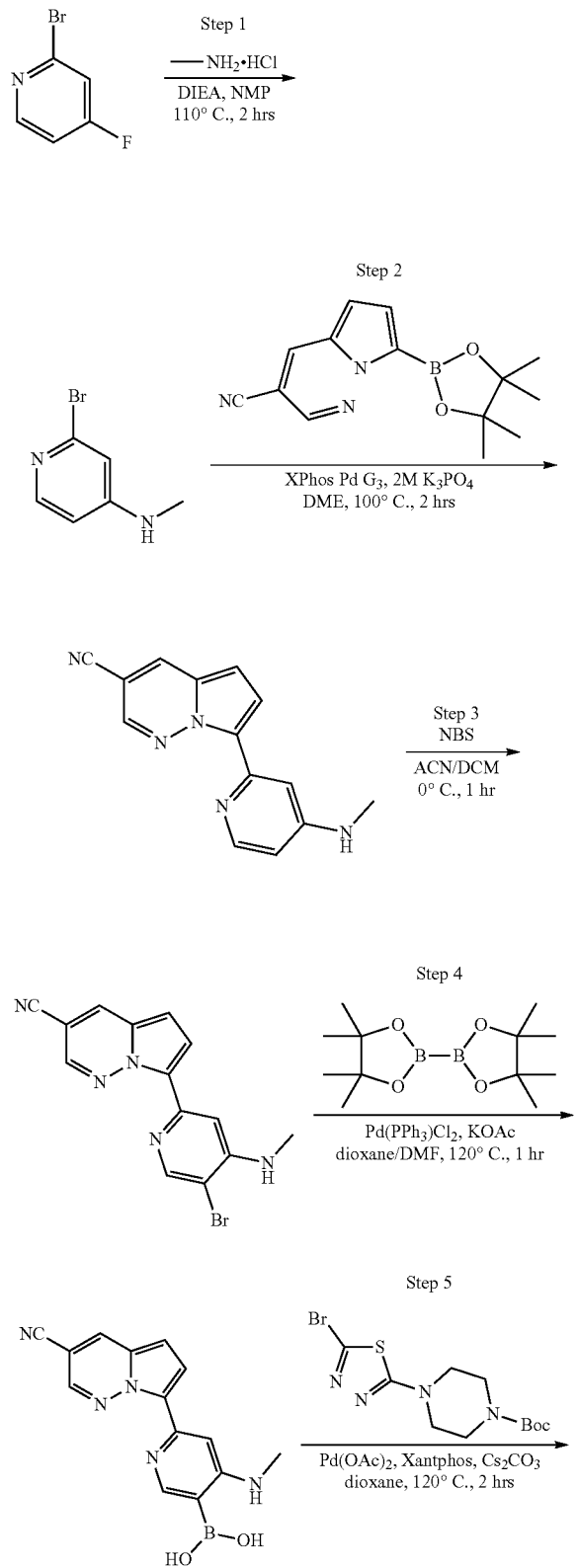

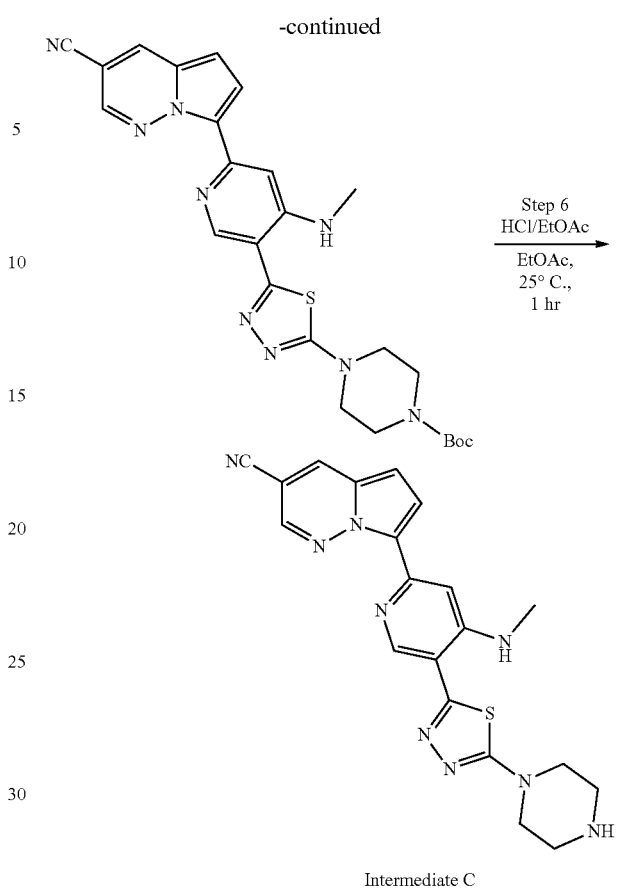

Intermediate C

Step 1: To a solution of 2-bromo-4-fluoropyridine(30.0 g, 170 mmol, 1.00 eq) in NMP (300 mL) was added methanamine hydrochloride (13.8 g, 204 mmol, 1.20 eq) and DIEA (66.1 g, 511 mmol, 89.1 mL, 3.00 eq). Then the reaction mixture was stirred at 110° C. for 2 hrs. The reaction mixture was poured into H$_2$O (600 mL) and extracted with DCM (200 mL*5). The organic layer was washed with saturated NaCl solution (200 mL*6). Then the organic layer dried over Na$_2$SO$_4$, filtered and concentrated under vacuum to obtain 2-bromo-N-methylpyridin-4-amine (29.2 g, crude) as a yellow liquid, which was used to next step without any purification. LCMS: m/z=188.9(M+H)$^+$ Step 2: To a solution of 2-bromo-N-methylpyridin-4-amine(19.2 g, 102 mmol, 1.00 eq) in DME (250 mL) was added 7-(4,4,5,5-tetramethyl-1,3,2-dioxaborolan-2-yl)pyrrolo[1,2-b]pyridazine-3-carbonitrile (31.7 g, 118 mmol, 1.15 eq), XPhos Pd G$_3$ (9.60 g, 11.3 mmol, 0.110 eq) and K$_3$PO$_4$ (2.00 M, 102 mL, 2.00 eq). The reaction mixture was stirred at 100° C. for 2 hrs at N$_2$. The reaction mixture was concentrated under reduced pressure. The resulting residue was purified by silica gel chromatography (DCM/MeOH=50/1 to 10/1) to provide 7-(4-(methylamino)pyridin-2-yl)pyrrolo[1,2-b]pyridazine-3-carbonitrile (16.9 g, 67.5 mmol, 65.7% yield) as a yellow solid. LCMS: m/z=250.0 (M+H)$^+$ Step 3: To a solution of 7-(4-(methylamino)pyridin-2-yl)pyrrolo[1,2-b]pyridazine-3-carbonitrile (16.9 g, 67.5 mmol, 1.00 eq) in DCM (355 mL) and ACN (355 mL) was added a solution of NBS (10.6 g, 59.4 mmol, 0.88 eq) in DCM (177 mL) and ACN (177 mL). The reaction mixture was stirred at 0° C. for 1 hr. The reaction mixture was concentrated under reduced pressure. The resulting residue was triturated with petroleum ether (30.0 mL) at 25° C. for 30 mins to give 7-(5-bromo-4-(methylamino)pyridin-2-yl)pyrrolo[1,2-b]

pyridazine-3-carbonitrile (28.4 g, 75.0 mmol) as a yellow solid. LCMS: m/z=329.9(M+H)+

Step 4: To a solution of 7-(5-bromo-4-(methylamino) pyridin-2-yl)pyrrolo[1,2-b]pyridazine-3-carbonitrile(24.2 g, 63.9 mmol, 1.00 eq) in dioxane (242 mL) and DMF (121 mL) was added 4,4,4',4',5,5,5',5'-octamethyl-2,2'-bi(1,3,2-dioxaborolane) (32.5 g, 127 mmol, 2.00 eq), KOAc (18.8 g, 191 mmol, 3.00 eq) and Pd(PPh$_3$)$_2$Cl$_2$ (6.71 g, 9.6 mmol, 0.150 eq) under N$_2$. The reaction mixture was stirred at 120° C. for 1 hr. The reaction mixture was filtered through kieselguhr, the filtrate was concentrated under vacuum to get a residue. The residue was purified by reversed-phase HPLC (0.1% TFA condition) to give (6-(3-cyanopyrrolo[1,2-b] pyridazin-7-yl)-4-(methylamino)pyridin-3-yl)boronic acid (12.93 g, 29.7 mmol, 46.4% yield, TFA) as a yellow solid. LCMS: m/z=293.9 (M+H)+

Step 5: To a solution of (6-(3-cyanopyrrolo[1,2-b] pyridazin-7-yl)-4-(methylamino)pyridin-3-yl)boronic acid (4.00 g, 9.2 mmol, 1.00 eq, TFA) in dioxane (210 mL) was added tert-butyl 4-(5-bromo-1,3,4-thiadiazol-2-yl)piperazine-1-carboxylate (3.39 g, 9.6 mmol, 1.05 eq), Cs$_2$CO$_3$ (7.47 g, 22.9 mmol, 2.50 eq), Xantphos (2.12 g, 3.67 mmol, 0.40 eq) and Pd(OAc)$_2$ (412 mg, 1.8 mmol, 0.20 eq) under N$_2$. The reaction mixture was stirred at 120° C. for 2 hrs. The reaction mixture was filtered directly at 120° C., the filter cake was washed by DCM (30.0 mL) and the filtrate was concentrated under vacuum to get a residue. The residue was triturated with EtOAc (30.0 mL) at 25° C. for 30 mins to give tert-butyl 4-(5-(6-(3-cyanopyrrolo[1,2-b]pyridazin-7-yl)-4-(methylamino)pyridin-3-yl)-1,3,4-thiadiazol-2-yl)piperazine-1-carboxylate (5.60 g, crude) as a yellow solid. LCMS: m/z=518.1 (M+H)+. $^1$H NMR: (400 MHz, CDCl$_3$) δ 8.53 (s, 1H), 8.35 (d, J=2.4 Hz, 1H), 8.19 (d, J=2.0 Hz, 1H), 8.10 (s, 1H), 7.92 (d, J=4.8 Hz, 1H), 6.99 (s, 1H), 3.62 (d, J=1.6 Hz, 8H), 3.12 (d, J=4.8 Hz, 3H), 1.49 (s, 9H).

Step 6: To a solution of tert-butyl 4-(5-(6-(3-cyanopyrrolo [1,2-b]pyridazin-7-yl)-4-(methylamino)pyridin-3-yl)-1,3,4-thiadiazol-2-yl)piperazine-1-carboxylate(5.60 g, 10.8 mmol, 1.00 eq) in EtOAc (28.0 mL) was added HCl/EtOAc (4.00 M, 28.0 mL, 10.3 eq). The reaction mixture was stirred at 25° C. for 1 hr. The reaction mixture was filtered; the filter cake was washed by DCM (50.0 mL) and concentrated under reduced pressure. The resulting residue was purified by prep-HPLC (basic condition) to give 7-(4-(methylamino)-5-(5-(piperazin-1-yl)-1,3,4-thiadiazol-2-yl)pyridin-2-yl)pyrrolo[1,2-b]pyridazine-3-carbonitrile (1.13 g, 2.6 mmol, 24.2% yield) as a yellow solid. LCMS: m/z=418.0 (M+H)+. $^1$H NMR (400 MHz, DMSO-d$_6$) δ 8.83 (d, J=2.0 Hz, 1H), 8.72 (d, J=2.0 Hz, 1H), 8.51-8.47 (m, 2H), 8.14 (s, 1H), 7.85 (d, J=5.2 Hz, 1H), 7.12 (d, J=4.4 Hz, 1H), 3.45 (t, J=4.8 Hz, 4H), 3.06 (d, J=4.8 Hz, 3H), 2.83 (t, J=5.2 Hz, 4H).

Intermediate C: Alternate Route

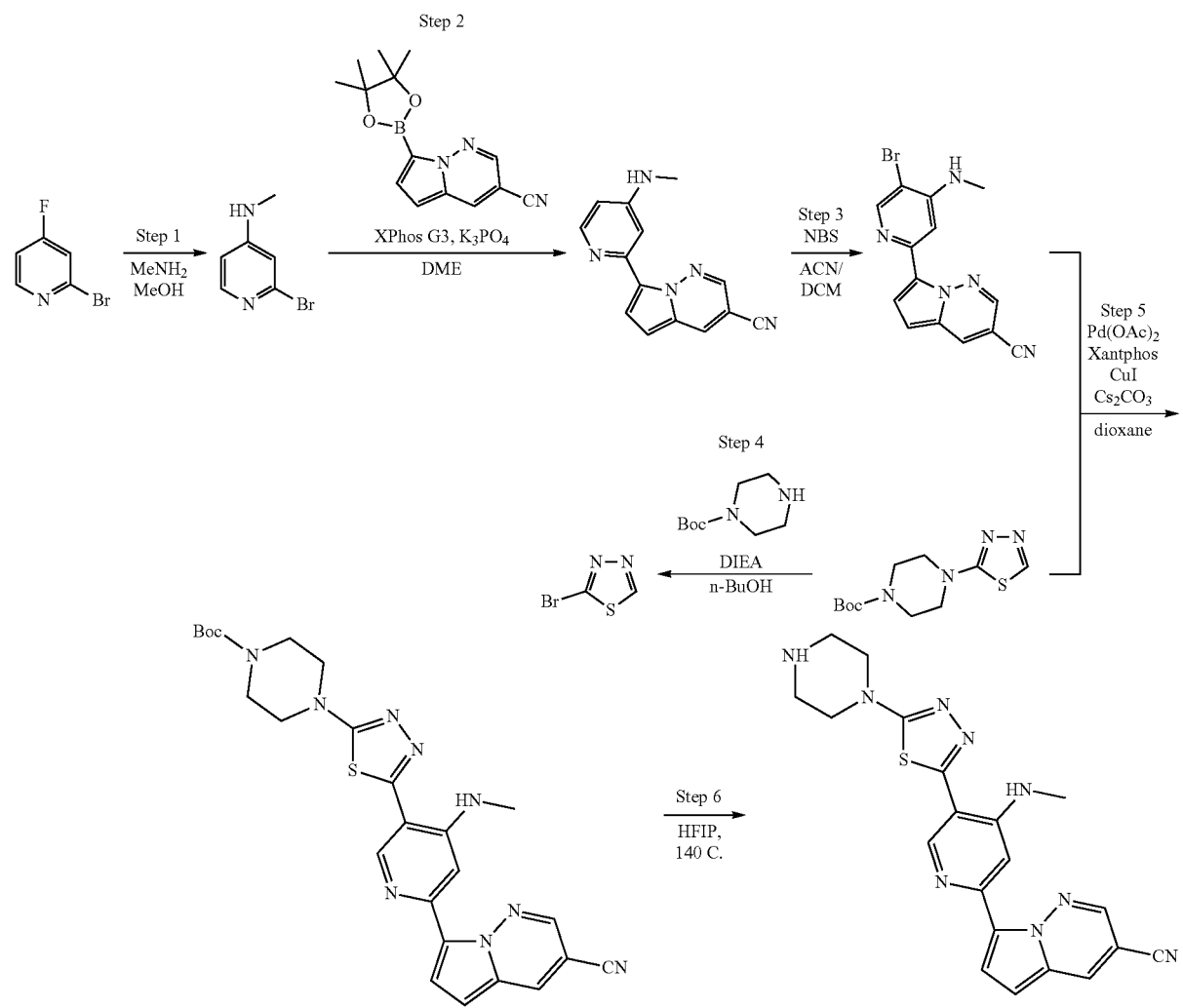

Intermediate C

Step 1: To a mixture of 2-bromo-4-fluoro-pyridine (25.0 g, 0.142 mol, 1.0 eq) the methylamine in methanol (9.8 M) (142 ml, 1.42 mol, 10 eq) was added, and the resulting mixture was heated at 80° C. overnight. After completion, the reaction mixture was cooled, evaporated all volatiles in vacuo, dissolved in EtOAc, and washed with water. The organic layer was dried over sodium sulfate, filtered, and concentrated to give 2-bromo-N-methylpyridin-4-amine (25 g, 89% yield). $^1$H NMR (300 MHz, DMSO-d$_6$), δ: 7.77 (d, J=5.8 Hz, 1H), 6.98-6.78 (m, 1H), 6.59 (m, 1H), 6.48 (m, 1H), 2.69 (d, J=4.9 Hz, 3H). LCMS: ESI(+)[M+H]$^+$=188.94.

Step 2: To a solution of 2-bromo-N-methylpyridin-4-amine (6.0 g, 32.1 mmol, 1.0 eq), 7-(4,4,5,5-tetramethyl-1,3,2-dioxaborolan-2-yl)pyrrolo[1,2-b]pyridazine-3-carbonitrile (12.09 g, 44.9 mmol, 1.4 eq) and Xphos G3 (2.17 g, 2.6 mmol, 0.08 eq) in anhydrous dimethoxyethane (80 ml, 0.4 M), 2M aq sol K$_3$PO$_4$ (32.1 ml, 64.2 mmol, 2.0 eq) was added. The solution was degassed with argon for 15 min and then heated at 120° C. with vigorous stirring overnight. The reaction mixture was filtrated through a pad of Celite and evaporated under reduced pressure to dryness. The crude residue obtained was purified by chromatography using methanol in dichloromethane (0-10%) to give 7-[4-(methylamino)-2-pyridyl]pyrrolo[1,2-b]pyridazine-3-carbonitrile as a yellow solid (6.1 g, 76% yield). $^1$H NMR (300 MHz, DMSO-d$_6$), δ: 8.79 (d, J=2.2 Hz, 1H), 8.64 (d, J=2.2 Hz, 1H), 8.19 (d, J=5.6, 1H), 7.87 (d, J=2.3, 1H), 7.76 (d, J=4.7 Hz, 1H), 7.08 (d, J=4.7, 1H), 6.80 (d, J=5.0, 1H), 6.45 (m, 1H), 2.77 (d, J=4.8 Hz, 3H). LCMS: ESI(+)[M+H]$^+$=250.36.

Step 3: 7-[4-(methylamino)-2-pyridyl]pyrrolo[1,2-b]pyridazine-3-carbonitrile (5.3 g, 20.1 mmol, 1.0 eq) was dissolved in acetonitrile (65 ml, 0.3 M) and dichloromethane (20 ml, 0.7 M) and N-bromosuccinimide (3.57 g, 20.1 mmol, 1.0 eq) was added by one portion at rt. The reaction was stirred at the ambient conditions for 30 min. The reaction progress was monitored by LCMS. After completion, the mixture was evaporated under reduced pressure and the resulting residue purified with chromatography using 0-5% ethyl acetate in dichloromethane to give 7-(5-bromo-4-(methylamino)pyridin-2-yl)pyrrolo[1,2-b]pyridazine-3-carbonitrile as a yellow solid (5.95 g, 88% yield). $^1$H NMR (300 MHz, DMSO-d$_6$), δ: 8.80 (d, J=2.2 Hz, 1H), 8.67 (d, J=2.2 Hz, 1H), 8.36 (s, 1H), 7.94 (s, 1H), 7.76 (d, J=4.8 Hz, 1H), 7.08 (d, J=4.8 Hz, 1H), 6.45 (q, J=4.3 Hz, 1H), 2.90 (d, J=4.7 Hz, 3H). LCMS: ESI(+)[M+H]$^+$=330.16.

Step 4: Tert-butyl 4-(1,3,4-thiadiazol-2-yl)piperazine-1-carboxylate was prepared in the same manner as in Step 1 of Intermediate B (alternate route). $^1$H NMR (300 MHz, DMSO-d$_6$), δ: 8.84 (s, 1H), 3.46 (s, 8H), 1.42 (s, 9H). LCMS: ESI(+)[M+2H]+=272.16.

Step 5: 7-[5-bromo-4-(methylamino)pyridin-2-yl]pyrrolo[1,2-b]pyridazine-3-carbonitrile (0.5 g, 1.52 mmol, 1.0 eq), palladium (II) acetate (0.051 g, 0.23 mmol, 0.15 eq), 4,5-bis(diphenylphosphino)-9,9-dimethylxanthene (0.26 g, 0.5 mmol, 0.3 eq), cesium carbonate (0.1 g, 3.1 mmol, 2.0 eq) and cuprous iodide (0.087 g, 0.5 mmol, 0.3 eq) were taken in a oven-dried screw-cap vial and tert-butyl 4-(1,3,4-thiadiazol-2-yl)piperazine-1-carboxylate (0.434 g, 1.5 mmol, 1 eq), anhydrous dioxane (25.39 ml, 0.06 M) were added to it. The reaction tube was evacuated-backfilled with argon for 20 minutes, sealed and stirred at 105° C. overnight. After completion of the reaction (confirmed by UPLC), all volatiles were evaporated in vacuo and the resulting residue was purified with chromatography (0 to 31 ethyl acetate in dichloromethane) to give tert-butyl 4-[5-(6-{3-cyanopyrrolo[1,2-b]pyridazin-7-yl}-4-(methylamino)-pyridin-3-yl)-1,3,4-thiadiazol-2-yl]piperazine-1-carboxylate as a yellow crystalline solid (0.57 g, 61% yield). $^1$H NMR (300 MHz, DMSO-d$_6$), δ: 8.83 (s, 1H), 8.73 (s, 1H), 8.48 (m, 2H), 8.14 (s, 1H), 7.86 (s, 1H), 7.12 (d, J=4.8 Hz, 1H), 3.54 (s, 8H), 3.06 (d, J=4.9 Hz, 3H), 1.44 (s, 9H). LCMS: ESI(+)[M+H]$^+$=518.64.

Step 6: The solution of tert-butyl 4-[5-(6-{3-cyanopyrrolo[1,2-b]pyridazin-7-yl}-4-(methylamino)-pyridin-3-yl)-1,3,4-thiadiazol-2-yl]piperazine-1-carboxylate (0.25 g, 0.5 mmol, 1 eq) in 1,1,1,3,3,3-hexafluoro-2-propanol (0.769 ml, 7.3 mmol, 15 eq) was heated at 140° C. with MW for 3 hrs. Afterwards, all volatiles were evaporated under reduced pressure and the remaining residue was purified via chromatography (0 to 7% methanol in dichloromethane) to give the titled product as a yellow solid (0.15 g, 73% yield). LCMS: ESI(+)[M+H]$^+$=418.06. $^1$H NMR (300 MHz, DMSO-d$_6$), δ: 8.83 (d, J=2.2 Hz, 1H), 8.72 (s, 1H), 8.54-8.42 (m, 2H), 8.13 (s, 1H), 7.85 (d, J=4.8 Hz, 1H), 7.11 (d, J=4.8 Hz, 1H), 3.46 (s, 4H), 3.06 (d, J=4.9 Hz, 3H), 2.84 (s, 4H), 2.61 (m, 1H).

Intermediate D: 7-[5-(5-{4-formylbicyclo[2.2.2]octan-1-yl}-1,3,4-thiadiazol-2-yl)-4-[(oxan-4-yl)amino]pyri-din-2-yl]pyrrolo[1,2-b]pyridazine-3-carbonitrile

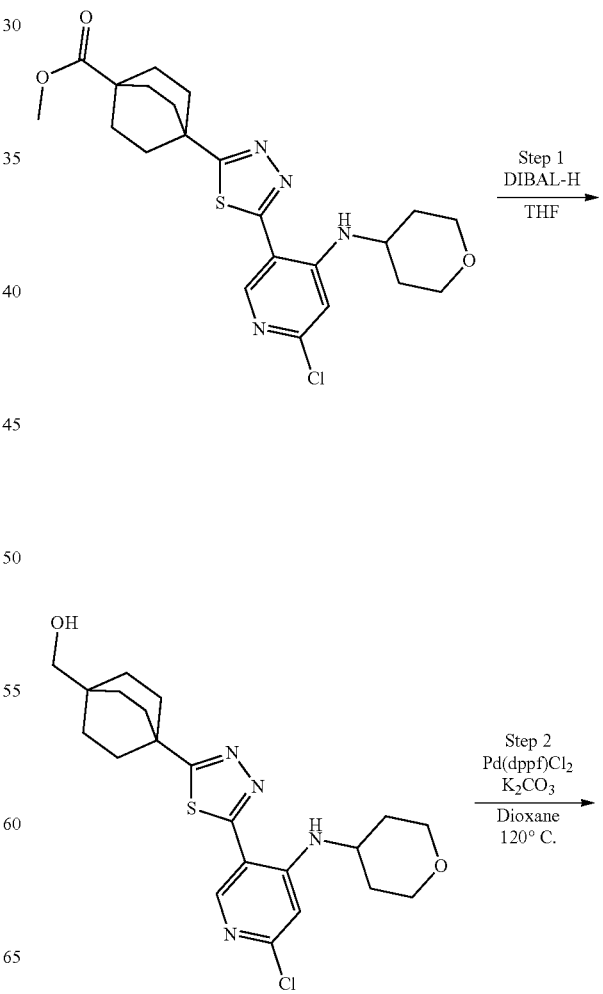

-continued

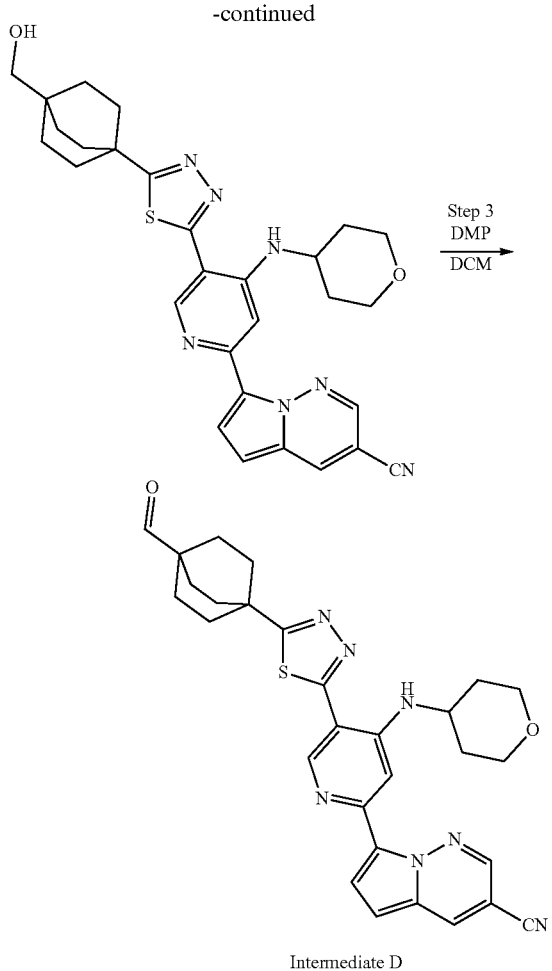

Intermediate D

Step 1: A solution of methyl 4-(5-{6-chloro-4-[(oxan-4-yl)amino]pyridin-3-yl}-1,3,4-thiadiazol-2-yl)bicyclo[2.2.2]octane-1-carboxylate (6 g, 13 mmol, 1 eq) in anhydrous THF (324.5 mL, 0.04 M) was cooled to −15° C. under argon atmosphere and treated with DIBAL-H (38.96 mL of a 1.0 M solution in THF, 39 mmol, 3 eq). After 30 min, the cooling bath was removed, the mixture was allowed to warm up to rt, and was stirred for 3 hrs. The reaction was quenched by adding MeOH (40 mL) and stirred vigorously for 20 min, followed by the addition of a sat aq solution of Rochelle salt. The reaction mixture was extracted with EtOAc. The combined organic layers were washed with brine and concentrated under reduced pressure. The resulting crude was purified by silica gel chromatography (0 to 10%, acetone/DCM) to afford [4-(5-{6-chloro-4-[(oxan-4-yl)amino]pyridin-3-yl}-1,3,4-thiadiazol-2-yl)bicyclo[2.2.2]-octan-1-yl]methanol as an off-white solid (3.65 g, 65% yield). LCMS: ESI(+)[M+H]$^+$=435.54. $^1$H NMR (300 MHz, DMSO-d$_6$), δ: 8.91 (d, J=7.7 Hz, 1H), 8.42 (s, 1H), 7.05 (s, 1H), 4.46 (t, J=5.4 Hz, 1H), 3.86 (m, 3H), 3.52 (t, J=11.0 Hz, 2H), 3.14 (dd, J=20.1, 5.3 Hz, 2H), 2.00-1.87 (m, 8H), 1.55-1.39 (m, 8H).

Step 2: To a solution of [4-(5-{6-chloro-4-[(oxan-4-yl)amino]pyridin-3-yl}-1,3,4-thiadiazol-2-yl)bicyclo[2.2.2]-octan-1-yl]methanol (3.78 g, 8.3 mmol, 1.0 eq), 7-(4,4,5,5-tetramethyl-1,3,2-dioxaborolan-2-yl)pyrrolo[1,2-b]pyridazine-3-carbonitrile (2.70 g, 9.9 mmol, 1.2 eq) and Pd(dppf)Cl$_2$·CH$_2$Cl$_2$ (1.69 g, 2.1 mmol, 0.25 eq) in anh dioxane (212 mL, 0.04 M), was added 2M aq K$_2$CO$_3$ (8.5 ml, 16.6 mmol, 2.0 eq). The mixture was degassed with argon for 30 min and then stirred at 120° C. overnight. The reaction mixture was diluted with DCM, filtrated through a pad of Celite, washed with DCM/MeOH (1:1) and concentrated under reduced pressure. The resulting crude was purified with flash chromatography (DCM/Acetone) to give [4-(5-{6-chloro-4-[(oxan-4-yl)amino]pyridin-3-yl}-1,3,4-thiadiazol-2-yl)bicyclo[2.2.2]octan-1-yl]methanol (3.3 g, 73% yield). LCMS: ESI(+)[M+H]$^+$=542.67. $^1$H NMR (300 MHz, DMSO-d$_6$), δ: 8.84 (m, 3H), 8.69 (s, 1H), 8.32 (s, 1H), 7.86 (d, J=4.8 Hz, 1H), 7.12 (d, J=4.8 Hz, 1H), 4.46 (t, J=5.4 Hz, 1H), 3.94 (d, J=15.3 Hz, 3H), 3.60 (t, J=10.2 Hz, 2H), 3.11 (d, J=5.4 Hz, 2H), 2.11-1.88 (m, 9H), 1.49 (s, 8H).

Step 3: To a solution of the [4-(5-{6-chloro-4-[(oxan-4-yl)amino]pyridin-3-yl}-1,3,4-thiadiazol-2-yl)bicyclo[2.2.2]octan-1-yl]methanol (3.3 g, 6.1 mmol, 1 eq) in DCM (609 mL, 0.01 M) was added Dess-Martin periodinane (3.36 g, 8.0 mmol, 1.3 eq). The reaction mixture was stirred at rt for 2 h, after which time it was quenched with 20% aq Na$_2$S$_2$O$_3$ and sat aq NaHCO$_3$. The resulting mixture was stirred until the aqueous layer becomes clear. Then the latter was extracted with DCM.

The combined organic layers were washed with sat aq NaHCO$_3$, water, and brine, dried over Na$_2$SO$_4$, and concentrated under reduced pressure. The crude product was triturated with Et$_2$O, filtered off, and wash on the filter with a mixture of DCM/Et$_2$O (1:1), Et$_2$O, and pentane to afford the title compound (2.8 g, 84% yield). LCMS: ESI(+)[M+H]$^+$= 540.20. $^1$H NMR (300 MHz, DMSO-d$_6$), δ: 9.49 (s, 1H), 8.90-8.73 (m, 3H), 8.70 (s, 1H), 8.32 (s, 1H), 7.86 (d, J=4.8 Hz, 1H), 7.12 (d, J=4.8 Hz, 1H), 3.95 (d, J=11.7 Hz, 3H), 3.60 (t, J=10.3 Hz, 2H), 2.18-1.96 (m, 8H), 1.78 (d, J=8.1 Hz, 6H), 1.60 (q, J=11.9, 9.9 Hz, 2H).

Intermediate E: 4-[5-(6-{3-cyanopyrrolo[1,2-b]pyridazin-7-yl}-4-[(oxan-4-yl)amino]pyridin-3-yl)-1,3,4-thiadiazol-2-yl]bicyclo[2.2.2]octane-1-carboxylic acid

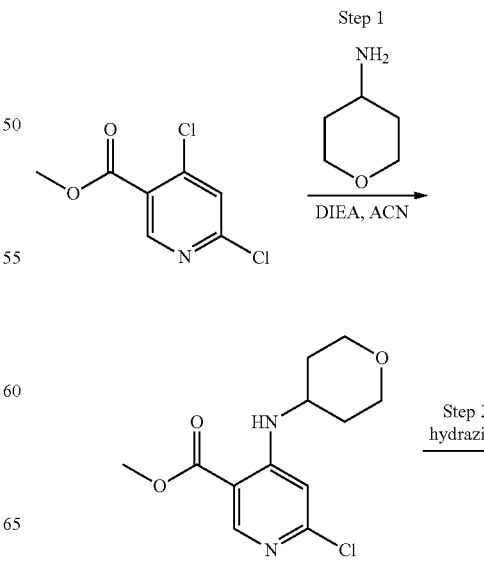

-continued

Step 3

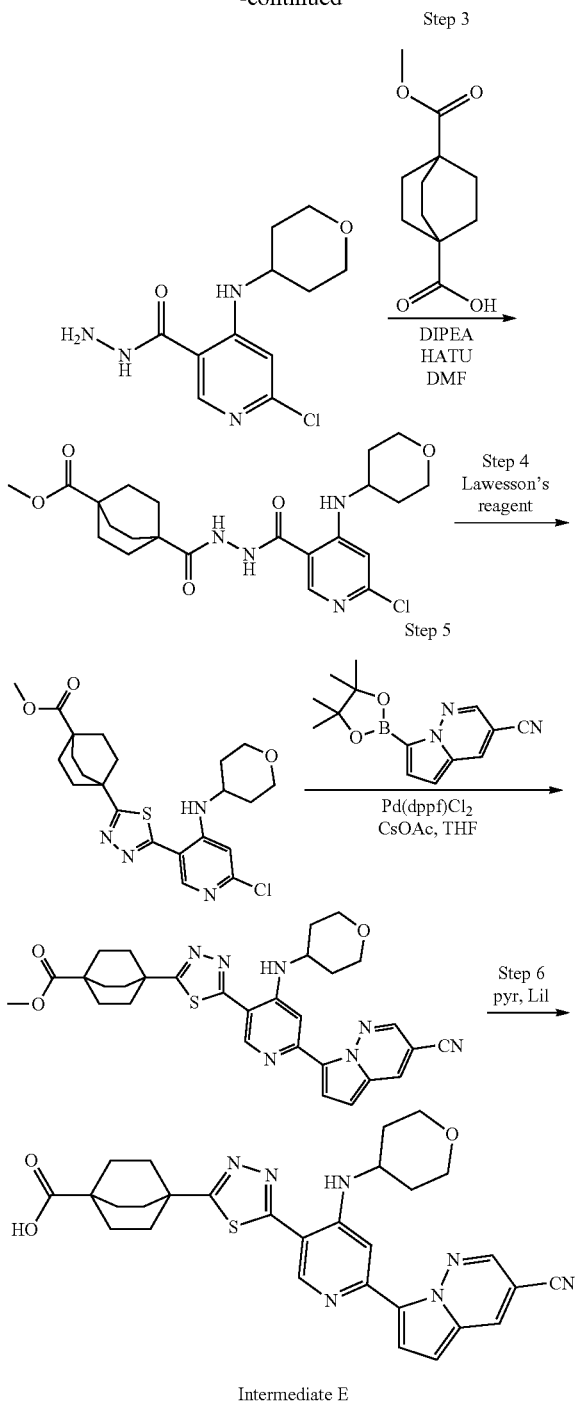

Intermediate E

Step 1: DIPEA (220 ml, 1.26 mol, 2.6 eq) was added to a cooled, stirred solution of methyl 4,6-dichloronicotinate (100 g, 485 mmol, 1.0 eq) in ACN (486 ml, 1 M). Tetrahydro-2H-pyran-4-amine (65 ml, 631 mmol, 1.3 eq) was added dropwise and the mixture was stirred at 70° C. for 36 hrs. The mixture was cooled, the solids were filtered off and the filtrate was concentrated in vacuo. The residue was partitioned between EtOAc and water. The organic layer was washed with brine, dried over $Na_2SO_4$, and concentrated under reduced pressure. The resulting residue was recrystallized from hexane to afford methyl 6-chloro-4-[(oxan-4-yl)amino]pyridine-3-carboxylate (124.8 g, 92% yield).

LCMS: ESI(+)[M+H]$^+$=272.25. $^1$H NMR (300 MHz, DMSO-d$_6$) δ: 8.54 (s, 1H), 8.06 (d, J=7.9 Hz, 1H), 7.00 (s, 1H), 3.84 (s, 6H), 3.48 (td, J=11.4, 2.0 Hz, 2H), 1.90 (d, J=10.7 Hz, 2H), 1.46 (qd, J=11.1, 4.5 Hz, 2H).

Step 2: To a solution of methyl 6-chloro-4-[(oxan-4-yl)amino]pyridine-3-carboxylate (40 g, 147.7 mmol, 1.0 eq) in EtOH (246 mL) was added hydrazine monohydrate 65% wt (88 mL, 1.18 mol, 8.0 eq) and the mixture was stirred at 80° C. for 2 hrs. The volatiles were evaporated, and then co-evaporated several times with toluene. The residue was dried overnight at 50° C. and 5 mBar to afford 6-chloro-4-[(oxan-4-yl)amino]pyridine-3-carbohydrazide (37.6 g, 89% yield). LCMS: ESI(+)[M+H]$^+$=272.05. $^1$H NMR (300 MHz, DMSO-d$_6$) δ: 9.87 (s, 1H), 8.40 (d, J=7.8 Hz, 1H), 8.27 (s, 1H), 6.84 (s, 1H), 4.49 (s, 2H), 3.91-3.78 (m, 2H), 3.77-3.64 (m, 1H), 3.58-3.39 (m, 2H), 1.89 (d, J=12.1 Hz, 2H), 1.39 (qd, J=10.7, 4.2 Hz, 2H).

Step 3: To a solution of monomethyl-1,4-cyclohexanedicarboxylate (31 g, 146 mmol, 1.1 eq) in DMF (460 mL) were added DIPEA (70 ml, 399 mmol, 3.0 eq) and HATU (60.7 g, 159.6 mmol, 1.2 eq), followed by portionwise addition of 6-chloro-4-[(oxan-4-yl)amino]pyridine-3-carbohydrazide (37.6 g, 133 mmol, 1.00 eq). The mixture was stirred at 25° C. for 1.5 hrs. The reaction was quenched with water and ice (600 mL) and extracted with EtOAc. The organic layers were washed with aq solution of NaHCO$_3$, aq solution of KHSO$_4$, water, brine, dried over Na$_2$SO$_4$, and concentrated under reduced pressure. The crude was purified by column chromatography eluted by DCM/MeOH (0-10%) to afford methyl 4-(N'-{6-chloro-4-[(oxan-4-yl)amino]pyridine-3-carbonyl}hydrazinecarbonyl)bicyclo[2.2.2]octane-1-carboxylate (45 g, 72% yield). LCMS: ESI(+)[M+H]$^+$=465.5. $^1$H NMR (300 MHz, DMSO-d$_6$) δ: 10.30 (s, 1H), 9.51 (s, 1H), 8.39 (s, 1H), 8.29 (d, J=7.9 Hz, 1H), 6.90 (s, 1H), 4.10 (d, J=4.8 Hz, 1H), 3.90-3.78 (m, 2H), 3.78-3.66 (m, 1H), 3.59 (s, 3H), 3.55-3.38 (m, 2H), 3.17 (d, J=4.0 Hz, 2H), 1.88 (d, J=10.8 Hz, 2H), 1.76 (s, 12H), 1.49-1.30 (m, 2H).

Step 4: To a solution of methyl 4-(N'-{6-chloro-4-[(oxan-4-yl)amino]pyridine-3-carbonyl}hydrazinecarbonyl)bicyclo[2.2.2]octane-1-carboxylate (45 g, 1 eq) in anh THF (0.06 M) was added Lawesson's reagent (1.5 eq) portionwise at 40° C. under vigorous stirring. The resulting suspension was stirred for 2 h at 75° C. At completion, the volatiles were evaporated and the residue was dissolved in DCM. The resulting solution was washed with aq K$_2$CO$_3$ and concentrated under reduced pressure. The crude was purified by chromatography (EtOAc in DCM, 0 to 10%) to afford methyl 4-(5-{6-chloro-4-[(oxan-4-yl)amino]pyridin-3-yl}-1,3,4-thiadiazol-2-yl)bicyclo[2.2.2]octane-1-carboxylate (15.6 g, 35% yield). LCMS: ESI(+)[M+H]$^+$=463.6. $^1$H NMR (300 MHz, DMSO-d$_6$) δ: 8.89 (d, J=7.8 Hz, 1H), 8.44 (s, 1H), 7.06 (s, 1H), 3.98-3.71 (m, 3H), 3.62 (s, 3H), 3.52 (t, J=10.1 Hz, 2H), 2.09-1.77 (m, 14H), 1.58-1.38 (m, 2H).

Step 5: Methyl 4-(5-{6-chloro-4-[(oxan-4-yl)amino]pyridin-3-yl}-1,3,4-thiadiazol-2-yl)bicyclo[2.2.2]octane-1-carboxylate (5 g, 10.8 mmol, 1.0 eq), 7-(4,4,5,5-tetramethyl-1,3,2-dioxaborolan-2-yl)pyrrolo[1,2-b]pyridazine-3-carbonitrile (3.78 g, 14 mmol, 1.3 eq) and CsOAc (6.4 g, 32.4 mmol, 3 eq) were dissolved anhydrous THF (216 ml, 0.05 M). The solution was degassed with argon for 15 min and [1,1-bis(diphenylphosphino)ferrocene]dichloropalladium(II) complex with dichloromethane (2.22 g, 2.7 mmol, 0.25 eq) was added. The pressure vessel was sealed and stirred to 90° C. overnight. The reaction was filtrated through a pad of Celite and washed with DCM and MeOH. The solvents were concentrated under reduced pressure and the residue was purified by column chromatography (5 to 50%, ACN in DCM) affording methyl 4-[5-(6-{3-cyanopyrrolo[1,2-b]pyridazin-7-yl}-4-[(oxan-4-yl)amino]pyridin-3-yl)-1,3,4-thiadiazol-2-yl]bicyclo[2.2.2]octane-1-carboxylate (5.1 g, 80% yield). LCMS: ESI(+)[M+H]$^+$=570.69. $^1$H NMR (300 MHz, DMSO-d$_6$) δ: 8.86 (d, J=2.2 Hz, 1H), 8.81 (d, J=7.1 Hz, 1H), 8.79 (d, J=2.2 Hz, 1H), 8.71 (s, 1H), 8.34 (s, 1H), 7.86 (d, J=4.9 Hz, 1H), 7.13 (d, J=4.8 Hz, 1H), 4.04-3.81 (m, 3H), 3.67-3.45 (m, 5H), 2.21-2.08 (m, 2H), 2.07-1.80 (m, 12H), 1.60 (q, J=10.1 Hz, 2H).

Step 6: To a solution of methyl 4-[5-(6-{3-cyanopyrrolo[1,2-b]pyridazin-7-yl}-4-[(oxan-4-yl)amino]pyridin-3-yl)-1,3,4-thiadiazol-2-yl]bicyclo[2.2.2]octane-1-carboxylate (4.1 g, 7.2 mmol, 1 eq) in pyridine (72 ml, 0.1 M), lithium iodide (9.73 g, 72 mmol, 10 eq) was added and the resulting mixture was stirred at 150° C. for 20 hrs. The reaction mixture was concentrated in vacuo and acidified with an equimolar amount of diluted HCl. The obtained residue was purified with column chromatography (0 to 15%, IPA/DCM) affording the titled compound (1.25 g, 30% yield). LCMS: ESI(+)[M+H]$^+$=556.20. $^1$H NMR (300 MHz, DMSO-d$_6$) δ: 12.22 (s, 1H), 9.51 (s, 1H), 8.96 (d, J=2.1 Hz, 1H), 8.86 (d, J=2.2 Hz, 1H), 8.77 (s, 1H), 8.16 (s, 1H), 8.03 (d, J=5.0 Hz, 1H), 7.22 (d, J=4.9 Hz, 1H), 4.08 (s, 1H), 4.01-3.89 (m, 2H), 3.60 (t, J=10.2 Hz, 2H), 2.16-1.78 (m, 14H), 1.75-1.56 (m, 2H).

Intermediate F: 7-[5-(5-{3,8-diazabicyclo[3.2.1]octan-3-yl}-1,3,4-thiadiazol-2-yl)-4-(oxan-4-ylamino)pyridin-2-yl]pyrrolo[1,2-b]pyridazine-3-carbonitrile

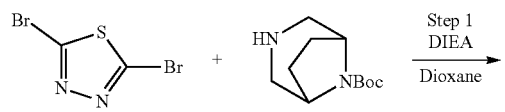

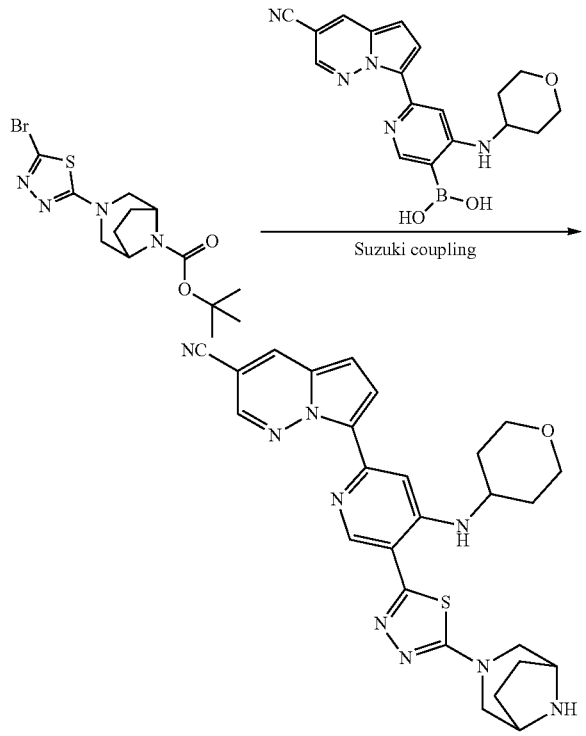

The title compound was synthesized following the same procedure as described for Intermediate T, except with tert-butyl 3,8-diazabicyclo[3.2.1]octane-8-carboxylate as a starting material instead of tert-butyl 4,7-diazaspiro[2.5]octane-4-carboxylate. LCMS C$_{26}$H$_{27}$N$_9$OS requires: 513.2, found: m/z=514.3 [M+H]$^+$.

Intermediate G: 7-[5-(5-{2,7-diazaspiro[3.5]nonan-2-yl}-1,3,4-thiadiazol-2-yl)-4-(methylamino)pyridin-2-yl]pyrrolo[1.2-b]pyridazine-3-carbonitrile

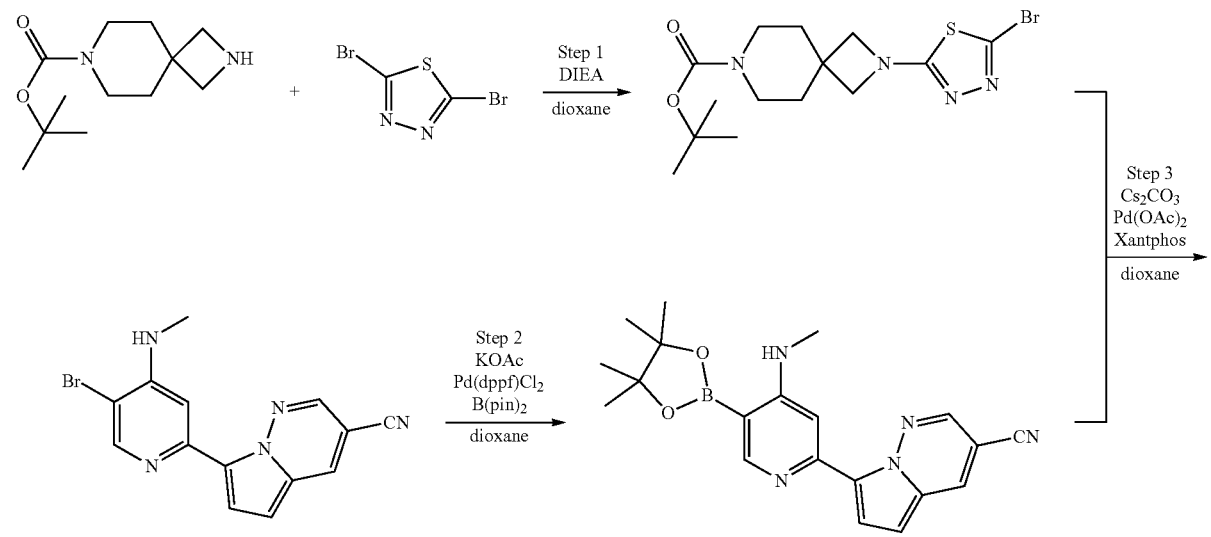

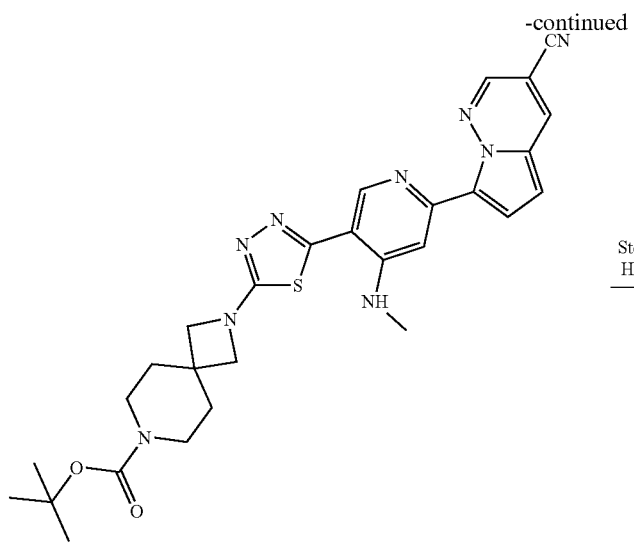

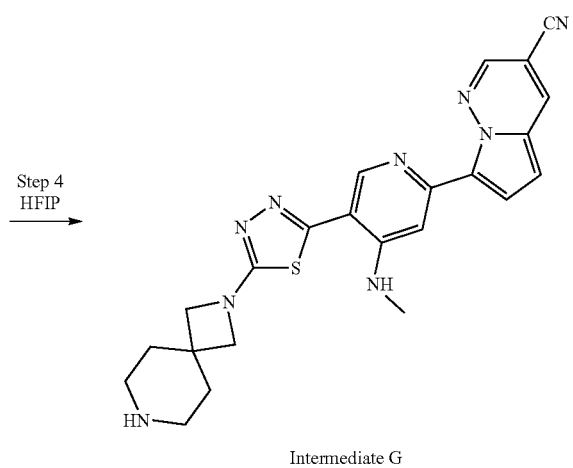

Intermediate G

Step 1: A suspension of 2,5-dibromo-1,3,4-thiadiazole (970 mg, 4.0 mmol, 1.0 eq.), tert-butyl 2,7-diazaspiro[3.5]nonane-7-carboxylate (990 mg, 4.4 mmol, 1.1 eq) and DIPEA (1.038 ml, 4.6 mmol, 1.5 eq) in dioxane (15 mL, 0.21 M) was stirred at 120° C. for 1 hour. The reaction mixture was diluted with water (10 mL) and extracted with DCM (20 mL). The crude material was purified by flash chromatography eluting by hexane/EtOAc to acquire the desired compound as a yellow oil (1.54 g, 96% yield). LCMS: ESI(+) [M+H]⁺=391.3 ¹H NMR (300 MHz, DMSO-d₆) δ 3.83 (s, 4H), 3.31-3.21 (m, 4H), 1.75-1.62 (m, 4H), 1.39 (s, 9H).

Step 2: 7-[5-bromo-4-(methylamino)pyridin-2-yl]pyrrolo[1,2-b]pyridazine-3-carbonitrile (1.5 g, 4.6 mmol, 1.0 eq) was dissolved in dioxane (25 ml) in pressure vessel followed by addition of bis(pinacolato)diboron (1.39 g, 5.49 mmol, 1.2 eq) and KOAc (0.89 g, 9.14 mmol, 2.0 eq). The solution was sparged with argon for 7 mins and Pd(dppf)Cl₂·DCM (0.375 g, 0.46 mmol, 0.1 eq) was added followed by additional sparging. The reaction mixture was then moved to preheated oil bath and stirred at 90° C. overnight. The UPLC showed the formation of the product. The reaction mixture was filtrated through Celite cake and evaporated to dryness. The crude was used in the next step without further purification. LCMS: ESI(+)[M+H]⁺=294.2.

Step 3: To a solution of tert-butyl 2-(5-bromo-1,3,4-thiadiazol-2-yl)-2,7-diazaspiro[3.5]nonane-7-carboxylate (1.377 g, 2.57 mmol, 1.0 eq) and 7-[4-(methylamino)-5-(4,4,5,5-tetramethyl-1,3,2-dioxaborolan-2-yl)pyridin-2-yl]pyrrolo[1,2-b]pyridazine-3-carbonitrile (1.0 g, 2. mmol, 1.0 eq) in dioxane (13 ml, 0.2 M) in pressure vessel were added cesium carbonate (2.09 g, 6.42 mmol, 2.5 eq) and palladium (II) acetate (0.115 g, 0.51 mmol, 0.2 eq). The reaction was sparged with argon for 7 mins followed by the addition of Xantphos (0.59 g, 1.03 mmol, 0.4 eq). The solution was degassed with argon for another 3 min and then stirred at 120° C. overnight. LCMS showed the formation of the product. The reaction mixture was filtrated through Celite cake and evaporated to dryness. The crude was purified by column chromatography eluting by DCM/MeOH (0-10%) to acquire 0.415 g (29% yield) of the desired product. LCMS: ESI(+)[M+H]⁺=558.8. ¹H NMR (300 MHz, DMSO-d₆) δ 8.83 (d, J=2.2 Hz, 1H), 8.73 (d, J=2.2 Hz, 1H), 8.48 (s, 2H), 8.14 (s, 1H), 7.85 (d, J=4.8 Hz, 1H), 7.12 (d, J=4.8 Hz, 1H), 3.91 (s, 4H), 3.06 (d, J=4.8 Hz, 3H), 1.75 (t, J=5.6 Hz, 4H), 1.40 (s, 9H).

Step 4: Tert-butyl 2-[5-(6-{3-cyanopyrrolo[1,2-b]pyridazin-7-yl}-4-(methylamino)pyridin-3-yl)-1,3,4-thiadiazol-2-yl]-2,7-diazaspiro[3.5]nonane-7-carboxylate (0.2 g, 0.36 mmol, 1.0 eq) was dissolved in 1,1,1,3,3,3-hexafluoro-2-propanol (1.13 mL, 30 eq) in a sealed reactor and put in a microwave for 2 h at 150° C. The UPLC showed full deprotection of the starting material. The solvent was evaporated to dryness and solid was triturated with Et₂O to get desired product 146 mg (87% yield) as a yellow solid. LCMS: ESI(+)[M+H]⁺=458.08. ¹H NMR (300 MHz, DMSO-d₆) δ 8.83 (d, J=2.2 Hz, 1H), 8.72 (d, J=2.2 Hz, 1H), 8.47 (s, 2H), 8.13 (s, 1H), 7.85 (d, J=4.8 Hz, 1H), 7.12 (d, J=4.8 Hz, 1H), 3.86 (s, 4H), 3.06 (d, J=4.8 Hz, 3H), 2.63 (t, J=5.4 Hz, 4H), 1.87-1.60 (m, 4H).

Intermediate H: 7-(5-(5-([4,4'-bipiperidin]-1-yl)-1,3,4-thiadiazol-2-yl)-4-(methylamino)pyridin-2-yl)pyrrolo[1,2-b]pyridazine-3-carbonitrile

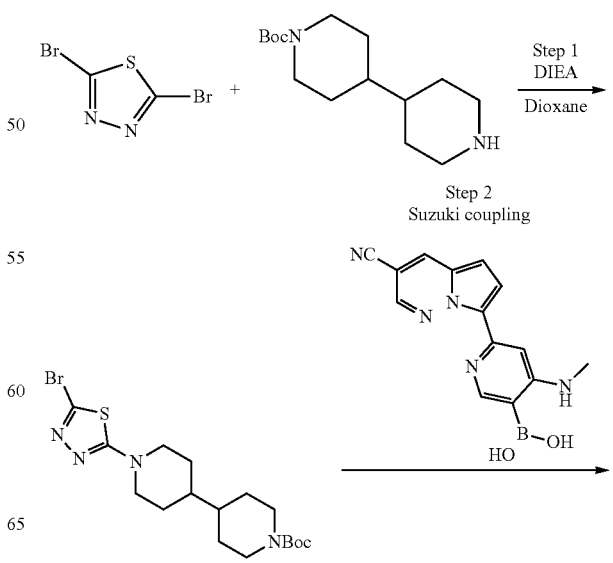

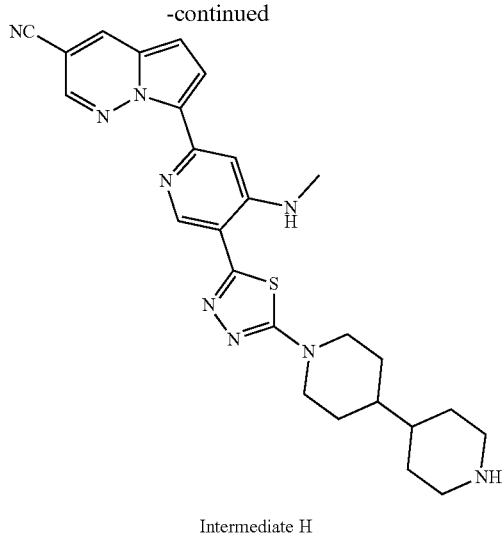

Intermediate H

The title compound was synthesized following the same procedures as described for Intermediate T, except with tert-butyl [4,4'-bipiperidine]-1-carboxylate as a starting material instead of tert-butyl 4,7-diazaspiro[2.5]octane-4-carboxylate. LCMS $C_{26}H_{29}N_9S$ requires: 499.2, found: m/z=500.4 [M+H]$^+$.

Intermediate I: 7-[4-(methylamino)-5-{5-[(1r,4r)-4-(methylamino)cyclohexyl]-1,3,4-thiadiazol-2-yl}pyridin-2-yl]pyrrolo[1,2-b]pyridazine-3-carbonitrile

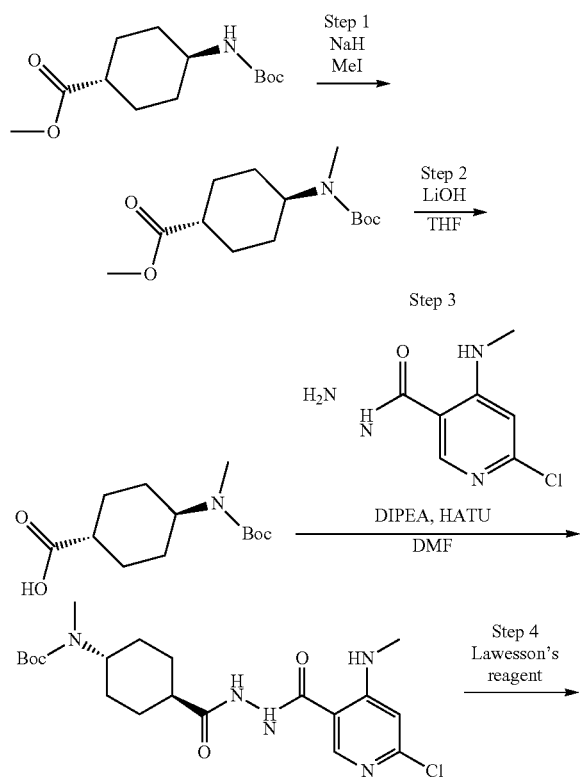

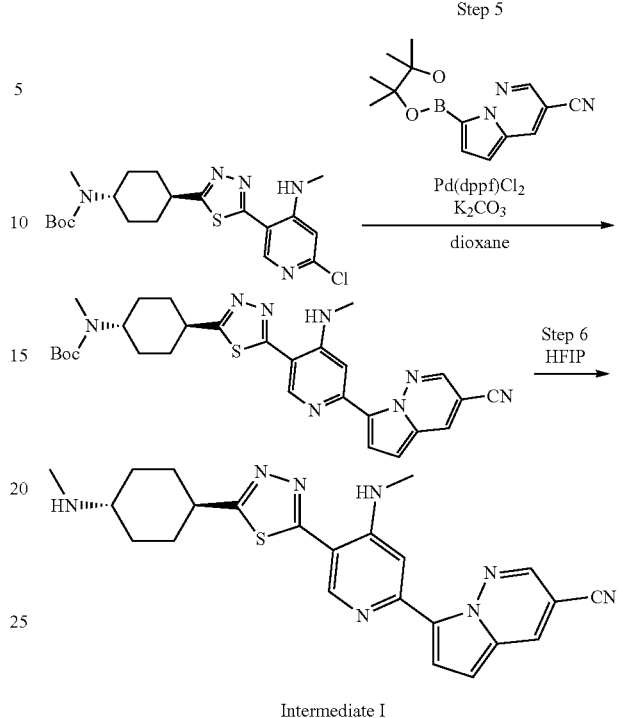

Intermediate I

Step 1: Methyl trans-4-(tert-butoxycarbonylamino)cyclohexanecarboxylate (3.0 g, 11.66 mmol, 1.0 eq) was dissolved in DMF (20 ml, 0.6M) and cooled down to 0° C. Then NaH (0.536 g, 13.99 mmol, 1.2 eq) was added and the reaction mixture was stirred at 0° C. for 30 min. Methyl iodide (1.09 ml, 17.49 mmol, 1.5 eq) was added, then the cooling bath was removed and the reaction mixture was stirred at RT overnight. TLC showed formation of new spot, the mixture was poured into a saturated aqueous ammonium chloride and extracted with ethyl acetate. The crude was purified by hexane:EtOAc to acquire 1.4 g (44% yield) of desired product. $^1$H NMR (300 MHz, DMSO-d$_6$) δ 3.58 (s, 3H), 2.64 (s, 3H), 2.25 (tt, J=11.7, 3.6 Hz, 1H), 1.94 (dt, J=12.3, 2.6 Hz, 2H), 1.60-1.41 (m, 4H), 1.38 (d, J=1.6 Hz, 12H).

Step 2: Methyl (1r,4r)-4-{[(tert-butoxy)carbonyl](methyl)amino}cyclohexane-1-carboxylate (1.3 g, 4.79 mmol, 1.0 eq) was dissolved in THF (18 ml, 0.27 M) followed by addition of solution of LiOH (4.8 ml, 4.79 mmol, 2.0 eq) and stirred at RT for 5 hrs. Then, another portion of LiOH (2.4 ml, 2.39 mmol, 1.0 eq) was added and the reaction mixture was stirred overnight. The reaction mixture was then quenched with saturated solution of KHSO$_4$ to pH<5 and extracted with DCM to acquire 1.18 g (96% yield) of desired product as a free acid. $^1$H NMR (300 MHz, DMSO-d$_6$) δ 3.90-3.52 (m, 1H) 2.65 (s, 3H), 2.13 (tt, J=11.7, 3.6 Hz, 1H), 2.02-1.91 (m, 2H), 1.66-1.45 (m, 4H), 1.39 (d, J=1.2 Hz, 11H).

Step 3: To a solution of 6-chloro-4-(methylamino)pyridine-3-carbohydrazide (0.84 g, 0.7975 mmol, 1.0 eq) and (1r,4r)-4-{[(tert-butoxy)carbonyl]amino}cyclohexane-1-carboxylic acid (1.19 g, 4.61 mmol, 1.1 eq) in DMF (10 mL) were added DIPEA (2.2 ml, 12.56 mmol, 3.0 eq) and HATU (1.91 g, 5.02 mmol, 1.2 eq). The mixture was stirred at 25° C. for 1 hour. The UPLC showed mass of desired product. The reaction mixture was quenched with water and extracted with ethyl acetate. The combined organic layers were washed with water, brine, dried over Na$_2$SO$_4$ and concentrated to get a crude product. The crude product was purified by column chromatography eluted by DCM:MeOH (0-10%) to acquire 1.18 g (64% yield) of desired product. LCMS: ESI(+)[M+H]$^+$=440.6. $^1$H NMR (300 MHz, DMSO-d$_6$) δ 10.30 (s, 1H), 9.78 (s, 1H), 8.33 (s, 1H), 8.11 (s, 1H), 6.66 (s, 1H), 2.82 (d, 3H), 2.65 (s, 3H), 2.13 (tt, J=11.7, 3.6 Hz, 1H), 2.02-1.91 (m, 2H), 1.66-1.45 (m, 4H), 1.39 (d, J=1.2 Hz, 12H).

Step 4: To a suspension of tert-butyl N-methyl-N-[(1r,4r)-4-{N'-[6-chloro-4-(methylamino)pyridine-3-carbonyl]hydrazinecarbonyl}cyclohexyl]carbamate (1.18 g, 2.68 mmol, 1.0 eq) in dry toluene (50 mL, 0.05 M) was added Lawesson's reagent (1.20 g, 2.95 mmol, 1.1 eq). The reaction mixture was stirred under reflux for 1.5 hrs and then quenched with water, washed with sat. solution of NaHCO$_3$, extracted with DCM and concentrated under reduced pressure. The crude was purified by flash column chromatography (DCM/MeOH) to give 0.7 g (60% yield) of the desired product as a white solid. LCMS: ESI(+)[M+H]$^+$=438.6. $^1$H NMR (300 MHz, DMSO-d$_6$) δ 8.66 (d, J=5.0 Hz, 1H), 8.40 (s, 1H), 6.83 (s, 1H), 3.25-3.09 (m, 1H), 2.98 (d, J=4.9 Hz, 3H), 2.71 (s, 3H), 2.21 (d, J=10.3 Hz, 2H), 1.69 (d, J=7.4 Hz, 6H), 1.41 (s, 9H).

Step 5: To a solution of tert-butyl N-methyl-N-[(1r,4r)-4-{5-[6-chloro-4-(methylamino)pyridin-3-yl]-1,3,4-thiadiazol-2-yl}cyclohexyl]carbamate (0.7 g, 1.6 mmol, 1.0 eq), 7-(4,4,5,5-tetramethyl-1,3,2-dioxaborolan-2-yl)pyrrolo[1,2-b]pyridazine-3-carbonitrile (0.6 g, 2.23 mmol, 1.4 eq) and Pd(dppf)Cl$_2$·CH$_2$Cl$_2$ (0.328 g, 0.4 mmol, 0.25 eq) in anh Dioxane (30 ml), was added 2M K$_2$CO$_3$ (1.6 ml, 3.2 mmol, 2.0 eq). The solution was degassed with argon for 2-3 min and then heated to 120° C. and stirred overnight. UPLC showed full conversion of the starting material. The resulting solution was diluted with MeOH, filtrated through a pad of Celite and concentrated to dryness. The crude was purified by chromatography eluted by DCM:MeOH (0-10%) to acquire 0.7 g (80% yield) of desired product. LCMS: ESI(+)[M+H]$^+$=546.1. $^1$H NMR (300 MHz, DMSO-d$_6$) δ 8.85 (d, J=2.2 Hz, 1H), 8.74 (d, J=2.2 Hz, 1H), 8.71-8.58 (m, 2H), 8.19 (s, 1H), 7.88 (d, J=4.8 Hz, 1H), 7.13 (d, J=4.8 Hz, 1H), 3.24-3.15 (m, 1H), 3.09 (d, J=4.9 Hz, 3H), 2.71 (s, 3H), 2.30-2.12 (m, 2H), 1.76-1.53 (m, 6H), 1.42 (s, 9H).

Step 6: Tert-butyl N-methyl-N-[(1r,4r)-4-[5-(6-{3-cyanopyrrolo[1,2-b]pyridazin-7-yl}-4-(methylamino)pyridin-3-yl)-1,3,4-thiadiazol-2-yl]cyclohexyl]carbamate (0.67 g, 1.23 mmol, 1.0 eq) was dissolved in hexafluoro-2-propanol (4.0 ml, 30.0 eq) in closed cup reactor and put in microwave for 2 h at 150° C. The UPLC showed full deprotection of the starting material. The solvent was evaporated to dryness to acquire desired product 0.54 g (99% yield) as yellow solid. LCMS: ESI(+)[M+H]$^+$=444.97. $^1$H NMR (300 MHz, DMSO-d$_6$) δ 8.84 (d, J=2.3 Hz, 1H), 8.73 (d, J=2.2 Hz, 1H), 8.68-8.47 (m, 2H), 8.18 (s, 1H), 7.88 (d, J=4.8 Hz, 1H), 7.13 (d, J=4.8 Hz, 1H), 3.20-3.10 (m, 1H), 3.09 (d, J=4.8 Hz, 3H), 2.36-2.26 (m, 4H), 2.20-2.08 (m, 2H), 2.07-1.96 (m, 2H), 1.70-1.49 (m, 3H), 1.33-1.11 (m, 2H).

Intermediate J: 7-[4-(methylamino)-5-{5-[4-(piperazin-1-yl)piperidin-1-yl]-1,3,4-thiadiazol-2-yl}pyridin-2-yl]pyrrolo[1,2-b]pyridazine-3-carbonitrile

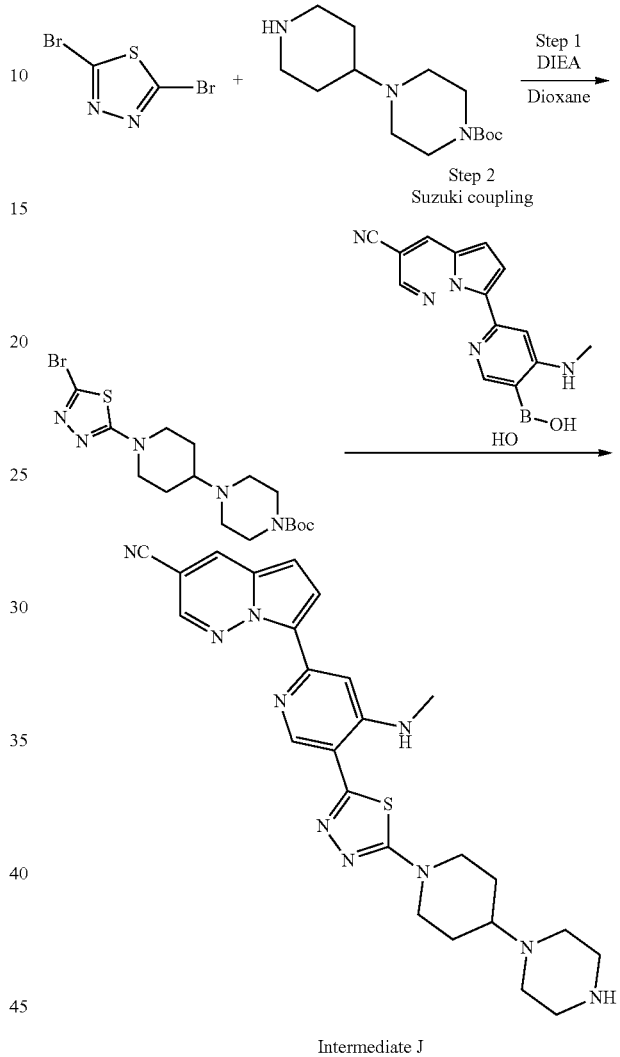

Intermediate J

The title compound was synthesized following the same procedures as described for Intermediate T, except with tert-butyl 4-(piperidin-4-yl)piperazine-1-carboxylate as a starting material instead of tert-butyl 4,7-diazaspiro[2.5]octane-4-carboxylate. LCMS C$_{25}$H$_{28}$N$_{10}$S requires: 500.2, found: m/z=501.4 [M+H]$^+$.

Intermediate K: 7-(5-(5-(4-aminobicyclo[2.2.2]octan-1-yl)-1,3,4-thiadiazol-2-yl)-4-(methylamino)pyridin-2-yl)pyrrolo[1,2-b]pyridazine-3-carbonitrile

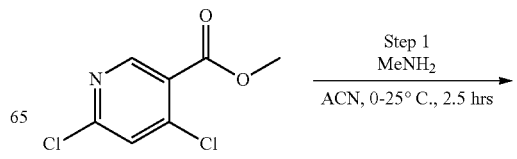

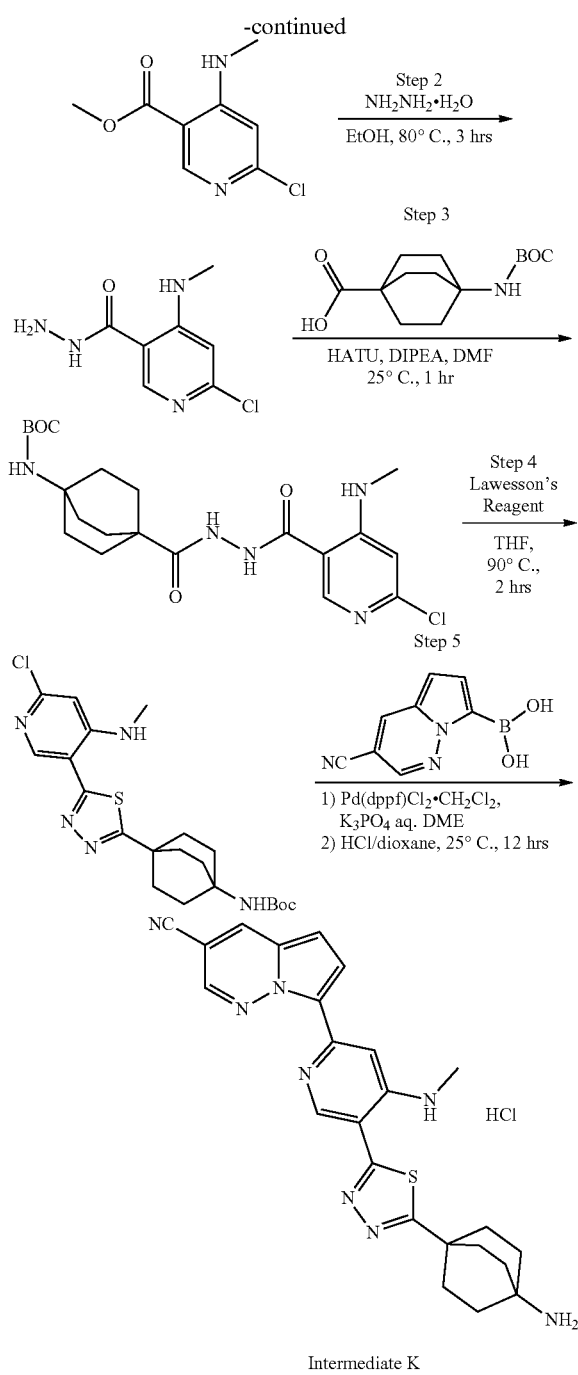

Intermediate K

Step 1: To a solution of methyl 4,6-dichloronicotinate (95.0 g, 461 mmol, 1.00 eq) in ACN (1000 mL) was added methylamine (288 g, 2.32 mol, 25% purity, 5.03 eq) slowly at 0° C., the mixture was stirred at 0° C. for 0.5 hr and then at 25° C. for 2 hrs. The reaction mixture was concentrated under reduced pressure and extracted with ethyl acetate (500 mL*3), the combined organic layers were washed with brine (500 mL*2), dried over Na$_2$SO$_4$, filtered and the filtrate was concentrated under reduced pressure to obtain the crude product. The crude product was purified by a column chromatography (SiO$_2$, petroleum ether: ethyl acetate=20: 1-10:1, R$_f$=30). Desired product (39.0 g, 184 mmol, 40.0% yield) was obtained as a white solid. LCMS: m/z=201.1 (M+H)+.

Step 2: To a solution of methyl 6-chloro-4-(methylamino) nicotinate (39.0 g, 184 mmol, 1.00 eq) in EtOH (300 mL) was added NH$_2$NH$_2$·H$_2$O (86.6 g, 1.47 mol, 84.1 mL, 7.97 eq), the mixture was stirred at 80° C. for 3 hrs. The reaction mixture was concentrated and extracted with ethyl acetate (500 mL*4). The combined organic layer was washed with brine (500 mL*4), dried over Na$_2$SO$_4$ and concentrated to get a crude product. The crude product was triturated with petroleum ether/ethyl acetate=15:1 (600 mL). Desired product (27.0 g, 120 mmol, 65.2% yield) was obtained as a white solid. LCMS: m/z=201.2 (M+H)$^+$ Step 3: To a solution of 6-chloro-4-(methylamino)nicotinohydrazide (8.00 g, 35.6 mmol, 1.00 eq) and 4-(((11-methyl)(11-oxidaneyl)boraneyl)amino)bicyclo[2.2.2]octane-1-carboxylic acid (10.5 g, 39.2 mmol, 1.10 eq) in DMF (100 mL) was added DIEA (13.8 g, 107 mmol, 18.6 mL, 3.00 eq) and HATU (16.2 g, 42.8 mmol, 1.20 eq) at 25° C., the mixture was stirred at 25° C. for 1 hr. The reaction mixture was poured into water (100 mL) and extracted with ethyl acetate (100 mL*3), the combined organic layer was washed with water (100 mL*3), brine (200 mL), dried and concentrated to get a crude product. The crude product was purified by prep-HPLC. Desired product (15.0 g, 32.0 mmol, 89.7% yield) was obtained as a white solid. LCMS: m/z=452.4 (M+H)$^+$ Step 4: To a solution of N'-(4-(((11-methyl)(11-oxidaneyl) boraneyl)amino)bicyclo[2.2.2]octane-1-carbonyl)-6-chloro-4-(methylamino)nicotinohydrazide (15.0 g, 32.0 mmol, 1.00 eq) in THF (300 mL) was added Lawesson's reagent (14.2 g, 35.2 mmol, 1.10 eq), the mixture was stirred at 90° C. for 2 hrs. The reaction mixture was concentrated to obtain the crude product. The crude product was purified by prep-HPLC. Desired product (4.30 g, 9.33 mmol, 29.1% yield) was obtained as an off-white solid. LCMS: m/z=450.3 (M+H)$^+$ Step 5: To a solution of tert-butyl (4-(5-(6-chloro-4-(methylamino)pyridin-3-yl)-1,3,4-thiadiazol-2-yl)bicyclo [2.2.2]octan-1-yl)carbamate (3.80 g, 8.44 mmol, 1.00 eq), (3-cyanopyrrolo[1,2-b]pyridazin-7-yl)boronic acid (2.37 g, 12.67 mmol, 1.50 eq) and K$_3$PO$_4$ (2 M, 8.44 mL, 2.00 eq) in DME (4.00 mL) was added Pd(dppf)Cl$_2$·CH$_2$Cl$_2$ (689 mg, 844 μmol, 0.10 eq) under N$_2$. The resulting mixture was stirred at 110° C. for 12 hrs. The reaction mixture was filtered, and the filtrate was extracted with DCM (80.0 mL*3). The combined organic phase was washed with brine (100 mL), dried over anhydrous Na$_2$SO$_4$, filtered and concentrated under vacuum. The crude product was purified by column chromatography (SiO$_2$, petroleum ether/ethyl acetate=10/1 to DCM/ethyl acetate=1/1) to give a residue. The residue and HCl/dioxane (4 M, 4.00 mL, 4.53 eq) in dioxane (20 mL) was stirred at 25° C. for 12 hrs. The mixture was concentrated under vacuum. The residue in EtOAc (20.0 mL) was heated to 90° C. for 30 mins and filtered for three times to give 7-(5-(5-(4-aminobicyclo [2.2.2]octan-1-yl)-1,3,4-thiadiazol-2-yl)-4-(methylamino) pyridin-2-yl)pyrrolo[1,2-b]pyridazine-3-carbonitrile (1.67 g, 3.22 mmol, 33.7% yield, HCl) as brown solid. LCMS: m/z=557.2

Intermediate L: 7-[5-(5-{3,8-diazabicyclo[3.2.1]octan-3-yl}-1,3,4-thiadiazol-2-yl)-4-(methylamino)pyridin-2-yl]pyrrolo[1,2-b]pyridazine-3-carbonitrile

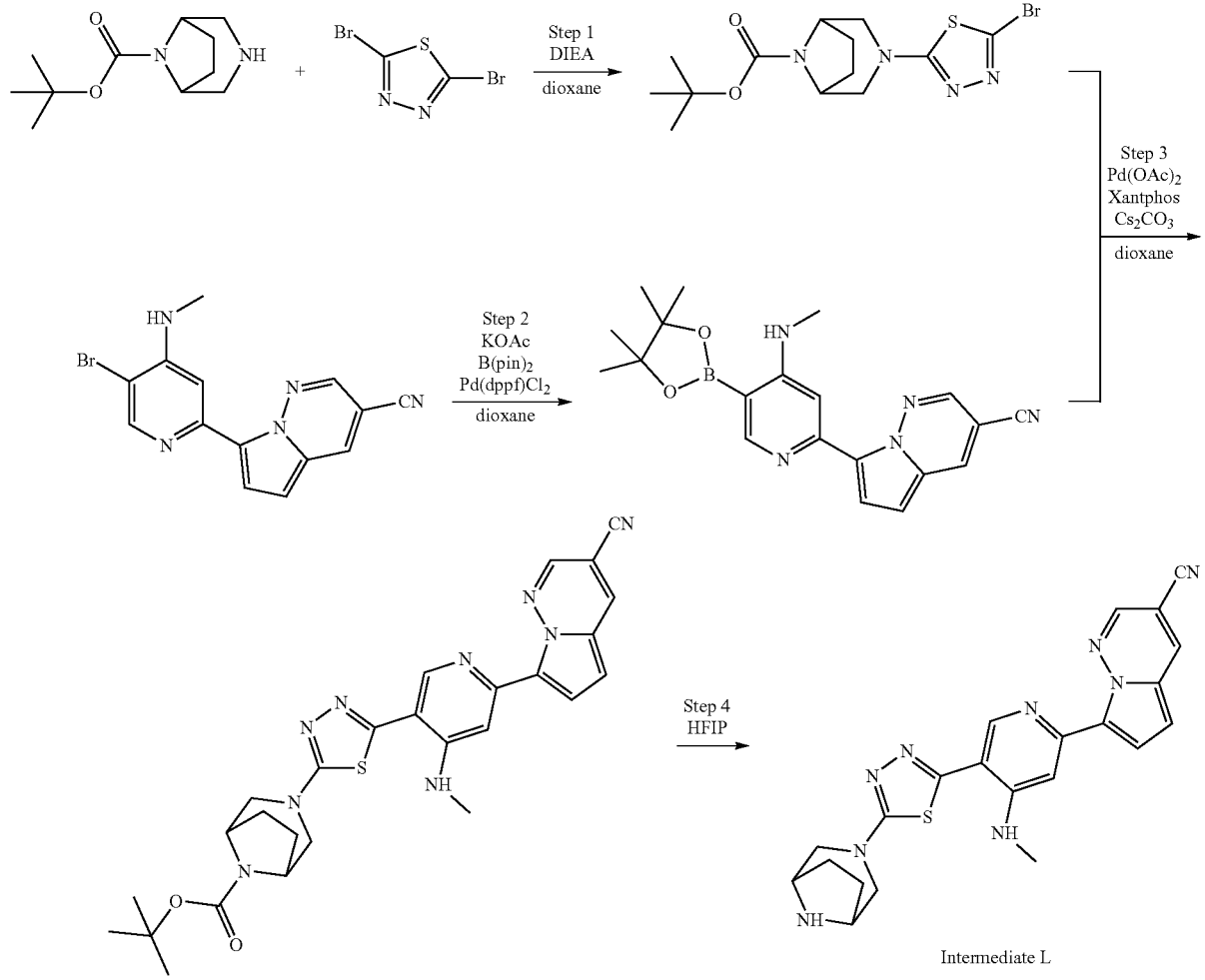

Intermediate L

Step 1: A stirred suspension of 2,5-dibromo-1,3,4-thiadiazole (1.05 g, 4.31 mmol, 1.0 eq), 8-Boc-3,8-diaza-bicyclo[3.2.1]octane (1.005 g, 4.73 mmol, 1.1 eq) and N,N-Diisopropylethylamine (1.125 ml, 6.46 mmol, 1.5 eq) in anhydrous dioxane (21.53 ml, 0.2 M) was heated at 120° C. for 1 hour. The reaction mixture was diluted with water, extracted with DCM, and the organic phase was concentrated onto silica gel. The crude material was purified by flash chromatography using an EtOAc/hexane gradient to afford 7-[5-bromo-4-(methylamino)pyridin-2-yl]pyrrolo[1,2-b]pyridazine-3-carbonitrile as a yellow oil (0.819 g, 2.18 mmol, 71%). LCMS: ESI(+)[M+H]+=337.3. $^1$H NMR (300 MHz, CDCl$_3$) δ 4.37 (s, 2H), 3.72-3.26 (m, 4H), 2.03 (m, 2H), 1.82 (m, 2H), 1.50 (d, J=0.8 Hz, 9H).

Step 2: 7-[5-bromo-4-(methylamino)pyridin-2-yl]pyrrolo[1,2-b]pyridazine-3-carbonitrile (1.5 g, 4.57 mmol, 1.0 eq) was dissolved in dioxane (25 ml, 0.18 M) in pressure reactor followed by addition of bis(pinacolato)diboron (1.39 g, 5.49 mmol, 1.2 eq) and KOAc (1.39 g, 14.17 mmol, 3.1 eq). The solution was sparged for a few minutes with argon and Pd(dppf)Cl$_2$·DCM (0.373 g, 0.46 mmol, 0.1 eq) was added followed by repeated sparging. The reaction mixture was then moved to preheated oil bath and stirred at 90° C. overnight. The reaction mixture was filtrated through a pad of Celite and evaporated to dryness. The crude was used in the next step without further purification.

Step 3: To a solution of 7-[4-(methylamino)-5-(4,4,5,5-tetramethyl-1,3,2-dioxaborolan-2-yl)pyridin-2-yl]pyrrolo[1,2-b]pyridazine-3-carbonitrile (0.58 g, 1.55 mmol, 1.0 eq), tert-butyl 3-(5-bromo-1,3,4-thiadiazol-2-yl)-3,8-diazabicyclo[3.2.1]octane-8-carboxylate (0.638 g, 1.70 mmol, 1.1 eq) in dioxane (40 ml, 0.04M) were added Cs$_2$CO$_3$ (1.26 g, 3.86 mmol, 2.5 eq) and Xantphos (0.358 g, 0.62 mmol, 0.4 eq). The reaction was sparged with argon for a few mins followed by the addition of Pd(OAc)$_2$ (0.069 g, 0.31 mmol, 0.2 eq). The solution was degassed with argon for 2-3 min and then stirred at 120° C. overnight. The reaction mixture was filtrated through a pad of Celite and evaporated to dryness. The crude was purified by FC eluting with DCM/MeOH (0-10%). The main fraction was repurified by pTLC eluting with DCM/MeOH (0-10%) and finally triturated with Et$_2$O to acquire 0.190 g (23% yield) of the desired product. LCMS: ESI(+)[M+H]$^+$=544.77. $^1$H NMR (300 MHz, DMSO-d$_6$) δ: 8.83 (d, J=2.2 Hz, 1H), 8.72 (d, J=2.3 Hz, 1H), 8.51-8.43 (m, 2H), 8.14 (s, 1H), 7.85 (d, J=4.8 Hz, 1H), 7.12 (d, J=4.8 Hz, 1H), 4.28 (s, 2H), 3.67 (d, J=11.8 Hz, 2H), 3.37 (d, 2H), 3.06 (d, J=4.9 Hz, 3H), 1.91 (d, J=6.3 Hz, 2H), 1.75 (d, J=7.4 Hz, 2H), 1.44 (s, 9H).

Step 4: To tert-butyl 3-[5-(6-{3-cyanopyrrolo[1,2-b]pyridazin-7-yl}-4-(methylamino)pyridin-3-yl)-1,3,4-thiadiazol-2-yl]-3,8-diazabicyclo[3.2.1]octane-8-carboxylate (0.120 g, 0.22 mmol, 1.0 eq) was added 1,1,1,3,3,3-hexafluoro-2-propanol (0.7 ml, 30 eq) in pressure vessel and heated in the microwave for 2.5 h at 150° C. The solvent was evaporated to dryness and triturated with Et$_2$O to give 0.080 g (82% yield) of the title compound. LCMS: ESI(+)[M+H]$^+$=444.05. $^1$H NMR (300 MHz, DMSO-d$_6$) δ: 8.83 (d, J=2.3 Hz, 1H), 8.72 (d, J=2.2 Hz, 1H), 8.52-8.44 (m, 2H), 8.13 (s, 1H), 7.85 (d, J=4.8 Hz, 1H), 7.12 (d, J=4.8 Hz, 1H), 3.61-3.46 (m, 4H), 3.29 (s, 3H), 3.06 (m, 3H), 1.70 (dd, J=9.8, 6.7 Hz, 4H).

Intermediate M: 4-[5-(6-{3-cyanopyrrolo[1,2-b]pyridazin-7-yl}-4-(methylamino)pyridin-3-yl)-1,3,4-thiadiazol-2-yl]cyclohexane-1-carboxylic acid hydrochloride

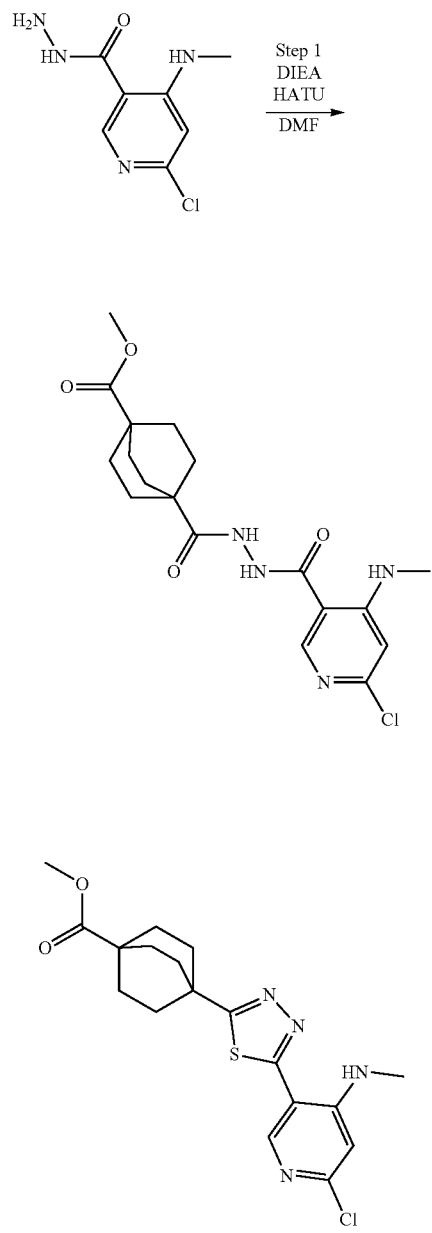

Intermediate M

Step 1: To a solution of 6-chloro-4-(methylamino)pyridine-3-carbohydrazide (10.0 g, 49.84 mmol, 1.0 eq) and 4-(methoxycarbonyl)bicyclo[2.2.2]octane-1-carboxylic acid (11.63 g, 54.83 mmol, 1.1 eq) in DMF (175 mL, 0.285 M) was added DIPEA (149.53 mmol, 26 mL, 3.0 eq) and HATU (22.74 g, 59.81 mmol, 1.2 eq). The mixture was stirred at 25° C. for 2 hrs. The reaction mixture was quenched with a water/ice mixture (600 mL) and extracted with EtOAc. The combined organic layers were washed with aq solution of NaHCO$_3$, aq. solution KHSO$_4$, water, brine and dried over Na$_2$SO$_4$. After evaporation of volatiles, the crude was purified by column chromatography (DCM/MeOH) to afford methyl 4-{N'-[6-chloro-4-(methylamino)pyridine-3-carbonyl]hydrazinecarbonyl}bicyclo-[2.2.2]octane-1-carboxylate as a white solid (15.6 g, 79% yield). LCMS: ESI(+)[M+H]$^+$=395.62. $^1$H NMR (300 MHz, DMSO-d$_6$), δ: 10.23 (1H, s), 9.48 (1H, s), 8.35 (1H, s), 8.14 (1H, br. q, J5.1), 6.66 (1H, s), 3.59 (3H, s), 2.82 (3H, d, J4.9), 1.76 (12H, m).

Step 2: Methyl 4-{N'-[6-chloro-4-(methylamino)pyridine-3-carbonyl]hydrazinecarbonyl}bicyclo-[2.2.2]octane-1-carboxylate (5.0 g, 12.66 mmol, 1 eq) was dissolved in THF (250 mL, 0.05 M) under argon. The solution was warmed up to 40° C. and P$_2$S$_5$ (4.22 g, 18.99 mmol, 1.5 eq) was added portionwise during vigorous stirring. Then, the resulting suspension was stirred for 2 h at reflux (controlled by UPLC). After completion, the volatiles were evaporated. The residue was dissolved in DCM and washed with sat. solution of K$_2$CO$_3$. The aqueous layer was removed with a separatory funnel and the organic layer was dried over Na$_2$SO$_4$ and concentrated under reduced pressure. The crude residue was purified by FC (DCM/EA) to give 4-{5-[6-chloro-4-(methylamino)pyridin-3-yl]-1,3,4-thiadiazol-2- yl}cyclohexane-1-carboxylate (2.66 g, 53% yield). LCMS: ESI(+)[M+H]$^+$=393.4. $^1$H NMR (300 MHz, DMSO-d$_6$), δ: 8.66 (1H, br. q, J5.2), 8.38 (1H, s), 6.82 (1H, s), 3.61 (3H, s), 2.97 (3H, d, J4.9), 2.05-1.94 (6H, m), 1.94-1.82 (6H, m).

Step 3: To an argon flashed flask containing methyl 4-{5-[6-chloro-4-(methylamino) pyridin-3-yl]-1,3,4-thiadiazol-2-yl}cyclohexane-1-carboxylate (4.04 g, 10.9 mmol, 1.0 eq), cesium acetate (5.2 g, 27.2 mmol, 2.5 eq) and Pd(dppf)Cl$_2$·DCM (1.74 g, 2.2 mmol, 0.2 eq) in THF (218 ml, 0.05 M), 7-(4,4,5,5-tetramethyl-1,3,2-dioxaborolan-2-yl)pyrrolo[1,2-b]pyridazine-3-carbonitrile (4.401 g, 16.35 mmol, 1.5 eq) was added. The mixture was stirred at 85° C. overnight. The mixture was filtered through a pad of Celite, concentrated in vacuo, re-dissolved in dichloromethane, and deposited onto silica gel. The resulting solid was purified by flash chromatography (0 to 10% gradient of acetonitrile in DCM) to give methyl 4-[5-(6-{3-cyanopyrrolo[1,2-b]pyridazin-7-yl}-4-(methylamino)pyridin-3-yl)-1,3,4-thiadiazol-2-yl]cyclohexane-1-carboxylate as a yellow crystalline solid (2.9 g, 56% yield). LCMS: ESI(+)[M+H]$^+$=474.60. $^1$H NMR (300 MHz, DMSO-d$_6$), δ: 8.83 (d, J=2.2 Hz, 1H), 8.72 (d, J=2.2 Hz, 1H), 8.62 (d, J=6.0 Hz, 2H), 8.22-8.12 (m, 1H), 7.87 (d, J=4.8 Hz, 1H), 7.11 (d, J=4.8 Hz, 1H), 3.62 (s, 3H), 3.19 (s, 1H), 3.08 (d, J=4.9 Hz, 3H), 2.42 (d, J=11.7 Hz, 1H), 2.19 (d, J=10.3 Hz, 2H), 2.03 (d, J=10.7 Hz, 2H), 1.59 (q, J=12.3, 11.2 Hz, 4H).

Step 4: To a solution of methyl 4-[5-(6-{3-cyanopyrrolo[1,2-b]pyridazin-7-yl}-4-(methylamino)pyridin-3-yl)-1,3,4-thiadiazol-2-yl]cyclohexane-1-carboxylate (2.9 g, 6.1 mmol, 1.0 eq) in dry pyridine (61.2 ml, 0.1 M), lithium iodide (8.3 g, 61.2 mmol, 10 eq) was added and the resulting mixture was stirred at 150° C. until completion (using UPLC control, 24-48 h). Then, the resulting mixture was acidified with an equimolar amount of dilute HCl. The obtained solid was purified by column chromatography (0 to 20% gradient of 2-propanol in DCM) to afford the target compound as a yellow solid (3.1 g, 95% yield). LCMS: ESI(+)[M+H]$^+$=460.23. $^1$H NMR (300 MHz, DMSO-d$_6$), δ: 12.17 (s, 1H), 9.59 (d, J=4.2 Hz, 1H), 8.99 (d, J=2.0 Hz, 1H), 8.86 (d, J=2.0 Hz, 1H), 8.69 (s, 1H), 8.15 (d, J=4.9 Hz, 1H), 7.95 (s, 1H), 7.24 (d, J=5.0 Hz, 1H), 3.32 (m, 1H), 3.22 (d, J=4.8 Hz, 3H), 2.40-2.28 (m, 1H), 2.21 (d, J=11.8 Hz, 2H), 2.04 (s, 2H), 1.72-1.46 (m, 4H).

Intermediate N: 7-[4-(methylamino)-5-{5-[(1r,4r)-4-formylcyclohexyl]-1,3,4-thiadiazol-2-yl}pyridin-2-yl]pyrrolo[1,2-b]pyridazine-3-carbonitrile

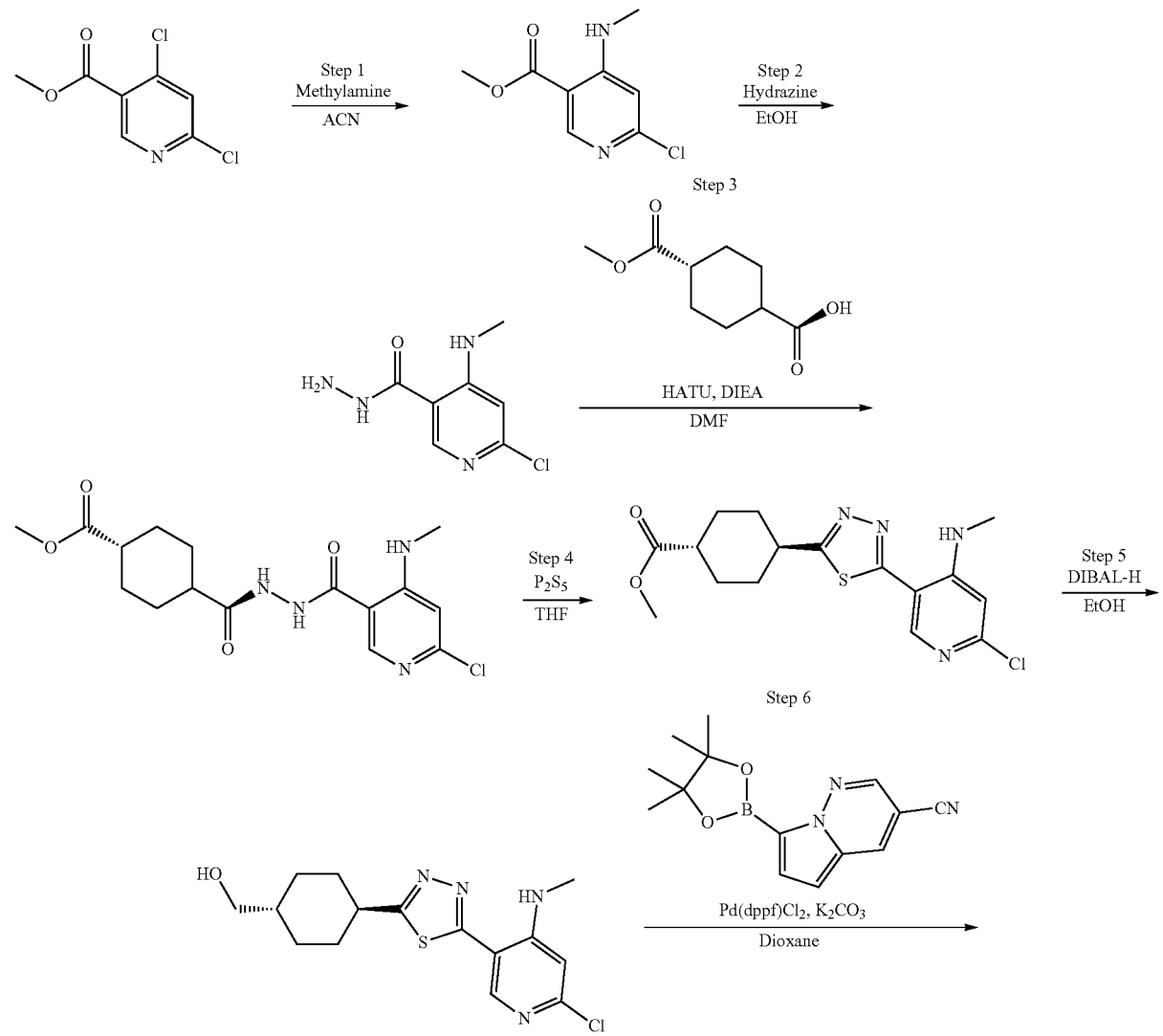

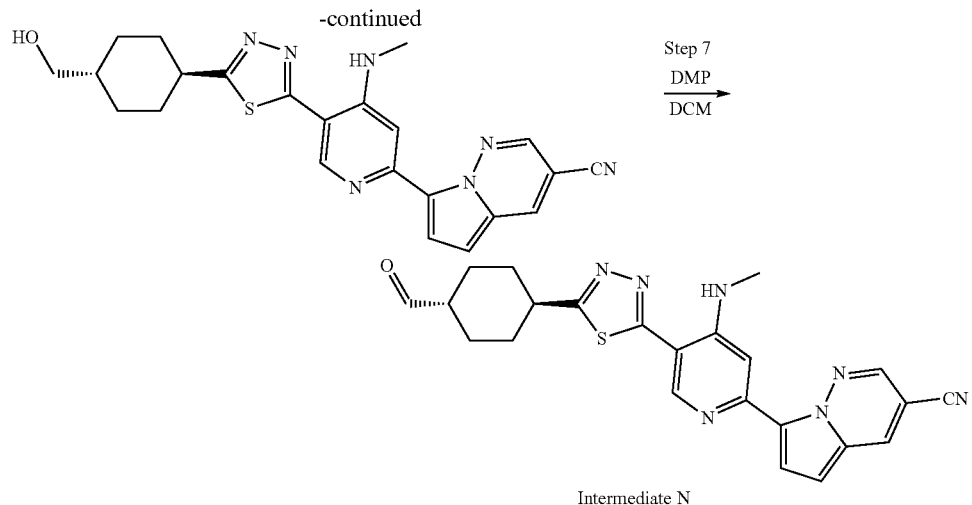

Intermediate N

Step 1: To a solution of methyl 4,6-dichloronicotinate (99.0 g, 481 mmol, 1.0 eq) in acetonitrile (990 mL, 0.49M) was added methylamine 40% wt (208 ml, 2403 mmol, 5.0 eq) slowly at −5° C., the mixture was stirred at 0° C. for 30 min and then at 25° C. for 2 hrs. The reaction mixture was concentrated under reduced pressure and extracted with ethyl acetate, the combined organic layers were washed with brine, dried over $Na_2SO_4$, filtered, and concentrated under reduced pressure. The crude was purified by column chromatography (hexane/EtOAc, 0 to 50%) affording methyl 6-chloro-4-(methylamino)pyridine-3-carboxylate as a white solid (65.3 g, 68% yield). LCMS: ESI(+)[M+H]$^+$=202.2. $^1$H NMR (300 MHz, DMSO-$d_6$) δ: 8.50 (s, 1H), 8.04 (d, J=5.5 Hz, 1H), 6.74 (s, 1H), 3.83 (3H, s), 2.88 (d, J=5.0 Hz, 3H).

Step 2: To a solution of methyl 6-chloro-4-(methylamino)pyridine-3-carboxylate (43 g, 0.21 mol, 1 eq) in EtOH (358 ml, 0.6 M), hydrazine hydrate (129 ml, 1.68 mol, 8.0 eq) was added and the resulting mixture was stirred at 80° C. for 4 hrs (UPLC control was applied). Afterward, the reaction mixture was cooled down to rt and extracted multiple times with DCM. The combined organic layers were dried over $Na_2SO_4$ and solvent concentrated in vacuo to afford 6-chloro-4-(methylamino)pyridine-3-carbohydrazide as a white crystalline solid (34.4 g, 79% yield). LCMS: ESI(+)[M+H]$^+$=200.95. $^1$H NMR (300 MHz, DMSO-$d_6$) δ: 9.81 (s, 1H), 8.21 (s, 1H), 8.11 (s, 1H), 6.62 (s, 1H), 4.46 (s, 2H), 2.82 (d, J=5.0 Hz, 3H).

Step 3: To a solution of 6-chloro-4-(methylamino)pyridine-3-carbohydrazide (12.0 g, 59.81 mmol, 1.0 eq) and monomethyl trans-1,4-cyclohexanedicarboxylate (12.25 g, 65.79 mmol, 1.1 eq) in DMF (150 mL) were added DIPEA (179.43 mmol, 32 mL, 3.0 eq) and HATU (27.29 g, 71.77 mmol, 1.2 eq). The mixture was stirred at 25° C. for 1 h and then quenched with water, added brine and extracted with EtOAc. The combined organic layers were washed with brine, dried over $Na_2SO_4$, and concentrated in vacuo. The residue was purified by column chromatography eluted by DCM/MeOH (0-10%) to afford methyl (1r,4r)-4-{N'-[6-chloro-4-(methylamino)pyridine-3-carbonyl]hydrazinecarbonyl}cyclohexane-1-carboxylate (15.5 g, 70% yield). LCMS: ESI(+)[M+H]$^+$=367.46. $^1$H NMR (300 MHz, DMSO-$d_6$) δ: 10.31 (s, 1H), 9.81 (s, 1H), 8.34 (s, 1H), 8.12 (q, J=4.9 Hz, 1H), 6.66 (s, 1H), 3.60 (s, 3H), 3.33 (s, 2H), 2.82 (d, J=4.9 Hz, 3H), 2.40-2.16 (m, 2H), 2.02-1.91 (m, 2H), 1.82 (t, J=7.2 Hz, 2H), 1.55-1.25 (m, 4H).

Step 4: To a solution of methyl (1r,4r)-4-{N'-[6-chloro-4-(methylamino)pyridine-3-carbonyl]hydrazinecarbonyl}cyclohexane-1-carboxylate (11.35 g, 30.77 mmol, 1 eq) in anh THF (1000 mL, 0.03 M), was added phosphorus pentasulfide (8.9 g, 40.01 mmol, 1.3 eq) at 20° C. The resulting mixture was aged for 3 h at 50° C. The reaction was filtered, washed with THF, and concentrated under reduced pressure. The residue was purified by column chromatography (hexane/EA) to afford methyl (1r,4r)-4-{5-[6-chloro-4-(methylamino)pyridin-3-yl]-1,3,4-thiadiazol-2-yl}cyclohexane-1-carboxylate (4.46 g, 40%). LCMS: ESI(+)[M+H]$^+$=367.48. $^1$H NMR (300 MHz, DMSO-$d_6$) δ: 8.65 (d, J=5.2 Hz, 1H), 8.39 (s, 1H), 6.82 (s, 1H), 3.62 (s, 3H), 3.21 (td, J=11.4 Hz, 3.5 Hz, 1H), 2.98 (d, J=4.9 Hz, 3H), 2.48-2.37 (m, 1H), 2.22-1.96 (m, 4H), 1.72-1.45 (m, 4H).

Step 5: A solution of methyl (1r,4r)-4-{5-[6-chloro-4-(methylamino)pyridin-3-yl]-1,3,4-thiadiazol-2-yl}cyclohexane-1-carboxylate (4.26 g, 11.61 mmol, 1 eq) in anhydrous THF (180.0 mL, 0.06 M) was cooled to −15° C. under argon atmosphere, and treated with DIBAL-H (35 mL of a 1.0 M solution in THF, 34.8 mmol, 3.0 eq). After 30 min, the cooling bath was removed and the mixture was allowed to warm up to rt and stir for 1 hrs. After this time, the reaction was quenched by adding MeOH (30 mL), stirred vigorously for 20 min followed by addition of sat aq Rochelle salt. The resulting mixture was extracted with DCM. The combined organic layers were washed with a diluted solution of $KHSO_4$, water, brine, dried over $Na_2SO_4$, and concentrated under reduced pressure. The residue was purified by column chromatography (DCM/ACN) to afford [(1r,4r)-4-{5-[6-chloro-4-(methylamino)pyridin-3-yl]-1,3,4-thiadiazol-2-yl}cyclohexyl]methanol (3.0 g, 8.85 mmol, 1.0 eq), 7-(4,4,5,5-tetramethyl-1,3,2-dioxaborolan-2-yl)pyrrolo[1,2-b]pyridazine-3-carbonitrile (3.19 g, 81% yield). LCMS: ESI(+)[M+H]$^+$=339.48. $^1$H NMR (300 MHz, DMSO-$d_6$) δ: 8.66 (d, J=4.6 Hz, 1H), 8.38 (s, 1H), 6.82 (s, 1H), 4.46 (t, J=5.3 Hz, 1H), 3.26 (t, J=5.8 Hz, 2H), 3.14 (tt, J=11.9 Hz, 3.6 Hz, 1H), 2.97 (d, J=4.9 Hz, 3H), 2.22-2.10 (m, 2H), 1.92-1.80 (m, 2H), 1.64-1.36 (m, 3H), 1.26-1.00 (m, 2H).

Step 6: To a solution of [(1r,4r)-4-{5-[6-chloro-4-(methylamino)pyridin-3-yl]-1,3,4-thiadiazol-2-yl}cyclohexyl]methanol (3.0 g, 8.85 mmol, 1.0 eq), 7-(4,4,5,5-tetramethyl-1,3,2-dioxaborolan-2-yl)pyrrolo[1,2-b]pyridazine-3- carbonitrile (3.4 g, 12.4 mmol, 1.4 eq) and Pd(dppf)Cl$_2$·CH$_2$Cl$_2$ (1.82 g, 2.21 mmol, 0.25 eq) in anh dioxane (130 ml, 0.07 M), was added 2M aq K$_2$CO$_3$ (9 ml, 17.71 mmol, 2.0 eq). The mixture was degassed with argon for 30 min and then stirred at 120° C. for 25 hrs. The reaction was diluted with DCM, filtrated though a pad of Celite, washed with DCM/MeOH (1:1) and concentrated in vacuo. The residue was purified twice with column chromatography (DCM/ACN and DCM/IPA respectively) to afford 7-[4-(methylamino)-5-{5-[(1r,4r)-4-(hydroxymethyl)cyclohexyl]-1,3,4-thiadiazol-2-yl}pyridin-2-yl]pyrrolo[1,2-b]pyridazine-3-carbonitrile (2.35 g, 60% yield). LCMS: ESI (+)[M+H]$^+$=446.38. $^1$H NMR (300 MHz, DMSO-d$_6$) δ: 8.84 (d, J=2.2 Hz, 1H), 8.73 (d, J=2.2 Hz, 1H), 8.64 (d, J=9.7 Hz, 2H), 8.17 (s, 1H), 7.87 (d, J=4.8 Hz, 1H), 7.12 (d, J=4.8 Hz, 1H), 4.47 (t, J=5.3 Hz, 1H), 3.27 (t, J=5.8 Hz, 2H), 3.22-3.11 (m, 1H), 3.09 (d, J=4.9 Hz, 3H), 2.23-2.13 (m, 2H), 1.93-1.83 (m, 2H), 1.66-1.39 (m, 3H), 1.26-1.00 (m, 4H).

Step 7: To a solution of the 7-[4-(methylamino)-5-{5-[(1r,4r)-4-(hydroxymethyl) cyclohexyl]-1,3,4-thiadiazol-2-yl}pyridin-2-yl]pyrrolo[1,2-b]pyridazine-3-carbonitrile (2.35 g, 5.27 mmol, 1 eq) in DCM (1.3 L, 0.004 M) was added Dess-Martin periodinane (2.91 g, 6.86 mmol, 1.3 eq). The mixture was stirred at rt overnight. The reaction was quenched with 20% aq Na$_2$S$_2$O$_3$ and sat aq NaHCO$_3$ and was stirred until the aqueous layer became clear. The latter was extracted with DCM. The combined organic layers were dried over Na$_2$SO$_4$ and concentrated in vacuo. The residue was purified by trituration with DCM/Et$_2$O (1:1) to afford the title compound (1.83 g, 78% yield).

LCMS: ESI(+)[M+H]$^+$=444.22. $^1$H NMR (300 MHz, DMSO-d$_6$) δ: 9.63 (br. d, J=1.1 Hz, 1H), 8.84 (d, J=2.3 Hz, 1H), 8.74 (d, J=2.2 Hz, 1H), 8.66 (s, 1H), 8.65 (q, J=2.7 Hz, 1H), 8.17 (s, 1H), 7.88 (d, J=4.8 Hz, 1H), 7.12 (d, J=4.8 Hz, 1H), 3.19 (ddt, J=11.7 Hz, 7.0 Hz, 3.6 Hz, 1H), 3.09 (d, J=4.9 Hz, 3H), 2.41 (ddt, J=12.2 Hz, 7.3 Hz, 3.7 Hz, 1H), 2.29-2.18 (m, 2H), 2.14-2.02 (m, 2H), 1.75-1.55 (m, 2H), 1.51-1.31 (m, 2H).

Intermediate O: 4-[5-(6-{3-cyanopyrrolo[1,2-b]pyridazin-7-yl}-4-(methylamino) pyridin-3-yl)-1,3,4-thiadiazol-2-yl]cyclohexane-1-carboxylic acid

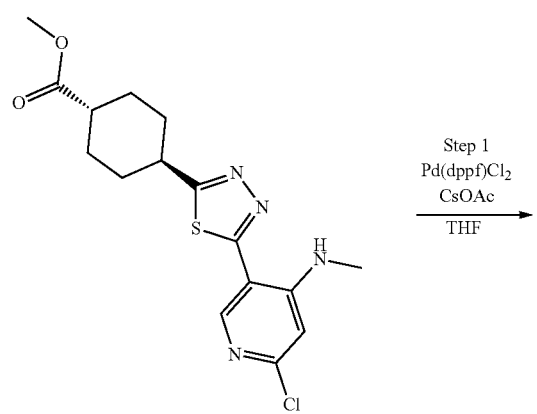

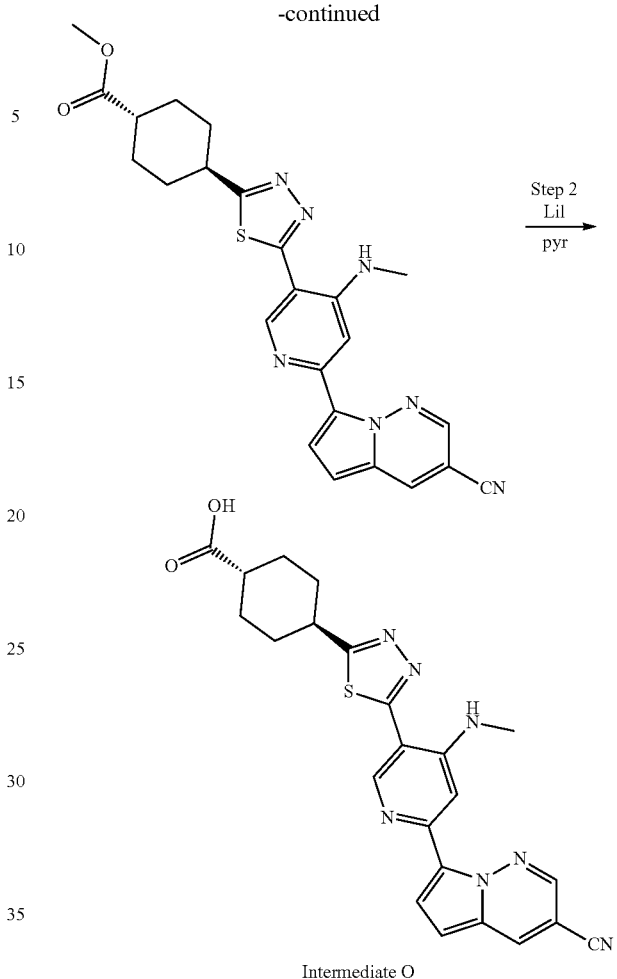

Intermediate O

Step 1: To an argon flushed flask containing methyl 4-{5-[6-chloro-4-(methylamino)pyridin-3-yl]-1,3,4-thiadiazol-2-yl}cyclohexane-1-carboxylate (4 g, 10.9 mmol, 1 eq), CsOAc (5.3 g, 27.3 mmol, 2.5 eq) and Pd(dppf)Cl$_2$·DCM (1.74 g, 2.18 mmol, 0.2 eq) in THF (218 ml, 0.05 M) was added a 7-(4,4,5,5-tetramethyl-1,3,2-dioxaborolan-2-yl)pyrrolo[1,2-b]pyridazine-3-carbonitrile (4.4 g, 16.35 mmol, 1.5 eq). The mixture was stirred at 85° C. overnight. The reaction was filtered, concentrated in vacuo, dissolved in DCM and adsorbed onto silica gel. This solid was purified by flash chromatography (0 to 10% of ACN in DCM) to afford the desired compound as a yellow crystalline solid (2.9 g, 56% yield). LCMS: ESI(+)[M+H]$^+$=474.60. $^1$H NMR (300 MHz, DMSO-d$_6$), δ: 8.83 (d, J=2.2 Hz, 1H), 8.72 (d, J=2.2 Hz, 1H), 8.62 (d, J=6.0 Hz, 2H), 8.22-8.12 (m, 1H), 7.87 (d, J=4.8 Hz, 1H), 7.11 (d, J=4.8 Hz, 1H), 3.62 (s, 3H), 3.19 (s, 1H), 3.08 (d, J=4.9 Hz, 3H), 2.42 (d, J=11.7 Hz, 1H), 2.19 (d, J=10.3 Hz, 2H), 2.03 (d, J=10.7 Hz, 2H), 1.59 (q, J=12.3, 11.2 Hz, 4H).

Step 2: To a solution of methyl 4-[5-(6-{3-cyanopyrrolo[1,2-b]pyridazin-7-yl}-4-(methylamino)pyridin-3-yl)-1,3,4-thiadiazol-2-yl]cyclohexane-1-carboxylate (2.9 g, 6.12 mmol, 1 eq) in dry pyridine (61 ml, 0.1 M), lithium iodide (8.27 g, 61.18 mmol, 10 eq) was added and the resulting mixture was stirred at 150° C. for 24 hrs. The resulting mixture was acidified with an equimolar amount of dilute HCl. The obtained solid was filtered off and purified by flash chromatography (0 to 20% of 2-propanol in DCM) to afford the desired compound as a yellow solid (2.5 g, 89% yield). LCMS: ESI(+)[M+H]$^+$=460.23. $^1$H NMR (300 MHz, DMSO-d$_6$), δ: 12.17 (s, 1H), 9.59 (d, J=4.2 Hz, 1H), 8.99 (d, J=2.0 Hz, 1H), 8.86 (d, J=2.0 Hz, 1H), 8.69 (s, 1H), 8.15 (d, J=4.9 Hz, 1H), 7.95 (s, 1H), 7.24 (d, J=5.0 Hz, 1H), 3.32 (m, 1H), 3.22 (d, J=4.8 Hz, 3H), 2.40-2.28 (m, 1H), 2.21 (d, J=11.8 Hz, 2H), 2.04 (s, 2H), 1.72-1.46 (m, 4H).
Intermediate P: 7-[4-(methylamino)-5-{5-[(1r,4r)-4-(ethylamino)cyclohexyl]-1,3,4-thiadiazol-2-yl}pyridin-2-yl]pyrrolo[1,2-b]pyridazine-3-carbonitrile
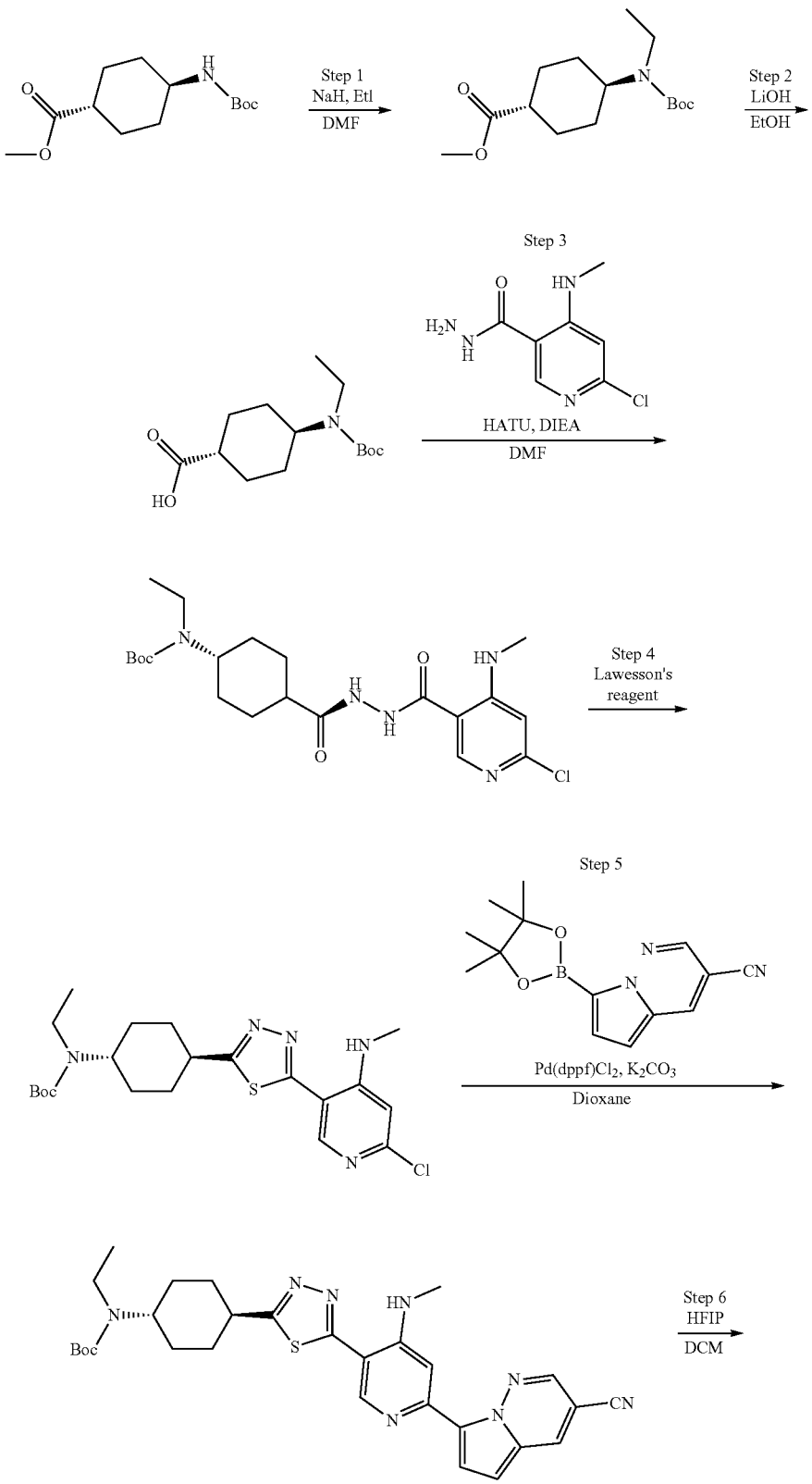

-continued

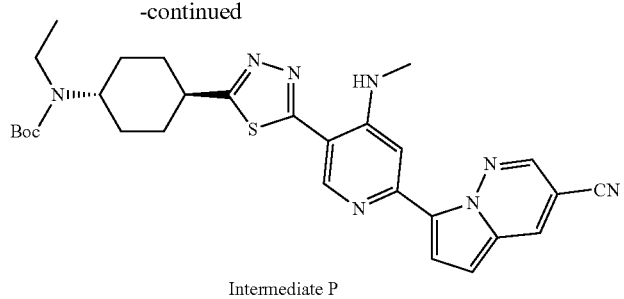

Intermediate P

Step 1: To a solution of methyl trans-4-(tert-butoxycarbonylamino)cyclohexane carboxylate (2.0 g, 7.8 mmol, 1.0 eq) in DMF (25 ml, 0.46 M) cooled down to 0° C. was added NaH (0.357 g, 9.32 mmol, 1.2 eq) and the resulting mixture was stirred at 0° C. for 30 min. After that ethyl iodide (0.937 ml, 11.66 mmol, 1.5 eq) was added, and the reaction mixture was stirred at room temperature overnight. DMF was then azeotropically removed by evaporation with PhMe (3×100 mL). 50 mL of sat aq solution of $NH_4Cl$ were added into the remaining solid. The resulting mixture was transferred into a separatory funnel and extracted with $Et_2O$ (4×50 mL). The combined organic layers were dried with $Na_2SO_4$ and concentrated in vacuo. The crude was purified by column chromatography (hexane/EtOAc, gradient 0% to 20%) to give methyl (1r,4r)-4-{[(tert-butoxy)carbonyl](ethyl)amino}cyclohexane-1-carboxylate as a yellowish, viscous oil (1.883 g, 85% yield). $^1H$ NMR (300 MHz, DMSO-$d_6$) δ 3.63 (s, 3H), 3.07 (q, J=7.1 Hz, 2H), 2.26 (t, J=11.9 Hz, 1H), 1.94 (d, J=12.5 Hz, 2H), 1.55 (d, J=27.9 Hz, 4H), 1.39 (d, J=1.7 Hz, 12H), 1.02 (t, J=6.8 Hz, 3H).

Step 2: To a solution of methyl (1r,4r)-4-{[(tert-butoxy)carbonyl](ethyl)amino}cyclohexane-1-carboxylate (1.88 g, 6.6 mmol, 1.0 eq) in mixture of THF (15 ml, 0.44 M) and water (3.0 mL, 2.41 M) was added LiOH*$H_2O$ (0.57 g, 13.2 mmol, 2.0 eq) and the reaction mixture was stirred at room temperature overnight. After NMR showed full substrate consumption, THF was then removed in vacuo and the obtained aqueous solution was acidified with 10% wt solution of $NaHSO_4$ to pH 5. The obtained suspension was then extracted with EtOAc (4×25 mL). The combined organic layers were dried over $Na_2SO_4$ and concentrated in vacuo to give (1r,4r)-4-{[(tert-butoxy)carbonyl](ethyl)amino}cyclohexane-1-carboxylic acid as a white solid (1.566 g, 87% yield). $^1H$ NMR (300 MHz, DMSO-$d_6$) δ 12.08 (s, 1H), 3.07 (d, J=7.3 Hz, 2H), 2.13 (tt, J=11.9, 3.4 Hz, 1H), 1.93 (dt, J=9.2, 2.8 Hz, 2H), 1.52 (dd, J=28.7, 16.5 Hz, 4H), 1.39 (s, 9H), 1.33 (dd, J=12.4, 3.8 Hz, 1H), 1.02 (t, J=6.8 Hz, 3H).

Step 3: To a solution of (1r,4r)-4-{[(tert-butoxy)carbonyl](ethyl)amino}cyclohexane-1-carboxylic acid (1.57 g, 5.77 mmol, 1.00 eq) in anh DMF (15 mL, 0.38 M) was added DIPEA (3.0 mL, 17.3 mmol, 3.00 eq) and HATU (3.29 g, 8.65 mmol, 1.5 eq). The mixture was stirred at 25° C. for 30 mins and 6-chloro-4-(methylamino)pyridine-3-carbohydrazide (1.216 g, 6.06 mmol, 1.05 eq) was added. After 2 hours at room temperature, the reaction was quenched with brine and extracted with EtOAc (5×50 mL). The combined organic layers were dried over $Na_2SO_4$ and concentrated in vacuo. The resulting crude was purified by column chromatography (DCM/MeOH, gradient 0 to 3%) to give the desired product as a light-brown solid (1.87 g, 71% yield). LCMS: ESI(+)[M+H]$^+$=454.4. $^1H$ NMR (300 MHz, DMSO-$d_6$) δ 10.31 (s, 1H), 9.82 (s, 1H), 8.35 (s, 1H), 8.12 (d, J=5.3 Hz, 1H), 6.67 (s, 1H), 3.13-3.06 (m, 2H), 2.83 (d, J=4.9 Hz, 3H), 2.23 (dd, J=14.7, 4.0 Hz, 1H), 1.85 (d, J=11.3 Hz, 2H), 1.69-1.46 (m, 5H), 1.41 (s, 9H), 1.04 (t, J=6.8 Hz, 3H).

Step 4: To a solution of tert-butyl N-ethyl-N-[(1r,4r)-4-{N'-[6-chloro-4-(methylamino) pyridine-3-carbonyl]hydrazinecarbonyl}cyclohexyl]carbamate (1.87 g, 4.11 mmol, 1.0 eq) in anhydrous THF (100 mL, 0.04 M) was added Lawesson's reagent (1.83 g, 4.52 mmol, 1.1 eq). The reaction mixture was stirred at 90° C. for 2 hrs. The volatiles were removed in vacuo, and the residue was dissolved in 50 mL DCM, washed with sat aq solution of $NaHCO_3$. The aqueous phase was extracted with DCM (3×50 mL). The organic layers were combined, dried over $Na_2SO_4$, and concentrated in vacuo. The crude was purified by double column chromatography (DCM/MeOH, gradient 0 to 4% and hexane/EtOAc, gradient 0 to 40%) to obtain tert-butyl N-ethyl-N-[(1r,4r)-4-{5-[6-chloro-4-(methylamino)pyridin-3-yl]-1,3,4-thiadiazol-2-yl}cyclohexyl] carbamate as a white foamy solid (0.794 g, 43% yield). LCMS: ESI(+)[M+H]$^+$=452.5. $^1H$ NMR (300 MHz, DMSO-$d_6$) δ 8.66 (d, J=5.9 Hz, 1H), 8.39 (d, J=1.6 Hz, 1H), 6.82 (d, J=1.7 Hz, 1H), 3.16 (t, J=12.0 Hz, 3H), 2.98 (d, J=4.9 Hz, 3H), 2.24-2.14 (m, 2H), 1.69 (d, J=20.3 Hz, 7H), 1.41 (d, J=2.0 Hz, 9H), 1.12-1.01 (m, 3H).

Step 5: The suspension of tert-butyl N-ethyl-N-[(1r,4r)-4-{5-[6-chloro-4-(methylamino) pyridin-3-yl]-1,3,4-thiadiazol-2-yl}cyclohexyl]carbamate (0.794 g, 1.76 mmol, 1.0 eq), 7-(4,4,5,5-tetramethyl-1,3,2-dioxaborolan-2-yl)pyrrolo[1,2-b]pyridazine-3-carbonitrile (0.662 g, 2.46 mmol, 1.4 eq), Pd(dppf)$Cl_2$·$CH_2Cl_2$ (0.36 g, 0.44 mmol, 0.25 eq), $K_2CO_3$ (0.485 g, 3.5 mmol, 2.0 eq) in anhydrous dioxane (25 mL, 0.07 M) was degassed with argon for 2-3 min and stirred at 120° C. overnight. After the full conversion of the starting material the reaction was diluted with MeOH, filtered through a pad of Celite and concentrated in vacuo. The crude was purified by FC (DCM/ACN, gradient 0 to 40%) to obtain tert-butyl N-ethyl-N-[(1r,4r)-4-[5-(6-{3-cyanopyrrolo[1,2-b]pyridazin-7-yl}-4-(methylamino)pyridin-3-yl)-1,3,4-thiadiazol-2-yl]cyclohexyl]carbamate as a yellow solid (0.676 g, 69% yield). LCMS: ESI(+)[M+H]$^+$= 559.85. $^1H$ NMR (300 MHz, DMSO-$d_6$) δ 8.85 (d, J=2.2 Hz, 1H), 8.74 (d, J=2.3 Hz, 1H), 8.67 (s, 1H), 8.63 (d, J=5.0 Hz, 1H), 8.19 (s, 1H), 7.88 (d, J=4.8 Hz, 1H), 7.13 (d, J=4.8 Hz, 1H), 3.26-3.12 (m, 3H), 3.09 (d, J=4.9 Hz, 3H), 2.21 (d, J=11.2 Hz, 2H), 1.83-1.57 (m, 6H), 1.42 (s, 9H), 1.12-1.02 (m, 3H).

Step 6: Tert-butyl N-ethyl-N-[(1r,4r)-4-[5-(6-{3-cyanopyrrolo[1,2-b]pyridazin-7-yl}-4-(methylamino)pyridin-3-yl)-1,3,4-thiadiazol-2-yl]cyclohexyl]carbamate (0.676 g, 1.21 mmol, 1.0 eq) was dissolved in 1,1,1,3,3,3-hexafluoro-2-propanol (3.185 mL, 25 eq) and stirred at 150° C. for 8 hours. After full consumption of the starting material the reaction mixture was coevaporated several times with DCM to remove the traces of HFIP. The crude was purified by column chromatography (DCM/MeOH, gradient 0 to 30%) to obtain the title compound as a dark-yellow solid (0.350 g, 63% yield). LCMS: ESI(+)[M+H]+=459.03. ¹H NMR (300 MHz, DMSO-d₆) δ 8.84 (s, 1H), 8.74 (s, 1H), 8.65 (s, 2H), 8.17 (d, J=3.1 Hz, 1H), 7.87 (d, J=4.8 Hz, 1H), 7.12 (d, J=4.7 Hz, 1H), 4.10 (s, 1H), 3.17 (s, 2H), 3.09 (d, J=4.7 Hz, 3H), 2.71-2.56 (m, 3H), 2.16 (d, J=12.8 Hz, 2H), 2.04 (t, J=11.7 Hz, 2H), 1.60 (q, J=12.4 Hz, 3H), 1.32-1.13 (m, 5H), 1.04 (t, J=6.8 Hz, 3H), 0.82-0.71 (m, 1H).

Intermediate Q: 7-[5-(5-{3,9-diazaspiro[5.5]undecan-3-yl}-1,3,4-thiadiazol-2-yl)-4-(oxan-4-ylamino)pyridin-2-yl]pyrrolo[1,2-b]pyridazine-3-carbonitrile Intermediate R: 7-[5-(5-{3,8-diazabicyclo[3.2.1]octan-3-yl}-1,3,4-thiadiazol-2-yl)-4-[(propan-2-yl)amino]pyridin-2-yl]pyrrolo[1,2-b]pyridazine-3-carbonitrile

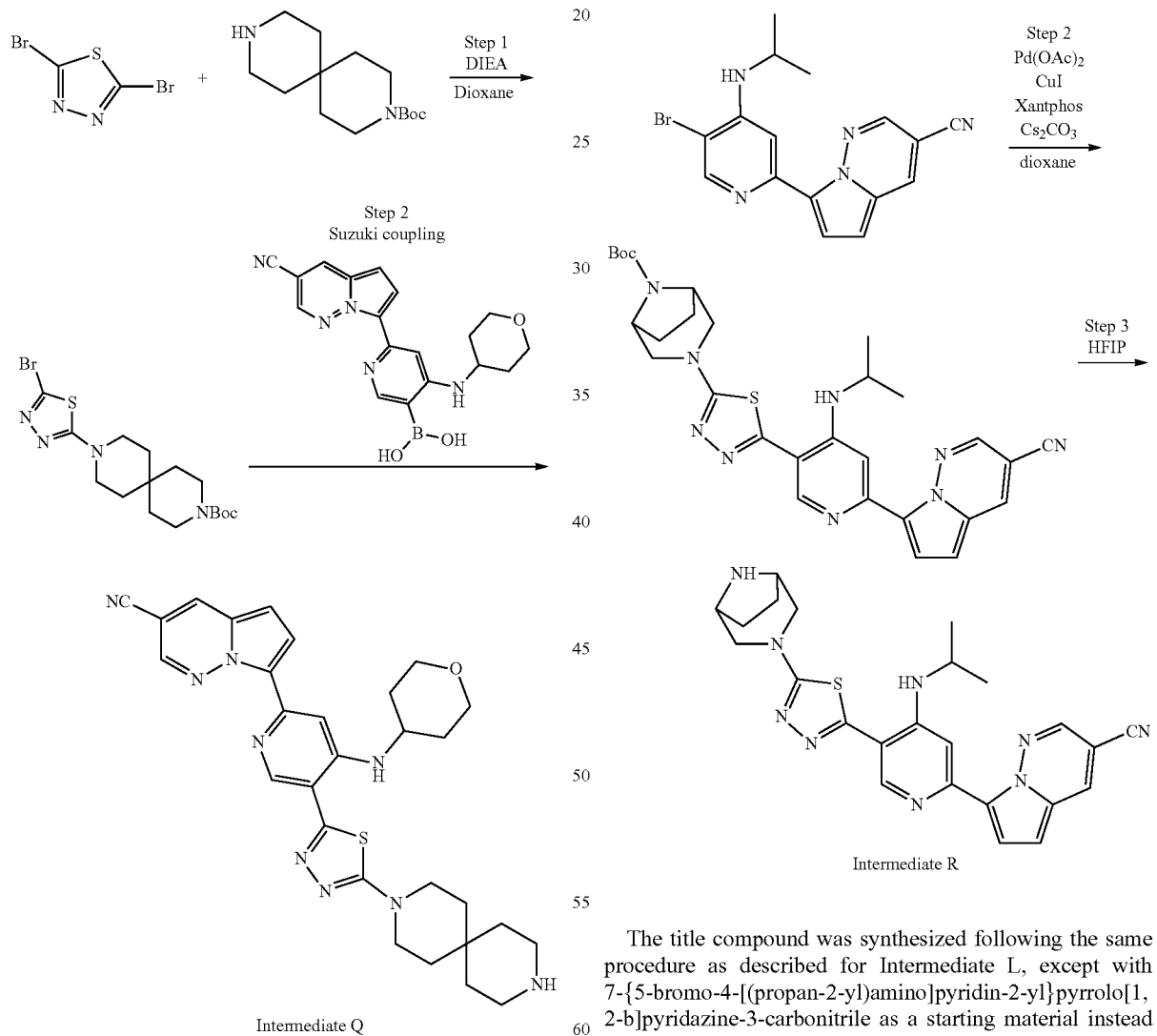

Intermediate Q

Intermediate R

Synthesized following same procedures as shown for Intermediate T, except with tert-butyl 3,9-diazaspiro[5.5]undecane-3-carboxylate starting material instead of tert-butyl 4,7-diazaspiro[2.5]octane-4-carboxylate. LCMS C₂₉H₃₃N₉OS requires: 555.3, found: m/z=556.3 [M+H]+.

The title compound was synthesized following the same procedure as described for Intermediate L, except with 7-{5-bromo-4-[(propan-2-yl)amino]pyridin-2-yl}pyrrolo[1,2-b]pyridazine-3-carbonitrile as a starting material instead of 7-[5-bromo-4-(methylamino)pyridin-2-yl]pyrrolo[1,2-b]pyridazine-3-carbonitrile. LCMS: ESI(+)[M+H]+=472.20. ¹H NMR (300 MHz, DMSO-d₆) δ: 8.82 (d, J=2.2 Hz, 1H), 8.71 (d, J=2.2 Hz, 1H), 8.56 (d, J=7.1 Hz, 1H), 8.46 (s, 1H), 8.18 (s, 1H), 7.83 (d, J=4.8 Hz, 1H), 7.11 (d, J=4.8 Hz, 1H), 3.91 (h, J=6.5 Hz, 1H), 3.60-3.44 (m, 4H), 3.32-3.24 (m, 3H), 1.69 (dd, J=10.0, 6.9 Hz, 4H), 1.34 (d, J=6.3 Hz, 6H).

Intermediate S: 7-(4-((4,4-difluorocyclohexyl)amino)-5-(5-(piperazin-1-yl)-1,3,4-thiadiazol-2-yl)pyridin-2-yl)pyrrolo[1,2-b]pyridazine-3-carbonitrile

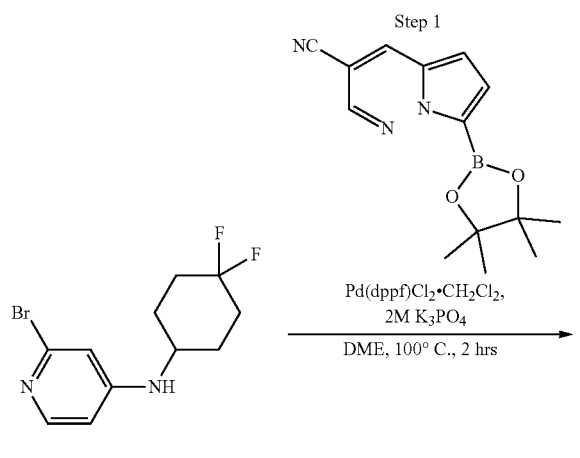

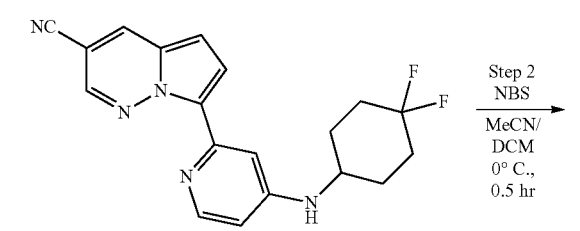

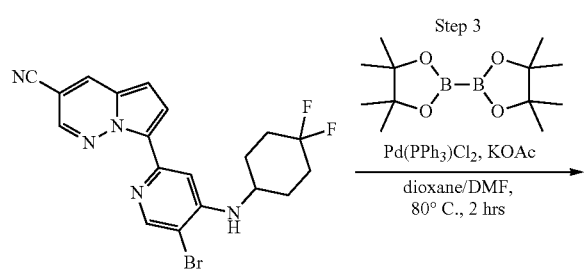

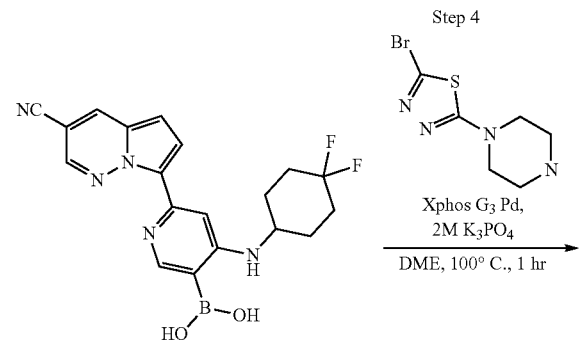

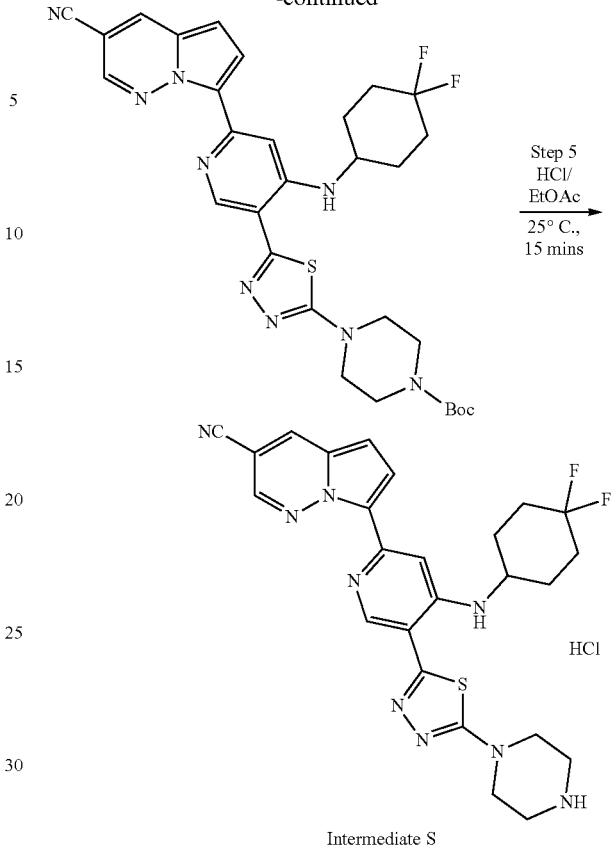

Intermediate S

Step 1: To a solution of 2-bromo-N-(4,4-difluorocyclohexyl)pyridin-4-amine (6.00 g, 20.6 mmol, 1.00 eq) and 7-(4,4,5,5-tetramethyl-1,3,2-dioxaborolan-2-yl)pyrrolo[1,2-b]pyridazine-3-carbonitrile (6.66 g, 24.7 mmol, 1.20 eq) in DME (60.0 mL) was added $K_3PO_4$ (2.00 M, 20.6 mL, 2.00 eq) and Pd(dppf)Cl$_2$·CH$_2$Cl$_2$ (1.68 g, 2.06 mmol, 0.10 eq) under N$_2$, the mixture was stirred at 100° C. for 2 hrs under N$_2$. The reaction mixture was poured into water (50.0 mL), then filtered and washed with ethyl acetate (100 mL*4), and collect the filter cake (4.0 g), concentrated under vacuum. The filtrate was extracted with ethyl acetate (100 mL*3), then concentrated under vacuum to give a residue (2.00 g). The residue (2.00 g) was purified by column chromatography (SiO$_2$, petroleum ether/ethyl acetate=1/1 to dichloromethane/Methanol=20/1, $R_f$=0.20). The product that was isolated by column chromatography was combined with the filtered product to yield the desired product (5.00 g, 14.1 mmol, 68.6% yield) as a yellow solid. LCMS: m/z=354.3 (M+H)+.

Step 2: To a solution of 7-(4-((4,4-difluorocyclohexyl)amino)pyridin-2-yl)pyrrolo[1,2-b]pyridazine-3-carbonitrile (5.50 g, 15.5 mmol, 1.00 eq) in MeCN (230 mL) and DCM (230 mL) was added a solution of NBS (2.49 g, 14.0 mmol, 0.90 eq) in MeCN (45.0 mL) and DCM (45.0 mL) at 0° C., the mixture was stirred at 0° C. for 0.5 hr. The reaction mixture was concentrated under vacuum. The crude product was triturated with ethyl acetate (20.0 mL) at 25° C. for 30 mins to give desired product (6.00 g, 13.8 mmol, 89.1% yield) as a yellow solid, which was confirmed by LCMS. LCMS: m/z=432.2 (M+H)+.

Step 3: To a solution of 7-(5-bromo-4-((4,4-difluorocyclohexyl)amino)pyridin-2-yl)pyrrolo[1,2-b]pyridazine-3- carbonitrile(480 mg, 1.11 mmol, 1.00 eq) and 4,4,4',4',5,5,5',5'-octamethyl-2,2'-bi(1,3,2-dioxaborolane) (563 mg, 2.22 mmol, 2.00 eq) in dioxane (10.0 mL) and DMF (5.00 mL) was added KOAc (326 mg, 3.33 mmol, 3.00 eq) and Pd(PPh$_3$)$_2$Cl$_2$ (116 mg, 166 μmol, 0.15 eq) under N$_2$, then the mixture was stirred at 80° C. for 2 hrs. The crude material was filtered, and the filtrate was concentrated under vacuum. The residue was purified by prep-HPLC (FA condition), then concentrated by lyophilization to yield the desired product (1.40 g, 2.87 mmol, 23.5% yield) as yellow solid. LCMS: m/z=398.2 (M+H)+.

Step 4: To a solution of (6-(3-cyanopyrrolo[1,2-b]pyridazin-7-yl)-4-((4,4-difluorocyclohexyl)amino)pyridin-3-yl)boronic acid (700 mg, 1.43 mmol, 1.00 eq, FA) and tert-butyl 4-(5-bromo-1,3,4-thiadiazol-2-yl)piperazine-1-carboxylate (525 mg, 1.51 mmol, 1.05 eq) in DME (15.0 mL) was added XPhos Pd G3 (121 mg, 143 μmol, 0.10 eq) and K$_3$PO$_4$ (2.00 M, 1.79 mL, 2.50 eq) under N$_2$. The mixture was stirred at 100° C. for 1 hr under N$_2$. The reaction was poured into water (20.0 mL), then filtered and washed by ethyl acetate (10.0 mL*4), the filtrate was extracted by ethyl acetate (20.0 mL*3), then concentrated under vacuum to give a residue. The residue confirmed by HPLC and purified by prep-HPLC was then concentrated by lyophilization to give desired product (600 mg, 965 μmol, 33.6% yield) as a yellow solid. LCMS: m/z=622.2 (M+H)+.

Step 5: To a solution of tert-butyl 4-(5-(6-(3-cyanopyrrolo[1,2-b]pyridazin-7-yl)-4-((4,4-difluorocyclohexyl)amino)pyridin-3-yl)-1,3,4-thiadiazol-2-yl)piperazine-1-carboxylate (600 mg, 965 μmol, 1.00 eq) in EtOAc (2.00 mL) was added HCl/EtOAc (4 M, 2.57 mL, 10.6 eq), then the mixture was stirred at 25° C. for 15 mins. The mixture was concentrated under vacuum. The crude product was triturated with ethyl acetate (1.00 mL) at 25° C. for 15 mins, then filtered and the filter cake was concentrated under vacuum to give 7-(4-((4,4-difluorocyclohexyl)amino)-5-(5-(piperazin-1-yl)-1,3,4-thiadiazol-2-yl)pyridin-2-yl)pyrrolo[1,2-b]pyridazine-3-carbonitrile (310 mg, 511 μmol, 52.9% yield, HCl) as a yellow solid, which was confirmed by LCMS. LCMS: m/z=522.1 (M+H)+. $^1$H NMR: 400 MHz, DMSO-d$_6$. δ 9.78 (d, J=7.2 Hz, 1H), 9.57 (s, 2H), 9.01 (d, J=2.0 Hz, 1H), 8.92 (d, J=2.0 Hz, 1H), 8.55 (s, 1H), 8.30 (d, J=5.2 Hz, 1H), 8.16 (s, 1H), 7.26 (d, J=4.8 Hz, 1H), 4.24-4.17 (m, 2H), 3.72-3.69 (m, 5H), 3.23 (s, 2H), 2.17-2.10 (m, 6H), 1.76-1.73 (m, 2H).

Intermediate T: 7-[5-(5-{4,7-diazaspiro[2.5]octan-7-yl}-1,3,4-thiadiazol-2-yl)-4-(isopropylamino)pyridin-2-yl]pyrrolo[1,2-b]pyridazine-3-carbonitrile

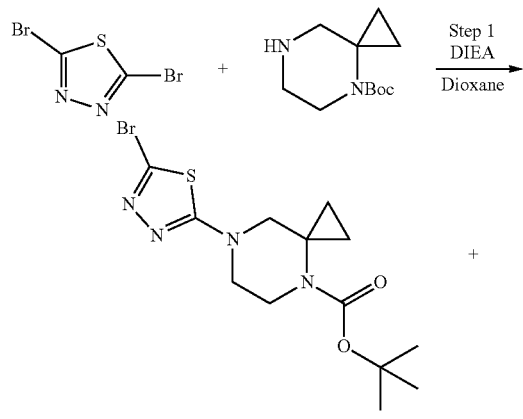

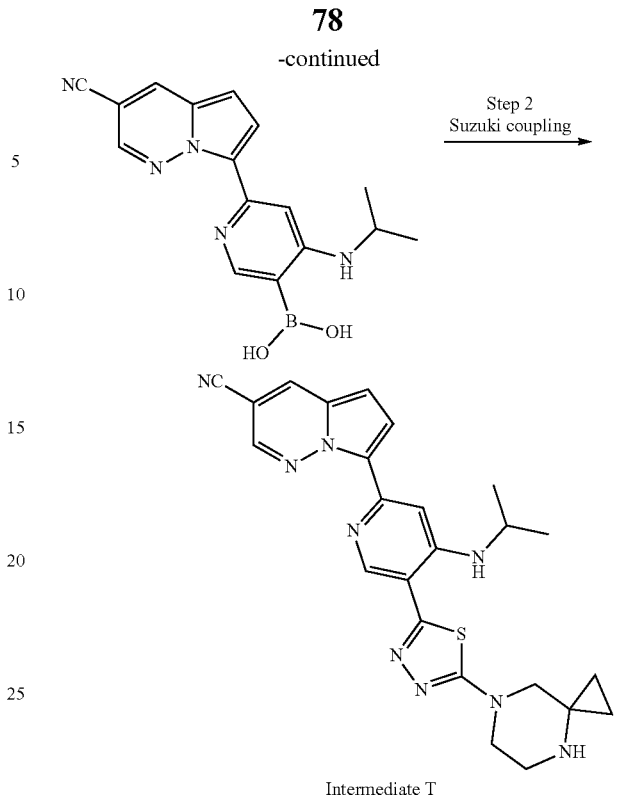

Intermediate T

Step 1: The dibromothiadiazole (500 mg, 2.05 mmol) and tert-butyl 4,7-diazaspiro[2.5]octane-4-carboxylate (435 mg, 1 eq) were dissolved in DIEA (0.6 mL, 1.75 eq) and dioxane (0.15M), followed by heating to 110° C. in a sealed vial. The reaction was stirred for 1.5 hr, followed by cooling and concentration onto silica gel. Silica gel column chromatography (0-5% methanol in DCM) provided the desired product (0.105 g, 14%). LCMS C$_{1-3}$H$_{19}$N$_4$BrO$_2$S requires: 374.0, found: m/z=320.9 [M-tert-butyl]+.

Step 2: 6-{3-cyanopyrrolo[1,2-b]pyridazin-7-yl}-4-(isopropylamino)pyridin-3-ylboronic acid (90 mg, 0.28 mmol), cesium carbonate (0.2 g, 2.2 eq), XantPhos (0.06 g, 0.4 eq), palladium acetate (13 mg, 0.2 eq), and tert-butyl 7-(5-bromo-1,3,4-thiadiazol-2-yl)-4,7-diazaspiro[2.5]octane-4-carboxylate (105 mg, 1 eq) were combined in a microwave vial, followed by addition of dioxane (8 mL). The reaction mixture was then purged with nitrogen for 1 min, and stirred at 145° C. for 30 min in the microwave reactor. The reaction was then filtered with celite and concentrated onto silica gel. Chromatography (0-10% methanol in DCM) provided desired intermediate. The material was dissolved in DCM:TFA (5:1 ratio of DCM to TFA, 0.1M), at room temperature and it was stirred for 3 hrs. The reaction was concentrated and purified by reverse phase chromatography on C18 column (0-100% ACN in water, 0.1% TFA) followed by overnight lyophilization to provide the desired product (28 mg, 21% yield).

LCMS C$_{24}$H$_{25}$N$_9$S requires: 471.2, found: m/z=472.3 [M+H]$^+$.

Intermediate U: [5-(5-{4-formylbicyclo[2.2.2]octan-1-yl}-1,3,4-thiadiazol-2-yl)-4-(methylamino)pyridin-2-yl]pyrrolo[1,2-b]pyridazine-3-carbonitrile

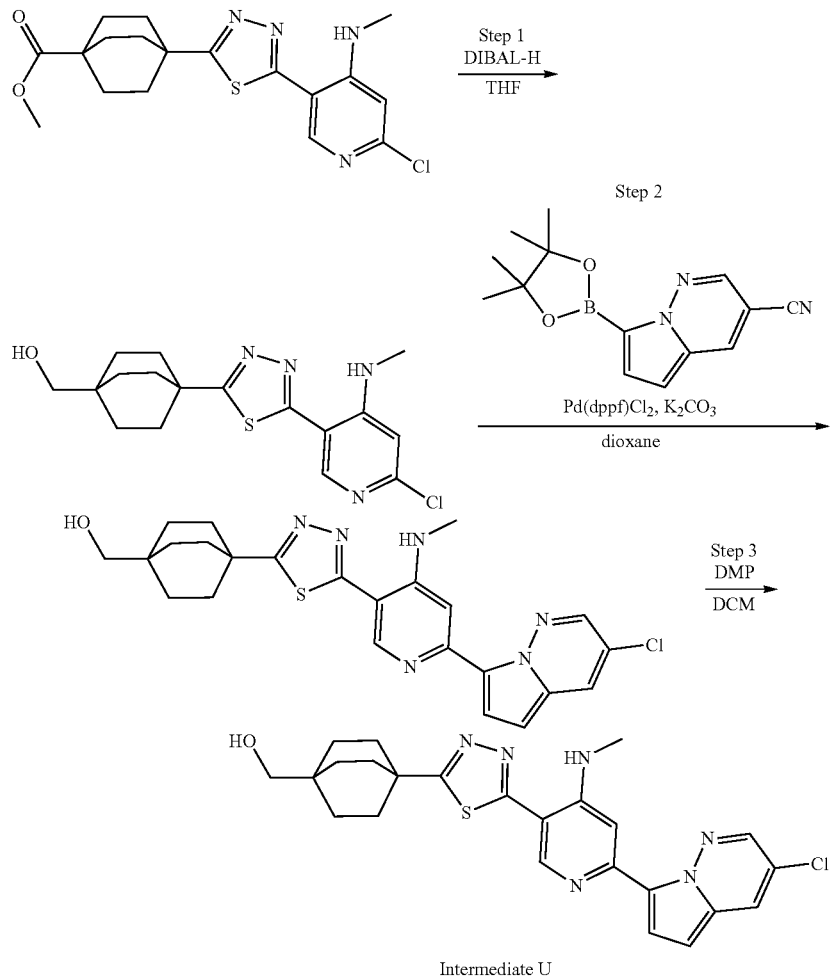

Intermediate U

Step 1: A solution of methyl 4-{5-[6-chloro-4-(methylamino)pyridin-3-yl]-1,3,4-thiadiazol-2-yl}bicyclo[2.2.2]octane-1-carboxylate (3.8 g, 9.67 mmol, 1 eq) in anhydrous THF (270 mL, 0.036 M) cooled to −15° C. under argon atmosphere and treated with DIBAL-H (29 mL, 1.0 M solution in THF, 29.02 mmol, 3 eq). After 30 min, the cooling bath was removed and the reaction warmed to rt and stirred for 1 hr. The mixture was then quenched by adding MeOH (30 mL) and stirred vigorously for 20 min followed by the addition of sat aq solution of Rochelle salt. The resulting mixture was extracted with DCM, and the combined organic layers were washed with sat. solution of NH$_4$Cl, dried over Na$_2$SO$_4$, concentrated under reduced pressure. The crude was purified by column chromatography (eluting with DCM/ACN) to afford 3.25 g of (4-{5-[6-chloro-4-(methylamino)pyridin-3-yl]-1,3,4-thiadiazol-2-yl}bicyclo[2.2.2]octan-1-yl)methanol (92% yield). LCMS: ESI(+)[M+H]$^+$=365.46. $^1$H NMR (300 MHz, DMSO-d$_6$) δ: 8.68 (q, J=5.2 Hz, 1H), 8.38 (s, 1H), 6.81 (s, 1H), 4.46 (t, J=5.4 Hz, 1H), 3.10 (d, J=5.0 Hz, 2H), 2.97 (d, J=4.9 Hz, 3H), 2.00-1.89 (m, 6H), 1.56-1.45 (m, 6H).

Step 2: To a solution of (4-{5-[6-chloro-4-(methylamino)pyridin-3-yl]-1,3,4-thiadiazol-2-yl}bicyclo[2.2.2]octan-1-yl)methanol (1.8 g, 4.93 mmol, 1.0 eq), 7-(4,4,5,5-tetramethyl-1,3,2-dioxaborolan-2-yl)pyrrolo[1,2-b]pyridazine-3-carbonitrile (1.59 g, 5.92 mmol, 1.2 eq) and Pd(dppf)Cl$_2$·CH$_2$Cl$_2$ (1.01 g, 1.23 mmol, 0.25 eq) in anh dioxane (125 mL, 0.04M), was added 2 M aq sol of K$_2$CO$_3$ (5 ml, 9.87 mmol, 2.0 eq). The reaction mixture was degassed with argon for 30 min and then stirred at 120° C. for 25 hrs. The reaction mixture was diluted with DCM, filtrated through a pad of Celite, washed with DCM/MeOH (1:1), and concentrated under reduced pressure. The crude was purified twice with column chromatography (DCM/Acetone and DCM/IPA) to afford 7-(5-{5-[4-(hydroxymethyl)bicyclo[2.2.2]octan-1-yl]-1,3,4-thiadiazol-2-yl}-4-(methylamino)pyridin-2-yl)pyrrolo[1,2-b]pyridazine-3-carbonitrile (1.46 g, 63% yield). LCMS: ESI(+)[M+H]$^+$=472.40. $^1$H NMR (300 MHz, DMSO-d$_6$) δ: 8.83 (d, J=2.2 Hz, 1H), 8.72 (d, J=2.3 Hz, 1H), 8.65 (br. q, J=4.9 Hz, 1H), 8.63 (s, 1H), 8.16 (s, 1H), 7.87 (d, J=4.8 Hz, 1H), 7.11 (d, J=4.8 Hz, 1H), 4.46 (t, J=5.4 Hz, 1H), 3.11 (d, J=5.4 Hz, 2H), 3.07 (d, J=4.8 Hz, 3H), 2.01-1.90 (m, 6H), 1.57-1.46 (m, 6H).

Step 3: To a solution of the 7-(5-{5-[4-(hydroxymethyl)bicyclo[2.2.2]octan-1-yl]-1,3,4-thiadiazol-2-yl}-4-(methylamino)pyridin-2-yl)pyrrolo[1,2-b]pyridazine-3-carbonitrile (1.46 g, 3.10 mmol, 1 eq) in DCM (900 mL, 3.44 mM) was added Dess-Martin periodinane (1.71 g, 4.02 mmol, 1.3 eq). The reaction mixture was stirred at RT for 2 h, then quenched with 20% aq Na₂S₂O₃ and sat aq NaHCO₃. The mixture was stirred until the aq layer became transparent. The aqueous layer was extracted with DCM. The combined organic layer was washed with sat. solution of NaHCO₃, water, and brine. The combined organic layers were dried over Na₂SO₄ and concentrated under reduced pressure. The resulting crude was triturated with Et₂O, filtrated, and the filtered solid was washed with a mixture of DCM/Et₂O (1:1), Et₂O, and pentane to afford the title compound (1.28 g, 88% yield). LCMS: ESI(+)[M+H]⁺=470.15. ¹H NMR (300 MHz, DMSO-d₆) δ: 9.49 (s, 1H), 8.85 (d, J=2.2 Hz, 1H), 8.75 (d, J=2.2 Hz, 1H), 8.67 (s, 1H), 8.64 (q, J=5.1 Hz, 1H), 8.19 (s, 1H), 7.88 (d, J=4.8 Hz, 1H), 7.13 (d, J=4.8 Hz, 1H), 3.09 (d, J=4.9 Hz, 3H), 2.09-1.98 (m, 6H), 1.82-1.71 (m, 6H).

Intermediate V: 7-[4-(methylamino)-5-{5-[4-(piperidin-4-yl)piperazin-1-yl]-1,3,4-thiadiazol-2-yl}pyridin-2-yl]pyrrolo[1,2-b]pyridazine-3-carbonitrile Synthesized following same procedures as shown for Intermediate T, except with tert-butyl 4-piperazin-1-ylpiperidine-1-carboxylate as a starting material instead of tert-butyl 4,7-diazaspiro[2.5]octane-4-carboxylate. LCMS C₂₅H₂₈N₁₀S requires: 500.2, found: m/z=501.5 [M+H]⁺.

Intermediate W: 7-{4-[(3-methyloxetan-3-yl)amino]-5-[5-(piperazin-1-yl)-1,3,4-thiadiazol-2-yl]pyridin-2-yl}pyrrolo[1,2-b]pyridazine-3-carbonitrile

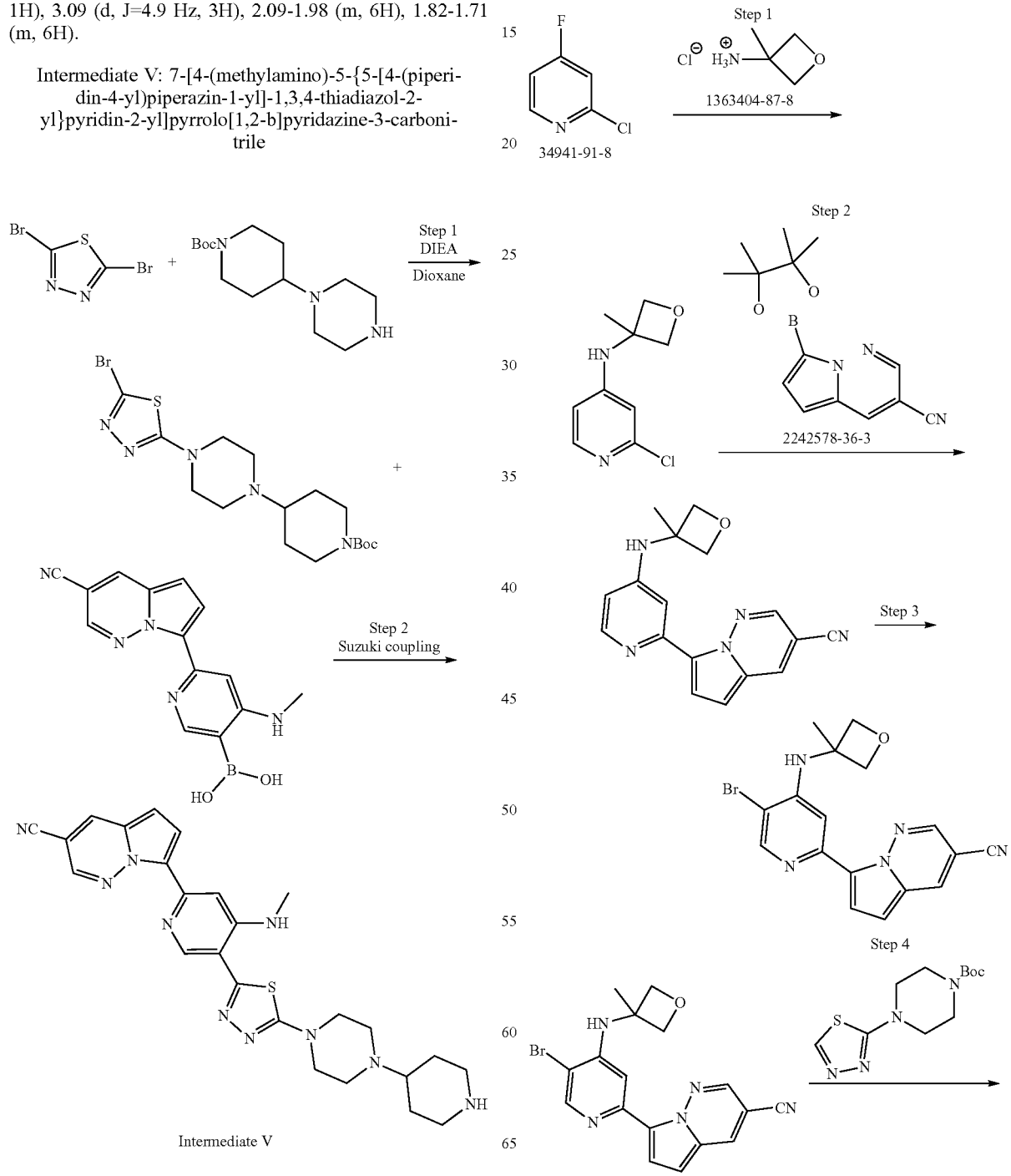

-continued

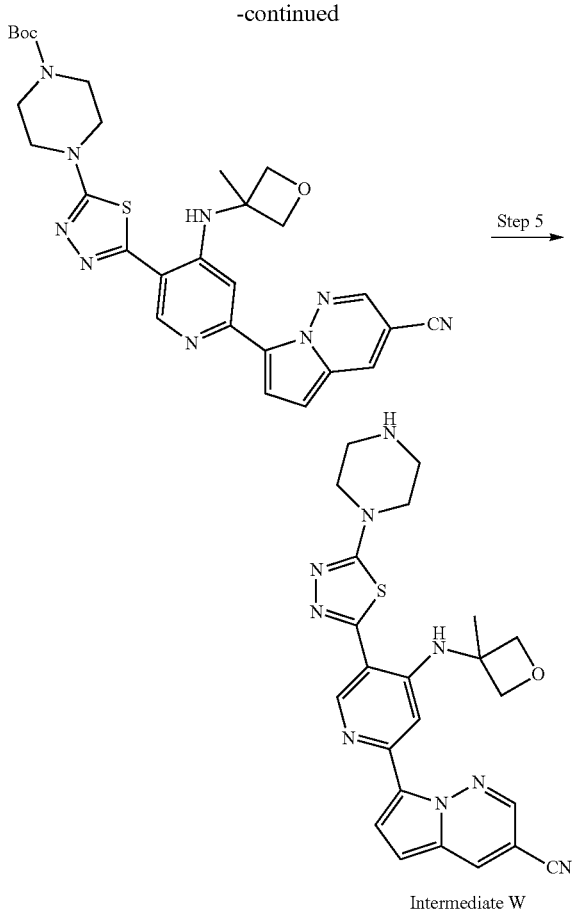

Intermediate W

Step 1: DIPEA (17.96 ml, 138.98 mmol, 3.5 eq) was added to a stirred solution of 3-Methyl-3-oxetanamine-HCl (4.9 g, 39.7 mmol, 1 eq) in DMF (39.7 ml, 1 M). Then, 2-chloro-4-Fluoropyridine (7.4 mL, 79.4 mmol, 2 eq) was added and the mixture was heated to 100° C. in a sealed tube for 32 h. The excess of reagents and DMF were removed by evaporation on rotavap. The residue (16.25 g) was diluted with DCM and brought to pH=8 by sat aq $NaHCO_3$. The layers were separated and the organic layer was extracted 4 times with DCM. The combined organic layers were washed with brine, dried with $Na_2SO_4$, and concentrated on rotavap. The crude was purified by FC (hexane/ethyl acetate) to give 5.17 g (54% yield) of 2-chloro-N-(3-methyloxetan-3-yl)pyridin-4-amine. [M+H]$^+$=199.50 m/z. $^1$H NMR (300 MHz, DMSO-d$_6$) δ 7.86 (d, J=5.8 Hz, 1H), 7.41 (s, 1H), 6.36-6.25 (m, 2H), 4.60 (d, J=6.1 Hz, 2H), 4.51 (d, J=6.2 Hz, 2H), 1.56 (s, 3H).

Step 2: To a solution of 2-chloro-N-(3-methyloxetan-3-yl)pyridin-4-amine (5.904 g, 24.668 mmol, 1.0 eq) in dimethoxyethane (123.33 ml, 0.2 M) in a 400 ml glass reactor was added 7-(4,4,5,5-tetramethyl-1,3,2-dioxaborolan-2-yl)pyrrolo[1,2-b]pyridazine-3-carbonitrile (9.293 g, 34.532 mmol, 1.4 eq) and potassium phosphate tribasic (10.686 g, 49.335 mmol, 2.0 eq). Mixture was degassed by evacuation of the reactor and backfilling it with argon (three times). Xphos Pd G3 (1.491 g, 1.726 mmol, 0.07 eq) was added and the evacuation-backfilling procedure was repeated three times. Reactor was sealed and the mixture was stirred at 120° C. overnight. Mixture was diluted with DCM and concentrated. Residue was purified via silica gel FC (DCM/ EA 100:0 to 0:100) to provide 4.83 g (55% yield) of 7-{4-[(3-methyloxetan-3-yl)amino]pyridin-2-yl}pyrrolo[1,2-b]pyridazine-3-carbonitrile as a yellow solid. [M+H]= 306.46 m/z. $^1$H NMR (300 MHz, DMSO-d6) δ 8.80 (d, J=2.2 Hz, 1H), 8.68 (d, J=2.2 Hz, 1H), 8.19 (d, J=5.7 Hz, 1H), 7.81-7.71 (m, 2H), 7.28 (s, 1H), 7.09 (d, J=4.8 Hz, 1H), 6.29 (dd, J=5.7, 2.3 Hz, 1H), 4.69 (d, J=6.0 Hz, 2H), 4.55 (d, J=6.0 Hz, 2H), 1.64 (s, 3H).

Step 3: To a solution of 7-{4-[(3-methyloxetan-3-yl)amino]pyridin-2-yl}pyrrolo[1,2-b]pyridazine-3-carbonitrile (3.944 g, 11.625 mmol, 1.0 eq) in acetonitrile anhydrous (136.78 ml, 0.085 M) and dimethylformamide anhydrous (35.23 ml, 0.33 M) at 0° C. was added a solution of N-bromo succinimide (1.966 g, 11.046 mmol, 0.95 eq) in anhydrous acetonitrile (14.53 ml, 0.8 M) in one go. Mixture was stirred at 0° C. for 45 minutes. Formed precipitate was filtered off and dried to obtain 7-{5-bromo-4-[(3-methyloxetan-3-yl)amino]pyridin-2-yl}pyrrolo[1,2-b]pyridazine-3-carbonitrile (2.1 g, 5.465 mmol, 47%). Filtrate was concentrated and purified by FC (silica gel, DCM to DCM/EA 7:3) to afford additional 1.57 g (35% yield) of 7-{5-bromo-4-[(3-methyl-oxetan-3-yl)amino]pyridin-2-yl}pyrrolo[1,2-b]pyridazine-3-carbonitrile. [M+H]$^+$=386.26 m/z. $^1$H NMR (300 MHz, DMSO-d6) δ 8.82 (d, J=2.2 Hz, 1H), 8.80 (d, J=2.2 Hz, 1H), 8.43 (s, 1H), 7.79 (d, J=4.8 Hz, 1H), 7.64 (s, 1H), 7.09 (d, J=4.8 Hz, 1H), 6.78 (s, 1H), 4.79 (d, J=6.3 Hz, 2H), 4.58 (d, J=6.4 Hz, 2H), 1.71 (s, 3H).

Step 4: To a solution of 7-{5-bromo-4-[(3-methyloxetan-3-yl)amino]pyridin-2-yl}pyrrolo[1,2-b]pyridazine-3-carbonitrile (3.65 g, 9.499 mmol, 1.0 eq) in dioxane anhydrous (279.39 ml, 0.034 M) in a glass pressure reactor was added tert-butyl 4-(1,3,4-thiadiazol-2-yl)piperazine-1-carboxylate (2.594 g, 9.499 mmol, 1.0 eq). Reactor was evacuated and backfilled with argon three times. Palladium (II) acetate (0.213 g, 0.949 mmol, 0.1 eq), 4,5-bis(diphenylphosphino)-9,9-dimethylxanthene (1.099 g, 1.899 mmol, 0.2 eq), cesium carbonate (12.38 g, 37.997 mmol, 4.0 eq) and copper (I) iodide (0.362 g, 1.901 mmol, 0.2 eq) were added and the reactor was sealed. Mixture was stirred at 105° C. for 3 hours. UPLC indicated partial conversion of SM. Palladium (II) acetate (0.107 g, 0.477 mmol, 0.05 eq), 4,5-bis(diphenyl phosphino)-9,9-dimethylxanthene (0.55 g, 0.951 mmol, 0.1 eq), cesium carbonate (6.19 g, 18.998 mmol, 2.0 eq) and copper (I) iodide (0.181 g, 0.95 mmol, 0.1 eq) were added and the reactor was evacuated and backfilled with argon three times. Reactor was resealed and the mixture was stirred at 105° C. overnight. Additional portions of palladium (II) acetate (0.107 g, 0.477 mmol, 0.05 eq), 4,5-bis (diphenylphosphino)-9,9-dimethylxanthene (0.55 g, 0.951 mmol, 0.1 eq), cesium carbonate (6.19 g, 18.998 mmol, 2.0 eq) and copper (I) iodide (0.181 g, 0.95 mmol, 0.1 eq) were added and after evacuation and backfilling with argon and sealing the mixture was stirred at 105° C. for 4 hours. Mixture was filtered through a pad of celite, washing with ethyl acetate. Filtrate was concentrated and the residue was purified by FC (silica gel, DCM to DCM/ethyl acetate 1:1) to provide 1.11 g (20% yield) of the titled compound. Two additional impure fractions (F2—0.97 g and F4—0.73 g) were repurified by FC (silica, DCM to DCM/ethyl acetate 1:1), combined and repurified again (silica, DCM to DCM/ ACN 6:4) to provide additional 0.31 g (6% yield) of tert-butyl 4-[5-(6-{3-cyanopyrrolo[1,2-b]pyridazin-7-yl}-4-[(3-methyloxetan-3-yl)amino]pyridin-3-yl)-1,3,4-thiadiazol-2-yl]piperazine-1-carboxylate. [M+H]$^+$=573.92 m/z. $^1$H NMR (300 MHz, DMSO-d6) δ 8.92 (s, 1H), 8.84 (t, J=1.8 Hz, 2H), 8.55 (s, 1H), 7.89-7.84 (m, 2H), 7.12 (d, J=4.8 Hz, 1H), 4.78 (d, J=6.4 Hz, 2H), 4.71 (d, J=6.2 Hz, 2H), 3.54 (q, J=5.5 Hz, 8H), 1.79 (s, 3H), 1.44 (s, 9H).

Step 5: To a solution of tert-butyl 4-[5-(6-{3-cyanopyrrolo[1,2-b]pyridazin-7-yl}-4-[(3-methyloxetan-3-yl)amino]pyridin-3-yl)-1,3,4-thiadiazol-2-yl]piperazine-1-carboxylate (1.134 g, 1.917 mmol, 1.0 eq) in dichloromethane anhydrous (35.2 ml, 32.0 vol) was added trifluoroacetic acid (1.477 ml, 19.171 mmol, 9.998 eq). The mixture was stirred at r.t. for 90 minutes. UPLC indicated no conversion. Trifluoroacetic acid (0.739 ml, 9.592 mmol, 5.003 eq) was added and stirring was continued for 90 minutes. UPLC indicated full conversion. The mixture was concentrated and evaporated with DCM three times. The residue was triturated with diethyl ether (150 ml). The resulting solid (TFA salt) was purified by RP FC (C18 silica, water to water/ACN 1:1, with 0.1% FA) to provide 0.545 g (59% yield) of 7-{4-[(3-methyloxetan-3-yl)amino]-5-[5-(piperazin-1-yl)-1,3,4-thiadiazol-2-yl]pyridin-2-yl}pyrrolo[1,2-b]pyridazine-3-carbonitrile as a TFA salt. LCMS: ESI(+) [M+H]$^+$= 474.32. $^1$H NMR (300 MHz, DMSO-d6) δ 8.92 (s, 3H), 8.86 (q, J=2.2 Hz, 2H), 8.58 (s, 1H), 7.87 (d, J=4.9 Hz, 2H), 7.13 (d, J=4.8 Hz, 1H), 4.78 (d, J=6.3 Hz, 2H), 4.73 (d, J=6.2 Hz, 2H), 3.83-3.72 (m, 4H), 3.32 (s, 4H), 1.79 (s, 3H).

Intermediate X: 7-{4-[(cyanomethyl)amino]-5-[5-(piperazin-1-yl)-1,3,4-thiadiazol-2-yl]pyridin-2-yl}pyrrolo[1,2-b]pyridazine-3-carbonitrile; trifluoroacetate

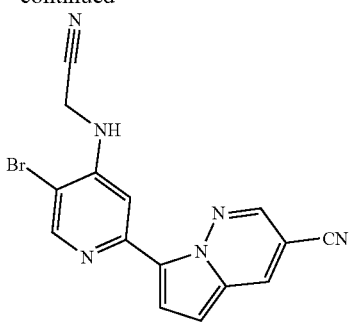

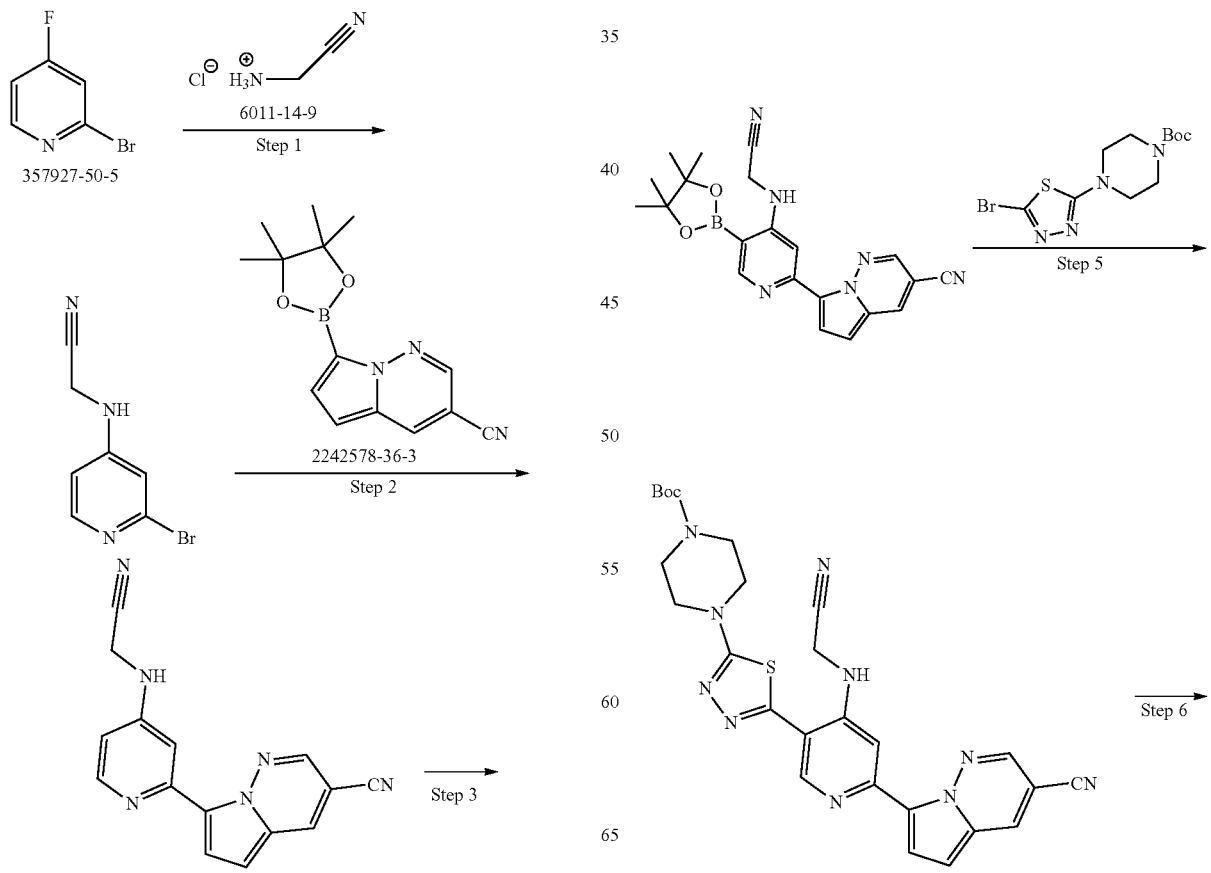

-continued

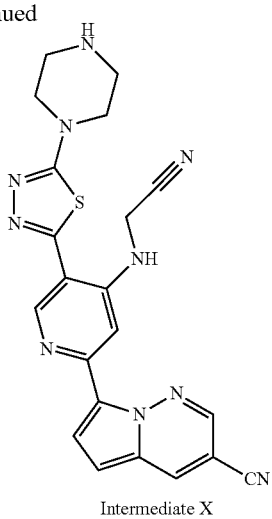

Intermediate X

Step 1: DIPEA (23.4 ml, 133.6 mmol, 3 eq) was added to stirred solution of 2-bromo-4-fluoropyridine (7.84 g, 44.55 mmol, 1 eq) in NMP (63 ml, 0.71 M). Aminoacetonitrile-HCl (6.31 g, 66.82 mmol, 1.5 eq) was added portion-wise and the mixture was heated to 120° C. in a pressure vial. After 12 h, an additional portion of aminoacetonitrile-HCl (3 g, 31.77 mmol, 0.7 eq) and DIPEA (16 ml, 91.35 mmol, 2 eq) were added. The reaction was stirred at 120° C. for 12 h. The reaction was diluted with water and extracted with EA. EA washed with water, brine, and dried over $Na_2SO_4$. Crude purified with FC hexane/EA (0 to 95%) to provide 6.0 g (64% yield) of 7-(4,4,5,5-tetramethyl-1,3,2-dioxaborolan-2-yl)pyrrolo[1,2-b]pyridazine-3-carbonitrile. $[M+H]^+$= 214.1 m/z. $^1$H NMR (300 MHz, DMSO-d6) 7.94 (1H, d, J=5.7 Hz), 7.43 (1H, t, J=6.4 Hz), 6.88 (1H, d, J=2.2 Hz), 6.70 (1H, dd, J=5.7, 2.2 Hz), 4.41 (2H, d, J=6.4 Hz).

Step 2: To a solution of 2-[(2-bromopyridin-4-yl)amino] acetonitrile (6.5 g, 30.65 mmol, 1.0 eq), 7-(4,4,5,5-tetramethyl-1,3,2-dioxaborolan-2-yl)pyrrolo[1,2-b]pyridazine-3-carbonitrile (11.55 g, 42.91 mmol, 1.4 eq) and Xphos Pd G3 (1.3 g, 1.53 mmol, 0.05 eq) in and DME (153 ml, 0.2 M), was added 2M aq. $K_3PO_4$ (31 ml, 61.31 mmol, 2.0 eq). The solution was degassed with argon for 2-3 min and then heated to 120° C. for 5 h. UPLC showed full conversion of the starting material. The resulting solution was diluted with DCM and concentrated to dryness. The crude was purified by FC eluted by EA:DCM (0 to 85%) to give 4.29 g (47% yield) of 7-{4-[(cyanomethyl)amino]pyridin-2-yl}pyrrolo[1,2-b]pyridazine-3-carbonitrile. [M+H]=275.38 m/z. $^1$H NMR (300 MHz, DMSO-d6) 8.82 (1H, d, J=2.2 Hz), 8.65 (1H, d, J=2.3 Hz), 8.36 (1H, d, J=5.6 Hz), 8.03 (1H, d, J=2.3 Hz), 7.79 (1H, d, J=4.7 Hz), 7.40 (1H, t, J=6.4 Hz), 7.10 (1H, d, J=4.8 Hz), 6.69 (1H, dd, J=5.7, 2.4 Hz), 4.42 (2H, d, J=6.3 Hz).

Step 3: 7-{4-[(cyanomethyl)amino]pyridin-2-yl}pyrrolo [1,2-b]pyridazine-3-carbonitrile (4.81 g, 17.54 mmol, 1 eq) was dissolved in ACN/DCM/DMF (10:5:1) mixture (1.5 L, 0.011 M) and N-bromosuccinimide (2.81 g, 15.78 mmol, 0.9 eq) was added by one portion at RT. The reaction was stirred at RT for 30 min. After completion, the mixture was evaporated and crude was purified with FC eluted by DCM/EtOAc to provide 2.0 g (35% yield) of 7-{5-bromo-4-[(cyanomethyl)amino]pyridin-2-yl}pyrrolo[1,2-b]pyridazine-3-carbonitrile. $[M+H]^+$=355.18 m/z. $^1$H NMR (300 MHz, DMSO-d6) 8.84 (1H, d, J=2.3 Hz), 8.64 (1H, d, J=2.2 Hz), 8.52 (1H, s), 8.14 (1H, s), 7.79 (1H, d, J=4.8 Hz), 7.12 (1H, d, J=4.8 Hz), 7.00 (1H, t, J=6.2 Hz), 4.47 (2H, d, J=6.2 Hz).

Step 4: 7-{5-bromo-4-[(cyanomethyl)amino]pyridin-2-yl}pyrrolo[1,2-b]pyridazine-3-carbonitrile (1.04 g, 2.83 mmol 1.0 eq) was dissolved in dioxane (30 ml, 0.1 M) and DMF (10 mL, 0.3 M) in a pressure vial followed by addition of bis(pinacolato)diboron (1.44 g, 5.66 mmol, 2.0 eq) and KOAc (0.86 g, 8.789 mmol, 3.1 eq). The solution was degassed for a few minutes with argon and $Pd(PPh_3)_2Cl_2$ (0.2 g, 0.283 mmol, 0.1 eq) was added followed by repeated degassing. The reaction mixture was stirred at 80° C. for 24 h. UPLC showed full conversion. The reaction mixture was diluted with EtOAc and washed with $H_2O$, brine, and dried over $Na_2SO_4$. The crude was triturated with hexane to remove excess of bis(pinacolato)diboron, filtrated off, dried, and used in the next step without additional purification.

Step 5: To a solution of 7-{4-[(cyanomethyl)amino]-5-(4,4,5,5-tetramethyl-1,3,2-dioxaborolan-2-yl)pyridin-2-yl}pyrrolo[1,2-b]pyridazine-3-carbonitrile (3.17 g, 7.93 mmol, 1.0 eq) in anh. dioxane (140 mL, 0.06 M) in a glass reactor was added tert-butyl 4-(5-bromo-1,3,4-thiadiazol-2-yl)piperazine-1-carboxylate (2.77 g, 7.93 mmol, 1.0 eq). The reactor was evacuated and backfilled with argon three times. Tri-tert-butylphosphonium tetrafluoroborate (0.23 g, 0.793 mmol, 0.1 eq), tris(dibenzylideneacetone)dipalladium(0) (0.363 g, 0.397 mmol, 0.05 eq) and cesium fluoride (3.61 g, 23.79 mmol, 3.0 eq) were added. Evacuation-backfilling was repeated three times, reactor was sealed, and the mixture was stirred at 70° C. for 12 hours. An additional amount of tri-tert-butylphosphonium tetrafluoroborate (0.23 g, 0.793 mmol, 0.1 eq), tris(dibenzylideneacetone)dipalladium(0) (0.363 g, 0.397 mmol, 0.05 eq) and cesium fluoride (3.61 g, 23.79 mmol, 3.0 eq) were added. Evacuation-backfilling was repeated three times, reactor was sealed, and the mixture was stirred at 70° C. for 12 hours. The mixture was cooled to r.t., diluted with DCM (200 ml) and filtered. Residue was purified twice by FC (DCM/i-PrOH and DCM/acetone) to provide 0.108 g (3% yield) of tert-butyl 4-(5-{4-[(cyanomethyl)amino]-6-{3-cyanopyrrolo[1,2-b]pyridazin-7-yl}pyridin-3-yl}-1,3,4-thiadiazol-2-yl)piperazine-1-carboxylate. $[M+H]^+$=543.65 m/z. $^1$H NMR (300 MHz, DMSO-d6) δ 8.91-8.83 (2H, m), 8.68 (1H, d, J=2.3 Hz), 8.61 (1H, s), 8.30 (1H, s), 7.88 (1H, d, J=4.8 Hz), 7.15 (1H, d, J=4.9 Hz), 4.70 (2H, d, J=6.1 Hz), 3.64-3.48 (9H, m), 1.44 (9H, s).

Step 6: To a solution of tert-butyl 4-(5-{4-[(cyanomethyl)amino]-6-{3-cyanopyrrolo[1,2-b]pyridazin-7-yl}pyridin-3-yl}-1,3,4-thiadiazol-2-yl)piperazine-1-carboxylate (108 mg, 0.199 mmol, 1.0 eq) in dichloromethane anhydrous (5 ml, 0.4 M) was added trifluoroacetic acid (5 ml, 65.68 mmol, 330 eq). The mixture was stirred at r.t. for 3 hours. The mixture was concentrated and co-evaporated with DCM three times. The residue was triturated with diethyl ether, filtrated, and washed with diethyl ether. The resulting solid was purified by RP FC (C18 silica, ACN/$H_2O$ with 0.1% FA) to provide 66.5 mg (58% yield) of 7-{4-[(cyanomethyl) amino]-5-[5-(piperazin-1-yl)-1,3,4-thiadiazol-2-yl]pyridin-2-yl}pyrrolo[1,2-b]pyridazine-3-carbonitrile; trifluoroacetate as a yellow solid (N—51). LCMS: ESI(+) $[M+H]^+$= 443.21. $^1$H NMR (300 MHz, DMSO-$d_6$) δ 9.08 (2H, br. s), 8.87 (1H, d, J=2.3 Hz), 8.83 (1H, t, J=6.2 Hz, overlaped), 8.68 (1H, d, J=2.2 Hz), 8.62 (1H, s), 8.30 (1H, s), 7.88 (1H, d, J=4.8 Hz), 7.15 (1H, d, J=4.8 Hz), 4.71 (2H, d, J=6.1 Hz), 3.86-3.68 (4H, m), 3.35-3.27 (4H, m).

Intermediate Y: 7-{4-[(oxetan-3-yl)amino]-5-[5-(piperazin-1-yl)-1,3,4-thiadiazol-2-yl]pyridin-2-yl}pyrrolo[1,2-b]pyridazine-3-carbonitrile

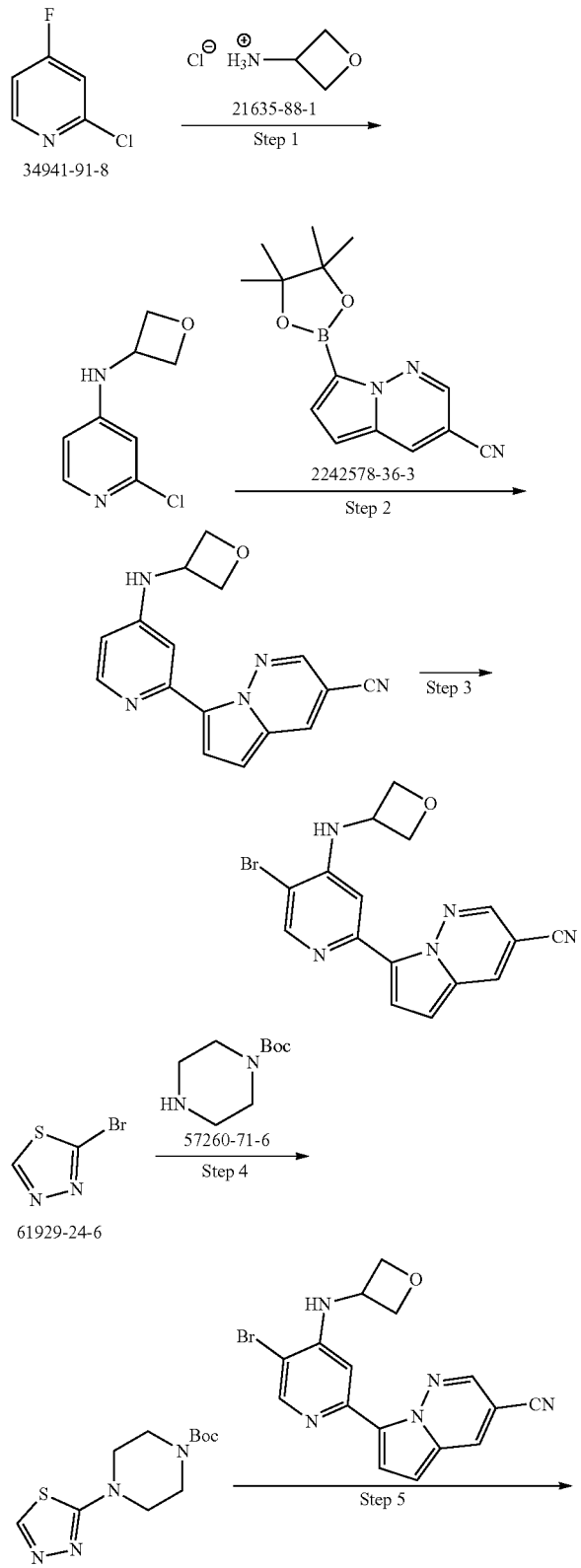

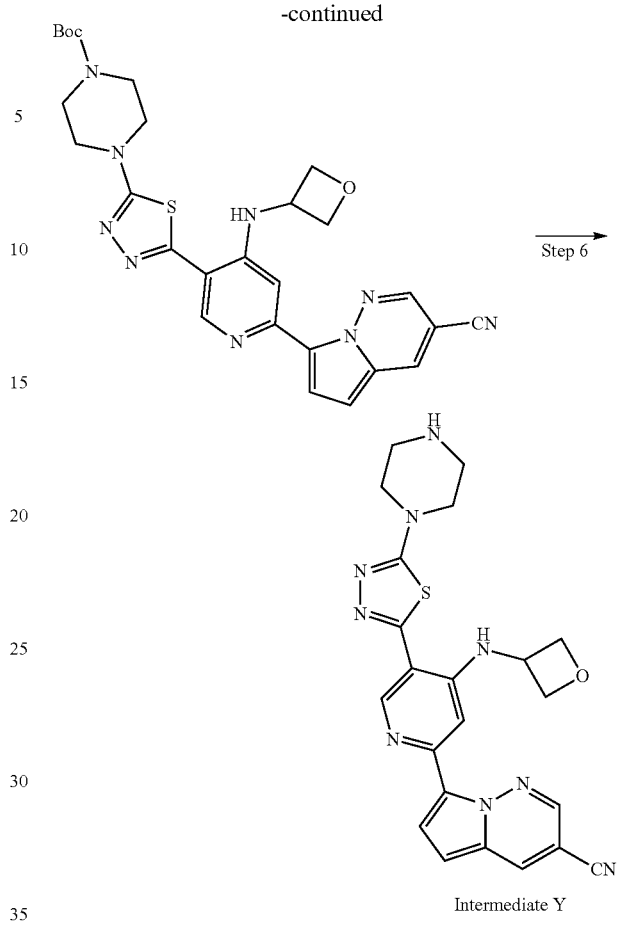

Intermediate Y

Step 1: DIPEA (27 ml, 156 mmol, 3.5 eq) was added to a cooled, stirred solution of Oxetan-3-amine-HCl (4.89 mg, 44.6 mmol, 1 eq) in DMF (45 ml, 1 M). Then, 2-chloro-4-fluoropyridine (8.3 ml, 90 mmol, 2 eq) was added and the mixture was heated to 90° C. in a sealed tube. At completion, the solvents were removed under reduced pressure. The residue was partitioned between EtOAc and water. The organic extract was washed with brine, dried with $Na_2SO_4$, filtrated, and evaporated under reduced pressure. The residue was purified by FC (Acetone/DCM 10 to 50%) gave 2-chloro-N—(oxetan-3-yl)pyridin-4-amine (3.2 g, 38% yield). LCMS: ESI(+)[M+H]$^+$=185.10. $^1$H NMR (300 MHz, DMSO-$d_6$) 7.85 (d, J=5.8 Hz, 1H), 7.63 (d, J=6.3 Hz, 1H), 6.55-6.33 (m, 2H), 4.85 (t, J=6.6 Hz, 2H), 4.65 (dt, J=12.8, 6.3 Hz, 1H), 4.41 (t, J=6.1 Hz, 2H).

Step 2: To a solution of 2-chloro-N—(oxetan-3-yl)pyridin-4-amine (2.59 g, 13.9 mmol, 1.0 eq) in DME (200 ml, 0.07 M) $K_3PO_4$ (6.09 g, 27.8 mmol, 2 eq) was added. The solution was degassed with argon for 20 min, then 7-(4,4,5,5-tetramethyl-1,3,2-dioxaborolan-2-yl)pyrrolo[1,2-b]pyridazine-3-carbonitrile (5.24 g, 19.5 mmol, 1.4 eq) and XPhos Pd G3 (841 mg, 0.97 mmol, 0.07 eq) were added. The pressure vessel was sealed and heated to 120° C. overnight. The reaction was filtrated on a pad of Celite. The latter was washed with DCM and MeOH. The mother liquor was evaporated under reduced pressure and the residue was purified by FC (5 to 50% of ACN in DCM) to give 7-{4-[(oxetan-3-yl)amino]pyridin-2-yl}pyrrolo[1,2-b]pyridazine-3-carbonitrile (1.9 g, 46% yield). LCMS: ESI(+)[M+H]$^+$=292.37. $^1$H NMR (300 MHz, DMSO-$d_6$) δ 8.80 (d, J=2.2 Hz, 1H), 8.67 (d, J=2.2 Hz, 1H), 8.21 (d, J=5.7 Hz, 1H), 7.85 (d, J=2.1 Hz, 1H), 7.76 (d, J=4.8 Hz, 1H), 7.52 (d, J=5.9 Hz, 1H), 7.08 (d, J=4.8 Hz, 1H), 6.40 (dd, J=5.7, 2.3 Hz, 1H), 4.89 (t, J=6.5 Hz, 2H), 4.68 (dt, J=12.6, 6.1 Hz, 1H), 4.50 (t, J=6.1 Hz, 2H).

Step 3: A solution of 7-{4-[(oxetan-3-yl)amino]pyridin-2-yl}pyrrolo[1,2-b]pyridazine-3-carbonitrile (1.9 g, 6.52 mmol, 1 eq) in a 4:1 mixture of ACN/DMF (75 ml, 0.086 M) was cooled down to 0° C. N-Bromosuccinimide (1.1 g, 6.2 mmol, 0.95 eq) was dissolved in ACN (5 ml) and added at once. The solution was stirred at 0° C. until completion (4 min) and monitored by TLC (AcOEt/Hex 1:1). A precipitate was formed. The precipitate was collected by filtration and the solid was dried extensively to get rid of the residual DMF and ACN to afford 2-bromo-1,3,4-thiadiazole (1.35 g, 56% yield). LCMS: ESI(+)[M+H]$^+$=370.20. $^1$H NMR (300 MHz, DMSO-d$_6$) δ 8.82 (d, J=2.2 Hz, 1H), 8.79 (d, J=2.2 Hz, 1H), 8.45 (s, 1H), 7.78 (d, J=4.8 Hz, 1H), 7.75 (s, 1H), 7.09 (d, J=4.8 Hz, 1H), 6.87 (d, J=3.1 Hz, 1H), 4.94 (d, J=3.2 Hz, 2H), 4.76-4.66 (m, 3H).

Step 4: To a solution of 2-bromo-1,3,4-thiadiazole (5 g, 30.3 mmol, 1.0 eq) and tert-butyl piperazine-1-carboxylate (14.4 g, 75.75 mmol, 2.5 eq) in n-butanol (63 mL, 0.48 M) was added DIPEA (22 mL, 121.2 mmol, 4.0 eq). The reaction mixture was heated in an oil bath at 120° C. for 1 hour. The reaction mixture was cooled, concentrated in vacuo to provide the crude product. It was diluted with 50 mL of AcOEt and 100 mL of H$_2$O and extracted with AcOEt (5×50 mL). The combined organic layers were dried with Na$_2$SO$_4$ and evaporated in vacuo to give the crude product a deep red crystalline solid. The compound was purified with FC (Hex/AcOEt 0 to 100%) to give 7-{5-bromo-4-[(oxetan-3-yl)amino]pyridin-2-yl}pyrrolo[1,2-b]pyridazine-3-carbonitrile (5.73 g, 69% yield). LCMS: ESI(+)[M+H]$^+$=271.20, $^1$H NMR (300 MHz, DMSO-d$_6$) δ: 8.85 (s, 1H), 3.47 (s, 8H), 1.43 (s, 9H).

Step 5: A suspension of 7-{5-bromo-4-[(oxetan-3-yl)amino]pyridin-2-yl}pyrrolo[1,2-b]pyridazine-3-carbonitrile (1.3 g, 3.51 mmol, 1 eq), tert-butyl 4-(1,3,4-thiadiazol-2-yl)piperazine-1-carboxylate (1.05 mg, 3.86 mmol, 1.1 eq), CuI (134 mg, 0.7 mmol, 0.2 eq), Xantphos (406 mg, 0.7 mmol, 0.2 eq) and Cs$_2$CO$_3$ (4.58 mg, 14 mmol, 4.0 eq) in anh. Dioxane (104 mL, 0.03 M) was degassed with argon for 15 min and Pd(OAc)$_2$ (80 mg, 0.35 mmol, 0.1 eq) was added. The pressure vessel was sealed and heated at 105° C. overnight. The reaction mixture was filtered through Celite, which was washed with AcOEt and the solvents were evaporated in vacuo. The crude was purified by FC (320 g column with 20 g silica dry loading, ACN/DCM gradient 0 to 100% in 25 CV). The residue was triturated with Et$_2$O (sonication for 15 min) and filtered to give 4-[5-(6-{3-cyanopyrrolo[1,2-b]pyridazin-7-yl}-4-[(oxetan-3-yl)amino]pyridin-3-yl)-1,3,4-thiadiazol-2-yl]piperazine-1-carboxylate (692 mg, 35% yield).LCMS: ESI(+)[M+H]$^+$=560.58. $^1$H NMR (300 MHz, DMSO-d$_6$) δ 8.94 (d, J=4.8 Hz, 1H), 8.85 (d, J=2.3 Hz, 1H), 8.82 (d, J=2.2 Hz, 1H), 8.56 (s, 1H), 7.91 (s, 1H), 7.86 (d, J=4.9 Hz, 1H), 7.12 (d, J=4.9 Hz, 1H), 5.07 (t, J=6.6 Hz, 2H), 4.88 (dd, J=11.4, 5.9 Hz, 1H), 4.59 (t, J=6.2 Hz, 2H), 3.55 (d, J=5.6 Hz, 7H), 3.47 (s, 5H), 1.44 (s, 7H), 1.43 (s, 6H).

Step 6: A solution of tert-butyl 4-[5-(6-{3-cyanopyrrolo[1,2-b]pyridazin-7-yl}-4-[(oxetan-3-yl)amino]pyridin-3-yl)-1,3,4-thiadiazol-2-yl]piperazine-1-carboxylate (692 mg, 1.24 mmol, 1.0 eq) in HFIP (4.0 mL) was heated in a microwave reactor at 140° C. for 1 h. The reaction mixture was purified by prep-HPLC affording the title compound (64 mg, 18% yield). LCMS: ESI(+)[M+H]+=459.96. $^1$H NMR (300 MHz, DMSO-d$_6$) δ 8.94 (d, J=4.6 Hz, 1H), 8.84 (d, J=2.3 Hz, 1H), 8.81 (d, J=2.2 Hz, 1H), 8.55 (s, 1H), 7.90 (s, 1H), 7.85 (d, J=4.8 Hz, 1H), 7.12 (d, J=4.9 Hz, 1H), 5.06 (t, J=6.7 Hz, 2H), 4.93-4.82 (m, 1H), 4.59 (t, J=6.2 Hz, 2H), 3.56-3.48 (m, 4H), 2.98-2.83 (m, 4H).

Intermediate Z: 7-[4-(cyclopropylamino)-5-[5-(piperazin-1-yl)-1,3,4-thiadiazol-2-yl]pyridin-2-yl]pyrrolo[1,2-b]pyridazine-3-carbonitrile

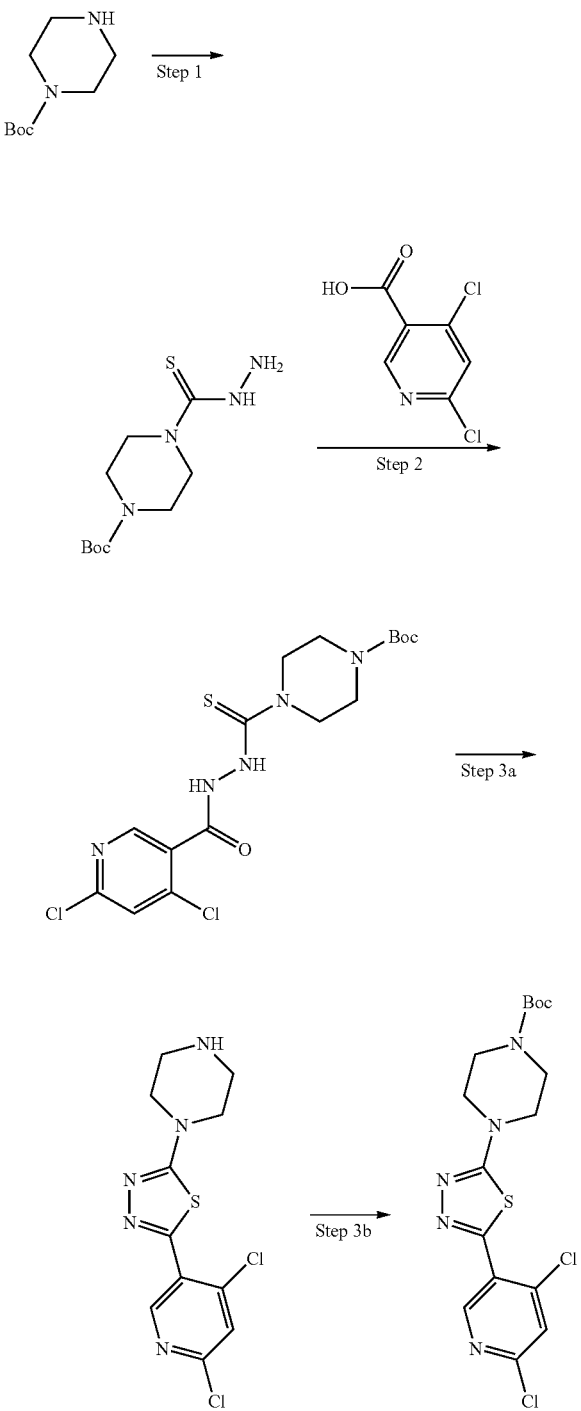

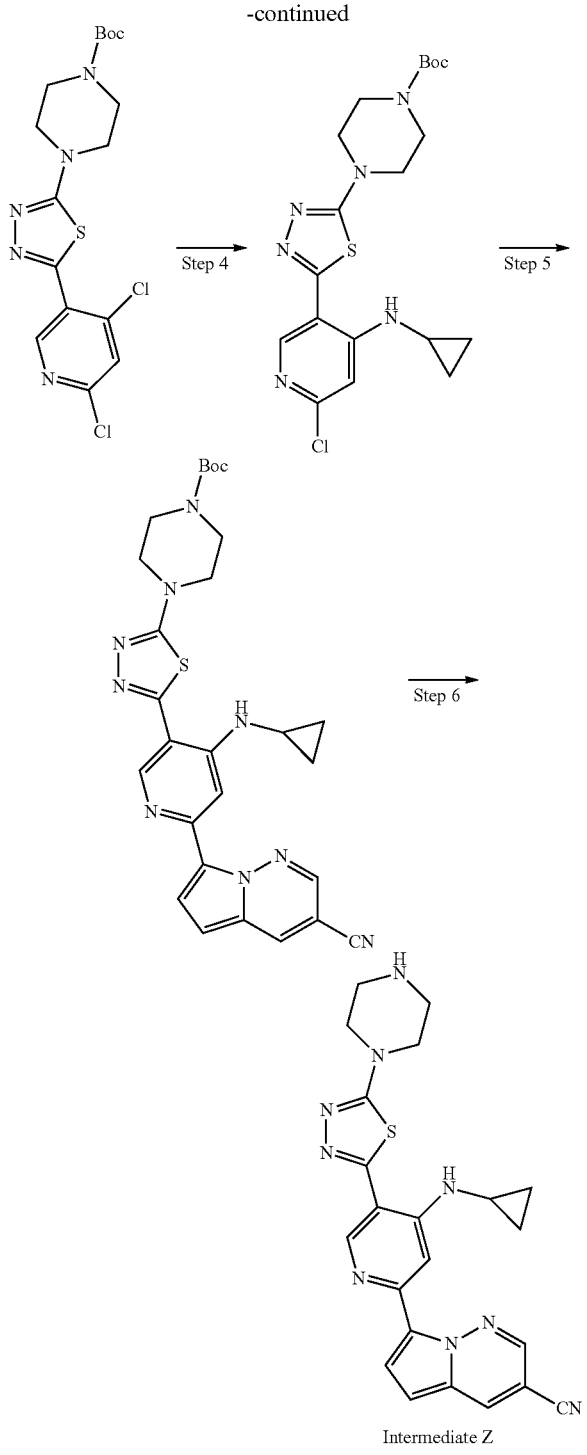

Intermediate Z

Step 1: To a stirred solution of tert-butyl piperazine-1-carboxylate (8 g, 42.9 mmol, 1.0 eq) in anhydrous THF (150 ml, 0.3 M) were added TEA (19 ml, 129 mmol, 3.0 eq) and 1,1'-thiocarbonyldiimidazole (11.5 g, 51.54 mmol, 1.2 eq) and the reaction mixture was stirred at rt for 2 h. Then, the solution was transferred dropwise to a solution of Hydrazine monohydrate (9.6 ml, 129 mmol, 3 eq) in THF (50 ml). Completion of the reaction was monitored by TLC. The reaction mixture was diluted with water (500 mL) and the aqueous layer was extracted with EtOAc (2×500 mL). The combined organic layers were washed with brine (500 mL), dried over $Na_2SO_4$, and concentrated under reduced pressure. The residue was recrystallized from AcOEt/Hex (1:2) to give tert-butyl 4-(amino carbamothioyl)piperazine-1-carboxylate (10.09 g, 89% yield). ESI(−)[M−H]+=259.38. $^1$H NMR (300 MHz, DMSO-d6) δ 9.13 (s, 1H), 4.76 (s, 2H), 3.79-3.62 (m, 4H), 3.42-3.25 (m, 4H), 1.41 (s, 9H).

Step 2: To a solution of starting 4,6-dichloronicotinic acid (5.645 g, 29.11 mmol, 1.1 eq) in dry DCM (90 ml, 0.3 M) under argon was added $Et_3N$ (4.4 ml, 1.2 eq) and the solution was cooled down to −15° C. Isobutyl-chloroformate (3.85 ml, 1.1 eq) was added dropwise maintaining the temperature at −15° C. The solution was, then, kept at −15° C. for 1 hour. Then, tert-butyl 4-(amino carbamothioyl)piperazine-1-carboxylate (6.89 g, 26.2 mmol, 1.0 eq) was added by portion and the reaction was stirred at rt overnight. At completion, the solution was treated with $NaHCO_3$ and extracted with DCM (3×50 ml). The combined organic layers were dried with $Na_2SO_4$, filtered, and evaporated to dryness. The crude residue was triturated with $Et_2O$ and filtered to afford tert-butyl 4-{[(4,6-dichloropyridin-3-yl)formohydrazido] methanethioyl} piperazine-1-carboxylate (8.2 g, 70% yield). ESI(−)[M−H]+=434.00. $^1$H NMR (300 MHz, DMSO-$d_6$) δ 10.68 (s, 1H), 9.94 (s, 1H), 8.71 (s, 1H), 7.97 (s, 1H), 3.99-3.80 (m, 4H), 3.47-3.37 (m, 4H), 1.42 (s, 9H).

Step 3a: A solution of tert-butyl 4-{[(4,6-dichloropyridin-3-yl)formohydrazido]methanethioyl}piperazine-1-carboxylate (4.211 g, 9.21 mmol, 1.0 eq) in sulfuric acid (31 ml, 552.6 mmol, 60 eq) was stirred overnight at rt. The reaction was poured into ice (~200 ml) while stirring vigorously. Then $K_2CO_3$ was carefully added portionwise until pH>9. $K_2SO_4$ was filtered off and washed with DCM several times. The product was extracted from the aqueous phase by DCM (3×200 ml). The combined organic layers were dried over $Na_2SO_4$, filtrated, and evaporated under reduced pressure to give 1-[5-(4,6-dichloropyridin-3-yl)-1,3,4-thiadiazol-2-yl] piperazine (2.276 g, 77% yield). ESI(+)[M+H]+=316.28. $^1$H NMR (300 MHz, DMSO-$d_6$) δ 8.94 (s, 1H), 8.02 (s, 1H), 3.50-3.45 (m, 4H), 2.87-2.78 (m, 4H).

Step 3b: To a solution of 1-[5-(4,6-dichloropyridin-3-yl)-1,3,4-thiadiazol-2-yl]piperazine (2.276 g, 7.2 mmol, 1.0 eq) in DCM (14 ml, 0.5 M) was added TEA (1.2 ml, 8.6 mmol, 1.2 eq) and the reaction was stirred for 5 min and $Boc_2O$ (1.9 g, 8.6 mmol, 1.2 eq) was added. The reaction mixture was stirred at rt for 1 h. At completion, the solution was evaporated to dryness under reduced pressure. The crude solid was suspended in hexane and filtered to give tert-butyl 4-[5-(4,6-dichloropyridin-3-yl)-1,3,4-thiadiazol-2-yl]piperazine-1-carboxylate (2.8 g, 93% yield).

ESI(+)[M+H]+=360.34. $^1$H NMR (300 MHz, DMSO-$d_6$) δ 8.94 (s, 1H), 8.04 (s, 1H), 3.63-3.46 (m, 8H), 1.43 (s, 9H).

Step 4: To a solution of tert-butyl 4-[5-(4,6-dichloropyridin-3-yl)-1,3,4-thiadiazol-2-yl]piperazine-1-carboxylate (1.4 g, 3.4 mmol, 1.0 eq) in a 1:3 mixture of t-Butanol/THF (45 ml, 0.075 M) was added cyclopropylamine (2.4 ml, 33.6 mmol, 10 eq) and the reaction mixture was heated to 90° C. for 24 h. At completion, the solution was evaporated under reduced pressure, diluted with water (100 ml), and extracted with DCM (20 ml×3). The organic phases were combined, dried with $Na_2SO_4$, filtrated, and concentrated under reduced pressure to give tert-butyl 4-{5-[6-chloro-4-(cyclopropylamino)pyridin-3-yl]-1,3,4-thiadiazol-2-yl}piperazine-1-carboxylate (1.33 g, 81%). ESI(+)[M+H]+=437.70. $^1$H NMR (300 MHz, DMSO-$d_6$) δ 8.73 (s, 1H), 8.23 (s, 1H), 7.05 (s, 1H), 3.52 (s, 8H), 2.73-2.59 (m, 1H), 1.43 (s, 9H), 0.90 (q, J=6.6 Hz, 2H), 0.57 (p, J=4.8 Hz, 2H).

Step 5: To a solution of tert-butyl 4-{5-[6-chloro-4-(cyclopropylamino)pyridin-3-yl]-1,3,4-thiadiazol-2- yl}piperazine-1-carboxylate (1.33 g, 3 mmol, 1.0 eq) in DME (40 ml, 0.07 M) was added $K_3PO_4$ (1.332 g, 6 mmol, 2.0 eq) and the mixture was degassed with argon for 10 min. 7-(4,4,5,5-tetramethyl-1,3,2-dioxaborolan-2-yl)pyrrolo[1,2-b]pyridazine-3-carbonitrile (1.147 g, 4.262 mmol, 1.4 eq) and XPhos Pd G3 (0.184 g, 0.213 mmol, 0.07 eq) were added and the pressure vessel was sealed. The mixture was stirred at 120° C. overnight. The solvent was evaporated under reduced pressure. The crude was purified by FC (0 to 10% of i-PrOH/DCM in 25 CV) to give tert-butyl 4-[5-(6-{3-cyanopyrrolo[1,2-b]pyridazin-7-yl}-4-(cyclopropylamino) pyridin-3-yl)-1,3,4-thiadiazol-2-yl]piperazine-1-carboxylate (120 mg, 20% yield). ESI(+)[M+H]$^+$=544.48. $^1$H NMR (300 MHz, DMSO-$d_6$) δ 9.36 (s, 2H), 9.12 (s, 1H), 8.92 (s, 1H), 8.84 (s, 1H), 8.60 (s, 1H), 8.52 (s, 1H), 8.05 (s, 1H), 7.19 (s, 1H), 3.80 (s, 4H), 3.30 (s, 4H), 2.83 (s, 1H), 1.41 (s, 9H), 1.06 (s, 2H), 0.70 (s, 2H).

Step 6: A solution of tert-butyl 4-[5-(6-{3-cyanopyrrolo[1,2-b]pyridazin-7-yl}-4-(cyclopropylamino)pyridin-3-yl)-1,3,4-thiadiazol-2-yl]piperazine-1-carboxylate (120 mg, 0.22 mmol, 1.0 eq) in DCM (1 ml, 0.3 M) was cooled down to 0° C. Then, TFA (0.17 ml, 2.2 mmol, 10 eq) was added dropwise and the mixture was stirred at rt for 3 h. At completion, the mixture was evaporated to dryness. The crude was suspended in $Et_2O$ and sonicated for 30 min. The suspension was filtrated to provide 95 mg (45% yield) of the title compound (TFA salt) as a yellow solid. LCMS: ESI(+)[M+H]$^+$=444.48. H NMR (300 MHz, DMSO-$d_6$) δ 9.36 (s, 2H), 9.12 (s, 1H), 8.92 (s, 1H), 8.84 (s, 1H), 8.60 (s, 1H), 8.52 (s, 1H), 8.05 (s, 1H), 7.19 (s, 1H), 3.80 (s, 4H), 3.30 (s, 4H), 2.83 (s, 1H), 1.06 (s, 2H), 0.70 (s, 2H).

Intermediate AA: 7-[4-(ethylamino)-5-[5-(piperazin-1-yl)-1,3,4-thiadiazol-2-yl]pyridin-2-yl]pyrrolo[1,2-b]pyridazine-3-carbonitrile

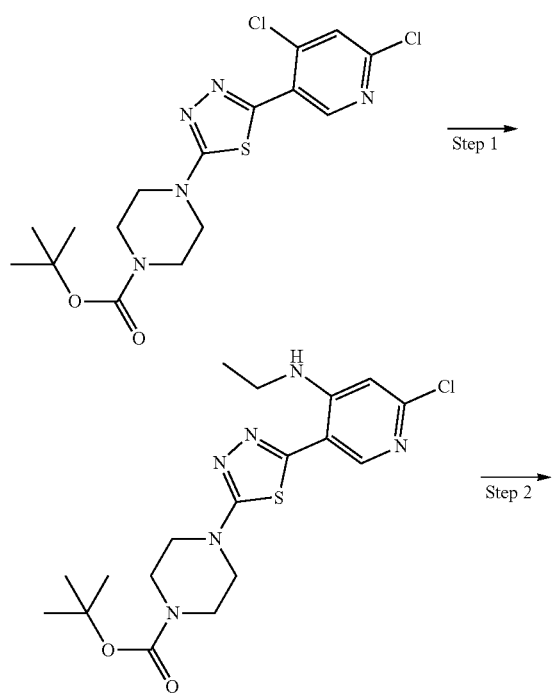

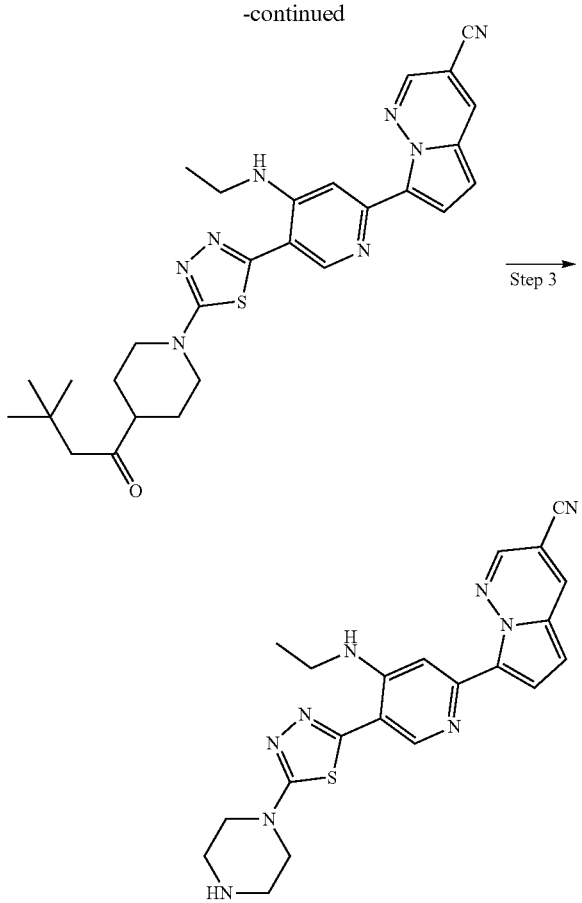

Intermediate AA

Step 1: A mixture of tert-butyl 4-[5-(4,6-dichloropyridin-3-yl)-1,3,4-thiadiazol-2-yl]piperazine-1-carboxylate (1.4 g, 3.36 mmol, 1.0 eq) in tert-butanol (22 ml, 0.15 M) and 2 M ethylamine solution in THF (2 ml, 7.1 mmol, 20.0 eq) was heated at 90° C. overnight. Then all volatiles were evaporated under reduced pressure, and the residue was dissolved in dichloromethane, washed with water, dried, and evaporated the solvent. The crude was triturated with hexane to provide 1.35 g (94% yield) of tert-butyl 4-{5-[6-chloro-4-(ethylamino)pyridin-3-yl]-1,3,4-thiadiazol-2-yl}piperazine-1-carboxylate. ESI(+)[M+H]$^+$=425.64. H NMR (300 MHz, DMSO-$d_6$), d: 8.59 (t, J=5.0 Hz, 1H), 8.20 (s, 1H), 6.81 (s, 1H), 3.52 (m, 8H), 3.32 (br q, 2H), 1.43 (s, 9H), 1.23 (t, J=7.2 Hz, 3H).

Step 2: Tert-butyl 4-{5-[6-chloro-4-(ethylamino)pyridin-3-yl]-1,3,4-thiadiazol-2-yl}piperazine-1-carboxylate (1.6 g, 3.77 mmol, 1.0 eq), 7-(4,4,5,5-tetramethyl-1,3,2-dioxaborolan-2-yl)pyrrolo[1,2-b]pyridazine-3-carbonitrile (1.42 g, 5.27 mmol, 1.4 eq), $K_3PO_4$ (1.648 g, 7.531 mmol, 2.0 eq) and XPhos Pd G3 (0.228 g, 0.264 mmol, 0.07 eq) were suspended in dimethoxymethane (54 ml, 0.07 M). The mixture was degassed with argon for 20 min and stirred at 120° C. overnight. The crude was purified via FC (silica gel, dichloromethane/acetonitrile 1:1) to provide 1.2 g (60% yield) of tert-butyl 4-[5-(6-{3-cyanopyrrolo[1,2-b]pyridazin-7-yl}-4-(ethylamino)pyridin-3-yl)-1,3,4-thiadiazol-2-yl]piperazine-1-carboxylate as a yellow solid. ESI(+)[M+H]$^+$=533.0. $^1$H NMR (300 MHz, DMSO-$d_6$), δ: 8.84 (d, J=2.2 Hz, 1H), 8.72 (d, J=2.2 Hz, 1H), 8.48 (m, 1H), 8.16

(s, 1H), 7.85 (d, J=4.8 Hz, 1H), 7.12 (d, J=4.8 Hz, 1H), 3.54 (br m, 10H), 1.44 (s, 9H), 1.34 (t, J=7.1 Hz, 3H).

Step 3: Tert-butyl 4-[5-(6-{3-cyanopyrrolo[1,2-b]pyridazin-7-yl}-4-(ethylamino)pyridin-3-yl)-1,3,4-thiadiazol-2-yl]piperazine-1-carboxylate (1.2 g, 2.25 mmol, 1.0 eq) was dissolved in acetic acid (15 ml, 0.15 M) and HCl in diethyl ether (6 g, 22.57 mmol, 10 eq) was added and reaction was stirred at r.t. for 2 h. UPLC monitoring was applied. Then, all volatiles were evaporated, and the crude residue was triturated with a mixture of 2-propanol and diethyl ether to provide 0.5 g (50% yield) of the title compound as a yellow solid. LCMS: ESI(+)[M+H]$^+$=432.21. $^1$H NMR (300 MHz, DMSO-d$_6$), δ: 8.83 (s, 1H), 8.71 (s, 1H), 8.49 (d, J=13.2 Hz, 2H), 8.15 (s, 1H), 7.84 (d, J=4.7 Hz, 1H), 7.11 (d, J=4.6 Hz, 1H), 4.12 (br m, 1H), 3.50 (m, 4H), 3.44 (br q, 2H), 2.90 (m, 4H), 1.34 (t, J=7.1 Hz, 3H).

Intermediate AB: 7-[4-(ethylamino)-5-[5-(piperazin-1-yl)-1,3,4-oxadiazol-2-yl]pyridin-2-yl]pyrrolo[1,2-b]pyridazine-3-carbonitrile tetrahydrochloride

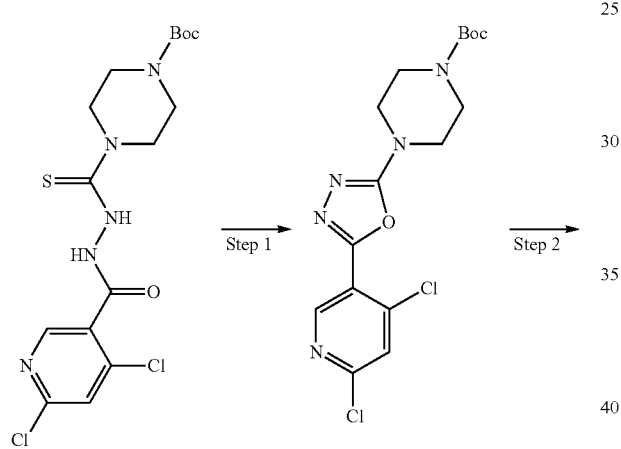

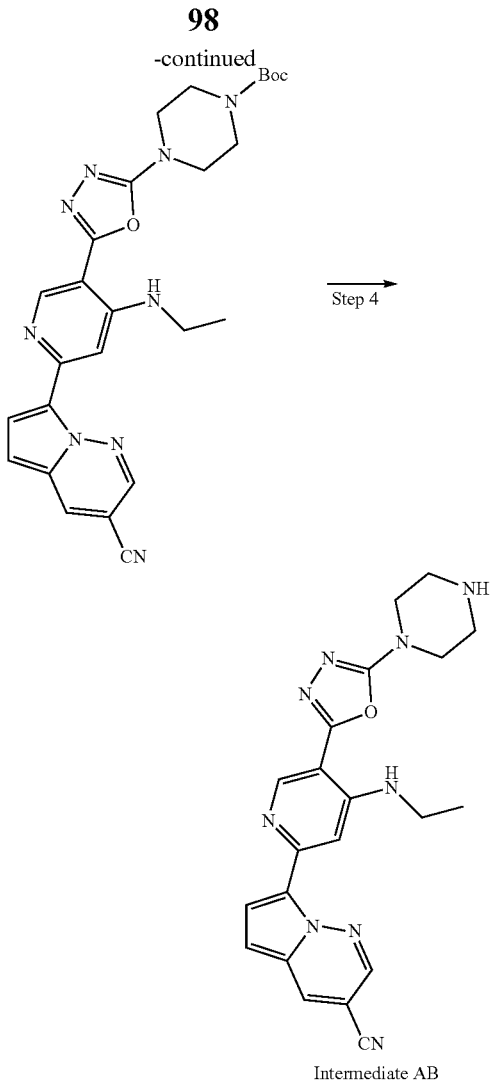

Intermediate AB

Step 1: The solution of tert-butyl 4-{[(4,6-dichloropyridin-3-yl)formohydrazido]methanethioyl}piperazine-1-carboxylate (0.11 g, 0.25 mmol, 1.0 eq) and p-toluenesulfonyl chloride (0.082 g, 0.43 mmol, 1.7 eq) in dry pyridine (1.3 ml, 0.2 M) was heated at 75° C. for 1.5 h with stirring. Then, all volatiles were evaporated at low pressure and the crude material was purified with flash chromatography (silica gel, DCM/2-PrOH, 9:1) to provide 0.06 g (52% yield) of tert-butyl 4-[5-(4,6-dichloropyridin-3-yl)-1,3,4-oxadiazol-2-yl]piperazine-1-carboxylate as an off-white crystalline product. ESI(+)[M+H]$^+$=418.8. $^1$H NMR (300 MHz, DMSO-d$_6$), d: 8.93 (s, 1H), 8.05 (s, 1H), 3.51 (s, 8H), 1.43 (s, 9H).

Step 2: Tert-butyl 4-[5-(4,6-dichloropyridin-3-yl)-1,3,4-oxadiazol-2-yl]piperazine-1-carboxylate (0.36 g, 0.865 mmol, 1.0 eq) was dissolved in tert-butanol (6 ml, 0.15 M) and 10% ethylamine in THF (2.0 ml, 4.32 mmol, 5 eq) was added. The resulting mixture was heated at 80° C. overnight and after cooling to room temperature was dissolved in dichloromethane, washed with water, and the organic phase was dried over Na$_2$SO$_4$, filtered, and evaporated to dryness under reduced pressure to provide 0.32 g (77% yield) of tert-butyl 4-{5-[6-chloro-4-(ethylamino)pyridin-3-yl]-1,3,4-oxadiazol-2-yl}piperazine-1-carboxylate as an off-white solid. ESI(+)[M+H]$^+$=409.63. $^1$H NMR (300 MHz, DMSO-d$_6$), δ: 8.46 (s, 1H), 7.83 (d, J=5.2 Hz, 1H), 6.85 (s, 1H), 3.51 (s, 8H), 3.39 (s, 2H), 1.43 (s, 9H), 1.23 (t, J=7.1 Hz, 3H).

Step 3: Tert-butyl 4-{5-[6-chloro-4-(ethylamino)pyridin-3-yl]-1,3,4-oxadiazol-2-yl}piperazine-1-carboxylate (0.3 g, 0.74 mmol, 1 eq), 7-(4,4,5,5-tetramethyl-1,3,2-dioxaborolan-2-yl)pyrrolo[1,2-b]pyridazine-3-carbonit-rile (0.28 g, 1.03 mmol, 1.4 eq), K₃PO₄ (0.35 g, 1.47 mmol, 2 eq) and XPhos Pd G3 (0.05 g, 0.052 mmol, 0.07 eq) were suspended in dimethoxyethane (11 ml, 0.07 M). The mixture was degassed with argon for 20 min, and stirred at 120° C. overnight. The crude was purified with flash chromatography (silica gel, dichloromethane/2-propanol) to provide 0.2 g (51% yield) of tert-butyl 4-[5-(6-{3-cyanopyrrolo[1,2-b]pyridazin-7-yl}-4-(ethylamino)pyridin-3-yl)-1,3,4-thiadiazol-2-yl] piperazine-1-carboxylate as a yellow solid. ESI (+)[M+H]⁺=516.71. ¹H NMR (300 MHz, DMSO-d₆), δ: 8.85 (d, J=2.2 Hz, 1H), 8.77 (s, 1H), 8.74 (d, J=2.2 Hz, 1H), 8.19 (s, 1H), 7.87 (d, J=4.8 Hz, 1H), 7.74 (t, J=5.3 Hz, 1H), 7.12 (d, J=4.8 Hz, 1H), 3.58-3.41 (m, 10H), 1.44 (s, 9H), 1.34 (t, J=7.1 Hz, 3H).

Step 4: To a solution of tert-butyl 4-[5-(6-{3-cyanopyrrolo[1,2-b]pyridazin-7-yl}-4-(ethylamino)pyridin-3-yl)-1,3,4-thiadiazol-2-yl]piperazine-1-carboxylate (0.2 g, 0.38 mmol, 1 eq) was dissolved in glacial acetic acid (2.51 ml, 0.15 M) and 1 M HCl in diethyl ether (0.915 g, 3.76 mmol, 10 eq) was added. The resulting mixture was stirred for 2 h. Then, all volatiles was evaporated at reduced pressure. The residue was triturated with dry diethyl ether to provide 0.18 g (81% yield) of the titled compound as a yellow crystalline solid. LCMS: ESI(+)[M+H]⁺=416.25.

¹H NMR (300 MHz, DMSO-d₆), δ: 9.53 (s, 2H), 9.00 (d, J=2.1 Hz, 1H), 8.86 (d, J=2.2 Hz, 1H), 8.75 (s, 2H), 8.28 (d, J=5.0 Hz, 1H), 8.12 (s, 1H), 7.24 (d, J=5.0 Hz, 1H), 3.86 (s, 4H), 3.65 (d, J=12.8 Hz, 2H), 3.29 (br m, 4H), 1.35 (t, J=7.1 Hz, 3H).

Intermediate AC: 7-(4-{[(1R)-1-cyanoethyl]amino}-5-[5-(piperazin-1-yl)-1,3,4-thiadiazol-2-yl]pyridin-2-yl)pyrrolo[1,2-b]pyridazine-3-carbonitrile

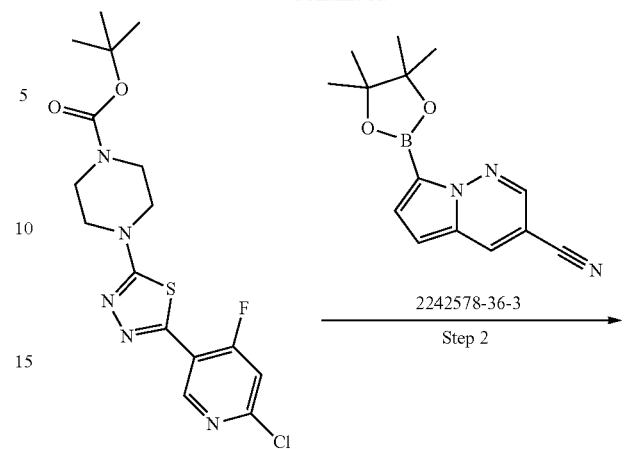

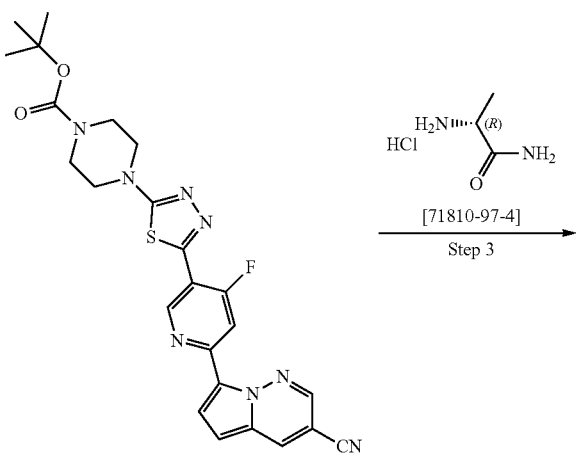

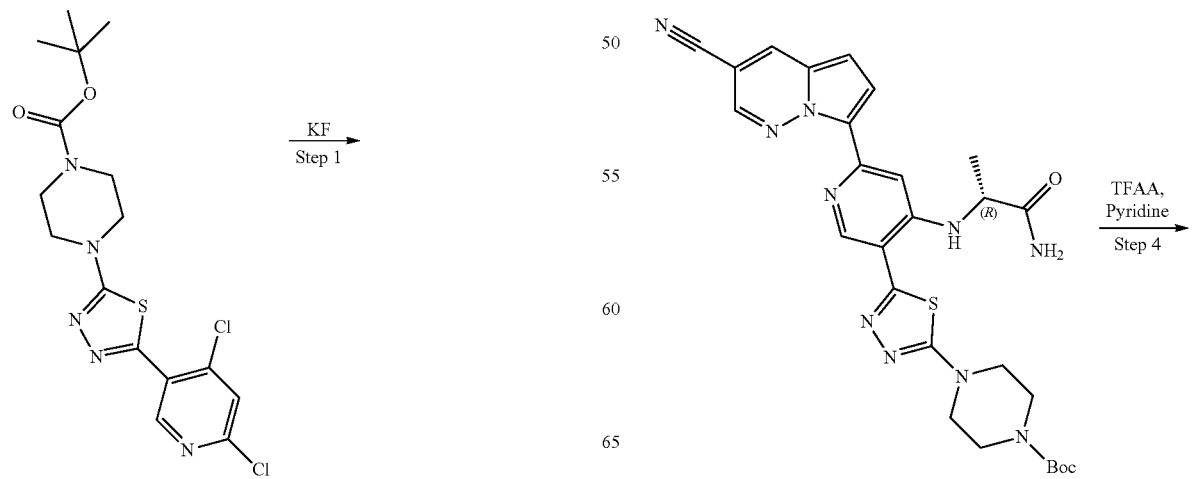

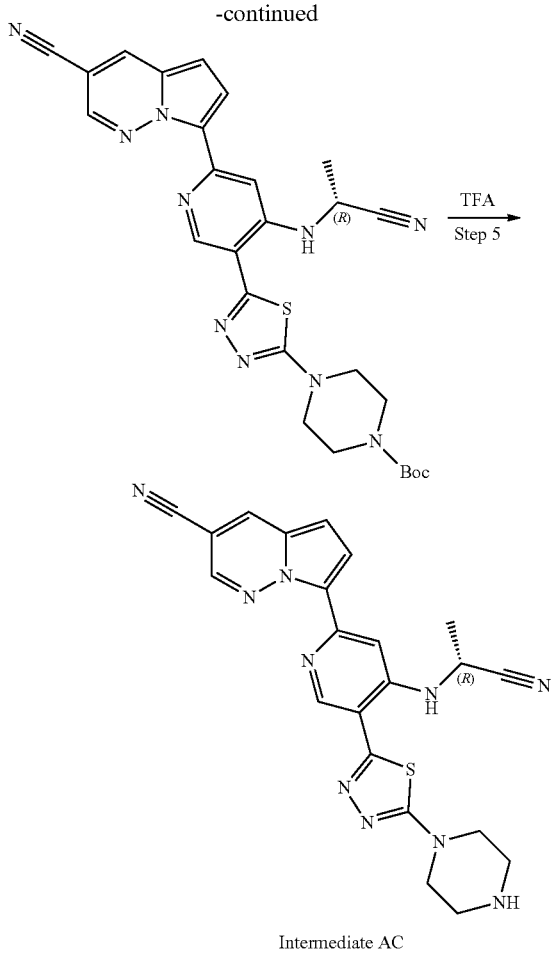

Intermediate AC

Step 1: To a solution of tert-butyl 4-[5-(4,6-dichloropyridin-3-yl)-1,3,4-thiadiazol-2-yl]piperazine-1-carboxylate (10.0 g, 24.02 mmol, 1.0 equiv.) in dimethyl sulfoxide anhydrous (80 mL, 0.3 M) were added potassium fluoride (1.61 g, 27.623 mmol, 1.15 equiv.) and 18-crown-6 (3.18 g, 12.01 mmol, 0.5 equiv.). The reaction mixture was stirred at 105° C. for 24 h. After completion of the reaction, it was diluted with water (100 mL) and the aqueous layer was extracted with DCM (3×500 mL). The combined organic layers were washed with brine (150 mL), dried over anhydrous $Na_2SO_4$, and concentrated under a vacuum. The residue was triturated with hexanes and then purified by silica gel flash chromatography eluting with 0-50% of EtOAc in hexanes to provide 6.7 g (70% yield) of tert-butyl 4-[5-(6-chloro-4-fluoropyridin-3-yl)-1,3,4-thiadiazol-2-yl]piperazine-1-carboxylate as an off-white solid. LCMS: [$C_{16}H_{19}ClFN_5O_2S$], desired mass 399.1, observed mass=399.9 [M+H+]. $^1$H NMR (300 MHz, CDCl$_3$) δ 9.21 (d, J=9.8 Hz, 1H), 7.22 (d, J=9.8 Hz, 1H), 3.62 (s, 8H), 1.49 (s, 9H).

Step 2: Tert-butyl 4-[5-(6-chloro-4-fluoropyridin-3-yl)-1,3,4-thiadiazol-2-yl]piperazine-1-carboxylate (6.7 g, 16.76 mmol, 1.0 equiv.), 7-(4,4,5,5-tetramethyl-1,3,2-dioxaborolan-2-yl) pyrrolo[1,2-b]pyridazine-3-carbonitrile (5.41 g, 20.10 mmol, 1.2 equiv.), potassium phosphate tribasic (7.11 g, 33.51 mmol, 2.0 equiv.) and XPhos Pd G3 (0.99 g, 1.17 mmol, 0.07 equiv.) were suspended in dimethoxyethane (240 mL, 0.07 M). The mixture was degassed with argon for 20 min and warmed up to 120° C. overnight. After completion of the reaction, it was concentrated under reduced pressure. The residue was purified by silica gel flash chromatography eluting with 100% of DCM (5 CV), 0-30% of ACN in DCM (15 CV), and 30% of ACN in DCM followed by trituration with Et$_2$O, to provide 950 mg (11% yield) of tert-butyl 4-[5-(6-{3-cyanopyrrolo[1,2-b]pyridazin-7-yl}-4-fluoropyridin-3-yl)-1,3,4-thiadiazol-2-yl]piperazine-1-carboxylate as a yellow solid. LCMS: [$C_{24}H_{23}FN_8O_2S$], desired mass 506.1, observed mass=507.0 [M+H+]. $^1$H NMR (300 MHz, CDCl$_3$) δ 9.50 (d, J=10.2 Hz, 1H), 8.69 (d, J=12.7 Hz, 1H), 8.36 (s, 1H), 8.22 (s, 1H), 8.04 (d, J=4.6 Hz, 1H), 7.02 (d, J=4.8 Hz, 1H), 3.64 (s, 8H), 1.50 (s, 9H).

Step 3: To a solution of tert-butyl 4-[5-(6-{3-cyanopyrrolo[1,2-b]pyridazin-7-yl}-4-fluoropyridin-3-yl)-1,3,4-thiadiazol-2-yl]piperazine-1-carboxylate (5.4 g, 8.00 mmol) in anhydrous DMSO (80.0 mL, 0.1 M) was added D-alaninamide hydrochloride (9.96 g, 80.0 mmol) and sodium bicarbonate (10.1 g, 120 mmol). The reaction mixture was stirred at 120° C. for 1 h. The product was precipitated by adding ice. The suspension was stirred at room temperature for 15 min. The solid was collected by filtration and washed with water till the filtrate was colorless. The solid was dried in vacuo. The residue was purified by silica gel flash chromatography eluting with 0 to 6% of MeOH in DCM to provide 1.36 g (30% yield) of tert-butyl 4-[5-(4-{[(1R)-1-carbamoylethyl]amino}-6-{3-cyanopyrrolo[1,2-b]pyridazin-7-yl}pyridin-3-yl)-1,3,4-thiadiazol-2-yl]piperazine-1-carboxylate as a yellow solid. LCMS: $C_{27}H_{30}N_{10}O_3S$ requires 574.2, observed m/z=575.2 [M+H]+. $^1$H NMR (300 MHz, DMSO-d$_6$) δ 8.85 (d, J=2.3 Hz, 1H), 8.64 (d, J=2.3 Hz, 1H), 8.52 (s, 1H), 8.13 (s, 1H), 7.83 (d, J=4.8 Hz, 1H), 7.77 (s, 1H), 7.23 (s, 1H), 7.13 (d, J=4.9 Hz, 1H), 6.87 (s, 1H), 4.27 (s, 1H), 3.54 (d, J=6.8 Hz, 8H), 1.50 (d, J=6.8 Hz, 3H), 1.44 (s, 9H).

Step 4: To a solution of tert-butyl 4-[5-(4-{[(1R)-1-carbamoylethyl]amino}-6-{3-cyanopyrrolo[1,2-b]pyridazin-7-yl}pyridin-3-yl)-1,3,4-thiadiazol-2-yl]piperazine-1-carboxylate (1.36 g, 2.37 mmol) in anhydrous DCM (23.7 mL, 0.1 M) was added trifluoroacetic anhydride (1.49 g, 7.1 mmol) and anhydrous pyridine (1.53 mL, 18.9 mmol) at 0° C. The reaction mixture was stirred at room temperature for 0.5 h. As the reaction was incomplete, another portion of trifluoroacetic anhydride (0.049 g, 0.24 mmol) and anhydrous pyridine (0.05 mL, 0.63 mmol) was added and the mixture was stirred 30 min under argon at room temperature. Aq sat NaHCO$_3$ was poured into the mixture and the mixture was extracted with DCM to get 671 mg of crude product. The crude was purified by silica gel flash chromatography eluting with 0 to 4% of MeOH in DCM to provide 0.33 g (24% yield) of tert-butyl 4-[5-(4-{[(1R)-1-cyanoethyl]amino}-6-{3-cyanopyrrolo[1,2-b]pyridazin-7-yl}pyridin-3-yl)-1,3,4-thiadiazol-2-yl]piperazine-1-carboxylate as an orange solid. LCMS: $C_{27}H_{28}N_{10}O_2S$ requires 556.2, observed m/z=557.2 [M+H]+. $^1$H NMR (300 MHz, DMSO-d$_6$) δ 8.88 (d, J=2.3 Hz, 1H), 8.83 (d, J=6.9 Hz, 1H), 8.68 (d, J=2.3 Hz, 1H), 8.64 (s, 1H), 8.37 (s, 1H), 7.88 (d, J=4.8 Hz, 1H), 7.15 (d, J=4.8 Hz, 1H), 5.04 (t, J=6.9 Hz, 1H), 3.55 (d, J=7.5 Hz, 8H), 1.78 (d, J=6.9 Hz, 3H), 1.44 (s, 9H).

Step 5: To a solution of tert-butyl 4-[5-(4-{[(1R)-1-cyanoethyl]amino}-6-{3-cyano pyrrolo[1,2-b]pyridazin-7-yl}pyridin-3-yl)-1,3,4-thiadiazol-2-yl]piperazine-1-carboxylate (0.97 g, 1.7 mmol) in anhydrous dichloromethane (34.8 mL, 0.05 M) was added trifluoroacetic acid (8 mL, 105 mmol) and anisole (0.381 mL, 3.48 mmol). The reaction mixture was stirred at room temperature for 1 h. The volatiles were evaporated, and the residue was triturated with diethyl ether four times to yield 790 mg of 7-(4-{[(1R)-

1-cyanoethyl]amino}-5-[5-(piperazin-1-yl)-1,3,4-thiadi-azol-2-yl]pyridin-2-yl)pyrrolo[1,2-b]pyridazine-3-carbonitrile as a TFA salt. The salt was dissolved in 20 mL of a mixture of DCM/MeOH (9:1, v/v) and was washed with 7% NaHCO$_3$ aqueous solution (30 mL). The aqueous layer was extracted twice with 10% of MeOH in DCM and the combined organic layers were washed with brine, dried over Na$_2$SO$_4$ and concentrated in vacuo to provide 0.562 g (63% yield) of the title compound as a yellow powder. LCMS: C$_{22}$H$_{20}$N$_{10}$S, desired mass=456.2, observed m/z=457.1 [M+H]$^+$, $^1$H NMR (300 MHz, DMSO-d$_6$) δ 8.90-8.80 (m, 2H), 8.68 (d, J=2.3 Hz, 1H), 8.64 (s, 1H), 8.37 (s, 1H), 7.88 (d, J=4.8 Hz, 1H), 7.15 (d, J=4.8 Hz, 1H), 5.04 (t, J=7.0 Hz, 1H), 3.53 (d, J=5.2 Hz, 4H), 2.89 (m, 4H), 1.78 (d, J=6.9 Hz, 3H).

Intermediate AD: 7-[4-(methylamino)-5-[5-(piperidin-4-yl)-1,3,4-thiadiazol-2-yl]pyridin-2-yl]pyrrolo[1,2-b]pyridazine-3-carbonitrile

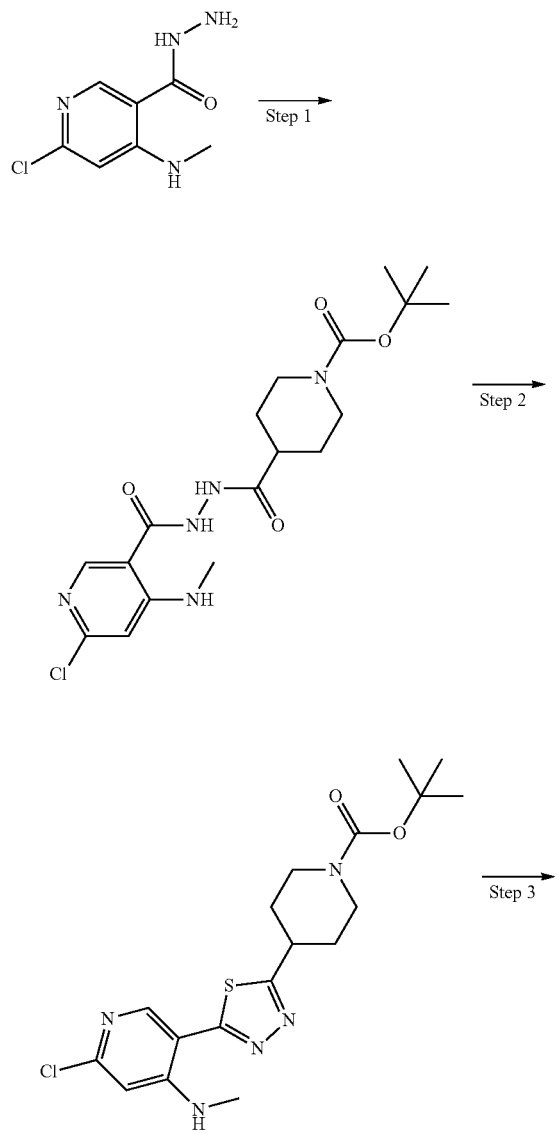

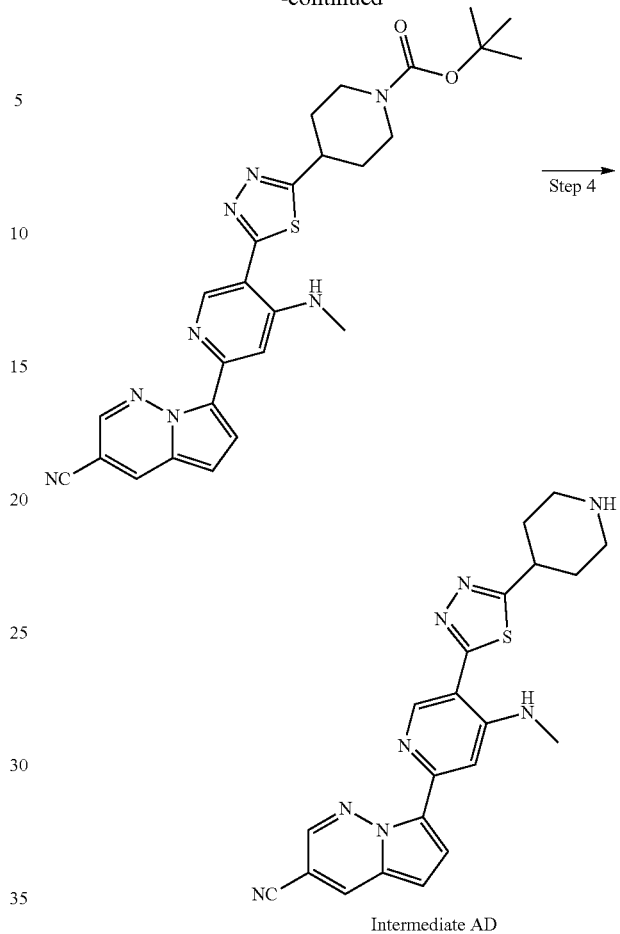

Intermediate AD

Step 1: To a solution of 6-chloro-4-(methylamino)pyridine-3-carbohydrazide (3.55 g, 17.69 mmol, 1 eq) and monomethyl 1-(tert-butoxycarbonyl)-4-piperidine carboxylic acid (4.46 g, 19.46 mmol, 1.1 eq) in DMF (60 mL, 0.3 M) were added DIPEA (9.3 mL, 53.08 mmol, 3 eq) and HATU (8.1 g, 21.23 mmol, 1.2 eq). The mixture was stirred at 25° C. overnight. The reaction mixture was quenched with ice/water (600 mL) and extracted with EtOAc. The combined organic layers were washed with brine, dried over Na$_2$SO$_4$, and concentrated under reduced pressure. The crude was purified by FC (DCM/MeOH, 0 to 10%) affording 6.44 g of tert-butyl 4-{N'-[6-chloro-4-(methylamino)pyridine-3-carbonyl]hydrazinecarbonyl}piperidine-1-carboxylate compound (85% yield). LCMS: ESI(+)[M−H]$^-$=410.40. $^1$H NMR (300 MHz, Chloroform-d) δ 10.33 (s, 1H), 9.89 (s, 1H), 8.34 (s, 1H), 8.10 (d, J=5.1 Hz, 1H), 6.66 (s, 1H), 3.95 (d, J=13.2 Hz, 2H), 2.82 (d, J=5.0 Hz, 5H), 2.47-2.36 (m, 1H), 1.71 (d, J=12.5 Hz, 2H), 1.51-1.40 (m, 11H).

Step 2: Tert-butyl 4-{N'-[6-chloro-4-(methylamino)pyridine-3-carbonyl]hydrazine carbonyl}piperidine-1-carboxylate (3.4 g, 8.25 mmol, 1 eq) was dissolved in anhydrous THF (275 ml, 0.03 M) under argon. The solution was warmed up to 40° C. and P$_2$S$_5$(2.75 mg, 12.38 mmol, 1.5 eq) was added portion wise during vigorous stirring. The resulting suspension was stirred for 1 h at reflux. After completion, the volatiles were evaporated under reduced pressure. The residue was dissolved in DCM (100 ml) and stirred vigorously with aq solution of K$_2$CO$_3$. The aqueous layer was removed with a separatory funnel and the organic solvent was dried over Na₂SO₄, and concentrated under reduced pressure. The crude residue was purified by FC (0 to 50% gradient of EtOAc in DCM) affording 1.82 g of tert-butyl 4-{5-[6-chloro-4-(methylamino) pyridin-3-yl]-1,3,4-thiadiazol-2-yl}piperidine-1-carboxylate (51% yield). LCMS: ESI(+)[M+H]⁺=410.4. ¹H NMR (300 MHz, DMSO-d₆) δ 8.66 (d, J=4.7 Hz, 1H), 8.40 (s, 1H), 6.84 (s, 1H), 4.01 (d, J=13.1 Hz, 2H), 3.53-3.36 (m, 1H), 2.98 (d, J=5.0 Hz, 5H), 2.09 (d, J=10.9 Hz, 2H), 1.64 (tt, J=12.0, 6.5 Hz, 2H), 1.42 (s, 9H).

Step 3: To a solution of tert-butyl 4-{5-[6-chloro-4-(methylamino)pyridin-3-yl]-1,3,4-thiadiazol-2-yl}piperidine-1-carboxylate (0.860 g, 2.097 mmol, 1.0 eq) and 7-(4,4,5,5-tetramethyl-1,3,2-dioxaborolan-2-yl)pyrrolo[1,2-b]pyridazine-3-carbonitrile (0.79 g, 2.936 mmol, 1.4 eq) in anhydrous dioxane (7 ml, 0.3 M), was added potassium carbonate (0.87 g, 6.295 mmol, 3 eq) dissolved in H₂O (0.35 ml, 6.0 M). The solution was degassed with argon for 15 min and [1,1-bis(diphenylphosphino)ferrocene]dichloropalladium(II) in complex with dichloromethane (0.43 g, 0.524 mmol, 0.25 eq) was added. The tube was sealed and stirred at 120° C. overnight. The reaction was filtrated through a pad of Celite and washed with DCM and MeOH. The solvents were evaporated under reduced pressure and the residue was purified by FC (5 to 50% of ACN in DCM) affording 363 mg of tert-butyl 4-[5-(6-{3-cyanopyrrolo[1,2-b]pyridazin-7-yl}-4-(methylamino)pyridin-3-yl)-1,3,4-thiadiazol-2-yl]piperidine-1-carboxylate (36% yield). LCMS: ESI(+)[M+H]⁺=517.44. ¹H NMR (300 MHz, DMSO-d₆) δ 8.86 (d, J=1.9 Hz, 1H), 8.75 (d, J=1.9 Hz, 1H), 8.68 (s, 1H), 8.65 (s, 1H), 8.21 (s, 1H), 7.89 (d, J=4.8 Hz, 1H), 7.13 (d, J=4.8 Hz, 1H), 4.03 (d, J=12.2 Hz, 2H), 3.10 (d, J=4.9 Hz, 3H), 3.06-2.86 (m, 2H), 2.11 (d, J=11.5 Hz, 2H), 1.76-1.56 (m, 2H), 1.43 (s, 9H).

Step 4: A solution of tert-butyl 4-[5-(6-{3-cyanopyrrolo[1,2-b]pyridazin-7-yl}-4-(methylamino)pyridin-3-yl)-1,3,4-thiadiazol-2-yl]piperidine-1-carboxylate (650 mg, 1.26 mmol) in HFIP (26 mL, 0.06 M) was stirred at 140° C. with MW irradiation for 4 h. The volatiles were evaporated, and the residue was co-evaporated with DCM three times. The crude was submitted for a short silica gel flash chromatography (5 to 30% of MeOH in DCM) affording 474 mg (85% yield) of the title compound. LCMS: ESI(+)[M+H]⁺=417.21. ¹H NMR (300 MHz, DMSO-d₆) δ 8.86 (d, J=2.2 Hz, 1H), 8.76 (d, J=2.2 Hz, 1H), 8.70 (s, 1H), 8.65 (q, J=4.3 Hz, 1H), 8.21 (s, 1H), 7.89 (d, J=4.8 Hz, 1H), 7.14 (d, J=4.8 Hz, 1H), 3.10 (d, J=4.9 Hz, 3H), 3.08-2.98 (m, 2H), 2.71-2.58 (m, 2H), 2.09-1.97 (m, 2H), 1.66 (qd, J=12.2, 3.6 Hz, 2H).

Intermediate AE: 7-(5-(5-((1r,4r)-4-(methylamino)cyclohexyl)-1,3,4-thiadiazol-2-yl)-4-((tetrahydro-2H-pyran-4-yl)amino)pyridin-2-yl)pyrrolo[1,2-b]pyridazine-3-carbonitrile hydrochloride

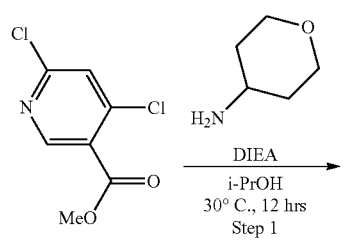

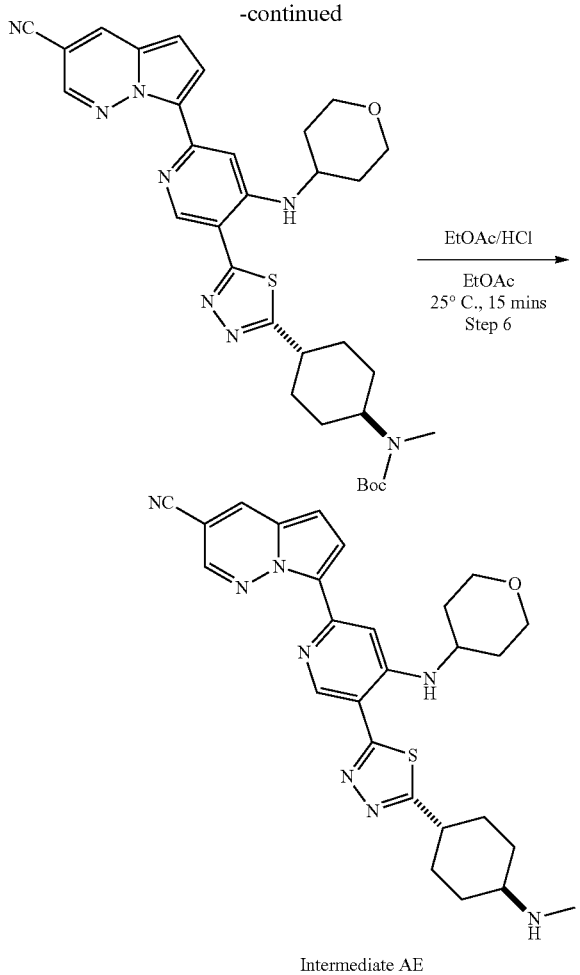

Intermediate AE

Step 1: To a solution of methyl 4,6-dichloronicotinate (71.6 g, 347 mmol, 1.00 eq) and tetrahydro-2H-pyran-4-amine (87.9 g, 869 mmol, 2.50 eq) in i-PrOH (700 mL) was added DIEA (157 g, 1.22 mol, 212 mL, 3.50 eq). The reaction mixture was kept under N$_2$ at 30° C. for 12 hrs. The reaction mixture was poured into H$_2$O (1.00 L), then was extracted with ethyl acetate (1.00 L*3). The combined organic layer was washed with brine (1.00 L*2), dried over Na$_2$SO$_4$, filtered and concentrated. The residue was purified by column chromatography (SiO$_2$, petroleum ether/ethyl acetate, gradient: 20/1-10/1-3/1) to give methyl 6-chloro-4-((tetrahydro-2H-pyran-4-yl)amino)nicotinate (43.0 g, 157 mmol, 45.4% yield, 99.4% purity) as a white solid. TLC R$_f$=0.30 (3:1 petroleum ether/ethyl acetate). LCMS: m/z=271.1 (M+H)+. $^1$H NMR (400 MHz, CDCl$_3$) δ 8.68 (s, 1H), 8.27 (d, J=8.0 Hz, 1H), 6.56 (s, 1H), 4.01 (t, J=3.8, 12.0 Hz, 2H), 3.89 (s, 3H), 3.63-3.53 (m, 3H), 2.04-1.98 (m, 2H), 1.64 (m, J=4.2, 10.2, 13.8 Hz, 2H)

Step 2: To the solution of methyl 6-chloro-4-((tetrahydro-2H-pyran-4-yl)amino)nicotinate (49.0 g, 179 mmol, 99.4% purity, 1.00 eq) in EtOH (300 mL) was added NH$_2$NH$_2$·H$_2$O (85.6 g, 1.45 mol, 83.2 mL, 85.0% purity, 8.03 eq). The reaction mixture was stirred at 80° C. for 3 hrs. The reaction mixture was poured into H$_2$O (300 mL), then was extracted with ethyl acetate (300 mL*3). The combined organic layer was washed with brine (600 mL*2), dried over Na$_2$SO$_4$, filtered and concentrated to give 6-chloro-4-((tetrahydro-2H-pyran-4-yl)amino)nicotino hydrazide (45.0 g, 166 mmol, 92.4% yield, 100% purity) as a white solid. LCMS: m/z=271.1 (M+H)+. $^1$H NMR (400 MHz, DMSO) δ 9.86 (s, 1H), 8.39 (d, J=7.8 Hz, 1H), 8.26 (s, 1H), 6.84 (s, 1H), 4.49 (br s, 2H), 3.82 (td, J=3.6, 11.6 Hz, 2H), 3.78-3.65 (m, 1H), 3.47 (dt, J=2.2, 11.2 Hz, 2H), 1.88 (br d, J=11.6 Hz, 2H), 1.48-1.27 (m, 2H)

Step 3: To a solution of 6-chloro-4-((tetrahydro-2H-pyran-4-yl)amino)nicotinohydrazide (15.0 g, 55.4 mmol, 100% purity, 1.00 eq) and (1r,4r)-4-((tert-butoxycarbonyl) (methyl)amino) cyclohexane-1-carboxylic acid (15.6 g, 60.9 mmol, 1.10 eq) in DMF (150 mL) was added HOBT (8.98 g, 66.4 mmol, 1.2 eq), EDCI (12.7 g, 66.4 mmol, 1.20 eq) and DIEA (21.4 g, 166 mmol, 28.9 mL, 3.00 eq). The mixture reaction was stirred at 25° C. under N$_2$ for 2 hrs. The reaction mixture was poured into H$_2$O (200 mL), then was extracted with ethyl acetate (200 mL*3). The combined organic layer was washed with brine (600 mL*2), dried over Na$_2$SO$_4$, filtered and concentrated. The residue was purified by column chromatography (SiO$_2$, petroleum ether/ethyl acetate=10/1-5/1) to give tert-butyl ((1r,4r)-4-(2-(6-chloro-4-((tetrahydro-2H-pyran-4-yl) amino)nicotinoyl)hydrazine-1-carbonyl)cyclohexyl)(methyl)carbamate (10.0 g, 17.3 mmol, 31.3% yield, 88.4% purity) as a yellow solid. TLC R$_f$=0.30 (petroleum ether/ethyl acetate=0/1). LCMS: m/z=510.1 (M+H)+. $^1$H NMR (400 MHz, DMSO) δ 10.37 (s, 1H), 9.85 (s, 1H), 8.39 (s, 1H), 8.27 (br d, J=7.8 Hz, 1H), 6.90 (s, 1H), 3.91-3.67 (m, 4H), 3.52-3.40 (m, 2H), 2.67 (s, 3H), 2.18 (br s, 1H), 1.93-1.80 (m, 4H), 1.71-1.44 (m, 6H), 1.40 (s, 9H), 1.38 (br s, 2H)

Step 4: To a solution of tert-butyl ((1r,4r)-4-(2-(6-chloro-4-((tetrahydro-2H-pyran-4-yl)amino)nicotinoyl)hydrazine-1-carbonyl)cyclohexyl)(methyl)carbamate (10.0 g, 17.3 mmol, 88.4% purity, 1.00 eq) in THF (100 mL) was added P$_2$S$_5$(5.78 g, 26.0 mmol, 2.76 mL, 1.50 eq) at 30° C., then the mixture was stirred at 70° C. for 2 hrs. After reaction completion volatiles was evaporated. The crude residue was dissolved in DCM (150 mL) and washed by vigorous stirring with 15% aqueous K$_2$CO$_3$ (150 mL). The organic layer was washed with water (200 mL) and brine (400 mL), dried over Na$_2$SO$_4$, and concentrated in vacuo. The residue was purified by column chromatography (SiO$_2$, petroleum ether/ethyl acetate=50/1-25/1-10/1) to give tert-butyl ((1r,4r)-4-(5-(6-chloro-4-((tetrahydro-2H-pyran-4-yl)amino) pyridin-3-yl)-1,3,4-thiadiazol-2-yl)cyclohexyl)(methyl)carbamate (6.00 g, 8.82 mmol, 50.9% yield, 74.7% purity) as a yellow solid. TLC R$_f$=0.20 (petroleum ether/ethyl acetate=1/1). LCMS: m/z=508.2 (M+H)$^+$. $^1$H NMR (400 MHz, CDCl$_3$) δ 9.08 (br d, J=7.4 Hz, 1H), 8.35 (s, 1H), 6.65 (s, 1H), 4.03 (td, J=3.8, 12.0 Hz, 2H), 3.75-3.64 (m, 1H), 3.63-3.55 (m, 2H), 3.09 (tt, J=3.6, 11.8 Hz, 1H), 2.78 (s, 3H), 2.37-2.27 (m, 2H), 2.11-2.01 (m, 2H), 1.89 (br dd, J=2.4, 12.2 Hz, 2H), 1.82-1.62 (m, 7H), 1.48 (s, 9H)

Step 5: To a solution of tert-butyl ((1r,4r)-4-(5-(6-chloro-4-((tetrahydro-2H-pyran-4-yl)amino)pyridin-3-yl)-1,3,4-thiadiazol-2-yl)cyclohexyl)(methyl)carbamate (6.00 g, 11.8 mmol, 1.00 eq) and 7-(4,4,5,5-tetramethyl-1,3,2-dioxaborolan-2-yl)pyrrolo[1,2-b]pyridazine-3-carbonitrile (4.13 g, 15.3 mmol, 1.30 eq) in DME (60.0 mL) was added K$_3$PO$_4$ (2.00 M, 11.8 mL, 2.00 eq) and XPhos Pd G$_3$ (999 mg, 1.18 mmol, 0.100 eq) under N$_2$, the mixture was stirred at 100° C. for 2 hrs under N$_2$. The reaction mixture was poured into H$_2$O (100 mL), then was extracted with ethyl acetate (100 mL*3). The combined organic layer was washed with brine (200 mL*2), dried over Na$_2$SO, filtered and concentrated. The crude product was purified by Prep-HPLC (column: Welch Ultimate XB-SiOH 250*70*10 um; mobile phase: [Hexane-EtOH (0.1% NH$_3$·H$_2$O];B %: 1%-40%, 20 min)

then concentrated by lyophilization to give tert-butyl ((1r,4r)-4-(5-(6-(3-cyanopyrrolo[1,2-b]pyridazin-7-yl)-4-((tetrahydro-2H-pyran-4-yl)amino) pyridin-3-yl)-1,3,4-thiadiazol-2-yl)cyclohexyl)(methyl)carbamate (2.00 g, 1.96 mmol, 16.7% yield, 60.6% purity) as a yellow solid. LCMS: m/z=615.2 (M+H)+

Step 6: To the solution of tert-butyl ((1r,4r)-4-(5-(6-(3-cyanopyrrolo[1,2-b]pyridazin-7-yl)-4-((tetrahydro-2H-pyran-4-yl)amino)pyridin-3-yl)-1,3,4-thiadiazol-2-yl)cyclohexyl)(methyl)carbamate (2.00 g, 1.96 mmol, 60.6% purity, 1.00 eq) in EtOAc (10.0 mL) was added HCl/EtOAc (4.00 M, 489 uL, 1.00 eq) kept under $N_2$ at 25° C. for 15 mins. The reaction mixture was concentrated under vacuum. The residue was treated with EtOAc (10.0 mL) at 25° C. for 1 hr, then filtered, and the filter cake was concentrated vacuum. 7-(5-(5-(((1r,4r)-4-(methylamino)cyclohexyl)-1,3,4-thiadiazol-2-yl)-4-((tetrahydro-2H-pyran-4-yl)amino) pyridin-2-yl)pyrrolo[1,2-b]pyridazine-3-carbonitrile hydrochloride (1.01 g, 1.67 mmol, 85.3% yield, 91.1% purity, HCl) was obtained as a yellow solid. LCMS: m/z=515.1 (M+H)+. $^1$H NMR: (400 MHz, MeOD) δ 8.80-8.76 (m, 2H), 8.71 (d, J=2.0 Hz, 1H), 8.16 (d, J=5.2 Hz, 1H), 8.00 (s, 1H), 7.25 (d, J=5.2 Hz, 1H), 4.42-4.26 (m, 1H), 4.04 (td, J=3.8, 12.0 Hz, 2H), 3.78-3.69 (m, 2H), 3.43-3.32 (m, 2H), 3.20 (tt, J=3.6, 11.8 Hz, 1H), 2.75 (s, 3H), 2.49-2.40 (m, 2H), 2.34 (br d, J=10.4 Hz, 2H), 2.20 (br d, J=12.2 Hz, 2H), 1.88-1.77 (m, 4H), 1.71-1.62 (m, 2H)

Intermediate AF: 7-(5-(5-(3,8-diazabicyclo[3.2.1]octan-3-yl)-1,3,4-thiadiazol-2-yl)-4-(((S)-tetrahydrofuran-3-yl)amino)pyridin-2-yl)pyrrolo[1,2-b]pyridazine-3-carbonitrile

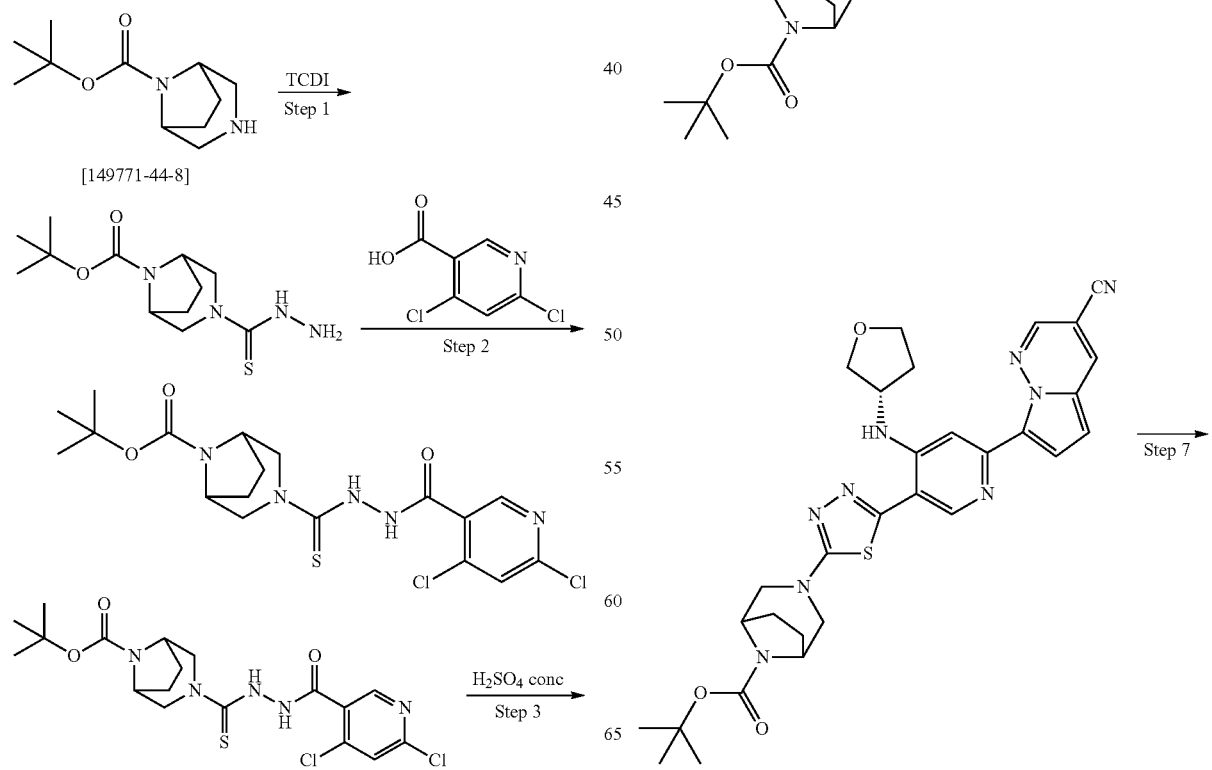

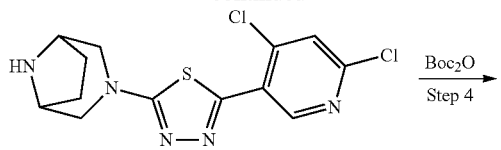

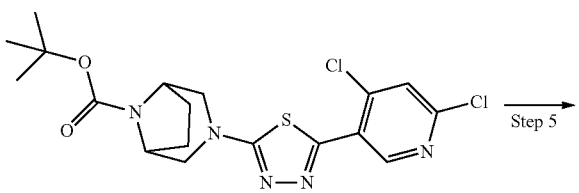

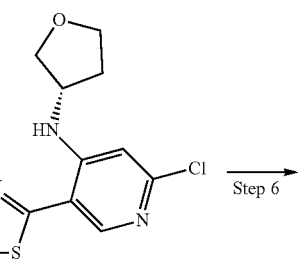

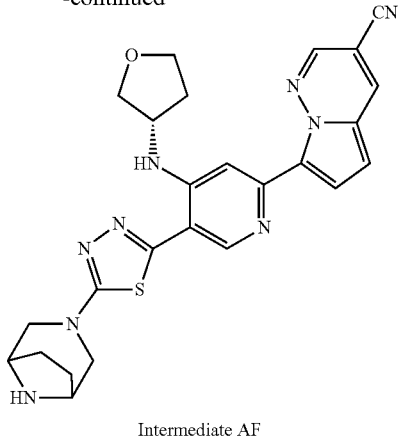

Intermediate AF

Step 1: To a stirred solution of tert-butyl 3,8-diazabicyclo [3.2.1], octane-8-carboxylate (29.4 g, 138.49 mmol, 1.0 eq) in THF (462 ml, 0.3 M) was added TEA (57.9 ml, 3.0 eq) and 1,1'-thiocarbonyldiimidazole (29.61 g, 1.2 eq) at room temperature and the reaction mixture was stirred for 2 h. Then, the solution was transferred dropwise to a solution of hydrazine monohydrate (20.80 g, 3 eq) in THF (130 ml). Completion of the reaction was monitored by TLC. The reaction mixture was diluted with water (500 mL) and the aqueous layer was extracted with EtOAc (2×500 mL). The combined organic layers were washed with brine (500 mL), dried over anhydrous $Na_2SO_4$, and concentrated under a vacuum. The residue was re-suspended in water (600 mL) and filtered off. It was then washed with water to remove the imidazole by-product to afford 35 g (88%) of tert-butyl 3-(aminocarbamothioyl)-3,8-diazabicyclo[3.2.1] octane-8-carboxylate as a light pink solid. LCMS: $[C_{12}H_{22}N_4O_2S]$, desired mass=286.4 observed mass=287.3 [M+H$^+$]. $^1$H NMR (300 MHz, DMSO-d6): δ 9.05 (s, 1H), 4.76 (s, 2H), 4.40-3.98 (m, 4H), 3.08-2.84 (m, 2H), 1.91-1.70 (m, 2H), 1.57 (d, J=7.2 Hz, 2H), 1.41 (s, 9H).

Step 2: To a solution of starting 4,6-dichloronicotinic acid (23.89 g, 124.45 mmol, 1.2 eq) in dry DCM (345 ml, 0.3 M) in the dry atmosphere was added TEA (17.35 ml, 124.45 mmol, 1.2 eq) and the solution was cooled down to −15° C. isobutyl-chloroformate (17.0 g, 124.45 mmol, 1.2 eq) was added dropwise maintaining the temperature at −15° C. The solution was kept at −15° C. for 1 h. Then, at this temperature, the tert-butyl 3-(amino carbamothioyl)-3,8-diazabicyclo [3.2.1]octane-8-carboxylate (30.0 g, 103.71 mmol, 1 eq) was added by portions and the reaction was allowed to turn back to 25° C. overnight. After completion, the solution was treated with solid NaHCO$_3$ (pH=8.0) and extracted with DCM 3×500 mL). The combined organic layers were dried with Na$_2$SO$_4$, filtered, and evaporated to dryness. The crude residue was triturated with hexane three times to yield 37.5 g (79%) of tert-butyl 3-{[(4,6-dichloropyridin-3-yl) formohydrazido]methanethioyl}-3,8-diazabicyclo [3.2.1]octane-8-carboxylate as a pale yellow solid which was used further without purification. LCMS: $[C_{18}H_{23}Cl_2N_5O_3S]$, desired mass=460.34 observed mass=459.9 [M−H$^-$]. $^1$H NMR (300 MHz, CDCl$_3$): δ 10.63 (s, 1H), 8.88 (s, 1H), 8.68 (d, J=19.5 Hz, 1H), 7.51 (s, 1H), 4.38 (s, 4H), 3.47-3.27 (m, 2H), 2.13-1.93 (m, 2H), 1.81 (t, J=6.9 Hz, 2H), 1.50 (d, J=3.4 Hz, 9H).

Step 3: Tert-butyl 3-{[(4,6-dichloropyridin-3-yl)formohydrazido]methanethioyl}-3,8-diazabicyclo[3.2.1] octane-8-carboxylate (37.5 g, 81.46 mmol, 1 eq) was dissolved in H$_2$SO$_4$ (272 ml, 0.3 M), and the solution stirred at rt overnight. The mixture was poured in ice under stirring and K$_2$CO$_3$ was added until pH~10. K$_2$SO$_4$ was filtered off and rinsed with DCM. The layers were separated, and the aqueous layer was further extracted with DCM (3×500 mL). The combined organic layer was washed with brine (1×500 mL), dried over Na$_2$SO$_4$, filtered, and evaporated under reduced pressure affording the crude which was triturated with hexane to yield 19.6 g (70%) of 3-[5-(4,6-dichloropyridin-3-yl)-1,3,4-thiadiazol-2-yl]-3,8-diazabicyclo[3.2.1] octane as a pale yellow solid. LCMS: $[C_{13}H_{13}Cl_2N_5S]$, desired mass=341.0 observed mass=341.8 [M+H$^+$]. $^1$H NMR (300 MHz, CDCl$_3$): δ 9.14 (s, 1H), 7.49 (s, 1H), 3.72 (dd, J=9.1, 3.1 Hz, 4H), 3.47 (dd, J=12.2, 2.8 Hz, 2H), 1.91 (d, J=2.1 Hz, 5H).

Step 4: To a solution of 3-[5-(4,6-dichloropyridin-3-yl)-1,3,4-thiadiazol-2-yl]-3,8-diazabicyclo[3.2.1] octane (19.6 g, 57.27 mmol, 1 eq) was dissolved in DCM (115 ml, 0.5 M), TEA (9.58 ml, 68.72 mmol, 1.2 eq) was added and the mixture was stirred for 5 min. Then, Boc$_2$O (15 g, 68.72 mmol 1.2 eq) was added and the solution was stirred until completion (2 h). The solution was evaporated to dryness under reduced pressure. Then, the crude was triturated with hexane (3×300 mL) to provide 21 g (83% yield) of tert-butyl 3-[5-(4,6-dichloropyridin-3-yl)-1,3,4-thiadiazol-2-yl]-3,8-diazabicyclo[3.2.1] octane-8-carboxylate as a pale yellow solid. LCMS: $[C_{18}H_{21}Cl_2N_5O_2S]$, desired mass=441.0 observed mass=441.9 [M+H$^+$]. $^1$H NMR (300 MHz, CDCl$_3$): δ 9.14 (s, 1H), 7.50 (s, 1H), 4.42 (s, 2H), 3.54 (s, 4H), 2.16-2.00 (m, 2H), 1.87 (d, J=7.4 Hz, 2H), 1.52 (s, 9H).

Step 5: A solution of tert-butyl 3-[5-(4,6-dichloropyridin-3-yl)-1,3,4-thiadiazol-2-yl]-3,8-diazabicyclo[3.2.1]octane-8-carboxylate (1.3 g, 2.94 mmol, 1.0 eq), (S)-3-aminotetrahydrofuran hydrochloride (2.18 g, 17.63 mmol, 6.0 eq), potassium carbonate anhydrous (3.24 g, 23.51 mmol, 8.0 eq) and DIPEA (2.56 ml, 14.69 mmol, 5.0 eq) in anhydrous ACN (30 ml, 0.1 M) and DMF (3 ml, 1 M) was stirred at 80° C. overnight. Then, all volatiles were removed under reduced pressure and the crude material was purified with silica gel flash chromatography eluting with dichloromethane/acetonitrile to provide 1.0 g (62% yield) of tert-butyl 3-(5-(6-chloro-4-(((S)-tetrahydrofuran-3-yl)amino)pyridin-3-yl)-1,3,4-thiadiazol-2-yl)-3,8-diazabicyclo[3.2.1]octane-8-carboxylate as an off-white crystalline product. ESI(+) [M+H]$^+$=494.0. $^1$H NMR (300 MHz, DMSO-d$_6$) d: 8.87 (d, J=7.0 Hz, 1H), 8.22 (s, 1H), 6.90 (s, 1H), 4.38 (m, 1H), 4.27 (m, 2H), 3.94-3.72 (m, 3H), 3.64 (m, 3H), 3.34 (m, 2H), 2.41-2.26 (m, 1H), 1.91 (m, 2H), 1.86-1.68 (m, 3H), 1.43 (s, 9H).

Step 6: tert-butyl 3-(5-(6-chloro-4-(((S)-tetrahydrofuran-3-yl)amino)pyridin-3-yl)-1,3,4-thiadiazol-2-yl)-3,8-diazabicyclo[3.2.1]octane-8-carboxylate (1.0 g, 1.82 mmol, 1.0 eq) 7-(4,4,5,5-tetramethyl-1,3,2-dioxaborolan-2-yl)pyrrolo-[1, 2-b]pyridazine-3-carbonitrile (0.709 g, 2.556 mmol, 1.4 eq), K$_3$PO$_4$ (0.775 g, 3.651 mmol, 2.0 eq) and XPhos Pd G3 (0.155 g, 0.18 mmol, 0.1 eq) were suspended in 1,2-dimethoxyethane (26.08 ml, 0.07 M). The mixture was degassed with argon for 20 min and stirred at 120° C. overnight. The crude material was purified with silica gel flash chromatography eluting with dichloromethane/2-propanol to provide 0.7 g (56% yield) of tert-butyl 3-(5-(6-(3-cyanopyrrolo[1,2-b]pyridazin-7-yl)-4-(((S)-tetrahydrofuran-3-yl)amino)pyridin-3-yl)-1,3,4-thiadiazol-2-yl)-3,8-diazabicyclo[3.2.1]octane-8-carboxylate as a yellow solid. ESI(+)[M+H]$^+$=600.47. $^1$H NMR (300 MHz, DMSO-d$_6$) δ: 8.82 (d, J=2.2 Hz, 1H), 8.76-8.68 (m, 2H), 8.49 (s, 1H), 8.18

(s, 1H), 7.83 (d, J=4.8 Hz, 1H), 7.11 (d, J=4.8 Hz, 1H), 4.30 (d, J=11.2 Hz, 3H), 4.08-3.99 (m, 1H), 3.93-3.78 (m, 2H), 3.70 (t, J=11.8 Hz, 3H), 2.49-2.38 (m, 3H), 1.98-1.85 (m, 3H), 1.75 (d, J=7.3 Hz, 2H), 1.44 (s, 9H).

Step 7: To a solution of tert-butyl 3-(5-(6-(3-cyanopyrrolo[1,2-b]pyridazin-7-yl)-4-(((S)-tetrahydrofuran-3-yl)amino)pyridin-3-yl)-1,3,4-thiadiazol-2-yl)-3,8-diazabicyclo[3.2.1]octane-8-carboxylate (0.7 g, 1.0 mmol, 1.0 eq) in anh. dichloromethane (3.5 ml, 0.3 M) the trifluoroacetic acid (1.5 ml, 20.5 mmol, 20 eq) was added, and the resulting mixture was stirred at room temperature for 3 h. After concentration under reduced pressure and conversion to the free amine, the crude was purified by silica gel flash chromatography eluting with dichloromethane/methanol to provide 0.34 g (62% yield) of 7-(5-(5-(3,8-diazabicyclo[3.2.1]octan-3-yl)-1,3,4-thiadiazol-2-yl)-4-(((S)-tetrahydrofuran-3-yl)amino)pyridin-2-yl)pyrrolo[1,2-b]pyridazine-3-carbonitrile as a yellow solid.

LCMS: ESI(+)[M+H]⁺=500.18. $^1$H NMR (300 MHz, DMSO-d$_6$) δ: 8.83 (d, J=2.2 Hz, 1H), 8.74 (d, J=2.3 Hz, 2H), 8.49 (s, 1H), 8.19 (s, 1H), 7.84 (d, J=4.8 Hz, 1H), 7.11 (d, J=4.8 Hz, 1H), 4.35 (m, 1H), 4.06 (m, 1H), 3.95-3.79 (m, 2H), 3.72 (m, 1H), 3.55 (m, 3H), 3.31-3.27 (m, 2H), 2.49-2.38 (m, 2H), 1.99-1.87 (m, 1H), 1.80-1.65 (m, 4H).

Intermediate AG: 7-[5-(5-{2,7-diazaspiro[3.5]nonan-2-yl}-1,3,4-thiadiazol-2-yl)-4-(oxan-4-ylamino)pyridin-2-yl]pyrrolo[1,2-b]pyridazine-3-carbonitrile

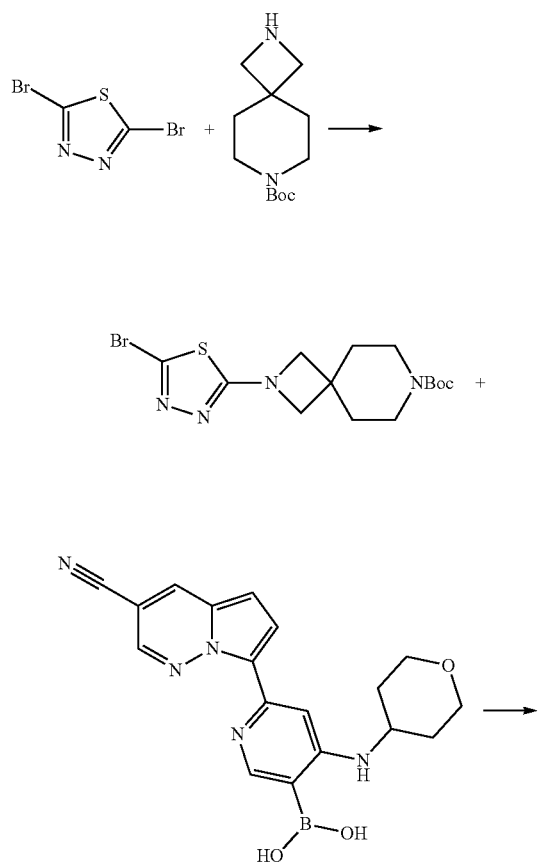

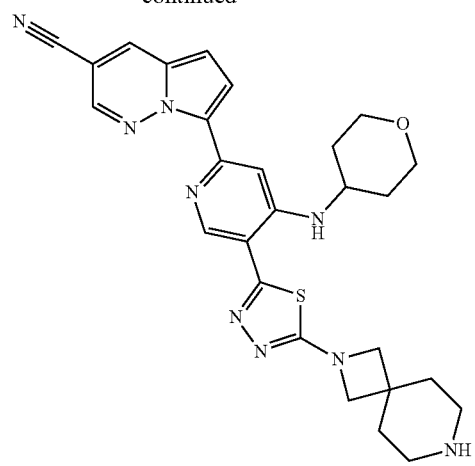

Intermediate AG

Synthesized following the same procedure for Intermediate T, except tert-butyl 2,7-diazaspiro[3.5]nonane-7-carboxylate was used. LCMS: ESI(+)[M+H]⁺=528.5. H NMR (500 MHz, Methanol-d$_4$) δ 8.78 (d, J=2.4 Hz, 1H), 8.70 (d, J=2.3 Hz, 1H), 8.56 (d, J=2.3 Hz, 1H), 8.13 (t, J=3.3 Hz, 1H), 7.94 (s, 1H), 7.30-7.09 (m, 2H), 4.31 (s, 1H), 4.13 (d, J=2.2 Hz, 4H), 4.11-3.97 (m, 3H), 3.74 (t, J=11.1 Hz, 2H), 3.26 (s, 5H), 2.19 (q, J=9.8, 6.5 Hz, 6H), 1.78 (d, J=11.5 Hz, 2H).

Intermediate AH: 7-[5-(5-{3,8-diazabicyclo[3.2.1]octan-3-yl}-1,3,4-thiadiazol-2-yl)-4-(ethylamino)pyridin-2-yl]pyrrolo[1,2-b]pyridazine-3-carbonitrile

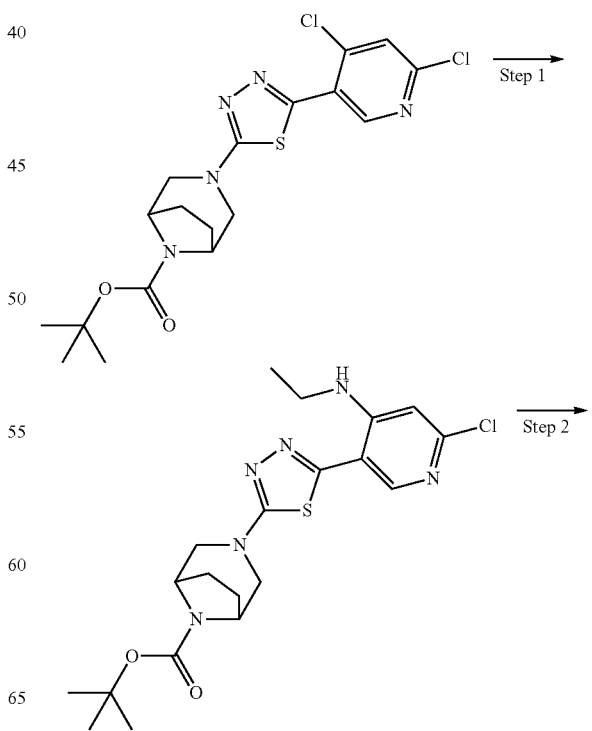

-continued

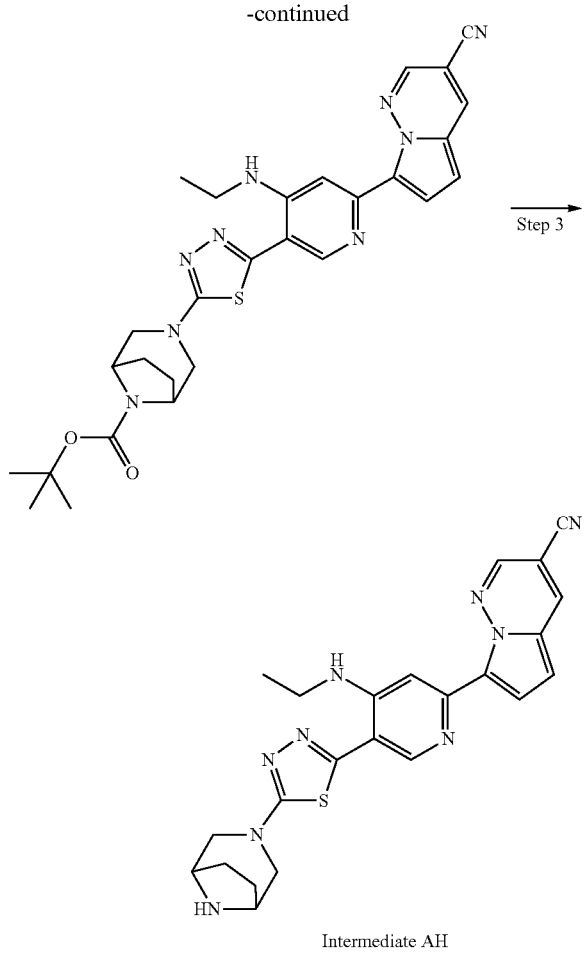

Intermediate AH

Step 1: A solution of tert-butyl 3-[5-(4,6-dichloropyridin-3-yl)-1,3,4-thiadiazol-2-yl]-3,8-diazabicyclo[3.2.1]octane-8-carboxylate (0.44 g, 0.10 mmol, 1.0 eq), ethylamine solution (5 ml, 1.0 mmol, 10.0 eq) in anh. acetonitrile (23 ml, 0.1 M) and DMF (2.5 ml, 1 M) was stirred at 80° C. for 21 h. Then, all volatiles were removed under reduced pressure and the crude material was purified by silica gel flash chromatography eluting with dichloromethane/acetonitrile to provide 0.44 g (98% yield) of tert-Butyl 3-{5-[6-chloro-4-(ethylamino)pyridin-3-yl]-1,3,4-thiadiazol-2-yl}-3,8-diazabicyclo[3.2.1]octane-8-carboxylate as an off-white crystalline product. ESI(+)[M+H]⁺=451.9. ¹H NMR (300 MHz, DMSO-d₆), d: 8.59 (t, J=5.4 Hz, 1H), 8.19 (s, 1H), 6.80 (s, 1H), 4.27 (s, 2H), 3.65 (m, 2H), 3.30 (m, 4H), 1.91 (m, 2H), 1.73 (m, 2H), 1.43 (s, 9H), 1.25 (t, 3H).

Step 2: tert-Butyl 3-{5-[6-chloro-4-(ethylamino)pyridin-3-yl]-1,3,4-thiadiazol-2-yl}-3,8-diazabicyclo[3.2.1]octane-8-carboxylate (0.44 g, 0.98 mmol, 1.0 eq), 7-(4,4,5,5-tetramethyl-1,3,2-dioxaborolan-2-yl)pyrrolo[1,2-b]pyridazine-3-carbonitrile (0.387 g, 1.4 mmol, 1.4 eq), K₃PO₄ (0.414 g, 1.951 mmol, 2.0 eq) and XPhos Pd G3 (0.083 g, 0.1 mmol, 0.1 eq) were suspended in 1,2-dimetoxyethane (13.94 ml, 0.07 M). The mixture was degassed with argon for 20 min and stirred at 120° C. overnight. The crude material was purified by silica gel flash chromatography eluting with dichloromethane/2-propanol (9:1) to provide 0.31 g (51% yield) of tert-butyl 3-[5-(6-{3-cyanopyrrolo[1,2-b]pyridazin-7-yl}-4-(ethylamino)pyridin-3-yl)-1,3,4-thiadiazol-2-yl]-3,8-diazabicyclo[3.2.1]octane-8-carboxylate as a yellow solid. ESI(+)[M+H]⁺=559.0. ¹H NMR (300 MHz, DMSO-d₆), δ: 8.83 (d, J=2.2 Hz, 1H), 8.72 (d, J=2.2 Hz, 1H), 8.49 (t, J=10.2 Hz, 2H), 8.16 (s, 1H), 7.85 (d, J=4.8 Hz, 1H), 7.11 (d, J=4.8 Hz, 1H), 4.29 (s, 2H), 3.68 (d, J=11.2 Hz, 2H), 3.50-3.37 (m, 4H), 1.93 (s, 2H), 1.76 (d, J=7.4 Hz, 2H), 1.45 (s, 9H), 1.34 (t, J=7.1 Hz, 3H).

Step 3: To a solution of tert-butyl 3-[5-(6-{3-cyanopyrrolo[1,2-b]pyridazin-7-yl}-4-(ethylamino)pyridin-3-yl)-1,3,4-thiadiazol-2-yl]-3,8-diazabicyclo[3.2.1]octane-8-carboxylate (0.31 g, 0.5 mmol, 1.0 eq) in anhydrous dichloromethane (5.0 ml, 0.1 M) trifluoroacetic acid (0.8 ml, 10.0 mmol, 20.0 eq) was added and the resulting mixture was stirred at room temperature for 1 h. After evaporation of all volatiles, the crude residue was triturated with anhydrous diethyl ether to provide 0.21 g (89% yield) of 7-[5-(5-{3,8-diazabicyclo[3.2.1]octan-3-yl}-1,3,4-thiadiazol-2-yl)-4-(ethylamino)pyridin-2-yl]pyrrolo[1,2-b]pyridazine-3-carbonitrile as a yellow solid. LCMS: ESI(+)[M+H]⁺=458.09. ¹H NMR (300 MHz, DMSO-d₆) δ: 9.19 (m, 3H), 8.95 (d, J=2.2 Hz, 1H), 8.82 (d, J=2.2 Hz, 1H), 8.57 (s, 1H), 8.11-7.95 (m, 2H), 7.21 (d, J=5.0 Hz, 1H), 4.23 (m, 2H), 3.95-3.82 (m, 2H), 3.65-3.60 (br m, 4H), 2.10-1.91 (m, 4H), 1.34 (t, J=7.1 Hz, 3H).

Intermediate AL: 7-(4-{[(3S)-oxolan-3-yl]amino}-5-[5-(piperazin-1-yl)-1,3,4-thiadiazol-2-yl]pyridin-2-yl)pyrrolo[1,2-b]pyridazine-3-carbonitrile

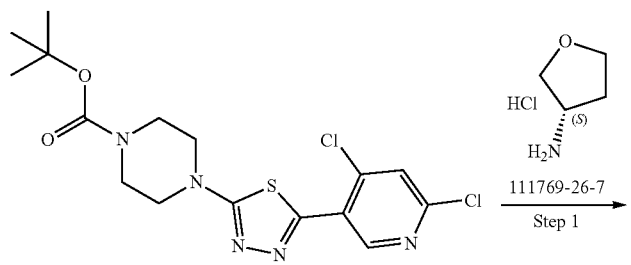

-continued

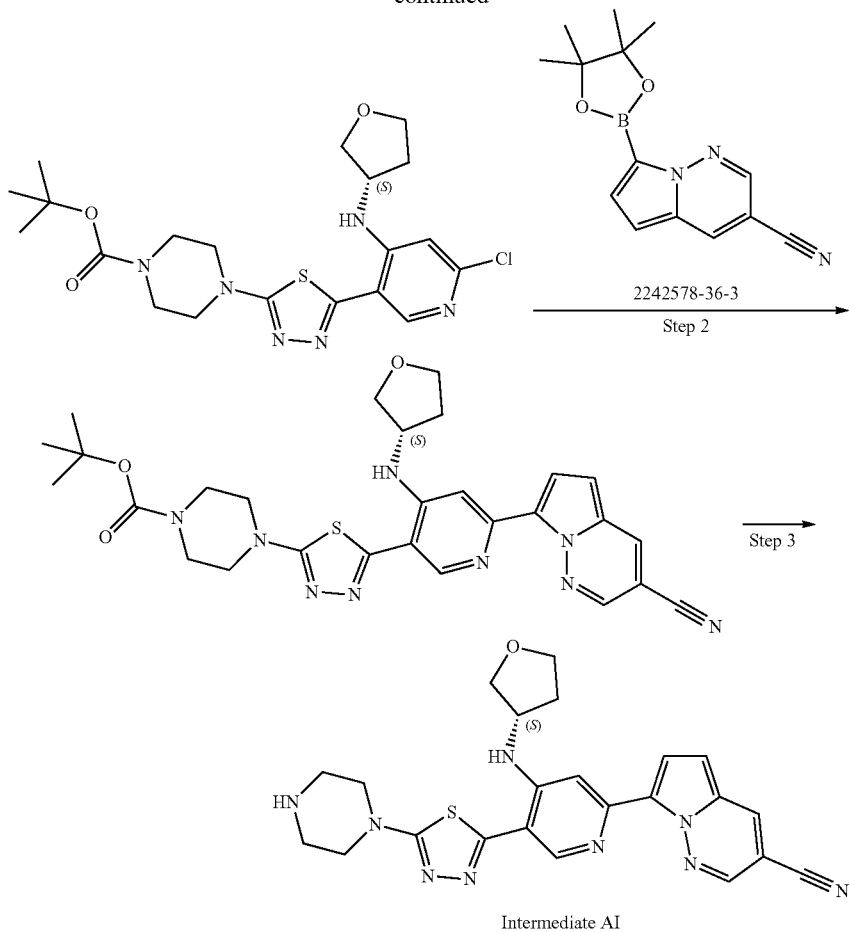

Intermediate AI

Step 1: To a solution of tert-butyl 4-[5-(4,6-dichloropyridin-3-yl)-1,3,4-thiadiazol-2-yl]piperazine-1-carboxylate (1.4 g, 1 eq) in DMF (3.3 ml, 1 M) and t-BuOH (11 ml, 0.3 M), was added DIPEA (8.7 ml, 15 eq) and (S)-3-aminotetrahydrofuran hydrochloride (4.12 g, 10 eq). The pressure vessel was sealed and the mixture was stirred at 100° C. overnight. Solvents were evaporated under reduced pressure. Then, the crude material was dissolved in DCM and washed with H$_2$O, NaHCO$_3$, brine. The organic phase was dried over Na$_2$SO$_4$, filtrated, and concentrated under reduced pressure to provide 420 mg (24% yield) of tert-butyl 4-[5-(6-chloro-4-{[(3S)-oxolan-3-yl]amino}pyridin-3-yl)-1,3,4-thiadiazol-2-yl]piperazine-1-carboxylate. ESI(+)[M+H]$^+$=467.26. $^1$H NMR (300 MHz, DMSO-d$_6$) δ 8.86 (d, J=6.9 Hz, 1H), 8.22 (s, 1H), 6.91 (s, 1H), 4.46-4.31 (m, 1H), 3.96-3.69 (m, 3H), 3.64 (dd, J=9.3, 2.5 Hz, 1H), 3.59-3.44 (m, 8H), 2.45-2.25 (m, 1H), 1.81 (dd, J=8.0, 5.0 Hz, 1H), 1.43 (s, 9H).

Step 2: tert-Butyl 4-[5-(6-chloro-4-{[(3S)-oxolan-3-yl]amino}pyridin-3-yl)-1,3,4-thiadiazol-2-yl]piperazine-1-carboxylate (420 mg, 0.9 mmol, 1 eq), 7-(4,4,5,5-tetramethyl-1,3,2-dioxaborolan-2-yl)pyrrolo[1,2-b]pyridazine-3-carbonitrile (0.267 g, 1.26 mmol, 1.4 eq), K$_3$PO$_4$ (0.382 g, 1.8 mmol, 2 eq) and XPhos Pd G3 (3.36 g, 0.0.063 mmol, 0.07 eq) were suspended in DME (13 ml, 0.07 M). The mixture was degassed with argon for 20 min and stirred at 120° C. overnight. The crude material was purified by silica gel flash chromatography eluting with DCM/acetonitrile and DCM/i-PrOH to provide 225 mg (53% yield) of tert-butyl 4-[5-(6-{3-cyanopyrrolo[1,2-b]pyridazin-7-yl}-4-{[(3S)-oxolan-3-yl]amino}pyridin-3-yl)-1,3,4-thiadiazol-2-yl]piperazine-1-carboxylate as a yellow solid. ESI(+)[M+H]$^+$=575.42. $^1$H NMR (300 MHz, DMSO-d$_6$) δ 8.85 (s, 1H), 8.80-8.69 (m, 2H), 8.52 (s, 1H), 8.22 (s, 1H), 7.85 (d, J=5.0 Hz, 1H), 7.12 (d, J=4.6 Hz, 1H), 4.43-4.27 (m, 1H), 4.10-4.00 (m, 1H), 4.00-3.79 (m, 2H), 3.79-3.70 (m, 1H), 3.59-3.48 (m, 8H), 2.01-1.87 (m, 1H), 1.44 (s, 9H).

Step 3: To a solution of tert-butyl 4-[5-(6-{3-cyanopyrrolo[1,2-b]pyridazin-7-yl}-4-{[(3S)-oxolan-3-yl]amino}pyridin-3-yl)-1,3,4-thiadiazol-2-yl]piperazine-1-carboxylate (225 mg, 0.384 mmol, 1 eq) in DCM (3 ml), TFA (2 ml) was added and the mixture was stirred at rt. After 1.5 h, the solvents were evaporated under reduced pressure. The crude material was suspended in Et$_2$O and sonicated for 30 min. The solid was filtrated off to provide 160 mg (81% yield) affording 7-(4-{[(3S)-oxolan-3-yl]amino}-5-[5-(piperazin-1-yl)-1,3,4-thiadiazol-2-yl]pyridin-2-yl)pyrrolo[1,2-b]pyridazine-3-carbonitrile (TFA salt) as a yellow solid. LCMS: ESI(+)[M+H]$^+$=473.98. $^1$H NMR (300 MHz, DMSO-d$_6$) δ 9.28 (s, 1H), 9.03-8.88 (m, 3H), 8.84 (d, J=1.9 Hz, 1H), 8.61 (s, 1H), 8.14 (s, 1H), 7.99 (d, J=4.8 Hz, 1H), 7.20 (d, J=4.9 Hz, 1H), 4.53 (s, 1H), 4.04 (dd, J=9.5, 5.4 Hz, 2H), 3.93-3.80 (m, 7H), 3.32 (s, 4H), 2.02-1.89 (s, 1H).

Intermediate AJ: 7-(4-{[(3R)-oxolan-3-yl]amino}-5-[5-(piperazin-1-yl)-1,3,4-thiadiazol-2-yl]pyridin-2-yl)pyrrolo[1,2-b]pyridazine-3-carbonitrile

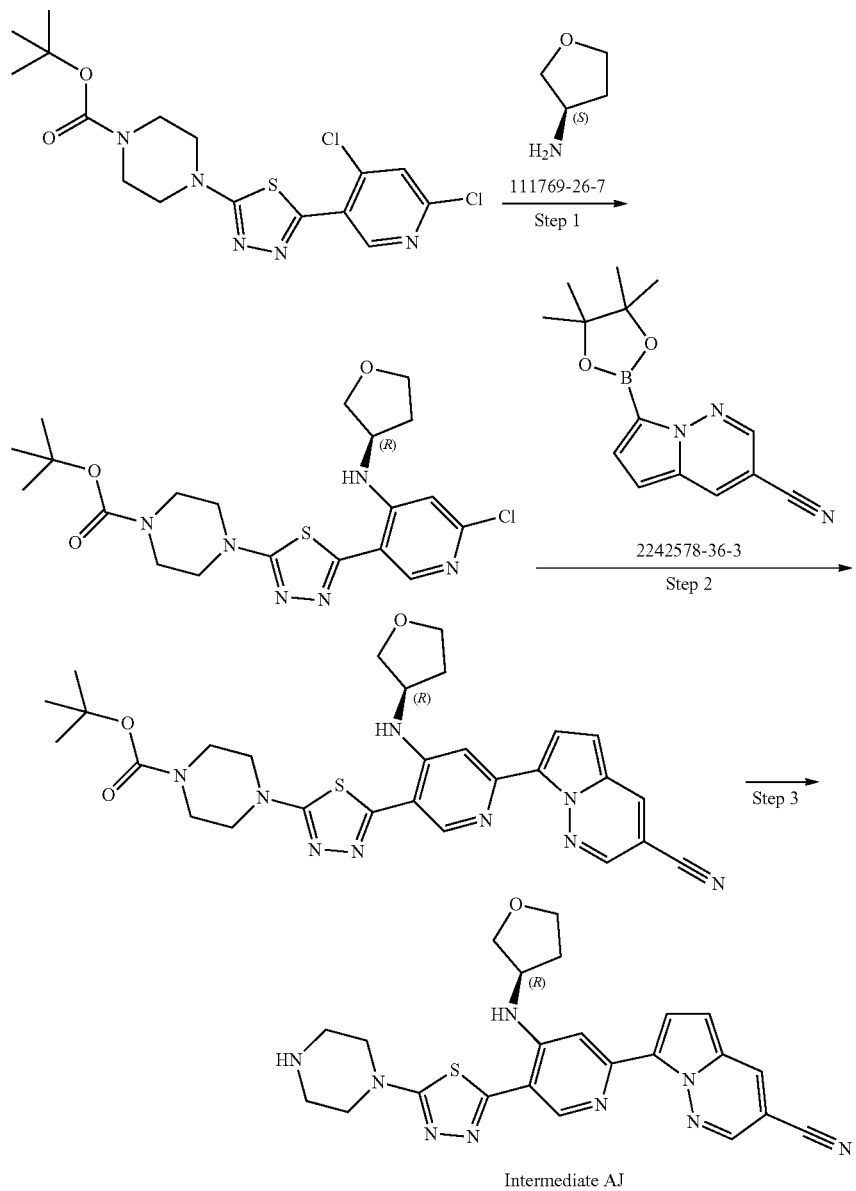

Intermediate AJ

Step 1: To a solution of tert-butyl 4-[5-(4,6-dichloropyridin-3-yl)-1,3,4-thiadiazol-2-yl]piperazine-1-carboxylate (1.74 g, 4.18 mmol, 1 eq) was dissolved in DMF (4 ml, 1 M) and t-BuOH (14 ml, 0.3 M). Then, was added DIPEA (9 ml, 15 eq) and (R)-3-aminotetrahydrofuran (3.6 g, 10 eq). The pressure vessel was sealed, and the mixture was stirred at 100° C. overnight. Solvents were evaporated under reduced pressure. Then, the crude material was dissolved in DCM and washed with H$_2$O, NaHCO$_3$, brine, and the organic phase was dried over Na$_2$SO$_4$, filtrated, and evaporated under reduced pressure to provide 1.7 g (79% yield) of tert-butyl 4-[5-(6-chloro-4-{[(3R)-oxolan-3-yl]amino}pyridin-3-yl)-1,3,4-thiadiazol-2-yl]piperazine-1-carboxylate. LCMS: ESI(+)[M+H]$^+$=467.27. $^1$H NMR (300 MHz, DMSO-d$_6$) δ 8.86 (d, J=6.9 Hz, 1H), 8.22 (s, 1H), 6.91 (s, 1H), 4.46-4.31 (m, 1H), 3.96-3.69 (m, 3H), 3.64 (dd, J=9.3, 2.5 Hz, 1H), 3.59-3.44 (m, 8H), 2.45-2.25 (m, 1H), 1.81 (dd, J=8.0, 5.0 Hz, 1H), 1.43 (s, 9H).

Step 2: tert-Butyl 4-[5-(6-chloro-4-{[(3R)-oxolan-3-yl]amino}pyridin-3-yl)-1,3,4-thiadiazol-2-yl]piperazine-1-carboxylate (1.7 g, 3.3 mmol, 1 eq), 7-(4,4,5,5-tetramethyl-1,3,2-dioxaborolan-2-yl)pyrrolo[1,2-b]pyridazine-3-carbonitrile (1.36 g, 5.04 mmol, 1.4 eq), K$_3$PO$_4$ (1.53 g, 7.2 mmol, 2 eq) and XPhos Pd G3 (0.213 g, 0.252 mmol, 0.07 eq) were suspended in DME (52 ml, 0.07 M). The mixture was degassed with argon for 20 min and stirred at 120° C. overnight. The crude material was purified by silica gel flash chromatography eluting with DCM/acetonitrile and DCM/i-PrOH) to provide 670 mg (33% yield) of tert-butyl 4-[5-(6-{3-cyanopyrrolo[1,2-b]pyridazin-7-yl}-4-{[(3R)-oxolan-3-yl]amino}pyridin-3-yl)-1,3,4-thiadiazol-2-yl]piperazine-1-carboxylate as a yellow solid. ESI(+)[M+H]$^+$=574.42. $^1$H NMR (300 MHz, DMSO-d$_6$) δ 8.84 (d, J=2.2 Hz, 1H), 8.76

(d, J=2.1 Hz, 1H), 8.51 (s, 1H), 8.21 (s, 1H), 7.85 (d, J=4.8 Hz, 1H), 7.12 (d, J=4.8 Hz, 1H), 4.35 (s, 2H), 4.12-3.71 (m, 6H), 3.61-3.42 (m, 8H), 1.93 (s, 1H), 1.44 (s, 9H).

Step 3: tert-Butyl 4-[5-(6-{3-cyanopyrrolo[1,2-b]pyridazin-7-yl}-4-{[(3R)-oxolan-3-yl]amino}pyridin-3-yl)-1,3,4-thiadiazol-2-yl]piperazine-1-carboxylate (670 mg, 1.11 mmol, 1.0 eq) was dissolved in DCM (10 ml, 0.3 M) and the solution was cooled down to 0° C. Then, TFA (7.6 g, 10 eq) was added dropwise and the mixture was stirred at rt for 3 h. At completion, the mixture was evaporated to dryness. The crude was suspended in Et$_2$O and sonicated for 30 min. The solid was filtrated off to provide 380 mg (65% yield) of 7-(4-{[(3R)-oxolan-3-yl]amino}-5-[5-(piperazin-1-yl)-1,3,4-thiadiazol-2-yl]pyridin-2-yl)pyrrolo[1,2-b]pyridazine-3-carbonitrile (TFA salt) as a yellow solid. LCMS: ESI(+)[M+H]$^+$=474.43. H NMR (300 MHz, DMSO-d$_6$): δ 8.96-8.83 (m, 4H), 8.80 (d, J=2.1 Hz, 1H), 8.58 (s, 1H), 8.22 (s, 1H), 7.90 (d, J=4.8 Hz, 1H), 7.16 (d, J=4.9 Hz, 1H), 4.43 (s, 1H), 4.06 (dd, J=9.3, 5.3 Hz, 1H), 3.95-3.72 (m, 8H), 3.35-3.21 (m, 4H), 2.01-1.86 (m, 1H).

Intermediate AK: 7-(5-(5-(3,8-diazabicyclo[3.2.1]octan-3-yl)-1,3,4-thiadiazol-2-yl)-4-(((R)-tetrahydro-furan-3-yl)amino)pyridin-2-yl)pyrrolo[1,2-b]pyridazine-3-carbonitrile

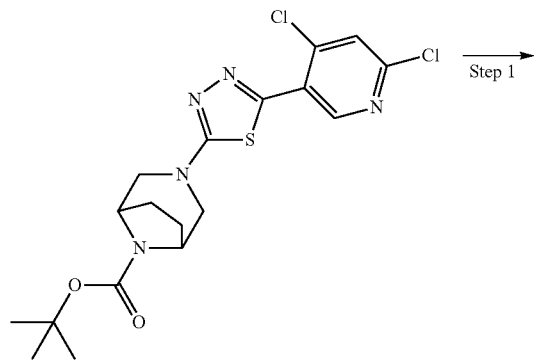

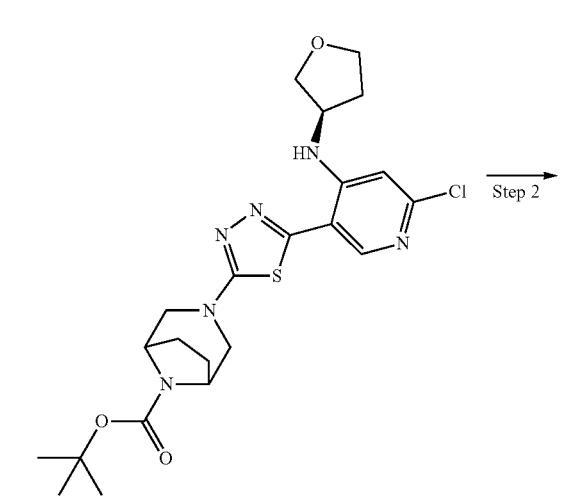

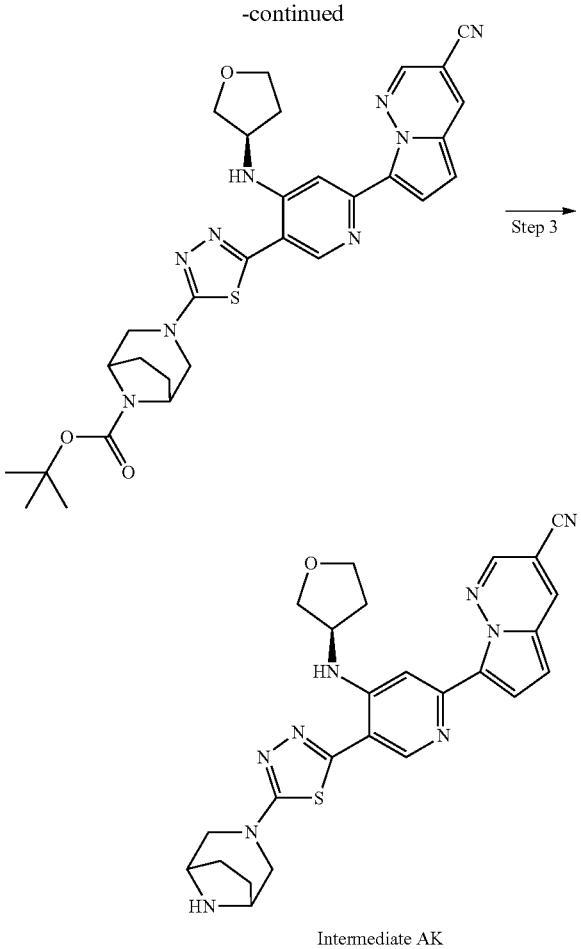

Intermediate AK

Step 1: A solution of tert-butyl 3-[5-(4,6-dichloropyridin-3-yl)-1,3,4-thiadiazol-2-yl]-3,8-diazabicyclo[3.2.1]octa-ne-8-carboxylate (1.0 g, 2.26 mmol, 1.0 eq), (R)-3-Aminotetrahydrofurane (1.38 g, 15.83 mmol, 7 eq), potassium carbonate anhydrous (2.5 g, 18.08 mmol, 8.0 eq) and DIPEA (1.5 ml, 11.30 mmol, 8.0 eq) in anh. acetonitrile (23 ml, 0.1 M) and DMF (2.5 ml, 1 M) was stirred at 80° C. overnight. Then, all volatiles were evaporated under reduced pressure and the crude material was purified with silica gel flash chromatography eluting with dichloromethane/acetonitrile to provide 1.1 g (94% yield) of tert-butyl 3-(5-(6-chloro-4-(((R)-tetrahydrofuran-3-yl)amino)pyridin-3-yl)-1,3,4-thiadiazol-2-yl)-3,8-diazabicyclo[3.2.1] octane-8-carboxylate as an off-white crystalline product. LCMS: ESI(+)[M+H]$^+$= 493.9. $^1$H NMR (300 MHz, DMSO-d$_6$), d: 8.87 (d, J=7.0 Hz, 1H), 8.22 (s, 1H), 6.90 (s, 1H), 4.37 (m, 1H), 4.27 (m, 2H), 3.87 (m, 3H), 3.65 (m, 3H), 3.34 (m, 2H), 2.39-2.26 (m, 1H), 1.91 (m, 2H), 1.77 (m, 3H), 1.43 (s, 9H).

Step 2: tert-butyl 3-(5-(6-chloro-4-(((R)-tetrahydrofuran-3-yl)amino)pyridin-3-yl)-1,3,4-thiadiazol-2-yl)-3,8-diazabicyclo[3.2.1]octane-8-carboxylate (1.1 g, 2.12 mmol, 1.0 eq), 7-(4,4,5,5-tetramethyl-1,3,2-dioxaborolan-2-yl)pyr-rolo[1,2-b]pyridazine-3-carbonitrile (1.35 g, 5.27 mmol, 1.4 eq), K$_3$PO$_4$(1.0 g, 5.1 mmol, 2.0 eq) and XPhos Pd G3 (0.220 g, 0.25 mmol, 0.1 eq) were suspended in 1,2-dimetoxyethane (36 ml, 0.07 M). The mixture was degassed with argon for 20 min and stirred at 120° C. overnight. The crude material was purified by silica gel flash chromatography eluting with DCM/2-propanol to provide 0.65 g (46% yield) of tert-butyl 3-(5-(6-(3-cyanopyrrolo[1,2-b]pyridazin-7-yl)-4-(((R)-tetrahydrofuran-3-yl)amino)pyridin-3-yl)-1,3,4-thiadiazol-2-yl)-3,8-diazabicyclo[3.2.1]octane-8-carboxylate as a yellow solid. LCMS: ESI(+)[M+H]$^+$=574.42. H NMR (300 MHz, DMSO-$d_6$) δ 8.84 (d, J=2.2 Hz, 1H), 8.76 (d, J=2.1 Hz, 1H), 8.51 (s, 1H), 8.21 (s, 1H), 7.85 (d, J=4.8 Hz, 1H), 7.12 (d, J=4.8 Hz, 1H), 4.35 (s, 2H), 4.12-3.71 (m, 6H), 3.61-3.42 (m, 8H), 1.93 (s, 1H), 1.44 (s, 9H).

Step 3: To a solution of tert-butyl 3-(5-(6-(3-cyanopyrrolo[1,2-b]pyridazin-7-yl)-4-(((R)-tetrahydrofuran-3-yl)amino)pyridin-3-yl)-1,3,4-thiadiazol-2-yl)-3,8-diazabicyclo[3.2.1]octane-8-carboxylate (0.64 g, 0.96 mmol, 1.0 eq) in dichloromethane (3.5 ml, 0.3 M) the trifluoroacetic acid (1.47 ml, 19.21 mmol, 20.0 eq) was added and the resulting mixture was stirred at room temperature for 3 h. After evaporation of all volatiles under reduced pressure and conversion to the free amine, the crude material was purified by silica gel flash chromatography eluting with dichloromethane/methanol to provide 0.1 g (19% yield) of 7-(5-(5-(3,8-diazabicyclo[3.2.1]octan-3-yl)-1,3,4-thiadiazol-2-yl)-4-(((R)-tetrahydrofuran-3-yl)amino)pyridin-2-yl)pyrrolo[1,2-b]pyridazine-3-carbonitrile as a yellow solid. LCMS: ESI(+)[M+H]$^+$=500.13. $^1$H NMR (300 MHz, DMSO-$d_6$) δ: 8.83 (d, J=2.2 Hz, 1H), 8.81-8.71 (m, 2H), 8.49 (s, 1H), 8.19 (s, 1H), 7.84 (d, J=4.8 Hz, 1H), 7.11 (d, J=4.8 Hz, 1H), 4.34 (s, 1H), 4.10-4.02 (m, 1H), 3.95-3.79 (m, 2H), 3.72 (m, 1H), 3.52 (d, J=9.5 Hz, 4H), 3.42 (s, 1H), 2.42 (s, 2H), 1.93 (d, J=8.3 Hz, 1H), 1.71 (d, J=5.7 Hz, 4H).

Intermediate AL: 7-[4-(cyclopropylamino)-5-(5-{3,8-diazabicyclo[3.2.1]octan-3-yl}-1,3,4-thiadiazol-2-yl)pyridin-2-yl]pyrrolo[1,2-b]pyridazine-3-carbonitrile bis(trifluoroacetate)

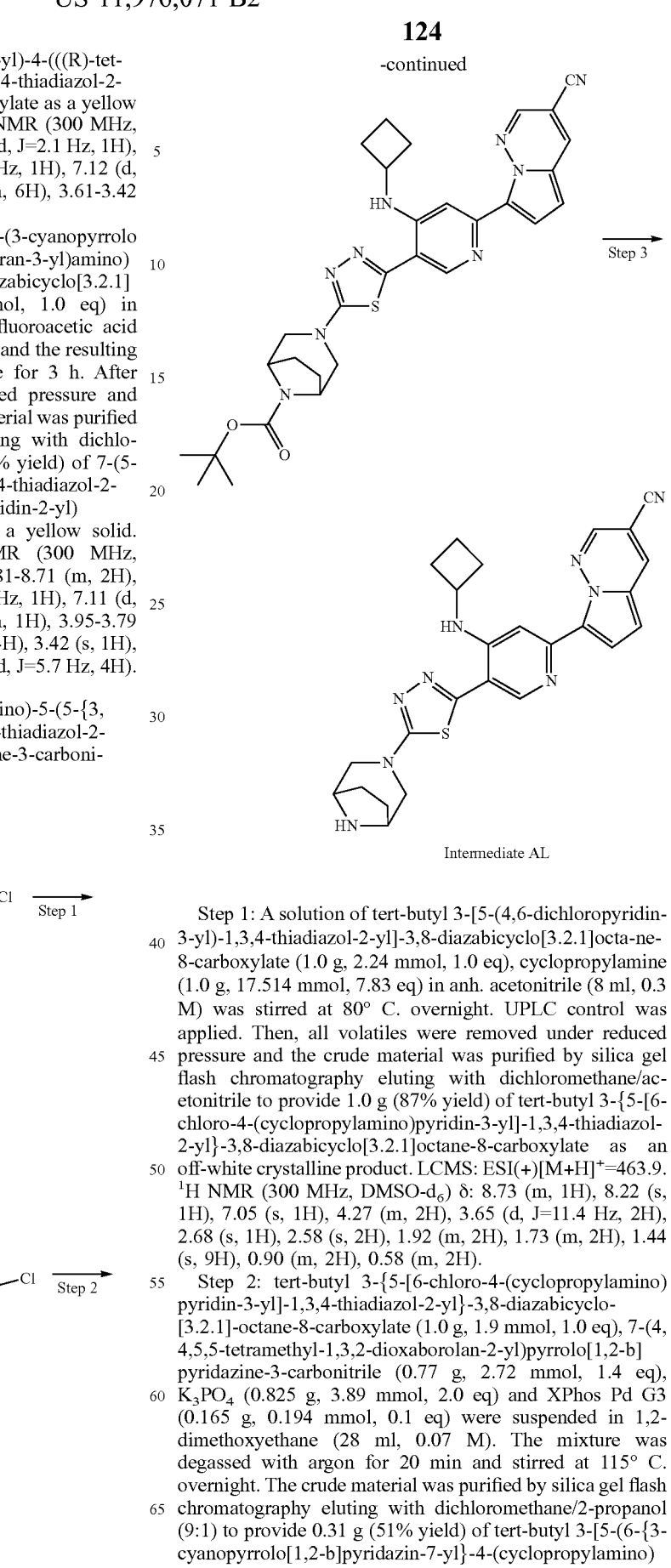

Intermediate AL

Step 1: A solution of tert-butyl 3-[5-(4,6-dichloropyridin-3-yl)-1,3,4-thiadiazol-2-yl]-3,8-diazabicyclo[3.2.1]octa-ne-8-carboxylate (1.0 g, 2.24 mmol, 1.0 eq), cyclopropylamine (1.0 g, 17.514 mmol, 7.83 eq) in anh. acetonitrile (8 ml, 0.3 M) was stirred at 80° C. overnight. UPLC control was applied. Then, all volatiles were removed under reduced pressure and the crude material was purified by silica gel flash chromatography eluting with dichloromethane/acetonitrile to provide 1.0 g (87% yield) of tert-butyl 3-{5-[6-chloro-4-(cyclopropylamino)pyridin-3-yl]-1,3,4-thiadiazol-2-yl}-3,8-diazabicyclo[3.2.1]octane-8-carboxylate as an off-white crystalline product. LCMS: ESI(+)[M+H]$^+$=463.9. $^1$H NMR (300 MHz, DMSO-$d_6$) δ: 8.73 (m, 1H), 8.22 (s, 1H), 7.05 (s, 1H), 4.27 (m, 2H), 3.65 (d, J=11.4 Hz, 2H), 2.68 (s, 1H), 2.58 (s, 2H), 1.92 (m, 2H), 1.73 (m, 2H), 1.44 (s, 9H), 0.90 (m, 2H), 0.58 (m, 2H).

Step 2: tert-butyl 3-{5-[6-chloro-4-(cyclopropylamino)pyridin-3-yl]-1,3,4-thiadiazol-2-yl}-3,8-diazabicyclo-[3.2.1]-octane-8-carboxylate (1.0 g, 1.9 mmol, 1.0 eq), 7-(4,4,5,5-tetramethyl-1,3,2-dioxaborolan-2-yl)pyrrolo[1,2-b]pyridazine-3-carbonitrile (0.77 g, 2.72 mmol, 1.4 eq), $K_3PO_4$ (0.825 g, 3.89 mmol, 2.0 eq) and XPhos Pd G3 (0.165 g, 0.194 mmol, 0.1 eq) were suspended in 1,2-dimethoxyethane (28 ml, 0.07 M). The mixture was degassed with argon for 20 min and stirred at 115° C. overnight. The crude material was purified by silica gel flash chromatography eluting with dichloromethane/2-propanol (9:1) to provide 0.31 g (51% yield) of tert-butyl 3-[5-(6-{3-cyanopyrrolo[1,2-b]pyridazin-7-yl}-4-(cyclopropylamino)

pyridin-3-yl)-1,3,4-thiadiazol-2-yl]-3,8-diazabicyclo[3.2.1]octane-8-carboxylate as a yellow solid. ESI(+)[M+H]⁺ =571.1. ¹H NMR (300 MHz, DMSO-d₆) δ: 8.84 (d, J=2.2 Hz, 1H), 8.76 (d, J=2.2 Hz, 1H), 8.66 (d, J=4.0 Hz, 2H), 8.49 (s, 1H), 7.87 (d, J=4.8 Hz, 1H), 7.13 (d, J=4.8 Hz, 1H), 4.28 (s, 2H), 3.67 (d, J=11.5 Hz, 2H), 3.37 (m, 2H), 2.74 (m, 1H), 1.93 (m, 2H), 1.74 (m, 2H), 1.44 (s, 9H), 1.00 (m, 2H), 0.64 (m, 2H).

Step 3: To a solution of tert-butyl 3-[5-(6-{3-cyanopyrrolo[1,2-b]pyridazin-7-yl}-4-(cyclopropylamino)pyridin-3-yl)-1,3,4-thiadiazol-2-yl]-3,8-diazabicyclo[3.2.1]octane-8-carboxylate (0.6 g, 0.85 mmol, 1.0 eq) in anh. dichloromethane (8.5 ml, 0.1 M) trifluoroacetic acid (1.3 ml, 17 mmol, 20.0 eq) was added and the resulting mixture was stirred at room temperature for 1 h. UPLC control was applied. After evaporation of all volatiles, the crude residue was triturated with anhydrous diethyl ether to provide 0.6 g (99% yield) of 7-[4-(cyclopropylamino)-5-(5-{3,8-diazabicyclo[3.2.1]octan-3-yl}-1,3,4-thiadiazol-2-yl)pyridin-2-yl]pyrrolo[1,2-b]pyridazine-3-carbonitrile bis(trifluoroacetate) as a yellow solid. LCMS: ESI(+)[M+H]⁺=470.194. ¹H NMR (300 MHz, DMSO-d₆) δ: 9.36 (m, 2H), 9.17 (s, 1H), 8.94 (s, 1H), 8.85 (s, 1H), 8.59 (d, J=6.9 Hz, 2H), 8.00 (d, J=4.9 Hz, 1H), 7.21 (d, J=4.9 Hz, 1H), 4.24 (s, 2H), 3.87 (d, J=12.1 Hz, 2H), 3.63 (d, J=12.1 Hz, 2H), 2.86 (s, 1H), 2.13-1.83 (m, 4H), 1.07 (m, 2H), 0.72 (m, 2H).

Intermediate AM: 7-[4-(cyclobutylamino)-5-(5-{3,8-diazabicyclo[3.2.1]octan-3-yl}-1,3,4-thiadiazol-2-yl)pyridin-2-yl]pyrrolo[1,2-b]pyridazine-3-carbonitrile trifluoroacetate

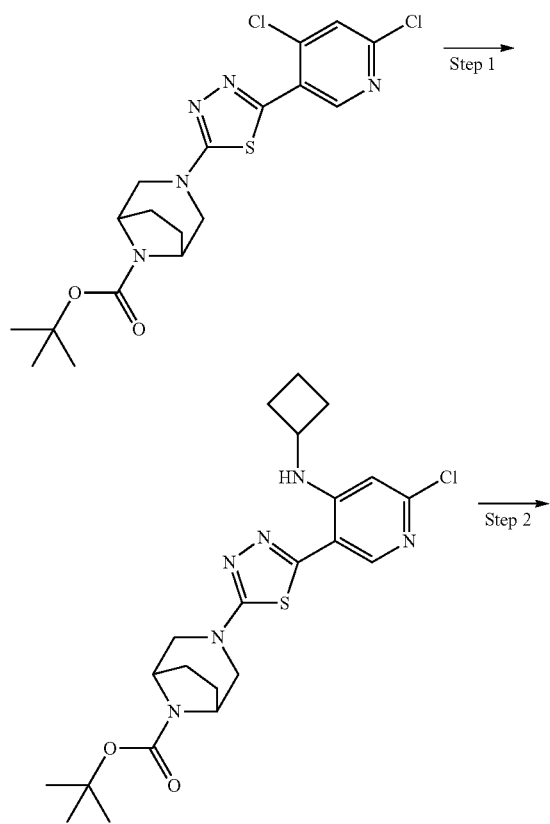

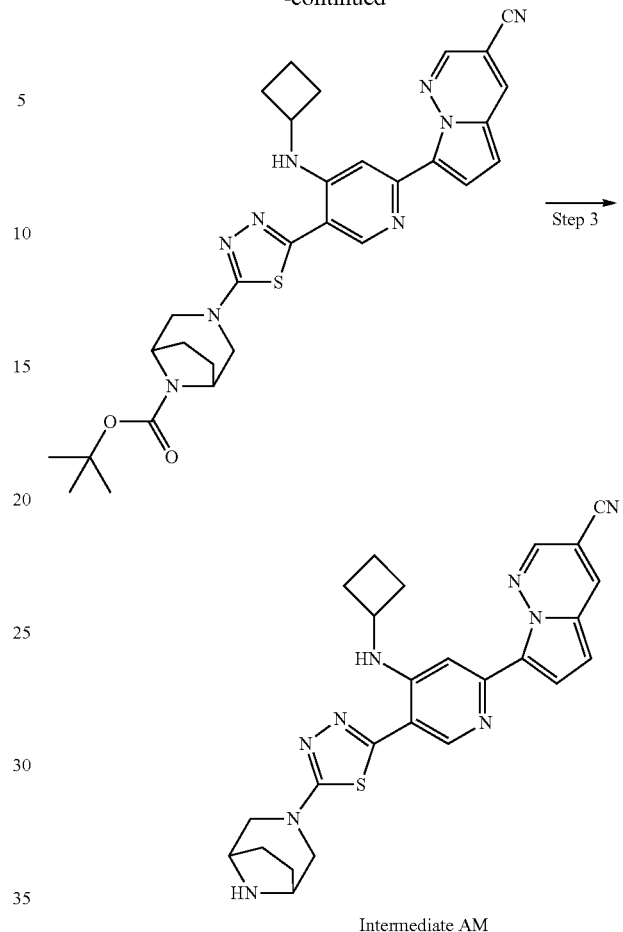

Intermediate AM

Step 1: A solution of tert-butyl 3-[5-(4,6-dichloropyridin-3-yl)-1,3,4-thiadiazol-2-yl]-3,8-diazabicyclo[3.2.1]octane-8-carboxylate (1.1 g, 2.5 mmol, 1.0 eq) and cyclobutylamine (1.751 g, 24.618 mmol, 10.0 eq) in dry acetonitrile (8 ml, 0.3 M) was heated at 80° C. overnight. All volatiles were removed under low pressure and the crude material was purified by silica gel flash chromatography eluting with dichloromethane/acetonitrile to provide 1.05 g (81% yield) of tert-butyl 3-{5-[6-chloro-4-(cyclobutylamino)pyridin-3-yl]-1,3,4-thiadiazol-2-yl}-3,8-diazabicyclo[3.2.1]octane-8-carboxylate as an off-white crystalline product. ESI(+)[M+H]⁺=479.0. ¹H NMR (300 MHz, DMSO-d₆) δ: 8.82 (d, J=6.2 Hz, 1H), 8.20 (s, 1H), 6.68 (s, 1H), 4.27 (m, 2H), 4.15 (m, 1H), 3.66 (d, J=11.1 Hz, 2H), 2.44 (s, 3H), 1.90 (s, 4H), 1.85-1.66 (m, 5H), 1.43 (s, 9H).

Step 2: tert-Butyl 3-{5-[6-chloro-4-(cyclobutylamino)pyridin-3-yl]-1,3,4-thiadiazol-2-yl}-3,8-diazabicyclo[3.2.1]-octane-8-carboxylate (1.0 g, 1.992 mmol, 1.0 eq), 7-(4,4,5,5-tetramethyl-1,3,2-dioxaborolan-2-yl)pyrrolo[1,2-b]pyridazine-3-carbonitrile (0.79 g, 2.788 mmol, 1.4 eq), K₃PO₄ (0.845 g, 3.983 mmol, 2.0 eq) and XPhos Pd G3 (0.169 g, 0.199 mmol, 0.1 eq) were suspended in 1,2-dimethoxyethane (8 ml, 0.07 M). The mixture was degassed with argon for 20 min and stirred at 117° C. overnight. The crude material was purified by silica gel flash chromatography eluting with dichloromethane/2-propanol to provide 0.47 g (38% yield) of tert-Butyl 3-[5-(6-{3-cyanopyrrolo[1,2-b]pyridazin-7-yl}-4-(cyclobutylamino)pyridin-3-yl)-1,3,4-thiadiazol-2-yl]-3,8-diazabicyclo[3.2.1]octane-8-carboxylate as a yellow solid. ESI(+)[M+H]⁺=584.65. ¹H NMR (300 MHz, DMSO-d₆) δ: 8.83 (d, J=2.2 Hz, 1H), 8.78 (d, J=2.2 Hz, 1H), 8.68 (d, J=5.2 Hz, 1H), 8.48 (s, 1H), 8.10 (s, 1H), 7.84 (d, J=4.8 Hz, 1H), 7.11 (d, J=4.8 Hz, 1H), 4.28 (s, 2H), 4.22-4.10 (m, 1H), 3.68 (d, J=11.3 Hz, 2H), 2.68-2.52 (m, 5H), 2.05-1.84 (m, 6H), 1.76 (d, J=11.3 Hz, 2H), 1.44 (s, 9H).

Step 3: To a solution of tert-butyl 3-[5-(6-{3-cyanopyrrolo[1,2-b]pyridazin-7-yl}-4-(cyclobutylamino)-pyridin-3-yl)-1,3,4-thiadiazol-2-yl]-3,8-diazabicyclo[3.2.1]octane-8-carboxylate (0.47 g, 0.76 mmol, 1.0 eq) in anhydrous dichloromethane (8.5 ml, 0.1 M) trifluoroacetic acid (1.7 ml, 15 mmol, 20.0 eq) was added and the resulting mixture was stirred at room temperature for 1 h. All volatiles were evaporated and the crude residue was triturated with anhydrous diethyl ether to provide 0.35 g (91% yield) of 7-[4-(cyclobutylamino)-5-(5-{3,8-diazabicyclo[3.2.1]octan-3-yl}-1,3,4-thiadiazol-2-yl)pyridin-2-yl]pyrrolo[1,2-b]pyridazine-3-carbonitrile trifluoroacetate as a yellow solid. LCMS: ESI(+)[M+H]⁺=484.24. ¹H NMR (300 MHz, DMSO-d₆) δ: 9.27 (br m, 3H), 8.94 (d, J=2.2 Hz, 1H), 8.86 (d, J=2.2 Hz, 1H), 8.59 (s, 1H), 7.99 (d, J=5.8 Hz, 2H), 7.20 (d, J=4.9 Hz, 1H), 4.32 (m, 2H), 4.23 (s, 2H), 3.88 (d, J=12.9 Hz, 2H), 3.69-3.58 (m, 2H), 2.61 (d, J=5.3 Hz, 2H), 2.14-1.82 (m, 8H).

Intermediate AN: 7-{4-[(1-cyanocyclopropyl)amino]-5-{5-[(1R,5S)-3,8-diazabicyclo[3.2.1]octan-3-yl]-1,3,4-thiadiazol-2-yl}pyridin-2-yl}pyrrolo[1,2-b]pyridazine-3-carbonitrile

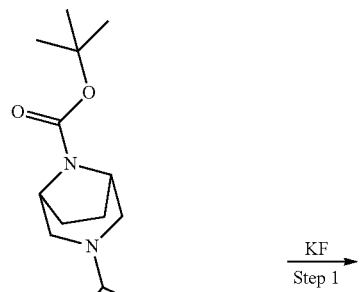

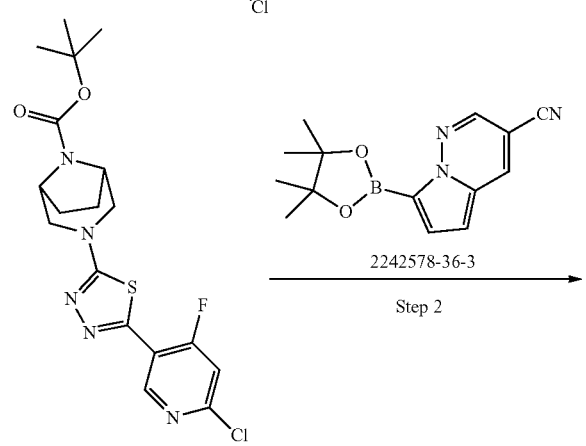

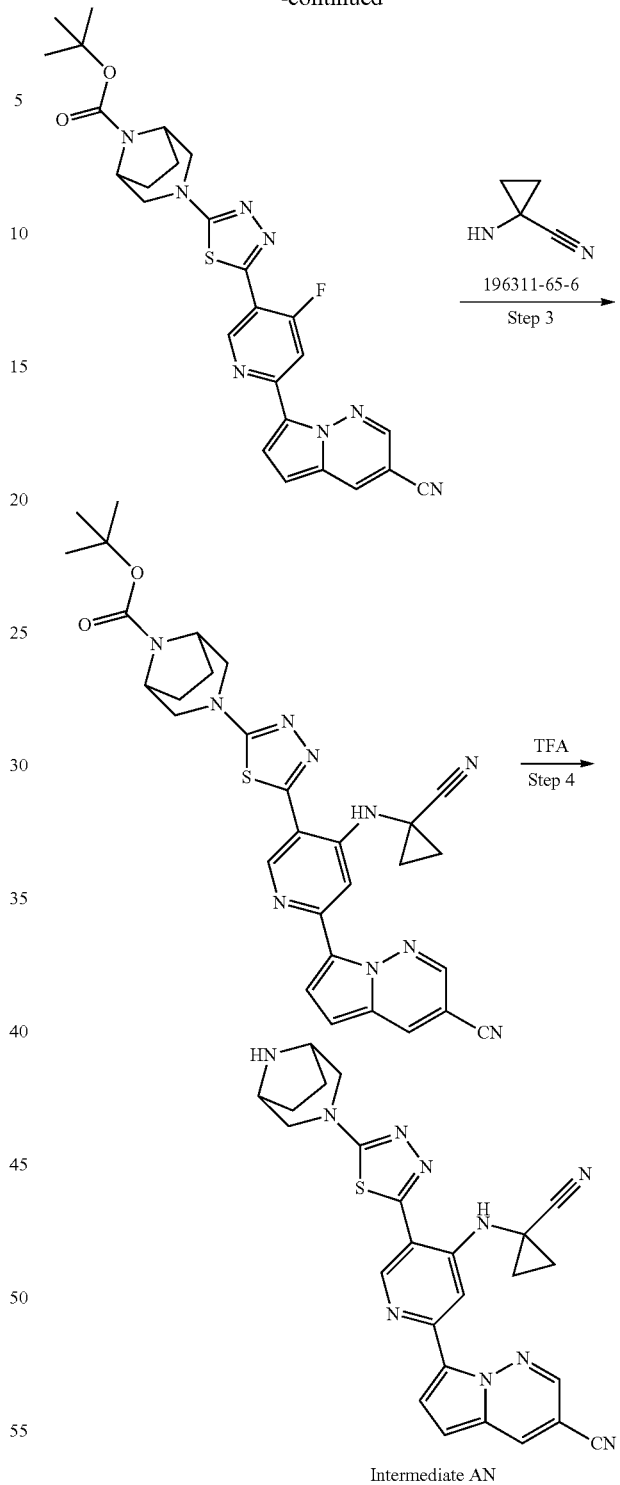

Intermediate AN

Step 1: Tert-butyl 3-[5-(4,6-dichloropyridin-3-yl)-1,3,4-thiadiazol-2-yl]-3,8-diazabicyclo[3.2.1]octane-8-carboxylate (5.0 g, 11.30 mmol, 1 eq), KF (755 mg, 12.99 mmol, 1.15 eq) and 18-crown-6 ether (1.49 g, 5.65 mmol, 0.5 eq) were dissolved in dimethyl sulfoxide anhydrous (41 mL), the reaction mixture was stirred at 105° C. for overnight. Then the reaction mixture was diluted with water (50 mL), extracted with DCM (3×100 mL). The DCM layer was washed 2 times with water and then with brine. The organic layer was dried over Na₂SO₄, filtered.

And solvent was removed under vacuum. The crude product 8.3 g was purified by FC using a gradient of 0 to 100% EtOAc in hexane to yield 4.1 g of tert-butyl 3-[5-(6-chloro-4-fluoropyridin-3-yl)-1,3,4-thiadiazol-2-yl]-3,8-diazabicyclo [3.2.1]octane-8-carboxylate as a white solid. LCMS: [C₁₈H₂₁ClFN₅O₂S], desired mass=425.9 observed mass=425.9 [M+H⁺]. ¹H NMR (300 MHz, DMSO-d6): δ 9.04 (d, J=10.0 Hz, 1H), 7.90 (d, J=10.4 Hz, 1H), 4.28 (s, 2H), 3.77-3.60 (m, 2H), 3.36-3.33 (m, 1H, merged with solvent residual peak), 3.39 (d, J=2.3 Hz, 1H), 1.91 (d, J=7.1 Hz, 2H), 1.74 (d, J=7.4 Hz, 2H), 1.44 (s, 9H).

Step 2: To a solution of tert-butyl 3-[5-(6-chloro-4-fluoropyridin-3-yl)-1,3,4-thiadiazol-2-yl]-3,8-diazabicyclo [3.2.1]octane-8-carboxylate (5.4 g, 12.68 mmol, 1.0 eq) in dimethoxyethane (181 mL, 0.07 M) in a glass reactor was added 7-(4,4,5,5-tetramethyl-1,3,2-dioxaborolan-2-yl)pyrrolo[1,2-b]pyridazine-3-carbonitrile (4.09 g, 15.21 mmol, 1.2 eq). The reactor was evacuated and backfilled with argon three times. Xphos Pd G3 (751 mg, 0.89 mmol, 0.07 eq) and potassium phosphate tribasic (5.38 g, 25.357 mmol, 2.0 eq) were added. Evacuation-backfilling was repeated three times, the reactor was sealed and the mixture was stirred at 120° C. for overnight. After completion of the reaction, the mixture was cooled to room temperature, diluted with DCM (200 ml), and concentrated. The residue was purified by FC using a gradient of ACN in DCM (0 to 100%) to yield 4.15 g (62% yield) of tert-butyl 3-[5-(6-{3-cyanopyrrolo[1,2-b]pyridazin-7-yl}-4-fluoropyridin-3-yl)-1,3,4-thiadiazol-2-yl]-3,8-diazabicyclo[3.2.1]octane-8-carboxylate as a pale yellow solid. LCMS: [C₂₆H₂₅FN₈O₂S], desired mass=532.6 observed mass=533.1 [M+H⁺]. ¹H NMR (300 MHz, CDCl₃): δ 9.52 (d, J=10.2 Hz, 1H), 8.71 (d, J=12.9 Hz, 1H), 8.39 (d, J=2.2 Hz, 1H), 8.25 (d, J=2.3 Hz, 1H), 8.06 (d, J=4.9 Hz, 1H), 7.04 (d, J=4.9 Hz, 1H), 4.43 (s, 2H), 3.64 (d, J=56.8 Hz, 4H), 2.06 (q, J=8.4, 6.9 Hz, 2H), 1.88 (d, J=7.4 Hz, 2H), 1.52 (s, 9H).

Step 3: To a solution of tert-butyl 3-[5-(6-{3-cyanopyrrolo[1,2-b]pyridazin-7-yl}-4-fluoropyridin-3-yl)-1,3,4-thiadiazol-2-yl]-3,8-diazabicyclo[3.2.1]octane-8-carboxylate (0.50 g, 0.76 mmol) and 1-aminocyclopropane-1-carbonitrile hydrochloride (2.5 g, 21 mmol) in DMSO anhydrous (10 ml, 0.1 M), was added DIPEA anhydrous (10 ml, 57 mmol). The reaction mixture was stirred at 130° C. overnight under an Ar atmosphere. The reaction mixture was cooled down to room temperature and diluted with CH₂Cl₂. The organic layer was washed with brine (3 times). The organic layer was dried over MgSO₄, then concentrated under reduced pressure. The residue was purified by silica gel flash chromatography eluting with CH₃CN/CH₂Cl₂ (gradient from 0% to 30% of CH₃CN) to provide 164 mg (36% yield) of tert-butyl 3-(5-{4-[(1-cyanocyclopropyl)amino]-6-{3-cyanopyrrolo[1,2-b]pyridazin-7-yl}pyridin-3-yl}-1,3,4-thiadiazol-2-yl)-3,8-diazabicyclo[3.2.1]octane-8-carboxylate as a yellow solid. LCMS: [C₃₀H₃₀N₁₀O₂S], observed mass=594.70 [M+H⁺]. ¹H NMR (300 MHz, DMSO-d₆): δ 9.03 (s, 1H), 8.90-8.87 (m, 1H), 8.86-8.83 (m, 2H), 8.62 (s, 1H), 7.92 (d, J=4.8 Hz, 1H), 7.16 (d, J=4.8 Hz, 1H), 4.36-4.24 (m, 2H), 3.78-3.60 (m, 2H), 3.43-3.35 (m, 2H), 1.96-1.81 (m, 4H), 1.80-1.70 (m, 2H), 1.58-1.47 (m, 2H), 1.44 (s, 9H).

Step 4: To a solution of tert-butyl 3-(5-{4-[(1-cyanocyclopropyl)amino]-6-{3-cyano pyrrolo[1,2-b]pyridazin-7-yl}pyridin-3-yl}-1,3,4-thiadiazol-2-yl)-3,8-diazabicyclo [3.2.1]octane-8-carboxylate (164 mg, 0.28 mmol) in anhydrous CH₂Cl₂ (2.8 ml, 0.1 M), TFA (0.40 ml, 5.6 mmol)

was added. The resulting mixture was stirred at room temperature for 2 h. The volatiles were removed under reduced pressure. The residue was triturated with anhydrous Et₂O to provide 149 mg (quantitative yield) of 7-{4-[(1-cyanocyclopropyl)amino]-5-{5-[(1R,5S)-3,8-diazabicyclo [3.2.1]octan-3-yl]-1,3,4-thiadiazol-2-yl}pyridin-2-yl}pyrrolo[1,2-b]pyridazine-3-carbonitrile (TFA salt) as a yellow solid. LCMS: ESI(+)[M+H]⁺=495.16. ¹H NMR (300 MHz, DMSO-d6): δ 9.30-9.02 (m, 3H), 8.92 (d, J=2.3 Hz, 1H), 8.88 (d, J=2.3 Hz, 1H), 8.86 (s, 1H), 8.67 (s, 1H), 7.95 (d, J=4.8 Hz, 1H), 7.19 (d, J=4.8 Hz, 1H), 4.30-4.15 (m, 2H), 3.93-3.80 (m, 2H), 3.68-3.53 (m, 2H), 2.10-1.94 (m, 4H), 1.95-1.83 (m, 2H), 1.56-1.49 (m, 2H).

Intermediate AO: 7-{4-[(cyanomethyl)amino]-5-{5-[(1R,5S)-3,8-diazabicyclo[3.2.1] octan-3-yl]-1,3,4-thiadiazol-2-yl}pyridin-2-yl}pyrrolo[1,2-b]pyridazine-3-carbonitrile

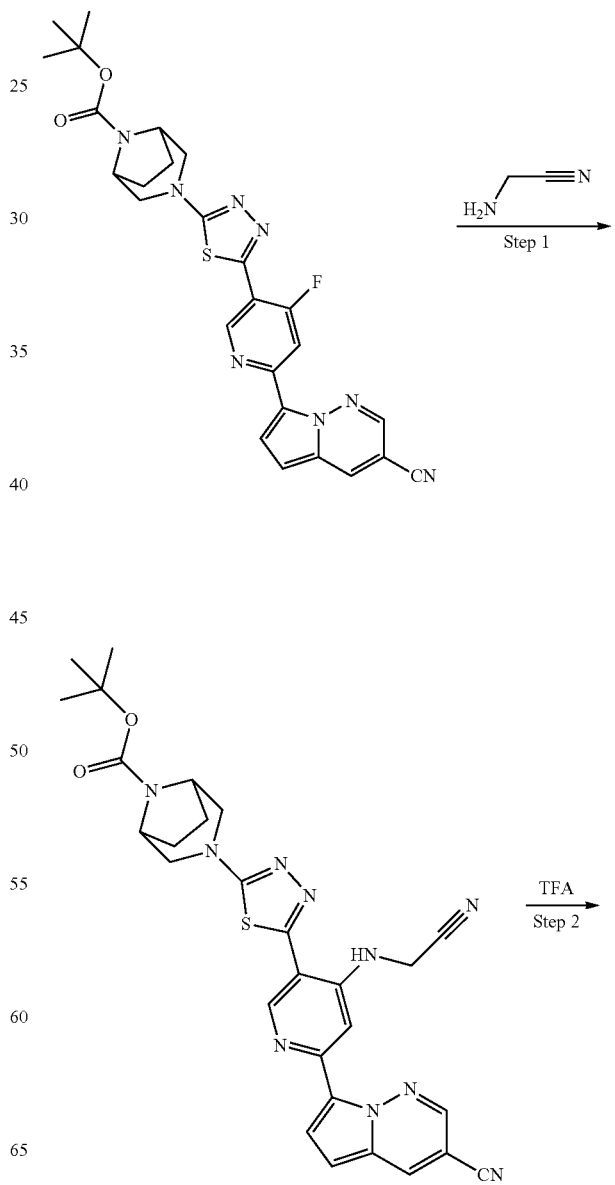

-continued

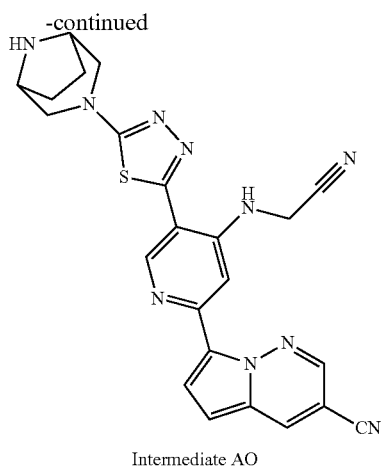

Intermediate AO

Step 1: To a solution of tert-butyl 3-[5-(6-{3-cyanopyrrolo[1,2-b]pyridazin-7-yl}-4-fluoropyridin-3-yl)-1,3,4-thiadiazol-2-yl]-3,8-diazabicyclo[3.2.1]octane-8-carboxylate (350 mg, 0.62 mmol) and 2-aminoacteonitrile hydrochloride (918 mg, 9.9 mmol) in DMA/CH$_3$CN (6.5:1) (23 ml, 0.1 M), was added DIPEA (2.6 ml, 15 mmol). The reaction mixture was stirred at 110° C. overnight under Ar atmosphere. The reaction mixture was cooled down to room temperature and the volatiles were removed under reduced pressure. The residue was purified by silica gel flash chromatography eluting with CH$_3$CN/CH$_2$Cl$_2$ (gradient from 0% to 20% of CH$_3$CN) to provide 250 mg (63% yield) of tert-butyl 3-(5-{4-[(cyanomethyl)amino]-6-{3-cyanopyrrolo[1,2-b]pyridazin-7-yl}pyridin-3-yl}-1,3,4-thiadiazol-2-yl)-3,8-diazabicyclo[3.2.1]octane-8-carboxylate as a yellow solid. LCMS: [C$_{28}$H$_{28}$N$_{10}$O$_2$S], observed mass=569.10 [M+H$^+$]. $^1$H NMR (300 MHz, DMSO-d$_6$): δ 8.90-8.78 (m, 2H), 8.68 (d, J=2.3 Hz, 1H), 8.60 (s, 1H), 8.30 (s, 1H), 7.87 (d, J=4.8 Hz, 1H), 7.15 (d, J=4.8 Hz, 1H), 4.69 (d, J=6.1 Hz, 2H), 4.34-4.22 (m, 2H), 3.75-3.64 (m, 2H), 3.43-3.35 (m, 2H), 1.96-1.87 (m, 2H), 1.81-1.65 (m, 2H), 1.44 (s, 9H).

Step 2: To a solution of tert-butyl 3-(5-{4-[(cyanomethyl)amino]-6-{3-cyanopyrrolo[1,2-b]pyridazin-7-yl}pyridin-3-yl}-1,3,4-thiadiazol-2-yl)-3,8-diazabicyclo[3.2.1]octane-8-carboxylate (0.25 g, 0.44 mmol) in CH$_2$Cl$_2$ anhydrous (4.4 ml, 0.1 M), TFA (0.67 ml, 8.8 mmol) was added. The resulting mixture was stirred at room temperature for 1 h. The solvent was removed under vacuum. And the residue was purified by prepHPLC (CH$_3$CN/H$_2$O+0.1% HCOOH) to provide 164 mg (75% yield) of 7-{4-[(cyanomethyl)amino]-5-{5-[(1R,5S)-3,8-diazabicyclo[3.2.1]octan-3-yl]-1,3,4-thiadiazol-2-yl}pyridin-2-yl}pyrrolo[1,2-b]pyridazine-3-carbonitrile (TFA salt) as a yellow solid. LCMS: ESI(+) [M+H]$^+$=469.39. $^1$H NMR (300 MHz, DMSO-d$_6$): δ 8.88 (d, J=2.3 Hz, 1H), 8.82 (t, J=6.2 Hz, 1H), 8.68 (d, J=2.3 Hz, 1H), 8.63 (s, 1H), 8.31 (s, 1H), 7.87 (d, J=4.8 Hz, 1H), 7.15 (d, J=4.8 Hz, 1H), 4.70 (d, J=6.2 Hz, 2H), 4.08-3.98 (m, 2H), 3.83-3.71 (m, 2H), 3.59-3.46 (m, 2H), 2.02-1.82 (m, 4H).

Intermediate AP: 7-[4-(cyclobutylamino)-5-[5-(piperazin-1-yl)-1,3,4-thiadiazol-2-yl]pyridin-2-yl]pyrrolo[1,2-b]pyridazine-3-carbonitrile

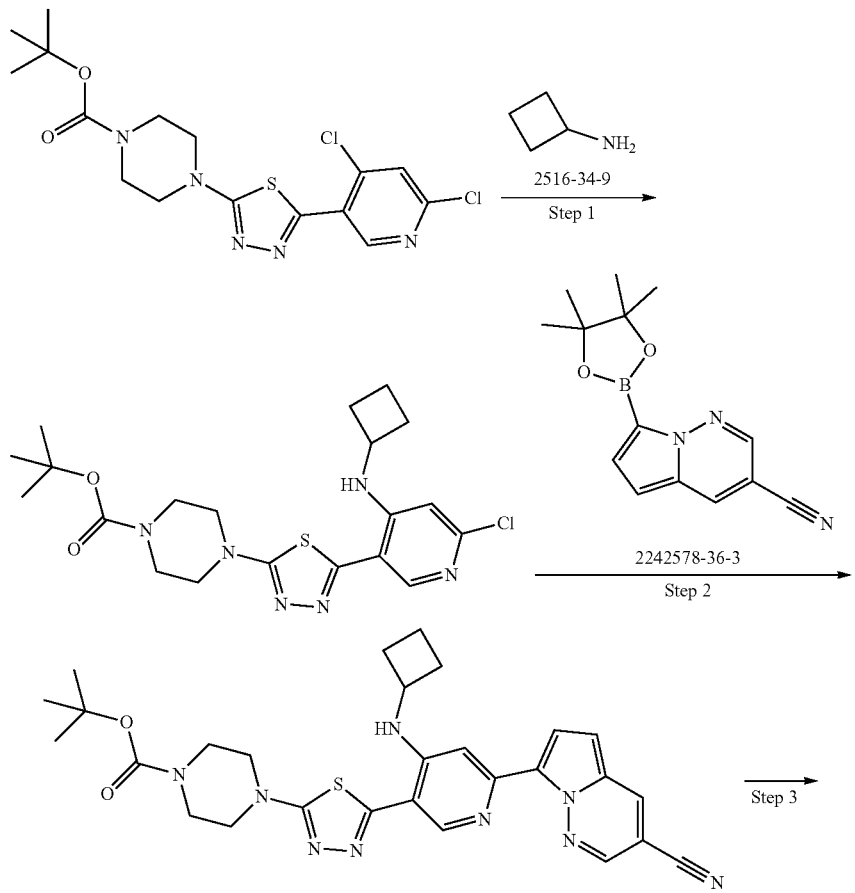

-continued

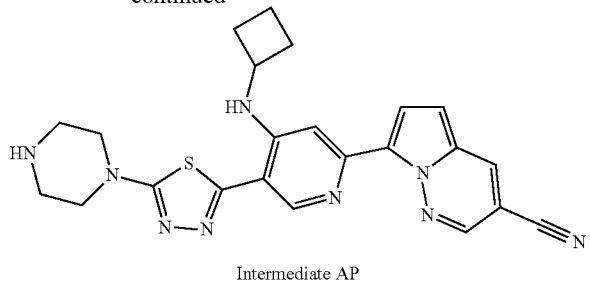

Intermediate AP

Step 1: In a pressure vessel, tert-butyl 4-(5-(4,6-dichloropyridin-3-yl)-1,3,4-thiadiazol-2-yl)piperazine-1-carboxylate (1.2 g, 1 eq) was dissolved in DMF (3 ml, 1 M) and t-BuOH (9.5 ml, 0.3 M). Then, was added DIPEA (7.4 ml, 15 eq) and cyclobutylamine (1.4 g, 7 eq). The pressure vessel was sealed and the mixture was warmed up to 80° C. overnight. Solvents were evaporated under reduced pressure, then, crude material was dissolved in DCM and washed with H$_2$O, NaHCO$_3$ and brine, dried over Na$_2$SO$_4$, filtrated and evaporated under reduced pressure affording tert-butyl 4-{5-[6-chloro-4-(cyclobutylamino)pyridin-3-yl]-1,3,4-thiadiazol-2-yl}piperazine-1-carboxylate (750 mg, 58%). LCMS: ESI(+)[M+H]$^+$=451.30. $^1$H NMR (300 MHz, DMSO-d$_6$) δ 8.82 (d, J=6.2 Hz, 1H), 8.21 (s, 1H), 6.69 (s, 1H), 4.15 (h, J=8.6, 8.1 Hz, 1H), 3.52 (d, J=3.9 Hz, 8H), 2.48-2.41 (m, 2H), 1.99-1.72 (m, 4H), 1.43 (s, 9H).

Step 2: tert-butyl 4-{5-[6-chloro-4-(cyclobutylamino)pyridin-3-yl]-1,3,4-thiadiazol-2-yl}piperazine-1-carboxylate (750 mg, 1.63 mmol, 1 eq), 7-(4,4,5,5-tetramethyl-1,3,2-dioxaborolan-2-yl)pyrrolo[1,2-b]pyridazine-3-carbonitrile (630 mg, 1.4 eq), K$_3$PO$_4$ (709 mg, 2 eq) and X Phos Pd G3 (101.6 mg, 0.07 eq) were suspended in DME (25 ml, 0.07 M). The mixture was degassed with argon for 20 min, and warmed-up to 120° C. overnight. Crude material was purified with FC (DCM/IPA 0 to 10%) to obtain tert-butyl 4-[5-(6-{3-cyanopyrrolo[1,2-b]pyridazin-7-yl}-4-(cyclobutylamino)pyridin-3-yl)-1,3,4-thiadiazol-2-yl]piperazine-1-carboxylate as a yellow solid (444 mg, 48%). LCMS: ESI(+)[M+H]$^+$=558.44. $^1$H NMR (300 MHz, DMSO-d$_6$) δ 8.83 (d, J=2.3 Hz, 1H), 8.78 (d, J=2.3 Hz, 1H), 8.68 (d, J=5.1 Hz, 1H), 8.49 (s, 1H), 8.11 (s, 1H), 7.84 (d, J=4.8 Hz, 1H), 7.11 (d, J=4.9 Hz, 1H), 4.24-4.09 (m, 1H), 3.60-3.46 (m, 8H), 2.60 (d, J=10.2 Hz, 2H), 2.10-1.82 (m, 4H), 1.44 (s, 9H).

Step 3: tert-butyl 4-[5-(6-{3-cyanopyrrolo[1,2-b]pyridazin-7-yl}-4-(cyclobutylamino)pyridin-3-yl)-1,3,4-thiadiazol-2-yl]piperazine-1-carboxylate (444 mg, 1 eq) was dissolved in DCM (5 ml), then TFA (2 ml) was added and the solution was stirred during 1.5 h. At completion, the mixture was evaporated to dryness, suspended in Et$_2$O and sonicated during 30 min. The suspension was filtered affording 7-[4-(cyclobutylamino)-5-[5-(piperazin-1-yl)-1,3,4-thiadiazol-2-yl]pyridin-2-yl]pyrrolo[1,2-b]pyridazine-3-carbonitrile as a TFA salt (477 mg, 87%). LCMS: ESI(+)[M+H]$^+$=458.09. $^1$H NMR (300 MHz, DMSO-d$_6$) δ 9.17 (s, 1H), 9.01 (s, 2H), 8.92 (d, J=2.2 Hz, 1H), 8.85 (d, J=2.2 Hz, 1H), 8.58 (s, 1H), 8.03 (s, 1H), 7.96 (d, J=4.9 Hz, 1H), 7.18 (d, J=4.9 Hz, 1H), 4.30 (dq, J=14.2, 7.0 Hz, 1H), 3.86-3.75 (m, 4H), 3.33 (s, 4H), 2.68-2.54 (m, 2H), 2.15-1.97 (m, 2H), 1.91 (dt, J=9.6, 5.5 Hz, 2H).

Intermediate AQ: 7-[5-(5-{3,8-diazabicyclo[3.2.1]oct-3-yl}-1,3,4-thiadiazol-2-yl)-4-{[(2R)-1-methoxypropan-2-yl]amino}pyridin-2-yl]pyrrolo[1,2-b]pyridazine-3-carbonitrile TFA salt

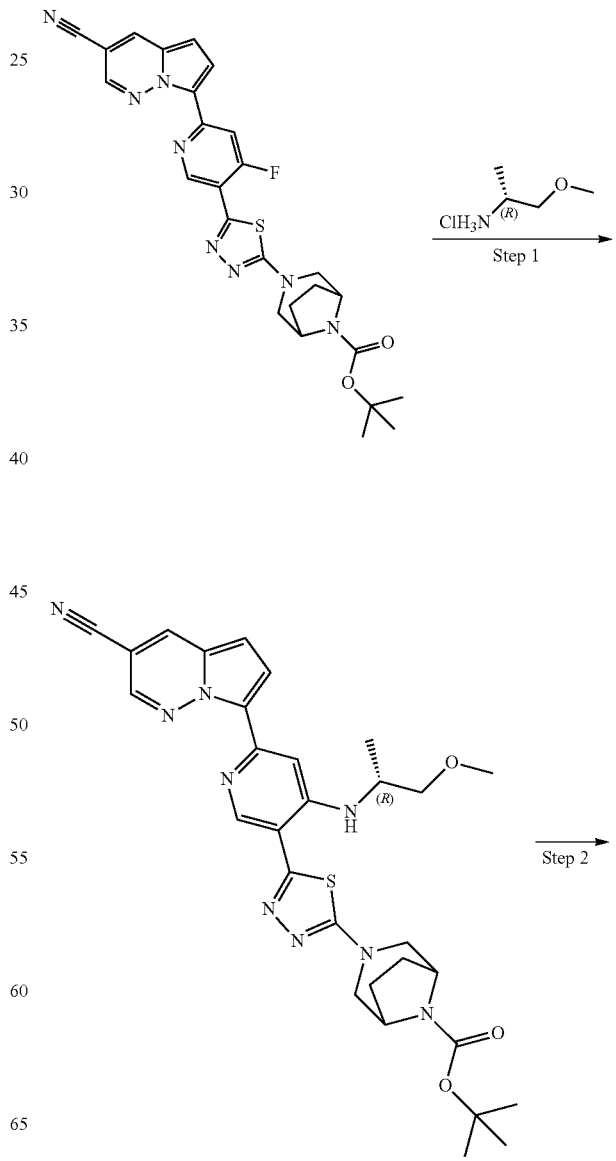

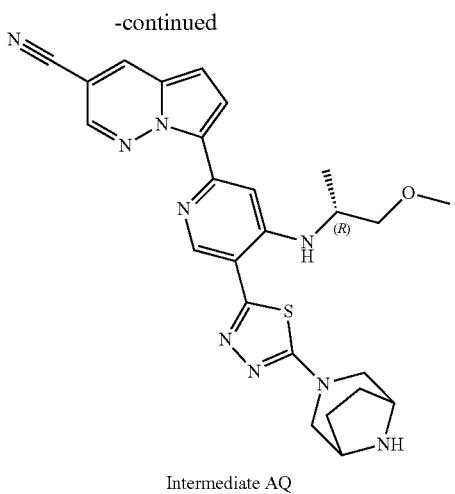

Intermediate AQ

Step 1: To a solution of tert-butyl 3-[5-(6-{3-cyanopyrrolo[1,2-b]pyridazin-7-yl}-4-fluoropyridin-3-yl)-1,3,4-thiadiazol-2-yl]-3,8-diazabicyclo[3.2.1]octane-8-carboxylate (660 mg, 1.24 mmol, 1 eq), (R)-1-methoxypropan-2-amine (2.21 g, 24.78 mmol, 20 eq) were suspended in anhydrous DMSO (12.4 mL, 0.1 M). To this anhydrous DIPEA (12.1 mL, 68.16 mmol, 55 eq) was added. The reaction mixture was heated to 120° C. for overnight. The reaction was cooled to room temperature and quenched by the addition of water (100 mL). The solid was filtered off and washed with water (till the washings were colorless). The solid obtained was dissolved in EtOAc. This EtOAc layer was dried over $Na_2SO_4$ to remove traces of water, filtered, and evaporated to yield 650 mg of crude. The crude was purified by FC using 0 to 100% ACN in DCM to yield 296 mg of semi pure product. Trituration using MTBE and ACN were attempted to remove impurity (m/z=656; possibly double substituted Suzuki product) but was unsuccessful. Therefore, the semi pure product was re-purified by RPFC using 5% to 95% ACN in water to yield 250 mg (32% yield) of tert-butyl 3-[5-(6-{3-cyanopyrrolo[1,2-b]pyridazin-7-yl}-4-{[(2R)-1-methoxypropan-2-yl]amino}pyridin-3-yl)-1,3,4-thiadiazol-2-yl]-3,8-diazabicyclo[3.2.1]octane-8-carboxylate as a yellow solid. LCMS: [$C_{30}H_{35}N_9O_3S$], desired mass=601.2 observed mass=602.2 [M+H$^+$]. $^1$H NMR (300 MHz, DMSO-d6): δ 8.84 (d, J=2.2 Hz, 1H), 8.73-8.63 (m, 2H), 8.49 (s, 1H), 8.24 (s, 1H), 7.84 (d, J=4.8 Hz, 1H), 7.12 (d, J=4.8 Hz, 1H), 4.28 (s, 2H), 4.09-3.94 (m, 1H), 3.74-3.62 (m, 2H), 3.58-3.47 (m, 2H), 3.39 (s, 1H), 3.36 (s, 4H), 1.91 (s, 2H), 1.76 (d, J=7.5 Hz, 2H), 1.44 (s, 9H), 1.32 (d, J=6.5 Hz, 3H).

Step 2: To a solution of tert-butyl 3-[5-(6-{3-cyanopyrrolo[1,2-b]pyridazin-7-yl}-4-{[(2R)-1-methoxypropan-2-yl]amino}pyridin-3-yl)-1,3,4-thiadiazol-2-yl]-3,8-diazabicyclo[3.2.1]octane-8-carboxylate (254 mg, 0.41 mmol, 1.0 eq) in anhydrous DCM (3.6 ml, 0.23 M) the TFA (0.83 ml, 7.28 mmol, 20 eq) was added and the resulting mixture was kept at RT for 1 h. The volatiles was removed by evaporation. The crude was triturated with $Et_2O$ (4×10 mL) to yield 251 mg (98%) of 7-[5-(5-{3,8-diazabicyclo[3.2.1]octan-3-yl}-1,3,4-thiadiazol-2-yl)-4-{[(2R)-1-methoxypropan-2-yl]amino}pyridin-2-yl]pyrrolo[1,2-b]pyridazine-3-carbonitrile (as TFA salt) as a pale yellow solid. LCMS: [$C_{25}H_{27}N_9OS$], desired mass=501.2 observed mass=502.2 [M+H$^+$]. $^1$H NMR (300 MHz, DMSO-d6): δ 9.35 (s, 2H), 9.25 (s, 1H), 8.94 (d, J=2.2 Hz, 1H), 8.80 (d, J=2.2 Hz, 1H), 8.59 (s, 1H), 8.12 (s, 1H), 8.00 (d, J=4.9 Hz, 1H), 7.20 (d, J=4.9 Hz, 1H), 4.23 (s, 3H), 3.94-3.81 (m, 2H), 3.69-3.51 (m, 4H), 3.36 (s, 3H), 1.98 (dd, J=11.8, 8.3 Hz, 4H), 1.33 (d, J=6.5 Hz, 3H).

Intermediate AR: 7-[4-(tert-butylamino)-5-[5-(piperazin-1-yl)-1,3,4-thiadiazol-2-yl]pyridin-2-yl]pyrrolo[1,2-b]pyridazine-3-carbonitrile

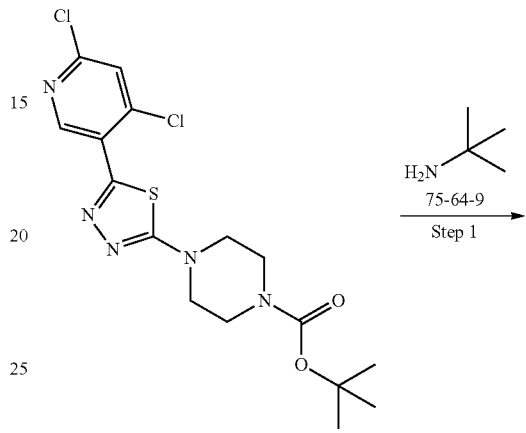

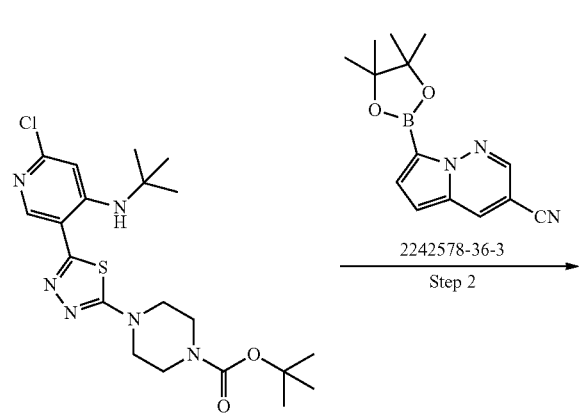

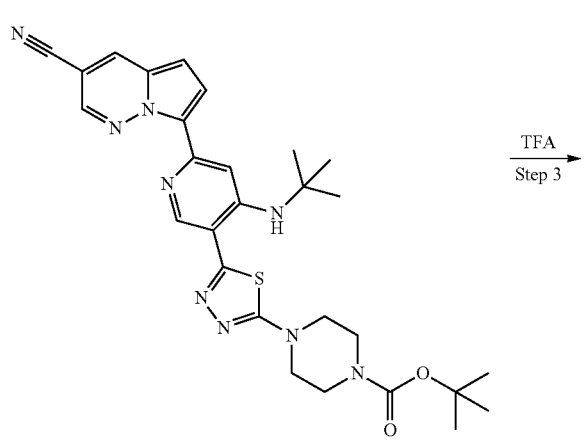

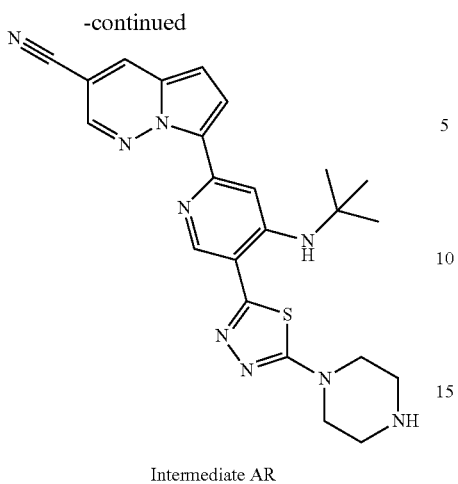

Intermediate AR

Step 1: To a suspension of tert-butyl 4-[5-(4,6-dichloropyridin-3-yl)-1,3,4-thiadiazol-2-yl]piperazine-1-carboxylate (1.5 g, 3.531 mmol) in dimethyl sulfoxide (35.31 mL, 0.1 M) were added tert-butylamine (7.45 mL, 70.89 mmol) and N,N-diisopropylethylamine (29.0 mL, 166.487 mmol). The reaction mixture was stirred at 110° C. for 24 h. After completion of the reaction, it was cooled to room temperature and quenched by the addition of ice. The precipitate formed was filtered off and dried under reduced pressure. The crude product was purified by silica gel flash chromatography with 0-100% of EtOAc in hexane provided 810 mg (51% yield) of tert-butyl 4-{5-[4-(tert-butylamino)-6-chloropyridin-3-yl]-1,3,4-thiadiazol-2-yl}piperazine-1-carboxylate as a white solid. LCMS: [$C_{20}H_{29}Cl_1N_6O_2S$], desired mass=452.2, observed mass=453.6 [M+H]$^+$. $^1$H NMR (300 MHz, DMSO-d$_6$) δ 9.02 (s, 1H), 8.20 (s, 1H), 6.86 (s, 1H), 3.57-3.45 (m, 8H), 1.43 (d, J=1.9 Hz, 18H).

Step 2: Tert-butyl 4-{5-[4-(tert-butylamino)-6-chloropyridin-3-yl]-1,3,4-thiadiazol-2-yl}piperazine-1-carboxylate (0.88 g, 1.94 mmol), 7-(4,4,5,5-tetramethyl-1,3,2-dioxaborolan-2-yl)pyrrolo[1,2-b]pyridazine-3-carbonitrile (0.732 g, 2.72 mmol), potassium phosphate tribasic (0.825 g, 3.89 mmol) and XPhos Pd G3 (0.2 g, 0.236 mmol, 0.122 equiv.) were suspended in dimethoxyethane (27.8 mL, 0.07 M). The mixture was degassed with argon for 20 min and stirred at 120° C. for overnight. After completion of the reaction, it was concentrated under reduced pressure. The residue was purified by silica gel flash chromatography with 0-100% of ACN in DCM to provide 532.9 mg (49% yield) of tert-butyl 4-{5-[4-(tert-butylamino)-6-{3-cyanopyrrolo[1,2-b]pyridazin-7-yl}pyridin-3-yl]-1,3,4-thiadiazol-2-yl}piperazine-1-carboxylate as a yellow solid. LCMS: [$C_{28}H_{33}N_9O_2S$], desired mass 559.3, observed mass=560.2 [M+H$^+$]. $^1$H NMR (300 MHz, DMSO-d$_6$) δ 8.84 (d, J=2.4 Hz, 2H), 8.76 (d, J=2.3 Hz, 1H), 8.56 (s, 1H), 8.49 (s, 1H), 7.85 (d, J=4.8 Hz, 1H), 7.12 (d, J=4.9 Hz, 1H), 3.53 (d, J=6.5 Hz, 8H), 1.55 (s, 9H), 1.43 (s, 9H).

Step 3: To a solution of tert-butyl 4-{5-[4-(tert-butylamino)-6-{3-cyanopyrrolo[1,2-b]pyridazin-7-yl}pyridin-3-yl]-1,3,4-thiadiazol-2-yl}piperazine-1-carboxylate (483 mg, 0.86 mmol) in dichloromethane anhydrous (8.6 mL, 0.1 M) was added trifluoroacetic acid (1.3 mL, 17.25 mmol). The reaction mixture was stirred at room temperature for 3 h. Then, the mixture was evaporated to dryness. The residue was triturated with diethyl ether. The product was collected by filtration affording 600 mg (100% yield) of 7-[4-(tert-butylamino)-5-[5-(piperazin-1-yl)-1,3,4-thiadiazol-2-yl]pyridin-2-yl]pyrrolo[1,2-b]pyridazine-3-carbonitrile (bis-TFA salt) as a yellow solid. LCMS: [$C_{23}H_{25}N_9S$], desired mass=459.2, observed mass=460.0 [M+H]$^+$. $^1$H NMR (300 MHz, DMSO-d$_6$) δ 9.34 (s, 1H), 9.04 (s, 2H), 8.92 (d, J=2.2 Hz, 1H), 8.83 (d, J=2.2 Hz, 1H), 8.56 (s, 1H), 8.51 (s, 1H), 7.93 (d, J=4.9 Hz, 1H), 7.18 (d, J=4.9 Hz, 1H), 3.83-3.75 (m, 4H), 3.31 (s, 4H), 1.57 (s, 9H).

Intermediate AS: tert-butyl 8-[5-(6-{3-cyanopyrrolo[1,2-b]pyridazin-7-yl}-4-[(oxan-4-yl)amino]pyridin-3-yl)-1,3,4-thiadiazol-2-yl]-3,8-diazabicyclo[3.2.1]octane-3-carboxylate

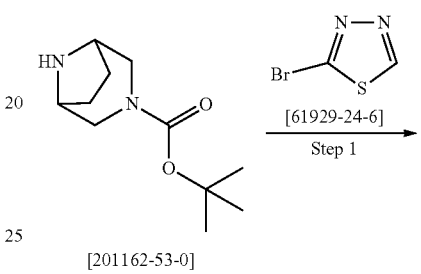

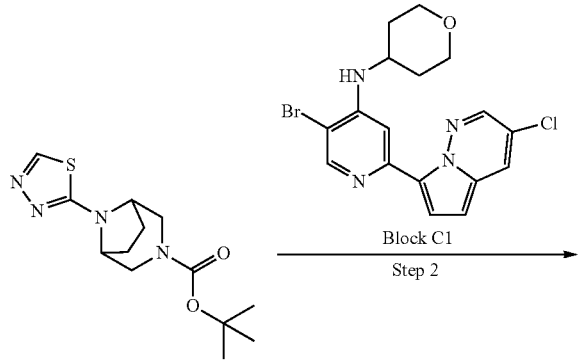

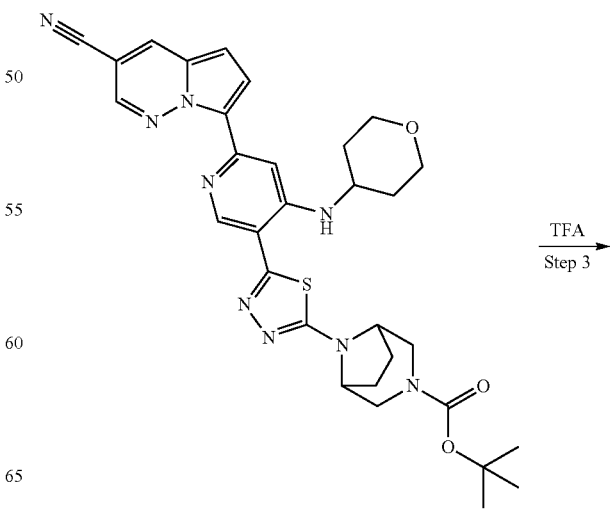

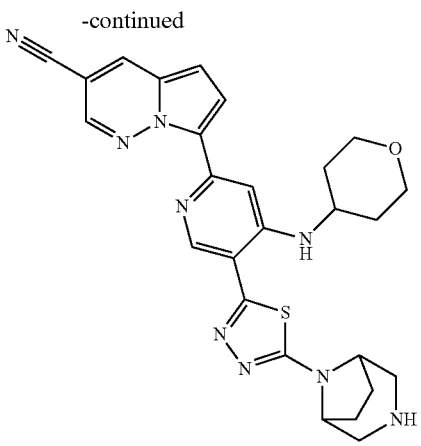

Intermediate AS

Step 1: To a solution of tert-butyl 3,8-diazabicyclo[3.2.1]octane-3-carboxylate (0.5 g, 2.36 mmol) and 2-Bromo-1,3,4-thiadiazole (0.972 g, 5.89 mmol) in n-butanol (4.71 mL, 0.5 M) was added N,N-diisopropylethylamine (1.611 mL, 9.42 mmol). The reaction mixture was stirred at 120° C. overnight. After completion of the reaction, it was cooled to room temperature. The volatiles were removed in vacuo and the residue was transferred into a separatory funnel using a mixture of EtOAc (20 mL) and H$_2$O (40 mL). The layers were separated, and the aqueous layer was extracted with EtOAc (3×20 mL). The combined organic layers were dried over Na$_2$SO$_4$ and concentrated in vacuo. The resulting crude was purified by silica gel flash chromatography eluting with 0 to 50% of MeCN in DCM to provide 271 mg (39% yield) of tert-butyl 8-(1,3,4-thiadiazol-2-yl)-3,8-diazabicyclo[3.2.1]octane-3-carboxylate as a red oil. LCMS: C$_{13}$H$_{20}$N$_4$O$_2$S requires 296.1, observed m/z=296.9 [M+H]$^+$. $^1$H NMR (300 MHz, Chloroform-d) δ 8.53 (s, 1H), 4.29 (d, J=25.9 Hz, 2H), 3.85 (dd, J=48.5, 13.1 Hz, 2H), 3.31 (dd, J=38.2, 13.1 Hz, 2H), 2.11 (dt, J=6.7, 3.8 Hz, 2H), 1.90 (d, J=17.8 Hz, 2H), 1.43 (s, 9H).

Step 2: A suspension of 7-{5-bromo-4-[(oxan-4-yl)amino]pyridin-2-yl}pyrrolo[1,2-b]pyridazine-3-carbonitrile (0.148 g, 0.37 mmol), tert-butyl 8-(1,3,4-thiadiazol-2-yl)-3,8-diazabicyclo[3.2.1] octane-3-carboxylate (0.1 g, 0.34 mmol), copper(I) iodide (0.013 g, 0.067 mmol), Xantphos (0.039 g, 0.067 mmol) and cesium carbonate (0.44 g, 1.35 mmol) in anhydrous dioxane (11.25 mL, 0.03 M) was degassed with argon for 15 min and palladium (II) acetate (8 mg, 0.034 mmol) was added. The pressure vessel was sealed and heated at 105° C. overnight. After completion of the reaction, the volatiles were evaporated in vacuo. The residue was purified by silica gel flash chromatography eluting with 0 to 100% of MeCN in DCM followed by 0 to 10% of IPA in DCM to afford semi-pure product. It was further triturated with diethyl ether (4×10 mL) to obtain 80 mg (34% yield) of tert-butyl 8-[5-(6-{3-cyanopyrrolo[1,2-b]pyridazin-7-yl}-4-[(oxan-4-yl)amino]pyridin-3-yl)-1,3,4-thiadiazol-2-yl]-3,8-diazabicyclo [3.2.1]octane-3-carboxylate as a bright yellow powder. LCMS: C$_{31}$H$_{35}$N$_9$O$_3$S requires 613.2, observed m/z=614.1 [M+H]$^+$. $^1$H NMR (300 MHz, DMSO-d$_6$) δ 8.85 (d, J=2.3 Hz, 1H), 8.78 (d, J=2.3 Hz, 1H), 8.67 (d, J=7.0 Hz, 1H), 8.52 (s, 1H), 8.31 (s, 1H), 7.85 (d, J=4.8 Hz, 1H), 7.13 (d, J=4.8 Hz, 1H), 4.35 (s, 2H), 4.01-3.81 (m, 5H), 3.61 (s, 3H), 2.14 (s, 2H), 2.03 (s, 2H), 1.75 (d, J=7.4 Hz, 3H), 1.58 (d, J=10.8 Hz, 3H), 1.42 (s, 9H).

Step 3: To a solution of tert-butyl 8-[5-(6-{3-cyanopyrrolo[1,2-b]pyridazin-7-yl}-4-[(oxan-4-yl)amino]pyridin-3-yl)-1,3,4-thiadiazol-2-yl]-3,8-diazabicyclo[3.2.1]octane-3-carboxylate (0.08 g, 0.12 mmol) in anhydrous dichloromethane (11.5 mL, 0.01 M) was added trifluoroacetic acid (0.785 g, 6.88 mmol). The reaction was stirred at room temperature for 2 h. After completion of the reaction, the volatiles were evaporated in vacuo and the residue was triturated with diethyl ether (4×10 mL). The residue was dried thoroughly to obtain 47 mg (77% yield) of 7-[5-(5-{3,8-diazabicyclo[3.2.1]octan-8-yl}-1,3,4-thiadiazol-2-yl)-4-[(oxan-4-yl)amino] pyridin-2-yl]pyrrolo[1,2-b]pyridazine-3-carbonitrile as a yellow solid. LCMS: C$_{26}$H$_{27}$N$_9$OS requires 513.2, observed m/z=514.1 [M+H]$^+$. $^1$H NMR (300 MHz, DMSO-d$_6$) δ 9.13 (s, 2H), 8.92 (d, J=2.2 Hz, 1H), 8.83 (d, J=2.2 Hz, 1H), 8.59 (s, 1H), 8.24 (s, 1H), 7.94 (d, J=4.9 Hz, 1H), 7.18 (d, J=4.9 Hz, 1H), 4.50 (s, 3H), 3.94 (d, J=11.7 Hz, 4H), 3.39 (q, J=6.9 Hz, 4H), 3.25 (d, J=12.5 Hz, 3H), 2.55 (s, 2H), 2.18-2.05 (m, 4H), 1.59 (d, J=10.5 Hz, 3H).

Intermediate AT: 7-[5-(5-{3,9-diazabicyclo[3.3.1]nonan-3-yl}-1,3,4-thiadiazol-2-yl)-4-[(oxan-4-yl)amino] pyridin-2-yl]pyrrolo[1,2-b]pyridazine-3-carbonitrile

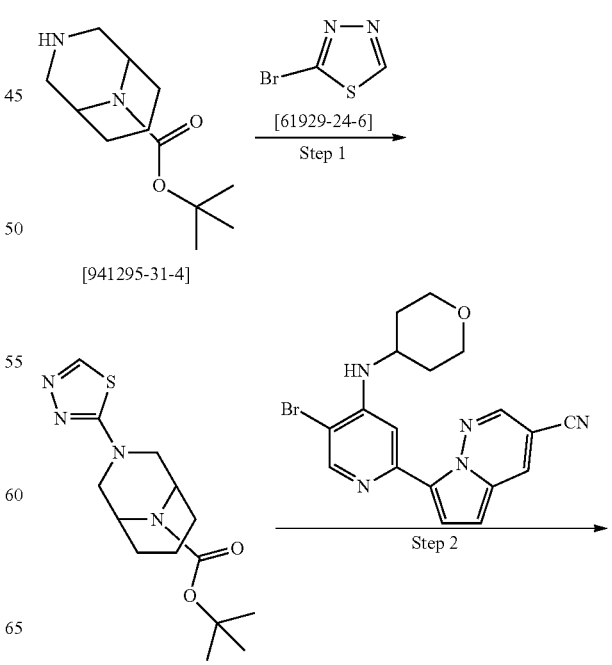

-continued

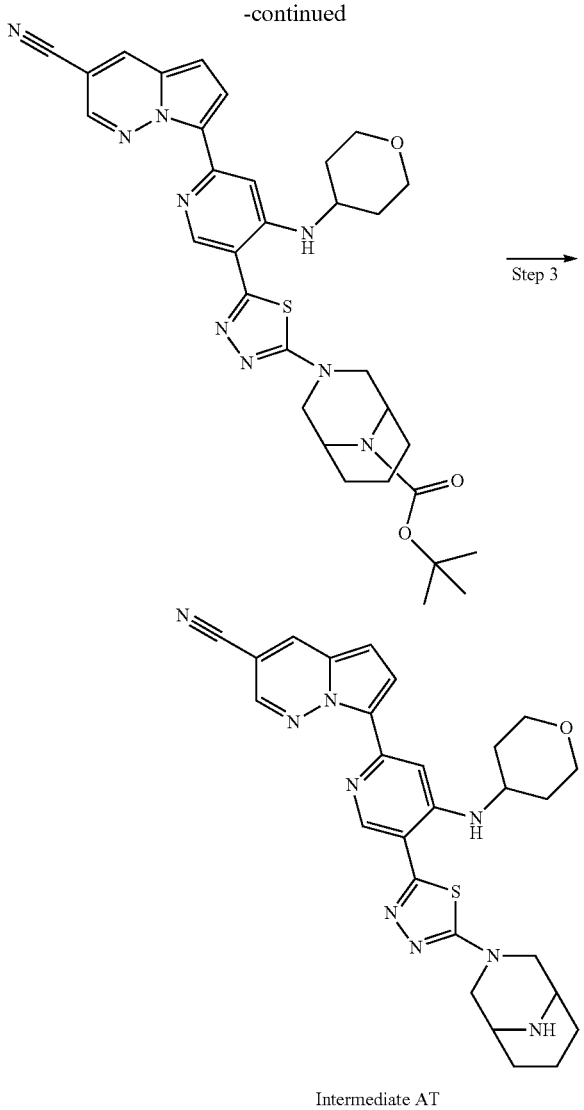

Intermediate AT

Step 1: To a solution of tert-butyl 3,9-diazabicyclo[3.3.1]nonane-9-carboxylate (0.55 g, 2.41 mmol) in n-butanol (4.82 mL, 0.5 M) was added 2-bromo-1,3,4-thiadiazole (1.00 g, 6.08 mmol) and DIPEA (1.66 mL, 9.72 mmol). The reaction mixture was stirred at 120° C. for 2 h. The volatiles were removed in vacuo and the residue was transferred into a separatory funnel using a mixture of EtOAc (50 mL) and H$_2$O (100 mL), and then extracted with EtOAc (5×50 mL). The combined organic layers were dried over Na$_2$SO$_4$ and concentrated in vacuo. The residue was purified by silica gel flash chromatography eluting with 0 to 70% of MeCN in DCM to provide 0.506 g (67% yield) of tert-butyl 3-(1,3,4-thiadiazol-2-yl)-3,9-diazabicyclo[3.3.1] nonane-9-carboxylate as a red oil. LCMS: C$_{13}$H$_{20}$N$_4$O$_3$S requires 310.2, observed m/z=311.3 [M+H]$^+$. $^1$H NMR (300 MHz, DMSO-d$_6$) δ 8.80 (s, 1H), 4.18 (d, J=12.3 Hz, 2H), 3.81 (dd, J=12.2, 4.4 Hz, 2H), 3.38 (d, J=4.3 Hz, 2H), 1.92 (dt, J=11.8, 5.7 Hz, 1H), 1.84-1.61 (m, 4H), 1.51 (s, 1H), 1.44 (m, 9H).

Step 2: A suspension of 7-{5-bromo-4-[(oxan-4-yl)amino]pyridin-2-yl}pyrrolo[1,2-b]pyridazine-3-carbonitrile (0.208 g, 0.522 mmol), tert-butyl 3-(1,3,4-thiadiazol-2-yl)-3,9-diazabicyclo [3.3.1]nonane-9-carboxylate (0.152 g, 0.475 mmol), CuI (0.018 g, 0.095 mmol), Xantphos (0.055 g, 0.095 mmol) and Cs$_2$CO$_3$ (0.619 g, 1.9 mmol) in anhydrous dioxane (15.83 mL, 0.03 M) was degassed with argon for 15 min and Pd(OAc)$_2$ (0.011 g, 0.047 mmol, 0.1 eq) was added. The reaction mixture was stirred at 130° C. for 2 h in a MW reactor. As the reaction was incomplete, additional Xantphos (0.055 g, 0.095 mmol), Cs$_2$CO$_3$ (0.619 g, 1.9 mmol), CuI (0.018 g, 0.095 mmol), Pd(OAc)$_2$ (0.011 g, 0.047 mmol) were added, and the reaction mixture was degassed by a vacuum/argon cycle. The reaction was heated at 130° C. with MW irradiation for an additional 2 h. After completion of the reaction, the reaction mixture was cooled to room temperature and the volatiles were evaporated in vacuo. The crude was purified by silica gel flash chromatography eluting with 0 to 100% of ACN in DCM followed by 0 to 10% of IPA in DCM to provide 0.056 g (19% yield) of tert-butyl 3-[5-(6-{3-cyanopyrrolo[1,2-b]pyridazin-7-yl}-4-[(oxan-4-yl)amino]pyridin-3-yl)-1,3,4-thiadiazol-2-yl]-3,9-diazabicyclo[3.3.1]nonane-9-carboxylate as a yellow solid. LCMS: C$_{32}$H$_{37}$N$_9$O$_3$S requires 627.3, observed m/z=628.2 [M+H]$^+$. $^1$H NMR (300 MHz, DMSO-d$_6$) δ 8.85 (d, J=2.3 Hz, 1H), 8.77 (d, J=2.3 Hz, 1H), 8.71 (d, J=7.1 Hz, 1H), 8.52 (s, 1H), 8.29 (s, 1H), 7.85 (d, J=4.8 Hz, 1H), 7.13 (d, J=4.8 Hz, 1H), 4.23 (d, J=12.6 Hz, 2H), 3.98-3.81 (m, 5H), 3.61 (t, J=10.7 Hz, 2H), 3.48 (d, J=10.5 Hz, 2H), 2.12 (d, J=13.4 Hz, 2H), 1.97 (s, 1H), 1.76 (d, J=25.0 Hz, 4H), 1.58 (d, J=11.3 Hz, 3H), 1.45 (s, 9H).

Step 3: To a solution of tert-butyl 3-[5-(6-{3-cyanopyrrolo[1,2-b]pyridazin-7-yl}-4-[(oxan-4-yl)amino] pyridin-3-yl)-1,3,4-thiadiazol-2-yl]-3,9-diazabicyclo[3.3.1]nonane-9-carboxylate (0.056 g, 0.09 mmol) in DCM (0.9 mL, 0.1 M) was added dropwise a solution of 4 M HCl in dioxane (0.707 mL, 2.83 mmol). The reaction mixture was allowed to stir at room temperature for overnight. After completion, the solid residue from the reaction mixture was filtered off and washed with DCM. The solid was collected and dried under vacuum to yield 0.038 g (75% yield) of 7-[5-(5-{3,9-diazabicyclo[3.3.1]nonan-3-yl}-1,3,4-thiadiazol-2-yl)-4-[(oxan-4-yl)amino] pyridin-2-yl]pyrrolo[1,2-b]pyridazine-3-carbonitrile (2×HCl salt) as a yellow solid. LCMS: C$_{27}$H$_{29}$N$_9$OS requires 527.2, observed m/z=528.2 [M+H]$^+$, $^1$H NMR (300 MHz, DMSO-d$_6$) δ 9.68-9.32 (m, 3H), 8.98 (d, J=2.3 Hz, 1H), 8.87 (d, J=2.2 Hz, 1H), 8.57 (s, 1H), 8.16 (s, 1H), 8.10 (s, 1H), 7.23 (d, J=5.0 Hz, 1H), 4.11 (d, J=13.1 Hz, 3H), 3.88 (dd, J=33.2, 15.8 Hz, 6H), 3.61 (t, J=10.8 Hz, 3H), 2.17-1.94 (m, 6H), 1.62 (d, J=11.5 Hz, 4H).

Intermediate AU: 7-(4-{[(1R)-1-cyanoethyl]amino}-5-(5-{3,8-diazabicyclo[3.2.1]octan-3-yl}-1,3,4-thiadiazol-2-yl)pyridin-2-yl)pyrrolo[1,2-b]pyridazine-3-carbonitrile

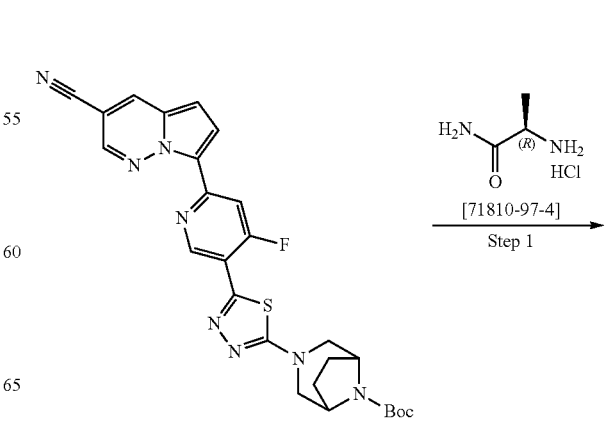

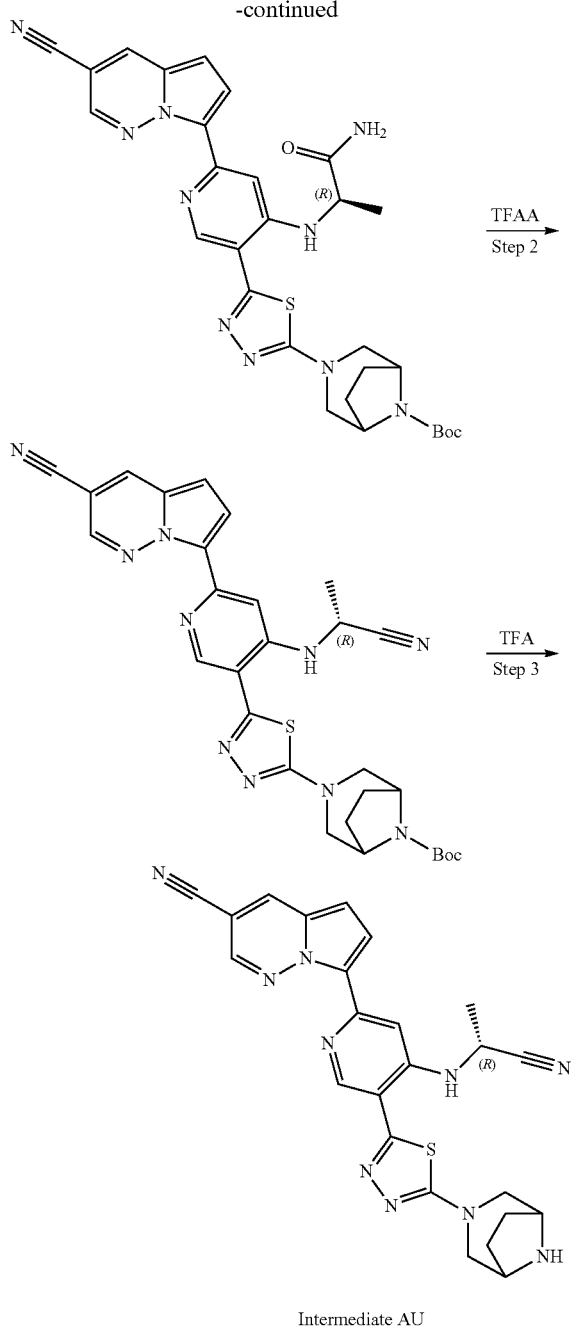

Intermediate AU

Step 1: Tert-butyl 3-[5-(6-{3-cyanopyrrolo[1,2-b]pyridazin-7-yl}-4-fluoropyridin-3-yl)-1,3,4-thiadiazol-2-yl]-3,8-diazabicyclo[3.2.1]octane-8-carboxylate (0.5 g, 0.94 mmol, 1.0 eq) was dissolved in dimethyl sulfoxide anhydrous (9.39 ml, 0.1 M). To this D-alaninamide hydrochloride (1.169 g, 9.4 mmol, 10.0 eq) and sodium bicarbonate (1.183 g, 14.08 mmol, 15.0 eq) were added. The resulting mixture was stirred at 120° C. for 1 h. After completion of the reaction, it was cooled down to rt and directly injected on the column and purified using water in ACN from 0-60% as a mobile phase to give 0.3 g (53% yield) of tert-butyl 3-[5-(4-{[(1R)-1-carbamoylethyl]amino}-6-{3-cyanopyrrolo[1,2-b]pyridazin-7-yl}pyridin-3-yl)-1,3,4-thiadiazol-2-yl]-3,8-diazabicyclo[3.2.1]octane-8-carboxylate as yellow solid. LCMS: [$C_{29}H_{32}N_{10}O_3S$], desired mass=600.7, observed mass=601.2 [M+H]$^+$. $^1$H NMR (300 MHz, DMSO-d$_6$) δ 8.90-8.81 (m, 2H), 8.64 (d, J=2.3 Hz, 1H), 8.51 (s, 1H), 8.12 (s, 1H), 7.83 (d, J=4.8 Hz, 1H), 7.79 (s, 1H), 7.23 (s, 1H), 7.13 (d, J=4.8 Hz, 1H), 4.38-4.19 (m, 3H), 3.79-3.63 (m, 2H), 3.44-3.35 (m, 2H), 1.93 (s, 2H), 1.86-1.69 (m, 3H), 1.50 (d, J=6.8 Hz, 3H), 1.45 (s, 9H).

Step 2: Tert-butyl 3-[5-(4-{[(1R)-1-carbamoylethyl]amino}-6-{3-cyanopyrrolo[1,2-b]pyridazin-7-yl}pyridin-3-yl)-1,3,4-thiadiazol-2-yl]-3,8-diazabicyclo[3.2.1]octane-8-carboxylate (0.3 g, 0.499 mmol, 1.0 eq) was suspended in dichloromethane anhydrous (9.99 ml, 0.05 M) followed by addition of anhydrous pyridine (0.322 ml, 3.995 mmol, 8.0 eq). Trifluoroacetic anhydride (0.315 g, 1.498 mmol, 3.0 eq) was added to the resulting suspension and the reaction mixture was stirred at rt for 30 minutes. Clear solution formation was observed. Then, the reaction mixture was concentrated in vacuo, dissolved in a minimum amount of DCM, and injected on the column. The crude was purified by flash chromatography using DCM-IPA 0-10% as a mobile phase to give 0.182 g (62% yield) of tert-butyl 3-[5-(4-{[(1R)-1-cyanoethyl]amino}-6-{3-cyanopyrrolo[1,2-b]pyridazin-7-yl}pyridin-3-yl)-1,3,4-thiadiazol-2-yl]-3,8-diazabicyclo[3.2.1]octane-8-carboxylate as a yellow solid. LCMS: [$C_{29}H_{30}N_{10}O_2S$], desired mass=582.6, observed mass=583.8 [M+H]$^+$. $^1$H NMR (300 MHz, DMSO-d$_6$) δ 8.87 (d, J=2.3 Hz, 1H), 8.84 (d, J=6.9 Hz, 1H), 8.68 (d, J=2.3 Hz, 1H), 8.63 (s, 1H), 8.36 (s, 1H), 7.88 (d, J=4.8 Hz, 1H), 7.15 (d, J=4.8 Hz, 1H), 5.11-4.97 (m, 1H), 4.40-4.22 (m, 2H), 3.76-3.64 (m, 2H), 3.42-3.37 (m, 2H), 2.04-1.86 (m, 2H), 1.84-1.69 (m, 5H), 1.44 (s, 9H).

Step 3: Tert-butyl 3-[5-(4-{[(1R)-1-cyanoethyl]amino}-6-{3-cyanopyrrolo[1,2-b]pyridazin-7-yl}pyridin-3-yl)-1,3,4-thiadiazol-2-yl]-3,8-diazabicyclo[3.2.1]octane-8-carboxylate (0.182 g, 0.312 mmol, 1.0 eq) was dissolved in anhydrous DCM (6.25 ml, 0.05 M). To this TFA (0.712 g, 6.247 mmol, 20.0 eq) was added. The resulting mixture was stirred at rt for 4 h. After completion of the reaction, it was concentrated in vacuo. The residue was triturated and sonicated with diethyl ether to give yellow precipitate, which was collected by filtration and dried in vacuo overnight to give 0.288 g (92% yield) of 7-(4-{[(1R)-1-cyanoethyl]amino}-5-(5-{3,8-diazabicyclo[3.2.1]octan-3-yl}-1,3,4-thiadiazol-2-yl)pyridin-2-yl)pyrrolo[1,2-b]pyridazine-3-carbonitrile as a yellow solid. LCMS: [$C_{28}H_{24}F_6N_{10}O_4S$], desired mass=482.5, observed mass=483.8 [M+H]$^+$. $^1$H NMR (300 MHz, DMSO-d$_6$) δ 9.13 (s, 1H), 9.05 (s, 1H), 8.89 (d, J=2.2 Hz, 1H), 8.84 (d, J=6.9 Hz, 1H), 8.70 (d, J=2.3 Hz, 1H), 8.67 (s, 1H), 8.37 (s, 1H), 7.90 (d, J=4.8 Hz, 1H), 7.17 (d, J=4.8 Hz, 1H), 5.08 (p, J=6.8 Hz, 1H), 4.28-4.19 (m, 2H), 3.92-3.83 (m, 2H), 3.64-3.58 (m, 2H), 2.12-1.93 (m, 4H), 1.78 (d, J=6.9 Hz, 3H).

Intermediate AV: 7-(5-(5-(3,8-diazabicyclo[3.2.1]
octan-3-yl)-1,3,4-thiadiazol-2-yl)-4-(isoxazol-4-
ylamino)pyridin-2-yl)pyrrolo[1,2-b]pyridazine-3-
carbonitrile

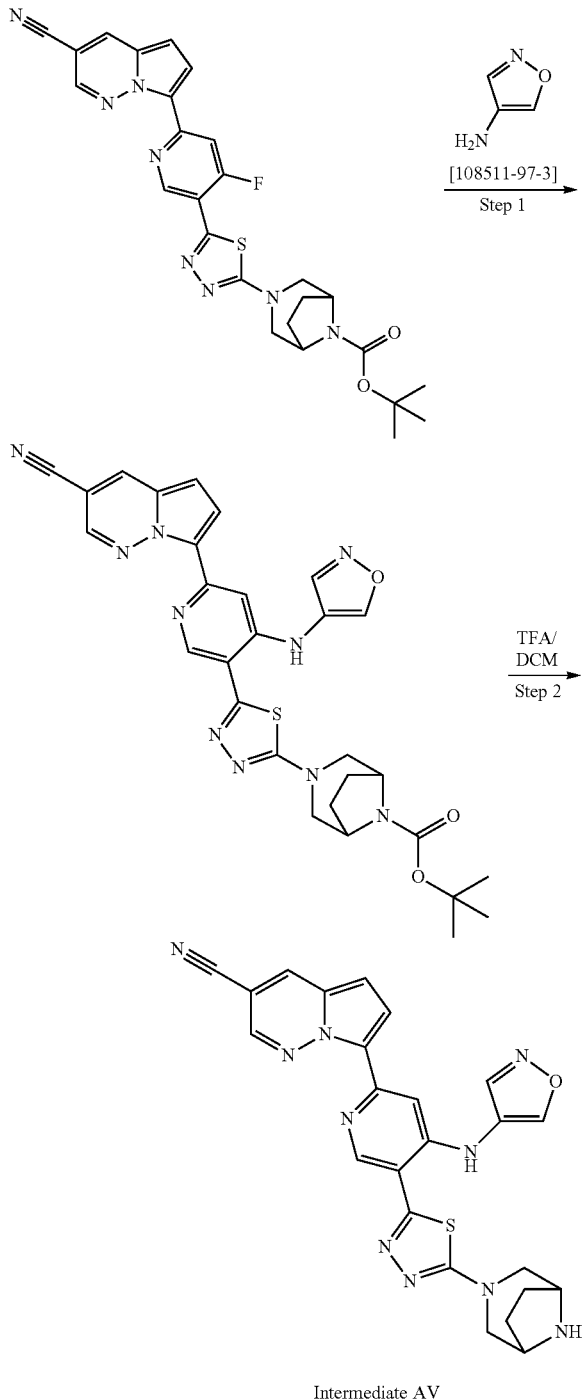

Intermediate AV

Step 1: To a solution of tert-butyl 3-[5-(6-{3-cyanopyrrolo[1,2-b]pyridazin-7-yl}-4-fluoropyridin-3-yl)-1,3,4-thiadiazol-2-yl]-3,8-diazabicyclo[3.2.1]octane-8-carboxylate (500 mg, 0.94 mmol) in AcOH (9.5 mL, 0.1 M) was added 1,2-oxazol-4-amine (789 mg, 9.4 mmol) was added. The reaction mixture was stirred at room temperature overnight. After completion of the reaction, acetic acid was evaporated, and the residue was partitioned between saturated NaHCO$_3$ (50 mL) and DCM (100 mL). The layers were separated, and the aqueous layer was further washed with DCM (2×100 mL). The combined organic layers were washed with brine (1×100 mL). The DCM layer was dried over anhydrous Na$_2$SO$_4$, filtered, and concentrated under reduced pressure to yield 900 mg of the crude. The crude was combined with trial reaction and purified by silica gel flash chromatography using 0 to 10% IPA in DCM to yield 600 mg of semi-pure product. It was then re-purified RPFC using ACN/water containing 0.1% FA, then was washed off the column using 95% THF, 0.1% TFA, and 4.9% water to yield 305 mg (54% yield) of tert-butyl 3-(5-(6-(3-cyanopyrrolo[1,2-b]pyridazin-7-yl)-4-(isoxazol-4-ylamino)pyridin-3-yl)-1,3,4-thiadiazol-2-yl)-3,8-diazabicyclo[3.2.1]octane-8-carboxylate as a pale yellow solid. LCMS: [C$_{29}$H$_{28}$N$_{10}$O$_3$S], desired mass=596.2 observed mass=597.1 [M+H]$^+$. $^1$H NMR (300 MHz, DMSO-d$_6$) δ 10.12 (s, 1H), 9.28 (s, 1H), 9.02 (s, 1H), 8.70-8.63 (m, 2H), 8.41 (s, 1H), 8.19 (d, J=5.8 Hz, 1H), 7.87 (d, J=4.8 Hz, 1H), 7.13 (d, J=4.9 Hz, 1H), 4.31 (s, 2H), 3.71 (d, J=11.6 Hz, 2H), 3.41 (d, J=11.1 Hz, 2H), 1.89 (d, J=24.9 Hz, 2H), 1.77 (d, J=7.5 Hz, 2H), 1.45 (s, 9H).

Step 2: To a solution of tert-butyl 3-(5-(6-(3-cyanopyrrolo[1,2-b]pyridazin-7-yl)-4-(isoxazol-4-ylamino)pyridin-3-yl)-1,3,4-thiadiazol-2-yl)-3,8-diazabicyclo[3.2.1]octane-8-carboxylate (305 mg, 0.511 mmol) in anhydrous DCM anhydrous (3.8 ml, 0.2 M) the TFA (1.72 g, 15.11 mmol) was added and the resulting mixture was kept at RT for 1 h. The volatiles were removed by evaporation. The crude was triturated with Et$_2$O (4×10 mL) to yield 315 mg (100% yield) of 7-(5-(5-(3,8-diazabicyclo[3.2.1]octan-3-yl)-1,3,4-thiadiazol-2-yl)-4-(isoxazol-4-ylamino)pyridin-2-yl)pyrrolo[1,2-b]pyridazine-3-carbonitrile as a pale yellow solid. LCMS: [C24H20N10OS], desired mass=496.15, observed mass=497.2 [M+H]$^+$. $^1$H NMR (300 MHz, DMSO-d$_6$) δ 10.12 (s, 1H), 9.29 (s, 3H), 9.01 (s, 1H), 8.85 (d, J=2.2 Hz, 1H), 8.69 (d, J=1.6 Hz, 2H), 8.38 (s, 1H), 7.87 (d, J=4.9 Hz, 1H), 7.13 (d, J=4.8 Hz, 1H), 4.24 (s, 2H), 3.88 (d, J=12.7 Hz, 2H), 3.63 (d, J=12.8 Hz, 2H), 2.09-1.92 (m, 4H).

Intermediate AW: 7-(4-{[(1S)-1-cyanoethyl]amino}-
5-(5-{3,8-diazabicyclo[3.2.1]octan-3-yl}-1,3,4-thia-
diazol-2-yl)pyridin-2-yl)pyrrolo[1,2-b]pyridazine-3-
carbonitrile

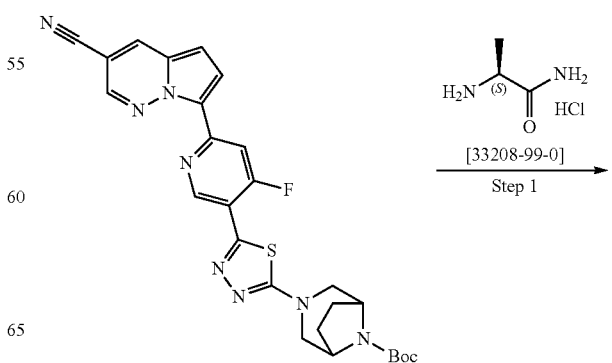

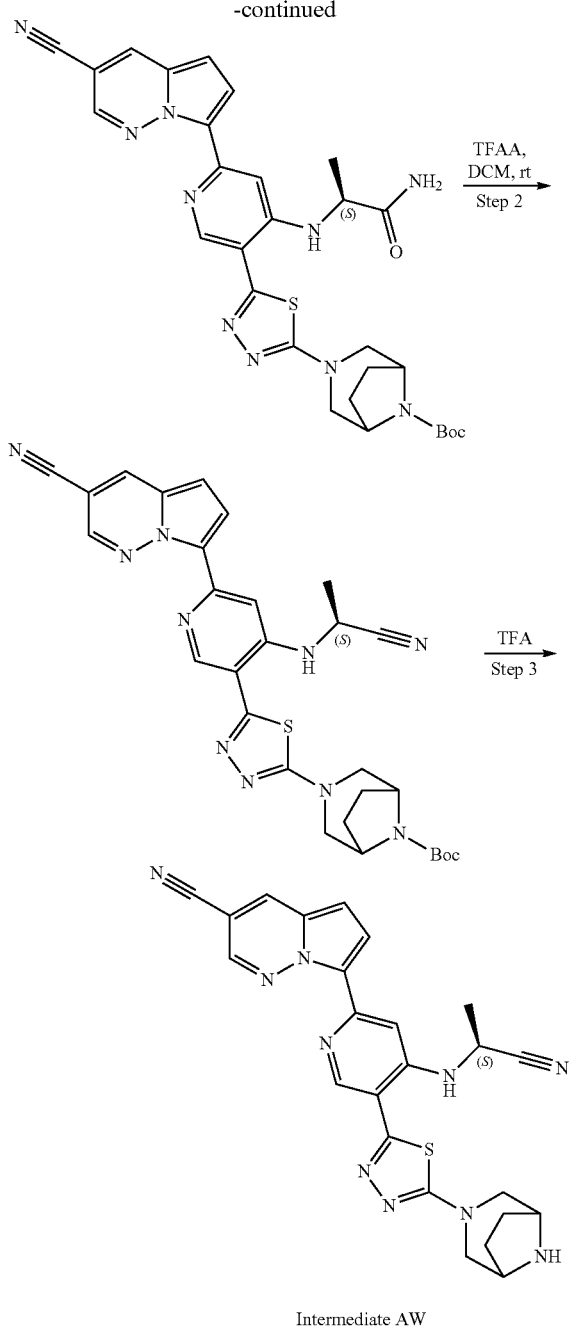

Intermediate AW

Step 1: To a solution of tert-butyl 3-[5-(6-{3-cyanopyrrolo[1,2-b]pyridazin-7-yl}-4-fluoropyridin-3-yl)-1,3,4-thiadiazol-2-yl]-3,8-diazabicyclo[3.2.1]octane-8-carboxylate (0.471 mg, 0.88 mmol) in N-methyl-pyrrolidone (5.9 mL, 0.15 M) was added L-alaninamide hydrochloride (0.33 g, 2.65 mmol) and N,N-diisopropylethylamine (0.79 mL, 4.42 mmol) at room temperature. The reaction mixture was stirred at 120° C. for overnight. After the completion of the reaction, the solvent was removed under reduced pressure. The residue was purified by silica gel flash chromatography eluting with 0-6% of MeOH in DCM to provide 0.332 g (62% yield) of tert-butyl 3-[5-(4-{[(1S)-1-carbamoylethyl]amino}-6-{3-cyanopyrrolo[1,2-b]pyridazin-7-yl}pyridin-3-yl)-1,3,4-thiadiazol-2-yl]-3,8-diazabicyclo[3.2.1]octane-8-carboxylate as a yellow gum. LCMS: [$C_{29}H_{32}N_{10}O_3S$], desired mass=600.2, observed mass=601.3 [M+H]$^+$. $^1$H NMR (300 MHz, DMSO-d$_6$) δ 8.85 (q, J=2.3, 1.6 Hz, 2H), 8.63 (d, J=2.2 Hz, 1H), 8.51 (s, 1H), 8.11 (s, 1H), 7.82 (d, J=4.8 Hz, 1H), 7.76 (s, 1H), 7.22 (s, 1H), 7.12 (d, J=4.8 Hz, 1H), 4.27 (d, J=7.1 Hz, 3H), 3.70 (d, J=11.8 Hz, 2H), 3.37 (d, J=11.8 Hz, 3H), 1.91 (s, 2H), 1.76 (d, J=7.4 Hz, 2H), 1.50 (d, J=6.7 Hz, 3H), 1.44 (s, 9H).

Step 2: To an ice-cooled solution of tert-butyl 3-[5-(4-{[(1S)-1-carbamoylethyl]amino}-6-{3-cyanopyrrolo[1,2-b]pyridazin-7-yl}pyridin-3-yl)-1,3,4-thiadiazol-2-yl]-3,8-diazabicyclo[3.2.1]octane-8-carboxylate (332 mg, 0.55 mmol) in dichloromethane anhydrous (42.5 mL, 0.01 M) were added trifluoroacetic anhydride (0.23 mL, 1.66 mmol) and pyridine anhydrous (0.36 mL, 4.42 mmol). The reaction mixture was stirred at room temperature for 30 min. After the completion of the reaction, the solvent was removed under reduced pressure. The residue was purified by silica gel flash chromatography eluting with 0-5% of MeOH in DCM to provide 0.195 g (63% yield) of tert-butyl 3-[5-(4-{[(1S)-1-cyanoethyl]amino}-6-{3-cyanopyrrolo[1,2-b]pyridazin-7-yl}pyridin-3-yl)-1,3,4-thiadiazol-2-yl]-3,8-diazabicyclo[3.2.1]octane-8-carboxylate as a yellow solid. LCMS: [$C_{29}H_{30}N_{10}O_2S$], desired mass=582.2, observed mass=583.1 [M+H]$^+$. $^1$H NMR (300 MHz, DMSO-d$_6$) δ 8.91-8.79 (m, 2H), 8.68 (d, J=2.3 Hz, 1H), 8.63 (s, 1H), 8.37 (s, 1H), 7.88 (d, J=4.8 Hz, 1H), 7.15 (d, J=4.9 Hz, 1H), 5.04 (t, J=6.8 Hz, 1H), 4.29 (s, 2H), 3.70 (d, J=11.8 Hz, 2H), 3.39 (d, J=11.7 Hz, 2H), 1.98-1.89 (m, 2H), 1.77 (t, J=6.7 Hz, 5H), 1.45 (s, 9H).

Step 3: To a solution of tert-butyl 3-[5-(4-{[(1S)-1-cyanoethyl]amino}-6-{3-cyanopyrrolo[1,2-b]pyridazin-7-yl}pyridin-3-yl)-1,3,4-thiadiazol-2-yl]-3,8-diazabicyclo[3.2.1]octane-8-carboxylate (0.195 g, 0.35 mmol) in dichloromethane anhydrous (1.75 mL, 0.2 M) was added trifluoroacetic acid (0.54 mL, 7.00 mmol) at room temperature. The reaction mixture was stirred at room temperature for 1 h. After the completion of the reaction, the solvent was removed under reduced pressure. The residue was purified by trituration with diethyl ether (3×20 mL) to provide 227.8 mg (96% yield) of 7-(4-{[(1S)-1-cyanoethyl]amino}-5-(5-{3,8-diazabicyclo[3.2.1]octan-3-yl}-1,3,4-thiadiazol-2-yl)pyridin-2-yl)pyrrolo[1,2-b]pyridazine-3-carbonitrile as a yellow solid. LCMS: [$C_{24}H_{22}N_{10}S$], desired mass=482.2, observed mass=483.0 [M+H]$^+$. $^1$H NMR (300 MHz, DMSO-d$_6$) δ 9.19-9.07 (m, 1H), 9.10-8.98 (m, 1H), 8.89 (d, J=2.3 Hz, 1H), 8.86 (d, J=8.1 Hz, 1H), 8.70 (d, J=2.3 Hz, 1H), 8.67 (s, 1H), 8.35 (s, 1H), 7.90 (d, J=4.7 Hz, 1H), 7.16 (d, J=4.9 Hz, 1H), 5.08 (t, J=6.9 Hz, 1H), 4.22 (s, 2H), 3.87 (d, J=13.1 Hz, 2H), 3.60 (d, J=12.7 Hz, 2H), 2.04-1.92 (m, 4H), 1.77 (d, J=6.9 Hz, 3H).

Intermediate AX: 7-{4-[(1-cyano-1-methylethyl)amino]-5-(5-{3,8-diazabicyclo[3.2.1]octan-3-yl}-1,3,4-thiadiazol-2-yl)pyridin-2-yl}pyrrolo[1,2-b]pyridazine-3-carbonitrile

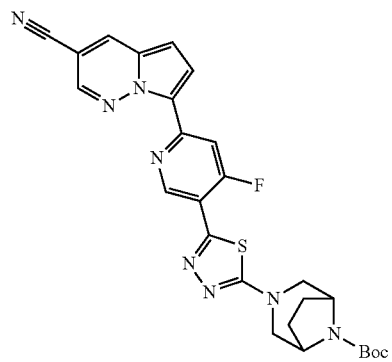
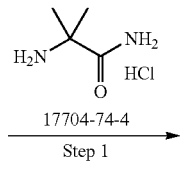
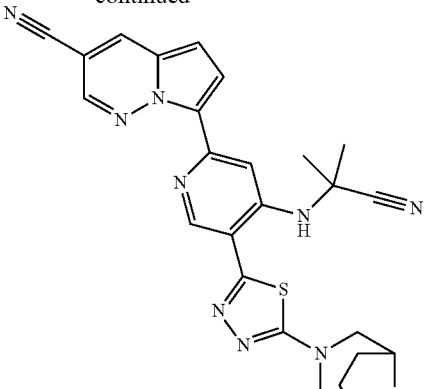

Intermediate AX

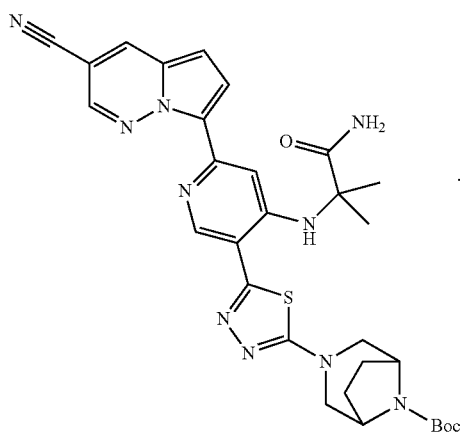

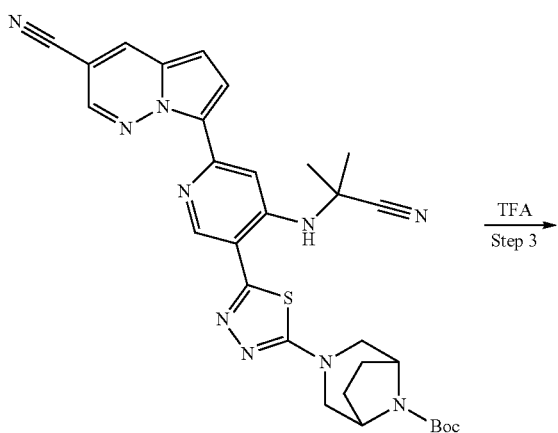

Step 1: Tert-butyl 3-[5-(6-{3-cyanopyrrolo[1,2-b]pyridazin-7-yl}-4-fluoropyridin-3-yl)-1,3,4-thiadiazol-2-yl]-3,8-diazabicyclo[3.2.1]octane-8-carboxylate (0.5 g, 0.939 mmol, 1.0 eq) was dissolved in dimethyl sulfoxide anhydrous (9.39 ml, 0.1 M) followed by addition of 2-amino-2-methylpropanamide hydrochloride (1.301 g, 9.388 mmol, 10.0 eq) and sodium bicarbonate (1.183 g, 14.082 mmol, 15.0 eq) the resulting mixture was stirred at 120° C. overnight. DMSO was removed in vacuo and the residue was mixed with water. The formed precipitate was collected by filtration and dried in vacuo to give crude 0.6 g (59% yield) tert-butyl 3-(5-{4-[(1-carbamoyl-1-methylethyl)amino]-6-{3-cyanopyrrolo[1,2-b]pyridazin-7-yl}pyridin-3-yl)-1,3,4-thiadiazol-2-yl)-3,8-diazabicyclo[3.2.1]octane-8-carboxylate as a yellow solid. LCMS: [$C_{30}H_{34}N_{10}O_3S$], desired mass=614.7, observed mass=615.8 [M+H]$^+$.

Step 2: The crude tert-butyl 3-(5-{4-[(1-carbamoyl-1-methylethyl)amino]-6-{3-cyanopyrrolo[1,2-b]pyridazin-7-yl}pyridin-3-yl)-1,3,4-thiadiazol-2-yl)-3,8-diazabicyclo[3.2.1]octane-8-carboxylate (0.6 g, 0.56 mmol, 1.0 eq) was suspended in dichloromethane anhydrous (11.13 ml, 0.05 M) followed by addition of anhydrous pyridine (0.359 ml, 4.451 mmol, 8.0 eq). Trifluoroacetic anhydride (0.351 g, 1.67 mmol, 3.0 eq) was added to the resulting suspension and the reaction mixture was stirred at rt for 30 minutes. Then, the reaction mixture was concentrated in vacuo, dissolved in a minimal amount of DCM and two FC purifications were performed using DCM-IPA 0-7% as a mobile phase followed by using DCM-ACN 0-30% as a mobile phase, to give 0.31 g (93% yield) of tert-butyl 3-(5-{4-[(1-cyano-1-methylethyl)amino]-6-{3-cyanopyrrolo[1,2-b]pyridazin-7-yl}pyridin-3-yl)-1,3,4-thiadiazol-2-yl)-3,8-diazabicyclo[3.2.1]octane-8-carboxylate as a yellow solid. LCMS: [$C_{30}H_{32}N_{10}O_2S$], desired mass=596.7, observed mass=597.9 [M+H]$^+$. $^1$H NMR (400 MHz, DMSO-d$_6$) δ 9.07 (s, 1H), 8.88 (d, J=2.2 Hz, 1H), 8.71 (d, J=2.2 Hz, 1H), 8.69 (s, 1H), 8.65 (s, 1H), 7.90 (d, J=4.8 Hz, 1H), 7.16 (d, J=4.8 Hz, 1H), 4.29 (s, 2H), 3.71 (d, J=11.9 Hz, 2H), 3.39 (d, J=11.3 Hz, 2H), 1.92 (s, 6H), 1.75 (d, J=7.4 Hz, 4H), 1.45 (s, 9H).

Step 3: Tert-butyl 3-(5-{4-[(1-cyano-1-methylethyl)amino]-6-{3-cyanopyrrolo[1,2-b]pyridazin-7-yl}pyridin-3-yl}-1,3,4-thiadiazol-2-yl)-3,8-diazabicyclo[3.2.1]octane-8-carboxylate (0.31 g, 0.52 mmol, 1.0 eq) was dissolved in anhydrous DCM (5.2 ml, 0.1 M) followed by TFA (1.185 g, 10.39 mmol, 20.0 eq). The resulting mixture was stirred at rt for 4 h, then concentrated in vacuo. The residue was triturated and sonicated with diethyl ether to give yellow precipitate, which was collected by filtration and dried in vacuo overnight to give 0.255 g (76% yield) of 7-{4-[(1-cyano-1-methylethyl)amino]-5-(5-{3,8-diazabicyclo[3.2.1]octan-3-yl}-1,3,4-thiadiazol-2-yl)pyridin-2-yl}pyrrolo[1,2-b]pyridazine-3-carbonitrile as a yellow solid. LCMS: [$C_{25}H_{24}N_{10}S$], desired mass=496.6, observed mass=497.8 [M+H]$^+$. $^1$H NMR (400 MHz, DMSO-$d_6$) δ 9.27-9.09 (m, 2H), 9.08 (s, 1H), 8.90 (d, J=2.2 Hz, 1H), 8.73 (d, J=2.2 Hz, 1H), 8.70 (s, 1H), 8.69 (s, 1H), 7.91 (d, J=4.8 Hz, 1H), 7.17 (d, J=4.8 Hz, 1H), 4.25-4.18 (m, 2H), 3.93-3.80 (m, 2H), 3.67-3.57 (m, 2H), 2.07-1.95 (m, 4H), 1.93 (s, 6H).

Intermediate AY: 7-[5-(5-{3-oxa-7,9-diazabicyclo[3.3.1]nonan-7-yl}-1,3,4-thiadiazol-2-yl)-4-[(oxan-4-yl)amino]pyridin-2-yl]pyrrolo[1,2-b]pyridazine-3-carbonitrile; 2× trifluoroacetate salt

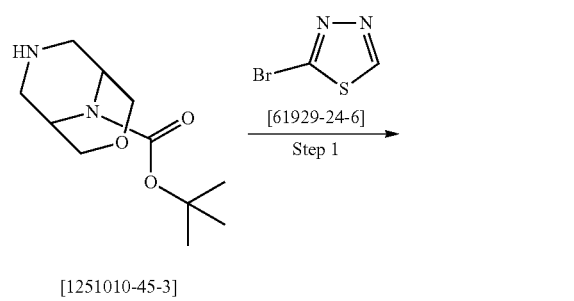

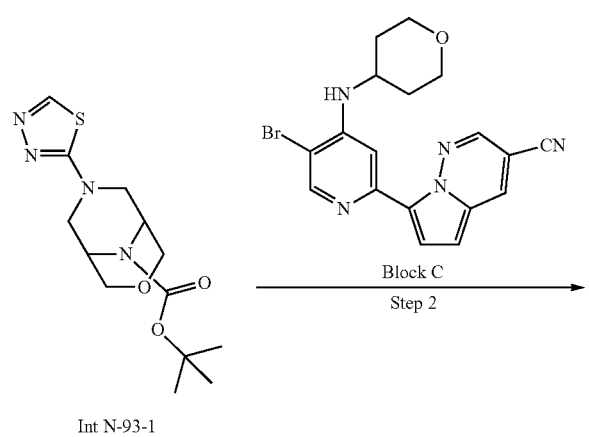

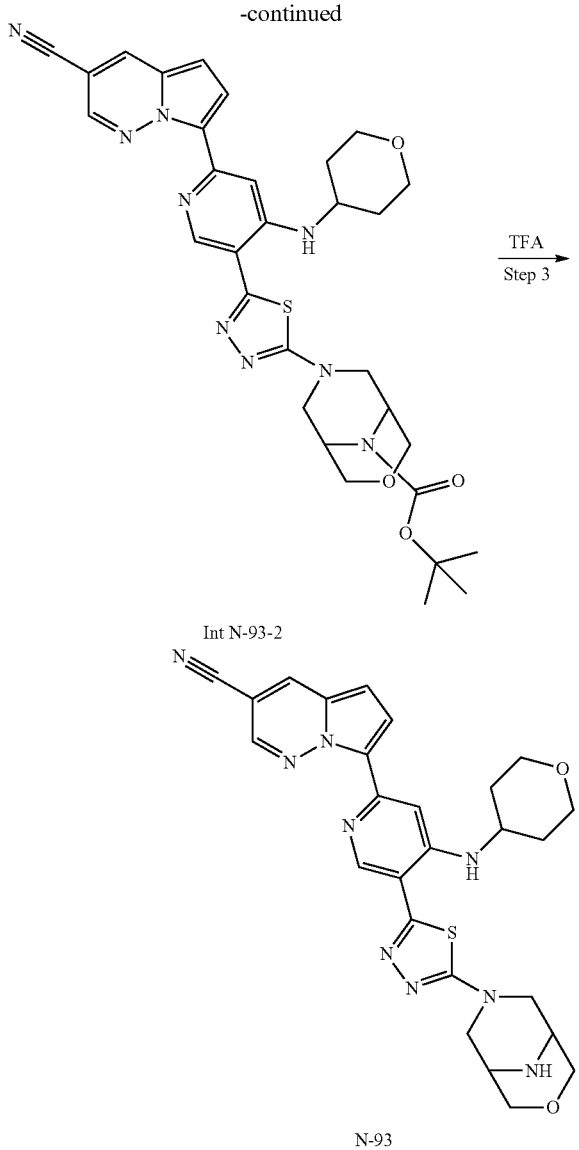

Step 1: To a solution of tert-butyl 3-oxa-7,9-diazabicyclo[3.3.1]nonane-9-carboxylate (0.55 g, 2.41 mmol) in n-butanol (4.82 mL, 0.5 M) was added 2-bromo-1,3,4-thiadiazole (0.99 g, 6.02 mmol) and DIPEA (1.65 mL, 9.64 mmol). The reaction mixture was stirred at 120° C. for 1 h. The volatiles were removed in vacuo and the residue was transferred into a separatory funnel using a mixture of EtOAc (50 mL) and H$_2$O (100 mL), and then extracted with EtOAc (5×50 mL). The combined organic layers were dried over Na$_2$SO$_4$, filtered, and concentrated in vacuo. The residue was purified by silica gel flash chromatography using 0 to 80% of ACN in DCM to provide 0.467 g (62% yield) of tert-butyl 7-(1,3,4-thiadiazol-2-yl)-3-oxa-7,9-diazabicyclo[3.3.1]nonane-9-carboxylate as a red solid. LCMS: $C_{13}H_{20}N_4O_3S$ requires 312.4, observed m/z=313.0 [M+H]$^+$. $^1$H NMR (300 MHz, DMSO-$d_6$) δ 8.75 (s, 1H), 4.01 (d, J=9.6 Hz, 2H), 3.97-3.84 (m, 4H), 3.62 (dt, J=11.5, 2.5 Hz, 2H), 3.44 (d, J=12.9 Hz, 2H), 1.44 (s, 9H).

Step 2: To a suspension of 7-{5-bromo-4-[(oxan-4-yl)amino]pyridin-2-yl}pyrrolo[1,2-b]pyridazine-3-carbonitrile (0.42 g, 1.06 mmol) in dioxane (32.0 mL, 0.03 M) were added tert-butyl 7-(1,3,4-thiadiazol-2-yl)-3-oxa-7,9-diazabicyclo[3.3.1]nonane-9-carboxylate (0.312 g, 0.959 mmol), CuI (0.037 g, 0.19 mmol), Xantphos (0.111 g, 0.19 mmol) and Cs$_2$CO$_3$ (1.25 g, 3.84 mmol). The reaction mixture was degassed with argon for 15 min and then Pd(OAc)$_2$ (0.022 g, 0.096 mmol) was added. The reaction mixture was stirred at 130° C. using microwave heating for 2 hours. Next, it was cooled to room temperature and additional Xantphos (0.111 g, 0.19 mmol), Cs$_2$CO$_3$ (1.25 g, 3.84 mmol), CuI (0.037 g, 0.19 mmol), Pd(OAc)$_2$ (0.022 g, 0.096 mmol) were added. The mixture was stirred at 130° C. for additional 2 h using microwave heating. The volatiles were evaporated in vacuo. The residue was purified by silica gel flash chromatography eluting with 0 to 100% of MeCN in DCM. The resulting semi-pure product was repurified using reversed-phase flash chromatography eluting with MeCN in water (5 to 75% of MeCN) to provide 0.09 g (15% yield) of tert-butyl 7-[5-(6-{3-cyanopyrrolo[1,2-b]pyridazin-7-yl}-4-[(oxan-4-yl)amino]pyridin-3-yl)-1,3,4-thiadiazol-2-yl]-3-oxa-7,9-diazabicyclo[3.3.1]nonane-9-carboxylate as a yellow solid. LCMS: C$_{31}$H$_{35}$N$_9$O$_4$S requires 629.7, observed m/z=630.2 [M+H]$^+$. $^1$H NMR (300 MHz, DMSO-d$_6$) δ 8.85 (d, J=2.3 Hz, 1H), 8.77 (d, J=2.3 Hz, 1H), 8.70 (s, 1H), 8.51 (s, 1H), 8.29 (s, 1H), 7.84 (d, J=4.8 Hz, 1H), 7.13 (d, J=4.8 Hz, 1H), 4.13-3.75 (m, 11H), 3.60 (dt, J=20.0, 10.5 Hz, 8H), 2.12 (d, J=15.5 Hz, 3H), 1.58 (d, J=10.0 Hz, 3H).

Step 3: To a solution of tert-butyl 7-[5-(6-{3-cyanopyrrolo[1,2-b]pyridazin-7-yl}-4-[(oxan-4-yl)amino]pyridin-3-yl)-1,3,4-thiadiazol-2-yl]-3-oxa-7,9-diazabicyclo[3.3.1]nonane-9-carboxylate (0.09 g, 0.143 mmol) in DCM (14.3 mL, 0.01 M) was added trifluoroacetic acid (0.978 g, 8.58 mmol). The reaction mixture was stirred at room temperature overnight. The volatiles were removed in vacuo. The resulting crude was triturated with Et$_2$O (4×20 mL) and dried to provide 0.08 g (83% yield) of 7-[5-(5-{3-oxa-7,9-diazabicyclo[3.3.1]nonan-7-yl}-1,3,4-thiadiazol-2-yl)-4-[(oxan-4-yl)amino]pyridin-2-yl]pyrrolo[1,2-b]pyridazine-3-carbonitrile; 2× trifluoroacetate salt as a yellow solid. LCMS: C$_{26}$H$_{27}$N$_9$O$_2$S requires 529.2, observed m/z=530.3 [M+H]$^+$, method: LCMS2-036-5-80-80-7-1-25-UV-Rot, RT=2.81 min, purity: 95.71% (254 nm). $^1$H NMR (300 MHz, DMSO-d$_6$) δ 8.99 (d, J=2.2 Hz, 1H), 8.87 (d, J=2.2 Hz, 1H), 8.62 (s, 1H), 8.14-8.04 (m, 2H), 7.25 (d, J=5.0 Hz, 1H), 4.32 (d, J=13.9 Hz, 2H), 4.12 (d, J=12.5 Hz, 3H), 4.03-3.83 (m, 6H), 3.67-3.54 (m, 2H), 2.57 (d, J=5.5 Hz, 4H), 2.10 (t, J=6.8 Hz, 2H), 1.72-1.57 (m, 2H).

B. Synthesis of LHM Building Blocks

HA-1: 1-(5-(2,6-dioxopiperidin-3-yl)pyridin-2-yl)piperidine-4-carbaldehyde

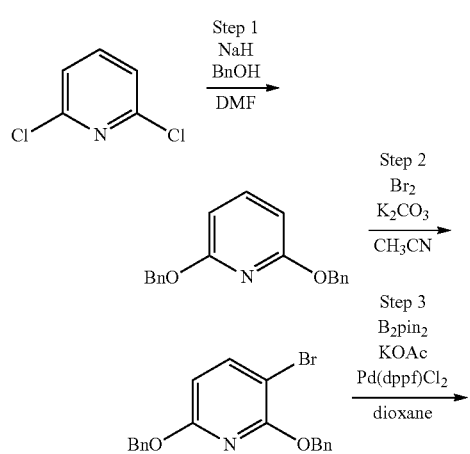

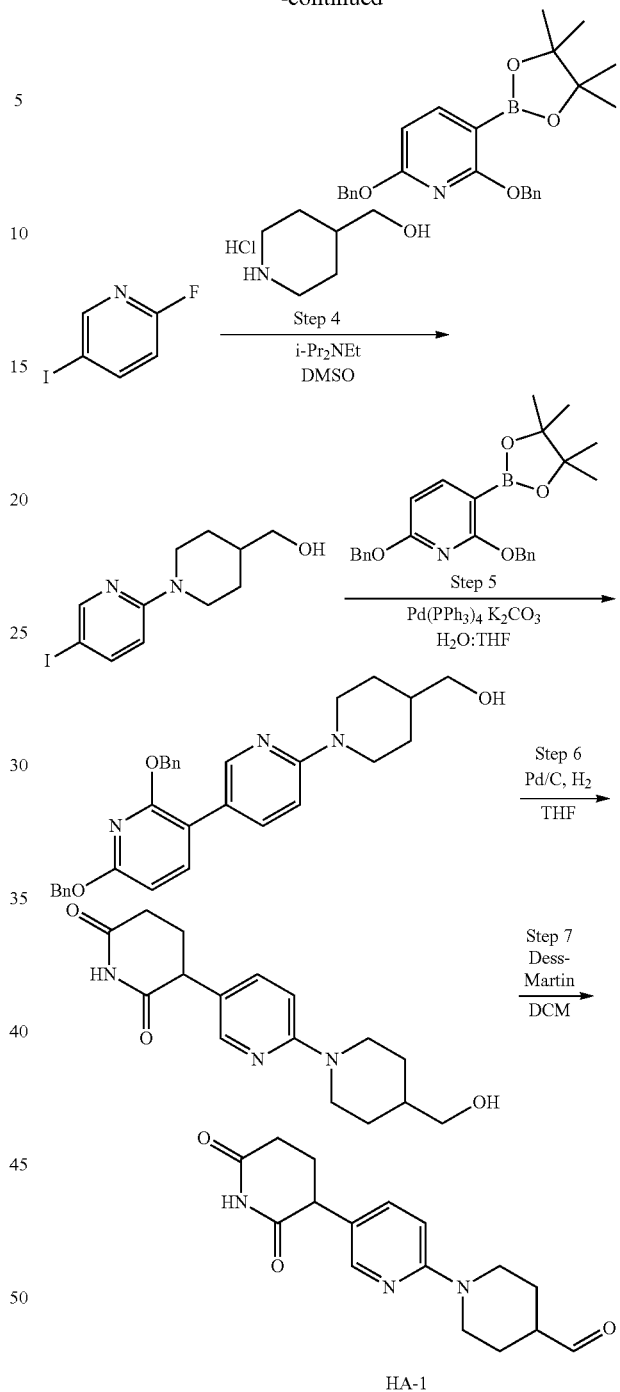

Step 1: Into a 5—L 4-necked round-bottom flask under an inert atmosphere of nitrogen, was added 2,6-dichloropyridine (150.00 g, 1013.58 mmol, 1.00 eq), dimethylformamide (3 L), NaH (272.00 g, 11334 mmol, 11.18 eq, 65%). This was followed by the addition of BnOH (329.50 g, 3050 mmol, 3.01 eq) dropwise with stirring at 0° C. The resulting solution was stirred for 4 h at 80° C. The reaction mixture was cooled. The reaction was then quenched by the addition of 7 L of water/ice. The solids were collected by filtration and concentrated. This resulted in 276 g (93.46%) of 2,6-bis(benzyloxy)pyridine as a grey solid. LCMS: (ES, m/z): [M+1]$^+$=292; T=1.48 min.

Step 2: Into a 3—L 4-necked round-bottom under an inert atmosphere of nitrogen, was added 2,6-bis(benzyloxy)pyridine (276.00 g, 947.3 mmol, 1.00 eq), CH$_3$CN (2.76 L), K$_2$CO$_3$ (445.00 g, 3196.54 mmol, 3.37 eq). This was followed by the dropwise addition of Br$_2$ (151.70 g, 949.26 mmol, 1.00 eq) at 0° C. The resulting solution was stirred for 4 h at room temperature. The resulting reaction mixture was concentrated. The residue was loaded onto a silica gel column with ethyl acetate/petroleum ether (10%). This resulted in 253 g (72.13%) of 2,6-bis(benzyloxy)-3-bromopyridine as a white solid. LCMS: [M+1]$^+$=370.

Step 3: Into a 3—L 4-necked round-bottom flask purged and maintained with an inert atmosphere of nitrogen, was placed 2,6-bis(benzyloxy)-3-bromopyridine (253.00 g, 683.32 mmol, 1.00 eq), Dioxane (2.53 L), bis(pinacolato) diboron (261.00 g, 1027.80 mmol, 1.50 eq), potassium acetate (134.00 g, 1365.36 mmol, 2.00 eq), Pd(dppf)Cl$_2$ (25.10 g, 34.29 mmol, 0.05 eq). The resulting solution was stirred overnight at 100° C. The reaction mixture was cooled. The resulting mixture was concentrated and loaded onto a silica gel column with ethyl acetate/petroleum ether (15%). This resulted in 200 g (70.14%) of 2,6-bis(benzyloxy)-3-(4,4,5,5-tetramethyl-1,3,2-dioxaborolan-2-yl)pyridine as a white solid.

Step 4: Into a 3—L 4-necked round-bottom flask purged and maintained with an inert atmosphere of nitrogen, was placed 2-fluoro-5-iodopyridine (200.00 g, 896.90 mmol, 1.00 eq), DMSO (2.00 L), piperidin-4-ylmethanol (128.90 g, 1119.15 mmol, 1.25 eq), DIEA (347.00 g, 2684.86 mmol, 3.00 eq). The resulting solution was stirred for 3 days at 90° C. The reaction mixture was cooled. The resulting mixture was exacted with 2×2 L of EA and the organic layer was combined. The resulting mixture was washed with 3×2 L of brine. The resulting mixture was concentrated. The residue was applied onto a silica gel column with ethyl acetate/petroleum ether (35%). This resulted in 182 g (63.78%) of [1-(5-iodopyridin-2-yl)piperidin-4-yl]methanol as yellow oil. LCMS: [M+1]$^+$=319.

Step 5: Into a 3—L 4-necked round-bottom flask purged and maintained with an inert atmosphere of nitrogen, was placed [1-(5-iodopyridin-2-yl)piperidin-4-yl]methanol (182.00 g, 572.04 mmol, 1.00 eq), tetrahydrofuran (1.82 L), water (364.00 mL), 2,6-bis(benzyloxy)-3-(4,4,5,5-tetramethyl-1,3,2-dioxaborolan-2-yl)pyridine (298.40 g, 715.05 mmol, 1.25 eq), K$_2$CO$_3$ (157.90 g, 1134.23 mmol, 1.98 equiv), tetrakis(triphenylphosphine)palladium(0) (66.00 g, 57.11 mmol, 0.10 eq). The resulting solution was stirred for overnight at 90° C. The reaction mixture was cooled. The resulting mixture was exacted with 2×3 L of EA and the organic layer was washed with 3×3 L of brine. The combined organic layers were concentrated. The residue was loaded onto a silica gel column with ethyl acetate/petroleum ether (85%). This resulted in 140 g (50.82%) of [1-[2',6'-bis(benzyloxy)-[3,3'-bipyridin]-6-yl]piperidin-4-yl]methanol as a green solid. LCMS: [M+1]$^+$=482.

Step 6: Into a 2—L round-bottom flask, was added [1-[2',6'-bis(benzyloxy)-[3,3'-bipyridin]-6-yl]piperidin-4-yl]methanol (35.00 g, 72.67 mmol, 1.00 eq), tetrahydrofuran (120 mL), Pd/C (10.00 g, 10%). The resulting solution was stirred overnight under hydrogen atmosphere (4 atm). The Pd/C was then filtered, followed by the addition of another 10 g of Pd/C(10%), then stirred overnight again. The filtration/addition sequence was repeated 3 times. The solids were filtered. The resulting filtrate was concentrated and washed with 3×100 mL EA, This resulted in 64 g crude product. The 8 g crude directly used into the next step and the remaining 56 g crude was further purified by flash chromatography. This resulted in 45 g of 6'-[4-(hydroxymethyl)piperidin-1-yl]-1,3-dihydro-[3,3'-bipyridine]-2,6-dione as a yellow solid. LCMS: [M+1]$^+$=304. $^1$H-NMR: (300 MHZ, DMSO-d, ppm):610.79 (s, 1H), 7.93 (d, J=2.3 Hz, 1H), 7.35 (dd, J=8.8, 2.5 Hz, 1H), 6.79 (d, J=8.8 Hz, 1H), 4.45 (t, J=5.1 Hz, 1H), 4.27 (d, J=12.9 Hz, 2H), 3.72 (dd, J=12.0, 4.9 Hz, 1H), 3.27 (t, J=5.1 Hz, 2H), 2.82-2.59 (m, 3H), 2.58-2.43 (m, 1H), 2.17 (qd, J=12.5, 4.4 Hz, 1H), 1.98 (dq, J=8.5, 4.7 Hz, 1H), 1.71 (d, J=13.3 Hz, 2H), 1.60 (br, 1H), 1.11 (qd, J=11.9, 3.8 Hz, 2H).

Step 7: Into a 1 L 3-necked round-bottom flask under an atmosphere of nitrogen, was added 3-[6-[4-(hydroxymethyl)piperidin-1-yl]pyridin-3-yl]piperidine-2,6-dione (8.00 g, 26.37 mmol, 1.00 eq), DCM (400.00 mL). This was followed by the addition of Dess-Martin periodinane (12.30 g, 31.59 mmol, 1.20 eq) at 0° C. The resulting solution was stirred for 2 h at 0° C. The reaction mixture was filtered, and the filtrate was washed with brine (200 mL), dried over Na$_2$SO$_4$ and concentrated in vacuum and purified by silica gel column with DCM/EA (3:2). The residue was loaded onto a silica gel column with ethyl acetate/petroleum ether (15%). This resulted in 5 g (62.92%) of 1-[5-(2,6-dioxopiperidin-3-yl)pyridin-2-yl]piperidine-4-carbaldehyde (HA-1) as a grey solid. LCMS: (ES, m/z): [M+1]=302. $^1$H-NMR: (300 MHZ, DMSO-d$_6$, ppm):610.80 (s, 1H), 9.62 (s, 1H), 7.95 (d, J=2.5 Hz, 1H), 7.39 (dd, J=8.9, 2.5 Hz, 1H), 6.83 (d, J=8.8 Hz, 1H), 4.12 (d, J=13.1, 4.2 Hz, 2H), 3.73 (dd, J=12.0, 4.9 Hz, 1H), 3.10-2.95 (m, 2H), 2.64 (tdd, J=24.6, 11.1, 4.8 Hz, 2H), 2.18 (qd, J=12.4, 4.4 Hz, 1H), 2.03-1.93 (m, 1H), 1.89 (dd, J=13.2, 3.6 Hz, 3H), 1.57-1.39 (m, 2H).

HA-2: rac-(R)-3-(6-(piperidin-4-yl)pyridin-3-yl) piperidine-2,6-dione

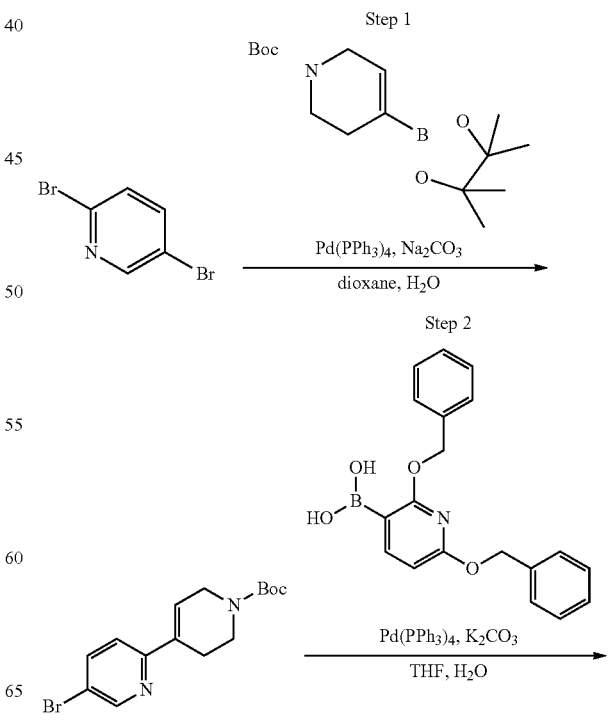

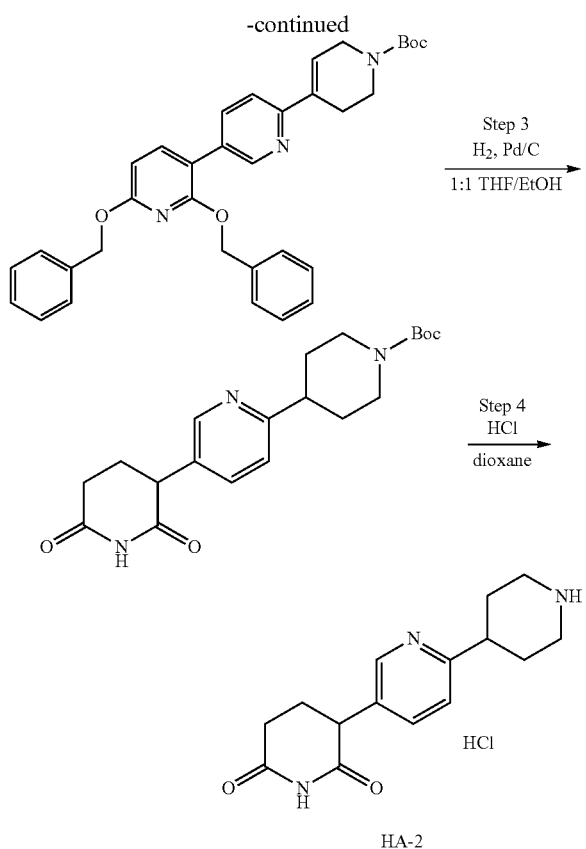

HA-2 reduced pressure. The resulting residue was purified by C18 reverse phase column chromatography with $CH_3CN/H_2O$ (1/1) to afford tert-butyl 4-[5-(2,6-dioxopiperidin-3-yl)pyridin-2-yl]piperidine-1-carboxylate (0.35 g, 39.63%) as a brown solid. LCMS (ESI) calculated for $(C_{20}H_{27}N_3O_4)$ $[M+1]^+$: 374.2; found: 374.0.

Step 4: A mixture of tert-butyl 4-[5-(2,6-dioxopiperidin-3-yl)pyridin-2-yl]piperidine-1-carboxylate (350 mg, 0.94 mmol, 1 eq) in HCl/dioxane (15 mL, 4M) was stirred at room temperature for 1 hr. The resulting mixture was concentrated under vacuum. This resulted in rac-(3R)-3-[6-(piperidin-4-yl)pyridin-3-yl]piperidine-2,6-dione hydrochloride salt (HA-2) (290 mg, 99.88%) as a pink solid. LCMS (ESI) calculated for $(C_{15}H_{19}N_3O_2)$ $[M+1]^+$: 274.2; found: 274.1. H NMR (400 MHz, DMSO-$d_6$) δ 10.98 (s, 1H), 9.19 (s, 1H), 9.09 (s, 1H), 8.68-8.63 (m, 1H), 8.22-8.15 (m, 1H), 7.73-7.66 (m, 1H), 4.20-4.12 (m, 1H), 3.44-3.36 (m, 2H), 3.32 (s, 1H), 3.09-3.02 (m, 1H), 3.02-2.96 (m, 1H), 2.80-2.67 (m, 1H), 2.64-2.55 (m, 1H), 2.43-2.27 (m, 1H), 2.18-2.11 (m, 2H), 2.06 (s, 2H), 2.11-1.96 (m, 1H).

HA-3: 1-(4-(2,6-dioxopiperidin-3-yl)-2-fluorophenyl)piperidine-4-carbaldehyde

Step 1: To a mixture of 2,5-dibromopyridine (10 g, 42.21 mmol, 1 eq) in 1,4-dioxane (100 mL) was added tert-butyl 4-(4,4,5,5-tetramethyl-1,3,2-dioxaborolan-2-yl)-3,6-dihydro-2H-pyridine-1-carboxylate (14.36 g, 46.43 mmol, 1.10 eq), $Na_2CO_3$ (6.71 g, 63.32 mmol, 1.5 eq) in $H_2O$ (10 mL) and $Pd(PPh_3)_4$ (1.46 g, 1.27 mmol, 0.03 eq). The resulting mixture was stirred at 100° C. overnight under nitrogen atmosphere. The resulting mixture was concentrated under vacuum. The residue was purified by silica gel column chromatography, eluted with PE/EA (2/1) to afford tert-butyl 5-bromo-3',6'-dihydro-2'H-[2,4'-bipyridine]-1'-carboxylate (10 g, 69.83%) as a yellow solid. LCMS (ESI) calculated for $(C_{15}H_{21}BrN_2O_2)$ $[M+1]^+$: 339.1; found: 339.1.

Step 2: To a mixture of tert-butyl 4-(5-bromopyridin-2-yl)piperidine-1-carboxylate (1 g, 2.93 mmol, 1eq) in THF (9 mL) was added 2,6-bis(benzyloxy)pyridin-3-ylboronic acid (1.18 g, 3.52 mmol, 1.2 equiv) and $K_2CO_3$ (0.81 g, 5.86 mmol, 2 eq) in $H_2O$ (3 mL) and $Pd(PPh_3)_4$ (0.34 g, 0.29 mmol, 0.1 eq). The resulting mixture was stirred at 110° C. overnight under nitrogen atmosphere. The resulting mixture was concentrated under vacuum. The residue was purified by silica gel column chromatography, eluted with PE/EA (5/1) to afford tert-butyl 5-[2,6-bis(benzyloxy)pyridin-3-yl]-3',6'-dihydro-2'H-[2,4'-bipyridine]-1'-carboxylate (1.3 g, 80.71%) as a white solid. LCMS (ESI) calculated for $(C_{34}H_{35}N_3O_4)$ $[M+1]^+$: 550.3; found: 550.3.

Step 3: To a mixture of tert-butyl 5-[2,6-bis(benzyloxy)pyridin-3-yl]-3',6'-dihydro-2'H-[2,4'-bipyridine]-1'-carboxylate (1.3 g, 2.37 mmol, 1eq) in THF (15 mL) was added Pd/C (1 g). The reaction mixture was stirred at room temperature for 5 h under a hydrogen atmosphere. The reaction mixture was filtered, then concentrated under

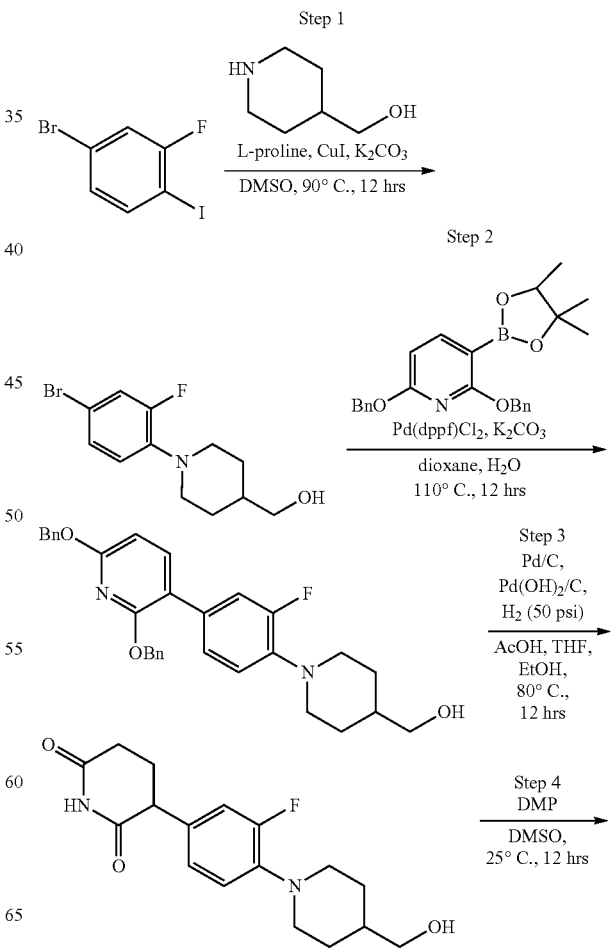

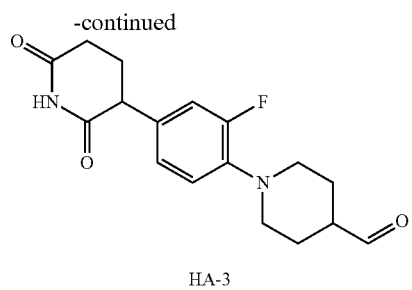

HA-3

Step 1: To a solution of 2-fluoro-4-bromo-iodobenzene (42.1 g, 365 mmol, 1.10 eq) and piperidin-4-ylmethanol (100 g, 332 mmol, 1.00 eq) in DMSO (1000 mL) was added L-proline (17.4 g, 132 mmol, 0.400 eq), $K_2CO_3$ (91.8 g, 664 mmol, 2.00 eq) and CuI (12.6 g, 66.4 mmol, 0.200 eq) under $N_2$. The reaction was stirred at 90° C. for 12 hrs. The reaction mixture was cooled to 20° C. and poured into saturated $NH_4Cl$ solution (1000 mL). The product was extracted with ethyl acetate (1000 mL*3), and the combined organic layers were washed with brine (1000 mL), dried over $Na_2SO_4$, filtered and concentrated. The residue was purified by column chromatography ($SiO_2$, petroleum ether/ethyl acetate=10/1 to 0/1, $R_f$=0.55). The desired product (10.7 g, 35.6 mmol, 10.7% yield) was obtained as a yellow solid. LCMS: m/z=290.0 (M+H)$^+$.

Step 2: To a solution of (1-(4-bromo-2-fluorophenyl)piperidin-4-yl)methanol(11.6 g, 38.6 mmol, 1.00 eq), 2,6-bis(benzyloxy)-3-(4,4,5-trimethyl-1,3,2-dioxaborolan-2-yl)pyridine(17.7 g, 42.4 mmol, 1.10 eq), $K_2CO_3$ (16.0 g, 115 mmol, 3.00 eq) in dioxane (116 mL) and $H_2O$ (23 mL) was added Pd(dppf)$Cl_2$·$CH_2Cl_2$ (3.15 g, 3.86 mmol, 0.100 eq) under $N_2$. Then the reaction mixture was stirred at 110° C. for 12 hrs. The mixture was cooled to 25° C. Then the reaction mixture was poured into $H_2O$ (300 mL), and was extracted with EtOAc (200 mL*3). The combined organic layers were washed with brine (200 mL), dried over $Na_2SO_4$ and concentrated. The crude product was purified by MPLC ($SiO_2$, petroleum ether/ethyl acetate=100/1 to 5/1) (petroleum ether/ethyl acetate=1/1, $R_f$=0.5). Compound 11 (10.7 g, 20.5 mmol, 53.2% yield) was obtained as a light yellow solid. LCMS: m/z=499.4 (M+H)$^+$.

Step 3: To a solution of (1-(4-(2,6-bis(benzyloxy)pyridin-3-yl)-2-fluorophenyl)piperidin-4-yl)methanol (11.6 g, 23.2 mmol, 1.00 eq) in THF (120 mL) and EtOH (120 mL) was added AcOH (4.19 g, 69.8 mmol, 3.99 mL, 3.00 eq), Pd/C (2.90 g, 10% purity) and Pd(OH)$_2$ (3.01 g, 4.29 mmol, 20% purity) under $N_2$. The suspension was degassed under vacuum and purged with $H_2$ several times. The mixture was stirred under $H_2$ (50 psi) at 80° C. for 12 hours. The reaction was cooled to 20° C. and filtered. The filtrate was concentrated. The crude product was used for next step without purification. The desired product (8.40 g, crude) was obtained as a yellow solid. LCMS: m/z=321.2 (M+H)$^+$.

Step 4: To a solution of 3-(3-fluoro-4-(4-(hydroxymethyl)piperidin-1-yl)phenyl) piperidine-2,6-dione(8.40 g, 26.2 mmol, 1.00 eq) in DMSO (90.0 mL) was added DMP (22.2 g, 52.4 mmol, 16.2 mL, 2.00 eq) in portions. The reaction was stirred at 25° C. for 12 hrs. The pH of the reaction mixture was adjusted to pH=10 with saturated aqueous $Na_2CO_3$, and the aqueous layer was extracted with ethyl acetate (400 mL*4). The combined organic layers were washed with $Na_2S_2O_3$ solution (500 mL*2) and brine (1000 mL), dried over $Na_2SO_4$, filtered and concentrated under vacuum. The crude product was triturated with ethyl acetate (100 mL) at 25° C. for 12 hrs. HA-3 (2.50 g, 7.60 mmol, 28.9% yield) was obtained as a yellow solid. LCMS: m/z=317.1 (M−H)$^+$. $^1$H NMR (400 MHz, DMSO-d$_6$) δ 10.8 (s, 1H), 9.64 (s, 1H), 7.06-6.90 (s, 3H), 3.83-3.76 (m, 1H), 3.29-3.24 (m, 2H), 2.76 (t, J=10.0 Hz, 2H), 2.69-2.60 (m, 1H), 2.48-2.41 (m, 2H), 2.24-2.13 (m, 1H), 2.04-1.91 (m, 3H), 1.71-1.58 (m, 2H).

HA-4: 1-(4-(2,6-dioxopiperidin-3-yl)-3-fluorophenyl)piperidine-4-carbaldehyde

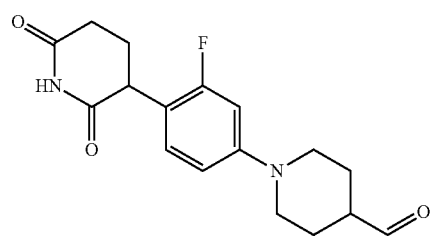 [SMILES: O=CC1CCN(c2ccc(C3CCC(=O)NC3=O)c(F)c2)CC1]

HA-4 was synthesized following the same procedure as HA-3 substituting 4-bromo-2-fluoro-1-iodobenzene with 1-bromo-2-fluoro-4-iodobenzene in Step 1 to give the titled compound. LCMS::m/z=317.1 (M−H)$^+$. $^1$H NMR: (400 MHz, DMSO-d$_6$) δ 10.79 (s, 1H), 9.62 (s, 1H), 7.07 (t, J=8.8 Hz, 1H), 6.77-6.69 (m, 2H), 3.91-3.84 (m, 1H), 3.67-3.59 (m, 2H), 2.91-2.81 (m, 2H), 2.76-2.65 (m, 1H), 2.56-2.52 (m, 1H), 2.49-2.45 (m, 1H), 2.20-2.07 (m, 1H), 1.97-1.86 (m, 3H), 1.61-1.49 (m, 2H).

HA-5: rac-(R)-3-(1,2,3,4-tetrahydroisoquinolin-6-yl)piperidine-2,6-dione

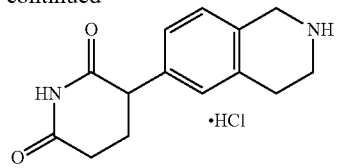

HA-5

Step 1: To a 40 mL vial was added tert-butyl 6-bromo-3,4-dihydro-1H-isoquinoline-2-carboxylate (1000.00 mg, 3.20 mmol), 2,6-bis(benzyloxy)-3-(4,4,5,5-tetramethyl-1,3,2-dioxaborolan-2-yl)pyridine (1470.31 mg, 3.52 mmol), tripotassium phosphate (2.04 g, 9.61 mmol), Pd(dppf)Cl₂DCM (0.26 g, 0.32 mmol), dioxane (7.00 mL), and water (2.50 mL). The reaction mixture was degassed with nitrogen for 15 min, then stirred at 90° C. for 16 hrs. The reaction mixture was then diluted with water and EtOAc, then filtered through celite. The product was extracted with EtOAc (3×), dried over MgSO₄, then concentrated. The resulting residue was purified by column chromatography (80 g silica, 0-25% EtOAc/hexanes) to yield tert-butyl 6-[2,6-bis(benzyloxy)pyridin-3-yl]-3,4-dihydro-1H-isoquinoline-2-carboxylate as a colorless oil (1.48 g, 88%). LCMS $C_{33}H_{34}N_2O_4$ requires: 522.3, found: m/z=523.3 [M+H]⁺.

Step 2: To a 40 mL vial was added tert-butyl 6-[2,6-bis(benzyloxy)pyridin-3-yl]-3,4-dihydro-1H-isoquinoline-2-carboxylate (1480.00 mg, 2.83 mmol), Pd/C (700.00 mg), THF (10.00 mL), and EtOH (10.00 mL). The reaction mixture was sparged with hydrogen for 5 min, then the reaction was stirred under hydrogen atmosphere (balloon) for 16 hrs. The reaction mixture was filtered through celite, then concentrated. The resulting residue was purified by column chromatography (40 g silica, 0-10% MeOH/DCM) to yield rac-tert-butyl 6-[(3R)-2,6-dioxopiperidin-3-yl]-3,4-dihydro-1H-isoquinoline-2-carboxylate as a white solid (852 mg, 87%). LCMS $C_{19}H_{24}N_2O_4$ requires: 344.2, found: m/z=345.2 [M+H]⁺.

Step 3: To a 40 mL vial was added rac-tert-butyl 6-[(3R)-2,6-dioxopiperidin-3-yl]-3,4-dihydro-1H-isoquinoline-2-carboxylate (852.00 mg, 2.47 mmol) and DCM (2.00 mL). To the reaction mixture was added 4 M hydrogen chloride in dioxane (6.18 mL, 0.90 g, 24.74 mmol) in a dropwise fashion. After 1 h, the reaction mixture was concentrated to yield the title compound as a white solid (707 mg, quantitative yield). LCMS $C_{14}H_{16}N_2O_2$ requires: 244.1, found: m/z=245.0 [M+H]⁺.

HA-6: 1-{4-[4-({4-[2-(6,6-dimethyl-1,4,5,7-tetrahydroindazol-3-yl)-1H-indole-5-carbonyl]piperazin-1-yl}methyl)piperidin-1-yl]-2-fluorophenyl}-1,3-diazinane-2,4-dione

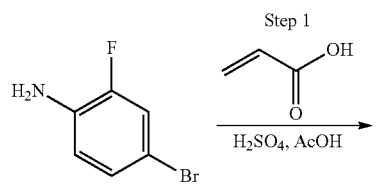

Step 1

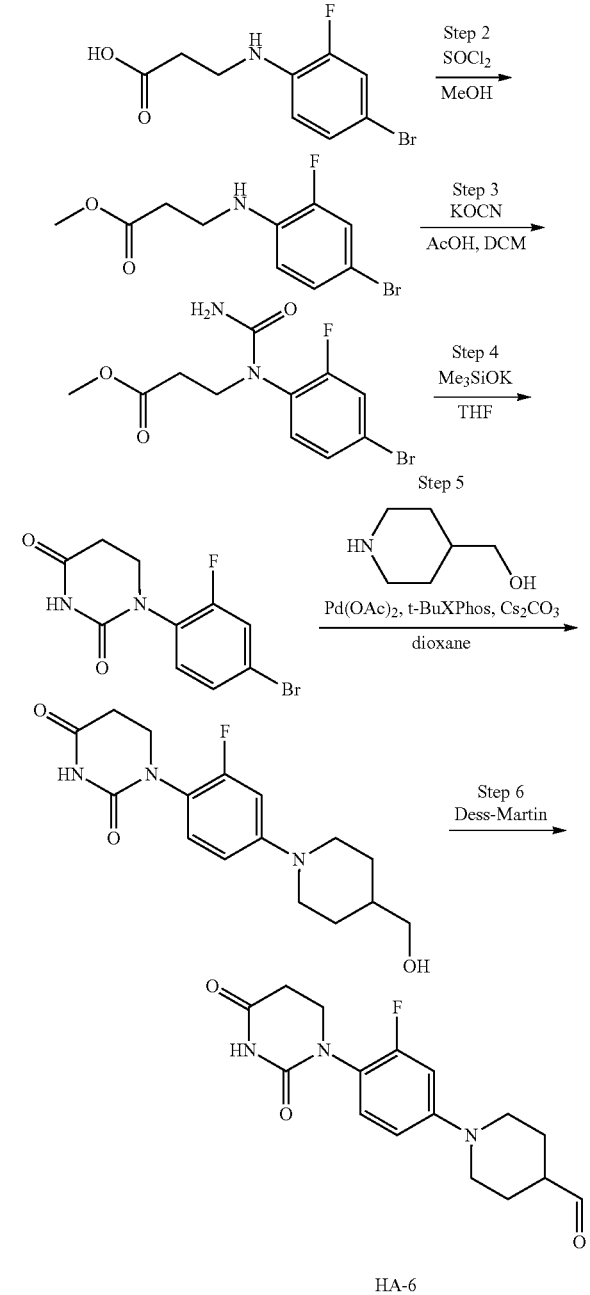

HA-6

Step 1: To a mixture of 4-bromo-2-fluoroaniline (20 g, 105.26 mmol, 1 eq) in AcOH (80 mL) and H₂SO₄ (1 mL) was added acrylic acid (22.75 g, 315.77 mmol, 3 eq) at room temperature. The resulting mixture was stirred at 100° C. for 2 hrs. The reaction mixture was concentrated under reduced pressure. The residue was purified by C18 reverse phase column with ACN/H₂O (1/4). This resulted in 3-[(4-bromo-2-fluorophenyl)amino]propanoic acid (13 g, 42.41%) as an off-white solid.

LCMS (ESI) calculated for ($C_9H_9BrFNO_2$) [M+1]⁺: 262.0; found: 262.0.

Step 2: To a mixture of 3-[(4-bromo-2-fluorophenyl)amino]propanoic acid (13 g, 49.6 mmol, 1 eq) in MeOH (30 mL) was added SOCl₂ (54 mL) at 0° C. The resulting mixture was stirred at room temperature for 2 hrs. The resulting mixture was concentrated under reduced pressure.

This resulted in methyl 3-[(4-bromo-2-fluorophenyl)amino]propanoate (9 g, crude) as a brown oil. LCMS (ESI) calculated for $(C_{10}H_{11}BrFNO_2)$ $[M+1]^+$: 276.0; found: 276.0.

Step 3: To a mixture of methyl 3-[(4-bromo-2-fluorophenyl)amino]propanoate (9 g, 32.6 mmol, 1 eq) in AcOH (40 mL) and DCM (40 mL) was added potassium cyanate (7.93 g, 97.79 mmol, 3 eq) at room temperature. The resulting mixture was stirred at room temperature for 3 hrs. The resulting mixture was extracted with EtOAc (3×30 mL). The combined organic layers were washed with water (3×10 mL), dried over anhydrous $Na_2SO_4$. After filtration, the filtrate was concentrated under reduced pressure. The residue was purified by C18 reverse phase column with ACN/$H_2O$ (3/7). This resulted in methyl 3-[(4-bromo-2-fluorophenyl)(carbamoyl)amino]propanoate (3.5 g, 30.28%) as a white solid. LCMS (ESI) calculated for $(C_{11}H_{12}BrFN_2O_3)$ $[M+1]^+$: 319.0; found: 319.0.

Step 4: To a mixture of methyl 3-[(4-bromo-2-fluorophenyl)(carbamoyl)amino]propanoate (3.5 g, 10.97 mmol, 1 eq) in THF (20 mL) was added potassium trimethylsilanolate (3.52 g, 27.42 mmol, 2.5 eq) at room temperature. The resulting mixture was stirred at room temperature for 1 hr. The resulting mixture was extracted with EtOAc (3×20 mL). The combined organic layers were washed with water (3×10 mL), dried over anhydrous $Na_2SO_4$. After filtration, the filtrate was concentrated under reduced pressure to give 1-(4-bromo-2-fluorophenyl)-1,3-diazinane-2,4-dione (2 g, crude) as a white solid. LCMS (ESI) calculated for $(C_{10}H_8BrFN_2O_2)$ $[M+1]^+$: 287.0; found: 287.0.

Step 5: To a mixture of 1-(4-bromo-2-fluorophenyl)-1,3-diazinane-2,4-dione (2.7 g, 9.41 mmol, 1 eq) in dioxane (25 mL) were added piperidin-4-ylmethanol (2.29 g, 19.85 mmol, 3 eq), $Pd(OAc)_2$ (0.21 g, 0.94 mmol, 0.1 eq), $Cs_2CO_3$ (9.19 g, 28.22 mmol, 3 eq) and t-BuXPhos (0.80 g, 1.88 mmol, 0.2 eq). The resulting mixture was stirred at 90° C. overnight under nitrogen atmosphere. The residue was purified by C18 reverse phase column with ACN/$H_2O$ (1/2) to give 1-{2-fluoro-4-[4-(hydroxymethyl)piperidin-1-yl]phenyl}-1,3-diazinane-2,4-dione (324 mg, 10.58%) as a grey solid. LMS (ESI) calculated for $(C_{16}H_{20}FN_3O_3)$ $[M+1]^+$: 322.1; found: 322.2. $^1$H NMR (400 MHz, DMSO-$d_6$) δ 7.93 (s, 1H), 7.22-7.13 (m, 1H), 6.84-6.72 (m, 1H), 6.01 (s, 2H), 3.79-3.72 (m, 2H), 3.66-3.58 (m, 2H), 3.28 (s, 2H), 2.75-2.65 (m, 4H), 1.76-1.69 (m, 2H), 1.56-1.52 (m, 1H), 1.31-1.03 (m, 2H).

Step 6: To a mixture of 1-{2-fluoro-4-[4-(hydroxymethyl)piperidin-1-yl]phenyl}-1,3-diazinane-2,4-dione (100 mg, 0.31 mmol, 1eq) in DCM (5 mL) was added Dess-Martin (197 mg, 0.47 mmol, 1.5 eq) in portions at 0° C. The resulting mixture was stirred at 0° C. for 2 hrs. The resulting mixture was concentrated under reduced pressure. The resulting mixture was purified by C18 reverse phase column with ACN/$H_2O$ (1/2). This resulted in the title compound as a brown solid (36 mg, 37.3%). LCMS (ESI) calculated for $(C_{16}H_{18}FN_3O_3)$ $[M+1]^+$: 320.1; found: 320.2.

HA-7: 1-(4-(2,6-dioxopiperidin-3-yl)phenyl)piperidine-4-carbaldehyde

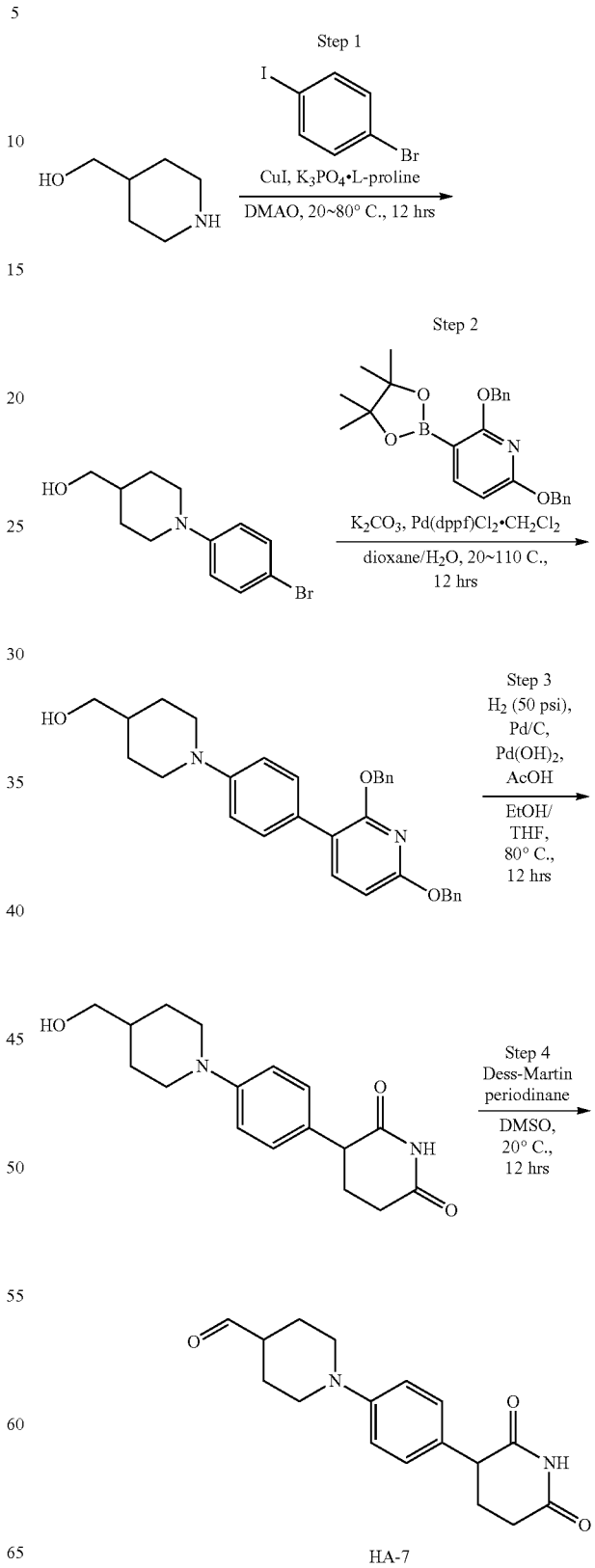

Step 1: To a solution of compound 1-bromo-4-iodobenzene (50.0 g, 176 mmol, 1.00 eq) in DMSO (250 mL) was added piperidin-4-ylmethanol (26.4 g, 229 mmol, 1.30 eq), $K_3PO_4$ (75.0 g, 353 mmol, 2.00 eq), CuI (6.73 g, 35.3 mmol, 0.200 eq) and L-proline (4.64 g, 35.3 mmol, 0.200 eq) at 20° C. under $N_2$. The reaction mixture was stirred at 80° C. for 12 hrs under $N_2$. The mixture was cooled to 20° C. and poured into water (1.00 L). The mixture was stirred at 0.5 hr. The mixture was extracted with ethyl acetate (500 mL*3). The organic layers were washed with $NH_3 \cdot H_2O$ in $H_2O$ (100 ml $NH_3 \cdot H_2O$ in 700 mL $H_2O$) (250 mL*3). The organic layers were washed with brine (1000 mL), dried over $Na_2SO_4$, filtered and concentrated. The residue was purified by column chromatography ($SiO_2$, petroleum ether/ethyl acetate=20/1 to 2/1, $R_f$=0.30). Desired product (31.0 g, 87.0 mmol, 49.2% yield) was obtained as yellow solid. LCMS: m/z=270.0 $(M+H)^+$.

Step 2: To a solution of (1-(4-bromophenyl)piperidin-4-yl)methanol (30.0 g, 84.2 mmol, 1.00 eq) and 2,6-bis(benzyloxy)-3-(4,4,5-trimethyl-1,3,2-dioxaborolan-2-yl)pyridine (35.1 g, 84.2 mmol, 1.00 eq) in dioxane (300 mL) and $H_2O$ (60.0 mL) was added $K_2CO_3$ (34.9 g, 252 mmol, 3.00 eq) and Pd(dppf)$Cl_2 \cdot CH_2Cl_2$ (6.88 g, 8.43 mmol, 0.100 eq) at 20° C. under $N_2$. The reaction was stirred at 110° C. for 12 hrs under $N_2$. The reaction was cooled to 20° C. and filtered. The filtrate was concentrated. The crude product was purified by re-crystallization from MeOH (100 mL) at 20° C. for 30 mins. The mixture was filtered and the filter cake was purified by column chromatography ($SiO_2$, petroleum ether/ethyl acetate=10/1 to 1/1, $R_f$=0.30). Desired product (22.5 g, 44.8 mmol, 53.2% yield) was obtained as yellow solid. LCMS: m/z=481.2 $(M+H)^+$.

Step 3: To a solution of (1-(4-(2,6-bis(benzyloxy)pyridin-3-yl)phenyl)piperidin-4-yl)methanol (20.0 g, 39.8 mmol, 1.00 eq) and AcOH (7.18 g, 119 mmol, 6.84 mL, 3.00 eq) in THF (200 mL) and EtOH (200 mL) was added Pd/C (5.00 g, 39.8 mmol, 10% purity, 1.00 eq) and Pd(OH)$_2$ (4.79 g, 34.1 mmol, 8.56e-1 eq) under $N_2$. The suspension was degassed under vacuum and purged with $H_2$ several times. The mixture was stirred under $H_2$ (50 psi) at 80° C. for 12 hrs. The mixture was cooled to 20° C. and filtered. The filtrate was concentrated. The crude product was triturated with petroleum ether/ethyl acetate=5/1 (200 mL) at 20° C. for 30 mins. Desired product (8.00 g, 24.2 mmol, 60.7% yield) was obtained as white solid. LCMS: m/z=303.2 $(M+H)^+$.

Step 4: To a solution of 3-(4-(4-(hydroxymethyl)piperidin-1-yl)phenyl)piperidine-2,6-dione (8.60 g, 28.4 mmol, 1.00 eq) in DMSO (90.0 mL) was slowly added Dess-Martin periodinane (24.1 g, 56.8 mmol, 17.6 mL, 2.00 eq) at 20° C. The reaction was stirred at 20° C. for 12 hrs. The mixture was adjusted with saturated aqueous $Na_2CO_3$ until pH=10 and the aqueous layer was extracted with ethyl acetate (350 mL*3). The combined organic layers were washed with $Na_2S_2O_3$ solution (500 mL) and brine (500 mL), dried over $Na_2SO_4$, concentrated under vacuum. The crude product was triturated with ethyl acetate (100 mL) at 20° C. for 30 mins. HA-7 (7.18 g, 22.8 mmol, 48.1% yield) was obtained as off-white solid. LCMS: m/z=299.1 $(M-H)^+$. $^1H$ NMR: (400 MHz, DMSO-$d_6$) δ 11.00-10.57 (m, 1H), 9.80-9.35 (m, 1H), 7.09-6.98 (m, 2H), 6.95-6.83 (m, 2H), 3.79-3.66 (m, 1H), 3.63-3.49 (m, 2H), 2.89-2.72 (m, 2H), 2.70-2.59 (m, 1H), 2.48-2.38 (m, 2H), 2.17-1.89 (m, 4H), 1.65-1.47 (m, 2H).

HA-8: rac-(R)-2-(1-(5-(2,6-dioxopiperidin-3-yl)pyridin-2-yl)piperidin-4-yl)acetic acid

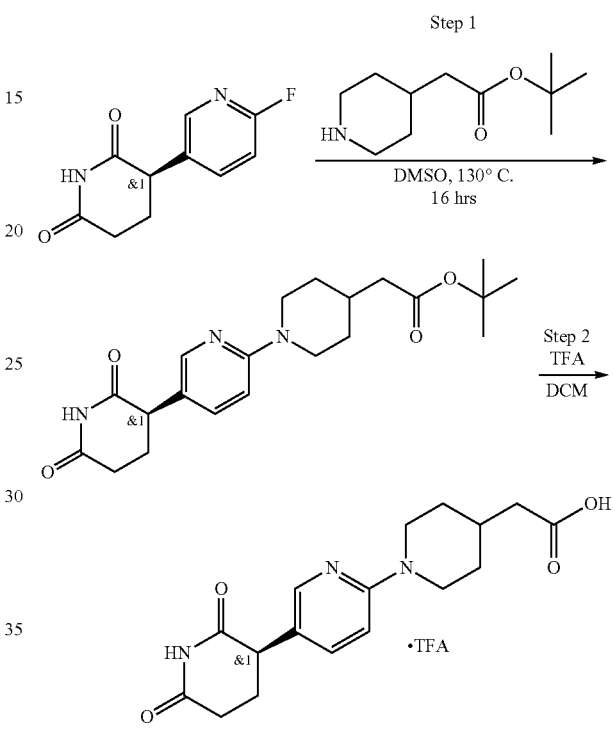

HA-8

Step 1: To a 40 mL vial was added rac-(3R)-3-(6-fluoropyridin-3-yl)piperidine-2,6-dione (1.00 g, 4.80 mmol), tert-butyl 2-(piperidin-4-yl)acetate (1.01 g, 5.04 mmol), DMSO (7.00 mL), and N,N-diisopropylethylamine (3.18 mL, 2.48 g, 19.21 mmol). The reaction mixture was stirred at 130° C. for 16 hrs. The reaction mixture was then diluted with EtOAc and brine. The product was extracted with EtOAc (2×). The combined organic layers were washed with brine (3×), dried over $MgSO_4$, then concentrated. The resulting residue was purified by column chromatography (80 g silica, 0-100% EtOAc/DCM) to yield rac-tert-butyl 2-(1-{5-[(3R)-2,6-dioxopiperidin-3-yl]pyridin-2-yl}piperidin-4-yl)acetate as a brown solid (456 mg, 25%). LCMS $C_{17}H_{21}N_3O_4$ requires: 387.2, found: 388.2 $[M+H]^+$.

Step 2: To a 40 mL vial was added rac-tert-butyl 2-(1-{5-[(3R)-2,6-dioxopiperidin-3-yl]pyridin-2-yl}piperidin-4-yl)acetate (456.00 mg, 1.18 mmol) and DCM (5.00 mL). To the reaction mixture was added trifluoroacetic acid (5.00 mL, 7.45 g, 65.34 mmol) in a dropwise fashion. After 30 min, the reaction mixture was concentrated under reduced pressure. The resulting residue was purified by chromatography (100 g C18 silica, 0-20% MeCN/$H_2O$) to yield the title compound as a white solid (1.04 g, 100%). LCMS $C_{21}H_{29}N_3O_4$ requires: 331.2, found: m/z=332.2 $[M+H]^+$.

HA-9: rac-1-[5-[(3R)-2,6-dioxopiperidin-3-yl]pyridin-2-yl]piperidine-4-carboxylic acid

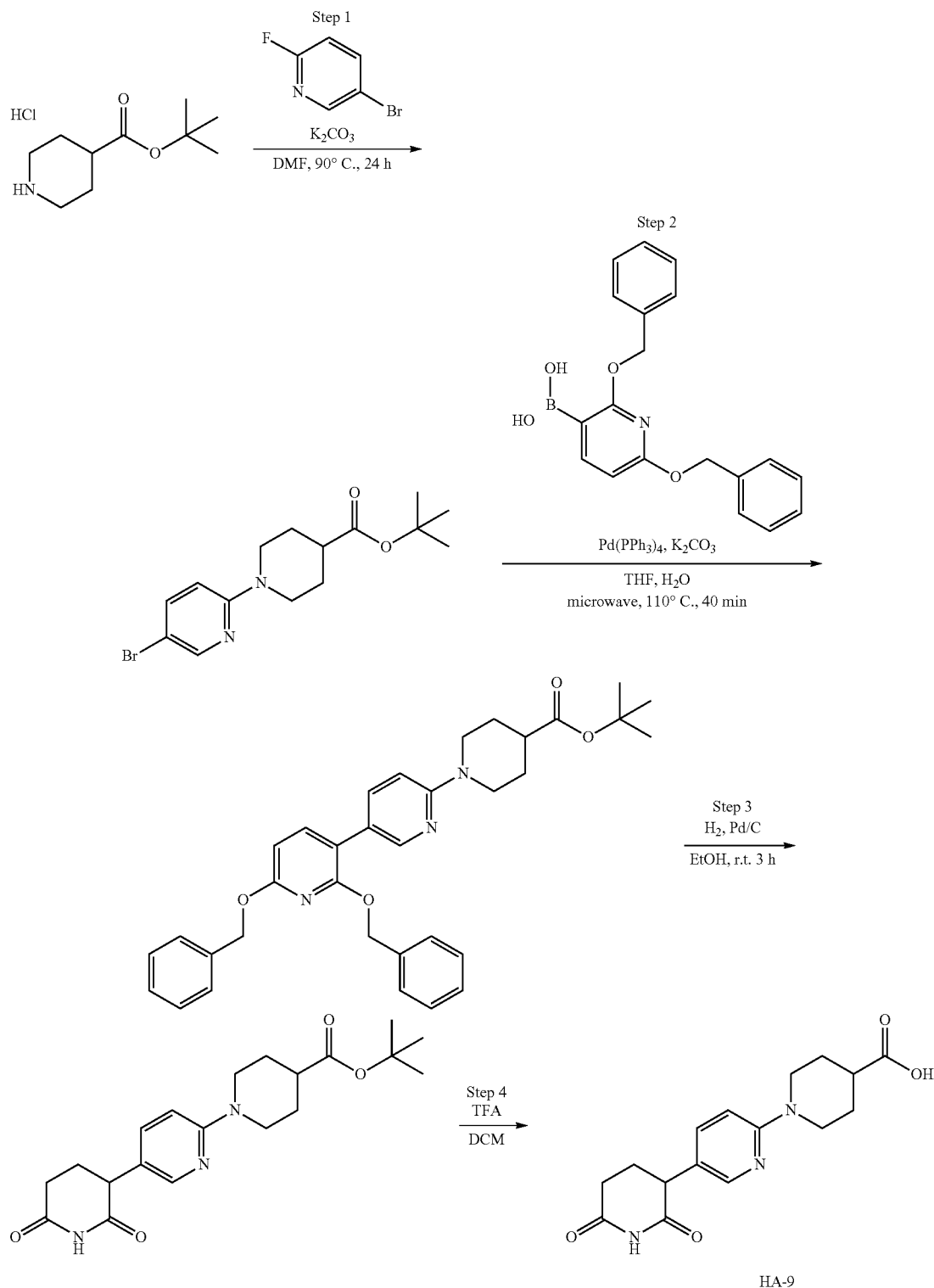

HA-9

Step 1: To a mixture of 5-bromo-2-fluoropyridine (6.64 g, 37.73 mmol, 1 eq) in DMF (50 mL) were added tert-butyl piperidine-4-carboxylate (8.39 g, 45.28 mmol, 1.2 eq) and $K_2CO_3$ (10.43 g, 75.46 mmol, 2 eq). The resulting mixture was stirred at 90° C. overnight. The resulting mixture was extracted with EtOAc (3×100 mL). The combined organic layers were washed with water (3×50 mL), dried over anhydrous $Na_2SO_4$. After filtration, the filtrate was concentrated under reduced pressure. The residue was purified by silica gel column chromatography, eluted with PE/EtOAc (1/1). This resulted in tert-butyl 1-(5-bromopyridin-2-yl)piperidine-4-carboxylate as a light yellow solid (10 g, 46.60% yield). LCMS (ESI) calculated for ($C_{15}H_{21}BrN_2O_2$) [M+H]$^+$: 341.2; found: 341.2.

Step 2: To a mixture of tert-butyl 1-(5-bromopyridin-2-yl)piperidine-4-carboxylate (2.40 g, 7.04 mmol, 1.6 eq), 2,6-bis(benzyloxy)pyridin-3-ylboronic acid (1.47 g, 4.39 mmol, 1.00 eq) and $K_2CO_3$ (1.2 g, 8.70 mmol, 2 eq) in THF (10 mL) and $H_2O$ (10 mL) were added Pd(PPh$_3$)$_4$(0.5 g, 0.43 mmol, 0.1 eq). The resulting mixture was stirred for 40 min at 110° C. under nitrogen atmosphere by microwave. The resulting mixture was concentrated under vacuum. The residue was purified by silica gel column chromatography, eluted with PE/EtOAc (1/1). This resulted in tert-butyl 1-[2,6-bis(benzyloxy)-[3,3-bipyridin]-6-yl]piperidine-4-carboxylate as a white solid (1.2 g, 49.36% yield). LCMS (ESI) calculated for ($C_{33}H_{35}N_3O_4$) [M+H]$^+$: 552.3; found: 552.0.

Step 3: To a mixture of tert-butyl 1-[2,6-bis(benzyloxy)-[3,3-bipyridin]-6-yl]piperidine-4-carboxylate (1.8 g, 3.26 mmol, 1 eq) in EtOH (50 mL) and THF (50 mL) was added Pd/C (0.9 g).

The resulting mixture was stirred at room temperature for 3 hrs under hydrogen atmosphere. The resulting mixture was filtered. The filtrate was concentrated under reduced pressure. The residue was purified by C18 reverse phase column chromatography with $CH_3CN/H_2O$ (2/1). This resulted in tert-butyl 1-[5-(2,6-dioxopiperidin-3-yl)pyridin-2-yl]piperidine-4-carboxylate as a yellow solid (390 mg, 28.81% yield). LCMS (ESI) calculated for ($C_{20}H_{27}N_3O_4$) [M+H]$^+$: 374.2; found: 374.2.

Step 4: To a mixture of tert-butyl 1-[5-(2,6-dioxopiperidin-3-yl)pyridin-2-yl]piperidine-4-carboxylate (650 mg, 1.74 mmol, 1 eq) in DCM (100 mL) were added TFA (10 mL) dropwise at 0° C. The resulting mixture was stirred at 0° C. for 2 hrs. The resulting mixture was concentrated under vacuum. The residue was purified by C18 reverse phase column chromatography with $CH_3CN/H_2O$ (1/1). This resulted in rac-1-[5-[(3R)-2,6-dioxopiperidin-3-yl]pyridin-2-yl]piperidine-4-carboxylic acid as a purple solid (540.8 mg, 96.08% yield). LCMS (ESI) calculated for ($C_{16}H_{19}N_3O_4$) [M+H]$^+$: 318.2; found: 318.2. $^1$H NMR (300 MHz, DMSO-d$_6$) δ 10.91 (s, 1H), 7.97-7.73 (m, 2H), 7.30 (d, J=9.3 Hz, 1H), 4.14-4.02 (m, 2H), 3.95-3.84 (m, 1H), 3.29-3.14 (m, 2H), 2.76-2.48 (m, 3H), 2.36-2.16 (m, 1H), 2.02-1.88 (m, 3H), 1.70-1.51 (m, 2H).

HA-10: rac-(R)-3-(6-(piperazin-1-yl)pyridin-3-yl)piperidine-2,6-dione

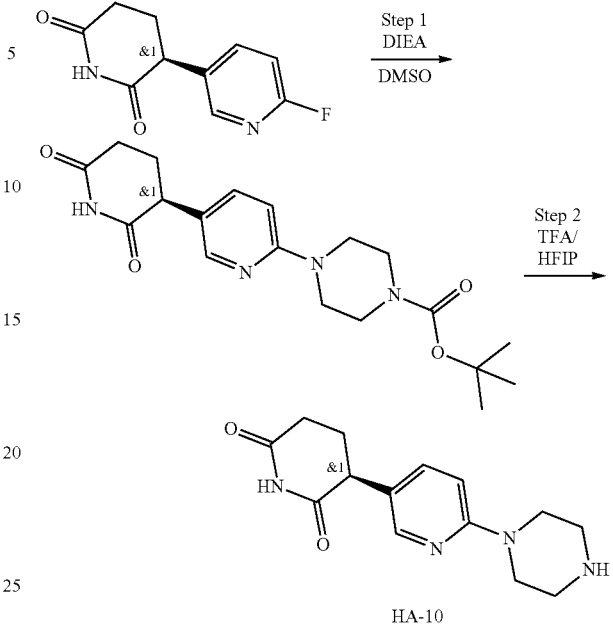

Step 1: Tert-butyl piperazine-1-carboxylate (0.895 g, 4.8 mmol), 3-(6-fluoropyridin-3-yl)piperidine-2,6-dione (0.5 mg, 2.40 mmol) were combined in DMSO (0.15M), followed by addition of N,N-diisopropylethylamine (1.68 mL, 9.61 mmol). The vial was capped, and stirred at 110° C. overnight. The reaction was then cooled to rt, concentrated onto silica gel and purified by column chromatography (0-100% EtOAc in hexane) to yield rac-tert-butyl (R)-4-(5-(2,6-dioxopiperidin-3-yl)pyridin-2-yl)piperazine-1-carboxylate (0.6 g, 67%). LCMS: $C_{19}H_{26}N_4O_4$ requires: 374.1, found: m/z=375.1 [M+H]$^+$.

Step 2: rac-tert-butyl (R)-4-(5-(2,6-dioxopiperidin-3-yl)pyridin-2-yl)piperazine-1-carboxylate was treated with 0.6 mL of TFA in HFIP (10 mL), and stirred at room temperature for 5 hr. LCMS showed the complete conversion of starting material. The reaction mixture was concentrated and purified with C18 reverse phase chromatography to afford rac-(R)-3-(6-(piperazin-1-yl)pyridin-3-yl)piperidine-2,6-dione as a pale white solid (0.31 g, 71%). $^1$H NMR (500 MHz, DMSO) δ 10.85 (s, 1H), 8.03 (d, J=2.4 Hz, 1H), 7.56 (dq, J=8.9, 2.1 Hz, 1H), 6.98 (dt, J=9.1, 2.1 Hz, 1H), 3.82 (dd, J=12.4, 4.9 Hz, 1H), 3.72 (t, J=5.2 Hz, 4H), 3.2 (t, J=5.2 Hz, 4H), 2.70 (ddd, J=17.6, 13.3, 5.3 Hz, 1H), 2.56 (q, J=2.8, 1.9 Hz, 1H), 2.23 (qd, J=12.6, 4.2 Hz, 1H), 2.08 (s, 1H), 1.98 (dtd, J=13.3, 5.2, 3.2 Hz, 1H). LCMS: $C_{14}H_{18}N_4O_2$ requires: 274.32, found: m/z=275.1 [M+H]$^+$.

HA-11: 3-[(3RS)-1-[5-[(3RS&)-2,6-dioxopiperidin-3-yl]pyridin-2-yl]pyrrolidin-3-yl]propanoic acid

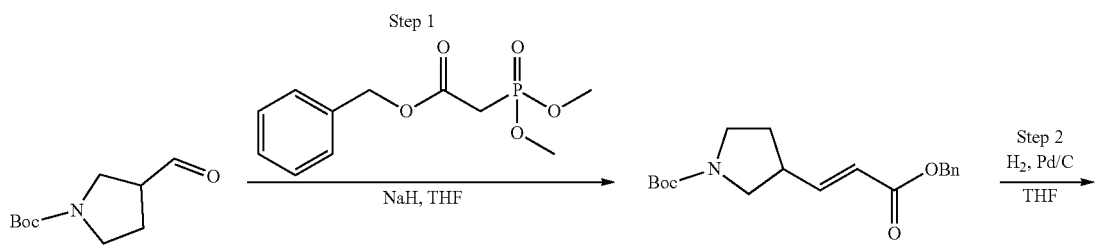

-continued
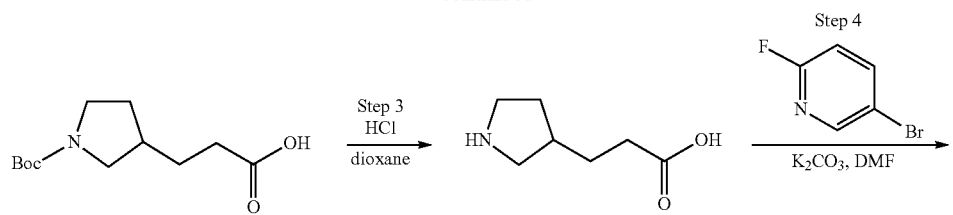
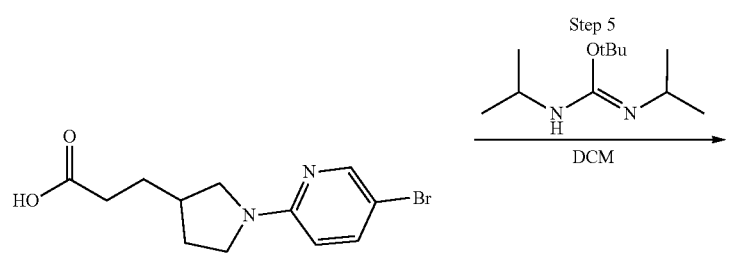
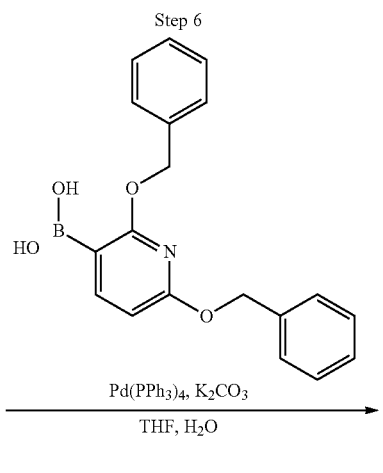
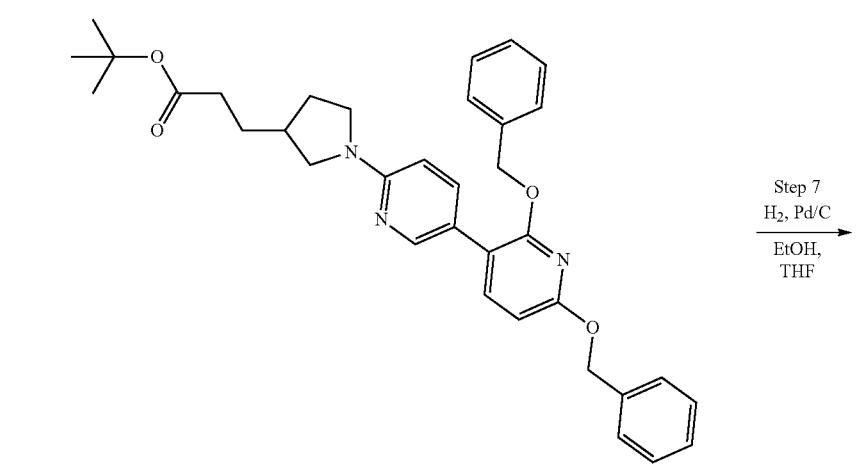

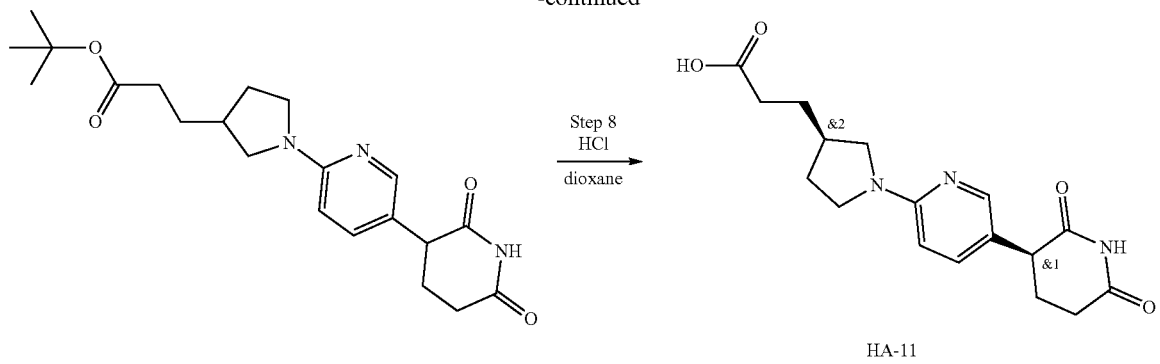

HA-11

Step 1: To a mixture of NaH (2.65 g, 110.4 mmol, 1.1 eq) in THF (500 mL) was added benzyl 2-(dimethoxyphosphoryl)acetate (28.51 g, 110.4 mmol, 1.10 eq) at 0° C. under nitrogen atmosphere. The resulting mixture was stirred for 30 min at room temperature under nitrogen atmosphere. To the above mixture was added tert-butyl 3-formylpyrrolidine-1-carboxylate (20 g, 100.4 mmol, 1 eq) at 0° C. The resulting mixture was stirred at room temperature overnight under nitrogen atmosphere. The aqueous layer was extracted with EtOAc (3×500 mL). The resulting mixture was concentrated under vacuum. The residue was purified by silica gel column chromatography, eluted with PE/EtOAc (1/1) to afford tert-butyl 3-[(1E)-3-(benzyloxy)-3-oxoprop-1-en-1-yl]pyrrolidine-1-carboxylate (31.6 g, 77.89% yield) as a colorless oil. LCMS (ESI) calculated for ($C_{19}H_{25}NO_4$) [M+H]$^+$: 332.1; found: 332.1.

Step 2: To a mixture of tert-butyl 3-[(1E)-3-(benzyloxy)-3-oxoprop-1-en-1-yl] pyrrolidine-1-carboxylate (12.70 g, 38.32 mmol, 1 eq) in THF (200 mL) was added Pd/C (2.04 g) at room temperature. The resulting mixture was stirred at room temperature overnight under hydrogen atmosphere. The resulting mixture was filtered. The filtrate was concentrated under reduced pressure. This resulted in 3-[1-(tert-butoxycarbonyl)pyrrolidin-3-yl]propanoic acid (3) as an off-white solid (9 g, crude). The crude product was used in the next step directly without further purification. LCMS (ESI) calculated for ($C_{12}H_{21}NO_4$) [M+1]$^+$: 244.1; found: 244.1.

Step 3: A mixture of 3-[1-(tert-butoxycarbonyl)pyrrolidin-3-yl]propanoic acid (9 g, crude) in HCl/dioxane (4 mol/L, 100 mL) was stirred at room temperature for 1 hr. The resulting mixture was concentrated under vacuum. This resulted in 3-(pyrrolidin-3-yl)propanoic acid as a pink solid (5.88 g, crude). LCMS (ESI) calculated for ($C_7H_{13}N_1O_2$) [M+1]$^+$: 144.0; found: 144.2.

Step 4: To a mixture of 3-(pyrrolidin-3-yl)propanoic acid (5.88 g, 41.07 mmol, 1 eq) and 5-bromo-2-fluoropyridine (7.23 g, 41.08 mmol, 1 eq) in DMF (30 mL) was added $K_2CO_3$ (8.5 g, 61.6 mmol, 1.5 eq) at room temperature. The resulting mixture was stirred at 80° C. overnight. The resulting mixture was extracted with EtOAc (3×100 mL). The combined organic layers were washed with water (3×50 mL), dried over anhydrous $Na_2SO_4$. After filtration, the filtrate was concentrated under reduced pressure. The residue was purified by C18 reverse phase column with $CH_3CN$/$H_2O$ (1/2). This resulted in 3-[1-(5-bromopyridin-2-yl)pyrrolidin-3-yl]propanoic acid as a crude brown oil (5) (12 g, 89.67% yield). LCMS (ESI) calculated for ($C_{12}H_{15}BrN_2O_2$) [M+1]$^+$: 299.0; found: 299.0.

Step 5: To a mixture of 3-[1-(5-bromopyridin-2-yl)pyrrolidin-3-yl]propanoic acid (12 g, 40.11 mmol, 1 eq) in DCM (100 mL) was added (Z)—N,N-diisopropyltert-butoxy methanimidamide (24.11 g, 120.4 mmol, 3 eq) at 0° C. The resulting mixture was stirred at room temperature for 3 hrs. The resulting mixture was concentrated under vacuum. The residue was purified by silica gel column chromatography, eluted with PE/EtOAc (1/1) to afford tert-butyl 3-[1-(5-bromopyridin-2-yl)pyrrolidin-3-yl]propanoate (4.2 g, 28.0% yield) as a brown oil. LCMS (ESI) calculated for ($C_{16}H_{23}BrN_2O_2$) [M+H]$^+$: 355.1; found: 355.0.

Step 6: To a mixture of tert-butyl 3-[1-(5-bromopyridin-2-yl)pyrrolidin-3-yl]propanoate (3 g, 8.44 mmol, 1 eq), 2,6-bis(benzyloxy)pyridin-3-ylboronic acid (4.25 g, 12.7 mmol, 1.5 eq) and $K_2CO_3$ (2.33 g, 16.89 mmol, 2 eq) in THF (30 mL) and $H_2O$ (10 mL) was added Pd(PPh$_3$)$_4$(0.98 g, 0.84 mmol, 0.1 eq) at room temperature under nitrogen atmosphere. The resulting mixture was stirred at 110° C. for 40 min under nitrogen atmosphere by microwave. The resulting mixture was concentrated under vacuum. The residue was purified by silica gel column chromatography, eluted with PE/EtOAc (1/1) to afford tert-butyl 3-[1-[2,6-bis(benzyloxy)-[3,3-bipyridin]-6-yl]pyrrolidin-3-yl]propanoate (7) (2.6 g, 53.34% yield) as a colorless oil. LCMS (ESI) calculated for ($C_{35}H_{39}N_3O_4$) [M+H]$^+$: 566.3; found: 566.2.

Step 7: To a mixture of tert-butyl 3-[1-[2',6'-bis(benzyloxy)-[3,3'-bipyridin]-6-yl] pyrrolidin-3-yl]propanoate (2.10 g, 3.71 mmol, 1 eq) in THF (6 mL) and EtOH (6 mL) was added Pd/C (1.70 g). The resulting mixture was stirred at room temperature for 3 h under hydrogen atmosphere. The resulting mixture was filtered. The filtrate was concentrated under vacuum. The residue was purified by silica gel column chromatography, eluted with $CH_2Cl_2$/EtOAc (1/2) to afford tert-butyl 3-[1-[5-(2,6-dioxopiperidin-3-yl)pyridin-2-yl]pyrrolidin-3-yl]propanoate (400 mg, 26.42% yield) as a colorless solid. MS (ESI) calculated for ($C_{21}H_{29}N_3O_4$) [M+1]$^+$: 388.2; found: 388.3.

Step 8: A mixture of tert-butyl 3-[1-[5-(2,6-dioxopiperidin-3-yl)pyridin-2-yl]pyrrolidin-3-yl]propanoate (490 mg, 1.27 mmol, 1 eq) in HCl/dioxane (5 mL, 4M) was stirred at room temperature for 2 hrs. The resulting mixture was concentrated under vacuum. This resulted in 3-[(3RS)-1-[5-[(3RS)-2,6-dioxopiperidin-3-yl]pyridin-2-yl]pyrrolidin-3-yl]propanoic acid HCl salt (HA-11) (379.1 mg, 81.56%) as a white solid. LCMS (ESI) calculated for ($C_{17}H_{21}N_3O_4$) [M+H]$^+$: 332.2; found: 332.1. $^1$H NMR (300 MHz, DMSO-d$_6$) δ 13.61 (s, 1H), 10.93 (s, 1H), 7.95-7.85 (m, 1H), 7.82 (d, J=2.1 Hz, 1H), 7.11-7.01 (m, 1H), 4.02-3.90 (m, 1H), 3.80-3.69 (m, 2H), 3.69-3.61 (m, 1H), 3.21-3.09 (m, 1H), 2.77-2.48 (m, 1H), 2.47-2.37 (m, 1H), 2.36-2.19 (m, 3H), 2.17 (s, 1H), 2-1.89 (m, 1H), 1.87-1.59 (m, 4H).

HA-12: rac-(R)-1-(5-((R)-2,6-dioxopiperidin-3-yl)pyridin-2-yl)pyrrolidine-3-carbaldehyde

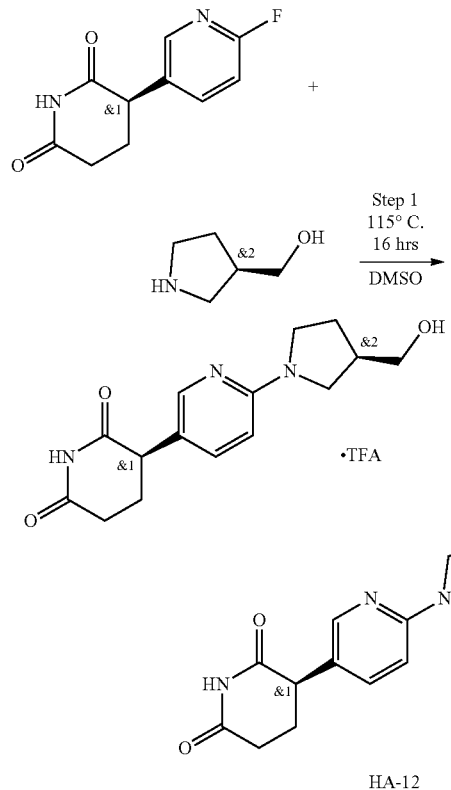

HA-13: 1-(5-(2,6-dioxopiperidin-3-yl)pyridin-3-yl)piperidine-4-carbaldehyde

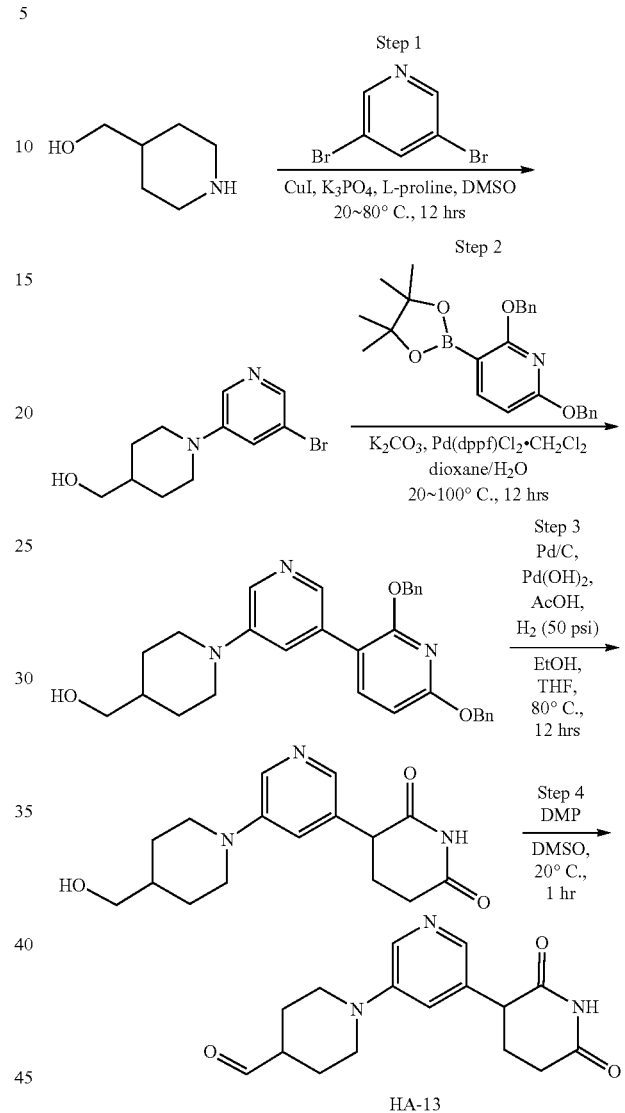

Step 1: To a 40 mL vial was added rac-(3R)-3-(6-fluoropyridin-3-yl)piperidine-2,6-dione (1000.00 mg, 4.80 mmol), rac-(3R)-pyrrolidin-3-ylmethanol (485.84 mg, 4.80 mmol), N,N-diisopropylethylamine (3.36 mL, 2.48 g, 19.21 mmol), and DMSO (7.00 mL). The reaction mixture was stirred at 115° C. for 16 hrs. The reaction mixture was then concentrated under reduced pressure, then purified by reverse phase column chromatography (415 g C18 silica, 0-10% MeCN/water+0.1% TFA) to give (3RS&)-3-{6-[(3RS)-3-(hydroxymethyl)pyrrolidin-1-yl]pyridin-3-yl}piperidine-2,6-dione; trifluoroacetic acid as an amorphous solid (954 mg, 69%). LCMS $C_{15}H_{19}N_3O_3$ requires: 289.1, found: m/z=290.1 [M+H]$^+$.

Step 2: To a 200 mL RBF was added (3RS&)-3-{6-[(3RS)-3-(hydroxymethyl)pyrrolidin-1-yl]pyridin-3-yl}piperidine-2,6-dione; trifluoroacetic acid (954.00 mg, 2.37 mmol), sodium bicarbonate (0.99 g, 11.83 mmol), and DCM (50.00 mL). The reaction mixture was cooled to 0 C, then 1,1-bis(acetyloxy)-3-oxo-1lambda5,2-benziodaoxol-1-yl acetate (1.10 g, 2.60 mmol) was added in one portion. The reaction was stirred warming to RT for 3 hrs. The crude reaction mixture was adsorbed onto silica, and purified by FC (40 g silica, 50-100% EtOAc/DCM+1% TEA) to yield the title compound as a white solid (177 mg, 26%). LCMS $C_{15}H_{17}N_3O_3$ requires: 287.1, found: m/z=288.0 [M+H]$^+$.

Step 1: To a solution of piperidin-4-ylmethanol (24.3 g, 211 mmol, 1.00 eq) and 3,5-dibromopyridine (50.0 g, 211 mmol, 1.00 eq) in DMSO (400 mL) was added $K_3PO_4$ (89.6 g, 422 mmol, 2.00 eq), CuI (8.04 g, 42.2 mmol, 0.200 eq) and L-proline (5.54 g, 42.2 mmol, 0.200 eq) at 20° C. under $N_2$. The mixture was stirred at 80° C. for 12 hrs under $N_2$. The mixture was cooled to 20° C. and poured into water (1.00 L). The mixture was stirred at 20° C. for 0.5 hr. The mixture was extracted with ethyl acetate (500 mL*3). The organic layers were washed with brine (1.00 L), dried over $Na_2SO_4$, filtered and concentrated. The residue was purified by column chromatography (SiO$_2$, petroleum ether/ethyl acetate=5/1 to 0/1, R$_f$=0.35). The desired product (33.0 g, 119 mmol, 56.5% yield) was obtained as an orange solid. LCMS: m/z=270.8 (M+H)$^+$.

Step 2: To a solution of (1-(5-bromopyridin-3-yl)piperidin-4-yl)methanol (20.0 g, 72.3 mmol, 1.00 eq) and 2,6-bis(benzyloxy)-3-(4,4,5,5-tetramethyl-1,3,2-dioxaborolan-2-yl)pyridine (30.2 g, 72.3 mmol, 1.00 eq) in dioxane (250 mL) and H$_2$O (50.0 mL) was added Pd(dppf)Cl$_2$·CH$_2$Cl$_2$ (5.91 g, 7.24 mmol, 0.100 eq) and K$_2$CO$_3$ (30.0 g, 217 mmol, 3.00 eq) at 20° C. under N$_2$. The mixture was degassed and then stirred at 100° C. for 12 hrs under N$_2$. The reaction was cooled to 20° C. and concentrated. The residue was poured into water (500 mL) and extracted with ethyl acetate (500 mL*4). The combined organic layers were washed with brine (1000 mL), dried over Na$_2$SO$_4$, filtered and concentrated. The residue was purified by column chromatography (SiO$_2$, petroleum ether/ethyl acetate=5/1 to 1/3, R$_f$=0.30). Desired product (25.0 g, 51.3 mmol, 70.9% yield) was obtained as a yellow solid. LCMS: m/z=482.1 (M+H)$^+$.

Step 3: To a solution of compound (1-(2',6'-bis(benzyloxy)-[3,3'-bipyridin]-5-yl)piperidin-4-yl)methanol (24.0 g, 49.2 mmol, 1.00 eq) and AcOH (8.88 g, 147 mmol, 8.46 mL, 3.00 eq) in THF (120 mL) and EtOH (120 mL) was added 10 wt % Pd/C (6.00 g, 49.2 mmol, 1.00 eq) and 20 wt % Pd(OH)$_2$ (5.93 g, 8.45 mmol, 0.17 eq) under N$_2$. The suspension was degassed under vacuum and purged with H$_2$ several times. The mixture was stirred under H$_2$ (50 psi) at 80° C. for 12 hrs. The mixture was cooled to 20° C. and filtered. The filtrate was concentrated. The residue was adjusted with saturated aqueous Na$_2$CO$_3$ until pH=10 and the aqueous layer was extracted with ethyl acetate: THF (1:1, 1000 mL*5). The combined organic layers were washed with brine (1000 mL), dried over Na$_2$SO$_4$, concentrated under vacuum. Desired product (9.91 g, 24.1 mmol, 48.9% yield) was obtained as pink solid without further purification. LCMS: m/z=304.2 (M+H)$^+$.

Step 4: To a solution of 3-(5-(4-(hydroxymethyl)piperidin-1-yl)pyridin-3-yl)piperidine-2,6-dione (9.91 g, 24.1 mmol, 1.00 eq) in DMSO (100 mL) was added DMP (20.4 g, 48.2 mmol, 14.93 mL, 2.00 eq) in portions at 20° C. The reaction was stirred at 20° C. for 1 hr. The mixture was poured into water (100 mL) and ethyl acetate (100 mL). The mixture was adjusted with saturated aqueous Na$_2$CO$_3$ until pH=10 and the aqueous layer was extracted with ethyl acetate (1000 mL*5) and THF: MeOH (1: 1, 1000 mL*5). The combined organic layers were washed with Na$_2$S$_2$O$_3$ solution (1000 mL) and brine (1000 mL), dried over Na$_2$SO$_4$, concentrated under vacuum. The crude product was triturated with ethyl acetate (100 mL) at 20° C. for 30 mins. HA-13 (4.92 g, 16.0 mmol, 66.5% yield) was obtained as an off-white solid. LCMS: m/z=300.1 (M−H)$^+$. $^1$H NMR: (400 MHz, CDCl$_3$) δ 9.72 (s, 1H), 8.34-8.21 (m, 2H), 7.99 (d, J=1.8 Hz, 1H), 7.02 (t, J=2.2 Hz, 1H), 3.77-3.72 (m, 1H), 3.68-3.61 (m, 2H), 3.00-2.92 (m, 2H), 2.84-2.76 (m, 1H), 2.75-2.65 (m, 1H), 2.50-2.41 (m, 1H), 2.34-2.24 (m, 2H), 2.11-2.04 (m, 2H), 1.82-1.74 (m, 2H).

HA-14: rac-(R)-2-(1-(5-(2,6-dioxopiperidin-3-yl)pyridin-2-yl)piperidin-4-yl)acetaldehyde

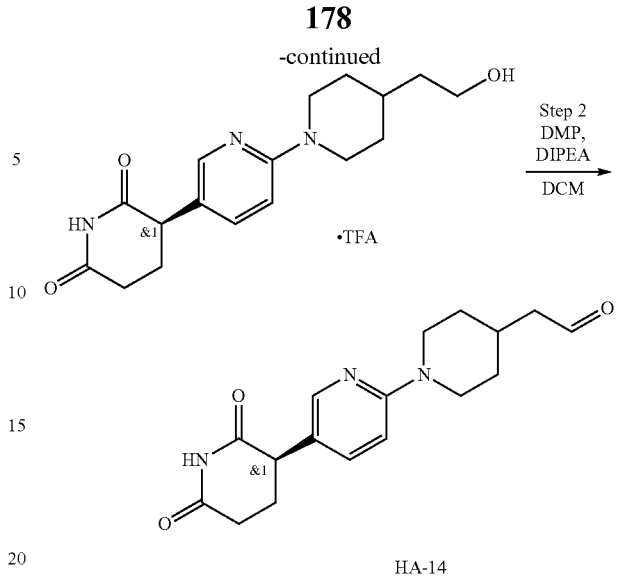

HA-14

Step 1: To a 40 mL vial was added rac-(3R)-3-(6-fluoropyridin-3-yl)piperidine-2,6-dione (1500.00 mg, 7.20 mmol), 4-piperidineethanol (977.44 mg, 7.57 mmol), N,N-diisopropylethylamine (5.03 mL, 3.72 g, 28.82 mmol), and DMSO (10.00 mL). Stirred at 130° C. for 16 hrs. The reaction mixture was concentrated and the resulting residue was purified by reverse phase column chromatography (415 g C18 silica, 5-50% MeCN/H2O+0.1% TFA) to yield rac-(3R)-3-{6-[4-(2-hydroxyethyl)piperidin-1-yl]pyridin-3-yl}piperidine-2,6-dione; trifluoroacetic acid as an amorphous solid (2.10 g, 92% yield). LCMS C$_{17}$H$_{23}$N$_3$O$_3$ requires: 317.2, found: 318.2 [M+H]$^+$.

Step 2: To a 40 mL vial was added rac-(3R)-3-{6-[4-(2-hydroxyethyl)piperidin-1-yl]pyridin-3-yl}piperidine-2,6-dione; trifluoroacetic acid (1600.00 mg, 3.71 mmol) and DCM (30.00 mL). The reaction mixture was cooled to 0° C., then 1,1-bis(acetyloxy)-3-oxo-1lambda5,2-benziodaoxol-1-yl acetate (1.73 g, 4.08 mmol) was added in one portion. After 10 min, the ice bath was removed, and the reaction was stirred warming to RT for 1 hr. 3 mL TEA was added to the reaction mixture, and the crude reaction mixture was adsorbed onto silica, then purified by column chromatography (80 g silica, 20-100% EtOAc+1% TEA/DCM) to yield the title compound as a white solid (278 mg, 47% yield). LCMS C$_{17}$H$_{21}$N$_3$O$_3$ requires: 315.2, found: m/z=316.2 [M+H]$^+$.

HA-15: rac-(R)-2-(4-(4-(2,6-dioxopiperidin-3-yl)pyridin-2-yl)piperazin-1-yl)acetic acid

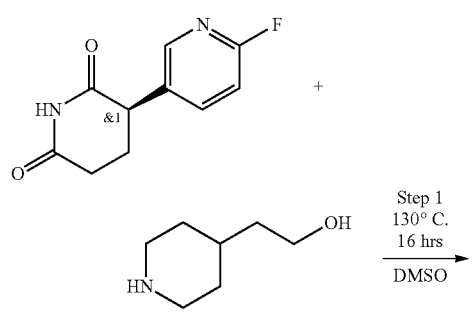

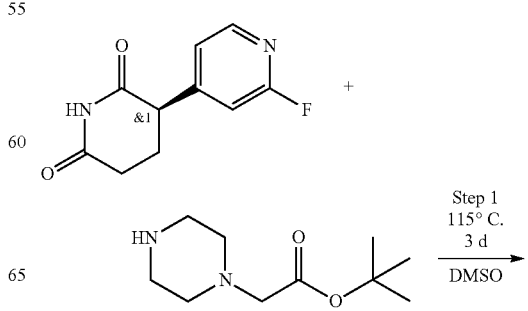

-continued

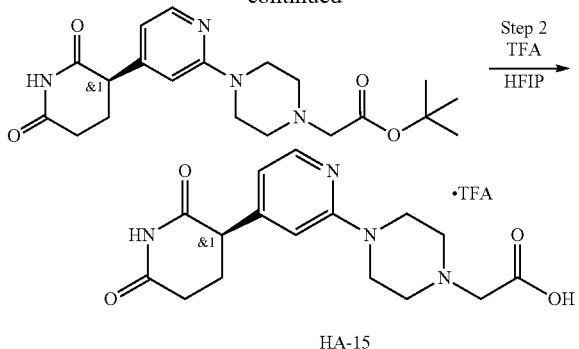

HA-15

Step 1: To a 40 mL vial was added rac-(3R)-3-(2-fluoro-pyridin-4-yl)piperidine-2,6-dione (1000.00 mg, 4.80 mmol), tert-butyl 2-(piperazin-1-yl)acetate (1443.01 mg, 7.20 mmol), DMSO (7.00 mL), and N,N-diisopropylethylamine (3.36 mL, 2.48 g, 19.21 mmol). The reaction mixture was stirred at 120° C. for 3 d. The reaction mixture was diluted with brine and EtOAc. The product was extracted with EtOAc (2×), and the combined organic layers were washed with brine (4×), dried over MgSO$_4$, then concentrated. The resulting residue was purified by column chromatography (80 g silica, 30-100% EtOAc/DCM+1% TEA) to yield rac-tert-butyl 2-(4-{4-[(3R)-2,6-dioxopiperidin-3-yl]pyridin-2-yl}piperazin-1-yl)acetate as an off-white solid (1.454 g, 78% yield). LCMS $C_{20}H_{28}N_4O_4$ requires: 388.2, found: m/z=389.2 [M+H]$^+$.

Step 2: To a 40 mL vial was added rac-tert-butyl 2-(4-{4-[(3R)-2,6-dioxopiperidin-3-yl]pyridin-2-yl}piperazin-1-yl)acetate (1454.30 mg, 3.74 mmol), HFIP (5.00 mL), and trifluoroacetic acid (2.85 mL, 4.27 g, 37.44 mmol). The reaction mixture was stirred at RT for 16 hrs. The reaction mixture was then concentrated. The resulting residue was purified by RP-FC (100 g C18 silica, 0-10% MeCN/H$_2$O) to yield the title compound as a white solid (813 mg, 65% yield). LCMS $C_{16}H_{20}N_4O_4$ requires: 332.1, found: m/z=333.1 [M+H]$^+$.

HA-16: rac-(R)-1-(4-(2,6-dioxopiperidin-3-yl)pyridin-2-yl)piperidine-4-carboxylic acid

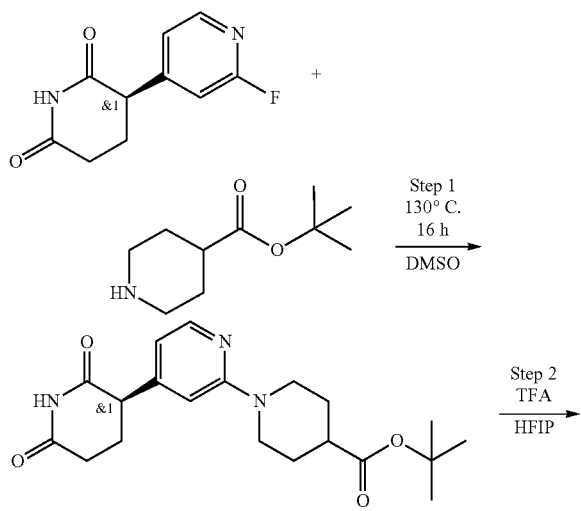

-continued

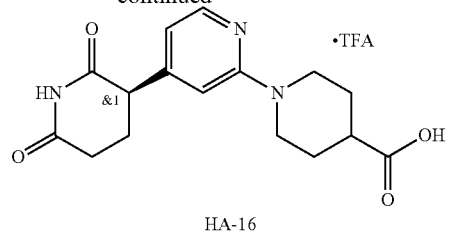

HA-16

Step 1: To a 40 mL vial was added rac-(3R)-3-(2-fluoro-pyridin-4-yl)piperidine-2,6-dione (1000 mg, 4.80 mmol), tert-butyl piperidine-4-carboxylate (978.87 mg, 5.28 mmol), N,N-diisopropylethylamine (3.36 mL, 2.48 g, 19.21 mmol), and DMSO (7.00 mL). The reaction mixture was stirred at 120° C. for 16 hrs. The reaction mixture was diluted with EtOAc and brine. The product was extracted with EtOAc (2×). The combined organic layers were washed with brine (4×), dried over MgSO$_4$, then concentrated. The resulting residue was purified by column chromatography (80 g silica, 0-70% EtOAc/DCM) to yield rac-tert-butyl 1-{4-[(3R)-2,6-dioxopiperidin-3-yl]pyridin-2-yl}piperidine-4-carboxylate as an off-white solid (1.235 g, 69% yield). LCMS $C_{20}H_{27}N_3O_4$ requires: 373.2, found: m/z=374.2 [M+H]$^+$.

Step 2: To a 40 mL vial was added rac-tert-butyl 1-{4-[(3R)-2,6-dioxopiperidin-3-yl]pyridin-2-yl}piperidine-4-carboxylate (630.00 mg, 1.69 mmol) and HFIP (4.00 mL). To the reaction mixture was added trifluoroacetic acid (1.28 mL, 1.92 g, 16.87 mmol) in a dropwise fashion. After 2 h, the reaction mixture was concentrated. The resulting residue was purified reverse phase column chromatography (100 g C18 silica, 0-15% MeCN/H$_2$O), to yield the title compound as a white solid (408 mg, 76% yield). LCMS $C_{16}H_{19}N_3O_4$ requires: 317.1, found: m/z=318.1 [M+H]$^+$.

HA-17: rac-(R)-1-(5-((R)-2,6-dioxopiperidin-3-yl)pyridin-2-yl)pyrrolidine-3-carboxylic acid

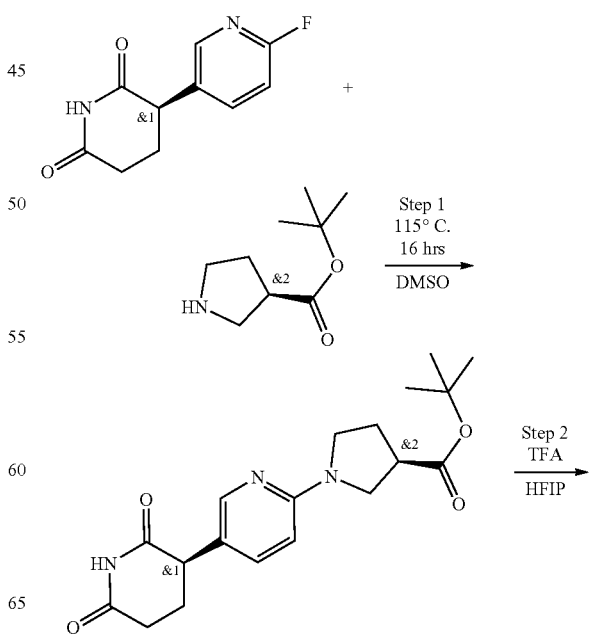

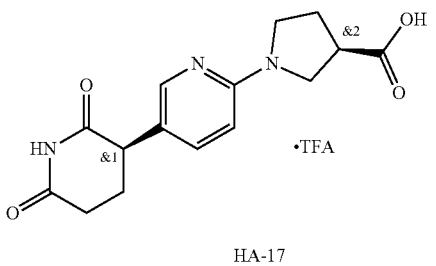

HA-17

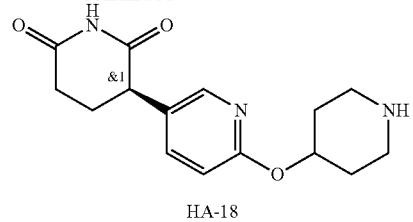

HA-18

Step 1: To a 40 mL vial was added rac-(3R)-3-(6-fluoro-pyridin-3-yl)piperidine-2,6-dione (1000.00 mg, 4.80 mmol), rac-tert-butyl (3R)-pyrrolidine-3-carboxylate (822.51 mg, 4.80 mmol), N,N-diisopropylethylamine (3.36 mL, 2.48 g, 19.21 mmol), and DMSO (7.00 mL). Stirred at 115° C. for 16 hrs. The reaction mixture was then diluted with EtOAc and brine. The product was extracted with EtOAc (2×), the combined organic layers were washed with brine (4×), dried over MgSO₄, then purified by column chromatography (80 g silica, 10-100% EtOAc/DCM) to yield tert-butyl (3RS)-1-{5-[(3RS&)-2,6-dioxopiperidin-3-yl]pyridin-2-yl}pyrrolidine-3-carboxylate as a white solid (779.1 mg, 45% yield). LCMS $C_{19}H_{25}N_3O_4$ requires: 359.2, found: m/z=360.2 [M+H]⁺.

Step 2: To a 40 mL vial was added tert-butyl (3RS)-1-{5-[(3RS&)-2,6-dioxopiperidin-3-yl]pyridin-2-yl}pyrrolidine-3-carboxylate (779.10 mg, 2.17 mmol), HFIP (4.00 mL), and trifluoroacetic acid (1.65 mL, 2.47 g, 21.68 mmol). The reaction mixture was stirred for 4 h, then concentrated. The resulting residue was purified by reverse phase chromatography (100 g C18 silica, 0-10% MeCN/water) to yield the title compound as a white solid (589 mg, 90% yield). LCMS $C_{15}H_{17}N_3O_4$ requires: 303.1, found: m/z=304.0 [M+H]⁺.

HA-18: rac-(R)-3-(6-(piperidin-4-yloxy)pyridin-3-yl)piperidine-2,6-dione

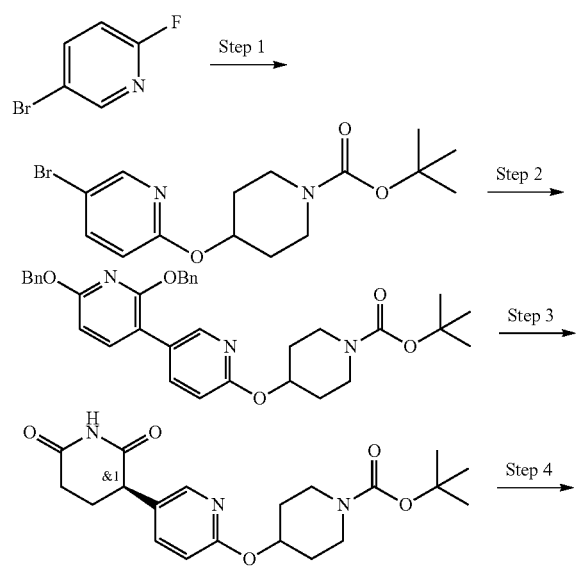

Step 1: tert-butyl 4-hydroxypiperidine-1-carboxylate (1.14 g, 5.68 mmol) was dissolved in NMP (10 ml) and the reaction was cooled to 0° C. Sodium hydride (0.27 g, 11.36 mmol) was added, and the reaction was stirred for 5 minutes before addition of 5-bromo-2-fluoropyridine (0.58 mL, 1.00 g, 5.68 mmol). The reaction was heated to 60° C. for 4 hours. The product was purified by reverse phase flash column chromatography (0-100% acetonitrile in water) via direct injection to yield tert-butyl 4-[(5-bromopyridin-2-yl)oxy]piperidine-1-carboxylate (0.751 g, 37% yield). LCMS: $C_{15}H_{21}BrN_2O_3$ requires 357.25, found: m/z=358.10 [M+H]⁺.

Step 2: tert-butyl 4-[(5-bromopyridin-2-yl)oxy]piperidine-1-carboxylate (0.750 g, 2.10 mmol), Pd(dppf)Cl₂·DCM (0.342 g, 0.42 mmol), cesium carbonate 1 N solution (5.25 mL, 1.71 g, 5.25 mmol), 2,6-bis(benzyloxy)pyridin-3-ylboronic acid (0.703 g, 2.10 mmol), and dioxane (5.00 mL) were combined in a sealed vial. The vial was purged with nitrogen gas and stirred at 100° C. for 60 minutes. The reaction was poured over brine and extracted with ethyl acetate, filtered, and concentrated on to silica gel. The reaction was purified by flash column chromatography (0-100% ethyl acetate in hexanes) to give tert-butyl 4-{[2',6'-bis(benzyloxy)-[3,3'-bipyridin]-6-yl]oxy}piperidine-1-carboxylate (1.05 g, 88% yield). LCMS: $C_{34}H_{37}N_3O_5$ requires 567.69, found: m/z=568.70 [M+H]⁺.

Step 3: tert-butyl 4-{[2',6'-bis(benzyloxy)-[3,3'-bipyridin]-6-yl]oxy}piperidine-1-carboxylate (1.05 g, 1.8 mmol) was dissolved in EtOH (20.00 mL). palladium on carbon 10% (0.20 g, 0.18 mmol) was added and the reaction was stirred under hydrogen balloon for 12 hours. The reaction was filtered through celite and concentrated to give tert-butyl 4-({5-[(3R)-2,6-dioxopiperidin-3-yl]pyridin-2-yl}oxy)piperidine-1-carboxylate (0.647 g, 95%). LCMS: $C_{20}H_{27}N_3O_5$ requires 389.45, found: m/z=390.20 [M+H]⁺.

Step 4: tert-butyl 4-({5-[(3R)-2,6-dioxopiperidin-3-yl]pyridin-2-yl}oxy)piperidine-1-carboxylate (0.647 g, 1.66 mmol) was dissolved in DCM (10 ml). 4M HCl in dioxane (3 ml) was added and the reaction was stirred at room temperature for 4 hours. The reaction mixture was concentrated on to silica gel and purified by reverse phase flash column chromatography (0-100% acetonitrile in water) to yield (3R)-3-[6-(piperidin-4-yloxy)pyridin-3-yl]piperidine-2,6-dione (0.427 g, 92% yield). LCMS: $C_{15}H_{19}N_3O_3$ requires 289.34, found: m/z=290.20 [M+H]⁺.

HA-19: 1-[5-(2,4-dioxo-1,3-diazinan-1-yl)pyridin-2-yl]piperidine-4-carbaldehyde

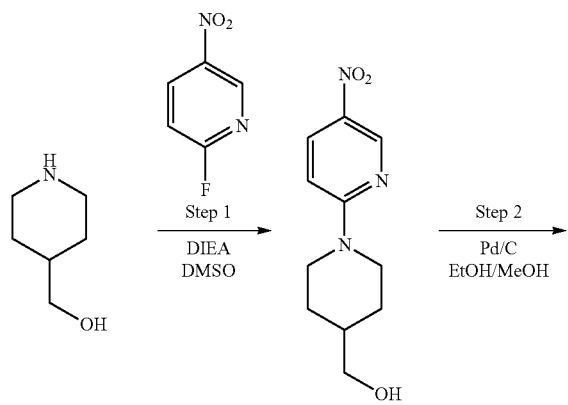

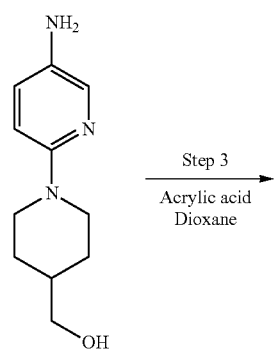

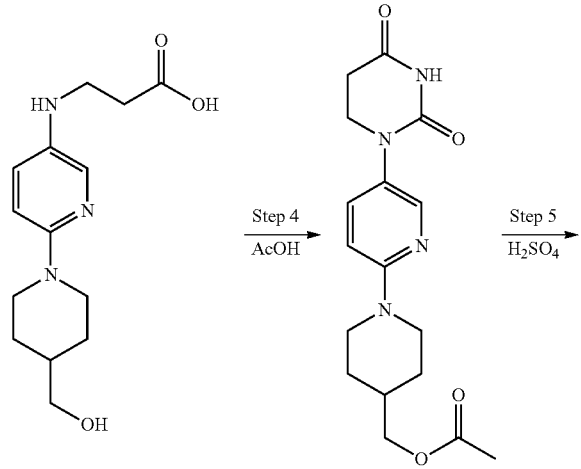

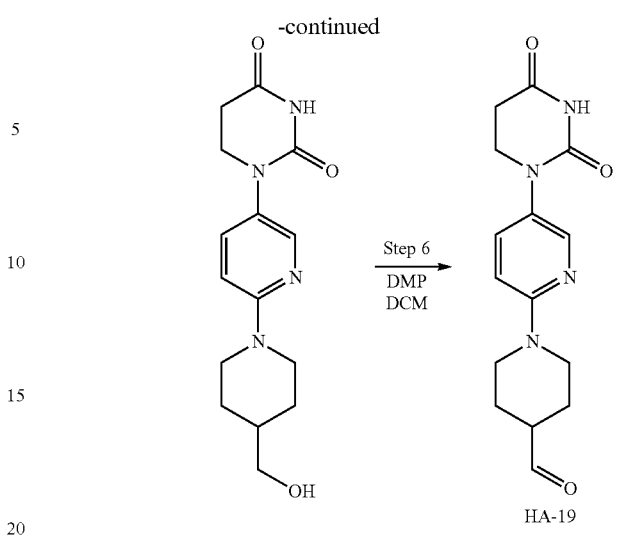

Step 1: A mixture of 2-fluoro-4-nitropyridine (20 g, 0.140 mol, 1 eq), piperidin-4-ylmethanol (24.318 g, 0.211 mol, 1.5 eq) and DIPEA (27.29 mL, 0.211 mol, 1.5 eq) in anhydrous DMSO (50 mL, 2.82 M) was stirred at 90° C. overnight. Then the reaction mixture was poured into ice water. The resulting precipitate was filtered and purified by FC (DCM/MeOH—9/1) to give 33.37 g of [1-(5-nitropyridin-2-yl)piperidin-4-yl]methanol (47% yield) as a yellow solid. LCMS: $(M+H)^+=237.7$ H NMR (300 MHz, $CDCl_3$) δ 9.05 (d, J=2.8 Hz, 1H), 8.20 (dd, J=9.6, 2.8 Hz, 1H), 6.60 (d, J=9.6 Hz, 1H), 4.59 (d, J=13.4 Hz, 2H), 3.57 (d, J=5.9 Hz, 2H), 3.11-2.95 (m, 2H), 1.98-1.84 (m, 3H), 1.31 (tdd, J=14.3, 11.8, 4.2 Hz, 2H).

Step 2: [1-(5-nitropyridin-2-yl)piperidin-4-yl]methanol (15.5 g, 0.065 mol, 1 eq) was dissolved in a mixture of EtOH/MeOH—1/1 (250 mL, 0.26 M), degassed and charged with Pd/C (50% wet, 2.32 g, 15% weight). The reaction mixture was evacuated and backfilled with $H_2$ and left to stir overnight (balloon, 1 atm), then filtered through a celite pad and concentrated to give 5.85 g of [1-(5-aminopyridin-2-yl)piperidin-4-yl]methanol (45% yield) as a pale yellow oil, which was used in the next step without additional purification. LCMS $(M+H)^+=208.25$ $^1H$ NMR (300 MHz, DMSO-$d_6$) δ 7.59 (dd, J=2.9, 0.7 Hz, 1H), 6.89 (dd, J=8.8, 2.9 Hz, 1H), 6.61 (dd, J=8.9, 0.8 Hz, 1H), 4.56-4.39 (m, 3H), 4.02-3.89 (m, 2H), 3.26 (dd, J=6.3, 5.3 Hz, 2H), 2.60-2.52 (m, 2H), 1.76-1.62 (m, 2H), 1.49 (s, 1H), 1.12 (dd, J=12.2, 4.0 Hz, 2H).

Step 3: A pressure vessel was charged with [1-(5-aminopyridin-2-yl)piperidin-4-yl] methanol (5.8 g, 27.9 mmol, 1eq) and acrylic acid (1.9 mL, 27.9 mmol, 1eq) dissolved in 1,4-dioxane (58 mL, 0.5 M). Obtained reaction mixture was stirred at 90° C. After 16 h 25% of starting amine was still present. An additional 0.25 eq of the acrylic acid was added and the reaction mixture was stirred at 90° C. for another 16 hrs. After that the mixture was concentrated, the obtained residue was diluted with EtOAc and refluxed, and the solution was decanted. The residue (black gum) was redissolved in MeOH and evaporated to yield 6.4 g of 3-({6-[4-(hydroxymethyl)piperidin-1-yl]pyridin-3-yl}amino)propanoic acid (78% yield). LCMS $(M+H)^+=280.25$. $(M-H)^-=278.025$. $^1H$ NMR (300 MHz, DMSO-$d_6$) δ 7.59 (d, J=2.9 Hz, 1H), 6.93 (dd, J=8.9, 3.0 Hz, 1H), 6.68 (d, J=8.9 Hz, 1H), 4.00 (dt, J=12.8, 3.3 Hz, 2H), 3.39 (t, J=7.1 Hz, 1H), 3.26 (d, J=6.3 Hz, 3H), 2.63-2.53 (m, 2H), 2.47-2.29 (m, 3H), 1.67 (s, 2H), 1.13 (dd, J=12.2, 4.0 Hz, 2H).

Step 4 and Step 5: 3-(\{6-[4-(hydroxymethyl)piperidin-1-yl]pyridin-3-yl\}amino)propanoic acid (6.4 g, 21.76 mmol, 1.0 eq.), urea (2.614 g, 43.53 mmol, 2.0 eq.) were dissolved in glacial acetic acid (64 mL, 10 vol) and left to stir at 90° C. for 48 hrs. The reaction mixture was concentrated, and the obtained residue was dissolved in EtOH (100 mL), followed by the addition of $H_2SO_4$ (0.012 mL, 0.022 mmol, 0.01eq) and stirred at room temperature for 48 hrs. The reaction mixture pH was adjusted to pH=10-11 with $KHSO_4$, concentrated and purified by chromatography (DCM/MeOH—9/1). The obtained material was further triturated with DCM to give 1.28 g 1-\{6-[4-(hydroxymethyl)piperidin-1-yl]pyridin-3-yl\}-1,3-diazinane-2,4-dione (18% yield). LCMS $(M+H)^+$=305.05. $^1$H NMR (300 MHz, DMSO-$d_6$) δ 10.34 (s, 1H), 8.04 (d, J=2.7 Hz, 1H), 7.47 (dd, J=9.0, 2.8 Hz, 1H), 6.84 (d, J=9.1 Hz, 1H), 4.47 (t, J=5.3 Hz, 1H), 4.29 (d, J=13.0 Hz, 2H), 3.70 (t, J=6.7 Hz, 2H), 3.27 (t, J=5.7 Hz, 2H), 2.83-2.65 (m, 4H), 1.77-1.54 (m, 3H), 1.18-1.03 (m, 2H).

Step 6: To the 1-\{6-[4-(hydroxymethyl)piperidin-1-yl]pyridin-3-yl\}-1,3-diazinane-2,4-dione (0.715 g, 2.3 mmol, 1eq) dissolved in anhydrous DCM (0.3M) the solution of Dess-Martin periodinane (1.073 g, 2.53 mmol, 1.1eq) in anhydrous DCM (0.15M) was added dropwise at 0° C. The reaction mixture was left to stir at room temperature for 1 h (TLC and LCMS control). The reaction mixture was diluted with aq. sat. $Na_2S_2O_3$, the organic layer was separated and washed with aq. sat. $NaHCO_3$. The aqueous layers were combined and back-extracted several times with DCM. The combined organic phase was dried over $Na_2SO_4$, concentrated to give 0.56 g of 1-[5-(2,4-dioxo-1,3-diazinan-1-yl)pyridin-2-yl]piperidine-4-carbaldehyde (HA-19) (yield 77%) as a beige solid. The product tends to form a stable hydrate. $^1$H NMR (300 MHz, DMSO-d6) δ 10.35 (s, 1H), 9.63 (d, J=0.9 Hz, 1H), 8.08-8.03 (m, 1H), 7.50 (dd, J=9.0, 2.8 Hz, 1H), 6.88 (d, J=9.1 Hz, 1H), 4.13 (dt, J=13.2, 4.1 Hz, 2H), 3.70 (t, J=6.7 Hz, 2H), 3.11-2.99 (m, 2H), 2.71 (d, J=6.7 Hz, 2H), 2.66-2.55 (m, 1H), 1.90 (dd, J=13.3, 3.9 Hz, 2H), 1.55-1.42 (m, 2H). LCMS ESI(+)[M+H]$^+$=305.11.

HA-20: rac-(R)-1-(4-(2,6-dioxopiperidin-3-yl)pyridin-2-yl)piperidine-4-carbaldehyde

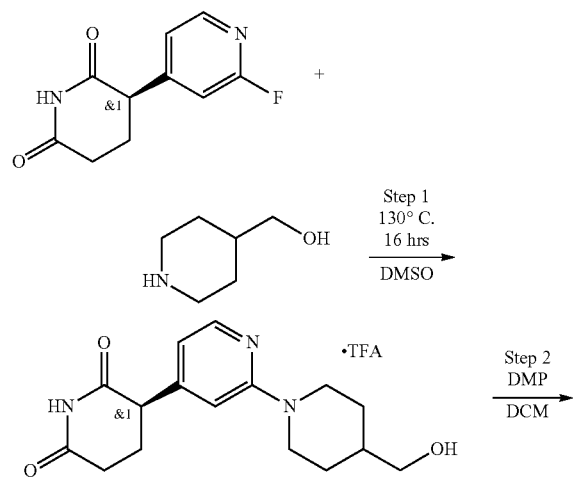

-continued

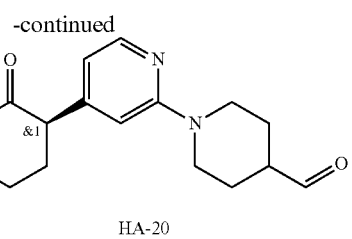

HA-20

Step 1: To a 40 mL vial was added rac-(3R)-3-(2-fluoropyridin-4-yl)piperidine-2,6-dione (1.0 g, 4.80 mmol), piperidin-4-ylmethanol (0.59 g, 5.04 mmol), N,N-diisopropylethylamine (3.36 mL, 2.48 g, 19.21 mmol), and DMSO (7.00 mL). The reaction mixture was stirred at 120° C. for 16 hrs. The reaction mixture was then concentrated and purified by RP-FC (415 g C18 silica, 5-20% MeCN/$H_2O$+ 0.1% TFA) to yield rac-(3R)-3-\{2-[4-(hydroxymethyl)piperidin-1-yl]pyridin-4-yl\}piperidine-2,6-dione; trifluoroacetic acid as a white solid (1.73 g, quantitative yield). LCMS. $C_{16}H_{21}N_3O_3$ requires: 303.2, found: m/z=304.5 $[M+H]^+$.

Step 2: To a 200 mL flask was added rac-(3R)-3-\{2-[4-(hydroxymethyl)piperidin-1-yl]pyridin-4-yl\}piperidine-2,6-dione; trifluoroacetic acid (1.71 g, 4.10 mmol), DCM (50.00 mL), and MeCN (10.00 mL). The reaction mixture was cooled to 0° C., and 1,1-bis(acetyloxy)-3-oxo-1-lambda-5,2-benziodaoxol-1-yl acetate (1.91 g, 4.51 mmol) was added in one portion. After stirring at 0° C. for 10 min, the reaction mixture was stirred while warming to RT for 3 hrs. 3 mL TEA was added to the reaction mixture, then the crude mixture was adsorbed onto silica, then purified by column chromatography (120 g silica, 10-100% EtOAc/DCM) to yield the title compound as a white solid (233 mg, 18%). LCMS $C_{16}H_{19}N_3O_3$ requires: 301.1, found: m/z=302.1 $[M+H]^+$.

HA-21: 1-(4-(2,4-dioxotetrahydropyrimidin-1(2H)-yl)phenyl)piperidine-4-carbaldehyde

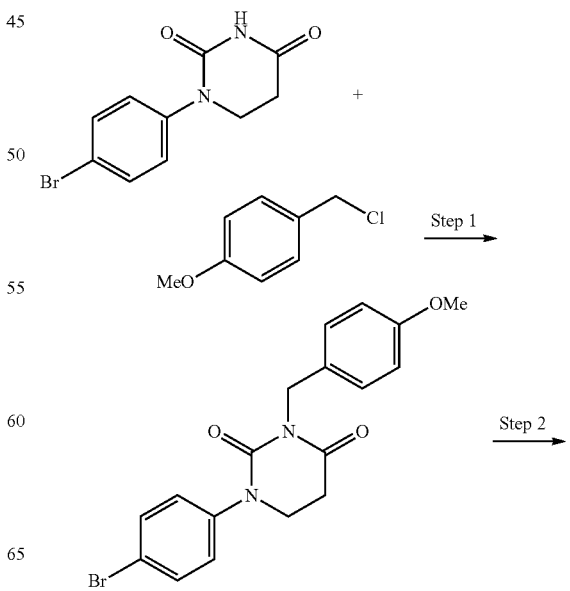

-continued

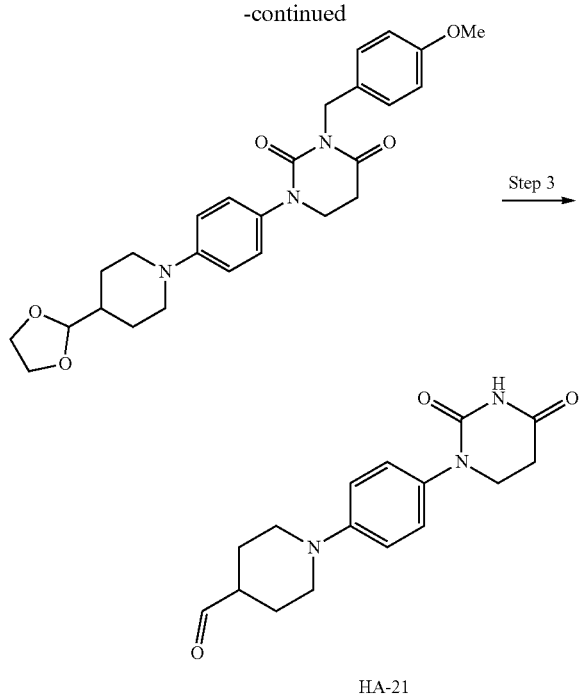

HA-21

Step 1: To a 40 mL vial was added 1-(4-bromophenyl)-1,3-diazinane-2,4-dione (6.40 g, 24 mmol), caesium carbonate (9.30 g, 28.5 mmol), and DMF (60.00 mL). To the reaction mixture was added 4-methoxybenzyl chloride (4.17 mL, 4.84 g, 30.9 mmol). The reaction mixture was stirred overnight, then quenched with water. The product was extracted with DCM (3×), dried over $Na_2SO_4$, then concentrated. The resulting residue was purified by FC (330 g silica, 0-50% EtOAc/DCM). The resulting purified residue was concentrated under reduced pressure into an amorphous solid and triturated with hexanes to yield 1-(4-bromophenyl)-3-(4-methoxybenzyl)dihydropyrimidine-2,4(1H,3H)-dione as a white solid (9.26 g, quantitative yield). LCMS: $C_{18}H_{17}BrN_2O_3$ requires: 388.0, found: m/z=389.2 $[M+H]^+$.

Step 2: To a 2 dram vial was added 1-(4-bromophenyl)-3-[(4-methoxyphenyl)methyl]-1,3-diazinane-2,4-dione (550 mg, 1.41 mmol), 4-(1,3-dioxolan-2-yl)piperidine (666 mg, 4.24 mmol), di-tert-butyl({2',4',6'-triisopropyl-[1,1'-biphenyl]-2-yl})phosphane (240 mg, 0.57 mmol), palladium (II) acetate (63 mg, 0.28 mmol), caesium carbonate (1.38 g, 4.24 mmol), and dioxane (5.00 mL). The reaction mixture was sparged with $N_2$ for 10 min, then stirred at 95° C. overnight. The crude reaction mixture was diluted with DCM and water, then filtered through celite. The product was extracted with DCM (3×), dried over $MgSO_4$, then concentrated. The resulting residue was purified by FC (40 g silica, 0-100% EtOAc/hex) to yield 1-(4-(4-(1,3-dioxolan-2-yl)piperidin-1-yl)phenyl)-3-(4-methoxybenzyl)dihydropyrimidine-2,4(1H,3H)-dione as a white solid (395 mg, 60%). LCMS: $C_{26}H_{31}N_3O_5$ requires: 465.2, found: m/z=466.4 $[M+H]^+$.

Step 3: To a 20 mL vial was added 1-{4-[4-(1,3-dioxolan-2-yl)piperidin-1-yl]phenyl}-3-[(4-methoxyphenyl)methyl]-1,3-diazinane-2,4-dione (395 mg, 0.85 mmol) and TFA (5.00 mL). To the reaction mixture was added trifluoromethanesulfonic acid (374 uL, 636 mg, 4.24 mmol). Full conversion after 10 min. The reaction mixture was diluted with minimal water, then purified by RP-FC (415 g C18 silica, 0-50% MeCN/water+0.1% TFA) to yield 1-(4-(2,4-dioxotetrahydropyrimidin-1(2H)-yl)phenyl)piperidine-4-carbaldehyde as a white solid (40 mg, 16%). LCMS: $C_{16}H_{21}N_3O_3$ requires: 301.1, found: m/z=302.2 $[M+H]^+$.

HA-22: 1-(3-(2,4-dioxotetrahydropyrimidin-1(2H)-yl)-4-fluorobenzoyl)piperidine-4-carbaldehyde

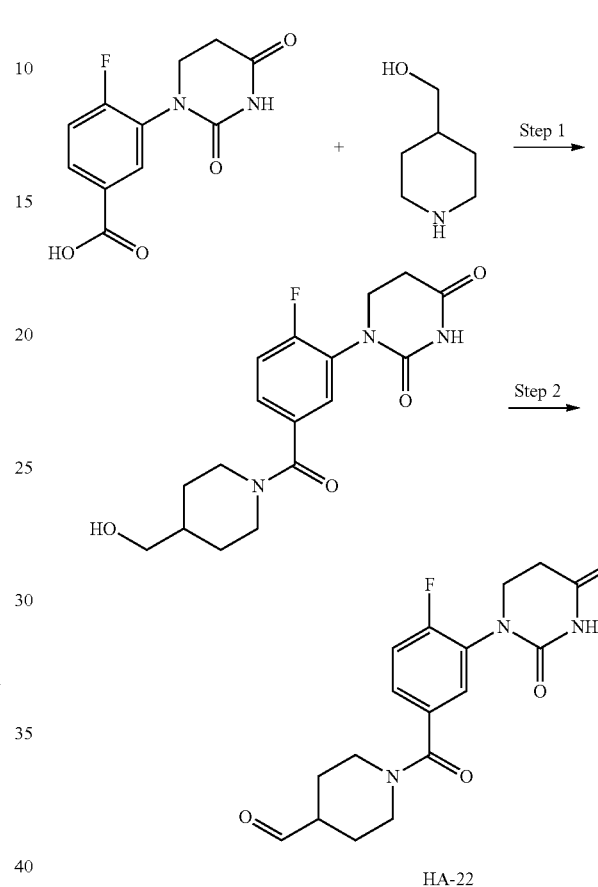

HA-22

Step 1: To a 20 mL vial was added 3-(2,4-dioxo-1,3-diazinan-1-yl)-4-fluorobenzoic acid (150 mg, 0.59 mmol), piperidin-4-ylmethanol (69 mg, 0.59 mmol), N,N-diiopropylethylamine (0.31 mL, 0.23 g, 1.78 mmol), and DMF (2 mL). To the reaction mixture was added a solution of [(dimethylamino)({[1,2,3]triazolo[4,5-b]pyridin-3-yloxy}) methylidene]dimethylazanium; hexafluoro-lambda5-phosphanuide (226 mg, 0.59 mmol) in DMF (1 mL). The reaction mixture was stirred for 16 h, and the crude reaction mixture was purified by RP-FC (100 g C18 silica, 0-30% MeCN/water+0.1% TFA) to yield 1-(2-fluoro-5-(4-(hydroxymethyl)piperidine-1-carbonyl) phenyl)dihydropyrimidine-2,4 (1H,3H)-dione as a white solid (263 mg, quantitative yield). LCMS: $C_{17}H_{20}FN_3O_4$ requires: 349.1, found: m/z=350.2 $[M+H]^+$.

Step 2: To a 2 dram vial was added 1-{2-fluoro-5-[4-(hydroxymethyl)piperidine-1-carbonyl]phenyl}-1,3-diazinane-2,4-dione (40 mg, 0.11 mmol), DMSO (0.50 mL), DCM (1.50 mL) 0, and IBX polystrene (1.22 mmol/g, 0.3 g). The reaction mixture was stirred for 1 d, then filtered with additional 20 mL DCM. The crude mixture was concentrated and carried forward to the next step as a solution in DMSO without further purification. LCMS: $C_{17}H_{18}FN_3O_4$ requires: 347.1, found: m/z=348.3 $[M+H]^+$.

HA-23: 1-(1,2,3,4-tetrahydroisoquinolin-6-yl)dihydropyrimidine-2,4(1H,3H)-dione

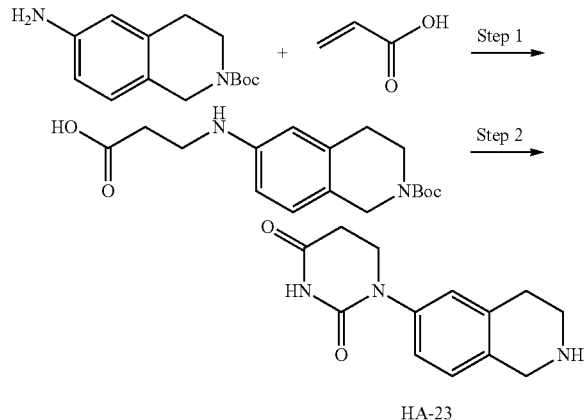

Step 1: Synthesis of 3-((2-(tert-butoxycarbonyl)-1,2,3,4-tetrahydroisoquinolin-6-yl)amino)propanoic acid: To a 20 mL vial was added tert-butyl 6-amino-3,4-dihydro-1H-isoquinoline-2-carboxylate (1.0 g, 4.0 mmol), acrylic acid (0.28 mL, 290 mg, 4.0 mmol), and toluene (7.0 mL). The reaction mixture was stirred at 80° C. for 16 h, then concentrated. The resulting crude product was used in the subsequent step without further purification. LCMS $C_{17}H_{24}N_2O_4$ requires: 320.2, found: m/z=321.2 [M+H]$^+$.

Step 2: Synthesis of 1-(1,2,3,4-tetrahydroisoquinolin-6-yl)dihydropyrimidine-2,4(1H,3H)-dione: To a 40 mL vial was added 3-{[2-(tert-butoxycarbonyl)-3,4-dihydro-1H-isoquinolin-6-yl]amino}propanoic acid (1.29 g, 4.0 mmol), urea (0.48 g, 8.1 mmol), and acetic acid (2.00 mL). The reaction mixture was stirred at 120° C. for 16 h. To the crude reaction mixture was added TFA (1 mL). The reaction mixture was stirred for 1 h, then purified by RP-FC (415 g C18 silica, 0-20% MeCN/water) to yield the title compound as an off-white solid (126 mg, 10%). LCMS $C_{13}H_{15}N_3O_2$ requires: 245.1, found: m/z=246.1 [M+H]$^+$.

HA-24: rac-(R)-2-(6-(2,6-dioxopiperidin-3-yl)-3,4-dihydroisoquinolin-2(1H)-yl)acetic acid

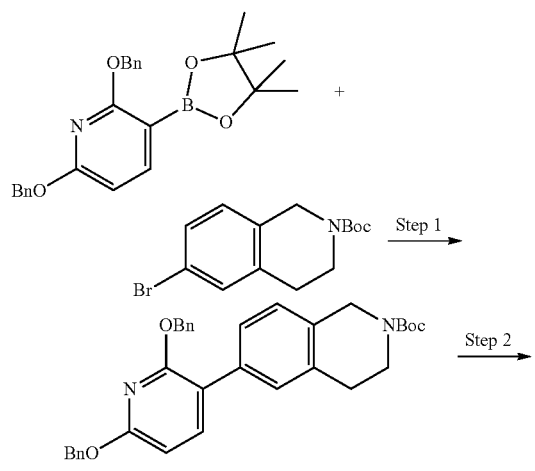

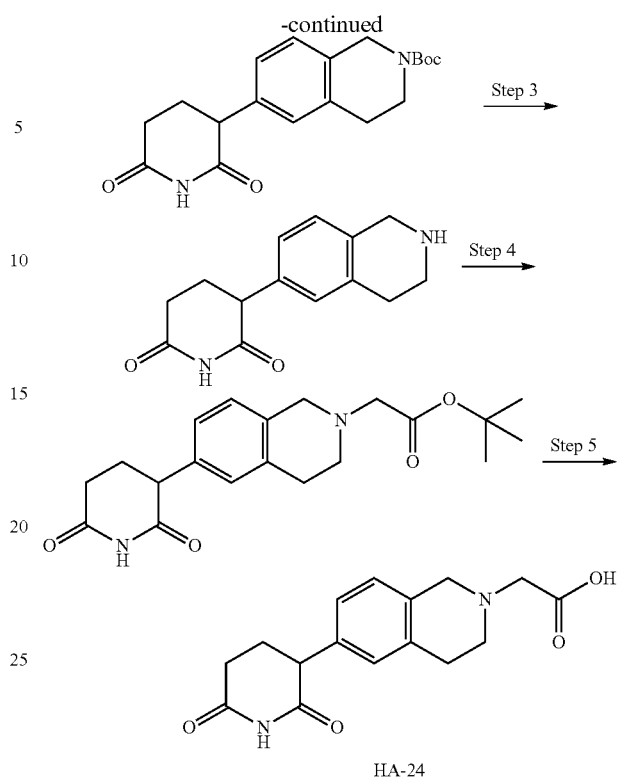

Step 1: To a 40 mL vial was added tert-butyl 6-bromo-3,4-dihydro-1H-isoquinoline-2-carboxylate (1.0 g, 3.2 mmol), 2,6-bis(benzyloxy)-3-(4,4,5,5-tetramethyl-1,3,2-dioxaborolan-2-yl)pyridine (1.47 g, 3.52 mmol), tripotassium phosphate (2.04 g, 9.61 mmol), Pd(dppf)Cl$_2$·DCM (0.26 g, 0.32 mmol), dioxane (7.00 mL), and water (2.50 mL). The reaction mixture was degassed with nitrogen for 15 min, then stirred at 90° C. for 16 h. The reaction mixture was then diluted with water and EtOAc, then filtered through celite. The product was extracted with EtOAc (3×), dried over MgSO$_4$, then concentrated. The resulting residue was purified by FC (80 g silica, 0-25% EtOAc/hexanes) to yield tert-butyl 6-bromo-3,4-dihydroisoquinoline-2(1H)-carboxylate as a colorless oil (1.48 g, 88%). LCMS: $C_{33}H_{34}N_2O_4$ requires: 522.3, found: m/z=523.3 [M+H]$^+$.

Step 2: To a 40 mL vial was added tert-butyl 6-[2,6-bis(benzyloxy)pyridin-3-yl]-3,4-dihydro-1H-isoquinoline-2-carboxylate (1.48 g, 2.83 mmol), Pd/C (700 mg), THF (10 mL), and EtOH (10 mL). The reaction mixture was sparged with hydrogen for 5 min, then the reaction was stirred under hydrogen atmosphere (balloon) for 16 h. The reaction mixture was filtered through celite, then concentrated. The resulting residue was purified by FC (40 g silica, 0-10% MeOH/DCM) to yield tert-butyl 6-(2,6-bis(benzyloxy)pyridin-3-yl)-3,4-dihydroisoquinoline-2(1H)-carboxylate as a white solid (852 mg, 87%). LCMS: $C_{19}H_{24}N_2O_4$ requires: 344.2, found: m/z=345.2 [M+H]$^+$.

Step 3: To a 40 mL vial was added rac-tert-butyl 6-[(3R)-2,6-dioxopiperidin-3-yl]-3,4-dihydro-1H-isoquinoline-2-carboxylate (852 mg, 2.47 mmol) and DCM (2.00 mL). To the reaction mixture was added 4 M hydrogen chloride in dioxane (6.18 mL, 0.90 g, 24.7 mmol) in a dropwise fashion. After 1 h, the reaction mixture was concentrated to yield tert-butyl 6-(2,6-dioxopiperidin-3-yl)-3,4-dihydroisoquinoline-2(1H)-carboxylate as a white solid (707 mg, quantitative yield). LCMS: $C_{14}H_{16}N_2O_2$ requires: 244.1, found: m/z=245.0 [M+H]$^+$.

Step 4: To a 1 dram vial was added rac-(3R)-3-(1,2,3,4-tetrahydroisoquinolin-6-yl)piperidine-2,6-dione hydrochloride (100 mg, 0.356 mmol), N,N-diisopropylethylamine (0.31 mL, 0.23 g, 1.78 mmol), and DMF (2.00 mL). To the reaction mixture was added tert-butyl 2-bromoacetate (53 uL, 76 mg, 0.39 mmol). After stirring for 16 h, the reaction mixture was purified by RP-FC (30 g C18 silica, 0-50% MeCN/water+0.1% TFA) to yield rac-tert-butyl (R)-2-(6-(2,6-dioxopiperidin-3-yl)-3,4-dihydroisoquinolin-2(1H)-yl)acetate as a white solid (165 mg, quantitative yield). LCMS: $C_{20}H_{26}N_2O_4$ requires: 358.2, found: m/z=359.4 [M+H]$^+$.

Step 5: To a 2 dram vial was added rac-tert-butyl 2-{6-[(3R)-2,6-dioxopiperidin-3-yl]-3,4-dihydro-1H-isoquinolin-2-yl}acetate (127 mg, 0.36 mmol), trifluoroacetic acid (0.50 mL, 0.74 g, 6.5 mmol), and DCM (0.50 mL). The reaction mixture was stirred at 40° C. for 4 h. The reaction mixture was concentrated under reduced pressure to yield rac-(R)-2-(6-(2,6-dioxopiperidin-3-yl)-3,4-dihydroisoquinolin-2(1H)-yl)acetic acid as a white solid (149 mg, quantitative yield). LCMS: $C_{16}H_{18}N_2O_4$ requires: 302.1, found: m/z=303.3 [M+H]$^+$.

HA-25: rac-(3R)-3-(6-{2-oxo-7-azaspiro[3.5]nonan-7-yl}pyridin-3-yl)piperidine-2,6-dione and N,N-diisopropylethylamine (173 uL, 0.13 g, 0.99 mmol), and DMSO (0.30 mL). Stirred at 130 C for 14 h. Added more amine (10 mg) and continued heating overnight. Used the solution directly in the next step. LCMS: ESI(+)[M+H]$^+$=374.3 Step 2: rac-(3R)-3-(6-{2-oxo-7-azaspiro[3.5]nonan-7-yl}pyridin-3-yl)piperidine-2,6-dione.

Removed the excess DIPEA from the previous reaction on the rotovap. Added 2 M aq HCl (0.25 mL, 18.23 mg, 0.50 mmol) and stirred at rt. After an hour, added more 2M HCl (0.1 mL) and heated to 40° C. then increased temp to 60° C. overnight. Reduced volume on the rotovap, diluted with MeCN and lyophilized. Redissolved in DCM and purified on the FC (4 g silica, 20-100% EtOAc in hexanes) to give rac-(3R)-3-(6-{2-oxo-7-azaspiro[3.5]nonan-7-yl}pyridin-3-yl)piperidine-2,6-dione (20 mg, 25%). LCMS: ESI(+)[M+H]$^+$=328.3

HA-26: 1-(4-(2,4-dioxotetrahydropyrimidin-1(2H)-yl)phenyl)pyrrolidine-3-carbaldehyde

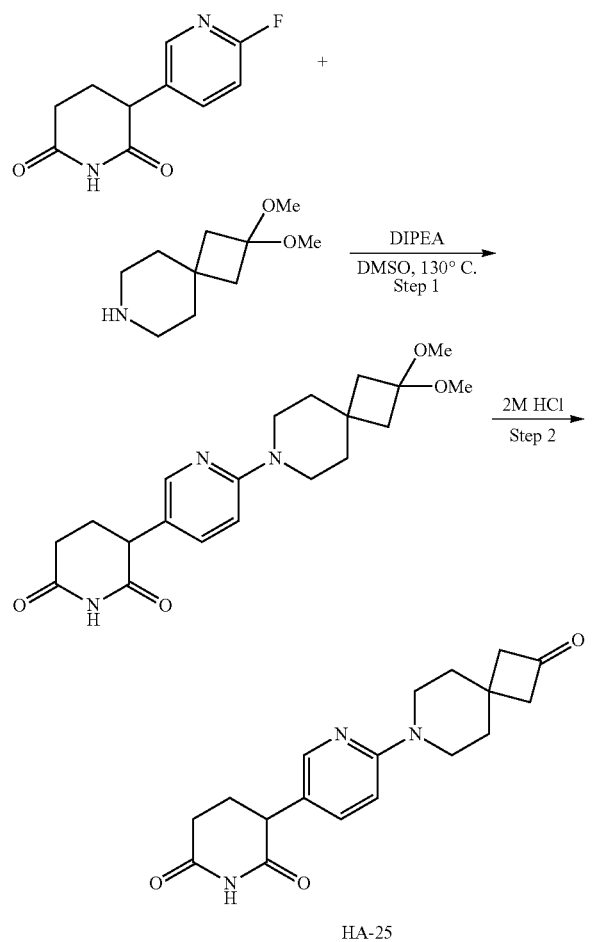

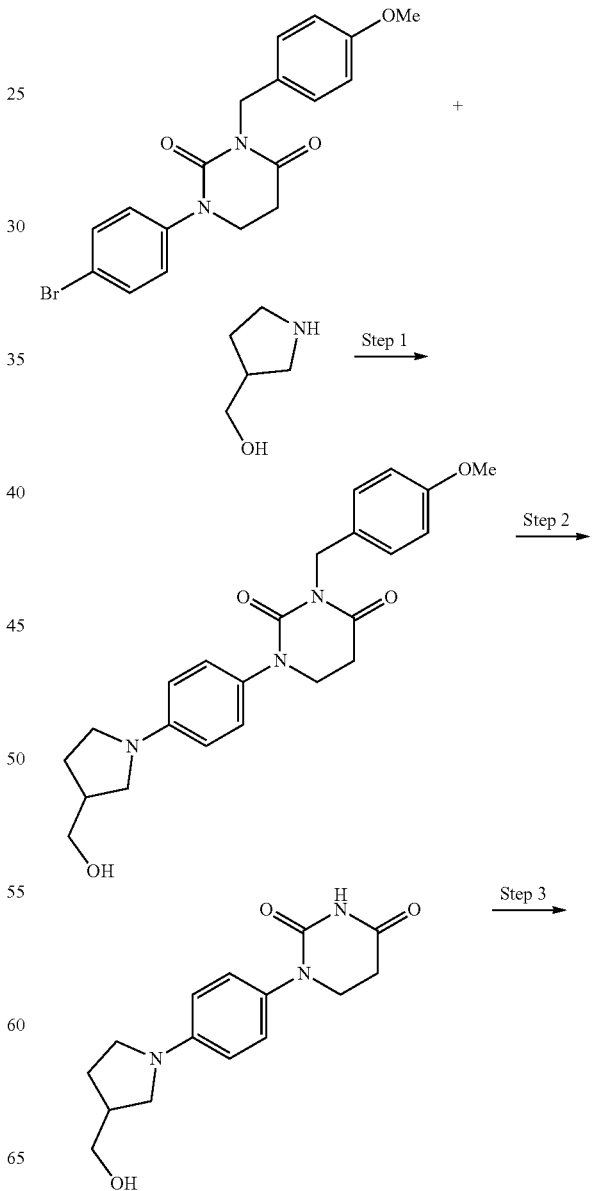

Step 1: To a 4 mL vial was added rac-(3R)-3-(6-fluoropyridin-3-yl)piperidine-2,6-dione (51.5 mg, 0.247 mmol), 2,2-dimethoxy-7-azaspiro[3.5]nonane (48 mg, 0.26 mmol)

-continued

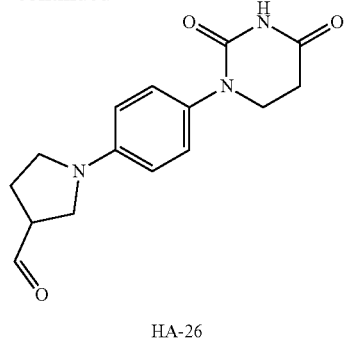

HA-26

Step 1: To a 40 mL vial was added 1-(4-bromophenyl)-3-[(4-methoxyphenyl)methyl]-1,3-diazinane-2,4-dione (500.00 mg, 1.28 mmol), rac-(3R)-pyrrolidin-3-ylmethanol (259.86 mg, 2.57 mmol), caesium carbonate (1.26 g, 3.85 mmol), (acetyloxy)palladio acetate (58 mg, 0.26 mmol), di-tert-butyl({2',4',6'-triisopropyl-[1,1'-biphenyl]-2-yl}) phosphane (0.22 g, 0.51 mmol), and dioxane (5.0 mL). The reaction mixture was stirred at 90° C. overnight. The reaction mixture was diluted with water, and the product was extracted with EtOAc (3×), dried over MgSO$_4$, then concentrated. The resulting residue was purified by FC (24 g silica, 0-100% DCM/EtOAc) to yield 1-(4-(3-(hydroxymethyl)pyrrolidin-1-yl)phenyl)-3-(4-methoxybenzyl)dihydropyrimidine-2,4(1H,3H)-dione as an off-white solid (295 mg, 56%). LCMS: $C_{23}H_{27}N_3O_4$ requires: 409.2, found: m/z=410.3 [M+H]$^+$.

Step 2: To a 40 mL vial was added rac-1-{4-[(3R)-3-(hydroxymethyl)pyrrolidin-1-yl]phenyl}-3-[(4-methoxyphenyl)methyl]-1,3-diazinane-2,4-dione (645.00 mg, 1.58 mmol) and TFA (10.00 mL). To the reaction mixture was added trifluoromethanesulfonic acid (0.70 mL, 1.18 g, 7.88 mmol). The reaction mixture was stirred for 1.5 h, then diluted with water (~5 mL). The resulting mixture was purified by RP-FC (400 g C18 silica, 0-50% MeCN/water+ 0.1% TFA) to yield 1-(4-(3-(hydroxymethyl)pyrrolidin-1-yl)phenyl)dihydropyrimidine-2,4(1H,3H)-dione as a white solid (513 mg, quantitative yield). LCMS: $C_{15}H_{19}N_3O_3$ requires: 289.1, found: m/z=290.2 [M+H]$^+$.

Step 3: To a 40 mL vial was added rac-1-{4-[(3R)-3-(hydroxymethyl)pyrrolidin-1-yl]phenyl}-1,3-diazinane-2,4-dione (456 mg, 1.58 mmol), DCM (7.5 mL) and DMSO (2.5 mL). The reaction mixture was cooled to 0° C., then sulfur trioxide pyridine complex (2.51 g, 16 mmol) was added to the reaction mixture. The reaction mixture was stirred warming to RT for 1 h; full conversion by LCMS. After 2 h, the reaction mixture was concentrated, and the resulting residue was purified by RP-FC (100 g C18 silica, 0-50% MeCN/ water+0.1% TFA) to yield 1-(4-(2,4-dioxotetrahydropyrimidin-1(2H)-yl)phenyl)pyrrolidine-3-carbaldehyde as a light brown solid (245 mg, 54%). LCMS: $C_{15}H_{17}N_3O_3$ requires: 287.1, found: m/z=288.2 [M+H]$^+$.

HA-27: rac-3-(5-((R)-2,6-dioxopiperidin-3-yl)pyridin-2-yl)-3-azabicyclo[3.1.0]hexane-6-OH -continued

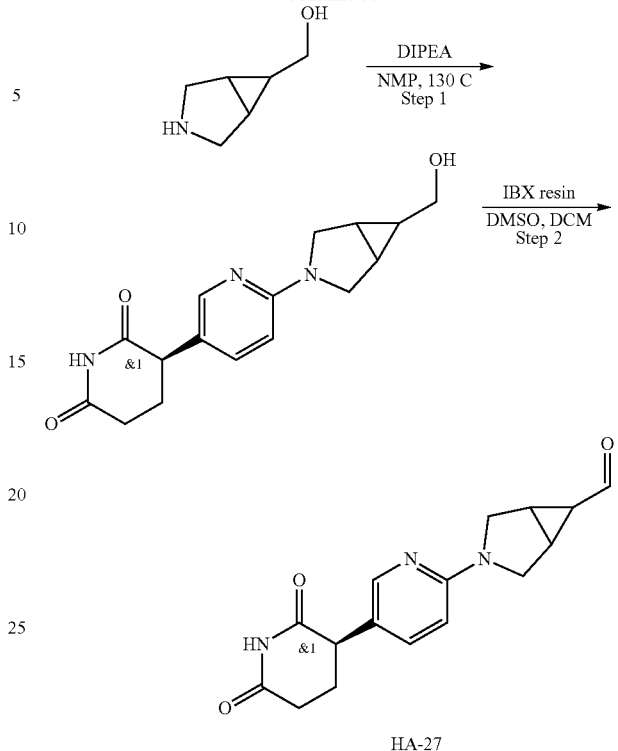

HA-27

Step 1: To a 4 mL vial was added (1R,5S,6R)-3-azabicyclo[3.1.0]hexan-6-ylmethanol (137 mg, 1.22 mmol), rac-(3R)-3-(6-fluoropyridin-3-yl)piperidine-2,6-dione (253 mg, 1.22 mmol), N,N-diisopropylethylamine (425 uL, 0.31 g, 2.4304 mmol), and NMP (1.0 mL). Stirred at 130° C. for 14 h. The excess DIPEA was removed by rotary evaporation. The reaction mixture was cooled to 0° C., acidified with TFA, and purified by reverse phase column chromatography (30 g C18 silica, 0-50% MeCN/H$_2$O+0.1% TFA). Elutes at ~25% MeCN. Product containing fractions were concentrated then lyophilized to yield rac-(3R)-3-(6-(6-(hydroxymethyl)-3-azabicyclo[3.1.0]hexan-3-yl)pyridin-3-yl)piperidine-2,6-dione (80 mg, 0.20 mmol, 17% yield). LCMS: ESI(+)[M+H]$^+$=302.2

Step 2: Dissolved rac-(3R)-3-(6-(6-(hydroxymethyl)-3-azabicyclo[3.1.0]hexan-3-yl)pyridin-3-yl)piperidine-2,6-dione (80 mg, 0.27 mmol) in DCM (4.00 mL) and DMSO (1.30 mL) then added IBX resin and stirred at rt overnight. (IBX resin 1.2 mmol/g loading, 3 eq; 0.80 mmol; 660 mg.) Filtered off the resin and washed with DCM (3×4 mL). Removed the DCM under vacuum and used the DMSO solution in the next step as is. LCMS: ESI(+)[M+H]$^+$=300.2

HA-28: rac-1-{6-[(3R)-2,6-dioxopiperidin-3-yl]pyridin-3-yl}piperidine-4-carbaldehyde

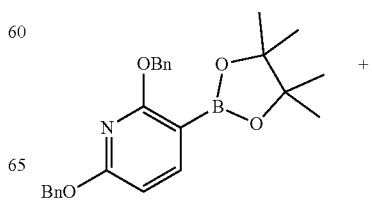

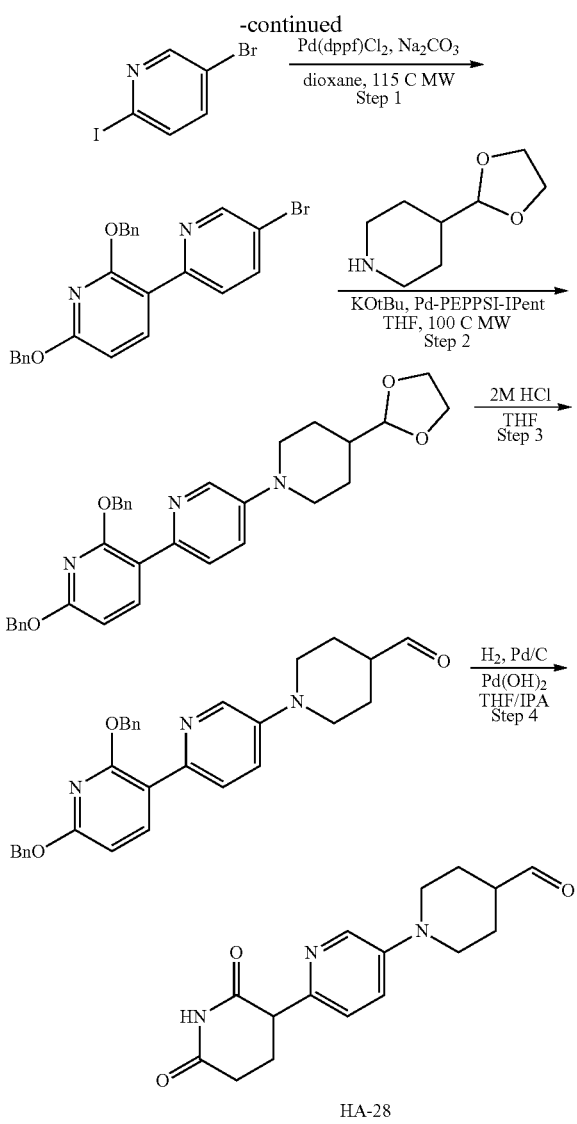

HA-28

Step 1: 5-bromo-2-iodopyridine (250.00 mg, 0.88 mmol) and 2,6-bis(benzyloxy)-3-(4,4,5,5-tetramethyl-1,3,2-dioxaborolan-2-yl)pyridine (367 mg, 0.88 mmol) were combined in 1,4-dioxane (2.50 mL) and 2 M sodium carbonate (1.10 mL, 0.23 g, 2.20 mmol) in a microwave vial. The reaction was degassed with nitrogen and then Pd(dppf)Cl2 (72 mg, 0.09 mmol) was added. The reaction was degassed again, sealed and heated in the microwave for 25 min at 115° C. Added EtOAc and water, filtered through celite, and then separated the layers. Concentrated down the organic layer which was then purified by flash chromatography (12 g silica, 0-100% EtOAc/hexanes, solid loading) to yield 2',6'-bis(benzyloxy)-5-bromo-2,3'-bipyridine (320 mg, 0.72 mmol, 81% yield). LCMS: ESI(+)[M+H]$^+$=447.2

Step 2: 2',6'-bis(benzyloxy)-5-bromo-2,3'-bipyridine (606 mg, 1.35 mmol) and 4-(1,3-dioxolan-2-yl)piperidine (256 mg, 1.63 mmol) were combined in THF (8.50 mL) under nitrogen in a microwave vial. Potassium tert-butoxide (1.63 mL, 0.18 g, 1.6256 mmol) and 1,3-bis[2,6-bis(pentan-3-yl)phenyl]-2H-imidazole; 3-chloropyridine; palladium chloride (Pd-PEPPSI-IPent) (53.76 mg, 0.0677 mmol) were added and the vial was sealed and heated to 100° C. for 15 min in the microwave. The reaction was quenched with sat NH4Cl and extracted with DCM (2×). The material was purified by flash chromatography (4 g silica, 5-100% EtOAc/hexanes; product eluted at 65%). Product containing fraction were combined and concentrated by rotary evaporation to yield 2',6'-bis(benzyloxy)-5-[4-(1,3-dioxolan-2-yl)piperidin-1-yl]-2,3'-bipyridine (0.50 g, 0.95 mmol, 70% yield). LCMS: ESI(+)[M+H]$^+$=524.4

Step 3: Dissolved 2',6'-bis(benzyloxy)-5-[4-(1,3-dioxolan-2-yl)piperidin-1-yl]-2,3'-bipyridine (102 mg, 0.19 mmol) in THF (2.00 mL) and 2M HCl (1.00 mL) at room temp. The reaction was stirred at 50° C. overnight. More THF and HCl were added and the reaction was stirred overnight at 50° C. and then was allowed to sit at rt for 3 days. Partitioned between EtOAc and sat sodium bicarbonate, dried the organic layer with sodium sulfate, filtered and concentrated by rotary evaporation to yield 1-[2',6'-bis(benzyloxy)-[2,3'-bipyridin]-5-yl]piperidine-4-carbaldehyde (90 mg 0.19 mmol, 96% yield). LCMS: ESI(+)[M+H]$^+$=480.3

Step 4: 1-[2',6'-bis(benzyloxy)-[2,3'-bipyridin]-5-yl]piperidine-4-carbaldehyde was stirred under hydrogen in THF (2.00 mL) and IPA (1.00 mL) with 40 mg of Pd/C overnight. Added 20 mg more Pd/C and continued stirring under hydrogen overnight. Filtered and concentrated the reaction mixture then redissolved in 2:1 THF/IPA (6 mL), and stirred under hydrogen with 20 mg Pd/C for 3 hours. Added Pd(OH)2 (20 mg) and stirred for 3 days under hydrogen. Filtered and concentrated the reaction mixture to yield rac-1-{6-[(3R)-2,6-dioxopiperidin-3-yl]pyridin-3-yl}piperidine-4-carbaldehyde (14 mg, 0.047 mmol, 25% yield). LCMS: ESI(+)[M+H]$^+$=302.2

HA-29: (1r,4r)-4-((5-(2,6-dioxopiperidin-3-yl)pyridin-2-yl)oxy)cyclohexane-1-carbaldehyde

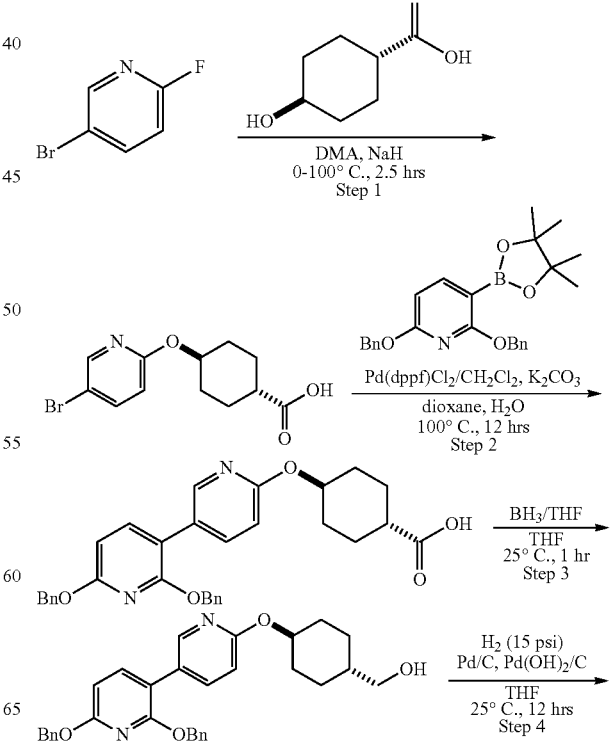

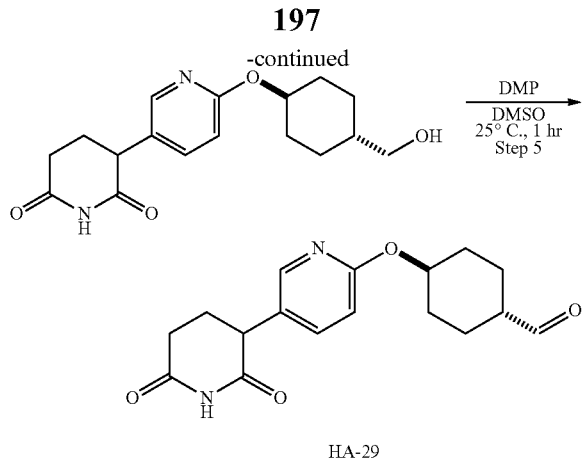

HA-29

Step 1: To a solution of 5-bromo-2-fluoropyridine (20.0 g, 138 mmol, 1.00 eq) in DMA (200 mL) was added NaH (11.1 g, 277 mmol, 60.0% purity, 2.00 eq) at 0° C. under $N_2$, the reaction mixture was stirred at 0° C. for 0.5 hr. Then (1r,4r)-4-hydroxycyclohexane-1-carboxylic acid (24.4 g, 139 mmol, 14.3 mL, 1.00 eq) was added at 0° C. Then reaction mixture was stirred at 100° C. for 2 hrs. The reaction was cooled to 10° C., diluted with $H_2O$ (1.00 L) and added 1N HCl (500 mL) to adjust to pH=3~4, and then the mixture was extracted with ethyl acetate (500 mL*4). The combined organic layers were dried over $Na_2SO_4$, filtered and dried by rotary evaporation. The residue was purified by column chromatography ($SiO_2$, Petroleum ether/ethyl acetate=50/1-25/1-10/1). (1r,4r)-4-((5-bromopyridin-2-yl)oxy)cyclohexane-1-carboxylic acid (10.0 g, 33.3 mmol, 24.0% yield) was obtained as a yellow solid. LCMS: m/z=299.9 (M+H)$^+$. $^1$H NMR: (400 MHz, $CDCl_3$) δ 8.17 (d, J=2.6 Hz, 1H), 7.63 (dd, J=2.6, 8.8 Hz, 1H), 6.61 (d, J=8.8 Hz, 1H), 5.01-4.89 (m, 1H), 2.40 (tt, J=3.6, 11.4 Hz, 1H), 2.25-2.17 (m, 2H), 2.16-2.08 (m, 2H), 1.72-1.62 (m, 2H), 1.54-1.43 (m, 2H).

Step 2: To the solution of (1r,4r)-4-((5-bromopyridin-2-yl)oxy)cyclohexane-1-carboxylic acid (10.0 g, 33.3 mmol, 1.00 eq) in dioxane (100 mL) and $H_2O$ (10.0 mL) was added 2,6-bis(benzyloxy)-3-(4,4,5,5-tetramethyl-1,3,2-dioxaborolan-2-yl)pyridine (15.3 g, 36.7 mmol, 1.10 eq) and $K_2CO_3$ (6.91 g, 49.9 mmol, 1.50 eq), then the solution was purged with $N_2$ three times, and to the solution was added Pd(dppf)$Cl_2$/$CH_2Cl_2$ (2.72 g, 3.33 mmol, 0.100 eq). The solution was stirred at 100° C. for 12 hrs. The reaction mixture was cooled to 25° C. and filtered. The reaction mixture was poured into $H_2O$ (300 mL), then was extracted with ethyl acetate (300 mL*3). The combined organic layer was washed with brine (500 mL*2), dried over $Na_2SO_4$, filtered and concentrated. The residue was purified by column chromatography ($SiO_2$, Petroleum ether/ethyl acetate=25/1-10/1-3/1). (1r,4r)-4-((2',6'-bis(benzyloxy)-[3,3'-bipyridin]-6-yl)oxy)cyclohexane-1-carboxylic acid (14.0 g, 27.4 mmol, 82.3% yield) was obtained as a yellow solid. LCMS: m/z=511.1 (M+H)$^+$. $^1$H NMR: (400 MHz, $CDCl_3$) δ 8.30 (s, 1H), 7.83 (d, J=7.8 Hz, 1H), 7.57 (d, J=8.2 Hz, 1H), 7.44-7.30 (m, 10H), 6.73 (d, J=8.6 Hz, 1H), 6.49 (d, J=8.2 Hz, 1H), 5.43 (s, 2H), 5.37 (s, 2H), 5.13-4.98 (m, 1H), 2.42 (tt, J=3.4, 11.4 Hz, 1H), 2.32-2.22 (m, 2H), 2.14 (d, J=11.0 Hz, 2H), 1.79-1.65 (m, 2H), 1.60-1.47 (m, 2H).

Step 3: To a solution of (1r,4r)-4-((2',6'-bis(benzyloxy)-[3,3'-bipyridin]-6-yl)oxy) cyclohexane-1-carboxylic acid (13.0 g, 25.5 mmol, 1.00 eq) in THF (130 mL) was added $BH_3$/THF (1 M, 76.4 mL, 3.00 eq) at 25° C. under $N_2$, The reaction mixture was stirred at 25° C. for 1 hr. Methanol (250 mL) was slowly dripped into the reaction solution, the reaction mixture was concentrated under vacuum to give ((1r,4r)-4-((2',6'-bis(benzyloxy)-[3,3'-bipyridin]-6-yl)oxy) cyclohexyl)methanol (12.6 g, 25.2 mmol, 99.1% yield, 99.4% purity) as a yellow solid. LCMS: m/z=497.3 (M+H)$^+$. $^1$H NMR: (400 MHz, DMSO d$_6$) δ 8.28 (d, J=2.0 Hz, 1H), 7.85 (dd, J=2.4, 8.6 Hz, 1H), 7.75 (d, J=8.2 Hz, 1H), 7.46-7.29 (m, 10H), 6.76 (d, J=8.6 Hz, 1H), 6.55 (d, J=8.0 Hz, 1H), 5.38 (d, J=12.8 Hz, 4H), 4.98-4.85 (m, 1H), 4.43 (t, J=5.2 Hz, 1H), 3.24 (br t, J=5.8 Hz, 2H), 2.09 (br d, J=9.4 Hz, 2H), 1.80 (br d, J=12.0 Hz, 2H), 1.38-1.30 (m, 2H), 1.09-0.98 (m, 2H).

Step 4: To a solution of ((1r,4r)-4-((2',6'-bis(benzyloxy)-[3,3'-bipyridin]-6-yl)oxy) cyclohexyl)methanol (12.6 g, 25.2 mmol, 99.4% purity, 1.00 eq) in THF (200 mL) was added Pd/C (5.00 g, 25.22 mmol, 10.0% purity, 1.00 eq) and Pd(OH)$_2$/C (5.00 g, 25.2 mmol, 20.0% purity, 1.00 eq) under $N_2$. The suspension was degassed under vacuum and purged with $H_2$ three times. The reaction mixture was stirred under $H_2$ (15 psi) at 25° C. for 12 hrs. The suspension was filtered through a pad of Celite and the pad was washed with THF (50.0 mL*2). The solution was concentrated by rotary evaporation to give 3-(6-(((1r,4r)-4-(hydroxymethyl)cyclohexyl)oxy)pyridin-3-yl)piperidine-2,6-dione (6.50 g, 20.1 mmol, 79.7% yield, 98.4% purity) as a yellow solid. LCMS: m/z=319.2 (M+H)$^+$. $^1$H NMR: (400 MHz, DMSO-d$_6$) δ 10.84 (s, 1H), 7.98 (d, J=2.4 Hz, 1H), 7.54 (dd, J=2.4, 8.6 Hz, 1H), 6.70 (d, J=8.6 Hz, 1H), 4.88 (tt, J=4.2, 10.8 Hz, 1H), 4.42 (t, J=5.4 Hz, 1H), 3.82 (dd, J=4.8, 12.6 Hz, 1H), 3.24 (t, J=5.8 Hz, 2H), 2.75-2.64 (m, 1H), 2.57-2.52 (m, 1H), 2.27-2.16 (m, 1H), 2.08 (br d, J=10.2 Hz, 2H), 2.03-1.94 (m, 1H), 1.83-1.76 (m, 2H), 1.53-1.46 (m, 1H), 1.40-1.35 (m, 2H), 1.10-0.96 (m, 2H).

Step 5: To a solution of 3-(6-(((1r,4r)-4-(hydroxymethyl) cyclohexyl)oxy)pyridin-3-yl)piperidine-2,6-dione (6.50 g, 20.1 mmol, 98.4% purity, 1.00 eq) in DMSO (65.0 mL) was added DMP (17.0 g, 40.2 mmol, 12.4 mL, 2.00 eq) slowly. The reaction was stirred at 25° C. for 1 hr. The mixture was adjusted with saturated aqueous $Na_2CO_3$ until pH=10 and the aqueous layer was extracted with ethyl acetate (100 mL*4). The combined organic layers were washed with $Na_2S_2O_3$ solution (200 mL*2) and brine (250 mL), dried over $Na_2SO_4$, filtered, and concentrated under vacuum to give (1r,4r)-4-((5-(2,6-dioxopiperidin-3-yl)pyridin-2-yl)oxy) cyclohexane-1-carbaldehyde (5.22 g, 16.3 mmol, 79.5% yield, 96.8% purity) as a white solid. LCMS: m/z=317.2 (M+H)$^+$. $^1$H NMR: (400 MHz, DMSO-d$_6$) δ 10.84 (s, 1H), 9.60 (s, 1H), 7.99 (d, J=2.4 Hz, 1H), 7.55 (dd, J=2.4, 8.6 Hz, 1H), 6.73 (d, J=8.6 Hz, 1H), 4.98-4.83 (m, 1H), 3.83 (dd, J=4.8, 12.5 Hz, 1H), 2.76-2.63 (m, 1H), 2.58-2.52 (m, 1H), 2.39-2.29 (m, 1H), 2.22 (dq, J=4.4, 12.8 Hz, 1H), 2.12-2.05 (m, 2H), 2.02-1.95 (m, 3H), 1.50-1.38 (m, 4H).

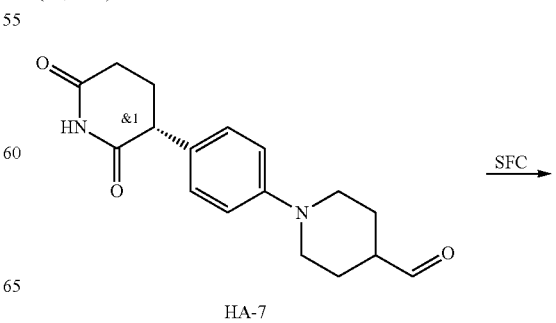

HA-7

-continued

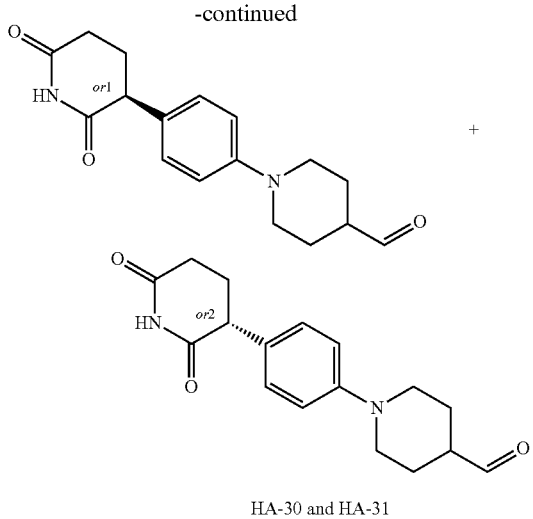

HA-30 and HA-31

(R)-1-(4-(2,6-dioxopiperidin-3-yl)phenyl)piperidine-4-carbaldehyde and (S)-1-(4-(2,6-dioxopiperidin-3-yl)phenyl)piperidine-4-carbaldehyde (HA-30, peak 1 and HA-31, peak 2)

rac-(R)-1-(4-(2,6-dioxopiperidin-3-yl)phenyl)piperidine-4-carbaldehyde (HA-7) was purified by prep-SFC (column: DAICEL CHIRALPAK AD (250 mm*30 mm, 10 um); mobile phase: [Neu-IPA]; B %: 65%-65%, 4.5; 650 mins) to give the first peak HA-30 (13.64 g, 45.41 mmol, 48.7% yield) as yellow solid and crude peak 2, HA-31. The crude peak 2 was purified by prep-SFC (column: DAICEL CHIRALPAK AD (250 mm*30 mm, 10 um); mobile phase: [IPA-ACN]; B %: 65%-65%, 4; 580 mins) to give HA-31 (8.13 g, 27.07 mmol, 29.04% yield) as an off-white solid.

HA-30 (peak 1):
LCMS: m/z=299.1 (M−H)⁻
SFC: ee %=98.3% under 220 nm
$^1$H NMR: 400 MHz, DMSO-d$_6$ δ 10.78 (s, 1H), 9.63 (s, 1H), 7.04 (d, J=8.4 Hz, 2H), 6.90 (d, J=8.8 Hz, 2H), 3.75-3.68 (m, 1H), 3.62-3.52 (m, 2H), 2.86-2.75 (m, 2H), 2.68-2.57 (m, 1H), 2.49-2.40 (m, 2H), 2.18-2.08 (m, 1H), 2.05-1.88 (m, 3H), 1.64-1.51 (m, 2H)

HA-31 (peak 2):
LCMS: m/z=299.1 (M−H)⁻
SFC: ee %=100% under 220 nm
$^1$H NMR: 400 MHz, DMSO-d$_6$ δ 10.75 (s, 1H), 9.63 (s, 1H), 7.07-7.01 (m, 2H), 6.89 (d, J=8.8 Hz, 2H), 3.75-3.68 (m, 1H), 3.61-3.53 (m, 2H), 2.85-2.75 (m, 2H), 2.68-2.58 (m, 1H), 2.49-2.42 (m, 2H), 2.19-2.07 (m, 1H), 2.05-1.87 (m, 3H), 1.64-1.51 (m, 2H)

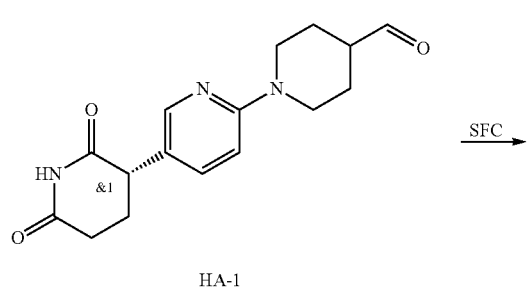

HA-1

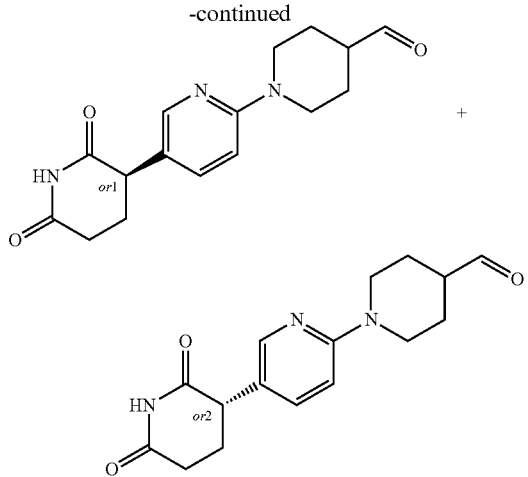

HA-32 (peak 1) and HA-3 (peak 2)

(R)-1-(5-(2,6-dioxopiperidin-3-yl)pyridin-2-yl)piperidine-4-carbaldehyde and (S)-1-(5-(2,6-dioxopiperidin-3-yl)pyridin-2-yl)piperidine-4-carbaldehyde (HA-32, peak1 and HA-33, peak 2)

rac-(R)-1-(5-(2,6-dioxopiperidin-3-yl)pyridin-2-yl)piperidine-4-carbaldehyde (HA-1) was purified by SFC (column: REGIS (s,s) WHELK-O1 (250 mm*50 mm, 10 um); mobile phase: [IPA-ACN];B %: 60%-60%,B2.7; 300 min) and concentrated under vacuum to give a residue. The residue was triturated with ethyl acetate (60.0 mL) at 20° C. for 2 hrs, filtered and the filter cake was concentrated under vacuum to give the first peak, HA-32 (17.79 g, 58.3 mmol, 40.5% yield) and second peak, HA-33 (16.05 g, 52.6 mmol, 36.5% yield) as white solids.

HA-32 (peak 1):
LCMS: m/z=320.0 (M+19)⁺
$^1$H NMR: 400 MHz, DMSO-d6 δ 10.79 (s, 1H), 9.61 (s, 1H), 7.94 (d, J=2.4 Hz, 1H), 7.38 (dd, J=2.4, 8.8 Hz, 1H), 6.82 (d, J=8.8 Hz, 1H), 4.13-4.08 (m, 2H), 3.73-3.70 (m, 1H), 3.04-2.97 (m, 2H), 2.67-2.53 (m, 3H), 2.22-2.12 (m, 1H). 2.00-1.93 (m, 1H).1.90-1.85 (m, 2H). 1.49-1.45 (m, 2H).
SFC: 100% ee under 220 nm.

HA-33 (peak 2):
LCMS: m/z=320.0 (M+19)⁺
$^1$H NMR: EC5149-12-P2B2, 400 MHz, DMSO-d$_6$e 10.79 (s, 1H), 9.61 (s, 1H), 7.94 (d, J=2.4 Hz, 1H), 7.38 (dd, J=2.4, 8.8 Hz, 1H), 6.82 (d, J=8.8 Hz, 1H), 4.13-4.09 (m, 2H), 3.74-3.70 (m, 1H), 3.04-2.97 (m, 2H), 2.67-2.53 (m, 3H), 2.22-2.12 (m, 1H). 2.00-1.93 (m, 1H). 1.90-1.85 (m, 2H). 1.49-1.46 (m, 2H).
SFC: 100% ee under 220 nm.

C. General Schemes for Coupling the IRAK4 Binder and LHM Building Blocks

The L moiety typically has up to four linker segments (—L$_1$—L$_2$—L$_3$—L$_4$—), one of which is formed by coupling a suitable IRAK4 building block or Intermediate (A-AY) and a suitable LHM block or HA (HA-1 through HA-33) described herein via a bond formation (e.g., amide). The following General Methods A-D illustrate the bond formations by which the building blocks may be coupled to afford the compounds of Formula (I).

General Method A (Amide coupling):

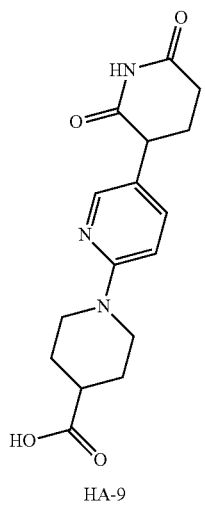

HA-9

+

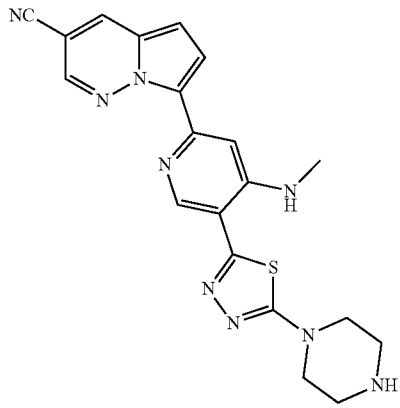

Intermediate C

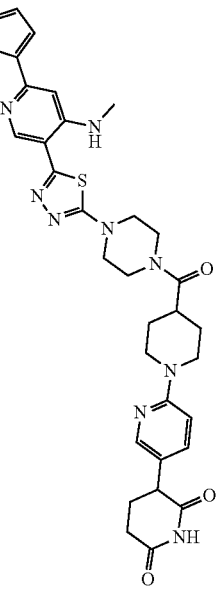

Example 51

Synthesis of 7-{5-[5-(4-{1-[5-(2,6-dioxopiperidin-3-yl)pyridin-2-yl]piperidine-4-carbonyl}piperazin-1-yl)-1,3,4-thiadiazol-2-yl]-4-(methylamino)pyridin-2-yl}pyrrolo[1,2-b]pyridazine-3-carbonitrile (Example 51)

HATU (22 mg, 1.15 eq) and 1-[5-(2,6-dioxopiperidin-3-yl)pyridin-2-yl]piperidine-4-carboxylic acid (HA-9) (16 mg, 0.05 mmol) were dissolved in DMF (0.15 M) and diisopropylethylamine (0.03 g, 5 eq). The reaction was stirred at room temperature for 10 minutes before addition of 7-[4-(methylamino)-5-[5-(piperazin-1-yl)-1,3,4-thiadiazol-2-yl]pyridin-2-yl]pyrrolo[1,2-b]pyridazine-3-carbonitrile (Intermediate C) (21 mg, 1.0 eq). The reaction was then stirred for 16 h, followed by filtration by syringe filter, and purification by HPLC to provide the title compound (12 mg, 33%).

General Method B (Reductive Amination):

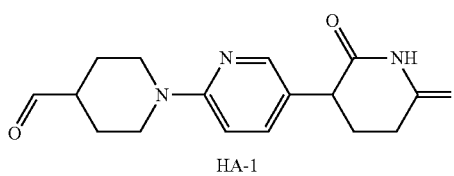

HA-1

+

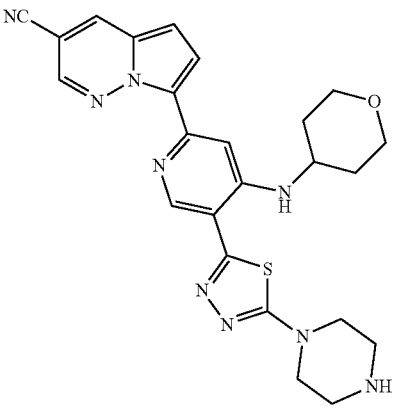

Intermediate A

-continued

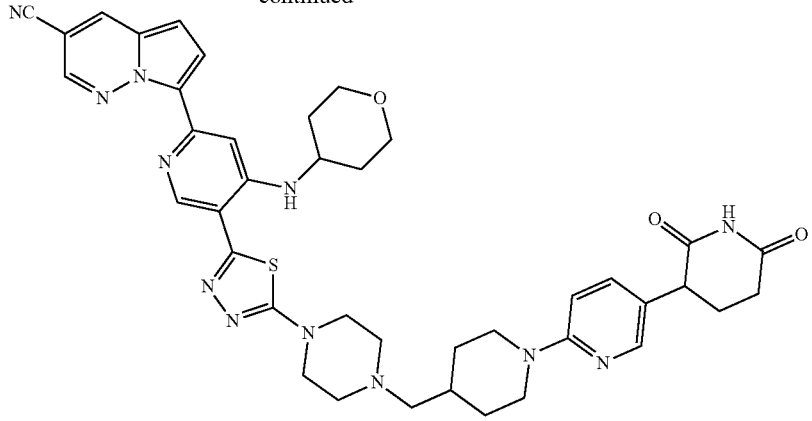

Example 43

Synthesis of 7-(5-{5-[4-({1-[5-(2,6-dioxopiperidin-3-yl)pyridin-2-yl]piperidin-4-yl}methyl)piperazin-1-yl]-1,3,4-thiadiazol-2-yl}-4-(oxan-4-ylamino)pyridin-2-yl)pyrrolo[1,2-b]pyridazine-3-carbonitrile (Example 43)

1-[5-(2,6-dioxopiperidin-3-yl)pyridin-2-yl]piperidine-4-carbaldehyde (HA-1) (20 mg, 0.07 mmol) and 7-[4-(oxan-4-ylamino)-5-[5-(piperazin-1-yl)-1,3,4-thiadiazol-2-yl]pyridin-2-yl]pyrrolo[1,2-b]pyridazine-3-carbonitrile (Intermediate A) (32 mg, 1 eq) were combined in a vial and dissolved in dichloroethane (0.03M) or another appropriate solvent such as DCM, DMF, DMSO, etc) and then triethylamine was added (0.09 mL, 10 eq) or another appropriate base such as DIPEA, NMM, etc. The reaction was stirred for 20 minutes before addition of sodium triacetoxyborohydride (35 mg, 2.5 eq). The reaction was stirred for 1 to 16 hrs, followed by concentration onto silica gel and chromatography (reverse phase C18 column, 0-100% acetonitrile in water with 0.1% TFA additive). Alternate purification method uses normal phase flash chromatography with methanol/DCM mobile phase or similar solvent system.

General Method C (parallel reductive amination in 96 deepwell plate):

To a 200 µL of a 0.2 M solution of 0.2 M solution of a suitable HA in anhydrous DMSO (0.04 mmol) were added 200 µL of a 0.2 M anhydrous DMSO solution of a suitable Intermediate in DMSO (1 eq), followed by the addition of diisopropylethylamine (10 eq)

The reaction plate was shaken at room temperature for 10 minutes and the reaction mixture transferred over to new plate containing borohydride (polymer-supported 2.5 mmol/g, 3 eq).

After reaction at room temperature for 14 hours, 300 µL of DMSO solution were transferred to a collection plate. After addition of 300 µL of DMSO the source plate was shaken for 5 minutes and 300 µL of solution were transferred into the collection plate. The operation was repeated twice after which the combined fractions were purified by preparative liquid chromatography to afford the expected compounds in yield ranging from 5% to 40%.

General Method D (parallel amide coupling in 96 deepwell plate)

450 µL of a 0.2M solution of a suitable HA in DMF (0.09 mmoles) were transferred into a 2 mL 96 Deepwell plate, followed by the addition of 150 µL of 1/1 Vol DMF/DIEA solution (4eq) and 270 µL of a 0.4 M solution of HATU in DMF (1.2 eq). After 15 minutes at room temperature, 450 µL of 0.2 M of a suitable Intermediate in DMF (1eq) was added to the reaction mixture.

The reaction was carried on for 2H at room temperature followed by purification by preparative liquid chromatography using a 5% to 90% ACN/Water gradient to afford desired product in yield ranging from 5% to 40%.

Definitions

The following description sets forth exemplary methods, parameters and the like. It should be recognized, however, that such description is not intended as a limitation on the scope of the present disclosure but is instead provided as a description of exemplary embodiments.

A dash ("-") that is not between two letters or symbols is used to indicate a point of attachment for a substituent. For example, —C(O)NH$_2$ is attached through the carbon atom. A dash at the front or end of a chemical group is a matter of convenience; chemical groups may be depicted with or without one or more dashes without losing their ordinary meaning. A wavy line drawn through a line in a structure indicates a point of attachment of a group. Unless chemically or structurally required, no directionality is indicated or implied by the order in which a chemical group is written or named.

The prefix "$C_{u-v}$" indicates that the following group has from u to v carbon atoms. For example, "$C_{1-6}$ alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount±10%. In other embodiments, the term "about" includes the indicated amount ±5%. In certain other embodiments, the term "about" includes the indicated amount ±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain containing no unsaturation. As used herein, alkyl has 1 to 20 carbon atoms (i.e., $C_{1-20}$ alkyl), 1 to 12 carbon atoms (i.e., $C_{1-12}$ alkyl), 1 to 8 carbon atoms (i.e., $C_{1-8}$ alkyl), 1 to 6 carbon atoms (i.e., $C_{1-6}$ alkyl), or 1 to 4 carbon atoms (i.e., $C_{1-4}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e., —$(CH_2)_3CH_3$), sec-butyl (i.e., —$CH(CH_3)CH_2CH_3$), isobutyl (i.e., —$CH_2CH(CH_3)_2$) and tert-butyl (i.e., —$C(CH_3)_3$); and "propyl" includes n-propyl (i.e., —$(CH_2)_2CH_3$) and isopropyl (i.e., —$CH(CH_3)_2$).

"Alkylene" or "alkylene chain" refers to an unbranched or branched divalent hydrocarbon chain, linking the rest of the molecule to a radical group, containing no unsaturation and having from 1 to 20 carbon atoms, or more typically 1 to 12 carbon atoms, or 1 to 8 carbon atoms, e.g., methylene, ethylene, propylene, n-butylene, and the like. The alkylene chain may be attached to the rest of the molecule and to the radical group through one carbon within the chain or through any two carbons within the chain.

"Alkenyl" refers to an alkyl group containing at least one carbon-carbon double bond and having from 2 to 20 carbon atoms (i.e., $C_{2-20}$ alkenyl), or more typically 2 to 12 carbon atoms (i.e., $C_{2-12}$ alkenyl), 2 to 8 carbon atoms (i.e., $C_{2-8}$ alkenyl), 2 to 6 carbon atoms (i.e., $C_{2-6}$ alkenyl), or 2 to 4 carbon atoms (i.e., $C_{2-4}$ alkenyl). Examples of alkenyl groups include ethenyl, propenyl, butadienyl (including 1,2-butadienyl and 1,3-butadienyl).

"Alkenylene" and "alkenylene chain" refer to an unbranched or branched divalent hydrocarbon chain linking the rest of the molecule to a radical group, containing at least one double bond and having from 2 to 20 carbon atoms, or more typically 2 to 12 carbon atoms, or 2 to 8 carbon atoms, e.g., ethenylene, propenylene, n-butenylene, and the like. The alkenylene chain is attached to the rest of the molecule through a single bond and to the radical group through a double bond or a single bond. The points of attachment of the alkenylene chain to the rest of the molecule and to the radical group can be through one carbon or any two carbons within the chain.

"Alkynyl" refers to an alkyl group containing at least one carbon-carbon triple bond and having from 2 to 20 carbon atoms (i.e., $C_{2-20}$ alkynyl), or more typically 2 to 12 carbon atoms (i.e., $C_{2-12}$ alkynyl), or more typically 2 to 8 carbon atoms (i.e., $C_{2-8}$ alkynyl), 2 to 6 carbon atoms (i.e., $C_{2-6}$ alkynyl), or 2 to 4 carbon atoms (i.e., $C_{2-4}$ alkynyl). The term "alkynyl" also includes those groups having one triple bond and one double bond.

"Alkynylene" and "alkynylene chain" refer to a unbranched or branched divalent hydrocarbon chain linking the rest of the molecule to a radical group, containing at least one triple bond and having from 2 to 20 carbon atoms, or more typically 2 to 12 carbon atoms, or 2 to 8 carbon atoms. The alkynylene chain is attached to the rest of the molecule through a single bond and to the radical group through a double bond or a single bond. The points of attachment of the alkynylene chain to the rest of the molecule and to the radical group can be through one carbon or any two carbons within the chain.

"Alkoxy" refers to the group "alkyl-O—". Examples of alkoxy groups include methoxy, ethoxy, n-propoxy, iso-propoxy, n-butoxy, tert-butoxy, sec-butoxy, n-pentoxy, n-hexoxy, and 1,2-dimethylbutoxy.

"Haloalkoxy" refers to an alkoxy group as defined above, wherein one or more hydrogen atoms are replaced by a halogen.

"Alkylthio" refers to the group "alkyl-S—".

"Amino" refers to the group —$NR^YR^Y$ wherein each $R^y$ is independently selected from the group consisting of hydrogen, alkyl, alkenyl, alkynyl, aryl, heterocyclyl, cycloalkyl or heteroaryl, each of which is optionally substituted, as defined herein.

"Aryl" refers to an aromatic carbocyclic group having a single ring (e.g., monocyclic) or multiple rings (e.g., bicyclic or tricyclic) including fused systems. As used herein, aryl has 6 to 20 ring carbon atoms (i.e., $C_{6-20}$ aryl), 6 to 15 carbon ring atoms (i.e., $C_{6-15}$ aryl), or 6 to 10 carbon ring atoms (i.e., $C_{6-10}$ aryl). Examples of aryl groups include phenyl, naphthyl, fluorenyl, and anthryl. Aryl, however, does not encompass or overlap in any way with heteroaryl defined below. If one or more aryl groups are fused with a heteroaryl, the resulting ring system is heteroaryl. If one or more aryl groups are fused with a heterocyclyl, the resulting ring system is heterocyclyl.

"Cyano" refers to the group —CN.

"Keto" or "oxo" refers to a group=O.

"Carbamoyl" refers to both an "O-carbamoyl" group which refers to the group —O—C(O)$NR^YR^Z$ and an "N-carbamoyl" group which refers to the group —$NR^YC(O)OR^Z$, wherein $R^y$ and $R^Z$ are independently selected from the group consisting of hydrogen, alkyl, aryl, haloalkyl, or heteroaryl; each of which may be optionally substituted.

"Carboxyl" or "carboxylic acid" refers to —C(O)OH.

"Ester" refers to both —OC(O)R and —C(O)OR, wherein R is a substituent; each of which may be optionally substituted, as defined herein.

"Cycloalkyl" refers to a saturated or partially unsaturated cyclic alkyl group having a single ring or multiple rings including fused, bridged, and spiro ring systems. The term "cycloalkyl" includes cycloalkenyl groups (i.e., the cyclic group having at least one double bond). As used herein, cycloalkyl has from 3 to 15 ring carbon atoms (i.e., $C_{3-20}$ cycloalkyl), 4 to 12 ring carbon atoms (i.e., $C_{4-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Examples of cycloalkyl groups include cyclopropyl, cyclobutyl, cyclopentyl, cyclohexyl, and bicyclo[2.2.2]octan-1-yl. Cycloalkyl may be attached to the remainder of a molecule by a single ring atom (e.g., as a substituent) or by two ring atoms (e.g., as a linker).

"Ethylene glycol unit" refers to a bivalent monomer having the structure of —$CH_2CH_2O$—, which may be repeated and extended into a longer chain. A linker segment may have up to 12 ethylene glycol units, or more typically up to 6 ethylene glycol units.

"Propylene glycol unit" refers to a bivalent monomer having the structure of —$CH(CH_3)$—$CH_2O$—, which may be repeated and extended into a longer chain. A linker segment may have up to 12 propylene glycol units, or more typically up to 6 propylene glycol units.

"Halogen" or "halo" includes fluoro, chloro, bromo, and iodo.

"Haloalkyl" refers to an unbranched or branched alkyl group as defined above, wherein one or more hydrogen atoms are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include difluoromethyl (—CHF$_2$) and trifluoromethyl (—CF$_3$).

"Heteroalkyl" refers to an alkyl group in which one or more of the carbon atoms (and any associated hydrogen atoms) are each independently replaced with the same or different heteroatoms such as N, O, S, and the likes. The term "heteroalkyl" includes unbranched or branched saturated chain having carbon and heteroatoms. By way of example, 1, 2 or 3 carbon atoms may be independently replaced with the same or different heteroatoms. Heteroatomic groups include, but are not limited to, —N(R)—, —O—, —S—, —S(O)—, —S(O)$_2$—, and the like, where R is H, alkyl, aryl, cycloalkyl, heteroalkyl, heteroaryl or heterocyclyl, each of which may be optionally substituted. Examples of heteroalkyl groups include —OCH$_3$, —CH$_2$OCH$_3$, —SCH$_3$, —CH$_2$SCH$_3$, —NRCH$_3$, and —CH$_2$NRCH$_3$, where R is hydrogen, alkyl, aryl, arylalkyl, heteroalkyl, or heteroaryl, each of which may be optionally substituted. As used herein, heteroalkyl include 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to a 5-15 membered, or more typically, 5-12 membered aromatic group having a single ring, multiple rings, or multiple fused rings, with 1-3 ring heteroatoms independently selected from nitrogen, oxygen, and sulfur. As used herein, heteroaryl includes 1 to 12 ring carbon atoms, or 3 to 8 carbon ring atoms; and 1 to 5 heteroatoms, 1 to 4 heteroatoms, 1 to 3 ring heteroatoms, 1 to 2 ring heteroatoms, or 1 ring heteroatom independently selected from nitrogen, oxygen, and sulfur. Examples of heteroaryl groups include pyrimidinyl, purinyl, pyridyl, pyridazinyl, benzothiazolyl, and pyrazolyl. Examples of the fused-heteroaryl rings include, but are not limited to, benzo[d]thiazolyl, quinolinyl, isoquinolinyl, benzo[b]thiophenyl, indazolyl, benzo[d]imidazolyl, pyrazolo[1,5-a]pyridinyl, and imidazo[1,5-a]pyridinyl, where the heteroaryl can be bound via either ring of the fused system. Any aromatic ring, having a single or multiple fused rings, containing at least one heteroatom, is considered a heteroaryl regardless of the attachment to the remainder of the molecule (i.e., through any one of the fused rings). Heteroaryl does not encompass or overlap with aryl as defined above. Heteroaryl may be attached to the remainder of a molecule by a single ring atom (e.g., as a substituent) or by two ring atoms (e.g., as a linker).

"Heterocyclyl" refers to a 3-15 membered, or more typically, 5-12 membered, saturated or unsaturated cyclic alkyl group, with 1-3 ring heteroatoms independently selected from nitrogen, oxygen and sulfur. The term "heterocyclyl" includes heterocycloalkenyl groups (i.e., the heterocyclyl group having at least one double bond), bicyclic heterocyclyl groups, bridged-heterocyclyl groups, fused-heterocyclyl groups, and spiro-heterocyclyl groups. A heterocyclyl may be a single ring or multiple rings wherein the multiple rings may be fused, bridged, or spiro. Any non-aromatic ring containing at least one heteroatom is considered a heterocyclyl, regardless of the attachment (i.e., can be bound through a carbon atom or a heteroatom). Further, the term heterocyclyl is intended to encompass any non-aromatic ring containing at least one heteroatom, which ring may be fused to an aryl or heteroaryl ring, regardless of the attachment to the remainder of the molecule. As used herein, heterocyclyl has 3 to 15 ring atoms (e.g., 3-15 membered heterocyclyl, 4-12 membered heterocyclyl, 4 to 10 membered heterocyclyl, 4-8 membered heterocyclyl or 4-6 membered heterocyclyl; having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. A heterocyclyl may contain one or more oxo and/or thioxo groups.

Examples of heterocyclyl groups include pyrrolidinyl, piperidinyl, piperazinyl, oxetanyl, dioxolanyl, azetidinyl, azetidinyl, morpholinyl, thiomorpholinyl, 4-7 membered sultam, 4-7 membered cyclic carbamate, 4-7 membered cyclic carbonate, 4-7 membered cyclic sulfide and morpholinyl. As used herein, heterocyclyl may include a bridged structure (i.e., "bridged heterocyclyl"), in which a four-to ten-membered cyclic moiety connected at two non-adjacent atoms of the heterocyclyl with one or more (e.g., 1 or 2) four- to ten-membered cyclic moiety having at least one heteroatom where each heteroatom is independently selected from nitrogen, oxygen, and sulfur. As used herein, bridged-heterocyclyl includes bicyclic and tricyclic ring systems. Also used herein, the term "spiro-heterocyclyl" refers to a ring system in which a three- to ten-membered heterocyclyl has one or more additional ring, wherein the one or more additional ring is three- to ten-membered cycloalkyl or three- to ten-membered heterocyclyl, where a single atom of the one or more additional ring is also an atom of the three- to ten-membered heterocyclyl. Examples of the spiro-heterocyclyl rings include bicyclic and tricyclic ring systems, such as 2-oxa-7-azaspiro[3.5]nonanyl, 2-oxa-6-azaspiro[3.4]octanyl, and 6-oxa-1-azaspiro[3.3]heptanyl. Examples of the fused-heterocyclyl rings include, but are not limited to, 1,2,3,4-tetrahydroisoquinolinyl, 1-oxo-1,2,3,4-tetrahydroisoquinolinyl, 1-oxo-1,2-dihydroisoquinolinyl, 4,5,6,7-tetrahydrothieno[2,3-c]pyridinyl, indolinyl, 2,3-dihydro-1H-isoindolyl, and isoindolinyl, where the heterocyclyl can be bound via either ring of the fused system. Examples of bridged heterocyclyl include, without limitation, 3,8-diazabicyclo[3.2.1]octan-3-yl, 3,9-diazabicyclo[3.3.1]nonan-3-yl, 3-oxa-7,9-diazabicyclo[3.3.1]nonan-7-yl. As used herein, a bicyclic heterocyclyl group is a heterocyclyl group attached at two points to another cyclic group, wherein the other cyclic group may itself be a heterocyclic group, or a carbocyclic group. Heterocyclyl may be attached to the remainder of a molecule by a single ring atom (e.g., as a substituent) or by two ring atoms (e.g., as a linker), the ring atom being carbon or heteroatom.

"Fused" refers to a ring which is joint to an adjacent ring and share two adjacent ring atoms that form a covalent bond.

"Bridged" refers to a ring fusion wherein non-adjacent atoms on a ring are joined by a divalent substituent, such as alkylenyl group, an alkylenyl group containing one or two heteroatoms, or a single heteroatom. Quinuclidinyl and admantanyl are examples of bridged ring systems.

"Spiro" refers to a ring substituent which is joined by two bonds at the same carbon atom. Examples of spiro groups include 1,1-diethylcyclopentane, dimethyl-dioxolane, and 4-benzyl-4-methylpiperidine, wherein the cyclopentane and piperidine, respectively, are the spiro substituents.

"Hydroxy" or "hydroxyl" refers to the group —OH. "Hydroxyalkyl" refers to an unbranched or branched alkyl group as defined above, wherein one or more hydrogen atoms are replaced by a hydroxyl.

"Nitro" refers to the group —NO$_2$.

"Imino" refers to a group that contains a C=N double bond, such as C=N—R$^y$, or =N—C(O)R$^y$, wherein R$^y$ is selected from the group consisting of hydrogen, alkyl, aryl, cyano, haloalkyl, or heteroaryl; each of which may be optionally substituted. Imino may be a linker segment by attaching to the remainder molecule at the carbon and nitrogen respectively.

"Sulfoximine" or "sulfoximino" refers to a substituted or unsubstituted moiety of the general formula

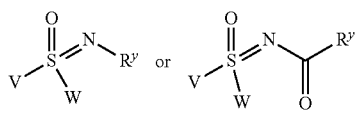

wherein $R^y$ is selected from the group consisting of hydrogen, alkyl, amino, aryl, cyano, haloalkyl, heterocyclyl, or heteroaryl; V and W are each independently selected from a bond, alkyl, amino, aryl, haloalkyl, heterocyclyl or heteroaryl; each of which may be optionally substituted and wherein $R^y$ and V, $R^y$ and W, and V and W together with the atoms to which they are attached may be joined together to form a ring.. Sulfoximine may be a linker segment by attaching to the remainder molecule at the sulfur and nitrogen respectively.

"Sulfonyl" refers to the group —$S(O)_2R$, where R is a substituent, or a defined group.

"Alkylsulfonyl" refers to the group —$S(O)_2R$, where R is a substituent, or a defined group.

"Alkylsulfinyl" refers to the group —$S(O)R$, where R is a substituent, or a defined group.

"Thiocyanate"—SCN.

"Thiol" refers to the group —SR, where R is a substituent, or a defined group.

"Thioxo" or "thione" refer to the group (=S) or (S).

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless indicated explicitly otherwise, where combinations of groups are referred to herein as one moiety, e.g., arylalkyl, the last mentioned group contains the atom by which the moiety is attached to the rest of the molecule.

The terms "optional" or "optionally" means that the subsequently described event or circumstance may or may not occur, and that the description includes instances where said event or circumstance occurs and instances in which it does not. Also, the term "optionally substituted" refers to any one or more hydrogen atoms on the designated atom or group may or may not be replaced by a moiety other than hydrogen. "Optionally substituted" may be zero to the maximum number of possible substitutions, and each occurrence is independent. When the term "substituted" is used, then that substitution is required to be made at a substitutable hydrogen atom of the indicated substituent. An optional substitution may be the same or different from a (required) substitution.

When a moiety is "optionally substituted," and reference is made to a general term, such as any "alkyl," "alkenyl," "alkynyl," "haloalkyl," "cycloalkyl," "aryl" or "heteroaryl," then the general term can refer to any antecedent specifically recited term, such as ($C_{1-3}$ alkyl), ($C_{4-6}$ alkyl), —$O(C_{1-4}$ alkyl), ($C_{3-10}$ cycloalkyl), O—($C_{3-10}$ cycloalkyl) and the like. For example, "any aryl" includes both "aryl" and "—O(aryl) as well as examples of aryl, such as phenyl or naphthyl and the like. Also, the term "any heterocyclyl" includes both the terms "heterocyclyl" and O-(heterocyclyl)," as well as examples of heterocyclyls, such as oxetanyl, tetrahydropyranyl (oxanyl), morpholino, piperidinyl and the like. In the same manner, the term "any heteroaryl" includes the terms "heteroaryl" and "O-(heteroryl)," as well as specific heteroaryls, such as pyridine and the like.

Some compounds of Formula (I) may exist as a "stereoisomer" or a mixture of stereoisomers. Stereoisomer refers to a compound made up of the same atoms bonded by the same bonds but having different three-dimensional structures, which are not interchangeable. The compounds of the disclosure, or their pharmaceutically acceptable salts may contain one or more asymmetric centers and may thus give rise to enantiomers (two stereoisomers whose molecules are non-superimposable mirror images of one another), diastereomers, and other stereoisomeric forms that may be defined, in terms of absolute stereochemistry, as (R)— or (S)—. The present disclosure is meant to include all such possible isomers, as well as their racemic mixture (i.e., equal amounts of (R) and (S) enantiomers) and optically pure forms. Optically active (+) and (−), (R)— and (S)— isomers may be prepared using chiral synthons or chiral reagents, or resolved using conventional techniques, such as HPLC using a chiral column.

In preferred embodiments, the compound of Formula (I) is a racemic mixture of two entiomers. It is possible, though not necessary, to separate the racemates into the two pure enantiomers by standard methods, e.g. by chemical resolution using optically active acid or base or by chromatography on chiral adsorbents, e.g. high-pressure liquid chromatography on acetyl cellulose. In some embodiments, one enatiomer is biologically far less active (the distomer), whereas the other enantiomer is highly bioactive (the eutomer).

The disclosure also includes "deuterated analogues" of compounds of Formula I in which from 1 to n hydrogens attached to a carbon atom is/are replaced by deuterium, in which n is the number of hydrogens in the molecule. Such compounds exhibit increased resistance to metabolism and are thus useful for increasing the half-life of any compound of Formula I when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F labeled compound may be useful for PET or SPECT studies. Isotopically labeled compounds of this disclosure can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of Formula I.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

In many cases, the compounds of this disclosure are capable of forming acid and/or base salts by virtue of the presence of amino and/or carboxyl groups or groups similar thereto.

Provided are also pharmaceutically acceptable salts, hydrates, or solvates of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The term "pharmaceutically acceptable salt" of a given compound refers to salts that retain the biological effectiveness and properties of the given compound, and which are not biologically or otherwise undesirable. "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts. Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. Likewise, pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines (i.e., $NH_2$(alkyl)), dialkyl amines (i.e., HN(alkyl)$_2$), trialkyl amines (i.e., N(alkyl)$_3$), substituted alkyl amines (i.e., $NH_2$(substituted alkyl)), di(substituted alkyl) amines (i.e., HN(substituted alkyl)$_2$), tri (substituted alkyl) amines (i.e., N(substituted alkyl)$_3$), alkenyl amines (i.e., $NH_2$(alkenyl)), dialkenyl amines (i.e., HN(alkenyl)$_2$), trialkenyl amines (i.e., N(alkenyl)$_3$), substituted alkenyl amines (i.e., $NH_2$(substituted alkenyl)), di(substituted alkenyl) amines (i.e., HN(substituted alkenyl)$_2$), tri(substituted alkenyl) amines (i.e., N(substituted alkenyl)$_3$, mono-, di- or tri- cycloalkyl amines (i.e., $NH_2$(cycloalkyl), HN(cycloalkyl)$_2$, N(cycloalkyl)$_3$), mono-, di- or tri- arylamines (i.e., $NH_2$(aryl), HN(aryl)$_2$, N(aryl)$_3$), or mixed amines, etc. Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine, and the like.

The term "substituted" means that any one or more hydrogen atoms on the designated atom or group is replaced with one or more substituents other than hydrogen, provided that the designated atom's normal valence is not exceeded. The one or more substituents include, but are not limited to, alkyl, alkenyl, alkynyl, alkoxy, acyl, amino, amido, amidino, aryl, azido, carbamoyl, carboxyl, carboxyl ester, cyano, guanidino, halo, haloalkyl, haloalkoxy, heteroalkyl, heteroaryl, heterocyclyl, hydroxy, hydrazino, imino, oxo, nitro, alkylsulfinyl, sulfonic acid, alkylsulfonyl, thiocyanate, thiol, thione, or combinations thereof. Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl)substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. Unless specified otherwise, where a group is described as optionally substituted, any substituents of the group are themselves unsubstituted. For example, in some embodiments, the term "substituted alkyl" refers to an alkyl group having one or more substituents including hydroxyl, halo, alkoxy, cycloalkyl, heterocyclyl, aryl, and heteroaryl. In other embodiments, the one or more substituents may be further substituted with halo, alkyl, haloalkyl, hydroxyl, alkoxy, cycloalkyl, heterocyclyl, aryl, or heteroaryl, each of which is substituted. In other embodiments, the substituents may be further substituted with halo, alkyl, haloalkyl, alkoxy, hydroxyl, cycloalkyl, heterocyclyl, aryl, or heteroaryl, each of which is unsubstituted. One skilled in the art will recognize that substituents and other moieties of the compounds of the generic formula herein should be selected in order to provide a compound which is sufficiently stable to provide a pharmaceutically useful compound which can be formulated into an acceptably stable pharmaceutical composition. Compounds which have such stability are contemplated as falling within the scope of the present invention. It should be understood by one skilled in the art that any combination of the definitions and substituents described above should not result in an inoperable species or compound.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

A "solvate" is formed by the interaction of a solvent and a compound. Solvates of salts of the compounds described herein are also provided. Hydrates of the compounds described herein are also provided.

Pharmaceutical Composition and Use of the Bifunctional Compounds of Formula (I)

The bifunctional compounds of Formula (I) are demonstrated to degrade IRAK4 and are therefore useful for treating disease indications or disorders involving the function of IRAK4, such as signaling or scaffolding.

Various embodiments provide pharmaceutical compositions of a compound of Formula (I), or any one of the substructures or compounds of Examples 1-147, and a pharmaceutically acceptable carrier.

Further embodiments provide methods for treating cancer, inflammatory disorders, autoimmune disorders or metabolic disorders, comprising administering to a subject in need thereof a therapeutically effective amount of a compound of Formula (I), or any one of the substructures or compounds of Examples 1-147.

Examples of cancer that may be treated include lymphomas, leukemia, including, e.g., acute myeloid leukemia (AML) and myelodysplastic syndrome (MDS), etc.

Examples of metabolic disorders include, without limitation, diabetes, including type I and type II diabetes, metabolic syndrome, dyslipidemia, obesity, glucose intolerance, hypertension, elevated serum cholesterol, and elevated triglycerides.

Examples of inflammatory disorders include rheumatoid arthritis (RA), inflammatory bowel disease (IBD), Crohn's disease, ulcerative colitis, necrotizing enterocolitis, gout, Lyme disease, arthritis, psoriasis, pelvic inflammatory disease, systemic lupus erythematosus (SLE), Sjogren's syndrome, inflammation associated with gastrointestinal infections, including *C. difficile*, viral myocarditis, acute and chronic tissue injury, non-alcoholic steatohepatitis (NASH), alcoholic hepatitis and kidney disease, including chronic kidney disease and diabetic kidney disease.

A further embodiment provides a method of treating an inflammation related disease or condition, or a metabolic disorder, gastrointestinal disorder, or cancer and the like comprising administering a compound of Formula (I) in combination with one or more compounds useful for the treatment of such diseases to a subject, particularly a human subject, in need thereof.

In some embodiments, a compound of the present disclosure is co-formulated with the additional one or more active ingredients. In some embodiments, the other active ingredient is administered at approximately the same time, in a separate dosage form. In some embodiments, the other active ingredient is administered sequentially, and may be administered at different times in relation to a compound of the present disclosure.

EXAMPLES

Depiction of Chemical Structures

The structures of Examples are depicted using the V3000 enhanced stereochemical representation to denote the known or unknown configuration(s) of each stereocenter. The following notations are used: "abs" denotes that the absolute configuration is known, "or1" denotes that the stereocenter is absolute but of unknown configuration, "&1" and "&2" each denote a racemic stereocenter and if each notation is contained in the same molecule means there is no known relationship between the racemic centers and therefore would be comprised of a mixture of 4 diastereomers.

Preparation of Compounds of Formula (I)

Example 1

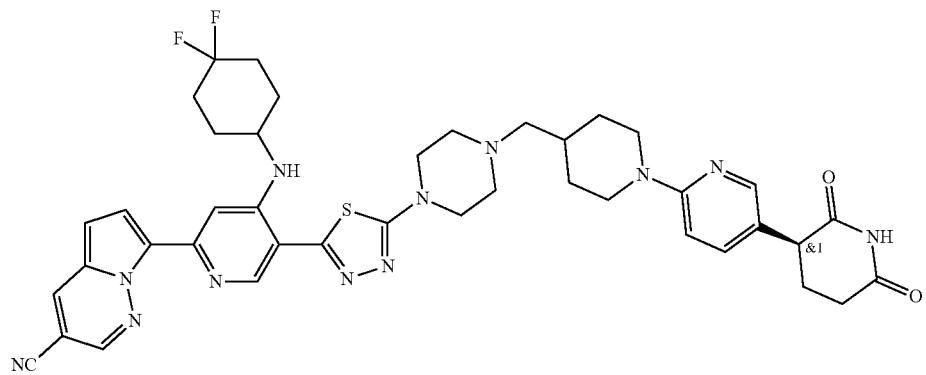 [SMILES: N#Cc1cnn2c(-c3cc(NC4CCC(F)(F)CC4)c(-c4nnc(N5CCN(CC6CCN(c7ccc([C@@H]8CCC(=O)NC8=O)cn7)CC6)CC5)s4)cn3)ccc2c1]

rac-7-{4-[(4,4-difluorocyclohexyl)amino]-5-(5-{4-[(1-{5-[(3R)-2,6-dioxopiperidin-3-yl]pyridin-2-yl}piperidin-4-yl)methyl]piperazin-1-yl}-1,3,4-thiadiazol-2-yl)pyridin-2-yl}pyrrolo[1,2-b]pyridazine-3-carbonitrile The title compound was synthesized from Intermediate S and HA-1 by reductive amination using General Method B. LCMS: $C_{41}H_{44}F2N_{12}O_2S$ requires: 806.3, found: m/z=807.6 [M+H]$^+$. $^1$H NMR (500 MHz, DMSO) δ 10.86 (s, 1H), 9.63 (s, 1H), 9.04 (s, 1H), 8.92 (d, J=2.2 Hz, 1H), 8.85 (d, J=2.2 Hz, 1H), 8.60 (s, 1H), 8.23 (s, 1H), 7.94 (d, J=3.0 Hz, 2H), 7.58 (s, 1H), 7.19 (d, J=4.8 Hz, 1H), 7.05 (s, 1H), 4.28 (d, J=13.0 Hz, 2H), 3.11 (pd, J=8.5, 4.3 Hz, 3H), 2.96 (s, 2H), 2.75-2.61 (m, 1H), 2.20-2.09 (m, 8H), 1.97 (dt, J=13.5, 4.1 Hz, 1H), 1.85 (d, J=12.7 Hz, 2H), 1.70 (d, J=10.3 Hz, 2H), 1.32-1.21 (m, 3H), 1.17 (t, J=7.3 Hz, 2H).

Example 2

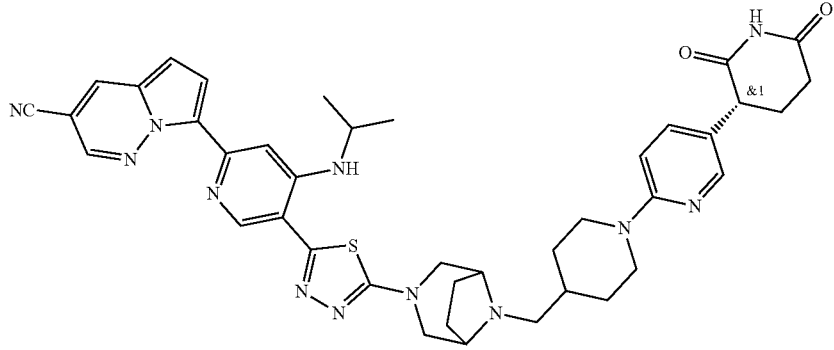 [SMILES: CC(C)Nc1cc(-c2ccc3cc(C#N)cnn23)ncc1-c1nnc(N2CC3CCC(C2)N3CC2CCN(c3ccc([C@H]4CCC(=O)NC4=O)cn3)CC2)s1]
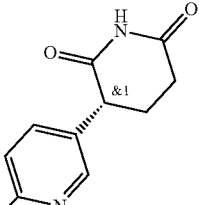

rac-7-[5-(5-{8-[(1-{5-[(3R)-2,6-dioxopiperidin-3-yl]pyridin-2-yl}piperidin-4-yl)methyl]-3,8-diazabicyclo[3.2.1]octan-3-yl}-1,3,4-thiadiazol-2-yl)-4-[(propan-2-yl)amino]pyridin-2-yl]pyrrolo[1,2-b]pyridazine-3-carbonitrile The title compound was synthesized from Intermediate R and HA-1 by reductive amination using General Method B. LCMS: $C_{40}H_{44}N_{12}O_2S$ requires: 756.3, found: m/z=757.6 [M+H]$^+$. $^1$H NMR (500 MHz, DMSO) δ 10.87 (s, 1H), 9.82 (s, 1H), 9.15 (s, 1H), 8.95 (d, J=2.2 Hz, 1H), 8.82 (d, J=2.2 Hz, 1H), 8.59 (d, J=6.1 Hz, 1H), 8.11 (s, 1H), 8.00 (d, J=4.9 Hz, 1H), 7.96 (d, J=2.5 Hz, 1H), 7.59 (s, 1H), 7.21 (d, J=4.8 Hz, 1H), 7.07 (s, 1H), 4.31 (d, J=12.5 Hz, 1H), 4.26 (s, 2H), 4.15-4.10 (m, 1H), 3.95 (d, J=13.4 Hz, 1H), 3.84 (s, 2H), 3.81 (d, J=6.0 Hz, 1H), 2.70 (ddd, J=17.5, 12.6, 5.3 Hz, 1H), 2.57 (t, J=3.9 Hz, 1H), 2.30-2.18 (m, 2H), 2.16 (s, 1H), 2.00 (dd, J=17.9, 8.4 Hz, 2H), 1.93 (d, J=12.5 Hz, 2H), 1.38 (d, J=6.3 Hz, 6H), 1.34-1.28 (m, 2H).

rac-7-[5-(5-{4-[(1-{4-[(3R)-2,6-dioxopiperidin-3-yl]-3-fluorophenyl}piperidin-4-yl)methyl]piperazin-1-yl}-1,3,4-thiadiazol-2-yl)-4-[(oxan-4-yl)amino]pyridin-2-yl]pyrrolo[1,2-b]pyridazine-3-carbonitrile The title compound was synthesized from Intermediate A and HA-3 by reductive amination using General Method B. LCMS: $C_{41}H_{44}FN_{11}O_3S$ requires: 789.3, found: m/z=790.5 [M+H]$^+$. $^1$H NMR (500 MHz, DMSO) δ 10.82 (s, 1H), 9.56 (s, 1H), 9.09 (s, 1H), 8.93 (d, J=2.2 Hz, 1H), 8.83 (d, J=2.2 Hz, 1H), 8.61 (s, 1H), 8.22 (s, 1H), 7.96 (d, J=4.9 Hz, 1H), 7.20 (d, J=4.9 Hz, 1H), 7.10 (t, J=8.9 Hz, 1H), 6.81-6.73 (m, 2H), 4.13 (d, J=13.8 Hz, 2H), 4.02 (s, 3H), 3.98-3.86 (m, 3H), 3.80 (d, J=12.4 Hz, 2H), 3.67 (s, 6H), 3.65-3.57 (m, 1H), 3.16 (s, 2H), 2.80-2.68 (m, 3H), 2.54 (s, 1H), 2.15 (ddt, J=18.5, 13.6, 6.4 Hz, 3H), 2.05 (s, 1H), 1.97 (ddd, J=10.3, 6.9, 3.3 Hz, 1H), 1.84 (d, J=12.5 Hz, 2H), 1.61 (ddt, J=13.3, 9.8, 5.2 Hz, 2H), 1.38-1.29 (m, 2H).

Example 3

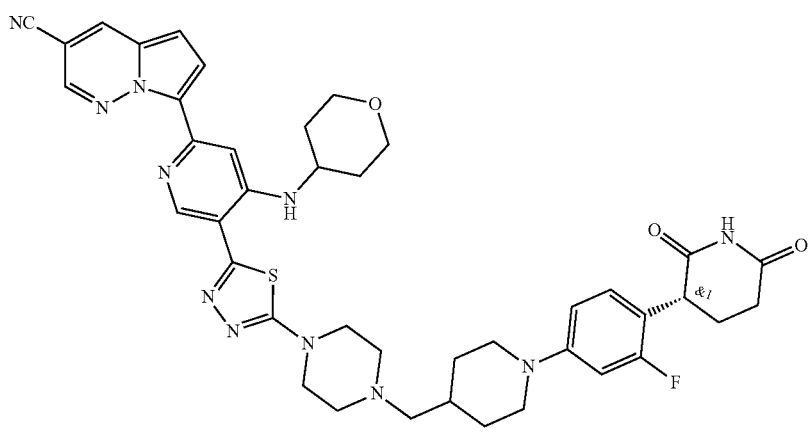

Example 4

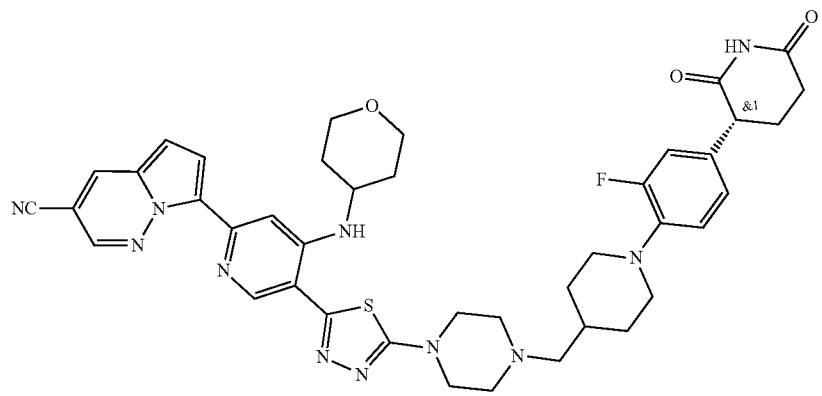 [SMILES: N#Cc1cnn2c(-c3cc(NC4CCOCC4)c(-c4nnc(N5CCN(CC6CCN(c7ccc([C@H]8CCC(=O)NC8=O)cc7F)CC6)CC5)s4)cn3)ccc2c1]

rac-7-[5-(5-{4-[(1-{4-[(3R)-2,6-dioxopiperidin-3-yl]-2-fluorophenyl}piperidin-4-yl)methyl]piperazin-1-yl}-1,3,4-thiadiazol-2-yl)-4-[(oxan-4-yl)amino]pyridin-2-yl]pyrrolo[1,2-b]pyridazine-3-carbonitrile The title compound was synthesized from Intermediate A and HA-4 by reductive amination using General Method B. LCMS: $C_{41}H_{44}FN_{11}O_3S$ requires: 789.3, found: m/z=790.5 [M+H]+. $^1$H NMR (500 MHz, DMSO) δ 10.83 (s, 1H), 9.53 (s, 1H), 8.92 (s, 1H), 8.83 (d, J=2.2 Hz, 1H), 8.60 (s, 1H), 8.23 (s, 1H), 7.95 (s, 1H), 7.19 (d, J=4.8 Hz, 1H), 7.08-6.95 (m, 3H), 4.13 (d, J=13.5 Hz, 2H), 4.01 (s, 1H), 3.94 (dt, J=11.8, 3.9 Hz, 2H), 3.82 (dd, J=11.8, 4.9 Hz, 1H), 3.68-3.58 (m, 2H), 3.40 (d, J=11.5 Hz, 2H), 2.75-2.64 (m, 3H), 2.21 (qd, J=12.5, 4.3 Hz, 1H), 2.12 (d, J=12.8 Hz, 2H), 2.05-1.97 (m, 2H), 1.88 (d, J=12.5 Hz, 2H), 1.61 (dd, J=13.8, 9.9 Hz, 2H), 1.44 (d, J=12.4 Hz, 2H).

Example 5

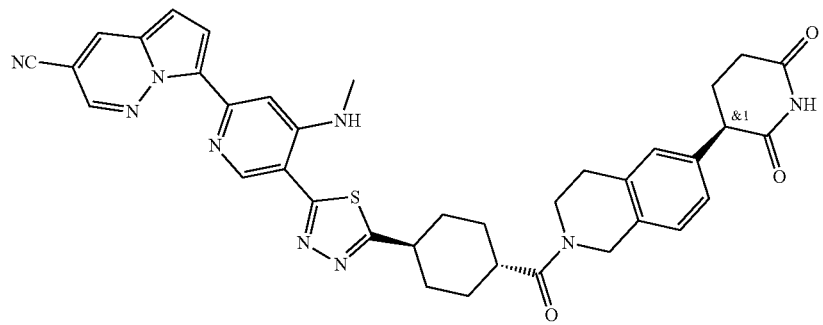 [SMILES: CNc1cc(-c2ccc3cc(C#N)cnn23)ncc1-c1nnc([C@H]2CC[C@H](C(=O)N3CCc4cc([C@H]5CCC(=O)NC5=O)ccc4C3)CC2)s1]

7-[4-(methylamino)-5-{5-[(1r,4r)-4-{6-[(3RS)-2,6-dioxopiperidin-3-yl]-1,2,3,4-tetrahydroisoquinoline-2-carbonyl}cyclohexyl]-1,3,4-thiadiazol-2-yl}pyridin-2-yl]pyrrolo[1,2-b]pyridazine-3-carbonitrile The title compound was synthesized from Intermediate O and HA-5 by amide coupling using General Method A. LCMS: $C_{37}H_{35}N_9O_3S$ requires: 685.3, found: m/z=686.2 [M+H]+. $^1$H NMR (500 MHz, DMSO) δ 10.82 (s, 1H), 8.95 (s, 1H), 8.83 (s, 1H), 8.73 (s, 1H), 8.04 (d, J=9.9 Hz, 2H), 7.23-7.13 (m, 2H), 7.05 (d, J=8.8 Hz, 2H), 4.75 (s, 1H), 4.61 (s, 1H), 3.80 (dq, J=10.8, 5.3 Hz, 2H), 3.69 (s, 1H), 3.30 (s, 1H), 3.19 (d, J=4.7 Hz, 3H), 2.87 (s, 3H), 2.75 (s, 1H), 2.71-2.63 (m, 1H), 2.21 (d, J=12.7 Hz, 4H), 2.06-1.98 (m, 1H), 1.90-1.75 (m, 3H), 1.73 (d, J=12.5 Hz, 1H), 1.64 (q, J=12.7 Hz, 2H), 1.24 (s, 1H).

Example 6

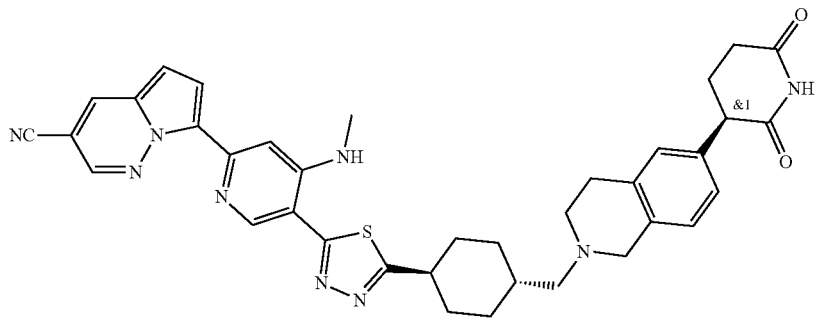 [SMILES: CNc1cc(-c2ccc3cc(C#N)cnn23)ncc1-c1nnc([C@H]2CC[C@H](CN3CCc4cc([C@H]5CCC(=O)NC5=O)ccc4C3)CC2)s1]

7-[4-(methylamino)-5-{5-[(1r,4r)-4-({6-[(3RS)-2,6-dioxopiperidin-3-yl]-1,2,3,4-tetrahydroisoquinolin-2-yl}methyl)cyclohexyl]-1,3,4-thiadiazol-2-yl}pyridin-2-yl]pyrrolo[1,2-b]pyridazine-3-carbonitrile The title compound was synthesized from Intermediate N and HA-5 by reductive amination using General Method B. LCMS: $C_{37}H_{37}N_9O_2S$ requires: 671.3, found: m/z=672.3 [M+H]$^+$. $^1$H NMR (500 MHz, DMSO) δ 10.86 (s, 1H), 9.47 (s, 1H), 8.91 (s, 1H), 8.80 (s, 1H), 8.73 (s, 1H), 8.14 (s, 1H), 7.96 (s, 1H), 7.23-7.12 (m, 4H), 4.61 (d, J=15.3 Hz, 1H), 4.32 (dd, J=15.6, 8.0 Hz, 1H), 3.86 (dd, J=11.7, 4.9 Hz, 1H), 3.77 (s, 1H), 3.15 (d, J=5.2 Hz, 7H), 3.08 (s, 1H), 2.75-2.65 (m, 1H), 2.23 (d, J=12.9 Hz, 4H), 2.03 (s, 4H), 1.96 (s, 1H), 1.69 (d, J=12.7 Hz, 2H), 1.35-1.19 (m, 3H).

Example 7

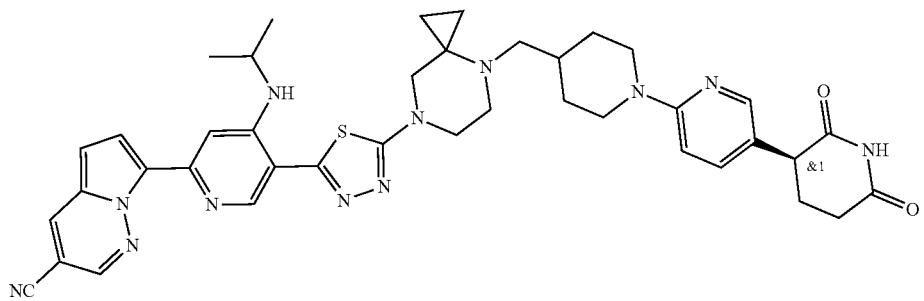 [SMILES: CC(C)Nc1cc(-c2ccc3cc(C#N)cnn23)ncc1-c1nnc(N2CCN(CC3CCN(c4ccc([C@@H]5CCC(=O)NC5=O)cn4)CC3)C3(CC3)C2)s1]

rac-7-[5-(5-{4-[(1-{5-[(3R)-2,6-dioxopiperidin-3-yl]pyridin-2-yl}piperidin-4-yl)methyl]-4,7-diazaspiro[2.5]octan-7-yl}-1,3,4-thiadiazol-2-yl)-4-[(propan-2-yl)amino]pyridin-2-yl]pyrrolo[1,2-b]pyridazine-3-carbonitrile The title compound was synthesized from Intermediate T and HA-1 by reductive amination using General Method B. LCMS: $C_{40}H_{44}N_{12}O_2S$ requires: 756.3, found: m/z=757.7 [M+H]$^+$; $^1$H NMR (500 MHz, DMSO-d$_6$) δ 10.81 (s, 1H), 8.85 (d, J=2.3 Hz, 1H), 8.74 (d, J=2.3 Hz, 1H), 8.59 (d, J=7.1 Hz, 1H), 8.48 (s, 1H), 8.22 (s, 1H), 7.95 (d, J=2.4 Hz, 1H), 7.85 (d, J=4.8 Hz, 1H), 7.47-7.32 (m, 1H), 7.13 (d, J=4.8 Hz, 1H), 6.80 (d, J=8.9 Hz, 1H), 4.27 (d, J=12.6 Hz, 2H), 4.15-4.06 (m, 4H), 3.94 (d, J=6.5 Hz, 1H), 3.73 (dd, J=12.0, 4.9 Hz, 1H), 3.58 (s, 2H), 3.39 (s, 5H), 3.21-3.16 (m, 8H), 3.05 (s, 2H), 2.77 (t, J=12.4 Hz, 3H), 2.70-2.61 (m, 3H), 2.24-2.11 (m, 2H), 2.04-1.87 (m, 2H), 1.74 (d, J=12.8 Hz, 2H), 1.63 (s, 2H), 1.36 (d, J=6.3 Hz, 6H), 1.25 (s, 7H), 1.17-1.02 (m, 6H), 0.87 (t, J=6.7 Hz, 2H), 0.62 (d, J=9.3 Hz, 5H).

Example 8

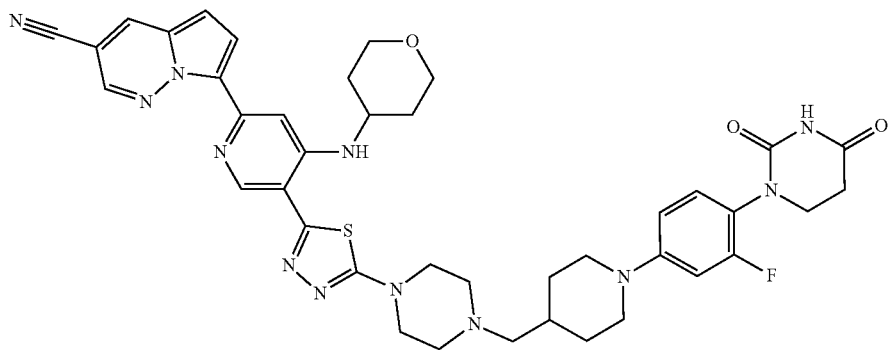 [SMILES: N#Cc1cnn2c(-c3cc(NC4CCOCC4)c(-c4nnc(N5CCN(CC6CCN(c7ccc(N8CCC(=O)NC8=O)c(F)c7)CC6)CC5)s4)cn3)ccc2c1]

7-(5-{5-[4-({1-[4-(2,4-dioxo-1,3-diazinan-1-yl)-3-fluorophenyl]piperidin-4-yl}methyl)piperazin-1-yl]-1,3,4-thiadiazol-2-yl}-4-[(oxan-4-yl)amino]pyridin-2-yl)pyrrolo[1,2-b]pyridazine-3-carbonitrile The title compound was synthesized from Intermediate A and HA-6 by reductive amination using General Method B. LCMS: $C_{40}H_{43}FN_{12}O_3S$ requires: 790.3, found: m/z=791.5 [M+H]$^+$. $^1$H NMR (500 MHz, DMSO) δ 10.38 (s, 1H), 9.57 (s, 1H), 9.13 (s, 1H), 8.93 (s, 1H), 8.83 (d, J=2.3 Hz, 1H), 8.60 (s, 1H), 8.20 (s, 1H), 7.96 (d, J=4.8 Hz, 1H), 7.25-7.17 (m, 2H), 6.87 (dd, J=14.1, 2.7 Hz, 1H), 6.79 (dd, J=9.0, 2.7 Hz, 1H), 4.02 (s, 1H), 3.93 (dt, J=11.9, 4.0 Hz, 2H), 3.82 (d, J=12.7 Hz, 2H), 3.68-3.57 (m, 8H), 3.15 (s, 2H), 2.78 (t, J=12.2 Hz, 2H), 2.70 (t, J=6.6 Hz, 2H), 2.14-2.08 (m, 2H), 1.93-1.73 (m, 2H), 1.65-1.54 (m, 2H), 1.31 (d, J=12.5 Hz, 2H).

Example 9

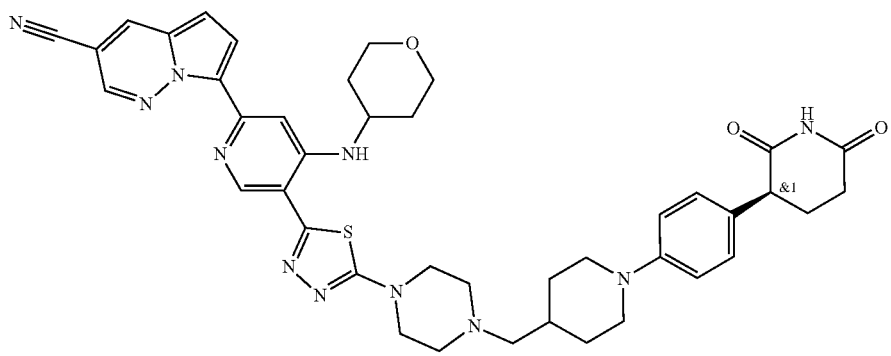 [SMILES: N#Cc1cnn2c(-c3cc(NC4CCOCC4)c(-c4nnc(N5CCN(CC6CCN(c7ccc([C@@H]8CCC(=O)NC8=O)cc7)CC6)CC5)s4)cn3)ccc2c1]

rac-7-[5-(5-{4-[(1-{4-[(3R)-2,6-dioxopiperidin-3-yl]phenyl}piperidin-4-yl)methyl]piperazin-1-yl}-1,3,4-thiadiazol-2-yl)-4-[(oxan-4-yl)amino]pyridin-2-yl]pyrrolo[1,2-b]pyridazine-3-carbonitrile The title compound was synthesized from Intermediate A and HA-7 by reductive amination using General Method B. LCMS: $C_{41}H_{45}N_{11}O_3S$ requires: 771.3, found: m/z=722.5 [M+H]$^+$. $^1$H NMR (500 MHz, DMSO) δ 10.77 (s, 1H), 8.84 (d, J=2.3 Hz, 1H), 8.76 (d, J=2.3 Hz, 1H), 8.66 (d, J=6.9 Hz, 1H), 8.51 (s, 1H), 8.29 (s, 1H), 7.84 (d, J=4.7 Hz, 1H), 7.12 (d, J=4.7 Hz, 1H), 7.03 (d, J=8.2 Hz, 2H), 6.89 (d, J=8.3 Hz, 2H), 3.97-3.80 (m, 3H), 3.72 (dd, J=10.8, 5.0 Hz, 1H), 3.68 (s, 1H), 3.66 (s, 1H), 3.64-3.53 (m, 6H), 3.29 (s, 3H), 2.69-2.58 (m, 3H), 2.25 (d, J=7.2 Hz, 2H), 2.12 (d, J=12.6 Hz, 3H), 2.04-1.97 (m, 1H), 1.82 (d, J=12.6 Hz, 2H), 1.71 (s, 1H), 1.62-1.57 (m, 1H), 1.56 (s, 1H), 1.23 (s, 4H).

Example 10

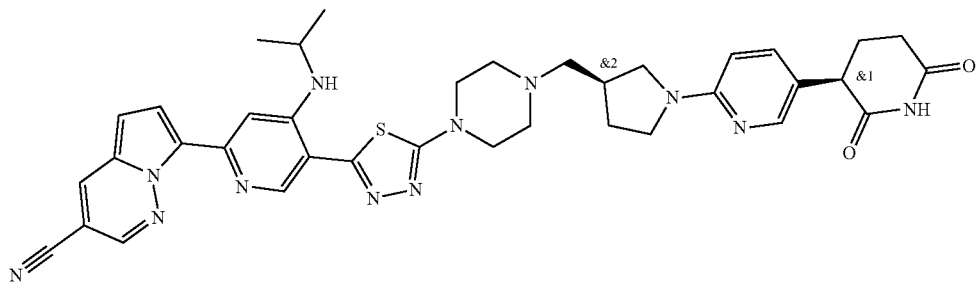 [SMILES: CC(C)Nc1cc(-c2ccc3cc(C#N)cnn23)ncc1-c1nnc(N2CCN(C[C@@H]3CCN(c4ccc([C@H]5CCC(=O)NC5=O)cn4)C3)CC2)s1]

7-{5-[5-(4-{[(3RS)-1-{5-[(3RS&)-2,6-dioxopiperidin-3-yl]pyridin-2-yl}pyrrolidin-3-yl]methyl}piperazin-1-yl)-1,3,4-thiadiazol-2-yl]-4-[(propan-2-yl)amino]pyridin-2-yl}pyrrolo[1,2-b]pyridazine-3-carbonitrile The title compound was synthesized from Intermediate B and HA-12 by reductive amination using General Method B. LCMS: $C_{37}H_{40}N_{12}O_2S$ requires: 716.3, found: m/z=717.6 [M+H]$^+$. $^1$H NMR (500 MHz, Methanol-d$_4$) δ 8.77 (q, J=2.1 Hz, 1H), 8.69 (t, J=2.3 Hz, 1H), 8.58 (d, J=2.4 Hz, 1H), 8.10 (dd, J=5.2, 2.0 Hz, 1H), 8.00 (dt, J=9.3, 2.3 Hz, 1H), 7.91 (dt, J=10.7, 2.8 Hz, 2H), 7.25 (dd, J=5.0, 2.2 Hz, 1H), 7.14 (dd, J=9.5, 2.0 Hz, 1H), 4.31 (ddq, J=10.8, 6.5, 4.4, 3.4 Hz, 1H), 4.07-3.90 (m, 6H), 3.90-3.74 (m, 1H), 3.68 (q, J=8.8 Hz, 1H), 3.49 (dt, J=21.6, 13.0 Hz, 5H), 3.11-2.99 (m, 1H), 2.80 (ddddd, J=20.2, 17.4, 15.0, 5.3, 2.3 Hz, 2H), 2.49 (tt, J=7.0, 3.9 Hz, 1H), 2.40-2.23 (m, 1H), 2.21 (ddt, J=10.2, 5.1, 2.8 Hz, 1H), 2.12-1.92 (m, 1H), 1.49 (dd, J=6.4, 2.0 Hz, 7H).

Example 11

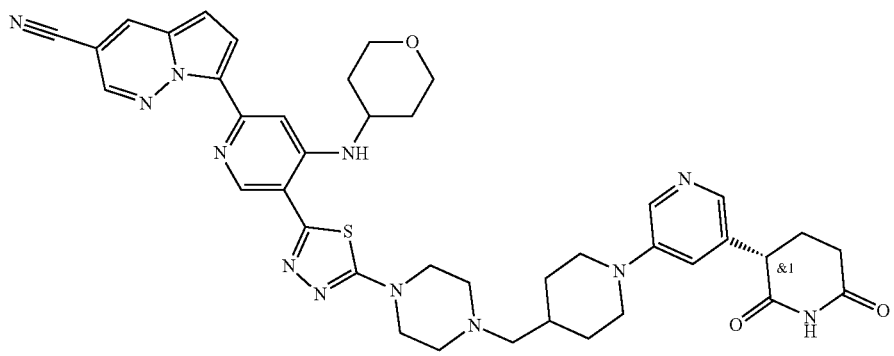 [SMILES: N#Cc1cnn2c(-c3cc(NC4CCOCC4)c(-c4nnc(N5CCN(CC6CCN(c7cncc([C@@H]8CCC(=O)NC8=O)c7)CC6)CC5)s4)cn3)ccc2c1]

rac-7-[5-(5-{4-[(1-{5-[(3R)-2,6-dioxopiperidin-3-yl]pyridin-3-yl}piperidin-4-yl)methyl]piperazin-1-yl}-1,3,4-thiadiazol-2-yl)-4-[(oxan-4-yl)amino]pyridin-2-yl]pyrrolo[1,2-b]pyridazine-3-carbonitrile The title compound was synthesized from Intermediate A and HA-13 by reductive amination using General Method C. LCMS: $C_{40}H_{44}N_{12}O_3S$ requires: 772.3, found: m/z=773.3 [M+H]$^+$.

Example 12

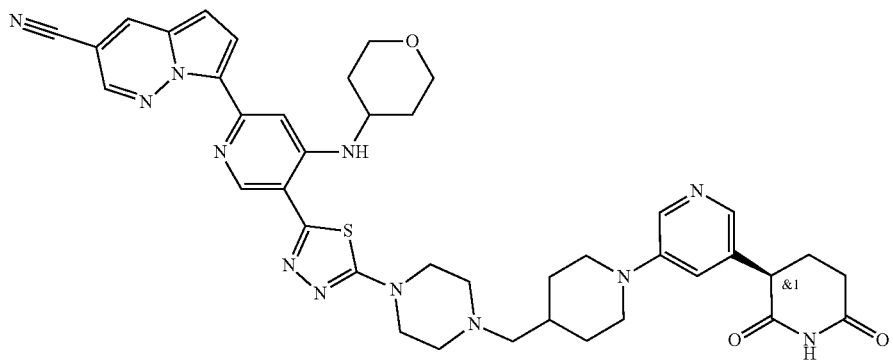 [SMILES: N#Cc1cnn2c(-c3cc(NC4CCOCC4)c(-c4nnc(N5CCN(CC6CCN(c7cncc([C@H]8CCC(=O)NC8=O)c7)CC6)CC5)s4)cn3)ccc2c1]

rac-7-[5-(5-{4-[(1-{4-[(3R)-2,6-dioxopiperidin-3-yl]
pyridin-2-yl}piperidin-4-yl)methyl]piperazin-1-yl}-
1,3,4-thiadiazol-2-yl)-4-[(oxan-4-yl)amino]pyridin-
2-yl]pyrrolo[1,2-b]pyridazine-3-carbonitrile The title compound was synthesized from Intermediate A and HA-20 by reductive amination using General Method C. LCMS: $C_{40}H_{44}N_{12}O_3S$ requires: 772.3, found: m/z=773.2 [M+H]$^+$.

Example 13

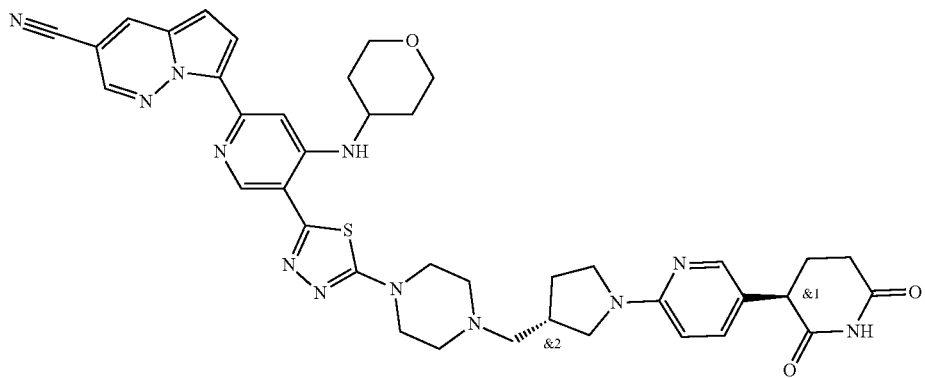 [SMILES: N#Cc1cnn2c(-c3cc(NC4CCOCC4)c(-c4nnc(N5CCN(C[C@@H]6CCN(c7ccc([C@H]8CCC(=O)NC8=O)cn7)C6)CC5)s4)cn3)ccc2c1]

7-{5-[5-(4-{[(3RS)-1-{5-[(3RS&)-2,6-dioxopiperi-
din-3-yl]pyridin-2-yl}pyrrolidin-3-yl]
methyl}piperazin-1-yl)-1,3,4-thiadiazol-2-yl]-4-
[(oxan-4-yl)amino]pyridin-2-yl}pyrrolo[1,2-b]
pyridazine-3-carbonitrile The title compound was synthesized from Intermediate A and HA-12 by reductive amination using General Method C. LCMS: $C_{39}H_{42}N_{12}O_3S$ requires: 758.3, found: m/z=759.3 [M+H]$^+$.

Example 14

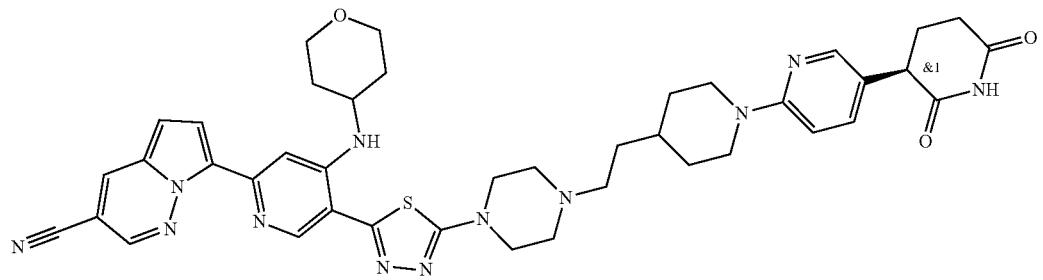 [SMILES: N#Cc1cnn2c(-c3cc(NC4CCOCC4)c(-c4nnc(N5CCN(CCC6CCN(c7ccc([C@H]8CCC(=O)NC8=O)cn7)CC6)CC5)s4)cn3)ccc2c1]

rac-7-[5-(5-{4-[2-(1-{5-[(3R)-2,6-dioxopiperidin-3-yl]pyridin-2-yl}piperidin-4-yl)ethyl]piperazin-1-yl}-1,3,4-thiadiazol-2-yl)-4-[(oxan-4-yl)amino]pyridin-2-yl]pyrrolo[1,2-b]pyridazine-3-carbonitrile The title compound was synthesized from Intermediate A and HA-14 by reductive amination using General Method C. LCMS: $C_{41}H_{46}N_{12}O_3S$ requires: 786.4, found: m/z=787.3 $[M+H]^+$.

Example 15

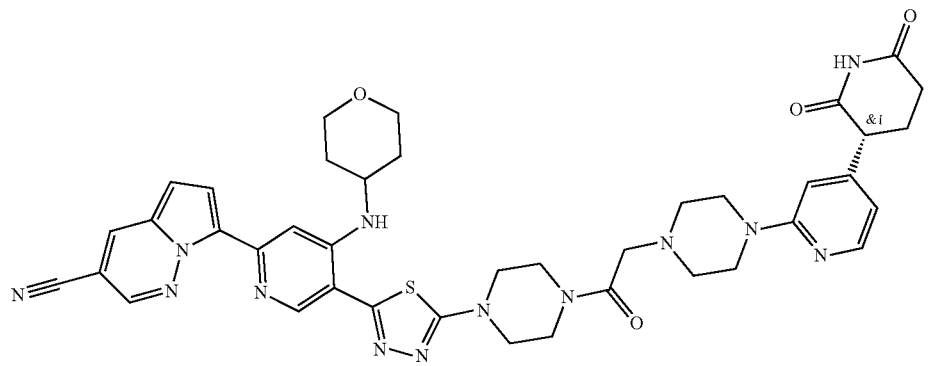 [SMILES: N#Cc1cnn2c(-c3cc(NC4CCOCC4)c(-c4nnc(N5CCN(C(=O)CN6CCN(c7cc([C@H]8CCC(=O)NC8=O)ccn7)CC6)CC5)s4)cn3)ccc2c1]

rac-7-[5-(5-{4-[2-(4-{4-[(3R)-2,6-dioxopiperidin-3-yl]pyridin-2-yl}piperazin-1-yl)acetyl]piperazin-1-yl}-1,3,4-thiadiazol-2-yl)-4-[(oxan-4-yl)amino]pyridin-2-yl]pyrrolo[1,2-b]pyridazine-3-carbonitrile The title compound was synthesized from Intermediate A and HA-14 by amide coupling using General Method D. LCMS: $C_{40}H_{43}N_{13}O_4S$ requires: 801.3, found: m/z=802.3 $[M+H]^+$.

Example 16

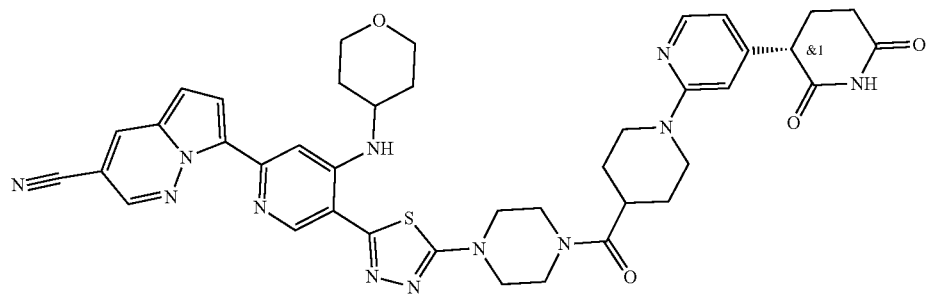 [SMILES: N#Cc1cnn2c(-c3cc(NC4CCOCC4)c(-c4nnc(N5CCN(C(=O)C6CCN(c7cc([C@@H]8CCC(=O)NC8=O)ccn7)CC6)CC5)s4)cn3)ccc2c1]

rac-7-(5-{5-[4-(1-{4-[(3R)-2,6-dioxopiperidin-3-yl]
pyridin-2-yl}piperidine-4-carbonyl)piperazin-1-yl]-
1,3,4-thiadiazol-2-yl}-4-[(oxan-4-yl)amino]pyridin-
2-yl)pyrrolo[1,2-b]pyridazine-3-carbonitrile The title compound was synthesized from Intermediate A and HA-15 by amide coupling using General Method D. LCMS: $C_{40}H_{42}N_{12}O_4S$ requires: 786.3, found: m/z=787.3 [M+H]$^+$.

Example 17

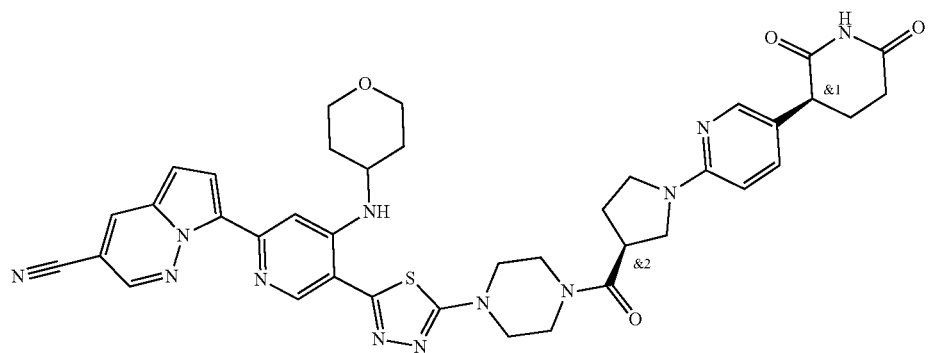 [SMILES: N#Cc1cnn2c(-c3cc(NC4CCOCC4)c(-c4nnc(N5CCN(C(=O)[C@H]6CCN(c7ccc([C@@H]8CCC(=O)NC8=O)cn7)C6)CC5)s4)cn3)ccc2c1]

7-[5-(5-{4-[(3RS)-1-{5-[(3RS&)-2,6-dioxopiperidin-
3-yl]pyridin-2-yl}pyrrolidine-3-carbonyl]piperazin-
1-yl}-1,3,4-thiadiazol-2-yl)-4-[(oxan-4-yl)amino]
pyridin-2-yl]pyrrolo[1,2-b]pyridazine-3-carbonitrile The title compound was synthesized from Intermediate A and HA-16 by amide coupling using General Method D. LCMS: $C_{39}H_{40}N_{12}O_4S$ requires: 772.3, found: m/z=773.2 [M+H]$^+$.

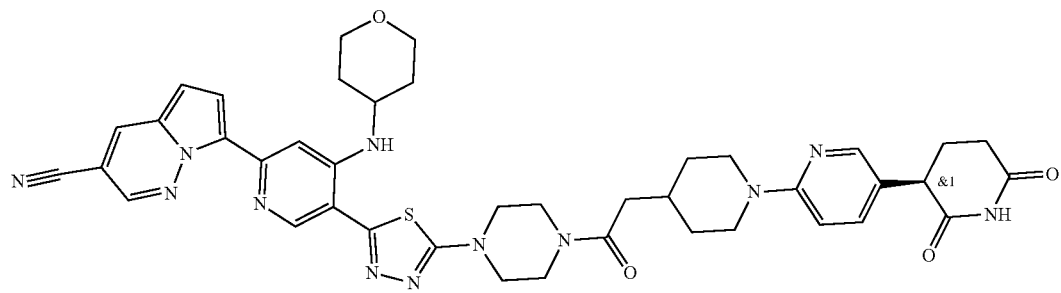 [SMILES: N#Cc1cnn2c(-c3cc(NC4CCOCC4)c(-c4nnc(N5CCN(C(=O)CC6CCN(c7ccc([C@H]8CCC(=O)NC8=O)cn7)CC6)CC5)s4)cn3)ccc2c1]

rac-7-[5-(5-{4-[2-(1-{5-[(3R)-2,6-dioxopiperidin-3-yl]pyridin-2-yl}piperidin-4-yl)acetyl]piperazin-1-yl}-1,3,4-thiadiazol-2-yl)-4-[(oxan-4-yl)amino]pyridin-2-yl]pyrrolo[1,2-b]pyridazine-3-carbonitrile The title compound was synthesized from Intermediate A and HA-8 by amide coupling using General Method D. LCMS: $C_{41}H_{44}N_{12}O_4S$ requires: 800.3, found: m/z=801.4 $[M+H]^+$.

Example 19

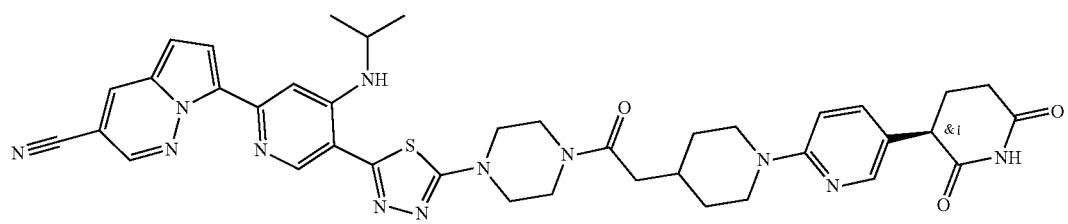 [SMILES: CC(C)Nc1cc(-c2ccc3cc(C#N)cnn23)ncc1-c1nnc(N2CCN(C(=O)CC3CCN(c4ccc([C@H]5CCC(=O)NC5=O)cn4)CC3)CC2)s1]

rac-7-[5-(5-{4-[2-(1-{5-[(3R)-2,6-dioxopiperidin-3-yl]pyridin-2-yl}piperidin-4-yl)acetyl]piperazin-1-yl}-1,3,4-thiadiazol-2-yl)-4-[(propan-2-yl)amino]pyridin-2-yl]pyrrolo[1,2-b]pyridazine-3-carbonitrile The title compound was synthesized from Intermediate B and HA-8 by amide coupling using General Method A. LCMS: $C_{39}H_{42}N_{12}O_3S$ requires: 758.3, found: m/z=759.7 $[M+H]^+$. $^1$H NMR (500 MHz, Methanol-$d_4$) δ 8.78 (t, J=1.9 Hz, 1H), 8.70 (d, J=1.9 Hz, 1H), 8.54 (s, 1H), 8.10 (d, J=5.0 Hz, 1H), 7.98 (dt, J=9.8, 1.9 Hz, 1H), 7.91 (s, 1H), 7.85 (t, J=1.9 Hz, 1H), 7.43 (d, J=9.6 Hz, 1H), 7.26 (dd, J=5.1, 1.4 Hz, 1H), 4.32 (p, J=6.4 Hz, 1H), 4.22 (d, J=13.6 Hz, 2H), 3.96 (dd, J=12.8, 4.9 Hz, 1H), 3.88-3.63 (m, 9H), 2.79 (q, J=6.4, 4.7 Hz, 2H), 2.53 (d, J=6.8 Hz, 2H), 2.41-2.13 (m, 3H), 2.04 (d, J=12.5 Hz, 2H), 1.49 (dd, J=6.3, 1.3 Hz, 8H).

Example 20

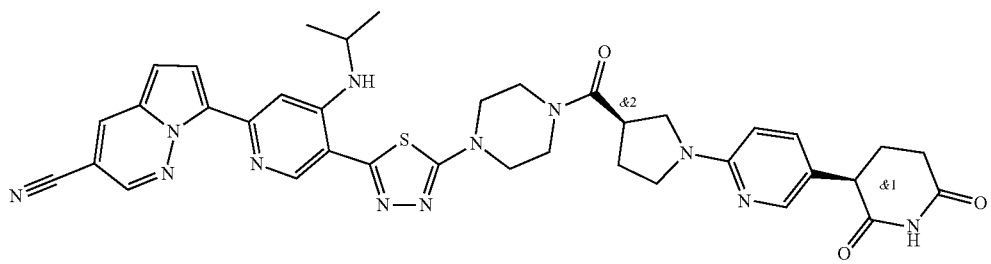 [SMILES: CC(C)Nc1cc(-c2ccc3cc(C#N)cnn23)ncc1-c1nnc(N2CCN(C(=O)[C@@H]3CCN(c4ccc([C@H]5CCC(=O)NC5=O)cn4)C3)CC2)s1]

7-[5-(5-{4-[(3RS)-1-{5-[(3RS&)-2,6-dioxopiperidin-3-yl]pyridin-2-yl}pyrrolidine-3-carbonyl]piperazin-1-yl}-1,3,4-thiadiazol-2-yl)-4-[(propan-2-yl)amino]pyridin-2-yl]pyrrolo[1,2-b]pyridazine-3-carbonitrile The title compound was synthesized from Intermediate B and HA-17 by amide coupling using General Method A. LCMS: $C_{37}H_{38}N_{12}O_3S$ requires: 730.3, found: m/z=731.6 [M+H]$^+$. $^1$H NMR (500 MHz, Methanol-d$_4$) δ 8.80 (td, J=4.9, 4.3, 2.1 Hz, 1H), 8.71 (td, J=5.0, 4.4, 2.1 Hz, 1H), 8.55 (t, J=4.8 Hz, 1H), 8.10 (q, J=4.9 Hz, 1H), 7.99 (ddt, J=11.3, 5.8, 2.7 Hz, 1H), 7.92 (t, J=4.8 Hz, 1H), 7.87 (dt, J=5.9, 2.9 Hz, 1H), 7.27 (q, J=4.9, 4.5 Hz, 1H), 7.18 (dt, J=9.5, 4.7 Hz, 1H), 4.38-4.28 (m, 1H), 4.01-3.81 (m, 11H), 3.75 (d, J=5.6 Hz, 4H), 2.85-2.73 (m, 2H), 2.60-2.46 (m, 1H), 2.43-2.29 (m, 2H), 2.23 (q, J=4.7 Hz, 1H), 1.55-1.47 (m, 7H).

Example 21

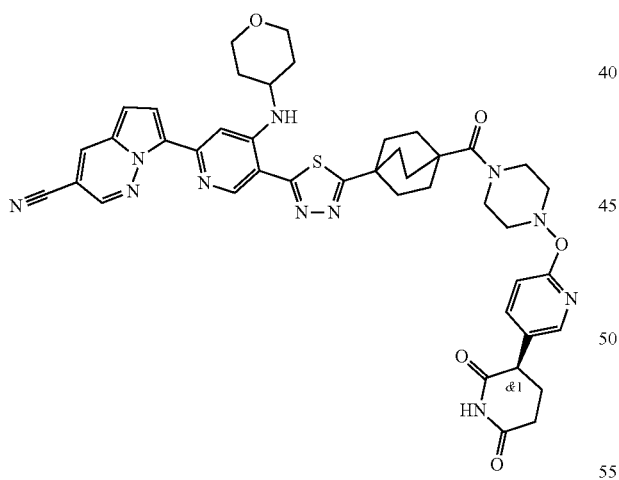

rac-7-[5-(5-{4-[4-({5-[(3R)-2,6-dioxopiperidin-3-yl]pyridin-2-yl}oxy)piperidine-1-carbonyl]bicyclo[2.2.2]octan-1-yl}-1,3,4-thiadiazol-2-yl)-4-[(oxan-4-yl)amino]pyridin-2-yl]pyrrolo[1,2-b]pyridazine-3-carbonitrile The title compound was synthesized from Intermediate E and HA-18 by amide coupling using General Method A. LCMS: $C_{44}H_{46}N_{10}O_5S$ requires: 826.3, found: m/z=827.7 [M+H]$^+$.

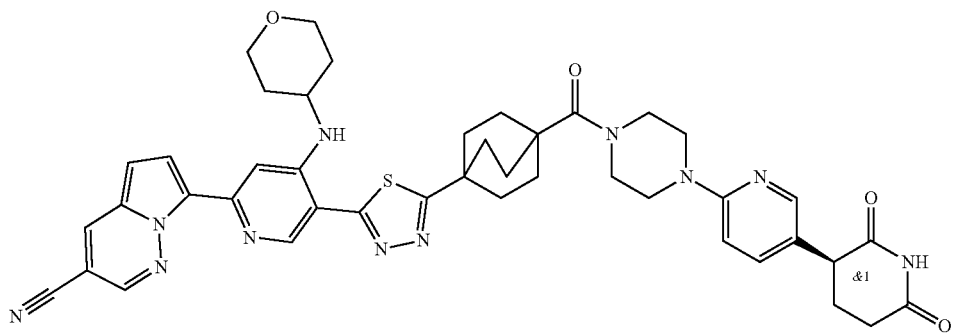 [SMILES: N#Cc1cnn2c(-c3cc(NC4CCOCC4)c(-c4nnc(C56CCC(C(=O)N7CCN(c8ccc([C@@H]9CCC(=O)NC9=O)cn8)CC7)(CC5)CC6)s4)cn3)ccc2c1]

rac-7-(5-{5-[4-(4-{5-[(3R)-2,6-dioxopiperidin-3-yl]
pyridin-2-yl}piperazine-1-carbonyl)bicyclo[2.2.2]
octan-1-yl]-1,3,4-thiadiazol-2-yl}-4-[(oxan-4-yl)
amino]pyridin-2-yl)pyrrolo[1,2-b]pyridazine-3-
carbonitrile The title compound was synthesized from Intermediate E and HA-10 by amide coupling using General Method A. LCMS: $C_{43}H_{45}N_{11}O_4S$ requires: 811.3, found: m/z=812.6 [M+H]$^+$. $^1$H NMR (500 MHz, Methanol-d$_4$) δ 8.80 (d, J=2.1 Hz, 1H), 8.77 (s, 1H), 8.71 (d, J=2.2 Hz, 1H), 8.13 (d, J=5.1 Hz, 1H), 8.03 (s, 1H), 7.99 (d, J=2.3 Hz, 1H), 7.87 (d, J=9.1 Hz, 1H), 7.25 (dd, J=12.9, 7.2 Hz, 2H), 4.34 (d, J=5.0 Hz, 1H), 4.07 (d, J=12.0 Hz, 2H), 3.99-3.88 (m, 5H), 3.82-3.64 (m, 7H), 3.04 (d, J=16.4 Hz, 1H), 2.85-2.71 (m, 2H), 2.31 (tt, J=12.8, 6.5 Hz, 2H), 2.20 (d, J=10.4 Hz, 15H), 1.88-1.76 (m, 2H).

Example 23

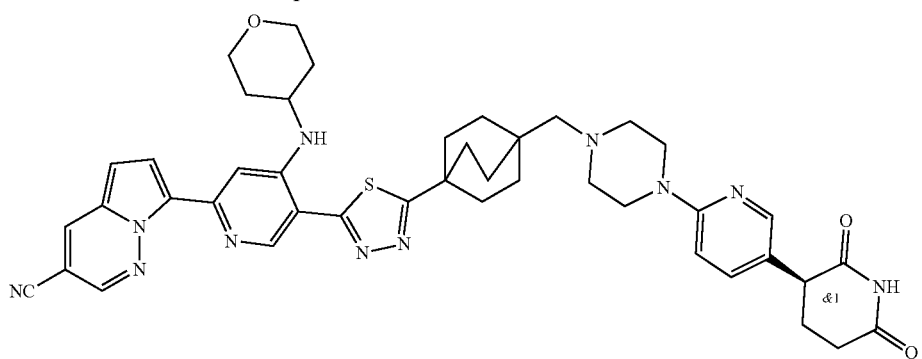

rac-7-[5-(5-{4-[(4-{5-[(3R)-2,6-dioxopiperidin-3-yl]
pyridin-2-yl}piperidin-1-yl)methyl]bicyclo[2.2.2]
octan-1-yl}-1,3,4-thiadiazol-2-yl)-4-[(oxan-4-yl)
amino]pyridin-2-yl]pyrrolo[1,2-b]pyridazine-3-
carbonitrile The title compound was synthesized from Intermediate D and HA-2 by reductive amination using General Method B. LCMS: $C_{44}H_{48}N_{10}O_3S$ requires: 796.4, found: m/z=797.7 [M+H]$^+$. $^1$H NMR (500 MHz, MeOD) δ 8.87-8.75 (m, 2H), 8.71 (d, J=2.2 Hz, 1H), 8.51 (s, 1H), 8.14 (d, J=5.0 Hz, 1H), 8.03 (s, 1H), 7.82 (d, J=8.2 Hz, 1H), 7.49-7.37 (m, 1H), 7.26 (d, J=5.0 Hz, 1H), 4.34 (tt, J=9.4, 4.3 Hz, 1H), 4.16-3.94 (m, 4H), 3.88-3.68 (m, 4H), 3.50 (s, 2H), 3.18 (s, 3H), 2.91-2.67 (m, 3H), 2.42-2.26 (m, 4H), 2.23 (dd, J=10.5, 5.0 Hz, 12H), 1.98-1.75 (m, 9H).

Example 24

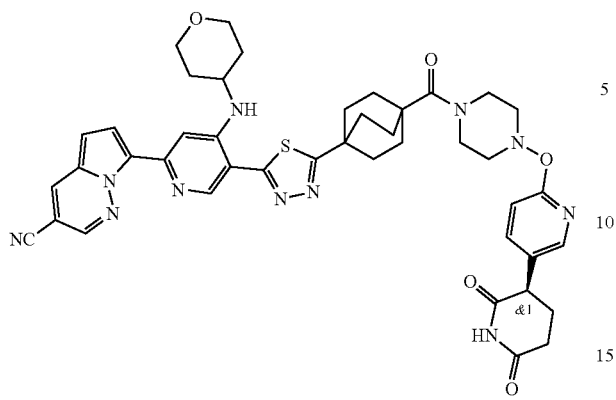

rac-7-{5-[5-(4-{[4-({5-[(3R)-2,6-dioxopiperidin-3-yl]pyridin-2-yl}oxy)piperidin-1-yl]methyl}bicyclo[2.2.2]octan-1-yl)-1,3,4-thiadiazol-2-yl]-4-[(oxan-4-yl)amino]pyridin-2-yl}pyrrolo[1,2-b]pyridazine-3-carbonitrile The title compound was synthesized from Intermediate D and HA-18 by reductive amination using General Method B. LCMS: $C_{44}H_{48}N_{10}O_4S$ requires: 812.4, found: m/z=813.7 [M+H]$^+$. $^1$H NMR (500 MHz, MeOD) δ 8.83-8.74 (m, 2H), 8.71 (d, J=2.2 Hz, 1H), 8.13 (d, J=5.0 Hz, 1H), 8.07 (d, J=2.9 Hz, 1H), 8.03 (s, 1H), 7.70-7.61 (m, 1H), 7.26 (d, J=5.0 Hz, 1H), 6.93-6.79 (m, 1H), 5.44-5.23 (m, 1H), 4.33 (dt, J=9.7, 5.3 Hz, 1H), 4.07 (dt, J=12.0, 4.0 Hz, 2H), 3.90 (dd, J=12.2, 5.0 Hz, 1H), 3.75 (ddd, J=12.3, 10.2, 2.5 Hz, 4H), 3.58 (d, J=12.0 Hz, 2H), 3.49 (s, 2H), 3.20 (d, J=9.3 Hz, 2H), 2.88-2.63 (m, 2H), 2.43 (d, J=13.5 Hz, 1H), 2.28 (dt, J=12.3, 6.7 Hz, 4H), 2.26-2.13 (m, 10H), 1.97-1.78 (m, 9H), 1.57-1.44 (m, 2H).

Example 25

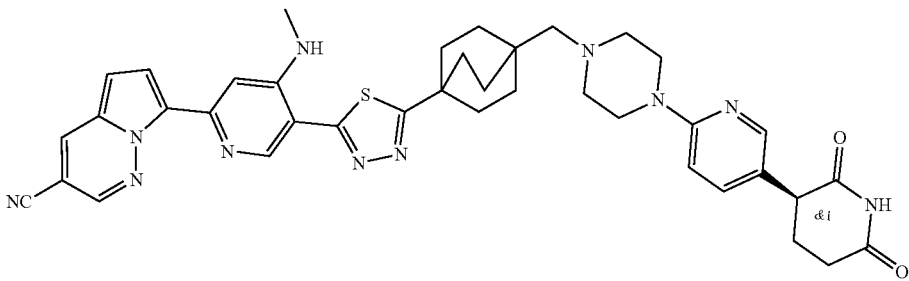 [SMILES: CNc1cc(-c2ccc3cc(C#N)cnn23)ncc1-c1nnc(C23CCC(CN4CCN(c5ccc([C@@H]6CCC(=O)NC6=O)cn5)CC4)(CC2)CC3)s1]

rac-7-[5-(5-{4-[(4-{5-[(3R)-2,6-dioxopiperidin-3-yl]pyridin-2-yl}piperazin-1-yl)methyl]bicyclo[2.2.2]octan-1-yl}-1,3,4-thiadiazol-2-yl)-4-(methylamino)pyridin-2-yl]pyrrolo[1,2-b]pyridazine-3-carbonitrile The title compound was synthesized from Intermediate U and HA-10 by reductive amination using General Method B. LCMS: $C_{39}H_{41}N_{11}O_2S$ requires: 727.3, found: m/z=728.7 [M+H]$^+$. $^1$H NMR (500 MHz, MeOD) δ 8.80 (s, 1H), 8.77-8.67 (m, 2H), 8.20-8.05 (m, 2H), 7.92 (d, J=4.2 Hz, 1H), 7.62 (d, J=8.9 Hz, 1H), 7.26 (d, J=6.7 Hz, 1H), 7.02 (s, 1H), 3.87 (d, J=12.0 Hz, 2H), 3.17 (s, 2H), 2.89-2.61 (m, 2H), 2.23 (d, J=8.5 Hz, 9H), 1.90 (d, J=10.8 Hz, 6H).

Example 26

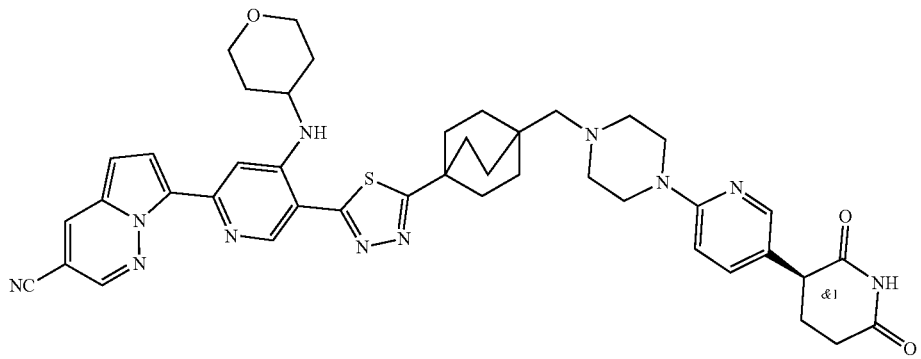 [SMILES: N#Cc1cnn2c(-c3cc(NC4CCOCC4)c(-c4nnc(C56CCC(CN7CCN(c8ccc([C@@H]9CCC(=O)NC9=O)cn8)CC7)(CC5)CC6)s4)cn3)ccc2c1]

rac-7-[5-(5-{4-[(4-{5-[(3R)-2,6-dioxopiperidin-3-yl]
pyridin-2-yl}piperazin-1-yl)methyl]bicyclo[2.2.2]
octan-1-yl}-1,3,4-thiadiazol-2-yl)-4-[(oxan-4-yl)
amino]pyridin-2-yl]pyrrolo[1,2-b]pyridazine-3-
carbonitrile The title compound was synthesized from Intermediate D and HA-10 by reductive amination using General Method B. LCMS: $C_{43}H_{47}N_{11}O_3S$ requires: 797.4, found: m/z=798.7 [M+H]$^+$. $^1$H NMR (500 MHz, MeOD) δ 8.79 (d, J=5.2 Hz, 2H), 8.72 (s, 1H), 8.19-8.07 (m, 2H), 8.03 (s, 1H), 7.63 (d, J=8.7 Hz, 1H), 7.26 (d, J=5.2 Hz, 1H), 7.02 (d, J=8.6 Hz, 1H), 4.34 (s, 2H), 4.07 (d, J=11.4 Hz, 3H), 3.87 (dd, J=12.1, 5.3 Hz, 1H), 3.75 (t, J=11.2 Hz, 3H), 3.17 (s, 2H), 2.88-2.65 (m, 2H), 2.37-2.14 (m, 11H), 1.98-1.86 (m, 6H), 1.86-1.74 (m, 2H).

Example 27

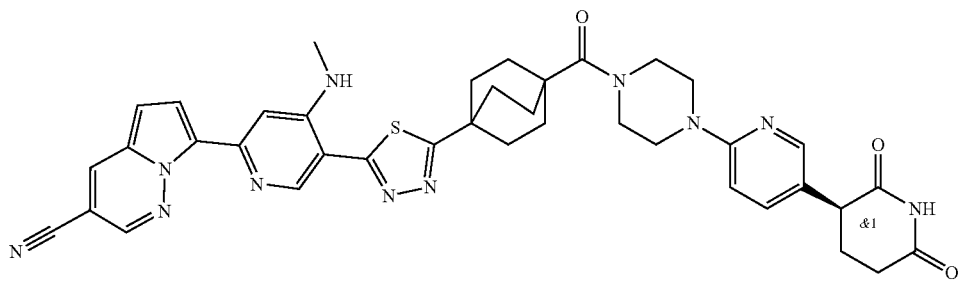 [SMILES: CNc1cc(-c2ccc3cc(C#N)cnn23)ncc1-c1nnc(C23CCC(C(=O)N4CCN(c5ccc([C@@H]6CCC(=O)NC6=O)cn5)CC4)(CC2)CC3)s1]

rac-7-(5-{5-[4-(4-{5-[(3R)-2,6-dioxopiperidin-3-yl]
pyridin-2-yl}piperazine-1-carbonyl)bicyclo[2.2.2]
octan-1-yl]-1,3,4-thiadiazol-2-yl}-4-(methylamino)
pyridin-2-yl)pyrrolo[1,2-b]pyridazine-3-carbonitrile The title compound was synthesized from Intermediate M and HA-10 by amide coupling using General Method A. LCMS: $C_{39}H_{39}N_{11}O_3S$ requires: 741.3, found: m/z=742.6 [M+H]$^+$. $^1$H NMR (500 MHz, MeOD) δ 8.80 (s, 1H), 8.72 (d, J=5.8 Hz, 2H), 8.12 (d, J=5.4 Hz, 1H), 8.01 (s, 1H), 7.92 (s, 1H), 7.83 (s, 1H), 7.26 (d, J=5.5 Hz, 1H), 7.19 (s, 1H), 3.94 (s, 5H), 3.70 (s, 4H), 2.92-2.50 (m, 4H), 2.31 (d, J=13.3 Hz, 1H), 2.20 (d, J=12.4 Hz, 14H), 2.06 (s, 1H), 1.40 (s, 1H).

Example 28

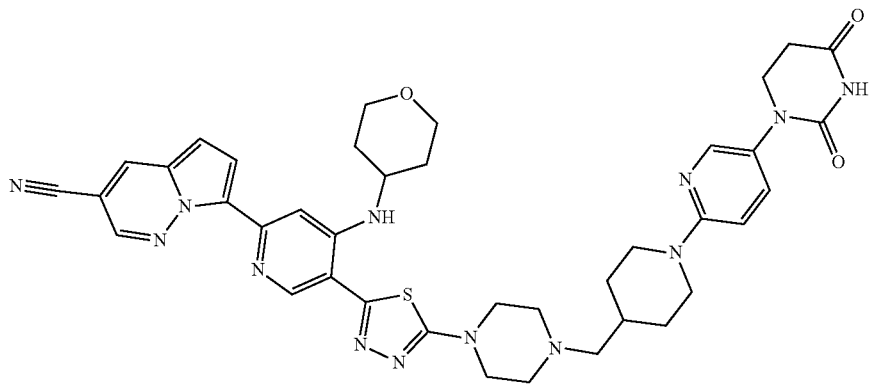 [SMILES: N#Cc1cnn2c(-c3cc(NC4CCOCC4)c(-c4nnc(N5CCN(CC6CCN(c7ccc(N8CCC(=O)NC8=O)cn7)CC6)CC5)s4)cn3)ccc2c1]

7-(5-{5-[4-({1-[5-(2,4-dioxo-1,3-diazinan-1-yl)pyridin-2-yl]piperidin-4-yl}methyl)piperazin-1-yl]-1,3,4-thiadiazol-2-yl}-4-[(oxan-4-yl)amino]pyridin-2-yl)pyrrolo[1,2-b]pyridazine-3-carbonitrile The title compound was synthesized from Intermediate A and HA-19 by reductive amination using General Method B. LCMS: $C_{39}H_{43}N_{13}O_3S$ requires: 773.3, found: m/z=774.2 [M+H]$^+$. $^1$H NMR (500 MHz, DMSO) δ 10.36 (s, 1H), 9.52 (s, 1H), 8.92 (s, 1H), 8.82 (s, 1H), 8.59 (s, 1H), 8.21 (s, 1H), 8.06 (d, J=2.7 Hz, 1H), 7.95 (s, 1H), 7.55-7.50 (m, 1H), 7.18 (d, J=4.9 Hz, 1H), 6.92 (d, J=9.0 Hz, 1H), 4.32 (d, J=12.8 Hz, 2H), 4.11 (s, 2H), 4.01 (s, 1H), 3.96-3.89 (m, 2H), 3.14 (s, 2H), 2.88 (t, J=12.5 Hz, 2H), 2.71 (t, J=6.7 Hz, 2H), 2.11 (d, J=13.0 Hz, 3H), 1.82 (d, J=12.7 Hz, 2H), 1.59 (d, J=11.2 Hz, 2H), 1.24 (s, 4H).

Example 29

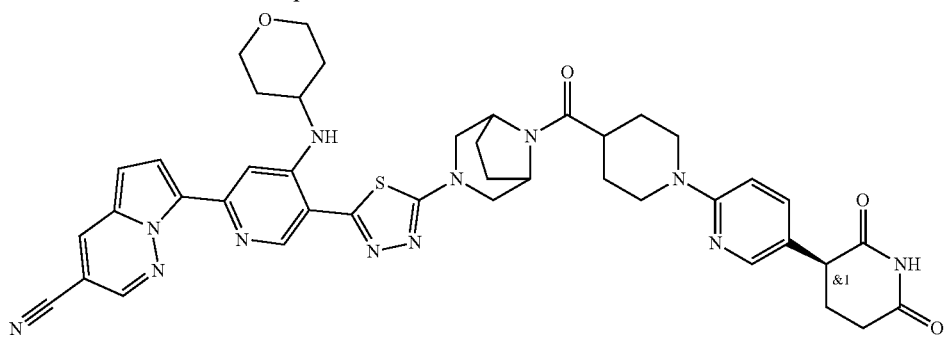

rac-7-(5-{5-[8-(1-{5-[(3R)-2,6-dioxopiperidin-3-yl]pyridin-2-yl}piperidine-4-carbonyl)-3,8-diazabicyclo[3.2.1]octan-3-yl]-1,3,4-thiadiazol-2-yl}-4-[(oxan-4-yl)amino]pyridin-2-yl)pyrrolo[1,2-b]pyridazine-3-carbonitrile The title compound was synthesized from Intermediate F and HA-9 by amide coupling using General Method A. LCMS: $C_{42}H_{44}N_{12}O_4S$ requires: 812.3, found: m/z=813.6 [M+H]$^+$. $^1$H NMR (500 MHz, Methanol-d$_4$) δ 8.84-8.77 (m, 1H), 8.72 (d, J=2.3 Hz, 1H), 8.61-8.55 (m, 1H), 8.17-8.08 (m, 1H), 8.00-7.87 (m, 3H), 7.38 (d, J=9.3 Hz, 1H), 7.27 (dd, J=7.2, 5.0 Hz, 1H), 4.79 (s, 1H), 4.30 (d, J=10.7 Hz, 4H), 4.16-3.89 (m, 5H), 3.79 (dt, J=21.8, 11.2 Hz, 4H), 3.61 (d, J=12.1 Hz, 3H), 3.42 (d, J=12.5 Hz, 3H), 3.16 (s, 1H), 2.81 (d, J=18.3 Hz, 2H), 2.34 (d, J=8.3 Hz, 1H), 2.23 (d, J=12.5 Hz, 5H), 2.16-1.67 (m, 12H).

Example 30

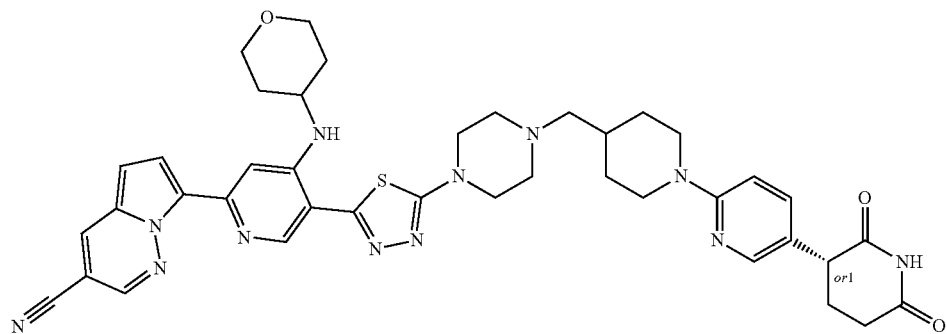 [SMILES: N#Cc1cnn2c(-c3cc(NC4CCOCC4)c(-c4nnc(N5CCN(CC6CCN(c7ccc([C@H]8CCC(=O)NC8=O)cn7)CC6)CC5)s4)cn3)ccc2c1]

7-[5-(5-{4-[(1-{5-[(3R)-2,6-dioxopiperidin-3-yl]
pyridin-2-yl}piperidin-4-yl)methyl]piperazin-1-yl}-
1,3,4-thiadiazol-2-yl)-4-[(oxan-4-yl)amino]pyridin-
2-yl]pyrrolo[1,2-b]pyridazine-3-carbonitrile The title compound was synthesized from Intermediate A and HA-1 by reductive amination using General Method B, and purified by chiral SFC. LCMS: $C_{40}H_{44}N_{12}O_3S$ requires: 772.3, found: m/z=773.5 [M+H]$^+$.

Example 31

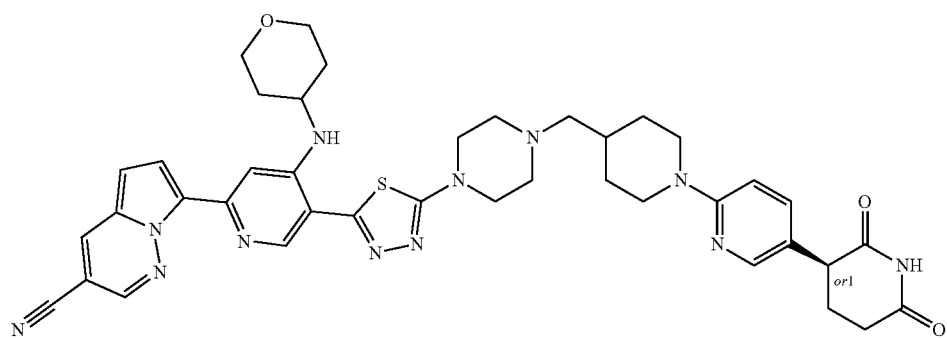 [SMILES: N#Cc1cnn2c(-c3cc(NC4CCOCC4)c(-c4nnc(N5CCN(CC6CCN(c7ccc([C@@H]8CCC(=O)NC8=O)cn7)CC6)CC5)s4)cn3)ccc2c1]

7-[5-(5-{4-[(1-{5-[(3S)-2,6-dioxopiperidin-3-yl]
pyridin-2-yl}piperidin-4-yl)methyl]piperazin-1-yl}-
1,3,4-thiadiazol-2-yl)-4-[(oxan-4-yl)amino]pyridin-
2-yl]pyrrolo[1,2-b]pyridazine-3-carbonitrile The title compound was synthesized from Intermediate A and HA-1 by reductive amination using General Method B, and purified by chiral SFC. LCMS: $C_{40}H_{44}N_{12}O_3S$ requires: 772.3, found: m/z=773.4 [M+H]$^+$.

Example 32

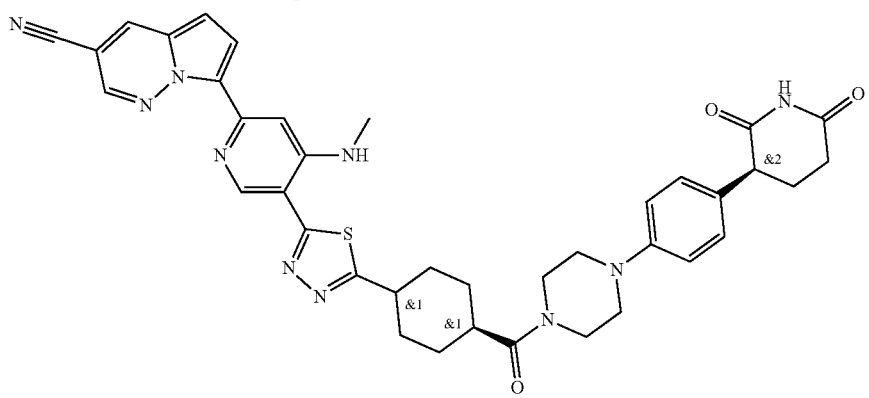

7-[4-(methylamino)-5-{5-[(1rs&,4rs&)-4-(4-{4-[(3RS)-2,6-dioxopiperidin-3-yl]phenyl}piperazine-1-carbonyl)cyclohexyl]-1,3,4-thiadiazol-2-yl}pyridin-2-yl]pyrrolo[1,2-b]pyridazine-3-carbonitrile The title compound was synthesized from Intermediate O and HA-10 by amide coupling using General Method A. LCMS: $C_{38}H_{38}N_{10}O_3S$ requires: 714.3, found: m/z=715.2 [M+H]+. 1H NMR (500 MHz, DMSO-$d_6$) δ 10.79 (s, 1H), 8.96 (s, 1H), 8.84 (s, 2H), 8.74 (s, 1H), 8.06 (d, J=17.8 Hz, 2H), 7.22 (d, J=5.0 Hz, 2H), 7.10 (d, J=8.3 Hz, 2H), 6.95 (d, J=8.4 Hz, 3H), 3.67 (d, J=38.3 Hz, 5H), 3.27-3.01 (m, 6H), 2.82 (d, J=12.3 Hz, 2H), 2.72-2.57 (m, 2H), 2.19 (dd, J=32.4, 12.3 Hz, 4H), 2.02 (dd, J=12.7, 5.7 Hz, 2H), 1.87 (d, J=12.5 Hz, 2H), 1.83-1.70 (m, 2H), 1.65 (t, J=12.1 Hz, 2H).

Example 33

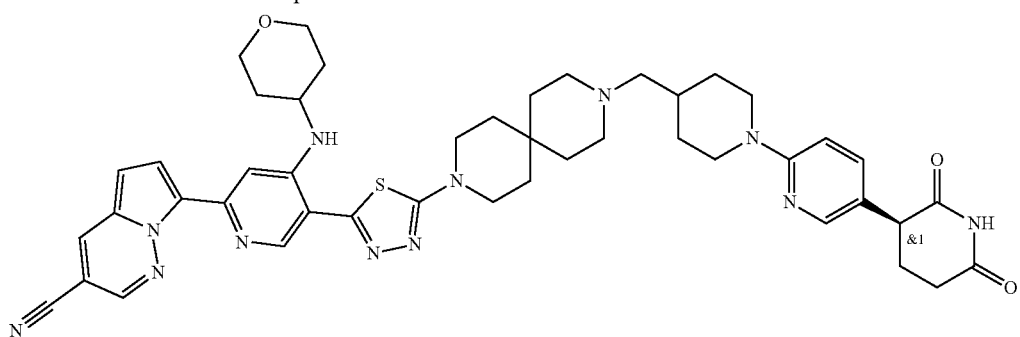

rac-7-[5-(5-{9-[(1-{5-[(3R)-2,6-dioxopiperidin-3-yl]pyridin-2-yl}piperidin-4-yl)methyl]-3,9-diazaspiro[5.5]undecan-3-yl}-1,3,4-thiadiazol-2-yl)-4-[(oxan-4-yl)amino]pyridin-2-yl]pyrrolo[1,2-b]pyridazine-3-carbonitrile The title compound was synthesized from Intermediate Q and HA-1 by reductive amination using General Method B. LCMS: $C_{45}H_{52}N_{12}O_3S$ requires: 840.4, found: m/z=841.9 [M+H]+. 1H NMR (500 MHz, MeOD) δ 8.79 (d, J=2.2 Hz, 1H), 8.70 (d, J=2.2 Hz, 1H), 8.55 (s, 1H), 8.13 (d, J=5.0 Hz, 1H), 8.03-7.92 (m, 2H), 7.90 (d, J=2.3 Hz, 1H), 7.40 (d, J=9.5 Hz, 1H), 7.26 (d, J=5.0 Hz, 1H), 4.29 (t, J=11.6 Hz, 3H), 4.06 (dt, J=12.2, 4.1 Hz, 3H), 3.96 (dd, J=12.9, 4.9 Hz, 1H), 3.79-3.69 (m, 6H), 3.58 (d, J=13.0 Hz, 2H), 3.25-3.11 (m, 4H), 2.86-2.72 (m, 2H), 2.32 (qd, J=12.5, 5.2 Hz, 2H), 2.20 (q, J=6.6 Hz, 3H), 2.08 (t, J=12.6 Hz, 5H), 1.95 (d, J=6.7 Hz, 2H), 1.90-1.65 (m, 7H), 1.51 (q, J=12.4 Hz, 2H).

Example 34

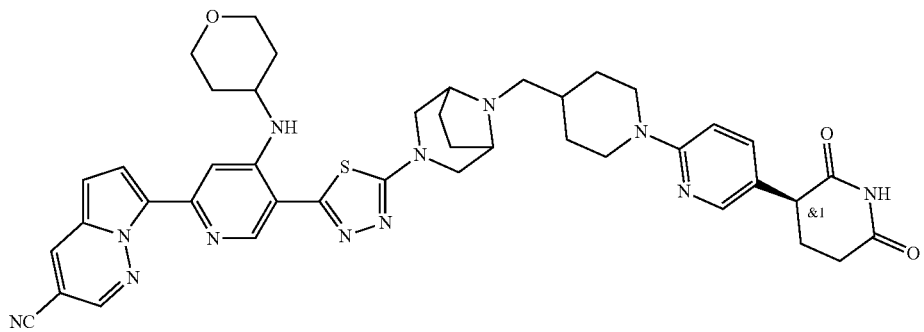 [SMILES: N#Cc1cnn2c(-c3cc(NC4CCOCC4)c(-c4nnc(N5CC6CCC(C5)N6CC5CCN(c6ccc([C@@H]7CCC(=O)NC7=O)cn6)CC5)s4)cn3)ccc2c1]

rac-7-[5-(5-{8-[(1-{5-[(3R)-2,6-dioxopiperidin-3-yl]
pyridin-2-yl}piperidin-4-yl)methyl]-3,8-diazabicyclo
[3.2.1]octan-3-yl}-1,3,4-thiadiazol-2-yl)-4-[(oxan-4-
yl)amino]pyridin-2-yl]pyrrolo[1,2-b]pyridazine-3-
carbonitrile The title compound was synthesized from Intermediate F and HA-1 by reductive amination using General Method B. LCMS: $C_{42}H_{46}N_{12}O_3S$ requires: 798.4, found: m/z=799.7 [M+H]$^+$. $^1$H NMR (500 MHz, MeOD) δ 8.79 (d, J=2.1 Hz, 1H), 8.70 (d, J=2.1 Hz, 1H), 8.60 (s, 1H), 8.13 (d, J=5.0 Hz, 1H), 7.98 (d, J=8.7 Hz, 2H), 7.90 (d, J=2.3 Hz, 1H), 7.42 (d, J=9.6 Hz, 1H), 7.26 (d, J=5.0 Hz, 1H), 4.38-4.26 (m, 5H), 4.12-4.04 (m, 4H), 4.02-3.91 (m, 4H), 3.74 (ddd, J=12.2, 10.2, 2.5 Hz, 2H), 3.21 (s, 2H), 2.87-2.68 (m, 2H), 2.44 (d, J=10.8 Hz, 3H), 2.32 (qd, J=13.3, 5.7 Hz, 2H), 2.25-2.07 (m, 8H), 1.80 (dtd, J=13.8, 10.0, 4.1 Hz, 2H), 1.56 (d, J=10.3 Hz, 2H).

Example 35

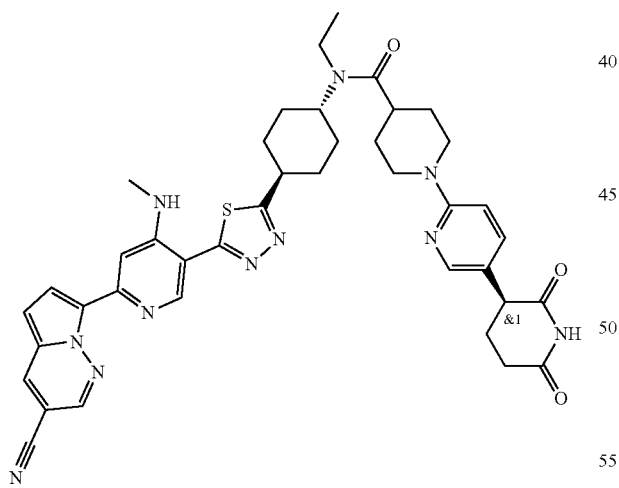

1-{5-[(3RS)-2,6-dioxopiperidin-3-yl]pyridin-2-yl}-
N-ethyl-N—[(1r,4r)-4-[5-(6-{3-cyanopyrrolo[1,2-b]
pyridazin-7-yl}-4-(methylamino)pyridin-3-yl)-1,3,4-
thiadiazol-2-yl]cyclohexyl]piperidine-4-carboxamide The title compound was synthesized from Intermediate P and HA-9 by amide coupling using General Method A. LCMS: $C_{40}H_{43}N_{11}O_3S$ requires: 757.3, found: m/z=758.5 [M+H]$^+$.

Example 36

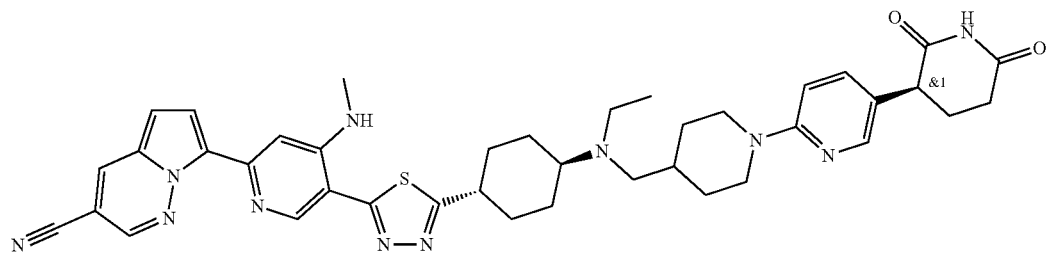 [SMILES: CCN(CC1CCN(c2ccc([C@@H]3CCC(=O)NC3=O)cn2)CC1)[C@H]1CC[C@H](c2nnc(-c3cnc(-c4ccc5cc(C#N)cnn45)cc3NC)s2)CC1]

7-[4-(methylamino)-5-{5-[(1r,4r)-4-{[(1-{5-[(3RS)-2,6-dioxopiperidin-3-yl]pyridin-2-yl}piperidin-4-yl)methyl](ethyl)amino}cyclohexyl]-1,3,4-thiadiazol-2-yl}pyridin-2-yl]pyrrolo[1,2-b]pyridazine-3-carbonitrile The title compound was synthesized from Intermediate P and HA-1 by reductive amination using General Method B. LCMS: $C_{40}H_{45}N_{11}O_2S$ requires: 743.3, found: m/z=744.2 [M+H]$^+$

Example 37

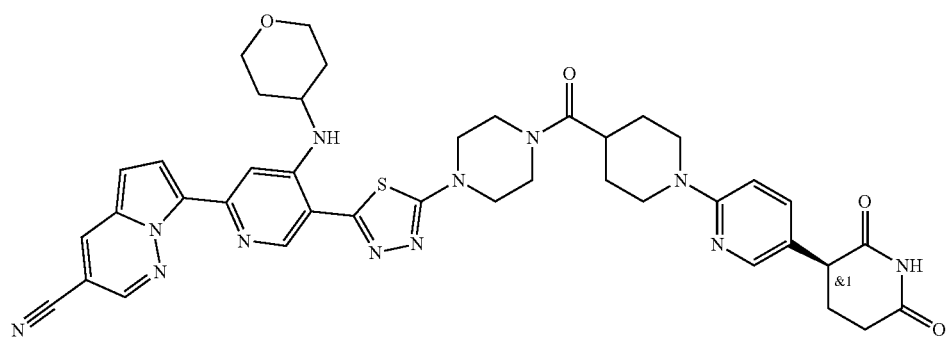 [SMILES: N#Cc1cnn2c(-c3cc(NC4CCOCC4)c(-c4nnc(N5CCN(C(=O)C6CCN(c7ccc([C@@H]8CCC(=O)NC8=O)cn7)CC6)CC5)s4)cn3)ccc2c1]

rac-7-(5-{5-[4-(1-{5-[(3R)-2,6-dioxopiperidin-3-yl]pyridin-2-yl}piperidine-4-carbonyl)piperazin-1-yl]-1,3,4-thiadiazol-2-yl}-4-[(oxan-4-yl)amino]pyridin-2-yl)pyrrolo[1,2-b]pyridazine-3-carbonitrile The title compound was synthesized from Intermediate A and HA-9 by amide coupling using General Method A. LCMS: $C_{40}H_{42}N_{12}O_4S$ requires: 786.3, found: m/z=787.7 [M+H]$^+$. $^1$H NMR (500 MHz, Methanol-d$_4$) δ 8.79 (d, J=2.2 Hz, 1H), 8.70 (d, J=2.2 Hz, 1H), 8.57 (s, 1H), 8.12 (d, J=5.0 Hz, 1H), 7.96 (d, J=7.5 Hz, 2H), 7.89 (d, J=2.3 Hz, 1H), 7.40 (d, J=9.5 Hz, 1H), 7.26 (d, J=5.0 Hz, 1H), 4.38-4.18 (m, 4H), 4.05 (dd, J=10.2, 5.9 Hz, 3H), 4.00-3.90 (m, 3H), 3.85 (d, J=17.2 Hz, 5H), 3.79-3.66 (m, 6H), 3.50-3.39 (m, 3H), 3.23 (d, J=10.7 Hz, 2H), 2.83-2.75 (m, 2H), 2.33 (qd, J=12.7, 5.4 Hz, 1H), 2.21 (d, J=12.2 Hz, 4H), 2.07-1.96 (m, 3H), 1.96-1.72 (m, 6H).

Example 38

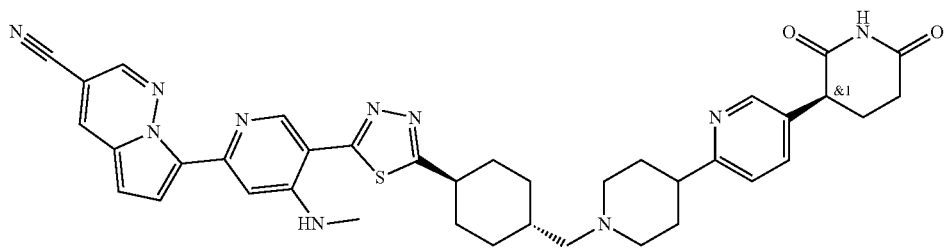 [SMILES: CNc1cc(-c2ccc3cc(C#N)cnn23)ncc1-c1nnc([C@H]2CC[C@H](CN3CCC(c4ccc([C@@H]5CCC(=O)NC5=O)cn4)CC3)CC2)s1]

7-[4-(methylamino)-5-{5-[(1r,4r)-4-[(4-{5-[(3RS)-2,
6-dioxopiperidin-3-yl]pyridin-2-yl}piperidin-1-yl)
methyl]cyclohexyl]-1,3,4-thiadiazol-2-yl}pyridin-2-
yl]pyrrolo[1,2-b]pyridazine-3-carbonitrile The title compound was synthesized from Intermediate N and HA-2 by reductive amination using General Method B. LCMS: $C_{38}H_{40}N_{10}O_2S$ requires: 700.3, found: m/z=701.6 [M+H]$^+$. $^1$H NMR (500 MHz, Methanol-d$_4$) δ 8.80 (d, J=2.1 Hz, 1H), 8.76-8.66 (m, 2H), 8.49 (d, J=2.3 Hz, 1H), 8.13 (d, J=5.1 Hz, 1H), 7.93 (s, 1H), 7.86-7.64 (m, 1H), 7.48-7.32 (m, 1H), 7.27 (d, J=5.0 Hz, 1H), 4.00 (dd, J=12.5, 5.0 Hz, 1H), 3.80 (d, J=12.4 Hz, 3H), 3.56 (d, J=36.8 Hz, 1H), 3.22-3.10 (m, 5H), 2.87-2.60 (m, 3H), 2.46-2.30 (m, 4H), 2.30-2.17 (m, 5H), 2.11 (d, J=11.9 Hz, 4H), 1.84 (q, J=12.2, 11.7 Hz, 3H), 1.42 (q, J=12.6 Hz, 2H).

Example 39

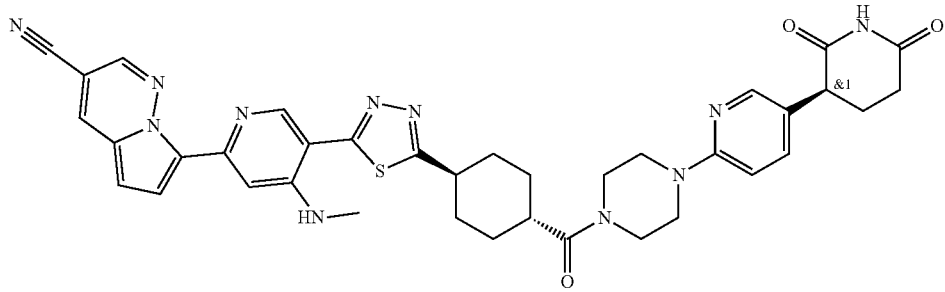 [SMILES: CNc1cc(-c2ccc3cc(C#N)cnn23)ncc1-c1nnc([C@H]2CC[C@H](C(=O)N3CCN(c4ccc([C@@H]5CCC(=O)NC5=O)cn4)CC3)CC2)s1]

7-[4-(methylamino)-5-{5-[(1r,4r)-4-(4-{5-[(3RS)-2,
6-dioxopiperidin-3-yl]pyridin-2-yl}piperazine-1-
carbonyl)cyclohexyl]-1,3,4-thiadiazol-2-yl}pyridin-
2-yl]pyrrolo[1,2-b]pyridazine-3-carbonitrile The title compound was synthesized from Intermediate O and HA-10 by amide coupling using General Method A. LCMS: $C_{37}H_{37}N_{11}O_3S$ requires: 715.3, found: m/z=716.2 [M+H]$^+$. $^1$H NMR (500 MHz, MeOD) δ 8.79 (d, J=2.1 Hz, 1H), 8.74-8.65 (m, 2H), 8.12 (d, J=5.1 Hz, 1H), 8.00 (d, J=2.3 Hz, 1H), 7.92 (s, 1H), 7.79 (d, J=9.2 Hz, 1H), 7.26 (d, J=5.1 Hz, 1H), 7.16 (d, J=9.2 Hz, 1H), 4.91 (s, 2H), 3.94-3.61 (m, 9H), 3.07-2.95 (m, 2H), 2.90 (d, J=13.2 Hz, 1H), 2.83-2.65 (m, 2H), 2.38 (d, J=12.2 Hz, 2H), 2.35-2.22 (m, 1H), 2.22-2.14 (m, 1H), 2.03 (d, J=12.7 Hz, 2H), 1.87-1.66 (m, 4H), 1.31 (s, 1H).

Example 40

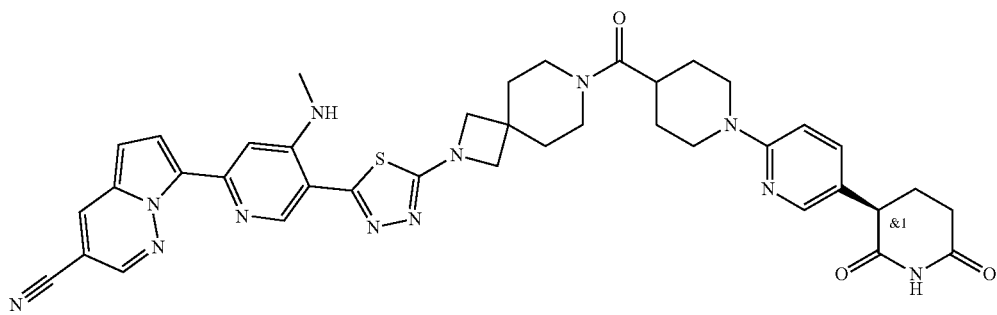 [SMILES: CNc1cc(-c2ccc3cc(C#N)cnn23)ncc1-c1nnc(N2CC3(CCN(C(=O)C4CCN(c5ccc([C@H]6CCC(=O)NC6=O)cn5)CC4)CC3)C2)s1]

rac-7-(5-{5-[7-(1-{5-[(3R)-2,6-dioxopiperidin-3-yl]
pyridin-2-yl}piperidine-4-carbonyl)-2,7-diazaspiro
[3.5]nonan-2-yl]-1,3,4-thiadiazol-2-yl}-4-(methyl-
amino)pyridin-2-yl)pyrrolo[1,2-b]pyridazine-3-
carbonitrile The title compound was synthesized from Intermediate G and HA-9 by amide coupling using General Method A. LCMS: $C_{39}H_{40}N_{12}O_3S$ requires: 756.3, found: m/z=757.1 [M+H]$^+$. $^1$H NMR (500 MHz, DMSO-d$_6$) δ 10.88 (s, 3H), 8.97 (s, 2H), 8.84 (s, 1H), 8.55 (s, 1H), 8.02 (d, J=28.7 Hz, 2H), 7.93 (s, 1H), 7.23 (d, J=4.9 Hz, 2H), 4.25 (d, J=12.8 Hz, 2H), 3.99 (d, J=6.9 Hz, 4H), 3.53 (d, J=49.2 Hz, 16H), 3.19 (d, J=4.6 Hz, 3H), 1.99 (d, J=9.2 Hz, 2H), 1.87 (s, 2H), 1.74 (d, J=28.1 Hz, 3H), 1.60 (d, J=12.0 Hz, 2H).

Example 41

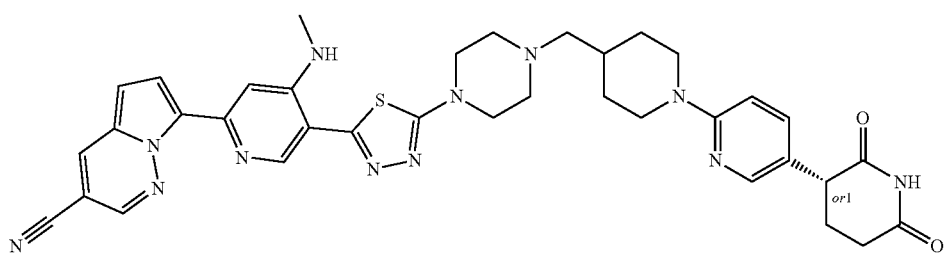 [SMILES: CNc1cc(-c2ccc3cc(C#N)cnn23)ncc1-c1nnc(N2CCN(CC3CCN(c4ccc([C@H]5CCC(=O)NC5=O)cn4)CC3)CC2)s1]

7-[5-(5-{4-[(1-{5-[(3R)-2,6-dioxopiperidin-3-yl]
pyridin-2-yl}piperidin-4-yl)methyl]piperazin-1-yl}-
1,3,4-thiadiazol-2-yl)-4-(methylamino)pyridin-2-yl]
pyrrolo[1,2-b]pyridazine-3-carbonitrile The title compound was synthesized from Intermediate C and HA-1 by reductive amination using General Method B, followed by chiral SFC to give the title compound. LCMS: $C_{38}H_{38}N_{12}O_2S$ requires: 702.3, found: m/z=703.4 [M+H]$^+$.

Example 42

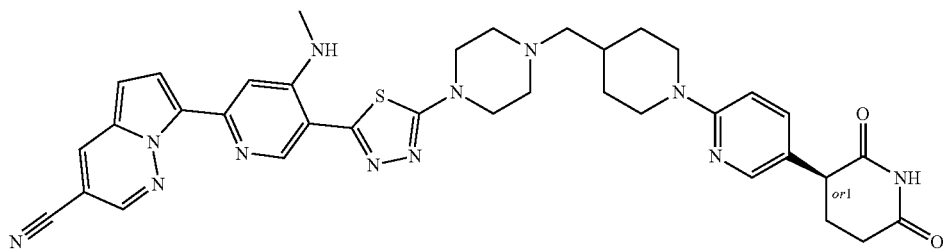 [SMILES: CNc1cc(-c2ccc3cc(C#N)cnn23)ncc1-c1nnc(N2CCN(CC3CCN(c4ccc([C@@H]5CCC(=O)NC5=O)cn4)CC3)CC2)s1]

7-[5-(5-{4-[(1-{5-[(3S)-2,6-dioxopiperidin-3-yl]
pyridin-2-yl}piperidin-4-yl)methyl]piperazin-1-yl}-
1,3,4-thiadiazol-2-yl)-4-(methylamino)pyridin-2-yl]
pyrrolo[1,2-b]pyridazine-3-carbonitrile The title compound was synthesized from Intermediate C and HA-1 by reductive amination using General Method B, followed by chiral SFC to give the title compound. LCMS: $C_{36}H_{38}N_{12}O_2S$ requires: 702.3, found: m/z=703.4 [M+H]$^+$.

Example 43

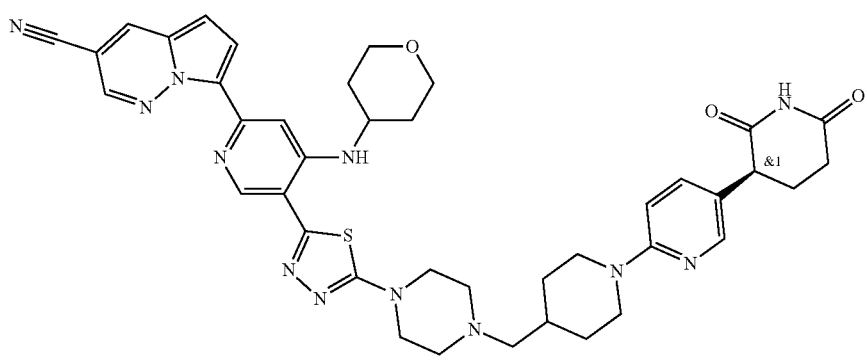 [SMILES: N#Cc1cnn2c(-c3cc(NC4CCOCC4)c(-c4nnc(N5CCN(CC6CCN(c7ccc([C@@H]8CCC(=O)NC8=O)cn7)CC6)CC5)s4)cn3)ccc2c1]

rac-7-[5-(5-{4-[(1-{5-[(3R)-2,6-dioxopiperidin-3-yl]
pyridin-2-yl}piperidin-4-yl)methyl]piperazin-1-yl}-
1,3,4-thiadiazol-2-yl)-4-[(oxan-4-yl)amino]pyridin-
2-yl]pyrrolo[1,2-b]pyridazine-3-carbonitrile The title compound was synthesized from Intermediate A and HA-1 by reductive amination using General Method B. LCMS: $C_{40}H_{44}N_{12}O_3S$ requires: 772.3, found: m/z=773.6 [M+H]$^+$. $^1$H NMR (500 MHz, MeOD) δ 8.78 (d, J=2.1 Hz, 1H), 8.70 (d, J=2.2 Hz, 1H), 8.62 (s, 1H), 8.14 (d, J=5.1 Hz, 1H), 8.05-7.93 (m, 2H), 7.89 (d, J=2.2 Hz, 1H), 7.45 (d, J=9.6 Hz, 1H), 7.25 (d, J=5.0 Hz, 1H), 4.39-4.21 (m, 3H), 4.05 (dt, J=12.3, 4.1 Hz, 6H), 4.02-3.89 (m, 2H), 3.74 (ddd, J=12.2, 10.2, 2.5 Hz, 3H), 3.61 (s, 4H), 3.39 (d, J=11.7 Hz, 2H), 3.25 (d, J=6.9 Hz, 3H), 2.86-2.70 (m, 2H), 2.52-2.39 (m, 1H), 2.33 (qd, J=12.8, 5.3 Hz, 1H), 2.21 (ddt, J=8.0, 5.6, 2.9 Hz, 3H), 2.12 (d, J=13.2 Hz, 2H), 1.80 (dtd, J=13.7, 9.9, 4.1 Hz, 2H), 1.54 (qd, J=12.5, 4.0 Hz, 2H).

Example 44

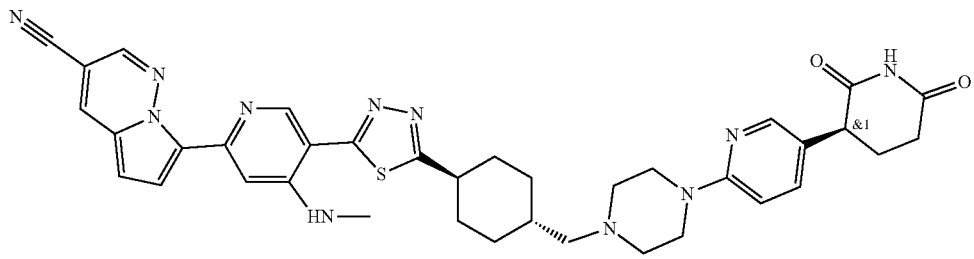 [SMILES: CNc1cc(-c2ccc3cc(C#N)cnn23)ncc1-c1nnc([C@H]2CC[C@H](CN3CCN(c4ccc([C@@H]5CCC(=O)NC5=O)cn4)CC3)CC2)s1]

7-[4-(methylamino)-5-{5-[(1r,4r)-4-[(4-{5-[(3RS)-2, 6-dioxopiperidin-3-yl]pyridin-2-yl}piperazin-1-yl) methyl]cyclohexyl]-1,3,4-thiadiazol-2-yl}pyridin-2-yl]pyrrolo[1,2-b]pyridazine-3-carbonitrile The title compound was synthesized from Intermediate N and HA-10 by reductive amination using General Method B. LCMS: $C_{37}H_{39}N_{11}O_2S$ requires: 701.3, found: m/z=702.6 [M+H]$^+$. $^1$H NMR (500 MHz, MeOD) δ 8.80 (d, J=2.1 Hz, 1H), 8.74 (s, 1H), 8.71 (d, J=2.1 Hz, 1H), 8.12 (dd, J=7.8, 3.8 Hz, 2H), 7.92 (s, 1H), 7.61 (dd, J=8.8, 2.5 Hz, 1H), 7.27 (d, J=5.1 Hz, 1H), 7.01 (d, J=8.8 Hz, 1H), 3.86 (dd, J=12.0, 5.1 Hz, 1H), 3.37 (s, 4H), 3.24 (q, J=7.3 Hz, 2H), 3.18 (d, J=6.5 Hz, 3H), 2.84-2.66 (m, 3H), 2.39 (d, J=13.0 Hz, 2H), 2.33-2.15 (m, 3H), 2.15-2.05 (m, 4H), 1.84 (q, J=12.6 Hz, 2H), 1.41 (q, J=11.8 Hz, 2H), 1.34 (t, J=7.4 Hz, 2H).

Example 45

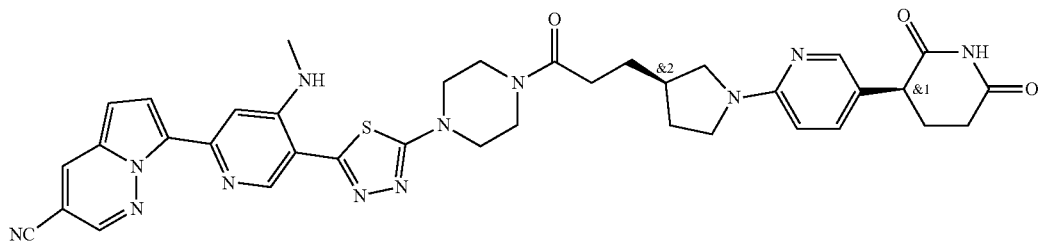 [SMILES: CNc1cc(-c2ccc3cc(C#N)cnn23)ncc1-c1nnc(N2CCN(C(=O)CC[C@@H]3CCN(c4ccc([C@@H]5CCC(=O)NC5=O)cn4)C3)CC2)s1]

7-{5-[5-(4-{3-[(3RS)-1-{5-[(3RS&)-2,6-dioxopiperidin-3-yl]pyridin-2-yl}pyrrolidin-3-yl]propanoyl}piperazin-1-yl)-1,3,4-thiadiazol-2-yl]-4-(methylamino)pyridin-2-yl}pyrrolo[1,2-b]pyridazine-3-carbonitrile The title compound was synthesized from Intermediate C and HA-11 by amide coupling using General Method A. LCMS: $C_{37}H_{38}N_{12}O_3S$ requires: 730.3, found: m/z=731.6 [M+H]$^+$. $^1$H NMR (500 MHz, Methanol-d$_4$) δ 8.79 (s, 1H), 8.70 (s, 1H), 8.53 (s, 1H), 8.12 (d, J=5.2 Hz, 1H), 7.95 (d, J=9.4 Hz, 1H), 7.84 (d, J=11.5 Hz, 2H), 7.26 (d, J=5.2 Hz, 1H), 7.13 (d, J=9.4 Hz, 1H), 3.95 (dd, J=12.8, 4.9 Hz, 2H), 3.89-3.73 (m, 9H), 3.71 (t, J=5.5 Hz, 2H), 3.61 (q, J=9.1 Hz, 2H), 2.85-2.71 (m, 2H), 2.64 (q, J=7.7 Hz, 2H), 2.60-2.45 (m, 1H), 2.45-2.23 (m, 3H), 2.21 (s, 1H), 1.97-1.79 (m, 3H).

Example 46

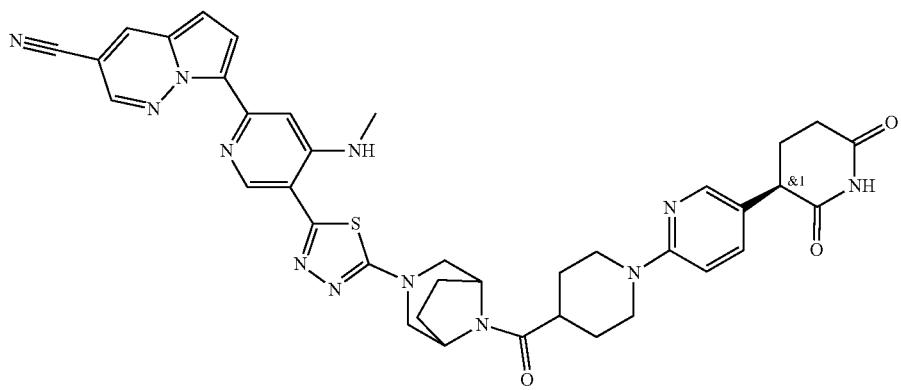 [SMILES: CNc1cc(-c2ccc3cc(C#N)cnn23)ncc1-c1nnc(N2CC3CCC(C2)N3C(=O)C2CCN(c3ccc([C@H]4CCC(=O)NC4=O)cn3)CC2)s1]

rac-7-(5-{5-[8-(1-{5-[(3R)-2,6-dioxopiperidin-3-yl]
pyridin-2-yl}piperidine-4-carbonyl)-3,8-diazabicyclo
[3.2.1]octan-3-yl]-1,3,4-thiadiazol-2-yl}-4-(methyl-
amino)pyridin-2-yl)pyrrolo [1,2-b]pyridazine-3-
carbonitrile The title compound was synthesized from Intermediate L and HA-9 by amide coupling using General Method A. LCMS: $C_{38}H_{38}N_{12}O_3S$ requires: 742.3, found: m/z=743.7 [M+H]$^+$. $^1$H NMR (500 MHz, Methanol-d$_4$) δ 8.79 (d, J=2.2 Hz, 1H), 8.70 (d, J=2.3 Hz, 1H), 8.52 (s, 1H), 8.11 (d, J=4.9 Hz, 1H), 7.99-7.91 (m, 1H), 7.90 (s, 1H), 7.85 (s, 1H), 7.38 (d, J=9.4 Hz, 1H), 7.26 (d, J=5.0 Hz, 1H), 4.27 (t, J=13.7 Hz, 2H), 4.05-3.84 (m, 3H), 3.81 (d, J=11.9 Hz, 1H), 3.58 (t, J=12.8 Hz, 4H), 3.42 (d, J=12.7 Hz, 3H), 3.14 (d, J=11.6 Hz, 2H), 2.83-2.71 (m, 2H), 2.32 (qd, J=12.7, 5.1 Hz, 1H), 2.21 (s, 2H), 2.12-1.78 (m, 8H).

Example 47

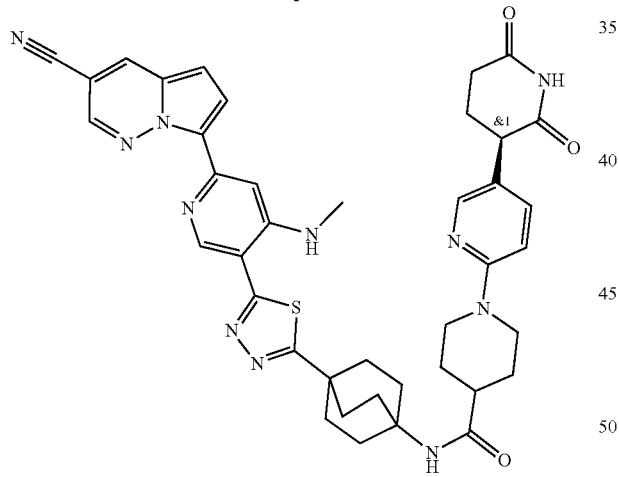

rac-N—{4-[5-(6-{3-cyanopyrrolo[1,2-b]pyridazin-7-
yl}-4-(methylamino)pyridin-3-yl)-1,3,4-thiadiazol-2-
yl]bicyclo[2.2.2]octan-1-yl}-1-{5-[(3R)-2,6-dioxopi-
peridin-3-yl]pyridin-2-yl}piperidine-4-carboxamide The title compound was synthesized from Intermediate K and HA-9 by amide coupling using General Method A. LCMS: $C_{40}H_{41}N_{11}O_3S$ requires: 755.3, found: m/z=756.7 [M+H]$^+$. $^1$H NMR (500 MHz, Methanol-d$_4$) δ 8.81 (d, J=4.6 Hz, 1H), 8.72 (d, J=4.9 Hz, 2H), 8.13 (d, J=5.3 Hz, 1H), 7.98 (d, J=9.2 Hz, 1H), 7.91 (dd, J=18.3, 5.6 Hz, 2H), 7.67 (d, J=5.0 Hz, 1H), 7.43 (t, J=7.7 Hz, 1H), 7.27 (d, J=5.3 Hz, 1H), 4.25 (d, J=13.3 Hz, 2H), 3.97 (dd, J=13.0, 5.5 Hz, 1H), 2.92-2.65 (m, 3H), 2.63 (d, J=11.2 Hz, 1H), 2.33 (tt, J=10.9, 5.5 Hz, 3H), 2.26-2.11 (m, 12H), 1.97 (d, J=13.6 Hz, 2H), 1.85 (t, J=12.0 Hz, 2H).

Example 48

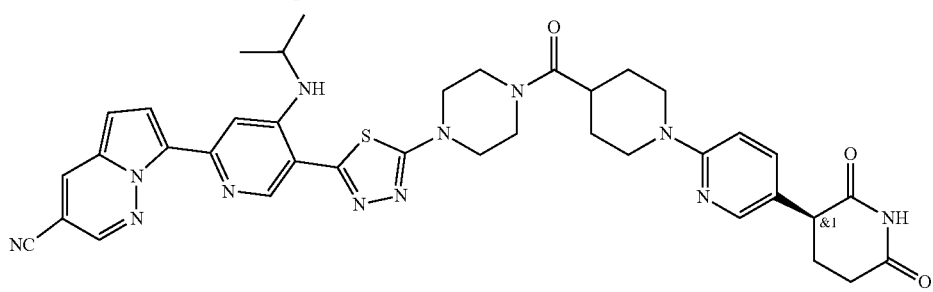 [SMILES: CC(C)Nc1cc(-c2ccc3cc(C#N)cnn23)ncc1-c1nnc(N2CCN(C(=O)C3CCN(c4ccc([C@@H]5CCC(=O)NC5=O)cn4)CC3)CC2)s1]

rac-7-(5-{5-[4-(1-{5-[(3R)-2,6-dioxopiperidin-3-yl] pyridin-2-yl}piperidine-4-carbonyl) piperazin-1-yl]-1,3,4-thiadiazol-2-yl}-4-[(propan-2-yl)amino]pyridin-2-yl)pyrrolo[1,2-b]pyridazine-3-carbonitrile The title compound was synthesized from Intermediate B and HA-9 by amide coupling using General Method A. LCMS: $C_{38}H_{40}N_{12}O_3S$ requires: 744.3, found: m/z=745.4 [M+H]$^+$. $^1$H NMR (500 MHz, Methanol-d$_4$) δ 8.79 (d, J=2.4 Hz, 1H), 8.70 (d, J=2.3 Hz, 1H), 8.54 (dd, J=3.3, 1.6 Hz, 1H), 8.09 (d, J=5.0 Hz, 1H), 7.99 (d, J=9.3 Hz, 1H), 7.90 (d, J=13.5 Hz, 2H), 7.51-7.34 (m, 1H), 7.26 (d, J=5.0 Hz, 1H), 4.43-4.16 (m, 3H), 4.06-3.89 (m, 3H), 3.84 (d, J=19.4 Hz, 4H), 3.71 (d, J=5.3 Hz, 2H), 3.43 (d, J=13.1 Hz, 4H), 3.25 (s, 1H), 2.88-2.66 (m, 2H), 2.32 (td, J=12.8, 5.2 Hz, 1H), 2.26-2.16 (m, 1H), 2.12-1.96 (m, 2H), 1.96-1.81 (m, 2H), 1.50 (d, J=6.3 Hz, 6H).

Example 49

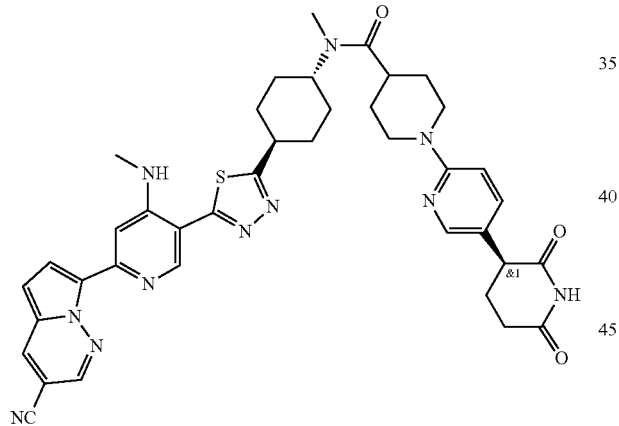

1-{5-[(3RS)-2,6-dioxopiperidin-3-yl]pyridin-2-yl}-N-methyl-N—[(1r,4r)-4-[5-(6-{3-cyanopyrrolo[1,2-b]pyridazin-7-yl}-4-(methylamino)pyridin-3-yl)-1,3,4-thiadiazol-2-yl]cyclohexyl]piperidine-4-carboxamide The title compound was synthesized from Intermediate I and HA-9 by amide coupling using General Method A. LCMS: $C_{39}H_{41}N_{11}O_3S$ requires: 743.3, found: m/z=744.5 [M+H]$^+$. $^1$H NMR (500 MHz, Methanol-d$_4$) δ 8.78 (d, J=2.2 Hz, 1H), 8.75-8.66 (m, 2H), 8.12 (dd, J=5.1, 2.3 Hz, 1H), 8.01-7.91 (m, 2H), 7.89 (d, J=2.3 Hz, 1H), 7.38 (dd, J=9.5, 5.1 Hz, 1H), 7.26 (d, J=4.9 Hz, 1H), 4.32-4.14 (m, 2H), 4.06 (s, 1H), 3.95 (dd, J=12.8, 4.9 Hz, 2H), 3.42 (t, J=6.4 Hz, 3H), 3.11 (s, 3H), 2.91 (s, 1H), 2.86-2.67 (m, 2H), 2.42 (d, J=17.1 Hz, 2H), 2.32 (tt, J=12.5, 6.2 Hz, 1H), 2.21 (dtd, J=11.3, 6.2, 5.7, 3.3 Hz, 2H), 2.09-1.90 (m, 6H), 1.86 (dt, J=16.3, 7.9 Hz, 5H).

Example 50

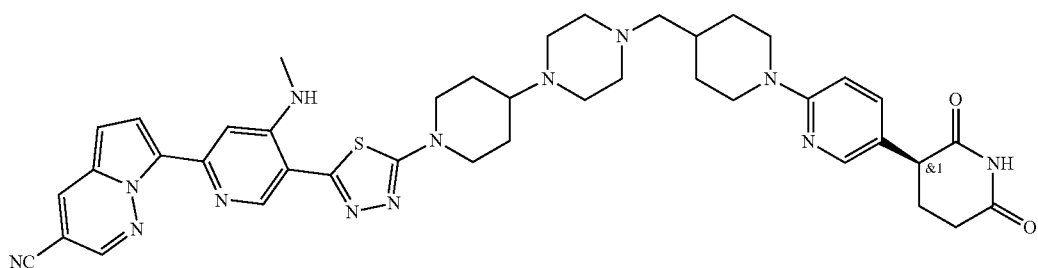 [SMILES: CNc1cc(-c2ccc3cc(C#N)cnn23)ncc1-c1nnc(N2CCC(N3CCN(CC4CCN(c5ccc([C@@H]6CCC(=O)NC6=O)cn5)CC4)CC3)CC2)s1]

7-[5-(5-{4-[4-({1-[5-(2,6-dioxopiperidin-3-yl)pyridin-2-yl]piperidin-4-yl}methyl)piperazin-1-yl]piperidin-1-yl}-1,3,4-thiadiazol-2-yl)-4-(methylamino)pyridin-2-yl]pyrrolo[1,2-b]pyridazine-3-carbonitrile The title compound was synthesized from Intermediate J and HA-1 by reductive amination using General Method B. LCMS: $C_{41}H_{47}N_{13}O_2S$ requires: 785.4, found: m/z=786.7 [M+H]$^+$. $^1$H NMR (500 MHz, Methanol-d$_4$) δ 8.79 (d, J=2.3 Hz, 1H), 8.70 (d, J=2.3 Hz, 1H), 8.52 (s, 1H), 8.12 (d, J=5.0 Hz, 1H), 7.96 (dd, J=9.5, 2.4 Hz, 1H), 7.86 (d, J=14.3 Hz, 2H), 7.40 (d, J=9.5 Hz, 1H), 7.26 (d, J=5.0 Hz, 1H), 4.23 (t, J=11.7 Hz, 4H), 3.95 (dd, J=13.0, 4.8 Hz, 1H), 2.89-2.67 (m, 5H), 2.41-2.09 (m, 6H), 2.05 (d, J=13.4 Hz, 3H), 1.87 (tt, J=12.6, 7.1 Hz, 3H), 1.42 (q, J=12.8, 11.8 Hz, 2H).

Example 51

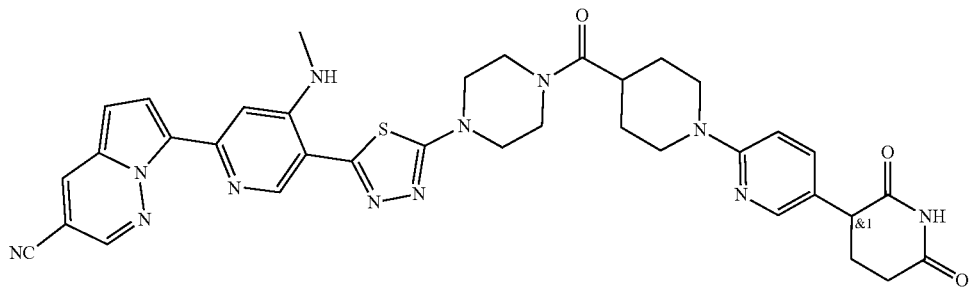 [SMILES: CNc1cc(-c2ccc3cc(C#N)cnn23)ncc1-c1nnc(N2CCN(C(=O)C3CCN(c4ccc(C5CCC(=O)NC5=O)cn4)CC3)CC2)s1]

7-{5-[5-(4-{1-[5-(2,6-dioxopiperidin-3-yl)pyridin-2-yl]piperidine-4-carbonyl}piperazin-1-yl)-1,3,4-thiadiazol-2-yl]-4-(methylamino)pyridin-2-yl}pyrrolo[1,2-b]pyridazine-3-carbonitrile The title compound was synthesized from Intermediate C and HA-9 by amide coupling using General Method A. LCMS: $C_{36}H_{36}N_{12}O_3S$ requires: 716.3, found: m/z=717.5 [M+H]$^+$. $^1$H NMR (500 MHz, Methanol-d$_4$) δ 8.78 (s, 1H), 8.70 (s, 1H), 8.52 (s, 1H), 8.15-8.05 (m, 1H), 7.90 (s, 2H), 7.86 (s, 1H), 7.34 (d, J=9.4 Hz, 1H), 7.25 (d, J=5.0 Hz, 1H), 4.27 (d, J=13.6 Hz, 3H), 3.94 (d, J=16.2 Hz, 4H), 3.84 (d, J=19.2 Hz, 5H), 3.71 (s, 3H), 3.22 (s, 2H), 2.79 (d, J=18.2 Hz, 2H), 2.31 (dd, J=15.8, 11.0 Hz, 1H), 2.21 (s, 1H), 2.00 (d, J=13.6 Hz, 2H), 1.89 (q, J=13.6, 12.9 Hz, 2H), 1.48 (s, 1H), 1.36 (d, J=41.4 Hz, 1H), 0.12 (s, 1H).

Example 52

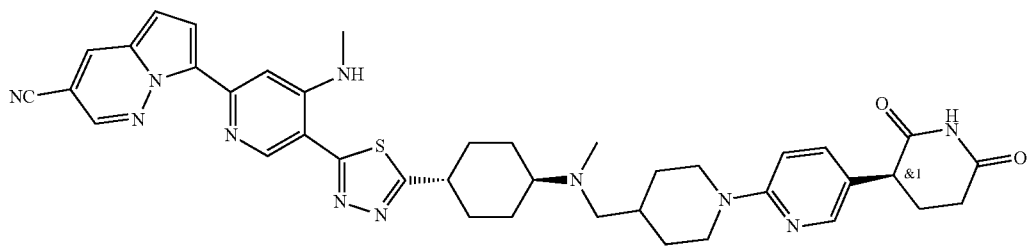 [SMILES: CNc1cc(-c2ccc3cc(C#N)cnn23)ncc1-c1nnc([C@H]2CC[C@H](N(C)CC3CCN(c4ccc([C@@H]5CCC(=O)NC5=O)cn4)CC3)CC2)s1]

7-[4-(methylamino)-5-{5-[(1r,4r)-4-{[(1-{5-[(3RS)-
2,6-dioxopiperidin-3-yl]pyridin-2-yl}piperidin-4-yl)
methyl](methyl)amino}cyclohexyl]-1,3,4-thiadiazol-
2-yl}pyridin-2-yl]pyrrolo[1,2-b]pyridazine-3-
carbonitrile The title compound was synthesized from Intermediate I and HA-1 by reductive amination using General Method B. LCMS: $C_{39}H_{43}N_{11}O_2S$ requires: 729.3, found: m/z=730.5 [M+H]$^+$. $^1$H NMR (500 MHz, Methanol-d$_4$) δ 8.79 (s, 1H), 8.75 (s, 1H), 8.71 (s, 1H), 8.13 (d, J=5.1 Hz, 1H), 7.94 (d, J=6.9 Hz, 2H), 7.87 (d, J=9.4 Hz, 1H), 7.28 (dd, J=22.0, 7.2 Hz, 2H), 4.32 (d, J=13.4 Hz, 3H), 3.93 (dd, J=12.8, 5.0 Hz, 2H), 3.52 (q, J=6.7 Hz, 10H), 3.12 (s, 2H), 2.98 (s, 3H), 2.84-2.65 (m, 3H), 2.50 (s, 3H), 2.37-2.23 (m, 5H), 2.23-1.80 (m, 9H), 1.51 (s, 3H), 1.21 (t, J=7.0 Hz, 9H).

Example 53

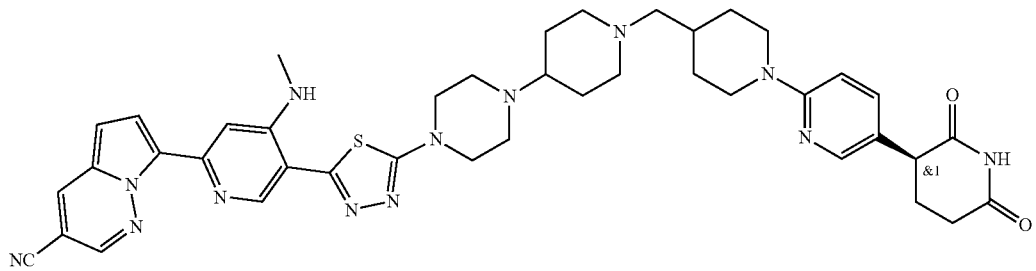 [SMILES: CNc1cc(-c2ccc3cc(C#N)cnn23)ncc1-c1nnc(N2CCN(C3CCN(CC4CCN(c5ccc([C@@H]6CCC(=O)NC6=O)cn5)CC4)CC3)CC2)s1]

rac-7-{5-[5-(4-{1-[(1-{5-[(3R)-2,6-dioxopiperidin-3-
yl]pyridin-2-yl}piperidin-4-yl)methyl]piperidin-4-
yl}piperazin-1-yl)-1,3,4-thiadiazol-2-yl]-4-(methyl-
amino)pyridin-2-yl}pyrrolo[1,2-b]pyridazine-3-
carbonitrile The title compound was synthesized from Intermediate V and HA-1 by reductive amination using General Method B. LCMS: $C_{41}H_{47}N_{13}O_2S$ requires: 785.4, found: m/z=786.8 [M+H]$^+$. $^1$H NMR (500 MHz, Methanol-d$_4$) δ 8.78 (d, J=2.3 Hz, 1H), 8.70 (d, J=2.3 Hz, 1H), 8.54 (d, J=2.9 Hz, 1H), 8.12 (d, J=4.9 Hz, 1H), 7.97 (dt, J=9.5, 2.6 Hz, 1H), 7.89 (d, J=2.4 Hz, 1H), 7.85 (d, J=2.6 Hz, 1H), 7.40 (dd, J=9.5, 2.6 Hz, 1H), 7.26 (d, J=5.0 Hz, 1H), 4.27 (d, J=13.5 Hz, 2H), 3.96 (dt, J=12.9, 3.9 Hz, 1H), 3.92-3.66 (m, 6H), 3.28-3.18 (m, 5H), 3.14 (d, J=6.8 Hz, 4H), 2.90-2.69 (m, 3H), 2.32 (dtd, J=17.9, 12.5, 11.4, 5.0 Hz, 4H), 2.24-2.12 (m, 3H), 2.07 (d, J=13.4 Hz, 3H), 1.50 (qd, J=13.0, 3.9 Hz, 2H), 1.40 (dq, J=8.1, 4.3, 3.6 Hz, 3H).

Example 54

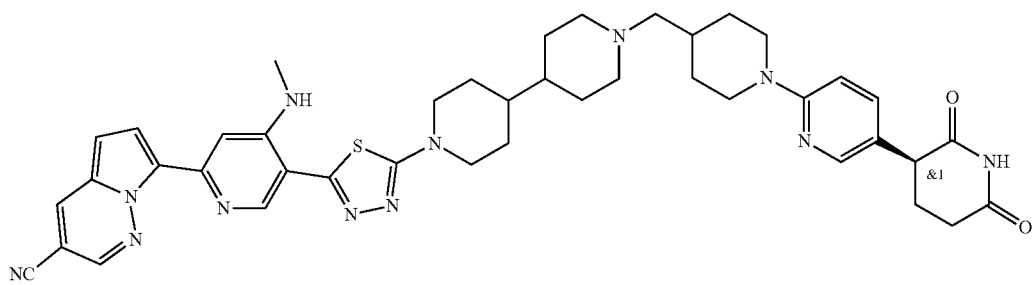 [SMILES: CNc1cc(-c2ccc3cc(C#N)cnn23)ncc1-c1nnc(N2CCC(C3CCN(CC4CCN(c5ccc([C@@H]6CCC(=O)NC6=O)cn5)CC4)CC3)CC2)s1]

rac-7-[5-(5-{1'-[(1-{5-[(3R)-2,6-dioxopiperidin-3-yl]pyridin-2-yl}piperidin-4-yl)methyl]-[4,4'-bipiperidin]-1-yl}-1,3,4-thiadiazol-2-yl)-4-(methylamino)pyridin-2-yl]pyrrolo[1,2-b]pyridazine-3-carbonitrile The title compound was synthesized from Intermediate H and HA-1 by reductive amination using General Method B. LCMS: $C_{42}H_{48}N_{12}O_2S$ requires: 784.4, found: m/z=785.8 $[M+H]^+$. $^1$H NMR (500 MHz, DMSO-$d_6$) δ 10.86 (s, 1H), 9.23 (d, J=97.6 Hz, 1H), 9.01 (dd, J=34.8, 2.2 Hz, 1H), 8.84 (d, J=2.1 Hz, 2H), 8.53 (s, 1H), 8.05 (d, J=4.9 Hz, 1H), 8.01-7.89 (m, 2H), 7.55 (s, 1H), 7.23 (d, J=5.0 Hz, 1H), 7.01 (s, 1H), 4.28 (d, J=12.9 Hz, 2H), 4.00 (d, J=12.4 Hz, 2H), 3.79 (s, 2H), 3.26 (t, J=12.1 Hz, 6H), 3.19 (d, J=5.0 Hz, 3H), 2.99 (q, J=4.5 Hz, 3H), 2.95-2.82 (m, 3H), 2.70 (ddd, J=17.5, 12.5, 5.3 Hz, 2H), 2.29-2.02 (m, 2H), 2.02-1.93 (m, 1H), 1.93-1.72 (m, 5H), 1.59-1.12 (m, 7H).

Example 55

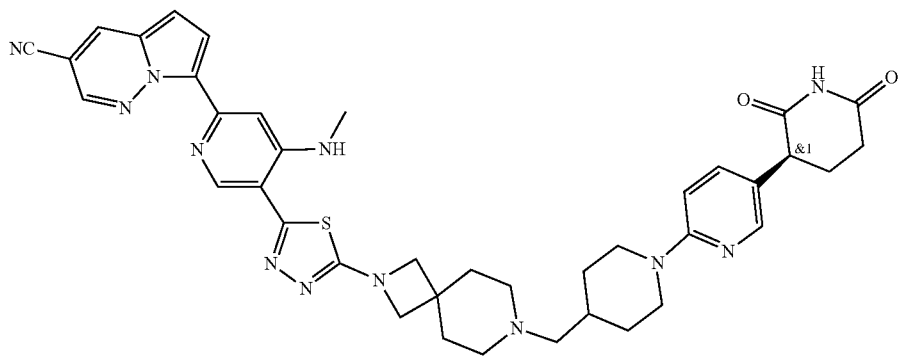 [SMILES: CNc1cc(-c2ccc3cc(C#N)cnn23)ncc1-c1nnc(N2CC3(CCN(CC4CCN(c5ccc([C@@H]6CCC(=O)NC6=O)cn5)CC4)CC3)C2)s1]

rac-7-[5-(5-{7-[(1-{5-[(3R)-2,6-dioxopiperidin-3-yl]pyridin-2-yl}piperidin-4-yl)methyl]-2,7-diazaspiro[3.5]nonan-2-yl}-1,3,4-thiadiazol-2-yl)-4-(methylamino)pyridin-2-yl]pyrrolo[1,2-b]pyridazine-3-carbonitrile Synthesized from Intermediate G and HA-1 by reductive amination using General Method B. LCMS: $C_{39}H_{42}N_{12}O_2S$ requires: 742.3, found: m/z=743.7 $[M+H]^+$.

Example 56

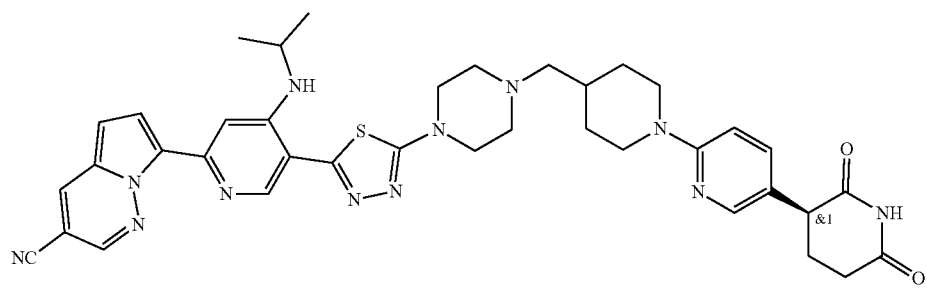 [SMILES: CC(C)Nc1cc(-c2ccc3cc(C#N)cnn23)ncc1-c1nnc(N2CCN(CC3CCN(c4ccc([C@@H]5CCC(=O)NC5=O)cn4)CC3)CC2)s1]

rac-7-[5-(5-{4-[(1-{5-[(3R)-2,6-dioxopiperidin-3-yl]
pyridin-2-yl}piperidin-4-yl)methyl]piperazin-1-yl}-
1,3,4-thiadiazol-2-yl)-4-[(propan-2-yl)amino]pyri-
din-2-yl]pyrrolo[1,2-b]pyridazine-3-carbonitrile The title compound was synthesized from Intermediate B and HA-1 by reductive amination using General Method B. LCMS: $C_{38}H_{42}N_{12}O_2S$ requires: 730.3, found: m/z=731.5 [M+H]$^+$. $^1$H NMR (500 MHz, DMSO-d$_6$) δ 10.88 (s, 1H), 9.74 (s, 1H), 9.20 (s, 1H), 8.96 (s, 1H), 8.82 (s, 1H), 8.60 (s, 1H), 8.11 (s, 1H), 8.01 (d, J=4.9 Hz, 1H), 7.95 (s, 1H), 7.62 (s, 1H), 7.22 (d, J=4.9 Hz, 1H), 7.10 (s, 1H), 4.29 (d, J=13.1 Hz, 3H), 4.13 (d, J=6.6 Hz, 4H), 3.82 (s, 6H), 3.13 (s, 4H), 2.99 (s, 5H), 2.69 (d, J=12.3 Hz, 3H), 2.34-2.10 (m, 4H), 1.99 (dt, J=13.4, 4.5 Hz, 2H), 1.87 (d, J=12.5 Hz, 2H), 1.38 (d, J=6.2 Hz, 8H), 1.28 (q, J=12.4 Hz, 3H).

Example 57

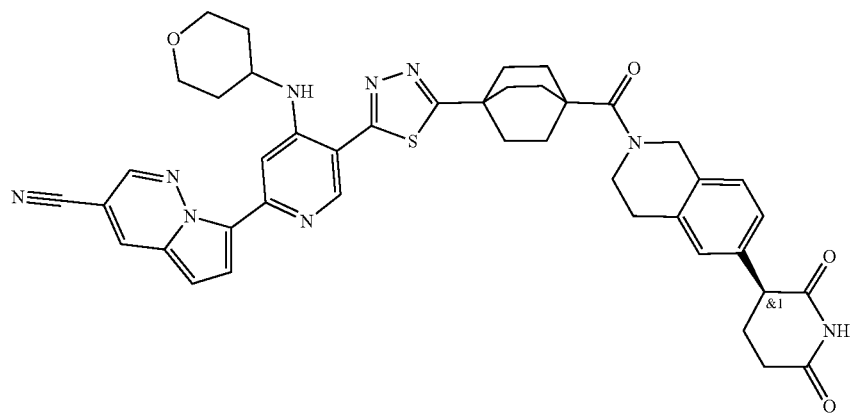 [SMILES: N#Cc1cnn2c(-c3cc(NC4CCOCC4)c(-c4nnc(C56CCC(C(=O)N7CCc8cc([C@@H]9CCC(=O)NC9=O)ccc8C7)(CC5)CC6)s4)cn3)ccc2c1]

rac-7-{5-[5-(4-{6-[(3R)-2,6-dioxopiperidin-3-yl]-1,
2,3,4-tetrahydroisoquinoline-2-carbonyl}bicyclo
[2.2.2]octan-1-yl)-1,3,4-thiadiazol-2-yl]-4-[(oxan-4-
yl)amino]pyridin-2-yl}pyrrolo[1,2-b]pyridazine-3-
carbonitrile The title compound was synthesized from Intermediate E and HA-5 by amide coupling using General Method A. LCMS: $C_{43}H_{43}N_9O_4S$ requires: 781.3, found: m/z=782.6 [M+H]$^+$. $^1$H NMR (500 MHz, DMSO) δ 10.82 (s, 1H), 9.18 (s, 1H), 8.91 (s, 1H), 8.83 (d, J=2.3 Hz, 1H), 8.76 (s, 1H), 8.26 (s, 1H), 7.95 (d, J=4.8 Hz, 1H), 7.19 (dd, J=10.6, 6.3 Hz, 2H), 7.07-7.00 (m, 2H), 4.72 (s, 2H), 4.01 (s, 1H), 3.95 (dt, J=11.7, 3.8 Hz, 2H), 3.86 (d, J=6.1 Hz, 2H), 3.80 (dd, J=11.5, 4.9 Hz, 1H), 3.65-3.56 (m, 2H), 2.81 (d, J=5.8 Hz, 2H), 2.65 (dt, J=17.0, 5.8 Hz, 1H), 2.23-2.09 (m, 3H), 2.09-1.98 (m, 16H), 1.73-1.58 (m, 2H), 1.23 (s, 1H).

Example 58

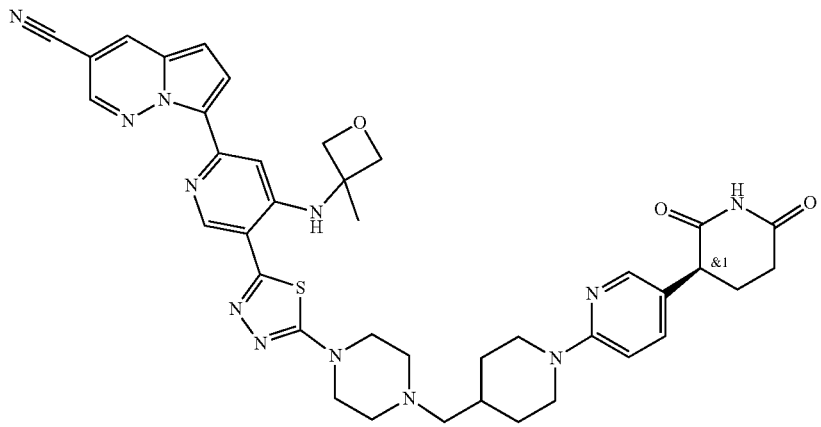 [SMILES: CC1(Nc2cc(-c3ccc4cc(C#N)cnn34)ncc2-c2nnc(N3CCN(CC4CCN(c5ccc([C@@H]6CCC(=O)NC6=O)cn5)CC4)CC3)s2)COC1]

rac-7-[5-(5-{4-[(1-{5-[(3R)-2,6-dioxopiperidin-3-yl]pyridin-2-yl}piperidin-4-yl)methyl]piperazin-1-yl}-1,3,4-thiadiazol-2-yl)-4-[(3-methyloxetan-3-yl)amino]pyridin-2-yl]pyrrolo[1,2-b]pyridazine-3-carbonitrile The title compound was synthesized from Intermediate W and HA-1 by reductive amination using General Method B. LCMS: $C_{39}H_{42}N_{12}O_3S$ requires: 758.3, found: m/z=759.5 [M+H]$^+$. $^1$H NMR (500 MHz, DMSO) δ 10.90 (s, 1H), 9.79 (s, 1H), 9.29 (s, 1H), 8.93-8.87 (m, 2H), 8.62 (s, 1H), 7.93 (d, J=4.9 Hz, 2H), 7.81 (s, 1H), 7.71 (s, 1H), 7.17 (d, J=4.8 Hz, 1H), 4.79 (d, J=6.4 Hz, 2H), 4.74 (d, J=6.4 Hz, 2H), 4.26 (d, J=13.2 Hz, 2H), 4.12 (s, 2H), 3.86 (dd, J=12.5, 4.9 Hz, 1H), 3.67 (s, 5H), 3.14 (s, 2H), 3.05 (s, 2H), 2.69 (ddd, J=17.7, 12.8, 5.4 Hz, 1H), 2.59-2.52 (m, 1H), 2.31-2.22 (m, 1H), 2.18 (s, 2H), 2.00-1.94 (m, 1H), 1.93-1.85 (m, 2H), 1.81 (s, 3H), 1.37-1.20 (m, 2H).

rac-7-{4-[(cyanomethyl)amino]-5-(5-{4-[(1-{5-[(3R)-2,6-dioxopiperidin-3-yl]pyridin-2-yl}piperidin-4-yl)methyl]piperazin-1-yl}-1,3,4-thiadiazol-2-yl)pyridin-2-yl}pyrrolo[1,2-b]pyridazine-3-carbonitrile The title compound was synthesized from Intermediate X and HA-1 by reductive amination using General Method B. LCMS: $C_{37}H_{37}N_{13}O_2S$ requires: 727.3, found: m/z=728.4 [M+H]$^+$. $^1$H NMR (500 MHz, DMSO) δ 10.85 (s, 1H), 9.54 (s, 1H), 8.89 (d, J=2.3 Hz, 1H), 8.69 (d, J=2.2 Hz, 1H), 8.66 (s, 1H), 8.31 (s, 1H), 7.94 (s, 1H), 7.90 (d, J=4.8 Hz, 1H), 7.16 (d, J=4.8 Hz, 1H), 4.73 (d, J=5.8 Hz, 2H), 4.29 (d, J=12.9 Hz, 2H), 4.11 (d, J=13.4 Hz, 2H), 3.15 (s, 2H), 2.92 (s, 3H), 1.91 (s, 1H), 1.84 (d, J=12.7 Hz, 2H), 1.25 (d, J=12.8 Hz, 5H).

Example 59

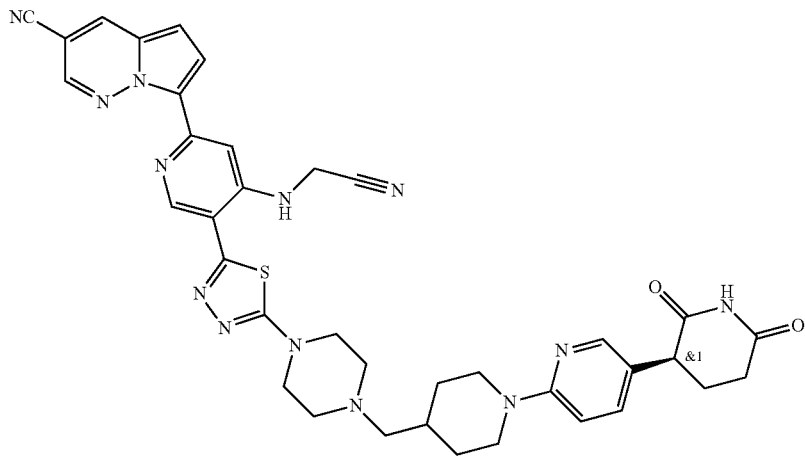 [SMILES: N#CCNc1cc(-c2ccc3cc(C#N)cnn23)ncc1-c1nnc(N2CCN(CC3CCN(c4ccc([C@@H]5CCC(=O)NC5=O)cn4)CC3)CC2)s1]

Example 60

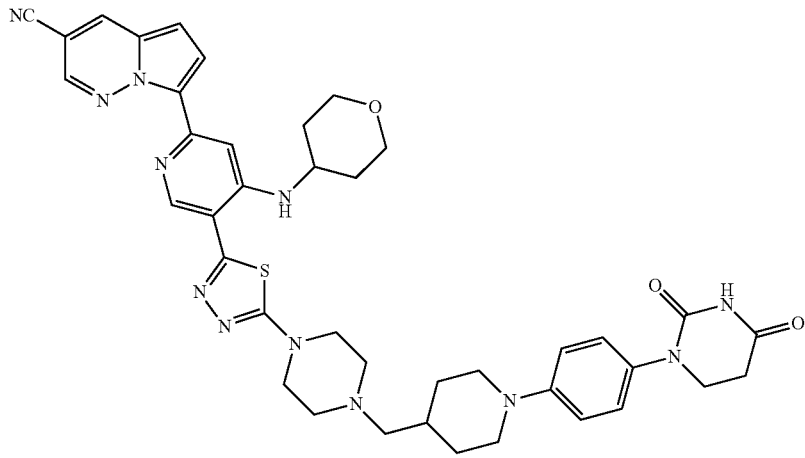 [SMILES: N#Cc1cnn2c(-c3cc(NC4CCOCC4)c(-c4nnc(N5CCN(CC6CCN(c7ccc(N8CCC(=O)NC8=O)cc7)CC6)CC5)s4)cn3)ccc2c1]

7-(5-{5-[4-({1-[4-(2,4-dioxo-1,3-diazinan-1-yl)phenyl]piperidin-4-yl}methyl)piperazin-1-yl]-1,3,4-thiadiazol-2-yl}-4-[(oxan-4-yl)amino]pyridin-2-yl)pyrrolo[1,2-b]pyridazine-3-carbonitrile The title compound was synthesized from Intermediate A and HA-21 by reductive amination using General Method B. LCMS: $C_{40}H_{44}N_{12}O_3S$ requires: 772.3, found: m/z=773.6 [M+H]$^+$. $^1$H NMR (500 MHz, DMSO) δ 10.27 (s, 1H), 9.51 (s, 1H), 8.90 (s, 1H), 8.81 (s, 1H), 8.58 (s, 1H), 8.24 (s, 1H), 7.91 (s, 1H), 7.16 (d, J=8.6 Hz, 2H), 6.97 (d, J=8.5 Hz, 2H), 4.12 (d, J=13.4 Hz, 2H), 3.93 (d, J=12.0 Hz, 2H), 3.28 (s, 3H), 3.16 (s, 2H), 2.73 (s, 2H), 2.69 (t, J=6.7 Hz, 2H), 2.11 (d, J=12.7 Hz, 2H), 2.03 (s, 1H), 1.85 (d, J=12.9 Hz, 2H), 1.58 (d, J=11.0 Hz, 2H), 1.35 (d, J=12.3 Hz, 2H), 1.24 (s, 1H).

rac-7-[5-(5-{4-[(1-{5-[(3R)-2,6-dioxopiperidin-3-yl]pyridin-2-yl}piperidin-4-yl)methyl] piperazin-1-yl}-1,3,4-thiadiazol-2-yl)-4-[(oxetan-3-yl)amino]pyridin-2-yl]pyrrolo[1,2-b]pyridazine-3-carbonitrile The title compound was synthesized from Intermediate Y and HA-1 by reductive amination using General Method B. LCMS: $C_{38}H_{40}N_{12}O_3S$ requires: 744.3, found: m/z=745.5 [M+H]$^+$. $^1$H NMR (500 MHz, DMSO) δ 10.80 (s, 1H), 8.94 (d, J=4.8 Hz, 1H), 8.86-8.79 (m, 2H), 8.55 (s, 1H), 7.96-7.89 (m, 2H), 7.85 (d, J=4.8 Hz, 1H), 7.36 (dd, J=8.9, 2.4 Hz, 1H), 7.12 (d, J=4.8 Hz, 1H), 6.79 (d, J=8.9 Hz, 1H), 5.06 (t, J=6.7 Hz, 2H), 4.91-4.84 (m, 1H), 4.59 (t, J=6.3 Hz, 2H), 4.27 (d, J=12.8 Hz, 2H), 3.72 (dd, J=12.1, 4.9 Hz, 1H), 3.57 (t, J=5.1 Hz, 4H), 2.78 (t, J=12.3 Hz, 2H), 2.73-2.63 (m, 1H), 2.23 (d, J=6.8 Hz, 2H), 2.16 (dd, J=14.4, 10.4 Hz, 1H), 1.97 (d, J=14.3 Hz, 1H), 1.79 (d, J=12.5 Hz, 3H), 1.23 (s, 1H), 1.11 (q, J=12.4 Hz, 2H).

Example 61

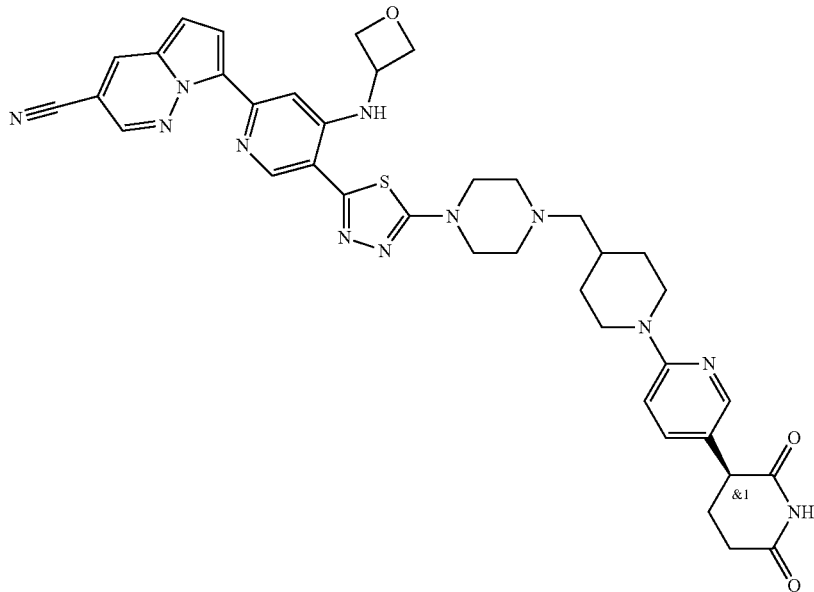 [SMILES: N#Cc1cnn2c(-c3cc(NC4COC4)c(-c4nnc(N5CCN(CC6CCN(c7ccc([C@@H]8CCC(=O)NC8=O)cn7)CC6)CC5)s4)cn3)ccc2c1]

Example 62

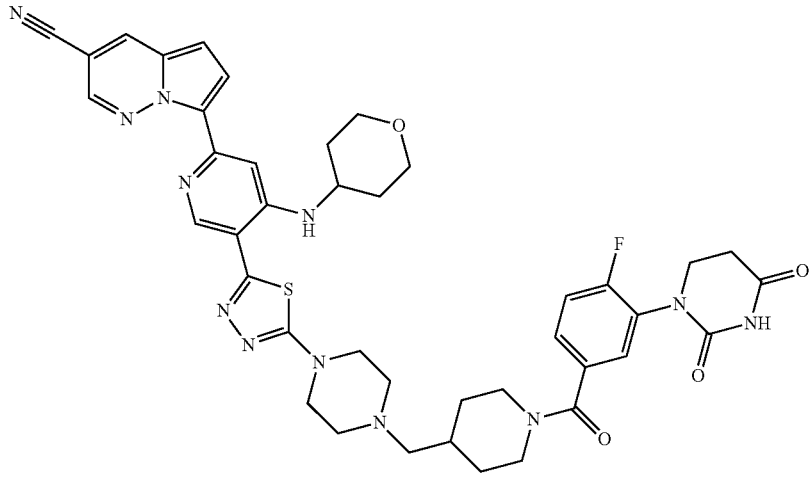 [SMILES: N#Cc1cnn2c(-c3cc(NC4CCOCC4)c(-c4nnc(N5CCN(CC6CCN(C(=O)c7ccc(F)c(N8CCC(=O)NC8=O)c7)CC6)CC5)s4)cn3)ccc2c1]

7-(5-{5-[4-({1-[3-(2,4-dioxo-1,3-diazinan-1-yl)-4-fluorobenzoyl]piperidin-4-yl}methyl) piperazin-1-yl]-1,3,4-thiadiazol-2-yl}-4-[(oxan-4-yl)amino]pyridin-2-yl)pyrrolo[1,2-b]pyridazine-3-carbonitrile The title compound was synthesized from Intermediate A and HA-22 by reductive amination using General Method B. LCMS: $C_{41}H_{43}FN_{12}O_4S$ requires: 818.3, found: m/z=819.4 [M+H]+. $^1$H NMR (500 MHz, DMSO) δ 10.54 (s, 1H), 9.55 (s, 1H), 8.90 (s, 1H), 8.81 (d, J=2.2 Hz, 1H), 8.58 (s, 1H), 8.23 (s, 1H), 7.92 (s, 1H), 7.51 (d, J=7.3 Hz, 1H), 7.40 (d, J=7.5 Hz, 2H), 7.17 (d, J=6.0 Hz, 2H), 7.08 (s, 1H), 6.98 (s, 1H), 4.47 (s, 1H), 4.11 (s, 2H), 3.98 (s, 1H), 3.93 (dt, J=11.9, 3.9 Hz, 2H), 3.76 (t, J=6.6 Hz, 2H), 3.66 (s, 2H), 3.59 (d, J=10.7 Hz, 1H), 3.27 (s, 2H), 3.13 (s, 3H), 2.84 (s, 2H), 2.74 (t, J=6.6 Hz, 2H), 2.54 (s, 1H), 2.11 (d, J=13.2 Hz, 2H), 1.86 (s, 1H), 1.73 (s, 1H), 1.62-1.55 (m, 2H), 1.24 (d, J=4.5 Hz, 2H).

Example 63

7-[5-(5-{4-[6-(2,4-dioxo-1,3-diazinan-1-yl)-1,2,3,4-tetrahydroisoquinoline-2-carbonyl]bicyclo[2.2.2]octan-1-yl}-1,3,4-thiadiazol-2-yl)-4-[(oxan-4-yl)amino]pyridin-2-yl]pyrrolo[1,2-b]pyridazine-3-carbonitrile The title compound was synthesized from Intermediate E and HA-23 by amide coupling using General Method A. LCMS: $C_{42}H_{42}N_{10}O_4S$ requires: 782.3, found: m/z=783.2 [M+H]+. $^1$H NMR (500 MHz, DMSO) δ 10.34 (s, 1H), 8.89 (s, 1H), 8.81 (d, J=2.3 Hz, 1H), 8.75 (s, 1H), 8.31 (s, 1H), 7.91 (s, 1H), 7.27 (d, J=8.3 Hz, 1H), 7.16 (dd, J=11.1, 6.6 Hz, 3H), 4.74 (s, 2H), 3.95 (d, J=11.6 Hz, 3H), 3.85 (s, 2H), 3.76 (t, J=6.6 Hz, 2H), 3.61 (t, J=10.9 Hz, 2H), 2.82 (s, 2H), 2.70 (t, J=6.7 Hz, 2H), 2.54 (s, 1H), 2.13 (d, J=12.6 Hz, 2H), 2.09-2.00 (m, 13H), 1.63 (d, J=10.8 Hz, 2H), 1.24 (s, 2H).

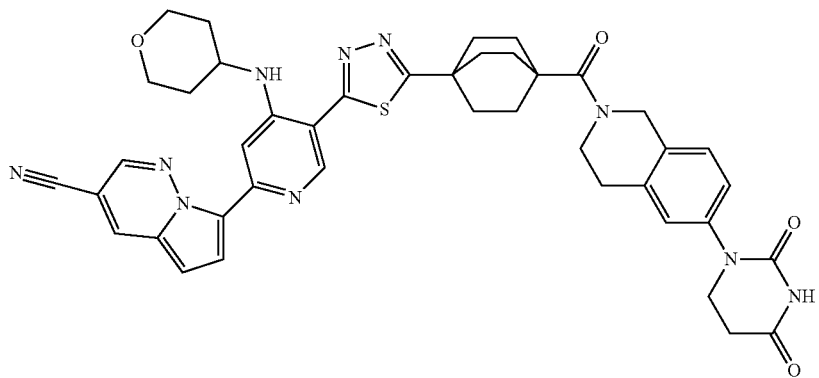 [SMILES: N#Cc1cnn2c(-c3cc(NC4CCOCC4)c(-c4nnc(C56CCC(C(=O)N7CCc8cc(N9CCC(=O)NC9=O)ccc8C7)(CC5)CC6)s4)cn3)ccc2c1]

Example 64

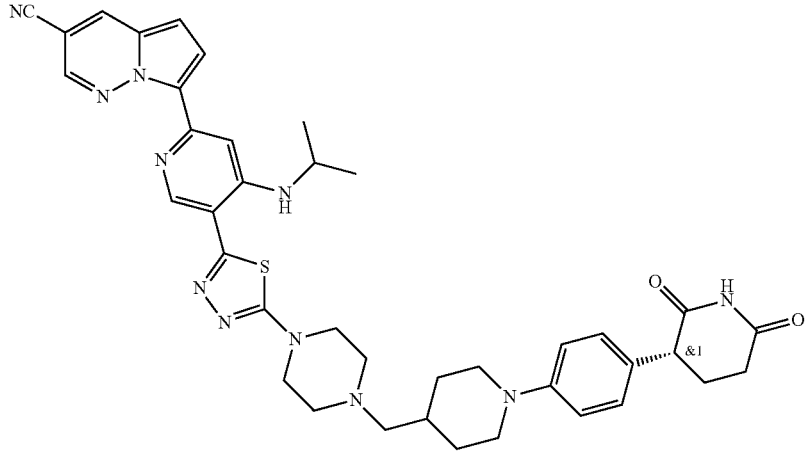 [SMILES: CC(C)Nc1cc(-c2ccc3cc(C#N)cnn23)ncc1-c1nnc(N2CCN(CC3CCN(c4ccc([C@H]5CCC(=O)NC5=O)cc4)CC3)CC2)s1]

rac-7-[5-(5-{4-[(1-{4-[(3R)-2,6-dioxopiperidin-3-yl]phenyl}piperidin-4-yl)methyl]piperazin-1-yl}-1,3,4-thiadiazol-2-yl)-4-[(propan-2-yl)amino]pyridin-2-yl]pyrrolo[1,2-b]pyridazine-3-carbonitrile The title compound was synthesized from Intermediate B and HA-7 by reductive amination using General Method B. LCMS: $C_{39}H_{43}N_{11}O_2S$ requires: 729.3, found: m/z=730.6 [M+H]$^+$. $^1$H NMR (500 MHz, DMSO) δ 10.79 (s, 1H), 9.57 (s, 1H), 8.94 (s, 1H), 8.81 (s, 1H), 8.58 (s, 1H), 8.14 (d, J=5.8 Hz, 1H), 8.01-7.96 (m, 1H), 7.20 (d, J=4.9 Hz, 1H), 7.08 (d, J=8.0 Hz, 2H), 6.95 (d, J=8.3 Hz, 2H), 4.11 (s, 3H), 3.78-3.71 (m, 3H), 3.17 (s, 2H), 2.74 (s, 1H), 2.65 (td, J=12.1, 5.6 Hz, 1H), 2.21-2.09 (m, 1H), 2.06-1.97 (m, 2H), 1.86 (d, J=12.6 Hz, 2H), 1.37 (d, J=6.3 Hz, 7H).

Example 65

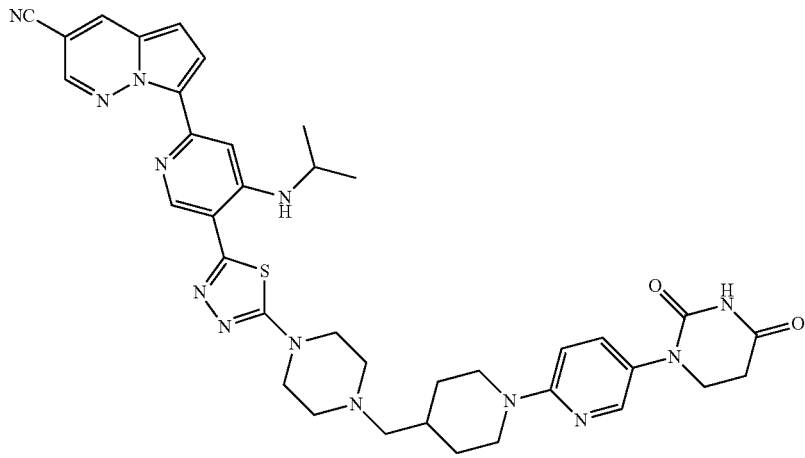 [SMILES: CC(C)Nc1cc(-c2ccc3cc(C#N)cnn23)ncc1-c1nnc(N2CCN(CC3CCN(c4ccc(N5CCC(=O)NC5=O)cn4)CC3)CC2)s1]

7-(5-{5-[4-({1-[5-(2,4-dioxo-1,3-diazinan-1-yl)pyridin-2-yl]piperidin-4-yl}methyl)piperazin-1-yl]-1,3,4-thiadiazol-2-yl}-4-[(propan-2-yl)amino]pyridin-2-yl)pyrrolo[1,2-b]pyridazine-3-carbonitrile The title compound was synthesized from Intermediate B and HA-19 by reductive amination using General Method B. LCMS: $C_{37}H_{41}N_{13}O_2S$ requires: 731.3, found: m/z=732.6 [M+H]$^+$. $^1$H NMR (500 MHz, DMSO) δ 10.37 (s, 1H), 9.59 (s, 1H), 9.11 (s, 1H), 8.94 (d, J=2.2 Hz, 1H), 8.81 (d, J=2.3 Hz, 1H), 8.59 (s, 1H), 8.12 (s, 1H), 8.07 (d, J=2.7 Hz, 1H), 7.99 (d, J=4.4 Hz, 1H), 7.54 (dd, J=9.0, 2.8 Hz, 1H), 7.21 (d, J=4.9 Hz, 1H), 6.93 (d, J=9.1 Hz, 1H), 4.33 (d, J=13.0 Hz, 2H), 4.12 (s, 3H), 3.81 (s, 2H), 3.71 (t, J=6.7 Hz, 2H), 3.67 (s, 10H), 3.17-3.13 (m, 2H), 2.89 (t, J=12.5 Hz, 2H), 2.72 (t, J=6.7 Hz, 2H), 2.14 (s, 1H), 1.84 (d, J=11.5 Hz, 2H), 1.38 (d, J=6.3 Hz, 6H), 1.25 (s, 2H).

Example 66

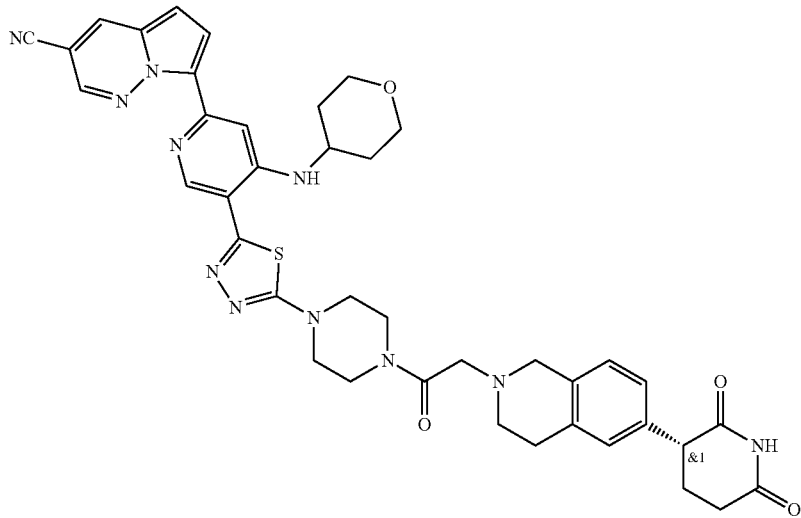 [SMILES: N#Cc1cnn2c(-c3cc(NC4CCOCC4)c(-c4nnc(N5CCN(C(=O)CN6CCc7cc([C@H]8CCC(=O)NC8=O)ccc7C6)CC5)s4)cn3)ccc2c1]

rac-7-(5-{5-[4-(2-{6-[(3R)-2,6-dioxopiperidin-3-yl]-1,2,3,4-tetrahydroisoquinolin-2-yl}acetyl)piperazin-1-yl]-1,3,4-thiadiazol-2-yl}-4-[(oxan-4-yl)amino]pyridin-2-yl)pyrrolo[1,2-b]pyridazine-3-carbonitrile The title compound was synthesized from Intermediate A and HA-24 by amide coupling using General Method A. LCMS: $C_{40}H_{41}N_{41}O_4S$ requires: 771.3, found: m/z=772.5 [M+H]$^+$. $^1$H NMR (500 MHz, DMSO) δ 10.86 (s, 1H), 10.22 (s, 1H), 8.92 (d, J=2.3 Hz, 1H), 8.82 (d, J=2.3 Hz, 1H), 8.58 (s, 1H), 8.19 (s, 1H), 7.95 (s, 1H), 7.19 (d, J=12.3 Hz, OH), 7.19 (s, 2H), 7.14 (d, J=6.1 Hz, 2H), 4.58 (d, J=15.6 Hz, 1H), 4.50 (s, 2H), 4.35 (d, J=14.2 Hz, 1H), 4.02 (s, 2H), 3.93 (dt, J=11.9, 3.8 Hz, 2H), 3.86 (dd, J=11.8, 4.9 Hz, 1H), 3.76 (d, J=6.6 Hz, 2H), 3.70 (d, J=6.0 Hz, 3H), 3.68-3.56 (m, 7H), 3.45 (s, 2H), 2.89 (s, 1H), 2.75-2.64 (m, 1H), 2.27-2.16 (m, 1H), 2.14-2.05 (m, 2H), 2.05-1.98 (m, 1H), 1.61 (dd, J=12.3, 8.5 Hz, 2H).

Example 67

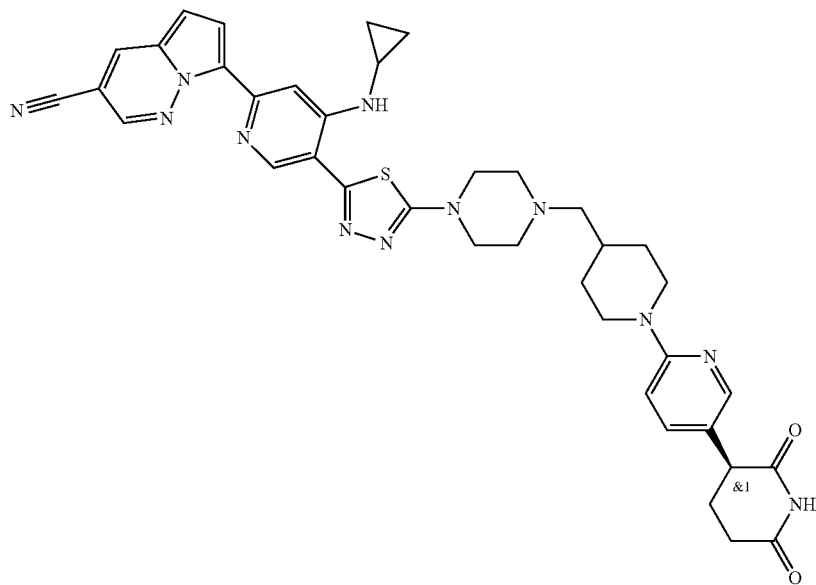 [SMILES: N#Cc1cnn2c(-c3cc(NC4CC4)c(-c4nnc(N5CCN(CC6CCN(c7ccc([C@@H]8CCC(=O)NC8=O)cn7)CC6)CC5)s4)cn3)ccc2c1]

rac-7-[4-(cyclopropylamino)-5-(5-{4-[(1-{5-[(3R)-2,6-dioxopiperidin-3-yl]pyridin-2-yl} piperidin-4-yl)methyl]piperazin-1-yl}-1,3,4-thiadiazol-2-yl)pyridin-2-yl]pyrrolo[1,2-b]pyridazine-3-carbonitrile The title compound was synthesized from Intermediate Z and HA-1 by reductive amination using General Method B. LCMS: $C_{38}H_{40}N_{12}O_2S$ requires: 728.3, found: m/z=729.5 [M+H]$^+$. $^1$H NMR (500 MHz, DMSO) δ 10.80 (s, 1H), 8.85 (d, J=2.3 Hz, 1H), 8.77 (d, J=2.2 Hz, 1H), 8.67 (s, 1H), 8.51 (s, 1H), 7.94 (d, J=2.6 Hz, 1H), 7.87 (d, J=4.8 Hz, 1H), 7.39-7.33 (m, 1H), 7.13 (d, J=4.8 Hz, 1H), 6.79 (d, J=8.9 Hz, 1H), 4.26 (d, J=12.9 Hz, 2H), 3.72 (dd, J=12.2, 4.9 Hz, 1H), 3.54 (d, J=5.6 Hz, 4H), 2.78 (t, J=12.4 Hz, 2H), 2.54 (s, 1H), 2.52 (s, 7H), 2.25-2.15 (m, 3H), 1.79 (d, J=12.7 Hz, 3H), 1.10 (d, J=12.3 Hz, 2H), 1.00 (d, J=6.6 Hz, 2H), 0.64 (s, 2H).

Example 68

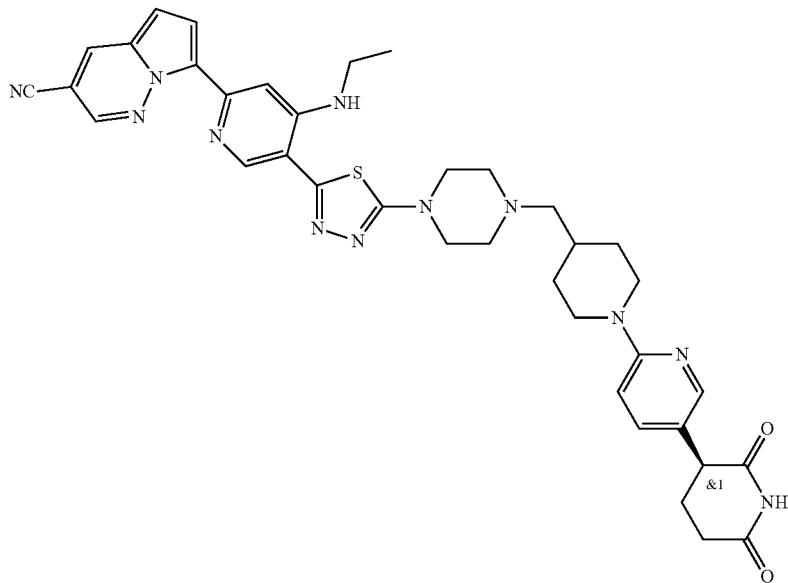

rac-7-[5-(5-{4-[(1-{5-[(3R)-2,6-dioxopiperidin-3-yl]pyridin-2-yl}piperidin-4-yl)methyl] piperazin-1-yl}-1,3,4-thiadiazol-2-yl)-4-(ethylamino)pyridin-2-yl]pyrrolo[1,2-b]pyridazine-3-carbonitrile The title compound was synthesized from Intermediate AA and HA-1 by reductive amination using General Method B. LCMS: $C_{37}H_{40}N_{12}O_2S$ requires: 716.3, found: m/z=717.5 [M+H]$^+$. $^1$H NMR (500 MHz, DMSO) δ 10.80 (s, 1H), 8.83 (d, J=2.2 Hz, 1H), 8.73 (d, J=2.2 Hz, 1H), 8.55-8.47 (m, 2H), 8.18 (s, 1H), 7.94 (d, J=2.4 Hz, 1H), 7.85 (d, J=4.8 Hz, 1H), 7.36 (dd, J=8.9, 2.5 Hz, 1H), 7.12 (d, J=4.8 Hz, 1H), 6.79 (d, J=8.8 Hz, 1H), 4.27 (d, J=12.8 Hz, 2H), 3.72 (dd, J=12.1, 4.9 Hz, 1H), 3.58-3.53 (m, 4H), 3.44 (p, J=6.9 Hz, 2H), 2.78 (t, J=12.1 Hz, 2H), 2.68 (td, J=12.2, 6.2 Hz, 1H), 2.26-2.21 (m, 2H), 2.17 (dt, J=12.4, 6.2 Hz, 1H), 2.01-1.94 (m, 1H), 1.79 (d, J=12.6 Hz, 3H), 1.34 (t, J=7.1 Hz, 3H), 1.11 (d, J=12.6 Hz, 2H).

Example 69

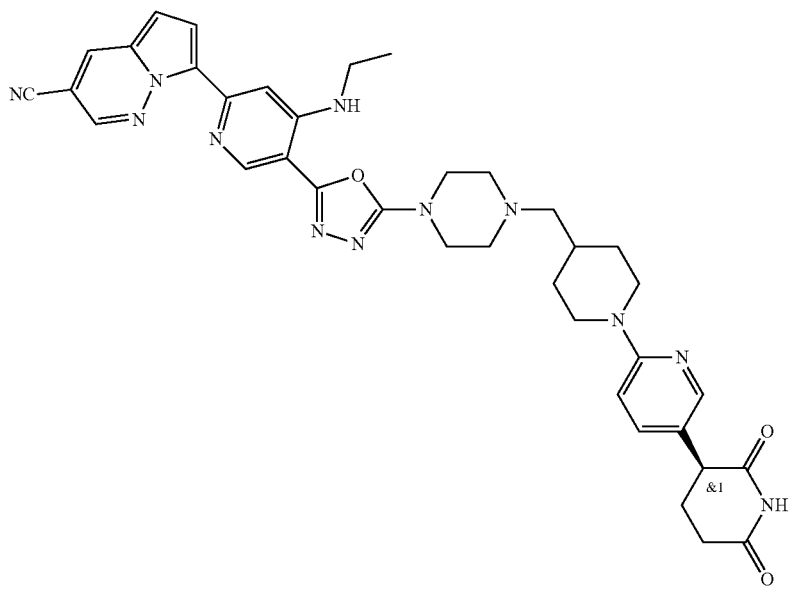 [SMILES: CCNc1cc(-c2ccc3cc(C#N)cnn23)ncc1-c1nnc(N2CCN(CC3CCN(c4ccc([C@@H]5CCC(=O)NC5=O)cn4)CC3)CC2)o1]

rac-7-[5-(5-{4-[(1-{5-[(3R)-2,6-dioxopiperidin-3-yl]
pyridin-2-yl}piperidin-4-yl)methyl] piperazin-1-yl}-
1,3,4-oxadiazol-2-yl)-4-(ethylamino)pyridin-2-yl]
pyrrolo[1,2-b]pyridazine-3-carbonitrile The title compound was synthesized from Intermediate AB and HA-1 by reductive amination using General Method B. LCMS: $C_{37}H_{40}N_{12}O_3$ requires: 700.3, found: m/z=701.3 [M+H]+. 1H NMR (500 MHz, DMSO) δ 10.88 (s, 1H), 9.75 (s, 1H), 8.95 (s, 1H), 8.83 (d, J=15.3 Hz, 2H), 8.42 (s, 1H), 8.09 (s, 1H), 8.03-7.89 (m, 2H), 7.66 (s, 1H), 7.23-7.18 (m, 1H), 7.14 (s, 1H), 4.27 (d, J=13.1 Hz, 2H), 3.61 (t, J=7.1 Hz, 4H), 3.11 (s, 2H), 3.01 (s, 3H), 2.88 (d, J=6.6 Hz, 1H), 2.75-2.61 (m, 2H), 2.31-2.11 (m, 2H), 1.97 (d, J=12.4 Hz, 1H), 1.87 (d, J=12.8 Hz, 2H), 1.38-1.22 (m, 6H).

rac-7-[5-(5-{4-[(1-{4-[(3R)-2,6-dioxopiperidin-3-yl]
phenyl}piperidin-4-yl)methyl]piperazin-1-yl}-1,3,4-
thiadiazol-2-yl)-4-(ethylamino)pyridin-2-yl]pyrrolo
[1,2-b]pyridazine-3-carbonitrile The title compound was synthesized from Intermediate AA and HA-7 by reductive amination using General Method B. LCMS: $C_{38}H_{41}N_1O_2S$ requires: 715.3, found: m/z=716.3 [M+H]+. 1H NMR (500 MHz, DMSO) δ 10.80 (s, 1H), 9.39-9.08 (m, 1H), 8.96 (s, 1H), 8.83 (s, 1H), 8.60 (d, J=3.1 Hz, 1H), 8.07 (s, 1H), 8.03 (s, 1H), 7.22 (q, J=6.6, 5.3 Hz, 1H), 7.09 (d, J=7.9 Hz, 2H), 6.97 (s, 2H), 3.74 (d, J=12.4 Hz, 3H), 3.68 (s, 4H), 3.29 (s, 2H), 3.17 (s, 2H), 2.76 (s, 2H), 2.15 (d, J=12.4 Hz, 1H), 2.03 (s, 2H), 1.87 (d, J=12.6 Hz, 2H), 1.37 (q, J=9.0, 7.9 Hz, 5H).

Example 70

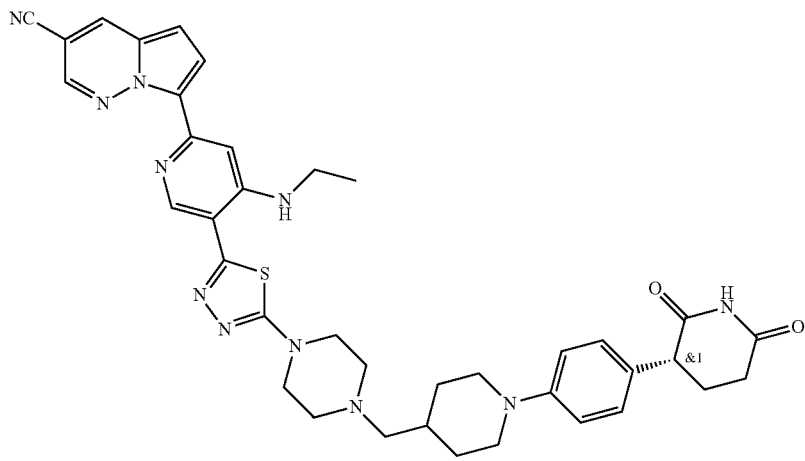 [SMILES: CCNc1cc(-c2ccc3cc(C#N)cnn23)ncc1-c1nnc(N2CCN(CC3CCN(c4ccc([C@H]5CCC(=O)NC5=O)cc4)CC3)CC2)s1]

Example 71

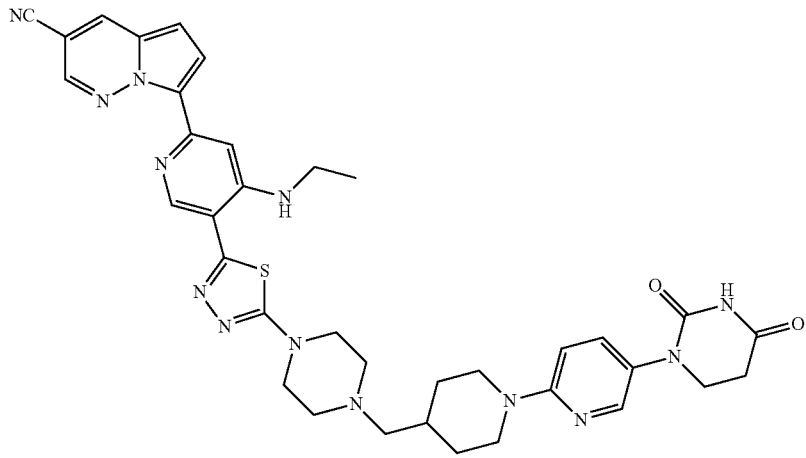 [SMILES: CCNc1cc(-c2ccc3cc(C#N)cnn23)ncc1-c1nnc(N2CCN(CC3CCN(c4ccc(N5CCC(=O)NC5=O)cn4)CC3)CC2)s1]

7-(5-{5-[4-({1-[5-(2,4-dioxo-1,3-diazinan-1-yl)pyridin-2-yl]piperidin-4-yl}methyl)piperazin-1-yl]-1,3,4-thiadiazol-2-yl}-4-(ethylamino)pyridin-2-yl)pyrrolo[1,2-b]pyridazine-3-carbonitrile The title compound was synthesized from Intermediate AA and HA-19 by reductive amination using General Method B. LCMS: $C_{36}H_{39}N_{13}O_2S$ requires: 717.3, found: m/z=718.4 [M+H]+. 1H NMR (500 MHz, DMSO) δ 10.38 (d, J=2.6 Hz, 1H), 9.80 (s, 1H), 9.40 (s, 1H), 8.99 (s, 1H), 8.85 (s, 1H), 8.62 (d, J=2.8 Hz, 1H), 8.07 (dd, J=6.9, 3.3 Hz, 2H), 8.03 (d, J=8.6 Hz, 1H), 7.57 (d, J=9.1 Hz, 1H), 7.24 (t, J=3.9 Hz, 1H), 6.97 (d, J=9.1 Hz, 1H), 4.33 (d, J=12.9 Hz, 2H), 4.13 (s, 2H), 3.81 (s, 1H), 3.71 (q, J=11.4, 9.7 Hz, 4H), 3.66-3.58 (m, 3H), 3.29 (s, 2H), 3.15 (s, 2H), 2.91 (s, 1H), 2.76-2.69 (m, 2H), 2.15 (s, 1H), 1.85 (d, J=12.7 Hz, 2H), 1.36 (t, J=7.2 Hz, 3H), 1.29 (d, J=12.3 Hz, 1H), 1.24 (d, J=12.2 Hz, 1H).

Example 72

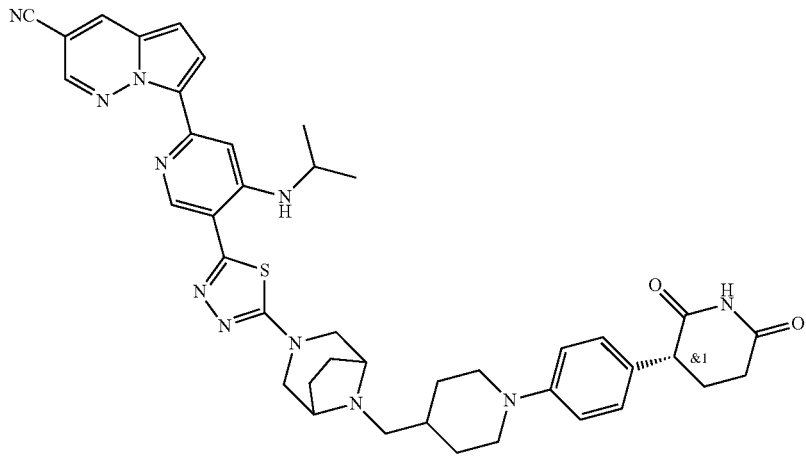 [SMILES: CC(C)Nc1cc(-c2ccc3cc(C#N)cnn23)ncc1-c1nnc(N2CC3CCC(C2)N3CC2CCN(c3ccc([C@H]4CCC(=O)NC4=O)cc3)CC2)s1]

rac-7-[5-(5-{8-[(1-{4-[(3R)-2,6-dioxopiperidin-3-yl]phenyl}piperidin-4-yl)methyl]-3,8-diazabicyclo[3.2.1]octan-3-yl}-1,3,4-thiadiazol-2-yl)-4-[(propan-2-yl)amino]pyridin-2-yl]pyrrolo[1,2-b]pyridazine-3-carbonitrile The title compound was synthesized from Intermediate R and HA-7 by reductive amination using General Method B. LCMS: $C_{41}H_{45}N_{11}O_2S$ requires: 755.3, found: m/z=756.6 [M+H]+. 1H NMR (500 MHz, DMSO) δ 10.78 (s, 1H), 9.72 (s, 1H), 9.19 (s, 2H), 8.95 (s, 1H), 8.81 (s, 1H), 8.58 (s, 1H), 8.08 (s, 1H), 8.00 (s, 1H), 7.20 (d, J=10.6 Hz, 2H), 7.08 (d, J=7.7 Hz, 3H), 6.97 (t, J=7.3 Hz, 2H), 4.25 (s, 2H), 4.12 (s, 2H), 3.82 (d, J=13.4 Hz, 3H), 3.74 (d, J=11.8 Hz, 4H), 3.04 (s, 2H), 2.75 (d, J=15.5 Hz, 3H), 2.63 (t, J=5.9 Hz, 1H), 2.29 (s, 2H), 2.14 (d, J=12.0 Hz, 1H), 2.01 (s, 5H), 1.92 (d, J=12.4 Hz, 2H), 1.41 (s, 1H), 1.36 (d, J=6.2 Hz, 8H).

Example 73

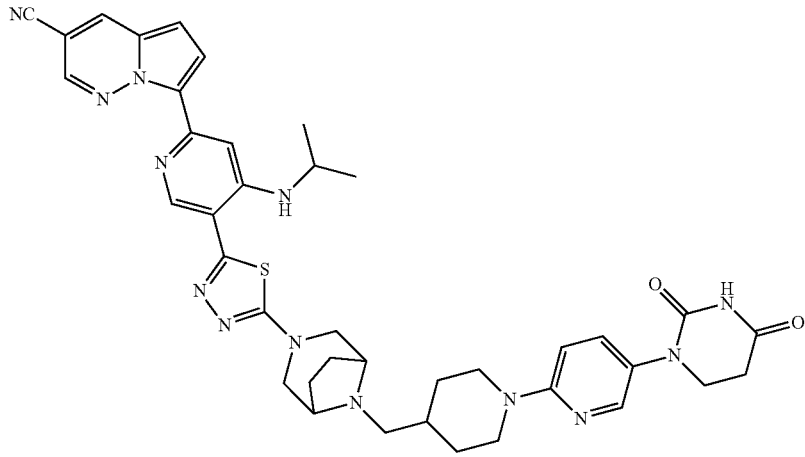 [SMILES: CC(C)Nc1cc(-c2ccc3cc(C#N)cnn23)ncc1-c1nnc(N2CC3CCC(C2)N3CC2CCN(c3ccc(N4CCC(=O)NC4=O)cn3)CC2)s1]

7-(5-{5-[8-({1-[5-(2,4-dioxo-1,3-diazinan-1-yl)pyridin-2-yl]piperidin-4-yl}methyl)-3,8-diazabicyclo[3.2.1]octan-3-yl]-1,3,4-thiadiazol-2-yl}-4-[(propan-2-yl)amino]pyridin-2-yl)pyrrolo[1,2-b]pyridazine-3-carbonitrile The title compound was synthesized from Intermediate R and HA-19 by reductive amination using General Method B. LCMS: $C_{39}H_{43}N_{13}O_2S$ requires: 757.3, found: m/z=758.5 [M+H]$^+$. $^1$H NMR (500 MHz, DMSO) δ 10.38 (s, 1H), 9.79 (s, 1H), 9.38 (s, 1H), 8.98 (s, 1H), 8.85 (s, 1H), 8.62 (d, J=8.4 Hz, 1H), 8.06 (t, J=7.2 Hz, 3H), 7.57 (d, J=9.0 Hz, 1H), 7.24 (d, J=4.8 Hz, 1H), 6.97 (d, J=9.1 Hz, 1H), 4.35 (d, J=13.0 Hz, 2H), 4.26 (s, 2H), 4.18 (s, 1H), 3.95 (d, J=13.3 Hz, 2H), 3.84 (d, J=13.2 Hz, 2H), 3.72 (t, J=6.8 Hz, 2H), 3.04 (s, 2H), 2.91 (s, 1H), 2.72 (t, J=7.4 Hz, 2H), 2.30 (s, 2H), 2.15 (s, 1H), 2.01 (d, J=9.7 Hz, 2H), 1.91 (d, J=12.4 Hz, 2H), 1.38 (d, J=6.3 Hz, 6H), 1.29 (q, J=16.1, 14.5 Hz, 3H).

Example 74

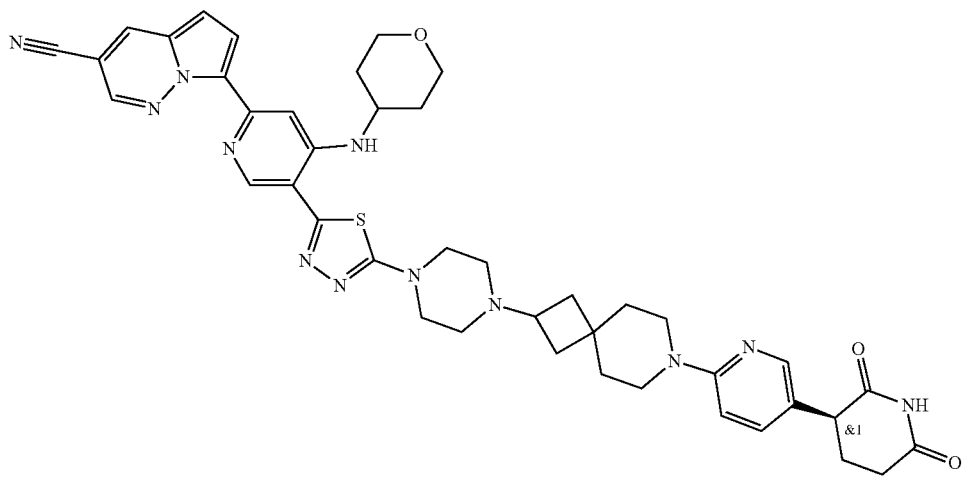 [SMILES: N#Cc1cnn2c(-c3cc(NC4CCOCC4)c(-c4nnc(N5CCN(C6CC7(CCN(c8ccc([C@@H]9CCC(=O)NC9=O)cn8)CC7)C6)CC5)s4)cn3)ccc2c1]

rac-7-(5-{5-[4-(7-{5-[(3R)-2,6-dioxopiperidin-3-yl]pyridin-2-yl}-7-azaspiro[3.5]nonan-2-yl)piperazin-1-yl]-1,3,4-thiadiazol-2-yl}-4-[(oxan-4-yl)amino]pyridin-2-yl)pyrrolo[1,2-b]pyridazine-3-carbonitrile The title compound was synthesized from Intermediate A and HA-25 by reductive amination using General Method B. LCMS: $C_{42}H_{46}N_{12}O_3S$ requires: 798.4, found: m/z=799.6 [M+H]$^+$. $^1$H NMR (500 MHz, DMSO) δ 10.81 (s, 1H), 8.85 (s, 1H), 8.78 (s, 1H), 8.67 (d, J=6.9 Hz, 1H), 8.52 (s, 1H), 8.30 (s, 1H), 7.94 (s, 1H), 7.85 (d, J=4.7 Hz, 1H), 7.37 (d, J=8.7 Hz, 1H), 7.13 (d, J=4.8 Hz, 1H), 6.81 (d, J=8.9 Hz, 1H), 3.94 (d, J=11.4 Hz, 2H), 3.87 (s, 1H), 3.77-3.70 (m, 1H), 3.61 (t, J=10.9 Hz, 2H), 3.57 (s, 4H), 3.50 (s, 2H), 2.83-2.76 (m, 1H), 2.68 (s, 1H), 2.43 (s, 3H), 2.17 (d, J=27.5 Hz, 2H), 2.11 (s, 1H), 2.04 (d, J=9.6 Hz, 2H), 1.59 (d, J=20.2 Hz, 6H), 1.53 (s, 2H).

Example 75

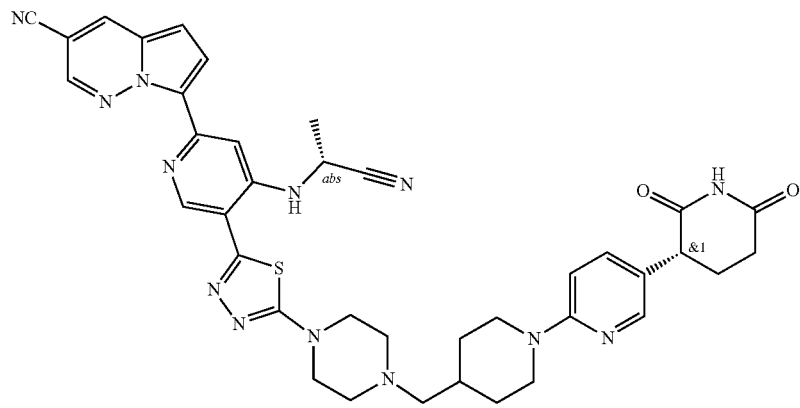 [SMILES: C[C@H](C#N)Nc1cc(-c2ccc3cc(C#N)cnn23)ncc1-c1nnc(N2CCN(CC3CCN(c4ccc([C@H]5CCC(=O)NC5=O)cn4)CC3)CC2)s1]

7-(4-{[(1R)-1-cyanoethyl]amino}-5-(5-{4-[(1-{5-[(3RS)-2,6-dioxopiperidin-3-yl]pyridin-2-yl}piperidin-4-yl)methyl]piperazin-1-yl}-1,3,4-thiadiazol-2-yl)pyridin-2-yl)pyrrolo[1,2-b]pyridazine-3-carbonitrile The title compound was synthesized from Intermediate AC and HA-1 by reductive amination using General Method B. LCMS: $C_{38}H_{39}N_{13}O_2S$ requires: 741.3, found: m/z=742.6 [M+H]$^+$. $^1$H NMR (500 MHz, DMSO) δ 10.81 (s, 1H), 8.90-8.83 (m, 2H), 8.68 (d, J=2.8 Hz, 1H), 8.64 (s, 1H), 8.37 (s, 1H), 7.95 (d, J=3.0 Hz, 1H), 7.89 (d, J=4.5 Hz, 1H), 7.37 (d, J=8.7 Hz, 1H), 7.16 (d, J=4.7 Hz, 1H), 6.80 (d, J=8.9 Hz, 1H), 5.05 (t, J=7.0 Hz, 1H), 4.28 (d, J=12.7 Hz, 2H), 3.73 (dd, J=12.2, 4.8 Hz, 1H), 3.58 (t, J=4.6 Hz, 4H), 2.79 (t, J=12.4 Hz, 2H), 2.74-2.66 (m, 1H), 2.55 (d, J=4.4 Hz, 3H), 2.24 (d, J=6.8 Hz, 2H), 2.22-2.13 (m, 1H), 1.98 (d, J=12.6 Hz, 1H), 1.80 (t, J=9.0 Hz, 6H), 1.25 (s, 2H), 1.12 (q, J=12.3 Hz, 2H).

rac-7-[5-(5-{4-[(1-{4-[(3R)-2,6-dioxopiperidin-3-yl]phenyl}piperidin-4-yl)methyl]piperazin-1-yl}-1,3,4-thiadiazol-2-yl)-4-[(3-methyloxetan-3-yl)amino]pyridin-2-yl]pyrrolo[1,2-b]pyridazine-3-carbonitrile The title compound was synthesized from Intermediate W and HA-7 by reductive amination using General Method B. LCMS: $C_{40}H_{43}N_{11}O_3S$ requires: 757.3, found: m/z=758.6 [M+H]$^+$. $^1$H NMR (500 MHz, DMSO) δ 10.78 (s, 1H), 9.56 (s, 1H), 9.20 (s, 1H), 8.89 (d, J=8.2 Hz, 2H), 8.60 (s, 1H), 7.91 (d, J=4.6 Hz, 1H), 7.82 (s, 1H), 7.16 (d, J=4.8 Hz, 1H), 7.08 (d, J=7.9 Hz, 2H), 6.97 (s, 2H), 4.79 (d, J=6.2 Hz, 2H), 4.73 (d, J=6.5 Hz, 2H), 4.10 (s, 2H), 3.72 (d, J=12.2 Hz, 3H), 3.27 (s, 2H), 3.16 (s, 2H), 2.74 (d, J=15.0 Hz, 2H), 2.14 (d, J=12.2 Hz, 1H), 2.01 (d, J=13.6 Hz, 2H), 1.86 (d, J=12.5 Hz, 2H), 1.80 (s, 3H), 1.37 (d, J=12.4 Hz, 2H).

Example 76

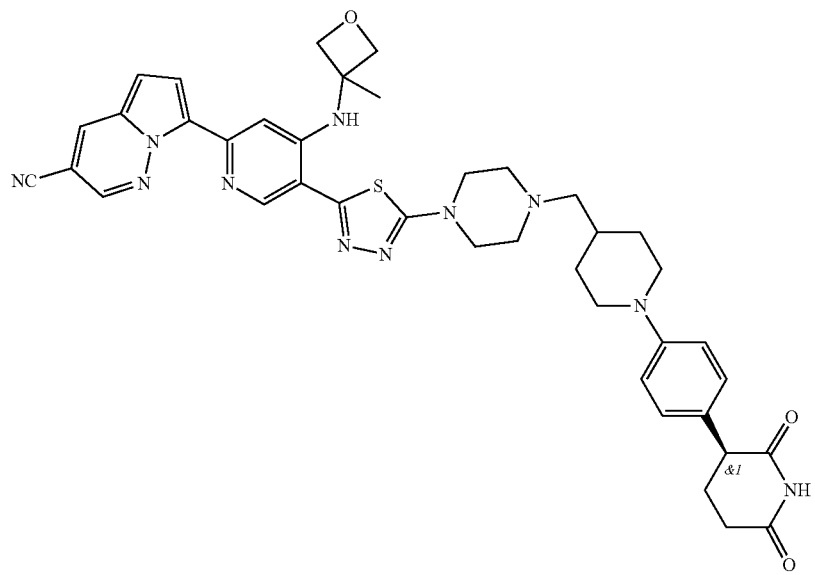 [SMILES: CC1(Nc2cc(-c3ccc4cc(C#N)cnn34)ncc2-c2nnc(N3CCN(CC4CCN(c5ccc([C@@H]6CCC(=O)NC6=O)cc5)CC4)CC3)s2)COC1]

Example 77

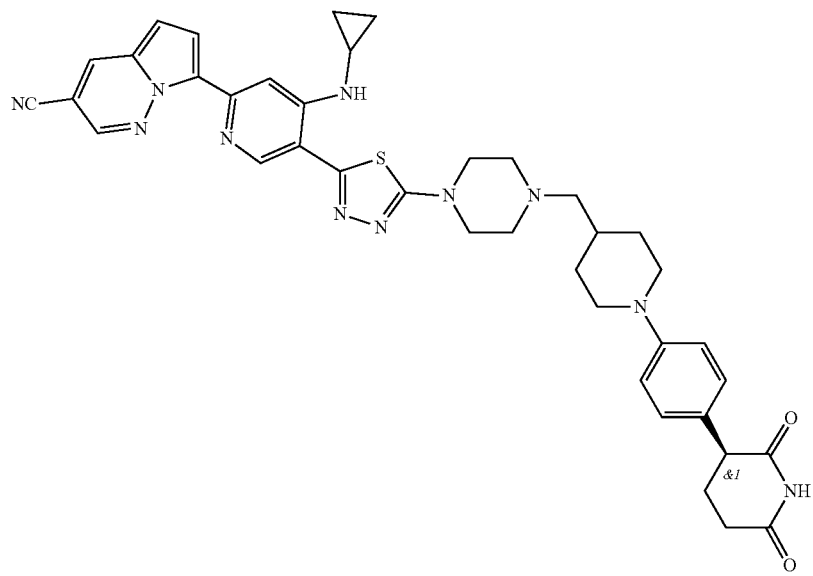 [SMILES: N#Cc1cnn2c(-c3cc(NC4CC4)c(-c4nnc(N5CCN(CC6CCN(c7ccc([C@@H]8CCC(=O)NC8=O)cc7)CC6)CC5)s4)cn3)ccc2c1]

rac-7-[4-(cyclopropylamino)-5-(5-{4-[(1-{4-[(3R)-2,6-dioxopiperidin-3-yl]phenyl}piperidin-4-yl)methyl]piperazin-1-yl}-1,3,4-thiadiazol-2-yl)pyridin-2-yl]pyrrolo[1,2-b]pyridazine-3-carbonitrile The title compound was synthesized from Intermediate Z and HA-7 by reductive amination using General Method B. LCMS: $C_{39}H_{41}N_{11}O_2S$ requires: 727.3, found: m/z=728.3 [M+H]$^+$. $^1$H NMR (500 MHz, DMSO) δ 10.79 (s, 1H), 9.60 (s, 1H), 9.12 (s, 1H), 8.94 (s, 1H), 8.84 (s, 1H), 8.59 (s, 2H), 7.98 (d, J=4.6 Hz, 1H), 7.23-7.18 (m, 1H), 7.09 (d, J=7.9 Hz, 2H), 6.97 (d, J=8.5 Hz, 2H), 4.10 (s, 2H), 3.27 (s, 3H), 3.15 (s, 2H), 2.84 (s, 1H), 2.75 (d, J=16.2 Hz, 2H), 2.63 (d, J=11.9 Hz, 1H), 2.14 (d, J=12.2 Hz, 1H), 2.01 (d, J=12.6 Hz, 3H), 1.86 (d, J=12.6 Hz, 2H), 1.37 (q, J=12.3 Hz, 2H), 1.06 (d, J=6.7 Hz, 2H), 0.69 (s, 2H).

Example 78

7-[4-(cyclopropylamino)-5-{5-[4-({1-[5-(2,4-dioxo-1,3-diazinan-1-yl)pyridin-2-yl]piperidin-4-yl}methyl)piperazin-1-yl]-1,3,4-thiadiazol-2-yl}pyridin-2-yl]pyrrolo[1,2-b]pyridazine-3-carbonitrile The title compound was synthesized from Intermediate Z and HA-19 by reductive amination using General Method B. LCMS: $C_{37}H_{39}N_{13}O_2S$ requires: 729.3, found: m/z=730.4 [M+H]$^+$. $^1$H NMR (500 MHz, DMSO) δ 10.37 (s, 1H), 9.63 (s, 1H), 9.17 (s, 1H), 8.94 (s, 1H), 8.85 (s, 1H), 8.59 (d, J=8.7 Hz, 2H), 8.06 (d, J=3.2 Hz, 1H), 7.99 (d, J=4.8 Hz, 1H), 7.56 (d, J=9.1 Hz, 1H), 7.21 (d, J=4.7 Hz, 1H), 6.95 (d, J=9.1 Hz, 1H), 4.31 (d, J=13.0 Hz, 2H), 4.09 (s, 4H), 3.70 (t, J=6.9 Hz, 2H), 3.13 (s, 2H), 2.94-2.83 (m, 4H), 2.75-2.68 (m, 2H), 2.13 (s, 1H), 1.83 (d, J=12.6 Hz, 2H), 1.24 (d, J=11.8 Hz, 2H), 1.07 (d, J=6.7 Hz, 2H), 0.70 (s, 2H).

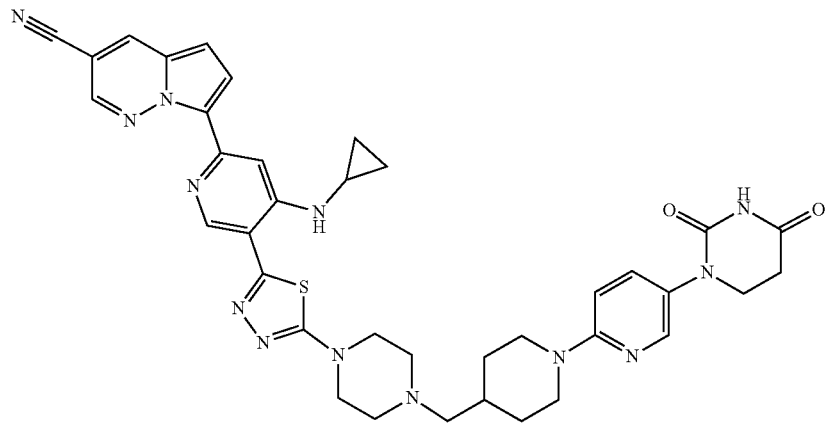 [SMILES: N#Cc1cnn2c(-c3cc(NC4CC4)c(-c4nnc(N5CCN(CC6CCN(c7ccc(N8CCC(=O)NC8=O)cn7)CC6)CC5)s4)cn3)ccc2c1]

Example 79

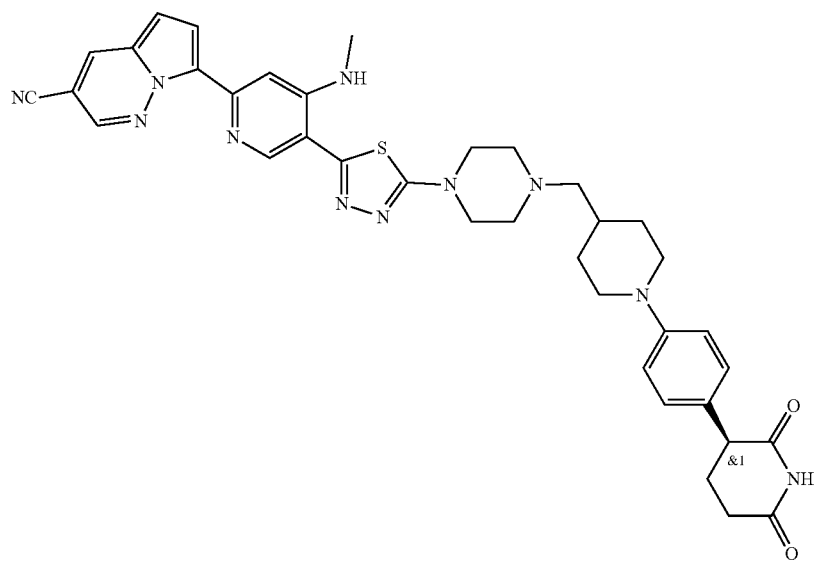 [SMILES: CNc1cc(-c2ccc3cc(C#N)cnn23)ncc1-c1nnc(N2CCN(CC3CCN(c4ccc([C@@H]5CCC(=O)NC5=O)cc4)CC3)CC2)s1]

rac-7-[5-(5-{4-[(1-{4-[(3R)-2,6-dioxopiperidin-3-yl]phenyl}piperidin-4-yl)methyl]piperazin-1-yl}-1,3,4-thiadiazol-2-yl)-4-(methylamino)pyridin-2-yl]pyrrolo[1,2-b]pyridazine-3-carbonitrile The title compound was synthesized from Intermediate C and HA-7 by reductive amination using General Method B. LCMS: $C_{37}H_{39}N_1O_2S$ requires: 701.3, found: m/z=702.5 [M+H]$^+$. $^1$H NMR (500 MHz, DMSO) δ 10.78 (s, 1H), 9.62 (s, 1H), 9.27 (s, 1H), 8.97 (s, 1H), 8.83 (s, 1H), 8.57 (d, J=2.7 Hz, 1H), 8.05 (s, 1H), 7.98 (s, 1H), 7.23 (t, J=3.8 Hz, 1H), 7.08 (d, J=7.9 Hz, 2H), 6.96 (s, 2H), 4.10 (s, 2H), 3.72 (d, J=12.6 Hz, 4H), 3.28 (s, 3H), 3.19 (t, J=3.6 Hz, 3H), 3.16 (s, 2H), 2.74 (d, J=11.3 Hz, 3H), 2.14 (d, J=12.3 Hz, 1H), 2.01 (s, 2H), 1.86 (d, J=12.6 Hz, 2H), 1.37 (d, J=12.5 Hz, 2H).

Example 80

7-(5-{5-[4-({1-[5-(2,4-dioxo-1,3-diazinan-1-yl)pyridin-2-yl]piperidin-4-yl}methyl)piperazin-1-yl]-1,3,4-thiadiazol-2-yl}-4-[(3-methyloxetan-3-yl)amino]pyridin-2-yl)pyrrolo[1,2-b]pyridazine-3-carbonitrile The title compound was synthesized from Intermediate W and HA-19 by reductive amination using General Method B. LCMS: $C_{38}H_{41}N_{13}O_3S$ requires: 759.3, found: m/z=760.6 [M+H]$^+$. $^1$H NMR (500 MHz, DMSO) δ 10.33 (s, 1H), 8.92 (s, 1H), 8.83 (d, J=4.0 Hz, 2H), 8.55 (s, 1H), 8.04 (s, 1H), 7.85 (d, J=6.8 Hz, 2H), 7.47 (d, J=8.3 Hz, 1H), 7.12 (d, J=4.8 Hz, 1H), 6.84 (d, J=9.1 Hz, 1H), 4.78 (d, J=6.2 Hz, 2H), 4.71 (d, J=6.3 Hz, 2H), 4.28 (d, J=12.9 Hz, 2H), 3.69 (t, J=6.8 Hz, 2H), 3.56 (s, 4H), 3.29 (s, 1H), 2.81 (t, J=12.3 Hz, 2H), 2.70 (t, J=6.9 Hz, 2H), 2.54 (s, 2H), 2.23 (d, J=6.7 Hz, 2H), 1.80 (d, J=10.7 Hz, 6H), 1.11 (d, J=12.5 Hz, 2H).

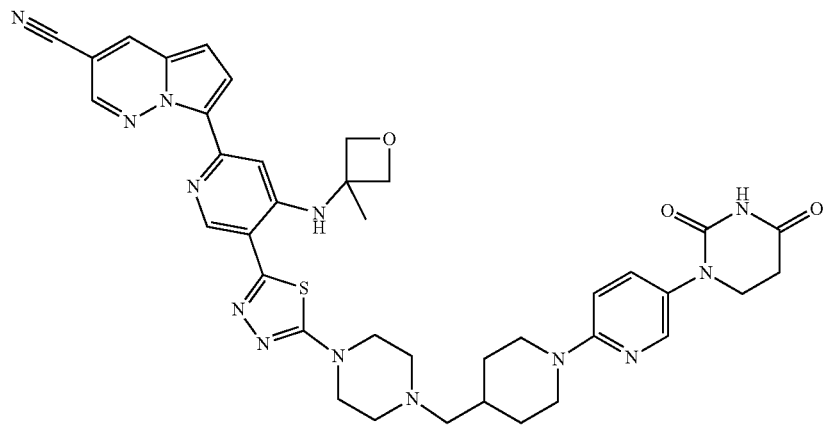 [SMILES: CC1(Nc2cc(-c3ccc4cc(C#N)cnn34)ncc2-c2nnc(N3CCN(CC4CCN(c5ccc(N6CCC(=O)NC6=O)cn5)CC4)CC3)s2)COC1]

Example 81

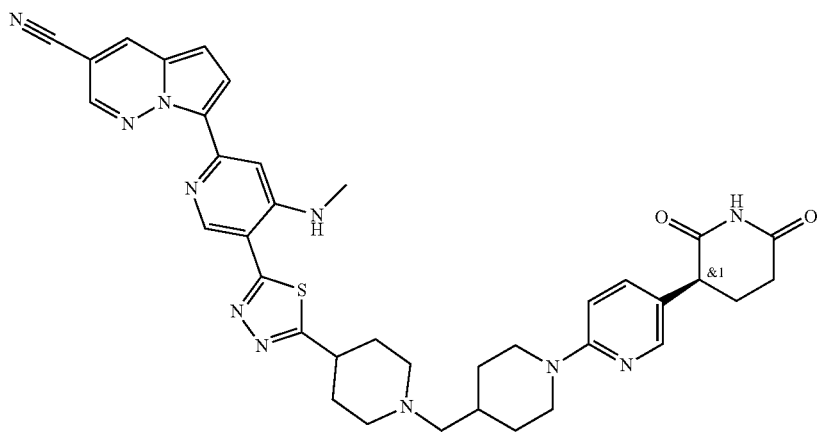 [SMILES: CNc1cc(-c2ccc3cc(C#N)cnn23)ncc1-c1nnc(C2CCN(CC3CCN(c4ccc([C@@H]5CCC(=O)NC5=O)cn4)CC3)CC2)s1]

rac-7-[5-(5-{1-[(1-{5-[(3R)-2,6-dioxopiperidin-3-yl]
pyridin-2-yl}piperidin-4-yl)methyl] piperidin-4-yl}-
1,3,4-thiadiazol-2-yl)-4-(methylamino)pyridin-2-yl]
pyrrolo[1,2-b]pyridazine-3-carbonitrile The title compound was synthesized from Intermediate AD and HA-1 by reductive amination using General Method B. LCMS: $C_{37}H_{39}N_1O_2S$ requires: 701.3, found: m/z=702.5 [M+H]$^+$. $^1$H NMR (500 MHz, DMSO-d$_6$) δ 10.89 (s, 1H), 9.15 (s, 1H), 8.96 (s, 1H), 8.81 (d, J=24.7 Hz, 1H), 8.18-7.88 (m, 2H), 7.64 (s, 1H), 7.35-7.17 (m, 1H), 7.11 (s, 1H), 4.29 (d, J=13.0 Hz, 2H), 3.78 (dd, J=60.9, 12.4 Hz, 4H), 3.26-3.06 (m, 3H), 2.95 (d, J=48.7 Hz, 1H), 2.72 (d, J=19.1 Hz, 1H), 2.38 (d, J=13.8 Hz, 2H), 2.17 (tt, J=29.5, 14.7 Hz, 2H), 2.05-1.82 (m, 2H), 1.40-1.12 (m, 2H).

Example 82

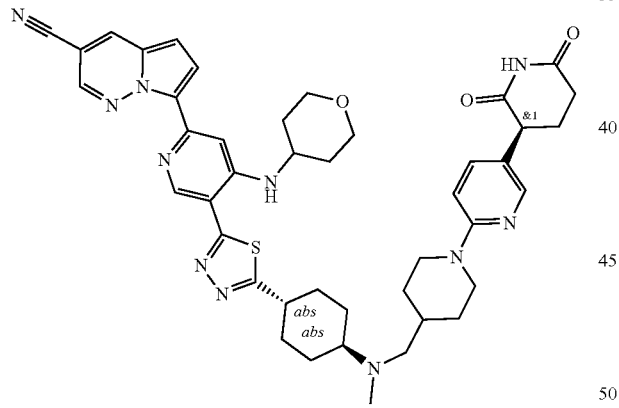

7-{4-[(oxan-4-yl)amino]-5-{5-[(1r,4r)-4-{[(1-{5-
[(3RS)-2,6-dioxopiperidin-3-yl]pyridin-2-
yl}piperidin-4-yl)methyl](methyl)
amino}cyclohexyl]-1,3,4-thiadiazol-2-yl}pyridin-2-
yl}pyrrolo[1,2-b]pyridazine-3-carbonitrile The title compound was synthesized from Intermediate AE and HA-1 by reductive amination using General Method B. LCMS: $C_{43}H_{49}N_{11}O_3S$ requires: 799.4, found: m/z=800.7 [M+H]$^+$. $^1$H NMR (500 MHz, DMSO-d$_6$) δ 10.88 (s, 1H), 8.93 (s, 1H), 8.87-8.72 (m, 1H), 8.28 (s, 1H), 7.95 (d, J=7.5 Hz, 1H), 7.19 (s, 1H), 4.29 (d, J=13.2 Hz, 2H), 4.06-3.88 (m, 2H), 3.83 (s, 1H), 3.62 (t, J=11.1 Hz, 1H), 3.43 (s, 1H), 3.30 (s, 1H), 3.19 (d, J=12.8 Hz, 1H), 2.98 (s, 1H), 2.82 (s, 1H), 2.12 (s, 3H), 1.97 (s, 2H), 1.78 (d, J=25.0 Hz, 2H), 1.63 (d, J=11.6 Hz, 2H), 1.26 (d, J=20.4 Hz, 2H).

Example 83

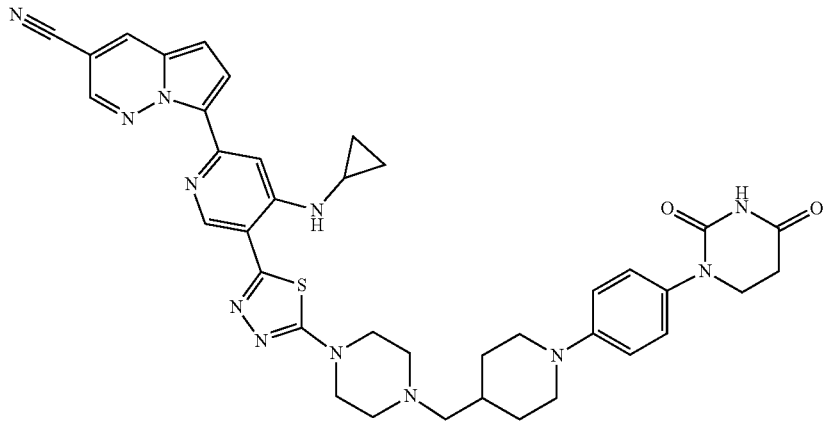 [SMILES: N#Cc1cnn2c(-c3cc(NC4CC4)c(-c4nnc(N5CCN(CC6CCN(c7ccc(N8CCC(=O)NC8=O)cc7)CC6)CC5)s4)cn3)ccc2c1]

7-[4-(cyclopropylamino)-5-{5-[4-({1-[4-(2,4-dioxo-1,3-diazinan-1-yl)phenyl]piperidin-4-yl}methyl)piperazin-1-yl]-1,3,4-thiadiazol-2-yl}pyridin-2-yl]pyrrolo[1,2-b]pyridazine-3-carbonitrile The title compound was synthesized from Intermediate Z and HA-21 by reductive amination using General Method B. LCMS: $C_{38}H_{40}N_{12}O_2S$ requires: 728.3, found: m/z=729.7 [M+H]⁺. ¹H NMR (500 MHz, DMSO) δ 10.28 (s, 1H), 10.08 (s, 1H), 8.93 (s, 1H), 8.84 (s, 1H), 8.62 (s, 1H), 8.56 (s, 1H), 8.00 (s, 1H), 7.19 (s, 3H), 6.99 (s, 2H), 4.09 (d, J=13.6 Hz, 2H), 3.71 (dd, J=17.9, 10.6 Hz, 7H), 3.66 (s, 1H), 3.15 (s, 2H), 2.83 (s, 1H), 2.75 (s, 1H), 2.69 (t, J=7.1 Hz, 2H), 2.54 (s, 2H), 2.05 (s, 1H), 1.90 (s, 2H), 1.38 (s, 2H), 1.06 (s, 2H), 0.69 (s, 2H).

Example 84

7-(5-{5-[8-({1-[4-(2,4-dioxo-1,3-diazinan-1-yl)phenyl]piperidin-4-yl}methyl)-3,8-diazabicyclo[3.2.1]octan-3-yl]-1,3,4-thiadiazol-2-yl}-4-[(oxan-4-yl)amino]pyridin-2-yl)pyrrolo[1,2-b]pyridazine-3-carbonitrile The title compound was synthesized from Intermediate F and HA-21 by reductive amination using General Method B. LCMS: $C_{42}H_{46}N_{12}O_3S$ requires: 798.4, found: m/z=799.7 [M+H]⁺. ¹H NMR (500 MHz, DMSO) δ 10.27 (s, 1H), 8.92 (s, 1H), 8.83 (s, 1H), 8.58 (s, 1H), 8.20 (s, 1H), 7.98 (s, 1H), 7.18 (s, 3H), 6.99 (s, 2H), 4.25 (s, 2H), 3.93 (d, J=9.4 Hz, 5H), 3.75 (d, J=12.2 Hz, 2H), 3.69 (d, J=7.9 Hz, 2H), 3.60 (t, J=11.3 Hz, 2H), 3.03 (s, 2H), 2.75 (s, 2H), 2.69 (d, J=14.7 Hz, 1H), 2.69 (s, 2H), 2.54 (s, 8H), 2.28 (s, 2H), 2.11 (d, J=13.4 Hz, 3H), 2.01 (d, J=8.9 Hz, 1H), 1.95 (s, 4H), 1.60 (s, 2H), 1.41 (s, 2H).

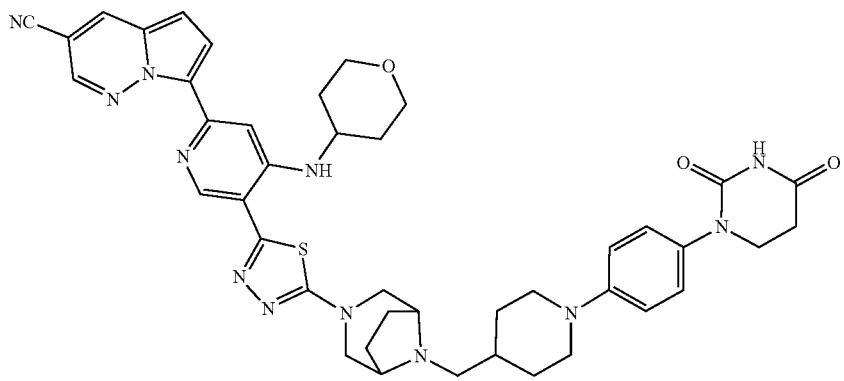 [SMILES: N#Cc1cnn2c(-c3cc(NC4CCOCC4)c(-c4nnc(N5CC6CCC(C5)N6CC5CCN(c6ccc(N7CCC(=O)NC7=O)cc6)CC5)s4)cn3)ccc2c1]

Example 85

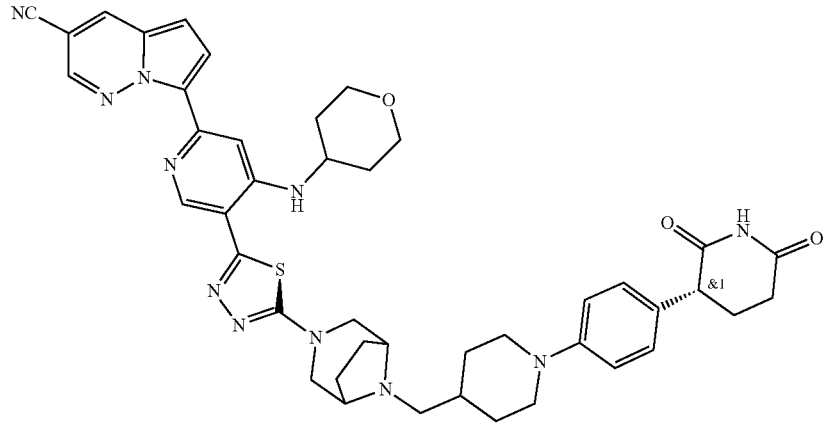

rac-7-[5-(5-{8-[(1-{4-[(3R)-2,6-dioxopiperidin-3-yl]
phenyl}piperidin-4-yl)methyl]-3,8-diazabicyclo
[3.2.1]octan-3-yl}-1,3,4-thiadiazol-2-yl)-4-[(oxan-4-
yl)amino]pyridin-2-yl]pyrrolo[1,2-b]pyridazine-3-
carbonitrile The title compound was synthesized from Intermediate F and HA-7 by reductive amination using General Method B. LCMS: $C_{43}H_{47}N_{11}O_3S$ requires: 797.4, found: m/z=798.6 [M+H]+. 1H NMR (500 MHz, DMSO) δ 10.79 (s, 1H), 9.74 (s, 1H), 9.17 (s, 1H), 8.94 (s, 1H), 8.84 (s, 1H), 8.61 (s, 1H), 8.20 (s, 1H), 7.98 (s, 1H), 7.20 (d, J=4.9 Hz, 1H), 7.09 (d, J=7.9 Hz, 2H), 6.97 (s, 2H), 4.26 (s, 2H), 4.05 (s, 1H), 3.94 (d, J=11.5 Hz, 4H), 3.84 (d, J=13.3 Hz, 2H), 3.75 (d, J=11.5 Hz, 3H), 3.05 (s, 2H), 2.75 (s, 2H), 2.30 (s, 2H), 2.12 (d, J=13.9 Hz, 3H), 2.02 (d, J=10.8 Hz, 4H), 1.93 (d, J=12.5 Hz, 2H), 1.61 (q, J=11.4 Hz, 2H), 1.41 (d, J=12.7 Hz, 2H).

Example 86

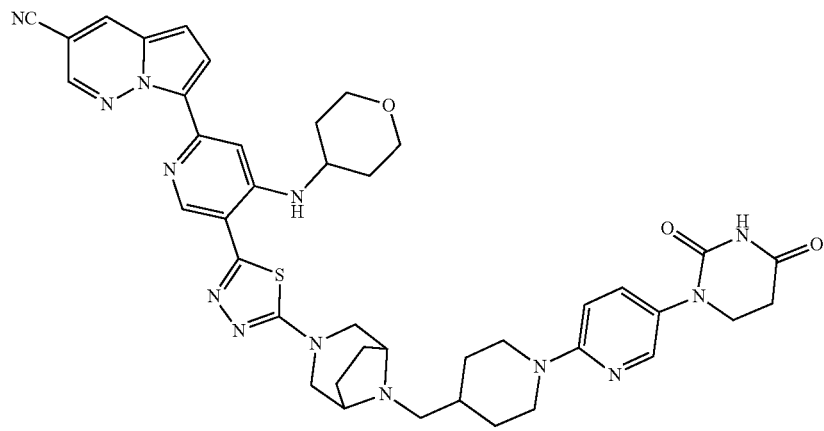 [SMILES: N#Cc1cnn2c(-c3cc(NC4CCOCC4)c(-c4nnc(N5CC6CCC(C5)N6CC5CCN(c6ccc(N7CCC(=O)NC7=O)cn6)CC5)s4)cn3)ccc2c1]

7-(5-{5-[8-({1-[5-(2,4-dioxo-1,3-diazinan-1-yl)pyri-
din-2-yl]piperidin-4-yl}methyl)-3,8-diazabicyclo
[3.2.1]octan-3-yl]-1,3,4-thiadiazol-2-yl}-4-[(oxan-4-
yl)amino]pyridin-2-yl)pyrrolo[1,2-b]pyridazine-3-
carbonitrile The title compound was synthesized from Intermediate F and HA-19 by reductive amination using General Method B. LCMS: $C_{41}H_{45}N_{13}O_3S$ requires: 799.3, found: m/z=800.6 [M+H]+. 1H NMR (500 MHz, DMSO) δ 10.39 (d, J=15.5 Hz, 1H), 9.77 (s, 1H), 9.19 (s, 1H), 8.96 (d, J=13.5 Hz, 1H), 8.86 (d, J=11.0 Hz, 1H), 8.63 (d, J=14.2 Hz, 1H), 8.21 (s, 1H), 8.09 (d, J=10.8 Hz, 1H), 7.99 (s, 1H), 7.55 (d, J=11.1 Hz, 1H), 7.21 (d, J=6.2 Hz, 1H), 6.95 (d, J=10.7 Hz, 1H), 4.35 (d, J=12.9 Hz, 3H), 4.26 (s, 3H), 3.95 (d, J=11.6 Hz, 6H), 3.04 (s, 2H), 2.92 (d, J=12.9 Hz, 4H), 2.74 (t, J=8.1 Hz, 3H), 2.32-2.28 (m, 3H), 2.12 (d, J=15.0 Hz, 7H), 2.03 (s, 2H), 1.90 (d, J=13.4 Hz, 4H), 1.62 (s, 3H), 1.30 (s, 3H).

Example 87

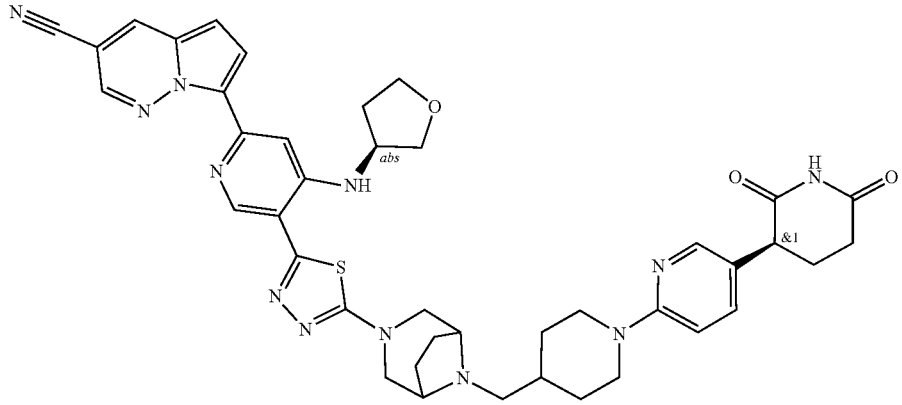 [SMILES: N#Cc1cnn2c(-c3cc(N[C@H]4CCOC4)c(-c4nnc(N5CC6CCC(C5)N6CC5CCN(c6ccc([C@@H]7CCC(=O)NC7=O)cn6)CC5)s4)cn3)ccc2c1]

7-[5-(5-{8-[(1-{5-[(3RS)-2,6-dioxopiperidin-3-yl]pyridin-2-yl}piperidin-4-yl)methyl]-3,8-diazabicyclo[3.2.1]octan-3-yl}-1,3,4-thiadiazol-2-yl)-4-{[(3S)-oxolan-3-yl]amino}pyridin-2-yl]pyrrolo[1,2-b]pyridazine-3-carbonitrile The title compound was synthesized from Intermediate AF and HA-1 by reductive amination using General Method B. LCMS: $C_{41}H_{44}N_{12}O_3S$ requires: 784.3, found: m/z=785.8 [M+H]$^+$. $^1$H NMR (500 MHz, DMSO-d$_6$) δ 10.87 (s, 1H), 9.91 (s, 1H), 9.79 (s, 1H), 9.14 (d, J=44.6 Hz, 3H), 8.93 (d, J=1.9 Hz, 2H), 8.83 (d, J=2.2 Hz, 2H), 8.60 (d, J=5.6 Hz, 3H), 8.32-8.09 (m, 2H), 7.96 (q, J=3.7, 2.9 Hz, 3H), 7.20 (d, J=4.9 Hz, 2H), 4.51 (s, 3H), 4.38-4.13 (m, 7H), 4.13-3.69 (m, 18H), 3.69-3.54 (m, 4H), 3.00 (d, J=28.8 Hz, 4H), 2.80-2.64 (m, 2H), 2.35-2.18 (m, 3H), 1.98 (dd, J=12.6, 9.1 Hz, 7H).

rac-7-[5-(5-{7-[(1-{5-[(3R)-2,6-dioxopiperidin-3-yl]pyridin-2-yl}piperidin-4-yl)methyl]-2,7-diazaspiro[3.5]nonan-2-yl}-1,3,4-thiadiazol-2-yl)-4-[(oxan-4-yl)amino]pyridin-2-yl]pyrrolo[1,2-b]pyridazine-3-carbonitrile The title compound was synthesized from Intermediate AG and HA-1 by reductive amination using General Method B. LCMS: $C_{43}H_{48}N_{12}O_3S$ requires: 812.4, found: m/z=814.0 [M+H]$^+$. $^1$H NMR (500 MHz, DMSO-d$_6$) δ 10.82 (s, 1H), 8.85 (d, J=2.3 Hz, 1H), 8.78 (d, J=2.3 Hz, 1H), 8.65 (d, J=7.0 Hz, 1H), 8.55 (s, 1H), 8.30 (s, 1H), 7.96 (s, 1H), 7.84 (d, J=4.8 Hz, 1H), 7.39 (d, J=8.8 Hz, 1H), 7.13 (d, J=4.8 Hz, 1H), 6.83 (s, 1H), 5.77 (s, 1H), 4.29 (s, 2H), 4.13-3.83 (m, 4H), 3.74 (dd, J=12.1, 4.9 Hz, 1H), 3.61 (t, J=10.9 Hz, 1H), 3.50 (s, 1H), 2.82 (s, 2H), 2.69 (s, 2H), 2.30-2.18 (m, 2H), 2.13 (d, J=13.1 Hz, 2H), 2.07-1.94 (m, 2H), 1.92 (s, 2H), 1.84-1.65 (m, 2H), 1.57 (d, J=10.3 Hz, 2H).

Example 88

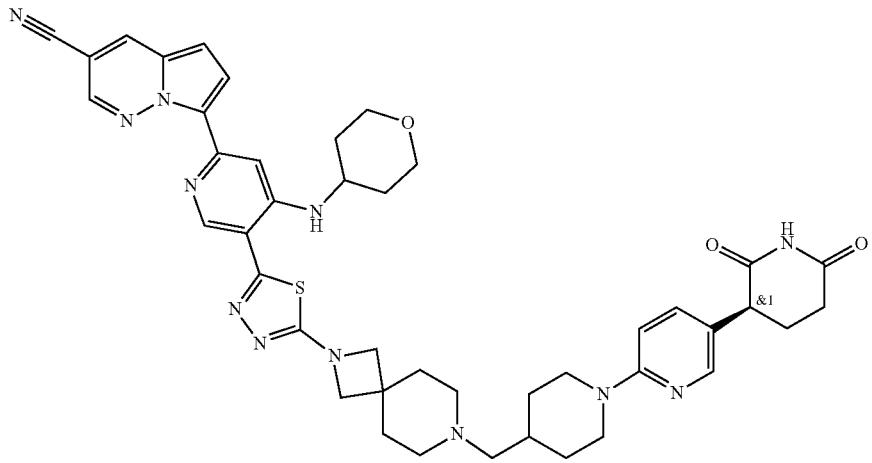 [SMILES: N#Cc1cnn2c(-c3cc(NC4CCOCC4)c(-c4nnc(N5CC6(CCN(CC7CCN(c8ccc([C@@H]9CCC(=O)NC9=O)cn8)CC7)CC6)C5)s4)cn3)ccc2c1]

Example 89

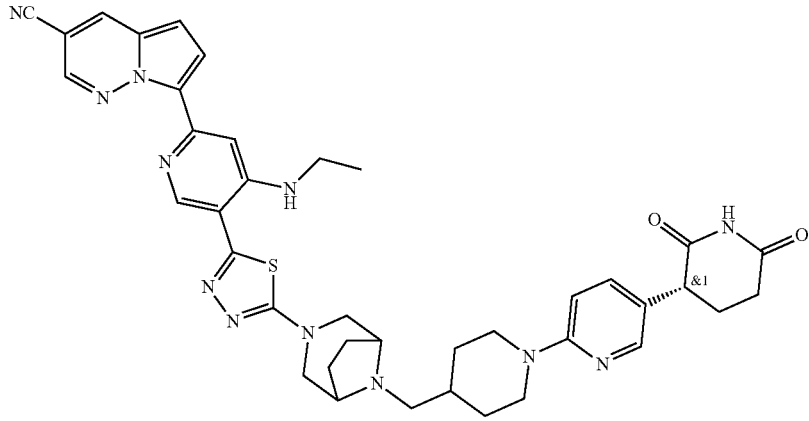 [SMILES: CCNc1cc(-c2ccc3cc(C#N)cnn23)ncc1-c1nnc(N2CC3CCC(C2)N3CC2CCN(c3ccc([C@H]4CCC(=O)NC4=O)cn3)CC2)s1]

rac-7-[5-(5-{8-[(1-{5-[(3R)-2,6-dioxopiperidin-3-yl]pyridin-2-yl}piperidin-4-yl)methyl]-3,8-diazabicyclo[3.2.1]octan-3-yl}-1,3,4-thiadiazol-2-yl)-4-(ethylamino)pyridin-2-yl]pyrrolo[1,2-b]pyridazine-3-carbonitrile The title compound was synthesized from Intermediate AH and HA-1 by reductive amination using General Method B. LCMS: $C_{39}H_{42}N_{12}O_2S$ requires: 742.3, found: m/z=743.6 [M+H]$^+$. $^1$H NMR (500 MHz, DMSO) δ 10.89 (s, 1H), 9.28 (s, 1H), 8.97 (s, 1H), 8.84 (d, J=2.3 Hz, 1H), 8.56 (d, J=8.5 Hz, 1H), 8.08 (s, 2H), 7.93 (dd, J=13.4, 2.5 Hz, 1H), 7.68 (s, 1H), 7.23 (d, J=4.9 Hz, 1H), 4.33 (d, J=13.0 Hz, 2H), 4.26 (s, 1H), 4.13 (d, J=13.0 Hz, 2H), 3.90 (d, J=12.6 Hz, 2H), 3.63-3.57 (m, 2H), 3.02 (t, J=6.2 Hz, 2H), 2.70 (ddd, J=17.7, 12.6, 5.3 Hz, 1H), 2.29 (s, 1H), 2.26 (d, J=13.6 Hz, 3H), 2.00 (q, J=12.2, 9.5 Hz, 5H), 1.36 (t, J=7.2 Hz, 3H), 1.33 (s, 1H).

Example 90

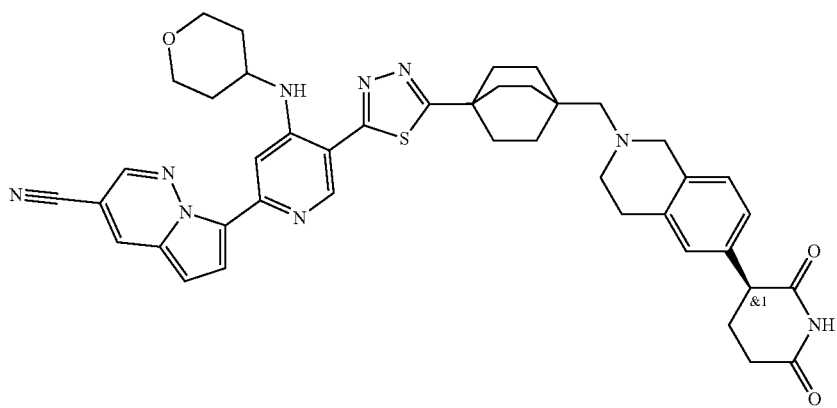

rac-7-(5-{5-[4-({6-[(3R)-2,6-dioxopiperidin-3-yl]-1,2,3,4-tetrahydroisoquinolin-2-yl}methyl)bicyclo[2.2.2]octan-1-yl]-1,3,4-thiadiazol-2-yl}-4-[(oxan-4-yl)amino]pyridin-2-yl)pyrrolo[1,2-b]pyridazine-3-carbonitrile The title compound was synthesized from Intermediate D and HA-5 by reductive amination using General Method B. LCMS: $C_{43}H_{45}N_9O_3S$ requires: 767.3, found: m/z=768.5 [M+H]$^+$. $^1$H NMR (500 MHz, DMSO) δ 10.85 (s, 1H), 9.25 (s, 2H), 8.92 (s, 1H), 8.83 (d, J=2.2 Hz, 1H), 8.77 (s, 1H), 8.27 (s, 1H), 7.94 (d, J=4.8 Hz, 1H), 7.23-7.13 (m, 4H), 4.56 (d, J=15.2 Hz, 1H), 4.41 (dd, J=15.6, 6.8 Hz, 1H), 4.01 (s, 1H), 3.94 (dt, J=11.7, 3.9 Hz, 2H), 3.86 (dd, J=11.8, 4.9 Hz, 1H), 3.74-3.68 (m, 1H), 3.65-3.57 (m, 2H), 3.50 (s, 1H), 3.21 (d, J=4.5 Hz, 1H), 3.13-3.06 (m, 2H), 2.69 (ddd, J=17.3, 12.0, 5.3 Hz, 1H), 2.21 (td, J=11.8, 5.9 Hz, 1H), 2.15-1.97 (m, 10H), 1.83-1.75 (m, 7H), 1.68-1.57 (m, 2H).

Example 91

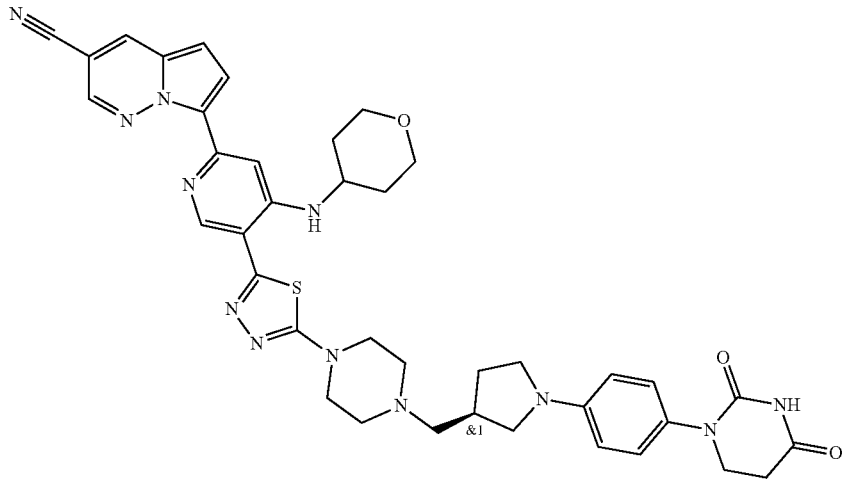 [SMILES: N#Cc1cnn2c(-c3cc(NC4CCOCC4)c(-c4nnc(N5CCN(C[C@H]6CCN(c7ccc(N8CCC(=O)NC8=O)cc7)C6)CC5)s4)cn3)ccc2c1]

rac-7-{5-[5-(4-{[(3R)-1-[4-(2,4-dioxo-1,3-diazinan-1-yl)phenyl]pyrrolidin-3-yl]methyl}piperazin-1-yl)-1,3,4-thiadiazol-2-yl]-4-[(oxan-4-yl)amino]pyridin-2-yl}pyrrolo[1,2-b]pyridazine-3-carbonitrile The title compound was synthesized from Intermediate A and HA-26 by reductive amination using General Method B. LCMS: $C_{39}H_{42}N_{12}O_3S$ requires: 758.3, found: m/z=759.4 [M+H]$^+$. $^1$H NMR (500 MHz, DMSO) δ 10.22 (s, 1H), 9.77 (s, 1H), 8.93 (s, 1H), 8.83 (d, J=2.1 Hz, 1H), 8.60 (s, 1H), 8.19 (s, 1H), 7.97 (s, 1H), 7.19 (d, J=5.0 Hz, 1H), 7.13 (d, J=8.5 Hz, 2H), 6.55 (d, J=8.6 Hz, 2H), 4.15 (s, 3H), 4.03 (s, 10H), 3.93 (dt, J=11.9, 3.9 Hz, 3H), 3.70-3.56 (m, 6H), 3.05 (t, J=8.5 Hz, 1H), 2.81 (s, 1H), 2.68 (t, J=6.7 Hz, 2H), 2.25 (s, 1H), 2.14-2.05 (m, 4H), 1.80 (s, 1H), 1.59 (d, J=11.1 Hz, 3H).

Example 92

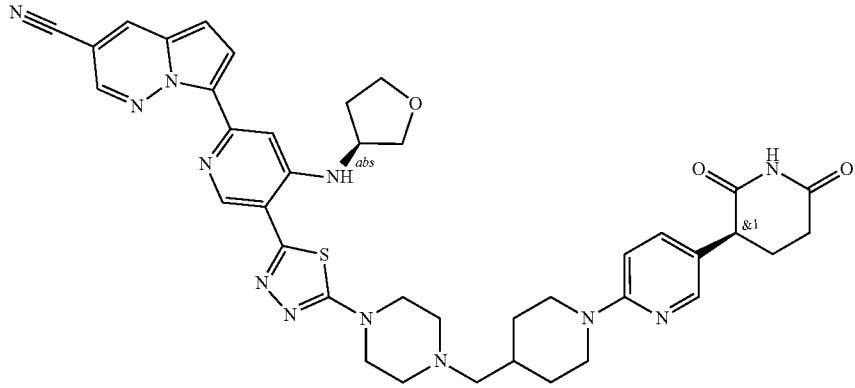 [SMILES: N#Cc1cnn2c(-c3cc(N[C@H]4CCOC4)c(-c4nnc(N5CCN(CC6CCN(c7ccc([C@@H]8CCC(=O)NC8=O)cn7)CC6)CC5)s4)cn3)ccc2c1]

7-[5-(5-{4-[(1-{5-[(3RS)-2,6-dioxopiperidin-3-yl]pyridin-2-yl}piperidin-4-yl)methyl]piperazin-1-yl}-1,3,4-thiadiazol-2-yl)-4-{[(3S)-oxolan-3-yl]amino}pyridin-2-yl]pyrrolo[1,2-b]pyridazine-3-carbonitrile The title compound was synthesized from Intermediate AI and HA-1 by reductive amination using General Method B. LCMS: $C_{39}H_{42}N_{12}O_3S$ requires: 758.3, found: m/z=759.4 [M+H]$^+$. $^1$H NMR (500 MHz, DMSO-d$_6$) δ 10.84 (s, 1H), 9.48 (s, 1H), 8.94-8.86 (m, 1H), 8.80 (d, J=2.3 Hz, 1H), 8.59 (s, 1H), 8.23 (s, 1H), 8.04-7.79 (m, 2H), 7.46 (s, 1H), 7.16 (d, J=4.8 Hz, 1H), 6.91 (s, 1H), 4.44 (s, 1H), 4.31 (d, J=12.9 Hz, 2H), 4.25-4.02 (m, 3H), 4.02-3.81 (m, 2H), 3.76 (d, J=9.3 Hz, 1H), 3.66 (d, J=10.8 Hz, 3H), 3.15 (s, 1H), 2.89 (s, 1H), 2.74-2.61 (m, 1H), 2.41-2.33 (m, 1H), 2.25-2.04 (m, 2H), 1.97 (d, J=19.9 Hz, 2H), 1.84 (d, J=12.7 Hz, 1H), 1.26 (d, J=9.8 Hz, 2H).

Example 93

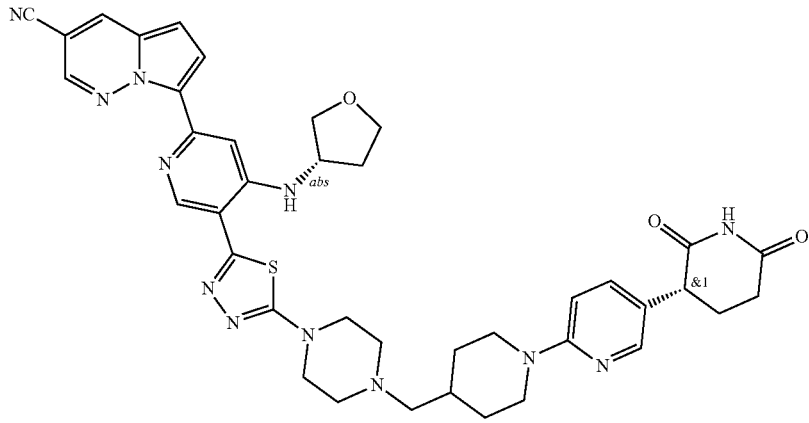 [SMILES: N#Cc1cnn2c(-c3cc(N[C@H]4CCOC4)c(-c4nnc(N5CCN(CC6CCN(c7ccc([C@H]8CCC(=O)NC8=O)cn7)CC6)CC5)s4)cn3)ccc2c1]

7-[5-(5-{4-[(1-{5-[(3RS)-2,6-dioxopiperidin-3-yl]pyridin-2-yl}piperidin-4-yl)methyl]piperazin-1-yl}-1,3,4-thiadiazol-2-yl)-4-{[(3R)-oxolan-3-yl]amino}pyridin-2-yl]pyrrolo[1,2-b]pyridazine-3-carbonitrile The title compound was synthesized from Intermediate AJ and HA-1 by reductive amination using General Method B. LCMS: $C_{39}H_{42}N_{12}O_3S$ requires: 758.3, found: m/z=759.6 [M+H]$^+$. $^1$H NMR (500 MHz, DMSO) δ 10.89 (s, 1H), 8.94 (s, 1H), 8.84 (s, 1H), 8.59 (s, 1H), 8.18 (s, 1H), 8.02 (s, 1H), 7.94 (s, 1H), 7.20 (d, J=4.8 Hz, 1H), 4.53 (s, 1H), 4.31 (d, J=13.1 Hz, 2H), 4.12 (d, J=13.5 Hz, 2H), 4.05 (dd, J=9.5, 5.4 Hz, 1H), 3.97-3.91 (m, 1H), 3.89 (s, 1H), 3.93-3.83 (m, 1H), 3.82 (s, 3H), 3.81 (dd, J=23.4, 7.1 Hz, 1H), 3.72-3.65 (m, 2H), 3.27 (d, J=11.5 Hz, 3H), 3.13 (s, 2H), 3.04 (s, 3H), 2.71 (td, J=13.5, 12.1, 6.4 Hz, 1H), 2.24 (s, 3H), 1.96 (s, 5H).

Example 94

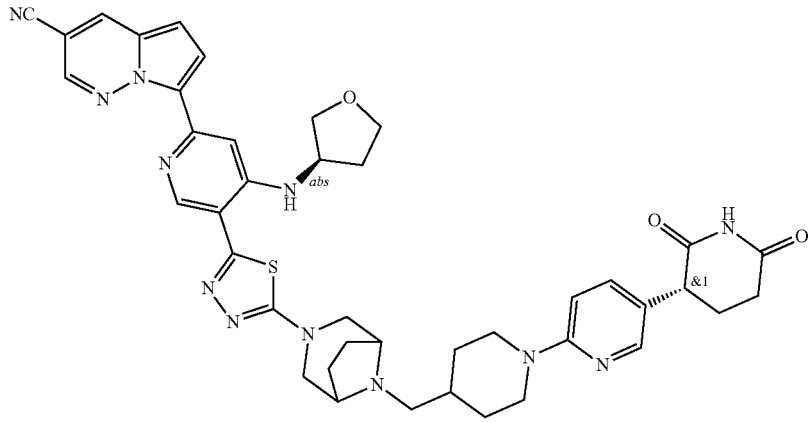 [SMILES: N#Cc1cnn2c(-c3cc(N[C@@H]4CCOC4)c(-c4nnc(N5CC6CCC(C5)N6CC5CCN(c6ccc([C@H]7CCC(=O)NC7=O)cn6)CC5)s4)cn3)ccc2c1]

7-[5-(5-{8-[(1-{5-[(3RS)-2,6-dioxopiperidin-3-yl]pyridin-2-yl}piperidin-4-yl)methyl]-3,8-diazabicyclo[3.2.1]octan-3-yl}-1,3,4-thiadiazol-2-yl)-4-{[(3R)-oxolan-3-yl]amino}pyridin-2-yl]pyrrolo[1,2-b]pyridazine-3-carbonitrile The title compound was synthesized from Intermediate AK and HA-1 by reductive amination using General Method B. LCMS: $C_{41}H_{44}N_{12}O_3S$ requires: 784.3, found: m/z=785.6 [M+H]$^+$. $^1$H NMR (500 MHz, DMSO) δ 10.91 (s, 1H), 8.96 (s, 1H), 8.86 (s, 1H), 8.60 (d, J=8.6 Hz, 1H), 8.16 (s, 1H), 8.07 (s, 1H), 7.93 (s, 1H), 7.22 (d, J=5.1 Hz, 1H), 4.56 (s, 1H), 4.33 (d, J=13.0 Hz, 2H), 4.28-4.20 (m, 2H), 4.13 (d, J=13.0 Hz, 2H), 4.05 (dd, J=9.5, 5.3 Hz, 1H), 3.98-3.80 (m, 5H), 3.83-3.77 (m, 1H), 3.09 (s, 3H), 3.02 (d, J=6.5 Hz, 1H), 2.70 (ddd, J=18.0, 12.6, 5.2 Hz, 1H), 2.59 (s, 1H), 2.28 (s, 5H), 2.01 (s, 6H), 1.98 (d, J=13.2 Hz, 1H), 1.36 (s, 2H).

Example 95

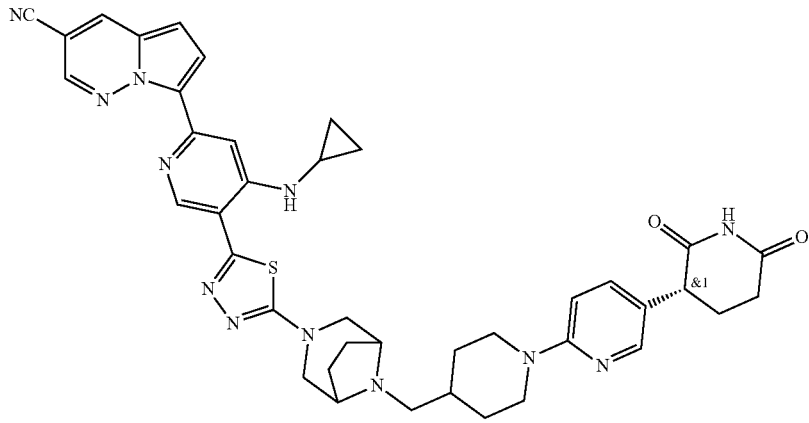 [SMILES: N#Cc1cnn2c(-c3cc(NC4CC4)c(-c4nnc(N5CC6CCC(C5)N6CC5CCN(c6ccc([C@H]7CCC(=O)NC7=O)cn6)CC5)s4)cn3)ccc2c1]

rac-7-[4-(cyclopropylamino)-5-(5-{8-[(1-{5-[(3R)-2,6-dioxopiperidin-3-yl]pyridin-2-yl}piperidin-4-yl)methyl]-3,8-diazabicyclo[3.2.1]octan-3-yl}-1,3,4-thiadiazol-2-yl)pyridin-2-yl]pyrrolo[1,2-b]pyridazine-3-carbonitrile The title compound was synthesized from Intermediate AL and HA-1 by reductive amination using General Method B. LCMS: $C_{40}H_{42}N_{12}O_2S$ requires: 754.3, found: m/z=755.6 [M+H]+. 1H NMR (500 MHz, DMSO) δ 10.92 (s, 1H), 8.97 (s, 1H), 8.88 (s, 1H), 8.59 (d, J=20.9 Hz, 2H), 8.08 (s, 1H), 7.93 (s, 1H), 7.29-7.21 (m, 1H), 4.33 (d, J=12.2 Hz, 2H), 4.26 (s, 2H), 4.11 (s, 2H), 3.89 (d, J=12.5 Hz, 3H), 3.10 (s, 3H), 3.02 (d, J=6.2 Hz, 1H), 2.87 (s, 1H), 2.70 (td, J=15.0, 12.9, 5.3 Hz, 1H), 2.28 (s, 5H), 2.00 (d, J=8.6 Hz, 2H), 1.36 (s, 2H), 1.08 (d, J=6.8 Hz, 2H), 0.73 (s, 2H).

Example 96

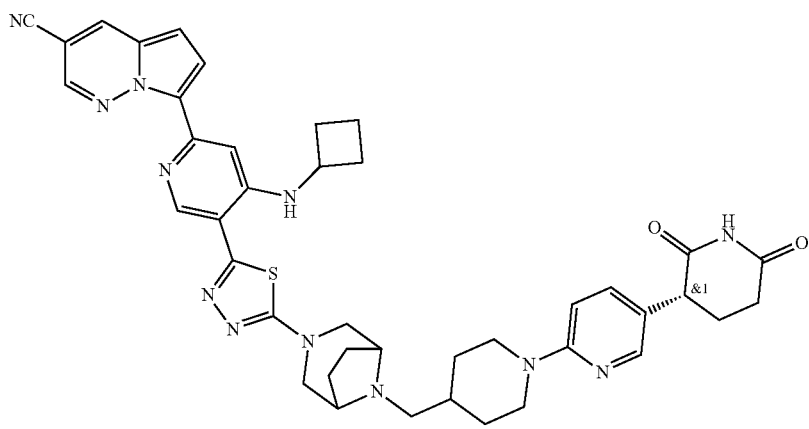 [SMILES: N#Cc1cnn2c(-c3cc(NC4CCC4)c(-c4nnc(N5CC6CCC(C5)N6CC5CCN(c6ccc([C@H]7CCC(=O)NC7=O)cn6)CC5)s4)cn3)ccc2c1]

rac-7-[4-(cyclobutylamino)-5-(5-{8-[(1-{5-[(3R)-2,6-dioxopiperidin-3-yl]pyridin-2-yl}piperidin-4-yl)methyl]-3,8-diazabicyclo[3.2.1]octan-3-yl}-1,3,4-thiadiazol-2-yl)pyridin-2-yl]pyrrolo[1,2-b]pyridazine-3-carbonitrile The title compound was synthesized from Intermediate AM and HA-1 by reductive amination using General Method B. LCMS: $C_{41}H_{44}N_{12}O_2S$ requires: 768.3, found: m/z=769.5 [M+H]+. 1H NMR (500 MHz, DMSO) δ 10.90 (s, 1H), 8.95 (s, 1H), 8.88 (s, 1H), 8.58 (d, J=8.9 Hz, 1H), 8.04 (s, 2H), 7.94 (s, 1H), 7.21 (s, 1H), 4.33 (d, J=13.0 Hz, 3H), 4.26 (s, 2H), 4.07 (s, 2H), 3.92 (d, J=12.7 Hz, 2H), 3.02 (s, 3H), 2.62 (s, 2H), 2.52 (s, 5H), 2.27 (s, 4H), 2.07 (d, J=10.3 Hz, 3H), 2.01 (d, J=10.3 Hz, 6H), 1.92 (h, J=5.1 Hz, 2H), 1.34 (s, 3H), 1.25 (s, 2H).

Example 97

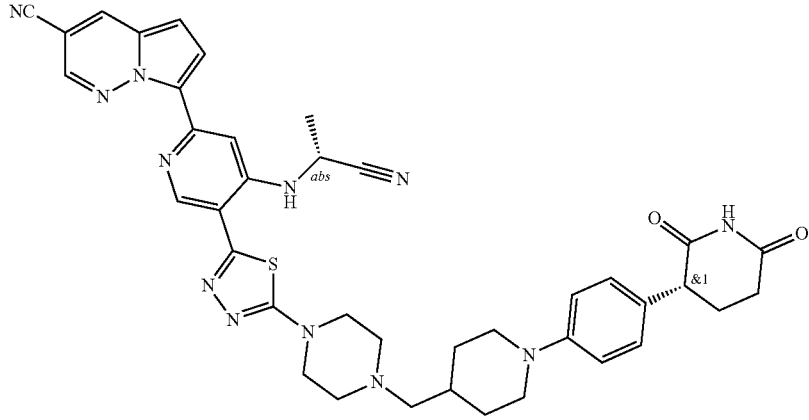 [SMILES: C[C@H](C#N)Nc1cc(-c2ccc3cc(C#N)cnn23)ncc1-c1nnc(N2CCN(CC3CCN(c4ccc([C@H]5CCC(=O)NC5=O)cc4)CC3)CC2)s1]

7-(4-{[(1R)-1-cyanoethyl]amino}-5-(5-{4-[(1-{4-[(3RS)-2,6-dioxopiperidin-3-yl]phenyl}piperidin-4-yl)methyl]piperazin-1-yl}-1,3,4-thiadiazol-2-yl)pyridin-2-yl)pyrrolo[1,2-b]pyridazine-3-carbonitrile The title compound was synthesized from Intermediate AC and HA-7 by reductive amination using General Method B. LCMS: $C_{39}H_{40}N_{12}O_2S$ requires: 740.3, found: m/z=741.6 [M+H]⁺. ¹H NMR (500 MHz, DMSO) δ 10.82 (s, 1H), 10.28 (s, 1H), 9.01 (s, 1H), 8.93 (d, J=2.3 Hz, 1H), 8.73 (d, J=2.2 Hz, 1H), 8.69 (s, 1H), 8.36 (s, 1H), 7.93 (d, J=36.0 Hz, 1H), 7.15 (s, 1H), 7.09 (s, 3H), 5.15 (s, 1H), 4.13 (d, J=14.1 Hz, 2H), 3.79 (d, J=12.0 Hz, 2H), 3.29 (d, J=10.9 Hz, 3H), 3.17 (s, 2H), 2.48 (s, 2H), 2.25-2.07 (m, 1H), 2.03 (dt, J=13.4, 4.8 Hz, 1H), 1.80 (d, J=6.9 Hz, 3H), 1.47 (s, 3H).

Example 98

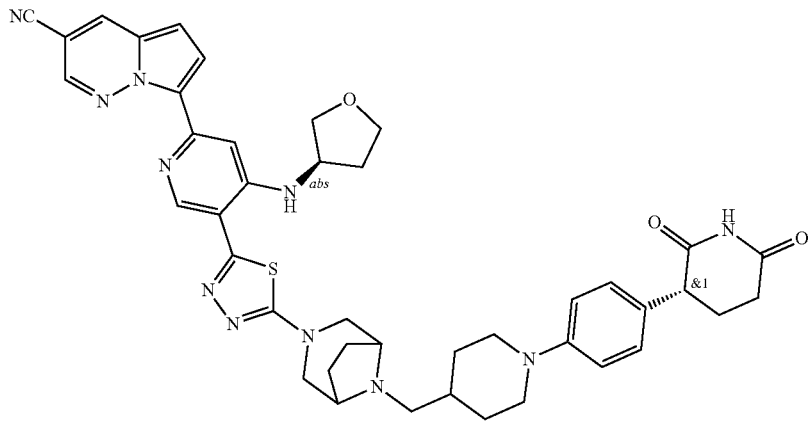 [SMILES: N#Cc1cnn2c(-c3cc(N[C@@H]4CCOC4)c(-c4nnc(N5CC6CCC(C5)N6CC5CCN(c6ccc([C@H]7CCC(=O)NC7=O)cc6)CC5)s4)cn3)ccc2c1]

7-[5-(5-{8-[(1-{4-[(3RS)-2,6-dioxopiperidin-3-yl]phenyl}piperidin-4-yl)methyl]-3,8-diazabicyclo[3.2.1]octan-3-yl}-1,3,4-thiadiazol-2-yl)-4-{[(3R)-oxolan-3-yl]amino}pyridin-2-yl]pyrrolo[1,2-b]pyridazine-3-carbonitrile The title compound was synthesized from Intermediate AK and HA-7 by reductive amination using General Method B. LCMS: $C_{42}H_{45}N_{11}O_3S$ requires: 783.3, found: m/z=784.6 [M+H]⁺. ¹H NMR (500 MHz, DMSO) δ 10.86 (s, 1H), 10.82 (s, 1H), 9.51 (s, 1H), 9.00-8.96 (m, 1H), 8.87 (d, J=2.2 Hz, 1H), 8.60 (d, J=10.2 Hz, 1H), 8.15 (s, 1H), 7.24 (d, J=4.9 Hz, 1H), 7.16 (s, 4H), 4.59 (s, 1H), 4.27 (s, 1H), 4.15 (d, J=12.9 Hz, 1H), 4.04 (dd, J=9.5, 5.3 Hz, 1H), 3.93 (td, J=13.6, 11.4, 7.8 Hz, 2H), 3.89-3.77 (m, 2H), 3.72 (d, J=11.9 Hz, 2H), 3.05 (s, 1H), 2.85 (s, 1H), 2.72-2.62 (m, 1H), 2.51 (s, 1H), 2.48 (s, 1H), 2.30 (s, 1H), 2.21-2.14 (m, 2H), 2.09-1.94 (m, 6H), 1.71 (s, 1H), 1.51 (s, 2H), 1.25 (s, 1H).

Example 99

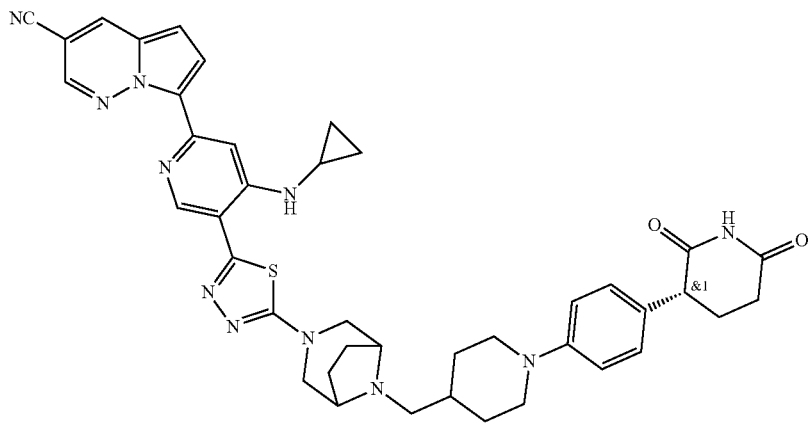 [SMILES: N#Cc1cnn2c(-c3cc(NC4CC4)c(-c4nnc(N5CC6CCC(C5)N6CC5CCN(c6ccc([C@H]7CCC(=O)NC7=O)cc6)CC5)s4)cn3)ccc2c1]

rac-7-[4-(cyclopropylamino)-5-(5-{8-[(1-{4-[(3R)-2,6-dioxopiperidin-3-yl]phenyl}piperidin-4-yl)methyl]-3,8-diazabicyclo[3.2.1]octan-3-yl}-1,3,4-thiadiazol-2-yl)pyridin-2-yl]pyrrolo[1,2-b]pyridazine-3-carbonitrile The title compound was synthesized from Intermediate AL and HA-7 by reductive amination using General Method B. LCMS: $C_{41}H_{43}N_{11}O_2S$ requires: 753.3, found: m/z=754.6 [M+H]$^+$. $^1$H NMR (500 MHz, DMSO) δ 10.82 (d, J=17.4 Hz, 2H), 10.47 (s, 1H), 8.95 (s, 1H), 8.87 (s, 1H), 8.61 (s, 1H), 8.57 (s, 1H), 8.05 (s, 1H), 7.22 (d, J=5.0 Hz, 1H), 7.12 (s, 4H), 6.99 (s, 3H), 4.26 (s, 2H), 4.03 (s, 2H), 3.90 (d, J=12.6 Hz, 3H), 3.74 (d, J=11.8 Hz, 1H), 3.04 (d, J=6.8 Hz, 2H), 2.86 (s, 2H), 2.76 (s, 2H), 2.69-2.61 (m, 1H), 2.29 (d, J=11.3 Hz, 2H), 2.21-2.13 (m, 2H), 2.06-1.98 (m, 7H), 1.85 (s, 1H), 1.46 (s, 4H), 1.25 (s, 4H), 1.08 (d, J=6.6 Hz, 3H), 0.87 (t, J=6.7 Hz, 1H), 0.72 (s, 3H).

Example 100

7-{5-[5-(4-{[(1RS&,5SR&,6RS&)-3-{5-[(3RS)-2,6-dioxopiperidin-3-yl]pyridin-2-yl}-3-azabicyclo[3.1.0]hexan-6-yl]methyl}piperazin-1-yl)-1,3,4-thiadiazol-2-yl]-4-[(oxan-4-yl)amino]pyridin-2-yl}pyrrolo[1,2-b]pyridazine-3-carbonitrile The title compound was synthesized from Intermediate A and HA-27 by reductive amination using General Method B. LCMS: $C_{40}H_{42}N_{12}O_3S$ requires: 770.3, found: m/z=771.5 [M+H]$^+$. $^1$H NMR (500 MHz, DMSO) δ 10.93 (s, 1H), 10.08 (s, 1H), 9.23 (s, 1H), 8.98-8.93 (m, 1H), 8.85 (d, J=2.3 Hz, 1H), 8.62 (s, 1H), 8.20 (s, 1H), 8.00 (dd, J=11.9, 4.9 Hz, 1H), 7.91 (d, J=2.2 Hz, 1H), 7.81 (s, 1H), 7.22 (t, J=4.7 Hz, 1H), 6.95 (s, 1H), 4.17 (s, 1H), 4.07 (s, 1H), 3.94 (dt, J=11.9, 3.9 Hz, 2H), 3.83 (t, J=8.1 Hz, 2H), 3.68 (s, 2H), 3.61 (t, J=10.7 Hz, 4H), 3.33 (s, 1H), 3.26 (s, 1H), 3.23 (d, J=7.2 Hz, 1H), 2.76-2.65 (m, 1H), 2.34-2.22 (m, 1H), 2.11 (d, J=12.8 Hz, 2H), 1.99 (s, 2H), 1.66-1.55 (m, 2H), 1.12 (s, 1H).

Example 101

7-{5-[5-(8-{[(1RS&,5SR&,6RS&)-3-{5-[(3RS)-2,6-dioxopiperidin-3-yl]pyridin-2-yl}-3-azabicyclo[3.1.0]hexan-6-yl]methyl}-3,8-diazabicyclo[3.2.1]octan-3-yl)-1,3,4-thiadiazol-2-yl]-4-[(oxan-4-yl)amino]pyridin-2-yl}pyrrolo[1,2-b]pyridazine-3-carbonitrile The title compound was synthesized from Intermediate F and HA-27 by reductive amination using General Method B. LCMS: $C_{42}H_{44}N_{12}O_3S$ requires: 796.3, found: m/z=797.3 [M+H]$^+$ $^1$H NMR (500 MHz, DMSO) δ 10.92 (s, 1H), 10.18 (s, 1H), 9.20 (s, 1H), 8.95 (t, J=3.3 Hz, 1H), 8.85 (t, J=2.8 Hz, 1H), 8.61 (d, J=4.1 Hz, 1H), 8.19 (d, J=12.7 Hz, 1H), 7.99 (t, J=7.0 Hz, 1H), 7.92 (d, J=2.2 Hz, 1H), 7.78 (s, 1H), 7.21 (t, J=4.3 Hz, 1H), 6.92 (s, 1H), 4.31 (s, 1H), 4.24 (s, 1H), 4.06 (s, 1H), 4.01-3.76 (m, 6H), 3.61 (t, J=11.7 Hz, 4H), 3.13 (s, 1H), 2.76-2.66 (m, 1H), 2.26 (s, 3H), 2.11 (d, J=12.6 Hz, 3H), 2.03 (s, 1H), 2.00 (s, 3H), 1.99 (dd, J=13.5, 9.1 Hz, 1H), 1.66-1.58 (m, 2H), 1.14 (s, 1H).

Example 102

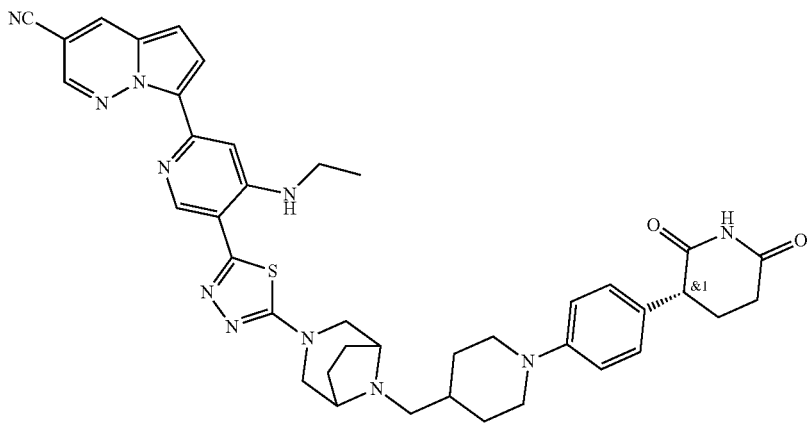 [SMILES: CCNc1cc(-c2ccc3cc(C#N)cnn23)ncc1-c1nnc(N2CC3CCC(C2)N3CC2CCN(c3ccc([C@H]4CCC(=O)NC4=O)cc3)CC2)s1]

rac-7-[5-(5-{8-[(1-{4-[(3R)-2,6-dioxopiperidin-3-yl]
phenyl}piperidin-4-yl)methyl]-3,8-diazabicyclo
[3.2.1]octan-3-yl}-1,3,4-thiadiazol-2-yl)-4-(ethyl-
amino)pyridin-2-yl]pyrrolo[1,2-b]pyridazine-3-
carbonitrile The title compound was synthesized from Intermediate AH and HA-7 by reductive amination using General Method B. LCMS: $C_{40}H_{43}N_{11}O_2S$ requires: 741.3, found: m/z=742.3 [M+H]$^+$. $^1$H NMR (500 MHz, DMSO) δ 10.80 (s, 1H), 9.67 (s, 1H), 8.96 (s, 1H), 8.83 (s, 1H), 8.59 (d, J=9.4 Hz, 1H), 8.06 (s, 1H), 8.02 (s, 1H), 7.22 (d, J=4.9 Hz, 1H), 7.09 (d, J=8.0 Hz, 2H), 6.97 (d, J=8.2 Hz, 2H), 4.26 (s, 2H), 3.94 (d, J=12.8 Hz, 2H), 3.83 (d, J=13.0 Hz, 1H), 3.79-3.72 (m, 3H), 3.06 (s, 2H), 2.75 (s, 2H), 2.71-2.60 (m, 1H), 2.30 (s, 2H), 2.23-2.10 (m, 1H), 2.08 (s, 1H), 2.02 (dq, J=8.4, 5.1 Hz, 3H), 1.93 (d, J=12.1 Hz, 2H), 1.41 (d, J=11.7 Hz, 2H), 1.35 (t, J=7.2 Hz, 3H), 1.25 (s, 1H).

Example 103

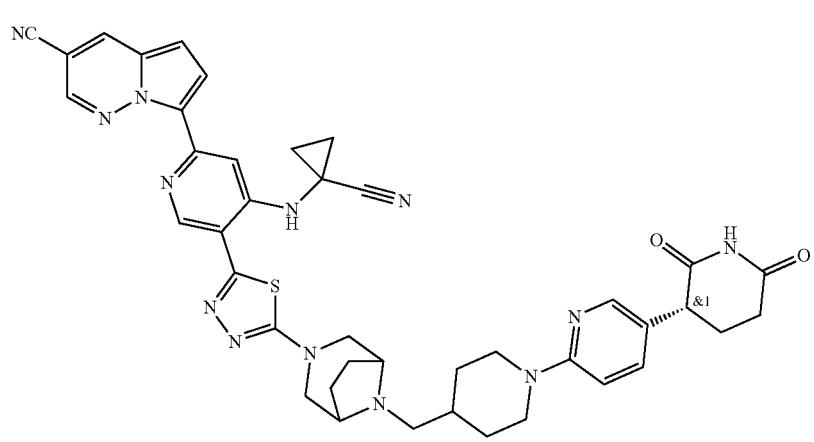 [SMILES: N#Cc1cnn2c(-c3cc(NC4(C#N)CC4)c(-c4nnc(N5CC6CCC(C5)N6CC5CCN(c6ccc([C@H]7CCC(=O)NC7=O)cn6)CC5)s4)cn3)ccc2c1]

rac-7-{4-[(1-cyanocyclopropyl)amino]-5-(5-{8-[(1-
{5-[(3R)-2,6-dioxopiperidin-3-yl]pyridin-2-
yl}piperidin-4-yl)methyl]-3,8-diazabicyclo[3.2.1]
octan-3-yl}-1,3,4-thiadiazol-2-yl)pyridin-2-
yl}pyrrolo[1,2-b]pyridazine-3-carbonitrile The title compound was synthesized from Intermediate AN and HA-1 by reductive amination using General Method B. LCMS: $C_{41}H_{41}N_{13}O_2S$ requires: 779.3, found: m/z=780.6 [M+H]$^+$. $^1$H NMR (500 MHz, DMSO) δ 10.92 (s, 1H), 9.07 (s, 1H), 8.90 (dd, J=18.0, 2.3 Hz, 2H), 8.87 (s, 1H), 8.69 (d, J=11.2 Hz, 1H), 7.99-7.91 (m, 2H), 7.74 (s, 1H), 7.19 (d, J=4.8 Hz, 1H), 4.33 (d, J=12.8 Hz, 2H), 4.26 (d, J=4.3 Hz, 2H), 4.06 (d, J=12.9 Hz, 1H), 3.90 (d, J=12.1 Hz, 3H), 3.11 (s, 2H), 3.05-2.99 (m, 2H), 2.76-2.65 (m, 1H), 2.59 (s, 1H), 2.31-2.22 (m, 5H), 2.00 (td, J=13.3, 11.5, 6.3 Hz, 5H), 1.91 (q, J=5.4, 4.9 Hz, 2H), 1.52 (q, J=5.4 Hz, 2H), 1.36 (d, J=12.1 Hz, 2H), 1.25 (s, 2H).

Example 104

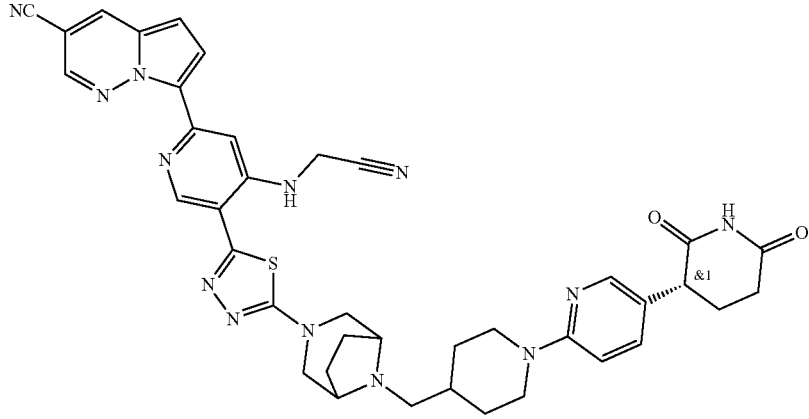 [SMILES: N#CCNc1cc(-c2ccc3cc(C#N)cnn23)ncc1-c1nnc(N2CC3CCC(C2)N3CC2CCN(c3ccc([C@H]4CCC(=O)NC4=O)cn3)CC2)s1]

rac-7-{4-[(cyanomethyl)amino]-5-(5-{8-[(1-{5-[(3R)-2,6-dioxopiperidin-3-yl]pyridin-2-yl}piperidin-4-yl)methyl]-3,8-diazabicyclo[3.2.1]octan-3-yl}-1,3,4-thiadiazol-2-yl)pyridin-2-yl}pyrrolo[1,2-b]pyridazine-3-carbonitrile The title compound was synthesized from Intermediate AO and HA-1 by reductive amination using General Method B. LCMS: C$_{39}$H$_{39}$N$_{13}$O$_2$S requires: 753.3, found: m/z=754.5 [M+H]$^+$. $^1$H NMR (500 MHz, DMSO) δ 10.86 (s, 1H), 9.62 (s, 1H), 8.90 (d, J=2.2 Hz, 1H), 8.73-8.65 (m, 2H), 8.32 (s, 1H), 7.96 (s, 1H), 7.91 (d, J=4.7 Hz, 1H), 7.18 (d, J=4.8 Hz, 1H), 4.74 (d, J=6.1 Hz, 2H), 4.32 (d, J=13.3 Hz, 2H), 4.26 (s, 2H), 3.94 (d, J=12.8 Hz, 2H), 3.82 (d, J=13.1 Hz, 2H), 3.04 (s, 2H), 2.69 (d, J=13.2 Hz, 1H), 2.28 (d, J=8.6 Hz, 2H), 2.22 (s, 3H), 2.14 (s, 1H), 2.04 (d, J=9.2 Hz, 1H), 1.99 (s, 2H), 1.91 (d, J=12.3 Hz, 2H), 1.30 (s, 2H), 1.25 (s, 2H).

Example 105

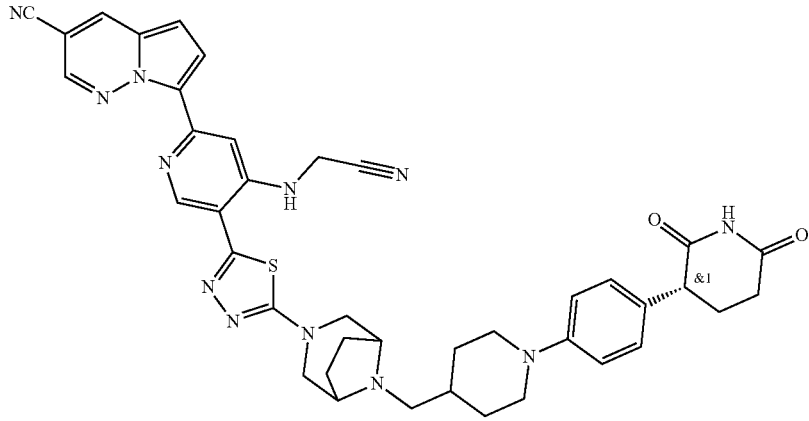 [SMILES: N#CCNc1cc(-c2ccc3cc(C#N)cnn23)ncc1-c1nnc(N2CC3CCC(C2)N3CC2CCN(c3ccc([C@H]4CCC(=O)NC4=O)cc3)CC2)s1]

rac-7-{4-[(cyanomethyl)amino]-5-(5-{8-[(1-{4-[(3R)-2,6-dioxopiperidin-3-yl]phenyl} piperidin-4-yl)methyl]-3,8-diazabicyclo[3.2.1]octan-3-yl}-1,3,4-thiadiazol-2-yl)pyridin-2-yl}pyrrolo[1,2-b]pyridazine-3-carbonitrile The title compound was synthesized from Intermediate AO and HA-7 by reductive amination using General Method B. LCMS: C$_{40}$H$_{40}$N$_{12}$O$_2$S requires: 752.3, found: m/z=753.4 [M+H]$^+$. $^1$H NMR (500 MHz, DMSO) δ 10.79 (s, 1H), 8.90 (s, 1H), 8.70 (s, 1H), 8.32 (s, 1H), 7.91 (s, 1H), 7.17 (d, J=4.8 Hz, 1H), 7.08 (d, J=8.4 Hz, 2H), 6.96 (s, 2H), 4.73 (d, J=5.9 Hz, 2H), 4.26 (s, 3H), 3.93 (d, J=12.3 Hz, 2H), 2.72 (s, 4H), 2.30 (d, J=7.0 Hz, 1H), 2.08 (s, 7H), 2.03 (s, 4H), 1.92 (d, J=11.0 Hz, 2H), 1.40 (s, 2H), 1.25 (s, 5H).

Example 106

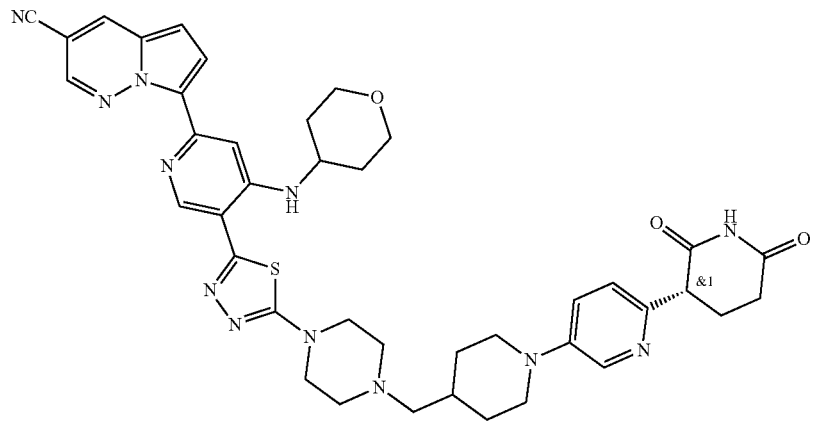 [SMILES: N#Cc1cnn2c(-c3cc(NC4CCOCC4)c(-c4nnc(N5CCN(CC6CCN(c7ccc([C@H]8CCC(=O)NC8=O)nc7)CC6)CC5)s4)cn3)ccc2c1]

rac-7-[5-(5-{4-[(1-{6-[(3R)-2,6-dioxopiperidin-3-yl]pyridin-3-yl}piperidin-4-yl)methyl] piperazin-1-yl}-1,3,4-thiadiazol-2-yl)-4-[(oxan-4-yl)amino]pyridin-2-yl]pyrrolo[1,2-b]pyridazine-3-carbonitrile The title compound was synthesized from Intermediate A and HA-28 by reductive amination using General Method B. LCMS: $C_{40}H_{44}N_{12}O_3S$ requires: 772.3, found: m/z=773.6 [M+H]$^+$. $^1$H NMR (500 MHz, DMSO) δ 11.06 (s, 1H), 11.01 (s, 1H), 10.81 (s, 1H), 8.99 (s, 1H), 8.88 (d, J=2.1 Hz, 1H), 8.60 (s, 1H), 8.35 (s, 1H), 8.18 (s, 1H), 8.14 (s, 1H), 7.88 (s, 1H), 7.57 (s, 2H), 7.25 (d, J=5.0 Hz, 1H), 4.13 (d, J=13.9 Hz, 4H), 3.98-3.85 (m, 5H), 3.83-3.73 (m, 1H), 3.72-3.58 (m, 4H), 2.88 (d, J=11.4 Hz, 2H), 2.61 (d, J=4.2 Hz, 1H), 2.34 (s, 1H), 2.12 (dt, J=19.0, 6.9 Hz, 4H), 2.01 (dd, J=18.3, 10.1 Hz, 2H), 1.77 (d, J=12.6 Hz, 1H), 1.64 (tt, J=10.4, 5.4 Hz, 2H), 1.46 (d, J=12.9 Hz, 1H), 1.37 (s, 2H), 1.25 (s, 6H), 0.87 (t, J=6.7 Hz, 1H).

7-{4-[(oxan-4-yl)amino]-5-[5-(4-{[(1r,4r)-4-({5-[(3RS)-2,6-dioxopiperidin-3-yl]pyridin-2-yl}oxy)cyclohexyl]methyl}piperazin-1-yl)-1,3,4-thiadiazol-2-yl}pyrrolo[1,2-b]pyridazine-3-carbonitrile The title compound was synthesized from Intermediate A and HA-29 by reductive amination using General Method B. LCMS: $C_{41}H_{45}N_{11}O_4S$ requires: 787.3, found: m/z=788.3 [M+H]$^+$. $^1$H NMR (500 MHz, DMSO) δ 10.87 (s, 1H), 9.43 (s, 1H), 8.92 (s, 1H), 8.83 (d, J=2.4 Hz, 1H), 8.59 (s, 1H), 8.24 (s, 1H), 8.00 (d, J=2.5 Hz, 1H), 7.94 (s, 1H), 7.58 (dd, J=8.6, 2.5 Hz, 1H), 7.18 (d, J=4.9 Hz, 1H), 6.75 (d, J=8.5 Hz, 1H), 4.95 (t, J=10.8 Hz, 1H), 4.13 (d, J=13.3 Hz, 2H), 3.97-3.91 (m, 2H), 3.85 (dd, J=12.3, 4.9 Hz, 1H), 3.67 (s, 3H), 3.63 (d, J=11.5 Hz, 4H), 3.12 (s, 2H), 2.73-2.66 (m, 1H), 2.50 (s, 3H), 2.31-2.19 (m, 1H), 2.14 (s, 4H), 2.11 (dd, J=13.3, 9.8 Hz, 1H), 2.00 (d, J=14.9 Hz, 1H), 1.90 (d, J=12.0 Hz, 4H), 1.60 (d, J=11.0 Hz, 2H), 1.47 (s, 1H), 1.43 (d, J=11.8 Hz, 1H), 1.24 (d, J=11.0 Hz, 4H).

Example 107

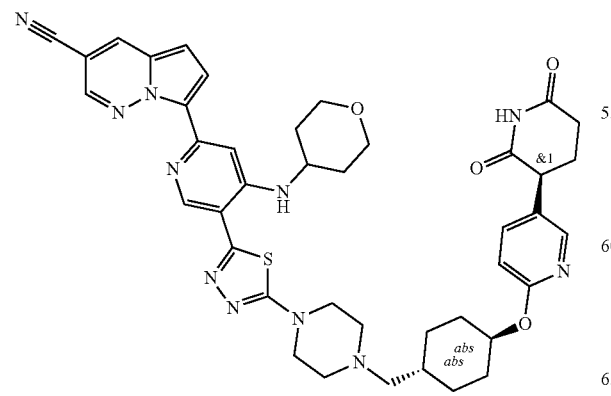

Example 108

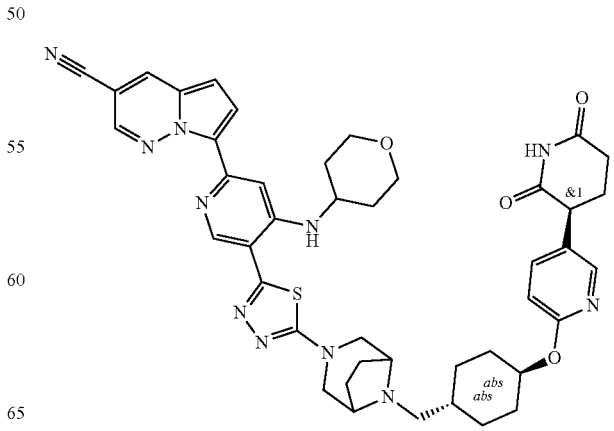

7-{4-[(oxan-4-yl)amino]-5-[5-(8-{[(1r,4r)-4-({5-[(3RS)-2,6-dioxopiperidin-3-yl]pyridin-2-yl}oxy)cyclohexyl]methyl}-3,8-diazabicyclo[3.2.1]octan-3-yl)-1,3,4-thiadiazol-2-yl]pyridin-2-yl}pyrrolo[1,2-b]pyridazine-3-carbonitrile The title compound was synthesized from Intermediate F and HA-29 by reductive amination using General Method B. LCMS: $C_{43}H_{47}N_{11}O_4S$ requires: 813.4, found: m/z=814.5 [M+H]$^+$. $^1$H NMR (500 MHz, DMSO) δ 10.87 (s, 1H), 9.65 (s, 1H), 9.31 (s, 1H), 8.96 (d, J=2.2 Hz, 1H), 8.85 (d, J=2.2 Hz, 1H), 8.62 (s, 1H), 8.16 (s, 1H), 8.01 (t, J=3.8 Hz, 2H), 7.58 (dd, J=8.6, 2.5 Hz, 1H), 7.22 (d, J=4.9 Hz, 1H), 6.75 (d, J=8.5 Hz, 1H), 5.00-4.92 (m, 1H), 4.25 (s, 2H), 4.09 (s, 1H), 3.94 (dq, J=7.6, 4.3, 3.8 Hz, 4H), 3.85 (dt, J=14.9, 7.9 Hz, 2H), 3.60 (d, J=10.6 Hz, 3H), 3.00 (s, 2H), 2.72 (ddd, J=17.6, 9.3, 4.5 Hz, 1H), 2.50 (s, 1H), 2.29 (s, 2H), 2.30-2.19 (m, 1H), 2.19-2.07 (m, 5H), 1.99 (dd, J=21.6, 11.9 Hz, 5H), 1.89 (s, 1H), 1.67-1.62 (m, 1H), 1.62-1.56 (m, 1H), 1.46 (q, J=12.2, 11.8 Hz, 2H), 1.31-1.23 (m, 2H).

Example 109

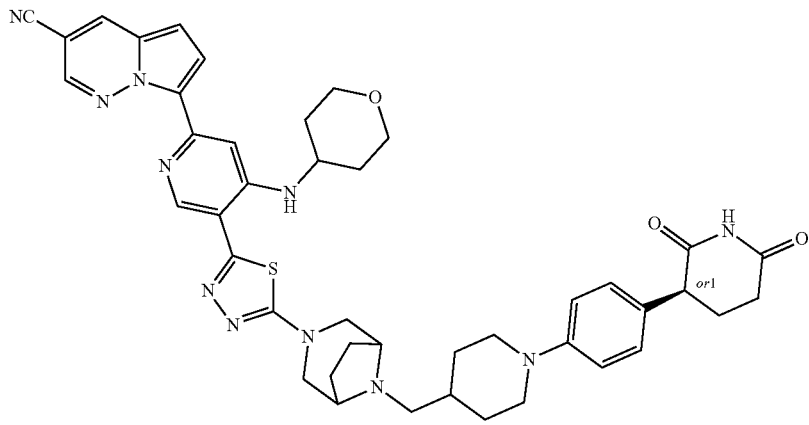 [SMILES: N#Cc1cnn2c(-c3cc(NC4CCOCC4)c(-c4nnc(N5CC6CCC(C5)N6CC5CCN(c6ccc([C@@H]7CCC(=O)NC7=O)cc6)CC5)s4)cn3)ccc2c1]

7-[5-(5-{8-[(1-{4-[(3S)-2,6-dioxopiperidin-3-yl]phenyl}piperidin-4-yl)methyl]-3,8-diazabicyclo[3.2.1]octan-3-yl}-1,3,4-thiadiazol-2-yl)-4-[(oxan-4-yl)amino]pyridin-2-yl]pyrrolo[1,2-b]pyridazine-3-carbonitrile The title compound was synthesized from Intermediate F and HA-30 by reductive amination using General Method B. LCMS: $C_{43}H_{47}N_{11}O_3S$ requires: 797.4, found: m/z=798.6 [M+H]$^+$. $^1$H NMR (500 MHz, DMSO) δ 10.81 (s, 1H), 9.42 (s, 1H), 8.98 (s, 1H), 8.87 (s, 1H), 8.60 (d, J=9.8 Hz, 1H), 8.17 (s, 1H), 8.10 (s, 1H), 7.23 (d, J=4.9 Hz, 1H), 7.14 (s, 2H), 7.08 (s, 3H), 4.27 (s, 2H), 4.12 (d, J=12.7 Hz, 2H), 3.93 (td, J=10.7, 9.5, 5.2 Hz, 4H), 3.79 (s, 1H), 3.73 (d, J=12.0 Hz, 3H), 3.61 (t, J=10.8 Hz, 2H), 3.05 (s, 2H), 2.80 (s, 2H), 2.72-2.61 (m, 1H), 2.32-2.26 (m, 2H), 2.14 (dd, J=27.7, 11.7 Hz, 5H), 2.07-1.98 (m, 4H), 1.69-1.58 (m, 2H), 1.25 (s, 3H).

Example 110

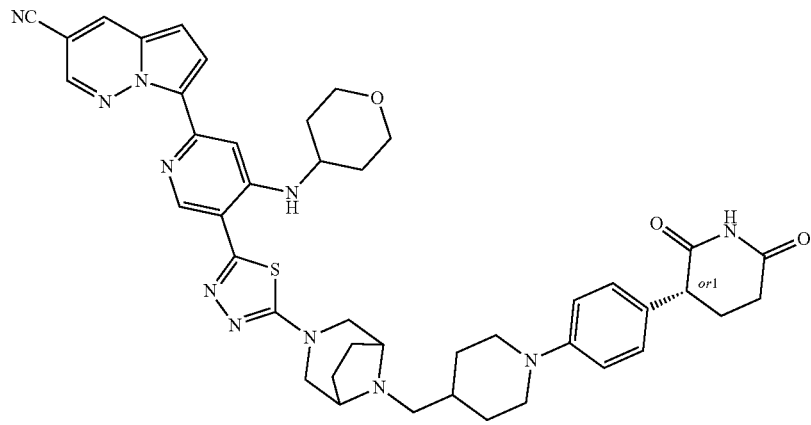 [SMILES: N#Cc1cnn2c(-c3cc(NC4CCOCC4)c(-c4nnc(N5CC6CCC(C5)N6CC5CCN(c6ccc([C@H]7CCC(=O)NC7=O)cc6)CC5)s4)cn3)ccc2c1]

7-[5-(5-{8-[(1-{4-[(3R)-2,6-dioxopiperidin-3-yl]phenyl}piperidin-4-yl)methyl]-3,8-diazabicyclo[3.2.1]octan-3-yl}-1,3,4-thiadiazol-2-yl)-4-[(oxan-4-yl)amino]pyridin-2-yl]pyrrolo[1,2-b]pyridazine-3-carbonitrile The title compound was synthesized from Intermediate F and HA-30 by reductive amination using General Method B. LCMS: $C_{43}H_{47}N_{11}O_3S$ requires: 797.4, found: m/z=798.6 [M+H]$^+$. $^1$H NMR (500 MHz, DMSO) δ 10.82 (s, 1H), 8.99 (s, OH), 8.88 (d, J=2.2 Hz, OH), 8.61 (d, J=10.0 Hz, OH), 8.14 (d, J=17.3 Hz, 1H), 7.25 (d, J=5.0 Hz, OH), 7.15 (s, 1H), 7.06 (s, 1H), 4.27 (s, 1H), 4.12 (d, J=13.0 Hz, 1H), 3.98-3.90 (m, 2H), 3.79 (s, 1H), 3.73 (d, J=11.7 Hz, 1H), 3.61 (t, J=10.9 Hz, 1H), 3.05 (s, 1H), 2.82 (s, 1H), 2.30 (d, J=9.7 Hz, 1H), 2.17 (d, J=12.1 Hz, 1H), 2.11 (d, J=13.4 Hz, 1H), 2.04 (dd, J=10.1, 5.3 Hz, 1H), 2.04-1.98 (m, 1H), 1.63 (tt, J=10.3, 5.9 Hz, 1H), 1.52 (s, 1H).

7-[5-(5-{8-[(1-{5-[(3S)-2,6-dioxopiperidin-3-yl]235yridine-2-yl}piperidin-4-yl)methyl]-3,8-diazabicyclo[3.2.1]octan-3-yl}-1,3,4-thiadiazol-2-yl)-4-[(oxan-4-yl)amino]235yridine-2-yl]pyrrolo[1,2-b]pyridazine-3-carbonitrile The title compound was synthesized from Intermediate F and HA-1 by reductive amination using General Method B, followed by chiral SFC to give the title compound. LCMS: $C_{42}H_{46}N_{12}O_3S$ requires: 798.4, found: m/z=799.4 [M+H]$^+$. $^1$H NMR (500 MHz, DMSO) δ 10.81 (s, 1H), 8.85 (d, J=2.2 Hz, 1H), 8.77 (d, J=2.3 Hz, 1H), 8.69 (d, J=6.9 Hz, 1H), 8.51 (s, 1H), 8.29 (s, 1H), 7.95 (d, J=2.5 Hz, 1H), 7.84 (d, J=4.8 Hz, 1H), 7.37 (dd, J=8.7, 2.5 Hz, 1H), 7.13 (d, J=4.8 Hz, 1H), 6.81 (d, J=8.8 Hz, 1H), 4.29 (d, J=12.6 Hz, 2H), 3.93 (dd, J=9.7, 6.1 Hz, 2H), 3.87 (s, 1H), 3.73 (dd, J=12.2, 4.9 Hz, 1H), 3.61 (t, J=10.9 Hz, 2H), 3.54 (d, J=11.7 Hz, 2H), 3.39 (d, J=11.2 Hz, 2H), 3.34 (s, 2H), 2.79 (t, J=12.4 Hz, 2H), 2.69 (td, J=12.2, 6.1 Hz, 1H), 2.28 (d, J=7.0 Hz, 2H), 2.24-2.07 (m, 3H), 1.96 (s, 3H), 1.87 (d, J=12.7 Hz, 2H), 1.72 (s, 1H), 1.59 (ddd, J=22.8, 12.8, 7.1 Hz, 3H), 1.15 (t, J=12.3 Hz, 2H).

Example 111

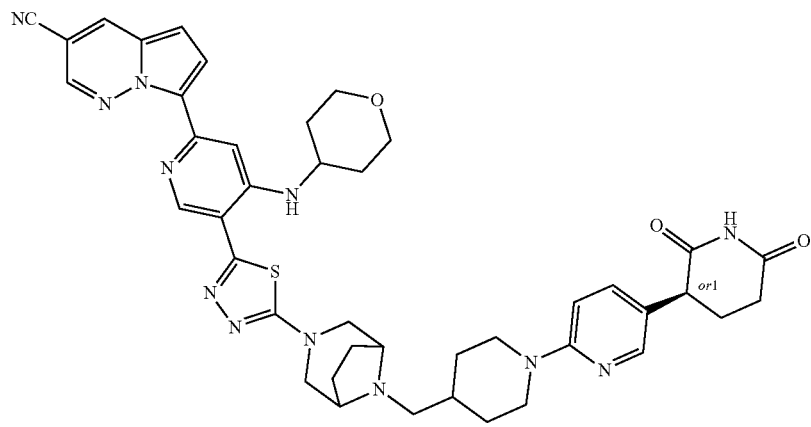

Example 112

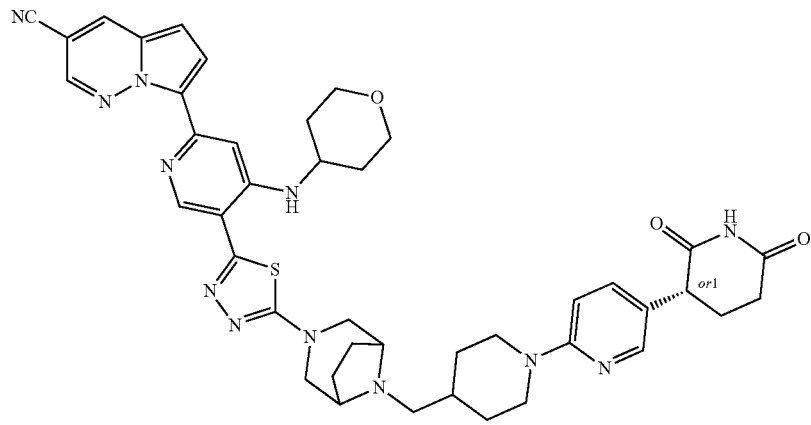 [SMILES: N#Cc1cnn2c(-c3cc(NC4CCOCC4)c(-c4nnc(N5CC6CCC(C5)N6CC5CCN(c6ccc([C@H]7CCC(=O)NC7=O)cn6)CC5)s4)cn3)ccc2c1]

7-[5-(5-{8-[(1-{5-[(3R)-2,6-dioxopiperidin-3-yl]pyridin-2-yl}piperidin-4-yl)methyl]-3,8-diazabicyclo[3.2.1]octan-3-yl}-1,3,4-thiadiazol-2-yl)-4-[(oxan-4-yl)amino]pyridin-2-yl]pyrrolo[1,2-b]pyridazine-3-carbonitrile The title compound was synthesized from Intermediate F and HA-1 by reductive amination using General Method B, followed by chiral SFC to give the title compound. LCMS: $C_{42}H_{46}N_{12}O_3S$ requires: 798.4, found: m/z=799.4 [M+H]$^+$. $^1$H NMR (500 MHz, DMSO) δ 10.81 (s, 1H), 8.85 (d, J=2.3 Hz, 1H), 8.77 (d, J=2.2 Hz, 1H), 8.68 (d, J=7.0 Hz, 1H), 8.51 (s, 1H), 8.29 (s, 1H), 7.95 (d, J=2.5 Hz, 1H), 7.84 (d, J=4.7 Hz, 1H), 7.37 (dd, J=8.9, 2.5 Hz, 1H), 7.13 (d, J=4.8 Hz, 1H), 6.81 (d, J=8.8 Hz, 1H), 4.29 (d, J=12.7 Hz, 2H), 3.94 (dt, J=11.8, 3.9 Hz, 2H), 3.73 (dd, J=12.1, 4.9 Hz, 1H), 3.65-3.56 (m, 2H), 3.53 (d, J=11.2 Hz, 2H), 3.39 (d, J=11.1 Hz, 2H), 3.34 (s, 3H), 2.79 (t, J=12.2 Hz, 2H), 2.74-2.66 (m, 1H), 2.28 (d, J=7.0 Hz, 2H), 2.24-2.12 (m, 2H), 2.11 (s, 1H), 1.96 (s, 2H), 1.87 (d, J=12.5 Hz, 2H), 1.72 (s, 1H), 1.59 (ddd, J=23.4, 12.8, 7.1 Hz, 3H), 1.16 (d, J=11.7 Hz, 1H), 1.11 (d, J=11.5 Hz, 1H).

Example 113

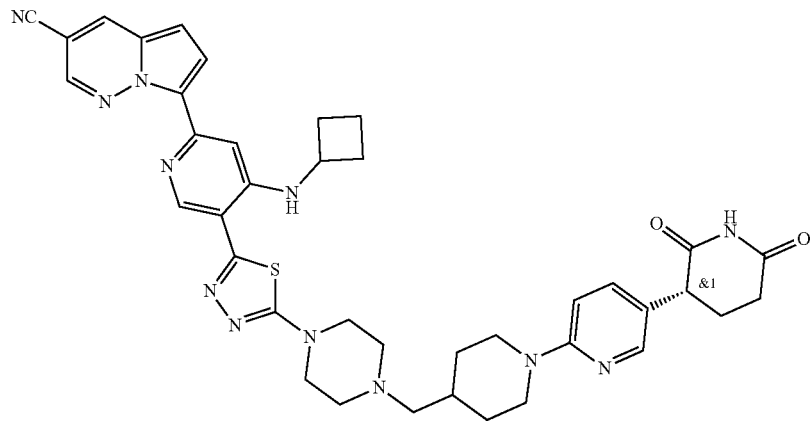 [SMILES: N#Cc1cnn2c(-c3cc(NC4CCC4)c(-c4nnc(N5CCN(CC6CCN(c7ccc([C@H]8CCC(=O)NC8=O)cn7)CC6)CC5)s4)cn3)ccc2c1]

rac-7-[4-(cyclobutylamino)-5-(5-{4-[(1-{5-[(3R)-2,6-dioxopiperidin-3-yl]pyridin-2-yl}piperidin-4-yl)methyl]piperazin-1-yl}-1,3,4-thiadiazol-2-yl)pyridin-2-yl]pyrrolo[1,2-b]pyridazine-3-carbonitrile The title compound was synthesized from Intermediate AP and HA-1 by reductive amination using General Method B. LCMS: $C_{39}H_{42}N_{12}O_2S$ requires: 742.3, found: m/z=743.5 [M+H]$^+$. $^1$H NMR (500 MHz, DMSO) δ 10.90 (s, 1H), 10.59 (s, 1H), 8.95 (s, 1H), 8.88 (s, 1H), 8.57 (s, 1H), 8.07-7.97 (m, 2H), 7.93 (s, 1H), 7.28-7.19 (m, 1H), 4.31 (d, J=13.6 Hz, 4H), 4.15-4.09 (m, 3H), 3.86 (d, J=14.0 Hz, 4H), 3.69 (s, 2H), 3.28 (s, 3H), 3.13 (s, 2H), 3.06 (s, 4H), 2.76-2.59 (m, 1H), 2.65-2.56 (m, 3H), 2.29-2.21 (m, 3H), 2.08 (t, J=9.6 Hz, 2H), 2.02-1.86 (m, 7H), 1.31 (d, J=12.3 Hz, 3H).

Example 114

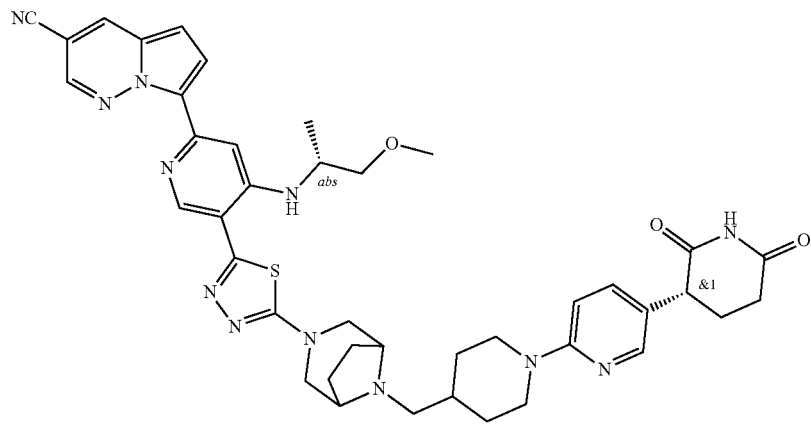 [SMILES: COC[C@@H](C)Nc1cc(-c2ccc3cc(C#N)cnn23)ncc1-c1nnc(N2CC3CCC(C2)N3CC2CCN(c3ccc([C@H]4CCC(=O)NC4=O)cn3)CC2)s1]

7-[5-(5-{8-[(1-{5-[(3RS)-2,6-dioxopiperidin-3-yl]pyridin-2-yl}piperidin-4-yl)methyl]-3,8-diazabicyclo[3.2.1]octan-3-yl}-1,3,4-thiadiazol-2-yl)-4-{[(2R)-1-methoxypropan-2-yl]amino}pyridin-2-yl]pyrrolo[1,2-b]pyridazine-3-carbonitrile The title compound was synthesized from Intermediate AQ and HA-1 by reductive amination using General Method B. LCMS: $C_{41}H_{46}N_{12}O_3S$ requires: 786.4, found: m/z=787.5 [M+H]$^+$

Example 115

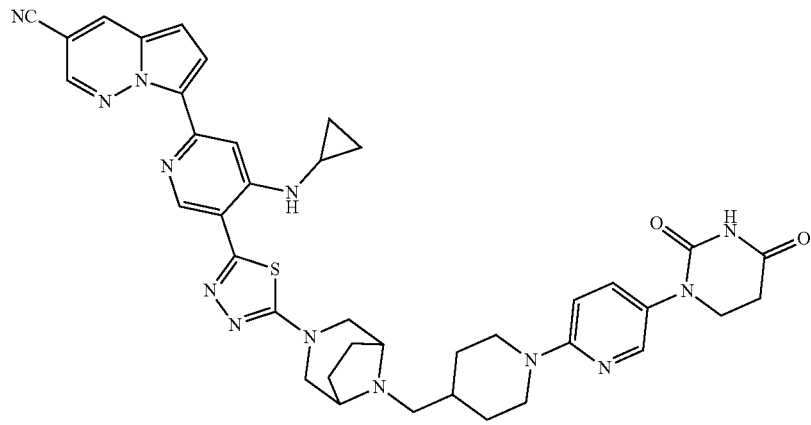 [SMILES: N#Cc1cnn2c(-c3cc(NC4CC4)c(-c4nnc(N5CC6CCC(C5)N6CC5CCN(c6ccc(N7CCC(=O)NC7=O)cn6)CC5)s4)cn3)ccc2c1]

7-[4-(cyclopropylamino)-5-{5-[8-({1-[5-(2,4-dioxo-1,3-diazinan-1-yl)pyridin-2-yl]piperidin-4-yl}methyl)-3,8-diazabicyclo[3.2.1]octan-3-yl]-1,3,4-thiadiazol-2-yl}pyridin-2-yl]pyrrolo[1,2-b]pyridazine-3-carbonitrile The title compound was synthesized from Intermediate AL and HA-19 by reductive amination using General Method B. LCMS: $C_{39}H_{41}N_{13}O_2S$ requires: 755.3, found: m/z=756.5 [M+H]$^+$ Example 116

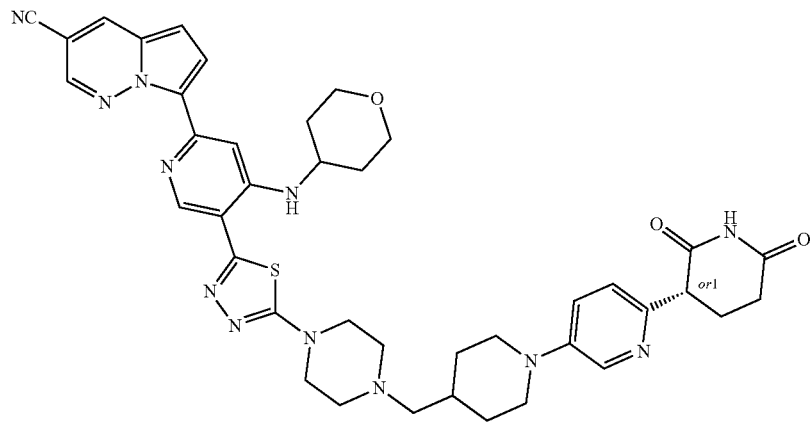 [SMILES: N#Cc1cnn2c(-c3cc(NC4CCOCC4)c(-c4nnc(N5CCN(CC6CCN(c7ccc([C@H]8CCC(=O)NC8=O)nc7)CC6)CC5)s4)cn3)ccc2c1]

7-[5-(5-{4-[(1-{6-[(3R)-2,6-dioxopiperidin-3-yl]
pyridin-3-yl}piperidin-4-yl)methyl] piperazin-1-yl}-
1,3,4-thiadiazol-2-yl)-4-[(oxan-4-yl)amino]pyridin-
2-yl]pyrrolo[1,2-b]pyridazine-3-carbonitrile The title compound was synthesized from Intermediate A and HA-28 by reductive amination using General Method B, followed by chiral SFC to give the title compound. LCMS: $C_{40}H_{44}N_{12}O_3S$ requires: 772.3, found: m/z=773.4 [M+H]$^+$ Example 117

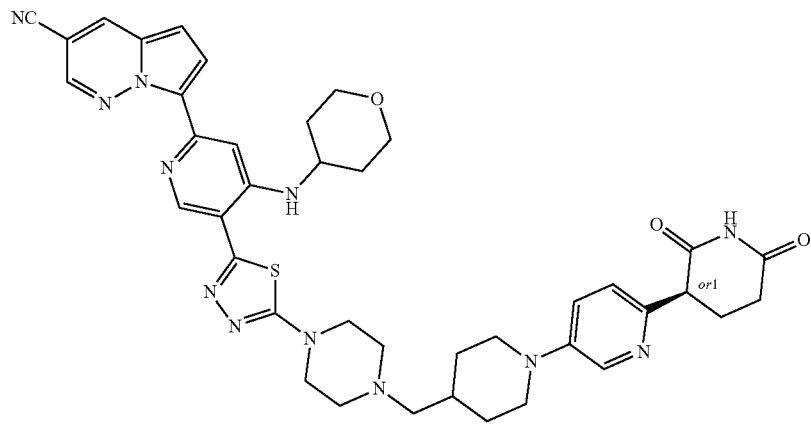 [SMILES: N#Cc1cnn2c(-c3cc(NC4CCOCC4)c(-c4nnc(N5CCN(CC6CCN(c7ccc([C@@H]8CCC(=O)NC8=O)nc7)CC6)CC5)s4)cn3)ccc2c1]

7-[5-(5-{4-[(1-{6-[(3S)-2,6-dioxopiperidin-3-yl]
pyridin-3-yl}piperidin-4-yl)methyl]piperazin-1-yl}-
1,3,4-thiadiazol-2-yl)-4-[(oxan-4-yl)amino]pyridin-
2-yl]pyrrolo[1,2-b]pyridazine-3-carbonitrile The title compound was synthesized from Intermediate A and HA-28 by reductive amination using General Method B, followed by chiral SFC to give the title compound. LCMS: $C_{40}H_{44}N_{12}O_3S$ requires: 772.3, found: m/z=773.3 [M+H]$^+$ Example 118

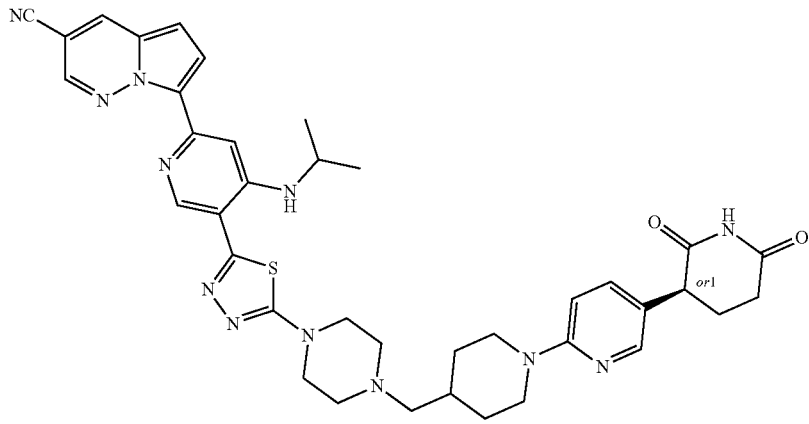 [SMILES: CC(C)Nc1cc(-c2ccc3cc(C#N)cnn23)ncc1-c1nnc(N2CCN(CC3CCN(c4ccc([C@@H]5CCC(=O)NC5=O)cn4)CC3)CC2)s1]

7-[5-(5-{4-[(1-{5-[(3S)-2,6-dioxopiperidin-3-yl]pyridin-2-yl}piperidin-4-yl)methyl]piperazin-1-yl}-1,3,4-thiadiazol-2-yl)-4-[(propan-2-yl)amino]pyridin-2-yl]pyrrolo[1,2-b]pyridazine-3-carbonitrile The title compound was synthesized from Intermediate B and HA-32 by reductive amination using General Method B. LCMS: $C_{38}H_{42}N_{12}O_2S$ requires: 730.3, found: m/z=731.5 [M+H]$^+$. $^1$H NMR (500 MHz, DMSO) δ 10.89 (s, 1H), 8.95 (s, 1H), 8.83 (s, 1H), 8.57 (s, 1H), 8.13 (s, 1H), 8.04 (s, 1H), 7.94 (s, 1H), 7.21 (d, J=4.5 Hz, 1H), 4.31 (d, J=13.0 Hz, 2H), 4.12 (d, J=13.7 Hz, 3H), 3.81 (s, 4H), 3.68 (d, J=12.0 Hz, 2H), 3.28 (s, 2H), 3.13 (s, 2H), 3.00 (s, 3H), 2.72-2.65 (m, 1H), 2.28-2.19 (m, 3H), 1.98 (d, J=12.3 Hz, 1H), 1.93 (s, 2H), 1.38 (d, J=6.3 Hz, 6H), 1.29 (s, 2H), 0.08 (s, 1H).

Example 119

7-[4-(cyclopropylamino)-5-(5-{4-[(1-{5-[(3S)-2,6-dioxopiperidin-3-yl]pyridin-2-yl}piperidin-4-yl)methyl]piperazin-1-yl}-1,3,4-thiadiazol-2-yl)pyridin-2-yl]pyrrolo[1,2-b]pyridazine-3-carbonitrile The title compound was synthesized from Intermediate Z and HA-32 by reductive amination using General Method B. LCMS: $C_{38}H_{40}N_{12}O_2S$ requires: 728.3, found: m/z=729.5 [M+H]$^+$. $^1$H NMR (500 MHz, DMSO) δ 10.91 (s, 1H), 10.75 (s, 1H), 9.17 (s, 1H), 8.96 (s, 1H), 8.87 (s, 1H), 8.64 (s, 1H), 8.56 (s, 1H), 8.07 (s, 1H), 7.93 (s, 1H), 7.75 (s, 1H), 7.22 (d, J=4.8 Hz, 1H), 4.32 (d, J=13.1 Hz, 2H), 4.10 (d, J=13.8 Hz, 2H), 3.87 (d, J=14.3 Hz, 3H), 3.69 (d, J=12.2 Hz, 2H), 3.27 (d, J=11.3 Hz, 2H), 3.13 (s, 3H), 2.86 (s, 1H), 2.76-2.65 (m, 1H), 2.30-2.21 (m, 2H), 1.98 (d, J=12.6 Hz, 3H), 1.32 (d, J=12.6 Hz, 2H), 1.08 (d, J=6.7 Hz, 2H), 0.72 (s, 2H).

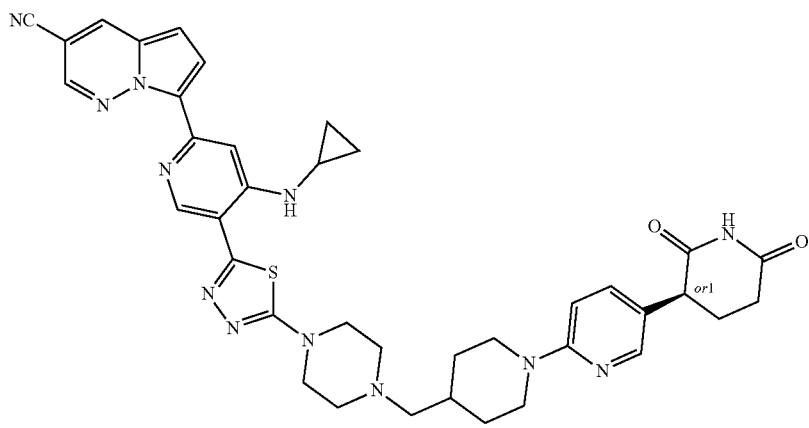 [SMILES: N#Cc1cnn2c(-c3cc(NC4CC4)c(-c4nnc(N5CCN(CC6CCN(c7ccc([C@@H]8CCC(=O)NC8=O)cn7)CC6)CC5)s4)cn3)ccc2c1]

Example 120

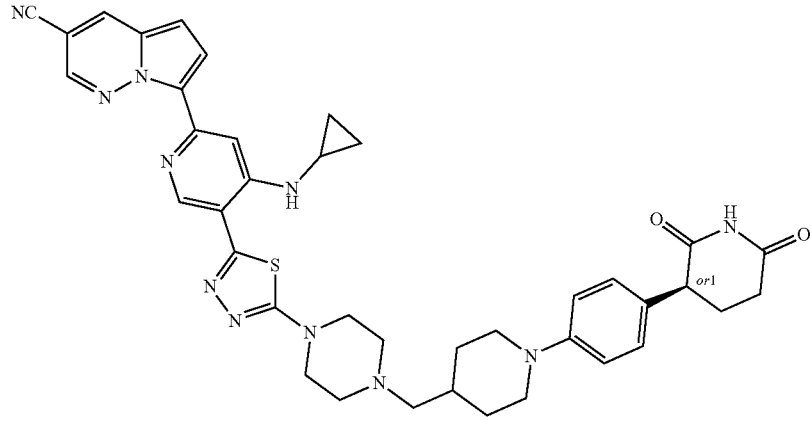 [SMILES: N#Cc1cnn2c(-c3cc(NC4CC4)c(-c4nnc(N5CCN(CC6CCN(c7ccc([C@@H]8CCC(=O)NC8=O)cc7)CC6)CC5)s4)cn3)ccc2c1]

7-[4-(cyclopropylamino)-5-(5-{4-[(1-{4-[(3S)-2,6-dioxopiperidin-3-yl]phenyl}piperidin-4-yl)methyl]piperazin-1-yl}-1,3,4-thiadiazol-2-yl)pyridin-2-yl]pyrrolo[1,2-b]pyridazine-3-carbonitrile The title compound was synthesized from Intermediate Z and HA-30 by reductive amination using General Method B. LCMS: $C_{39}H_{41}N_{11}O_2S$ requires: 727.3, found: m/z=728.4 [M+H]$^+$. $^1$H NMR (500 MHz, DMSO-d$_6$) δ 11.30 (s, 1H), 10.86 (s, 1H), 9.56 (s, 1H), 9.02 (s, 1H), 8.93 (s, 1H), 8.62 (s, 1H), 8.52 (s, 1H), 8.37-8.17 (m, 1H), 7.28 (t, J=12.5 Hz, 2H), 4.12 (d, J=13.7 Hz, 2H), 3.94 (dd, J=29.7, 17.0 Hz, 5H), 3.42-3.07 (m, 7H), 2.95 (s, 2H), 2.69 (ddd, J=17.6, 12.1, 5.7 Hz, 2H), 2.30-1.91 (m, 6H), 1.77 (s, 2H), 1.23-0.94 (m, 2H), 0.78 (t, J=4.8 Hz, 2H).

Example 121

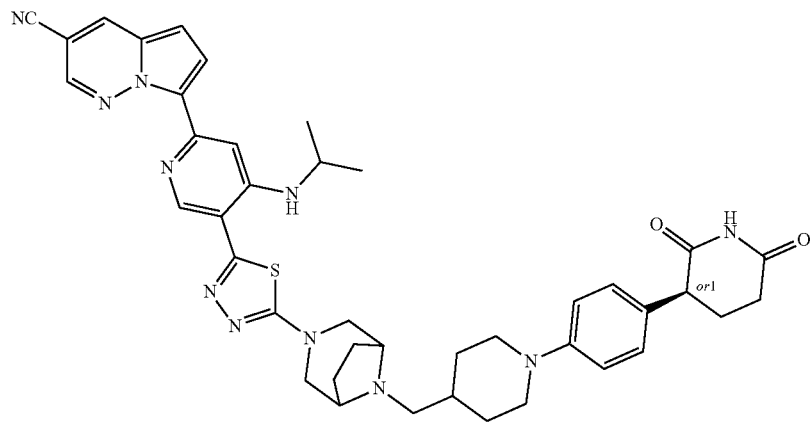 [SMILES: CC(C)Nc1cc(-c2ccc3cc(C#N)cnn23)ncc1-c1nnc(N2CC3CCC(C2)N3CC2CCN(c3ccc([C@@H]4CCC(=O)NC4=O)cc3)CC2)s1]

7-[5-(5-{8-[(1-{4-[(3S)-2,6-dioxopiperidin-3-yl]phenyl}piperidin-4-yl)methyl]-3,8-diazabicyclo[3.2.1]octan-3-yl}-1,3,4-thiadiazol-2-yl)-4-[(propan-2-yl)amino]pyridin-2-yl]pyrrolo[1,2-b]pyridazine-3-carbonitrile The title compound was synthesized from Intermediate R and HA-30 by reductive amination using General Method B. LCMS: $C_{41}H_{45}N_{11}O_2S$ requires: 755.4, found: m/z=756.5 [M+H]$^+$. $^1$H NMR (500 MHz, DMSO-d$_6$) δ 11.38 (s, 1H), 10.84 (s, 1H), 9.60 (s, 1H), 9.01 (s, 1H), 8.87 (s, 1H), 8.55 (d, J=4.0 Hz, 1H), 8.24 (t, J=6.6 Hz, 1H), 8.09 (s, 1H), 7.36-7.10 (m, 4H), 4.44-4.06 (m, 5H), 4.06-3.78 (m, 4H), 3.70 (d, J=11.8 Hz, 3H), 3.07 (s, 3H), 2.69 (td, J=11.8, 6.0 Hz, 2H), 2.46-2.10 (m, 7H), 2.03 (dt, J=17.9, 6.8 Hz, 4H), 1.39 (d, J=6.3 Hz, 7H).

Example 122

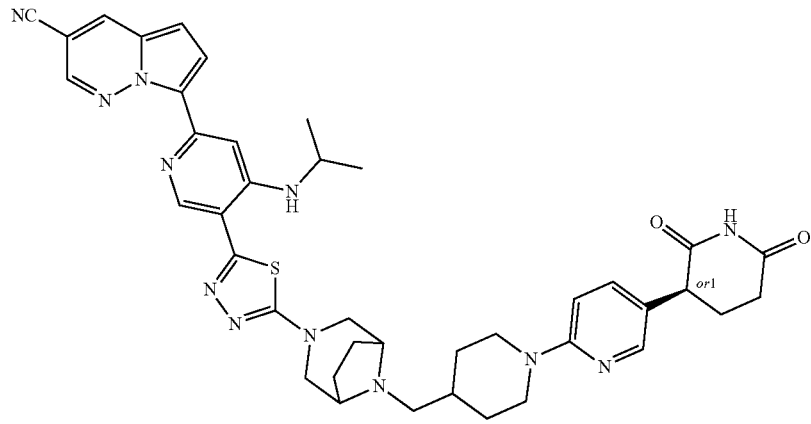

7-[5-(5-{8-[(1-{5-[(3S)-2,6-dioxopiperidin-3-yl]pyridin-2-yl}piperidin-4-yl)methyl]-3,8-diazabicyclo[3.2.1]octan-3-yl}-1,3,4-thiadiazol-2-yl)-4-[(propan-2-yl)amino]pyridin-2-yl]pyrrolo[1,2-b]pyridazine-3-carbonitrile The title compound was synthesized from Intermediate R and HA-32 by reductive amination using General Method B. LCMS: $C_{40}H_{44}N_{12}O_2S$ requires: 756.3, found: m/z=757.3 [M+H]+. $^1$H NMR (500 MHz, DMSO-$d_6$) δ 10.92 (s, 2H), 8.99 (s, 1H), 8.86 (s, 1H), 8.58 (d, J=8.0 Hz, 1H), 8.12 (d, J=25.3 Hz, 2H), 7.92 (d, J=12.6 Hz, 2H), 7.81 (s, 1H), 7.24 (d, J=4.9 Hz, 2H), 4.41-4.00 (m, 10H), 3.91 (d, J=12.4 Hz, 5H), 3.20-2.92 (m, 5H), 2.77-2.61 (m, 2H), 2.40-2.10 (m, 6H), 2.10-1.86 (m, 8H), 1.60 (d, J=11.6 Hz, 1H).

Example 123

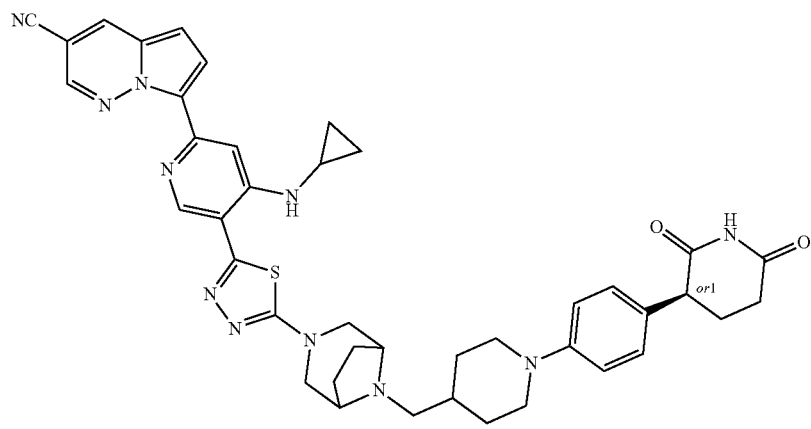 [SMILES: N#Cc1cnn2c(-c3cc(NC4CC4)c(-c4nnc(N5CC6CCC(C5)N6CC5CCN(c6ccc([C@@H]7CCC(=O)NC7=O)cc6)CC5)s4)cn3)ccc2c1]

7-[4-(cyclopropylamino)-5-(5-{8-[(1-{4-[(3S)-2,6-dioxopiperidin-3-yl]phenyl}piperidin-4-yl)methyl]-3,8-diazabicyclo[3.2.1]octan-3-yl}-1,3,4-thiadiazol-2-yl)pyridin-2-yl]pyrrolo[1,2-b]pyridazine-3-carbonitrile The title compound was synthesized from Intermediate AL and HA-30 by reductive amination using General Method B. LCMS: $C_{41}H_{43}N_{11}O_2S$ requires: 753.3, found: m/z=754.6 [M+H]+. $^1$H NMR (500 MHz, DMSO-$d_6$) δ 10.81 (s, 2H), 9.66 (s, 1H), 8.93 (d, J=46.4 Hz, 1H), 8.57 (s, 1H), 7.19 (d, J=48.8 Hz, 8H), 4.26 (s, 3H), 3.60 (d, J=12.1 Hz, 5H), 3.05 (s, 3H), 2.89 (s, 2H), 2.65 (dd, J=3.9, 2.1 Hz, 5H), 2.29 (s, 3H), 2.21-2.09 (m, 4H), 2.02 (d, J=13.6 Hz, 10H), 1.70 (s, 2H), 1.25 (s, 2H), 1.09 (s, 2H), 0.73 (s, 2H).

Example 124

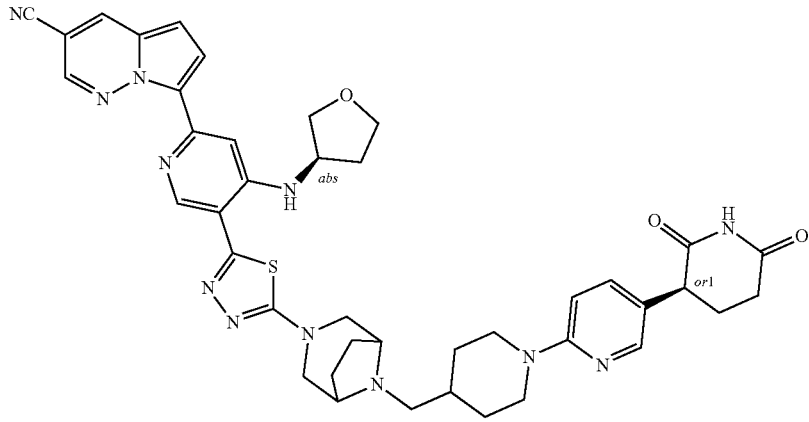 [SMILES: N#Cc1cnn2c(-c3cc(N[C@@H]4CCOC4)c(-c4nnc(N5CC6CCC(C5)N6CC5CCN(c6ccc([C@@H]7CCC(=O)NC7=O)cn6)CC5)s4)cn3)ccc2c1]

7-[5-(5-{8-[(1-{5-[(3S)-2,6-dioxopiperidin-3-yl]
pyridin-2-yl}piperidin-4-yl)methyl]-3,8-diazabicyclo
[3.2.1]octan-3-yl}-1,3,4-thiadiazol-2-yl)-4-{[(3R)-
oxolan-3-yl]amino}pyridin-2-yl]pyrrolo[1,2-b]
pyridazine-3-carbonitrile The title compound was synthesized from Intermediate AK and HA-32 by reductive amination using General Method B. LCMS: $C_{41}H_{44}N_{12}O_3S$ requires: 784.3, found: m/z=785.5 [M+H]$^+$. $^1$H NMR (500 MHz, DMSO-d$_6$) δ 10.89 (s, 1H), 8.94 (s, 1H), 8.84 (s, 1H), 8.60 (d, J=8.0 Hz, 1H), 8.18 (s, 1H), 7.97 (d, J=29.2 Hz, 2H), 7.20 (s, 1H), 4.52 (s, 1H), 4.45-4.19 (m, 5H), 4.05 (dd, J=9.6, 5.6 Hz, 3H), 3.92 (d, J=12.2 Hz, 3H), 3.90-3.73 (m, 5H), 3.09-2.93 (m, 3H), 2.82-2.63 (m, 3H), 2.27 (s, 4H), 1.96 (d, J=35.7 Hz, 6H), 1.33 (s, 2H).

Example 125

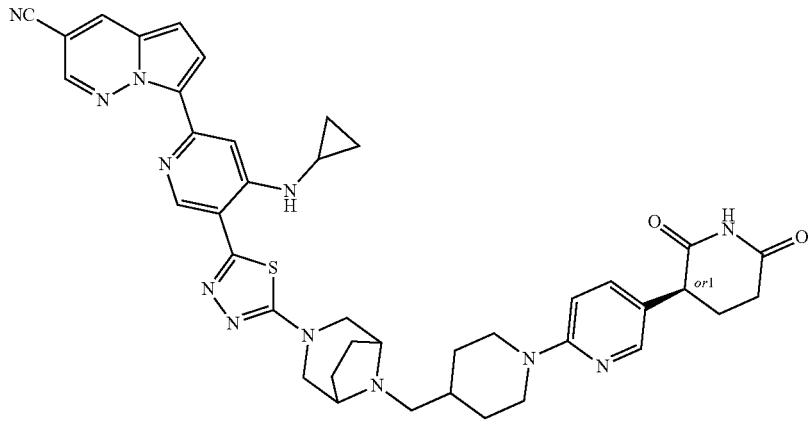 [SMILES: N#Cc1cnn2c(-c3cc(NC4CC4)c(-c4nnc(N5CC6CCC(C5)N6CC5CCN(c6ccc([C@@H]7CCC(=O)NC7=O)cn6)CC5)s4)cn3)ccc2c1]

7-[4-(cyclopropylamino)-5-(5-{8-[(1-{5-[(3S)-2,6-
dioxopiperidin-3-yl]pyridin-2-yl}piperidin-4-yl)
methyl]-3,8-diazabicyclo[3.2.1]octan-3-yl}-1,3,4-
thiadiazol-2-yl)pyridin-2-yl]pyrrolo[1,2-b]
pyridazine-3-carbonitrile The title compound was synthesized from Intermediate AL and HA-32 by reductive amination using General Method B. LCMS: $C_{40}H_{42}N_{12}O_2S$ requires: 754.3, found: m/z=755.2 [M+H]$^+$. $^1$H NMR (500 MHz, DMSO-d$_6$) δ 10.88 (s, 1H), 8.92 (s, 1H), 8.84 (s, 1H), 8.64 (s, 1H), 8.57 (s, 1H), 7.93 (d, J=17.8 Hz, 2H), 7.19 (s, 1H), 4.39-4.16 (m, 5H), 4.09 (d, J=13.9 Hz, 2H), 3.91 (s, 7H), 3.02 (s, 4H), 2.81 (s, 3H), 2.65 (s, 7H), 2.27 (s, 4H), 2.14-1.85 (m, 8H), 1.28 (d, J=32.5 Hz, 5H), 1.06 (d, J=6.4 Hz, 2H), 0.69 (s, 2H).

Example 126

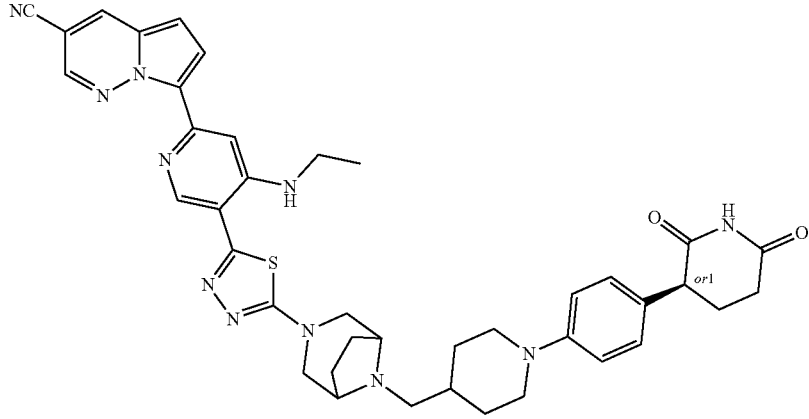 [SMILES: CCNc1cc(-c2ccc3cc(C#N)cnn23)ncc1-c1nnc(N2CC3CCC(C2)N3CC2CCN(c3ccc([C@@H]4CCC(=O)NC4=O)cc3)CC2)s1]

7-[5-(5-{8-[(1-{4-[(3S)-2,6-dioxopiperidin-3-yl]phenyl}piperidin-4-yl)methyl]-3,8-diazabicyclo[3.2.1]octan-3-yl}-1,3,4-thiadiazol-2-yl)-4-(ethylamino)pyridin-2-yl]pyrrolo[1,2-b]pyridazine-3-carbonitrile The title compound was synthesized from Intermediate AH and HA-30 by reductive amination using General Method B. LCMS: $C_{40}H_{43}N_{11}O_2S$ requires: 741.3, found: m/z=742.4 [M+H]$^+$. $^1$H NMR (500 MHz, DMSO-d$_6$) δ 10.80 (s, 1H), 8.89 (d, J=64.0 Hz, 1H), 8.57 (s, 1H), 8.08 (s, 1H), 7.22 (s, 2H), 7.09 (s, 2H), 6.96 (s, 1H), 4.26 (s, 2H), 3.93 (s, 3H), 3.75 (d, J=11.5 Hz, 4H), 3.33 (s, 3H), 3.05 (s, 1H), 2.65 (s, 40H), 2.30 (s, 2H), 2.23-2.08 (m, 2H), 2.10-1.87 (m, 6H), 1.82 (s, 2H), 1.43 (s, 1H), 1.36 (t, J=7.1 Hz, 3H).

Example 127

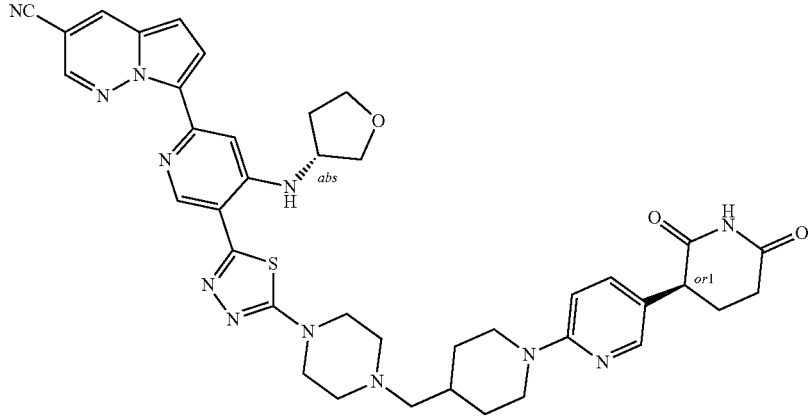 [SMILES: N#Cc1cnn2c(-c3cc(N[C@@H]4CCOC4)c(-c4nnc(N5CCN(CC6CCN(c7ccc([C@@H]8CCC(=O)NC8=O)cn7)CC6)CC5)s4)cn3)ccc2c1]

7-[5-(5-{4-[(1-{5-[(3S)-2,6-dioxopiperidin-3-yl]pyridin-2-yl}piperidin-4-yl)methyl]piperazin-1-yl}-1,3,4-thiadiazol-2-yl)-4-{[(3R)-oxolan-3-yl]amino}pyridin-2-yl]pyrrolo[1,2-b]pyridazine-3-carbonitrile The title compound was synthesized from Intermediate AJ and HA-32 by reductive amination using General Method B. LCMS: $C_{39}H_{42}N_{12}O_3S$ requires: 758.3, found: m/z=759.6 [M+H]$^+$. $^1$H NMR (500 MHz, DMSO) δ 10.91 (s, 1H), 10.74 (s, 1H), 9.36 (s, 1H), 8.96 (s, 1H), 8.85 (s, 1H), 8.59 (s, 1H), 8.17 (s, 1H), 8.07 (s, 1H), 7.93 (s, 1H), 7.75 (s, 1H), 7.35 (s, 1H), 7.22 (d, J=4.9 Hz, 1H), 4.56 (s, 1H), 4.32 (d, J=13.2 Hz, 2H), 4.12 (d, J=13.5 Hz, 2H), 4.05 (dd, J=9.4, 5.3 Hz, 1H), 3.94 (q, J=7.7 Hz, 1H), 3.89 (s, 2H), 3.85 (td, J=8.3, 5.1 Hz, 2H), 3.80 (dd, J=9.4, 2.7 Hz, 1H), 3.69 (d, J=12.2 Hz, 2H), 3.27 (d, J=10.6 Hz, 2H), 3.12 (s, 3H), 2.70 (ddd, J=17.6, 12.8, 5.3 Hz, 1H), 2.59 (s, 1H), 2.30-2.21 (m, 3H), 1.99 (dd, J=11.4, 6.5 Hz, 4H), 1.35-1.29 (m, 2H).

Example 128

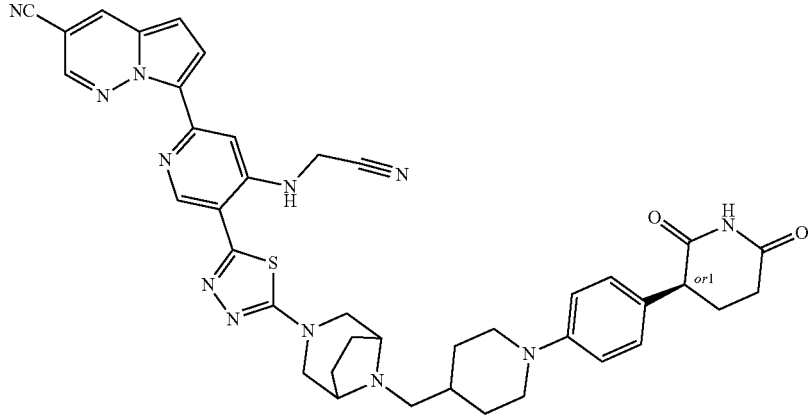 [SMILES: N#CCNc1cc(-c2ccc3cc(C#N)cnn23)ncc1-c1nnc(N2CC3CCC(C2)N3CC2CCN(c3ccc([C@@H]4CCC(=O)NC4=O)cc3)CC2)s1]

7-{4-[(cyanomethyl)amino]-5-(5-{8-[(1-{4-[(3S)-2,6-dioxopiperidin-3-yl]phenyl}piperidin-4-yl)methyl]-3,8-diazabicyclo[3.2.1]octan-3-yl}-1,3,4-thiadiazol-2-yl)pyridin-2-yl}pyrrolo[1,2-b]pyridazine-3-carbonitrile The title compound was synthesized from Intermediate AO and HA-30 by reductive amination using General Method B. LCMS: $C_{40}H_{40}N_{12}O_2S$ requires: 752.3, found: m/z=753.5 [M+H]$^+$. $^1$H NMR (500 MHz, DMSO) δ 10.81 (s, 1H), 10.54 (s, 1H), 9.11 (s, 1H), 8.96-8.92 (m, 1H), 8.75 (s, 1H), 8.68 (d, J=11.5 Hz, 1H), 8.27 (s, 1H), 8.02-7.98 (m, 1H), 7.21 (d, J=4.9 Hz, 1H), 7.15 (s, 4H), 4.78 (d, J=6.1 Hz, 2H), 4.27 (s, 1H), 4.06 (d, J=12.9 Hz, 2H), 3.91 (d, J=12.5 Hz, 2H), 3.76 (d, J=15.6 Hz, 3H), 3.72 (s, 1H), 3.06 (s, 2H), 2.82 (s, 3H), 2.72-2.61 (m, 1H), 2.30 (d, J=9.7 Hz, 2H), 2.19-2.14 (m, 3H), 2.07-2.00 (m, 5H), 1.50 (s, 3H), 1.25 (s, 1H), 0.08 (s, 1H).

Example 129

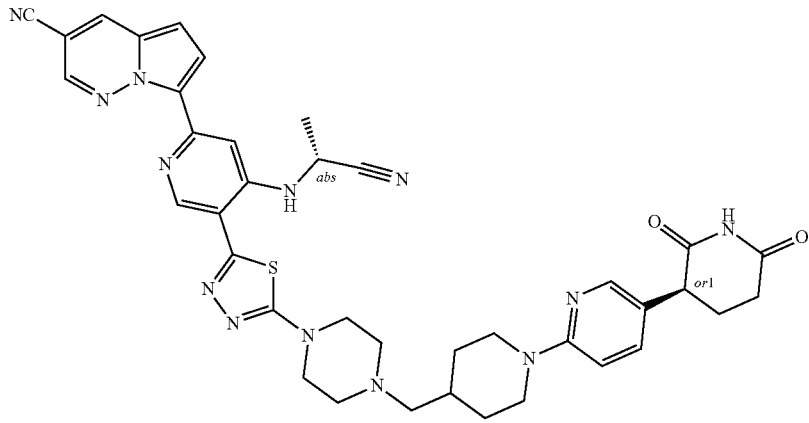 [SMILES: C[C@H](C#N)Nc1cc(-c2ccc3cc(C#N)cnn23)ncc1-c1nnc(N2CCN(CC3CCN(c4ccc([C@@H]5CCC(=O)NC5=O)cn4)CC3)CC2)s1]

7-(4-{[(1R)-1-cyanoethyl]amino}-5-(5-{4-[(1-{5-[(3S)-2,6-dioxopiperidin-3-yl]pyridin-2-yl}piperidin-4-yl)methyl]piperazin-1-yl}-1,3,4-thiadiazol-2-yl)pyridin-2-yl)pyrrolo[1,2-b]pyridazine-3-carbonitrile The title compound was synthesized from Intermediate AC and HA-32 by reductive amination using General Method B. LCMS: $C_{38}H_{39}N_{13}O_2S$ requires: 741.3, found: m/z=742.6 [M+H]$^+$. $^1$H NMR (500 MHz, DMSO) δ 10.92 (s, 1H), 10.63 (s, 1H), 8.92 (d, J=2.2 Hz, 1H), 8.73 (d, J=2.2 Hz, 1H), 8.69 (s, 1H), 8.37 (s, 1H), 7.96 (d, J=4.8 Hz, 1H), 7.92 (d, J=2.3 Hz, 1H), 7.80 (s, 1H), 7.31 (s, 1H), 7.19 (d, J=4.8 Hz, 1H), 5.17-5.10 (m, 1H), 4.31 (d, J=13.2 Hz, 2H), 4.12 (d, J=13.7 Hz, 2H), 3.85 (s, 1H), 3.75 (s, 19H), 3.69 (d, J=12.2 Hz, 2H), 3.28 (d, J=11.3 Hz, 3H), 3.13 (s, 4H), 2.71 (td, J=12.7, 6.5 Hz, 1H), 2.59 (s, 1H), 2.26 (s, 3H), 2.02-1.95 (m, 3H), 1.80 (d, J=6.8 Hz, 3H), 1.33 (d, J=11.9 Hz, 3H).

Example 130

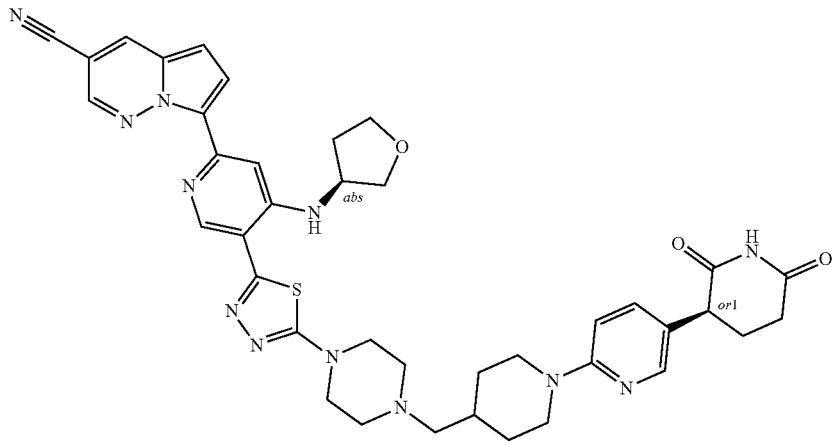 [SMILES: N#Cc1cnn2c(-c3cc(N[C@H]4CCOC4)c(-c4nnc(N5CCN(CC6CCN(c7ccc([C@@H]8CCC(=O)NC8=O)cn7)CC6)CC5)s4)cn3)ccc2c1]

7-[5-(5-{4-[(1-{5-[(3S)-2,6-dioxopiperidin-3-yl]pyridin-2-yl}piperidin-4-yl)methyl]piperazin-1-yl}-1,3,4-thiadiazol-2-yl)-4-{[(3S)-oxolan-3-yl]amino}pyridin-2-yl]pyrrolo[1,2-b] pyridazine-3-carbonitrile The title compound was synthesized from Intermediate AI and HA-32 by reductive amination using General Method B. LCMS: $C_{39}H_{42}N_{12}O_3S$ requires: 758.3, found: m/z=759.5 [M+H]$^+$. $^1$H NMR (500 MHz, DMSO-d$_6$) δ 10.90 (s, 1H), 8.95 (s, 1H), 8.85 (s, 1H), 8.60 (s, 1H), 8.17 (s, 1H), 8.04 (s, 1H), 7.93 (s, 1H), 7.21 (d, J=4.9 Hz, 1H), 4.55 (s, 1H), 4.31 (d, J=13.1 Hz, 2H), 4.22-3.97 (m, 2H), 3.93 (q, J=7.8 Hz, 1H), 3.27 (d, J=11.2 Hz, 1H), 3.13 (s, 2H), 2.77-2.62 (m, 1H), 2.24 (s, 1H), 1.97 (s, 2H), 1.31 (s, 2H).

Example 131

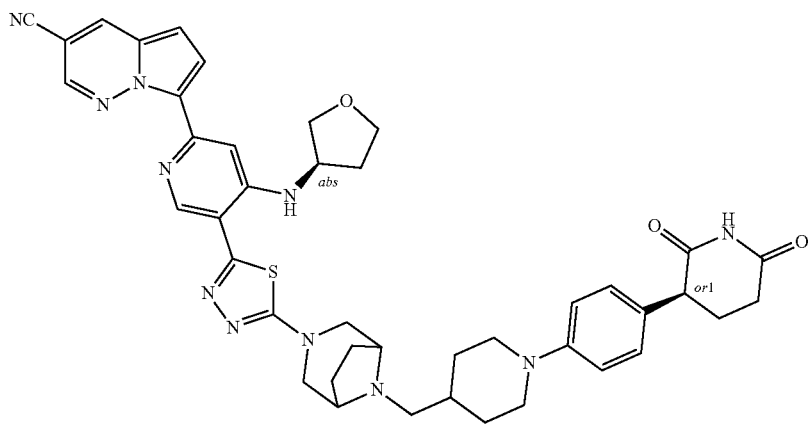 [SMILES: N#Cc1cnn2c(-c3cc(N[C@@H]4CCOC4)c(-c4nnc(N5CC6CCC(C5)N6CC5CCN(c6ccc([C@@H]7CCC(=O)NC7=O)cc6)CC5)s4)cn3)ccc2c1]

7-[5-(5-{8-[(1-{4-[(3S)-2,6-dioxopiperidin-3-yl]phenyl}piperidin-4-yl)methyl]-3,8-diazabicyclo[3.2.1]octan-3-yl}-1,3,4-thiadiazol-2-yl)-4-{[(3R)-oxolan-3-yl]amino}pyridin-2-yl]pyrrolo[1,2-b]pyridazine-3-carbonitrile The title compound was synthesized from Intermediate AK and HA-30 by reductive amination using General Method B. LCMS: $C_{42}H_{45}N_{11}O_3S$ requires: 783.3, found: m/z=784.8 [M+H]$^+$. $^1$H NMR (500 MHz, DMSO-d$_6$) δ 10.80 (s, 1H), 8.93 (s, 1H), 8.83 (s, 1H), 8.61 (d, J=9.6 Hz, 1H), 8.18 (s, 1H), 7.99 (s, 1H), 7.20 (s, 1H), 7.09 (s, 2H), 6.97 (s, 2H), 4.51 (s, 2H), 4.26 (s, 3H), 4.06 (dd, J=9.4, 5.4 Hz, 2H), 3.92 (dd, J=9.9, 5.9 Hz, 5H), 3.86 (dd, J=8.4, 5.4 Hz, 2H), 3.76 (t, J=13.7 Hz, 7H), 3.05 (s, 3H), 2.85-2.58 (m, 6H), 2.29 (s, 3H), 2.20-1.84 (m, 9H), 1.44 (s, 2H).

Example 132

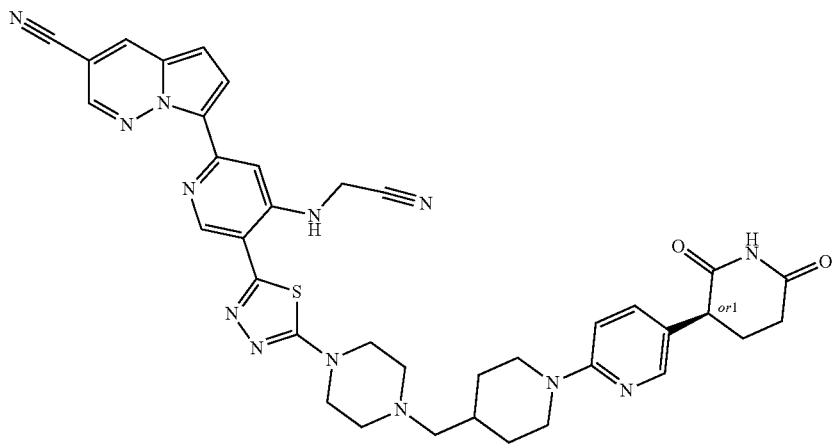 [SMILES: N#CCNc1cc(-c2ccc3cc(C#N)cnn23)ncc1-c1nnc(N2CCN(CC3CCN(c4ccc([C@@H]5CCC(=O)NC5=O)cn4)CC3)CC2)s1]

7-{4-[(cyanomethyl)amino]-5-(5-{4-[(1-{5-[(3S)-2,
6-dioxopiperidin-3-yl]pyridin-2-yl} piperidin-4-yl)
methyl]piperazin-1-yl}-1,3,4-thiadiazol-2-yl)pyri-
din-2-yl}pyrrolo[1,2-b]pyridazine-3-carbonitrile The title compound was synthesized from Intermediate X and HA-32 by reductive amination using General Method B. LCMS: $C_{37}H_{37}N_{13}O_2S$ requires: 727.3, found: m/z=728.8 [M+H]$^+$.

Example 133

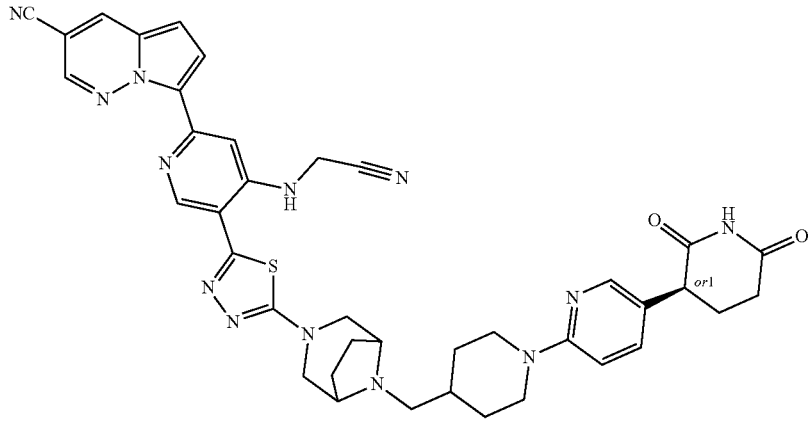 [SMILES: N#CCNc1cc(-c2ccc3cc(C#N)cnn23)ncc1-c1nnc(N2CC3CCC(C2)N3CC2CCN(c3ccc([C@@H]4CCC(=O)NC4=O)cn3)CC2)s1]

7-{4-[(cyanomethyl)amino]-5-(5-{8-[(1-{5-[(3S)-2,
6-dioxopiperidin-3-yl]pyridin-2-yl} piperidin-4-yl)
methyl]-3,8-diazabicyclo[3.2.1]octan-3-yl}-1,3,4-
thiadiazol-2-yl)pyridin-2-yl}pyrrolo[1,2-b]
pyridazine-3-carbonitrile The title compound was synthesized from Intermediate AO and HA-32 by reductive amination using General Method B. LCMS: $C_{39}H_{39}N_{13}O_2S$ requires: 753.3, found: m/z=754.7 [M+H]$^+$. $^1$H NMR (500 MHz, DMSO) δ 10.92 (s, 1H), 10.85 (s, 1H), 9.11 (s, 1H), 8.94 (d, J=2.4 Hz, 1H), 8.76-8.72 (m, 1H), 8.68 (d, J=10.5 Hz, 1H), 8.28 (s, 1H), 8.01-7.98 (m, 1H), 7.93 (d, J=2.4 Hz, 1H), 7.81 (s, 1H), 7.20 (d, J=4.8 Hz, 1H), 4.78 (d, J=6.0 Hz, 2H), 4.33 (d, J=12.9 Hz, 2H), 4.27 (s, 2H), 4.11 (d, J=12.7 Hz, 2H), 3.90 (d, J=12.3 Hz, 3H), 3.13 (s, 2H), 3.03 (d, J=6.5 Hz, 2H), 2.70 (ddd, J=17.6, 12.7, 5.3 Hz, 1H), 2.28 (d, J=11.5 Hz, 5H), 2.07-1.94 (m, 6H), 1.40-1.34 (m, 2H).

Example 134

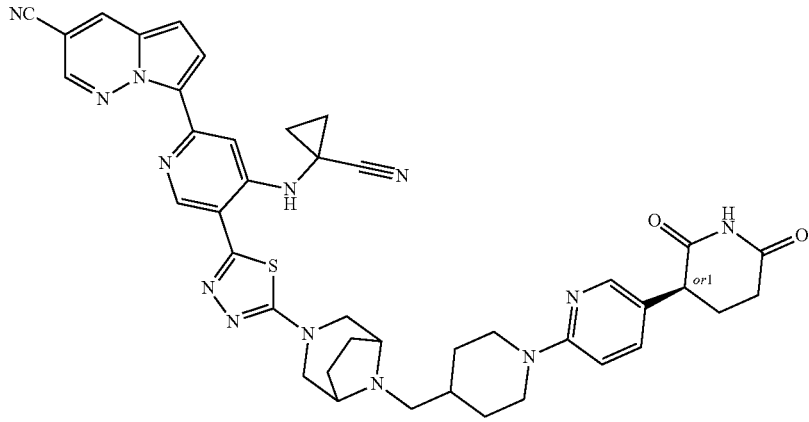 [SMILES: N#Cc1cnn2c(-c3cc(NC4(C#N)CC4)c(-c4nnc(N5CC6CCC(C5)N6CC5CCN(c6ccc([C@@H]7CCC(=O)NC7=O)cn6)CC5)s4)cn3)ccc2c1]

7-{4-[(1-cyanocyclopropyl)amino]-5-(5-{8-[(1-{5-[(3S)-2,6-dioxopiperidin-3-yl]pyridin-2-yl}piperidin-4-yl)methyl]-3,8-diazabicyclo[3.2.1]octan-3-yl}-1,3,4-thiadiazol-2-yl)pyridin-2-yl}pyrrolo[1,2-b]pyridazine-3-carbonitrile The title compound was synthesized from Intermediate AN and HA-32 by reductive amination using General Method B. LCMS: $C_{41}H_{41}N_{13}O_2S$ requires: 779.3, found: m/z=780.6 [M+H]⁺. ¹H NMR (500 MHz, DMSO) δ 10.92 (s, 1H), 9.08 (s, 1H), 8.90 (dd, J=18.0, 2.2 Hz, 2H), 8.69 (d, J=11.7 Hz, 1H), 7.95 (dd, J=23.3, 3.7 Hz, 2H), 7.31 (s, 1H), 7.19 (d, J=4.8 Hz, 1H), 4.33 (d, J=13.0 Hz, 2H), 4.26 (s, 1H), 4.11 (d, J=12.8 Hz, 2H), 3.89 (d, J=12.7 Hz, 3H), 3.13 (s, 2H), 3.02 (t, J=6.3 Hz, 2H), 2.70 (ddd, J=17.6, 12.7, 5.4 Hz, 1H), 2.34-2.25 (m, 5H), 2.01 (q, J=16.8, 16.3 Hz, 6H), 1.91 (q, J=5.4, 5.0 Hz, 2H), 1.52 (q, J=5.4 Hz, 2H), 1.37 (d, J=12.8 Hz, 2H).

Example 135

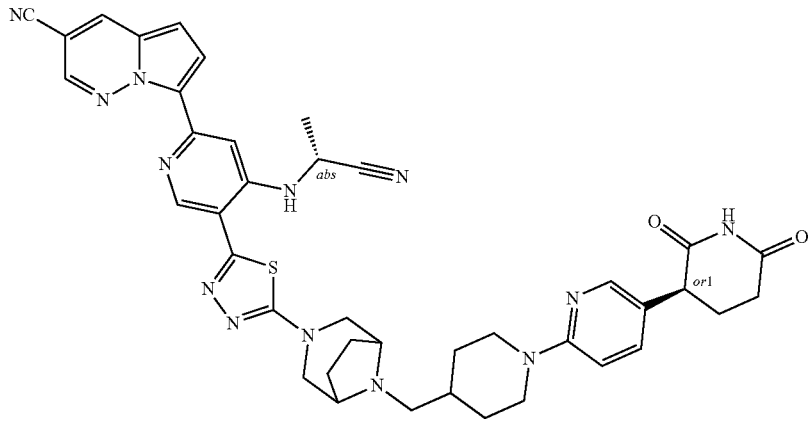 [SMILES: C[C@H](C#N)Nc1cc(-c2ccc3cc(C#N)cnn23)ncc1-c1nnc(N2CC3CCC(C2)N3CC2CCN(c3ccc([C@@H]4CCC(=O)NC4=O)cn3)CC2)s1]

7-(4-{[(1R)-1-cyanoethyl]amino}-5-(5-{8-[(1-{5-[(3S)-2,6-dioxopiperidin-3-yl]pyridin-2-yl}piperidin-4-yl)methyl]-3,8-diazabicyclo[3.2.1]octan-3-yl}-1,3,4-thiadiazol-2-yl)pyridin-2-yl)pyrrolo[1,2-b]pyridazine-3-carbonitrile The title compound was synthesized from Intermediate AU and HA-32 by reductive amination using General Method B. LCMS: $C_{40}H_{41}N_{13}O_2S$ requires: 767.3, found: m/z=768.6 [M+H]⁺. ¹H NMR (500 MHz, DMSO) δ 10.93 (s, 1H), 8.99 (s, 1H), 8.92 (d, J=2.3 Hz, 1H), 8.75-8.67 (m, 2H), 8.36 (s, 1H), 7.96 (d, J=5.1 Hz, 1H), 7.94-7.90 (m, 1H), 7.82 (s, 1H), 7.33 (s, 1H), 7.19 (d, J=4.8 Hz, 1H), 5.14 (t, J=7.3 Hz, 1H), 4.34 (d, J=13.0 Hz, 2H), 4.26 (s, 2H), 4.14 (d, J=12.8 Hz, 2H), 3.91 (d, J=12.6 Hz, 3H), 3.14 (s, 2H), 3.02 (t, J=6.2 Hz, 2H), 2.70 (ddd, J=17.6, 12.7, 5.2 Hz, 1H), 2.59 (s, 1H), 2.28 (d, J=12.5 Hz, 5H), 2.02 (td, J=15.6, 10.4 Hz, 5H), 1.79 (d, J=6.8 Hz, 3H), 1.37 (d, J=12.6 Hz, 2H).

Example 136

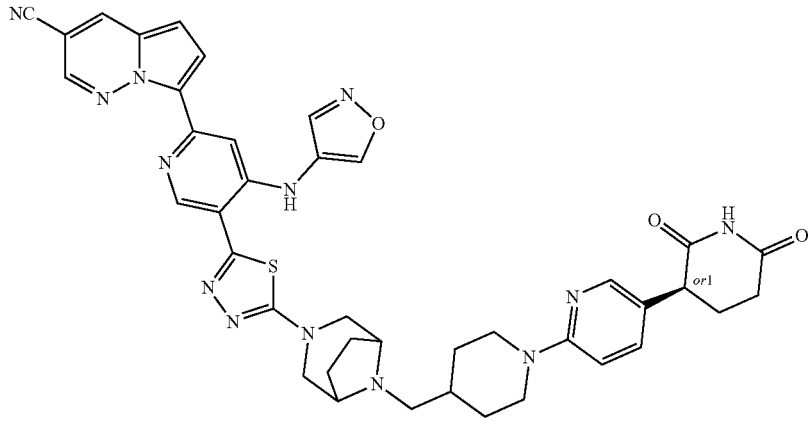 [SMILES: N#Cc1cnn2c(-c3cc(Nc4cnoc4)c(-c4nnc(N5CC6CCC(C5)N6CC5CCN(c6ccc([C@@H]7CCC(=O)NC7=O)cn6)CC5)s4)cn3)ccc2c1]

7-[5-(5-{8-[(1-{5-[(3S)-2,6-dioxopiperidin-3-yl]pyridin-2-yl}piperidin-4-yl)methyl]-3,8-diazabicyclo[3.2.1]octan-3-yl}-1,3,4-thiadiazol-2-yl)-4-[(1,2-oxazol-4-yl)amino]pyridin-2-yl]pyrrolo[1,2-b]pyridazine-3-carbonitrile The title compound was synthesized from Intermediate AV and HA-32 by reductive amination using General Method B. LCMS: $C_{40}H_{39}N_{13}O_3S$ requires: 781.3, found: m/z=782.4 [M+H]$^+$. $^1$H NMR (300 MHz, DMSO-d$_6$) δ 11.14 (s, 1H), 10.95 (s, 1H), 10.21 (s, 1H), 9.33 (s, 1H), 9.03 (d, J=2.6 Hz, 1H), 8.89 (d, J=2.2 Hz, 1H), 8.79-8.67 (m, 2H), 8.41 (s, 1H), 8.01-7.80 (m, 3H), 7.39 (s, 1H), 7.17 (d, J=4.9 Hz, 1H), 4.42-4.14 (m, 6H), 3.90 (d, J=13.1 Hz, 3H), 3.19 (s, 3H), 3.03 (s, 2H), 2.78-2.64 (m, 2H), 2.42-2.19 (m, 4H), 2.03 (q, J=14.2 Hz, 5H), 1.39 (d, J=12.4 Hz, 2H).

7-[5-(5-{4-[(1-{5-[(3R)-2,6-dioxopiperidin-3-yl]pyridin-2-yl}piperidin-4-yl)methyl] piperazin-1-yl}-1,3,4-thiadiazol-2-yl)-4-{[(3R)-oxolan-3-yl]amino}pyridin-2-yl]pyrrolo[1,2-b]pyridazine-3-carbonitrile The title compound was synthesized from Intermediate AJ and HA-33 by reductive amination using General Method B. LCMS: $C_{39}H_{42}N_{12}O_3S$ requires: 758.3, found: m/z=759.7 [M+H]$^+$. $^1$H NMR (500 MHz, DMSO) δ 11.02 (s, 1H), 10.92 (s, 1H), 9.43 (s, 1H), 8.97 (d, J=2.2 Hz, 1H), 8.86 (d, J=2.2 Hz, 1H), 8.58 (s, 1H), 8.17 (s, 1H), 8.12 (s, 1H), 7.92 (d, J=2.3 Hz, 1H), 7.80 (s, 1H), 7.23 (d, J=4.9 Hz, 1H), 4.57 (s, 1H), 4.33 (d, J=13.2 Hz, 2H), 4.12 (d, J=13.7 Hz, 2H), 4.05 (dd, J=9.5, 5.3 Hz, 1H), 3.94 (d, J=7.7 Hz, 1H), 3.91 (s, 3H), 3.83 (ddt, J=23.4, 9.4, 4.1 Hz, 2H), 3.69 (d, J=12.1 Hz, 2H), 3.32-3.27 (m, 1H), 3.26 (s, 1H), 3.12 (s, 4H), 2.70 (ddd, J=17.7, 12.8, 5.3 Hz, 1H), 2.57 (d, J=18.6 Hz, 1H), 2.51 (s, 1H), 2.33-2.23 (m, 2H), 2.05-1.93 (m, 4H), 1.33 (d, J=12.4 Hz, 2H).

Example 137

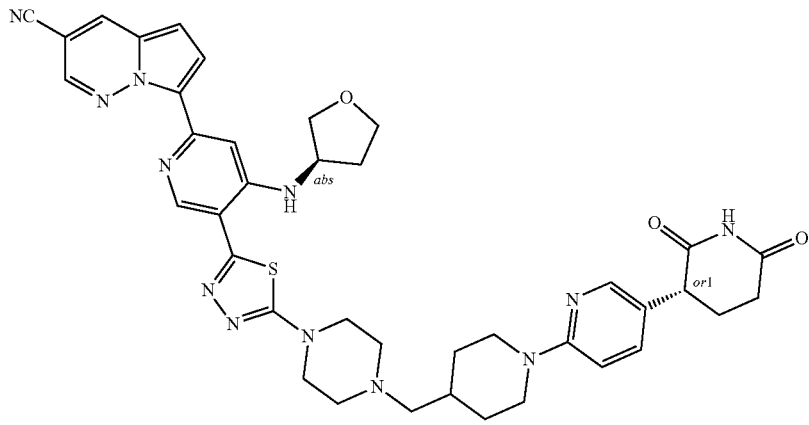 [SMILES: N#Cc1cnn2c(-c3cc(N[C@@H]4CCOC4)c(-c4nnc(N5CCN(CC6CCN(c7ccc([C@H]8CCC(=O)NC8=O)cn7)CC6)CC5)s4)cn3)ccc2c1]

Example 138

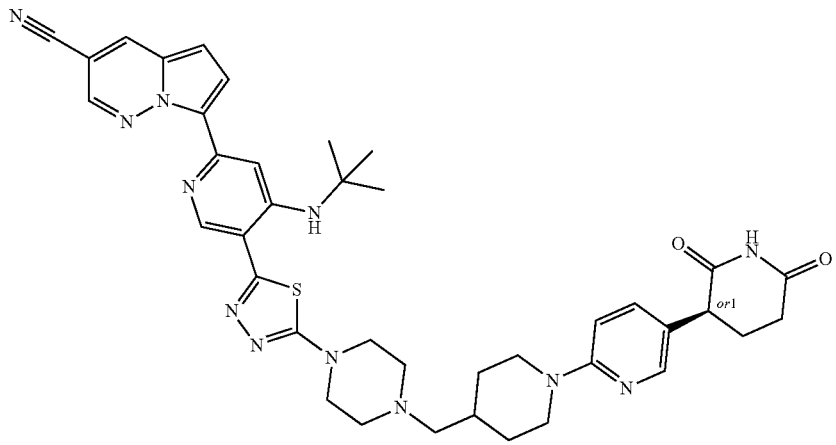 [SMILES: CC(C)(C)Nc1cc(-c2ccc3cc(C#N)cnn23)ncc1-c1nnc(N2CCN(CC3CCN(c4ccc([C@@H]5CCC(=O)NC5=O)cn4)CC3)CC2)s1]

7-[4-(tert-butylamino)-5-(5-{4-[(1-{5-[(3S)-2,6-di-oxopiperidin-3-yl]pyridin-2-yl}piperidin-4-yl)methyl]piperazin-1-yl}-1,3,4-thiadiazol-2-yl)pyridin-2-yl]pyrrolo[1,2-b]pyridazine-3-carbonitrile The title compound was synthesized from Intermediate AR and HA-32 by reductive amination using General Method B. LCMS: $C_{39}H_{44}N_{12}O_2S$ requires 744.9, found m/z=745.4 [M+H]$^+$. $^1$H NMR (300 MHz, DMSO-d$_6$) δ 10.81 (s, 1H), 8.90-8.82 (m, 2H), 8.76 (d, J=2.2 Hz, 1H), 8.56 (s, 1H), 8.49 (s, 1H), 7.94 (s, 1H), 7.86 (d, J=4.8 Hz, 1H), 7.37 (d, J=8.9 Hz, 1H), 7.13 (d, J=4.9 Hz, 1H), 6.80 (d, J=8.8 Hz, 1H), 4.27 (d, J=12.8 Hz, 2H), 3.79-3.67 (m, 2H), 3.54 (d, J=13.6 Hz, 5H), 2.81 (d, J=11.6 Hz, 2H), 2.22 (s, 2H), 1.99 (s, 2H), 1.80 (d, J=12.3 Hz, 3H), 1.56 (s, 9H), 1.13 (s, 3H), 0.85 (d, J=7.2 Hz, 2H).

Example 139

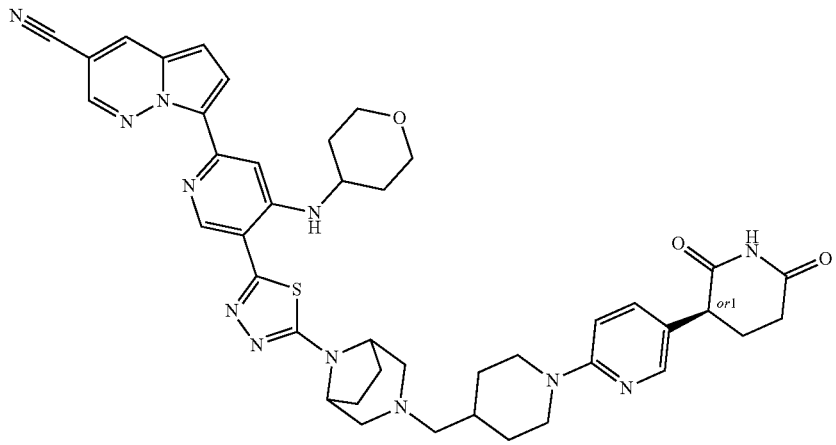 [SMILES: N#Cc1cnn2c(-c3cc(NC4CCOCC4)c(-c4nnc(N5C6CCC5CN(CC5CCN(c7ccc([C@@H]8CCC(=O)NC8=O)cn7)CC5)C6)s4)cn3)ccc2c1]

7-[5-(5-{3-[(1-{5-[(3S)-2,6-dioxopiperidin-3-yl]pyridin-2-yl}piperidin-4-yl)methyl]-3,8-diazabicyclo[3.2.1]octan-8-yl}-1,3,4-thiadiazol-2-yl)-4-[(oxan-4-yl)amino]pyridin-2-yl]pyrrolo[1,2-b]pyridazine-3-carbonitrile The title compound was synthesized from Intermediate AS and HA-32 by reductive amination using General Method B. LCMS: $C_{42}H_{46}N_{12}O_3S$ requires: 798.4, found: m/z=799.8 [M+H]$^+$. $^1$H NMR (500 MHz, DMSO) δ 10.90 (d, J=19.8 Hz, 1H), 8.95 (d, J=16.3 Hz, 1H), 8.85 (s, 1H), 8.58 (d, J=20.9 Hz, 1H), 8.26 (s, 1H), 7.91 (d, J=13.4 Hz, 1H), 7.20 (s, 1H), 4.57 (d, J=4.4 Hz, 2H), 4.34 (s, 1H), 4.24 (d, J=13.1 Hz, 2H), 4.03 (s, 2H), 3.98-3.92 (m, 2H), 3.82 (s, 2H), 3.62 (s, 4H), 3.06 (s, 2H), 2.75 (d, J=11.6 Hz, 1H), 2.29 (s, 1H), 2.19-2.09 (m, 3H), 2.00 (s, 3H), 1.85 (s, 3H), 1.62 (s, 3H), 1.26 (d, J=13.3 Hz, 3H), 1.17 (s, 1H).

Example 140

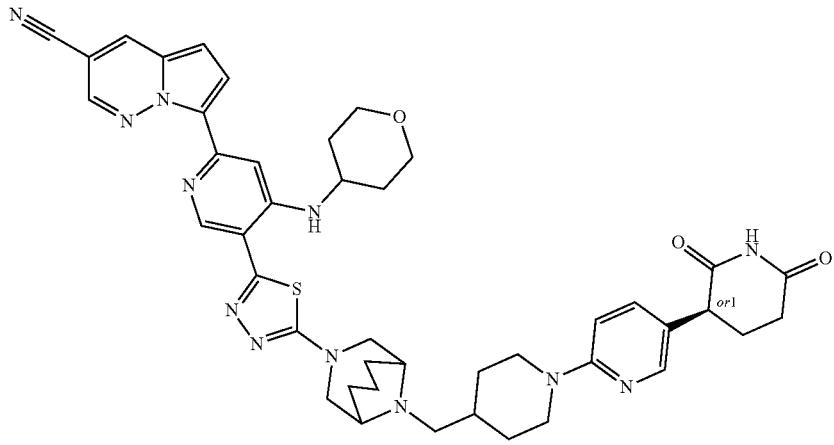 [SMILES: N#Cc1cnn2c(-c3cc(NC4CCOCC4)c(-c4nnc(N5CC6CCCC(C5)N6CC5CCN(c6ccc([C@@H]7CCC(=O)NC7=O)cn6)CC5)s4)cn3)ccc2c1]

7-(5-{5-[(1R,5S)-9-[(1-{5-[(3S)-2,6-dioxopiperidin-3-yl]pyridin-2-yl}piperidin-4-yl)methyl]-3,9-diazabicyclo[3.3.1]nonan-3-yl]-1,3,4-thiadiazol-2-yl}-4-[(oxan-4-yl)amino]pyridin-2-yl)pyrrolo[1,2-b]pyridazine-3-carbonitrile The title compound was synthesized from Intermediate AT and HA-32 by reductive amination using General Method B. LCMS: $C_{43}H_{48}N_{12}O_3S$ requires 812.4, found m/z=813.5 [M+H]$^+$. $^1$H NMR (300 MHz, DMSO-d$_6$) δ 11.37 (s, 1H), 10.95 (s, 1H), 9.77 (s, 1H), 9.02 (d, J=2.2 Hz, 1H), 8.91 (d, J=2.2 Hz, 1H), 8.58 (d, J=6.0 Hz, 1H), 8.28 (s, 1H), 8.18 (d, J=2.5 Hz, 1H), 7.93 (d, J=12.3 Hz, 2H), 7.44 (s, 1H), 7.27 (d, J=5.0 Hz, 1H), 4.41 (dd, J=28.3, 13.1 Hz, 3H), 4.15 (d, J=13.4 Hz, 3H), 4.08-3.89 (m, 7H), 3.62 (t, J=10.9 Hz, 4H), 3.39 (d, J=7.0 Hz, 2H), 3.23 (t, J=12.5 Hz, 2H), 2.71-2.57 (m, 3H), 2.18-1.82 (m, 8H), 1.65 (d, J=11.9 Hz, 3H), 1.43 (d, J=11.8 Hz, 2H).

Example 141

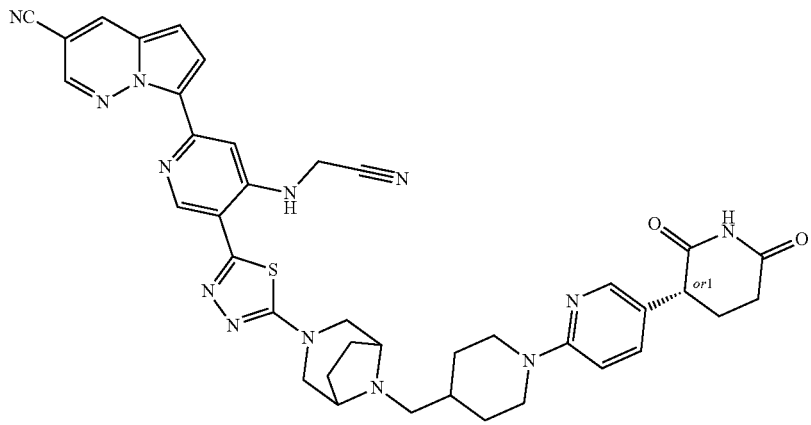

7-{4-[(cyanomethyl)amino]-5-(5-{8-[(1-{5-[(3R)-2,6-dioxopiperidin-3-yl]pyridin-2-yl} piperidin-4-yl)methyl]-3,8-diazabicyclo[3.2.1]octan-3-yl}-1,3,4-thiadiazol-2-yl)pyridin-2-yl}pyrrolo[1,2-b]pyridazine-3-carbonitrile The title compound was synthesized from Intermediate AO and HA-33 by reductive amination using General Method B. LCMS: $C_{39}H_{39}N_{13}O_2S$ requires: 753.3, found: m/z=754.6 [M+H]$^+$. $^1$H NMR (500 MHz, DMSO) δ 10.91 (s, 1H), 9.04 (s, 1H), 8.93 (s, 1H), 8.73 (s, 1H), 8.68 (d, J=10.7 Hz, 1H), 8.29 (s, 1H), 7.97 (s, 1H), 7.93 (s, 1H), 7.76 (s, 1H), 7.20 (d, J=4.9 Hz, 1H), 4.77 (d, J=6.0 Hz, 2H), 4.33 (d, J=12.9 Hz, 2H), 4.26 (s, 2H), 4.08 (d, J=12.8 Hz, 2H), 3.90 (d, J=12.4 Hz, 3H), 3.73 (s, 5H), 3.10 (s, 2H), 3.02 (t, J=6.0 Hz, 2H), 2.70 (ddd, J=17.6, 12.5, 5.2 Hz, 1H), 2.59 (s, 1H), 2.55 (s, 1H), 2.28 (s, 5H), 2.02 (s, 5H), 1.36 (s, 2H).

Example 142

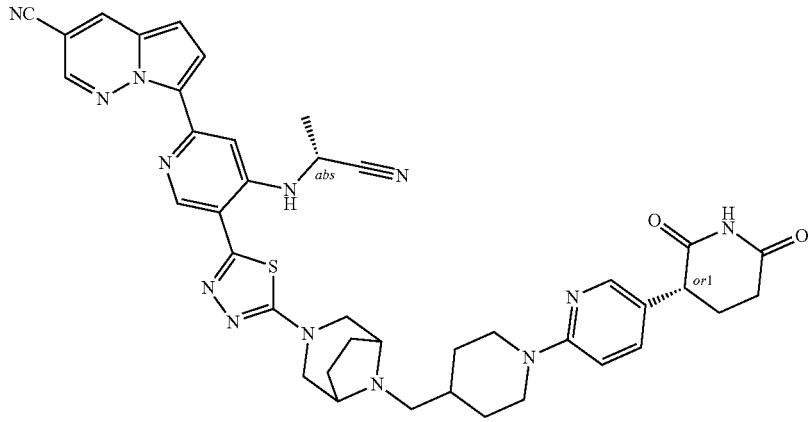 [SMILES: C[C@H](C#N)Nc1cc(-c2ccc3cc(C#N)cnn23)ncc1-c1nnc(N2CC3CCC(C2)N3CC2CCN(c3ccc([C@H]4CCC(=O)NC4=O)cn3)CC2)s1]

7-(4-{[(1R)-1-cyanoethyl]amino}-5-(5-{8-[(1-{5-[(3R)-2,6-dioxopiperidin-3-yl]pyridin-2-yl}piperidin-4-yl)methyl]-3,8-diazabicyclo[3.2.1]octan-3-yl}-1,3,4-thiadiazol-2-yl)pyridin-2-yl)pyrrolo[1,2-b]pyridazine-3-carbonitrile The title compound was synthesized from Intermediate AU and HA-33 by reductive amination using General Method B. LCMS: $C_{40}H_{41}N_{13}O_2S$ requires: 767.3, found: m/z=768.0 [M+H]$^+$. $^1$H NMR (500 MHz, DMSO) δ 10.92 (s, 1H), 8.94-8.90 (m, 1H), 8.74-8.67 (m, 2H), 8.36 (s, 1H), 7.97-7.91 (m, 2H), 7.78 (s, 1H), 7.34 (s, 1H), 7.19 (d, J=4.8 Hz, 1H), 5.16-5.09 (m, 1H), 4.34 (d, J=13.0 Hz, 2H), 4.26 (s, 1H), 4.13 (d, J=12.8 Hz, 1H), 3.91 (d, J=12.6 Hz, 3H), 3.20-2.96 (m, 4H), 2.76-2.65 (m, 1H), 2.61-2.54 (m, 1H), 2.31-2.25 (m, 5H), 2.07-1.95 (m, 6H), 1.79 (d, J=6.8 Hz, 3H), 1.44-1.20 (m, 4H).

7-(4-{[(1S)-1-cyanoethyl]amino}-5-(5-{8-[(1-{5-[(3R)-2,6-dioxopiperidin-3-yl]pyridin-2-yl}piperidin-4-yl)methyl]-3,8-diazabicyclo[3.2.1]octan-3-yl}-1,3,4-thiadiazol-2-yl)pyridin-2-yl)pyrrolo[1,2-b]pyridazine-3-carbonitrile The title compound was synthesized from Intermediate AW and HA-33 by reductive amination using General Method B. LCMS: $C_{40}H_{41}N_{13}O_2S$ requires: 767.3, found: m/z=768.7 [M+H]$^+$. $^1$H NMR (500 MHz, DMSO) δ 10.91 (s, 1H), 10.68 (s, 1H), 8.92 (d, J=2.2 Hz, 1H), 8.74-8.67 (m, 2H), 8.36 (s, 1H), 7.94 (d, J=6.2 Hz, 2H), 7.76 (s, 1H), 7.19 (d, J=4.8 Hz, 1H), 5.15-5.09 (m, 1H), 4.36-4.25 (m, 4H), 4.07 (d, J=12.3 Hz, 2H), 3.91 (d, J=12.9 Hz, 3H), 3.09 (s, 3H), 3.02 (t, J=6.2 Hz, 2H), 2.70 (ddd, J=17.8, 12.7, 5.3 Hz, 1H), 2.59 (s, 1H), 2.28 (s, 5H), 2.02 (d, J=11.9 Hz, 5H), 1.79 (d, J=6.8 Hz, 3H), 1.38-1.32 (m, 2H).

Example 143

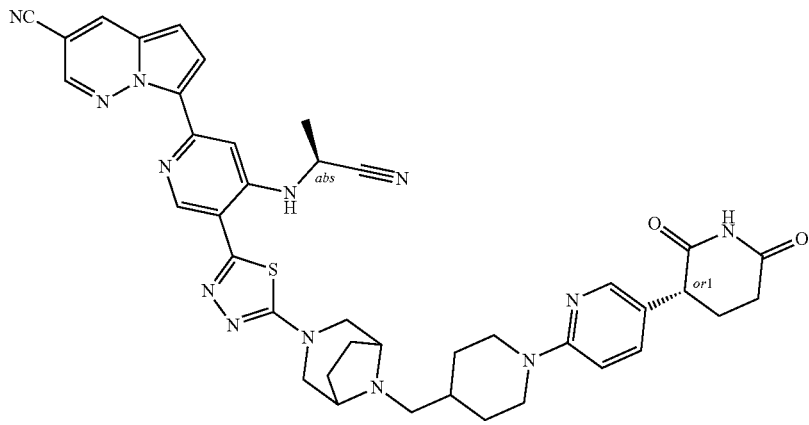 [SMILES: C[C@@H](C#N)Nc1cc(-c2ccc3cc(C#N)cnn23)ncc1-c1nnc(N2CC3CCC(C2)N3CC2CCN(c3ccc([C@H]4CCC(=O)NC4=O)cn3)CC2)s1]

Example 144

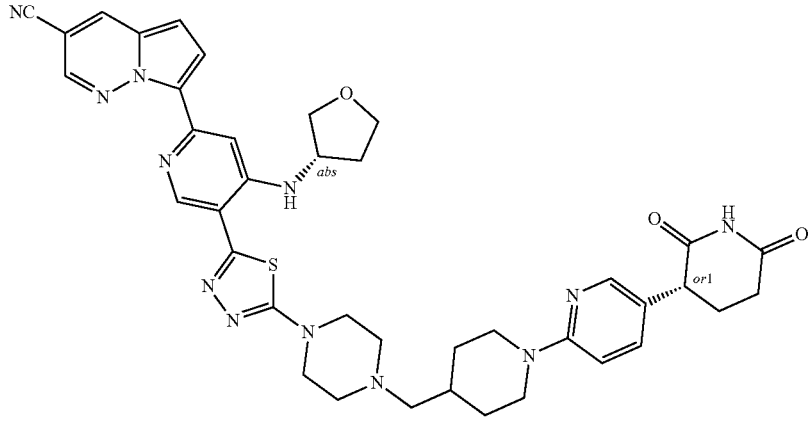 [SMILES: N#Cc1cnn2c(-c3cc(N[C@H]4CCOC4)c(-c4nnc(N5CCN(CC6CCN(c7ccc([C@H]8CCC(=O)NC8=O)cn7)CC6)CC5)s4)cn3)ccc2c1]

7-[5-(5-{4-[(1-{5-[(3R)-2,6-dioxopiperidin-3-yl]pyridin-2-yl}piperidin-4-yl)methyl] piperazin-1-yl}-1,3,4-thiadiazol-2-yl)-4-{[(3S)-oxolan-3-yl]amino}pyridin-2-yl]pyrrolo[1,2-b]pyridazine-3-carbonitrile The title compound was synthesized from Intermediate AI and HA-33 by reductive amination using General Method B. LCMS: $C_{39}H_{42}N_{12}O_3S$ requires: 758.3, found: m/z=759.7 [M+H]$^+$. $^1$H NMR (500 MHz, DMSO) δ 10.92 (d, J=13.5 Hz, 1H), 8.96 (s, 1H), 8.85 (s, 1H), 8.60 (s, 1H), 8.18 (s, 1H), 8.06 (s, 1H), 7.93 (s, 1H), 7.75 (s, 1H), 7.22 (d, J=4.8 Hz, 1H), 4.55 (s, 1H), 4.31 (d, J=13.1 Hz, 2H), 4.12 (d, J=13.8 Hz, 2H), 4.05 (dd, J=9.5, 5.4 Hz, 1H), 3.94 (q, J=7.8 Hz, 1H), 3.88 (s, 8H), 3.89-3.77 (m, 3H), 3.72-3.59 (m, 3H), 3.29 (s, 1H), 3.14 (td, J=8.0, 4.5 Hz, 3H), 2.70 (td, J=12.7, 6.4 Hz, 1H), 2.30-2.23 (m, 3H), 2.02-1.95 (m, 4H), 1.27 (dt, J=7.5, 5.8 Hz, 6H).

Example 145

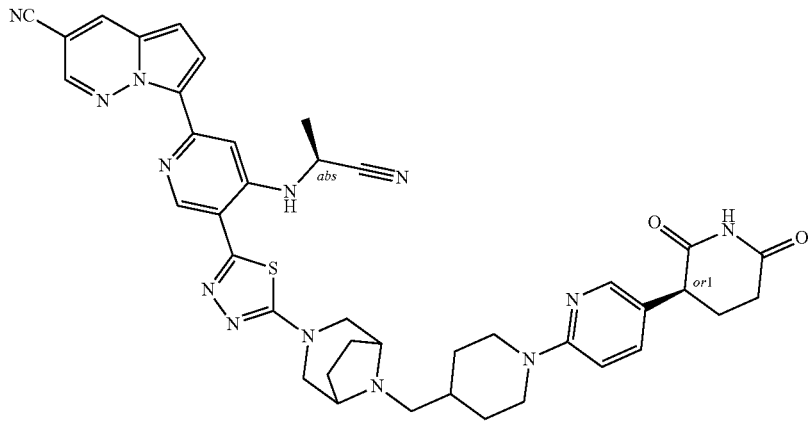 [SMILES: C[C@@H](C#N)Nc1cc(-c2ccc3cc(C#N)cnn23)ncc1-c1nnc(N2CC3CCC(C2)N3CC2CCN(c3ccc([C@@H]4CCC(=O)NC4=O)cn3)CC2)s1]

7-(4-{[(1S)-1-cyanoethyl]amino}-5-(5-{8-[(1-{5-[(3S)-2,6-dioxopiperidin-3-yl]pyridin-2-yl}piperidin-4-yl)methyl]-3,8-diazabicyclo[3.2.1]octan-3-yl}-1,3,4-thiadiazol-2-yl)pyridin-2-yl)pyrrolo[1,2-b]pyridazine-3-carbonitrile The title compound was synthesized from Intermediate AW and HA-32 by reductive amination using General Method B. LCMS: $C_{40}H_{41}N_{13}O_2S$ requires: 767.3, found: m/z=768.6 [M+H]$^+$. $^1$H NMR (500 MHz, DMSO) δ 10.89 (s, 1H), 8.91 (d, J=2.3 Hz, 1H), 8.88 (s, 1H), 8.70 (d, J=10.7 Hz, 2H), 8.38 (s, 1H), 7.97-7.89 (m, 2H), 7.18 (d, J=4.8 Hz, 1H), 5.10 (s, 1H), 4.33 (d, J=12.9 Hz, 2H), 4.24 (d, J=15.3 Hz, 3H), 3.94 (s, 5H), 3.84 (s, 1H), 3.77 (s, 1H), 3.03 (t, J=6.4 Hz, 2H), 2.72 (d, J=13.6 Hz, 1H), 2.28 (d, J=12.3 Hz, 6H), 2.03 (d, J=9.5 Hz, 1H), 1.98 (s, 5H), 1.79 (d, J=6.9 Hz, 4H), 1.32 (s, 3H), 1.25 (s, 1H).

Example 146

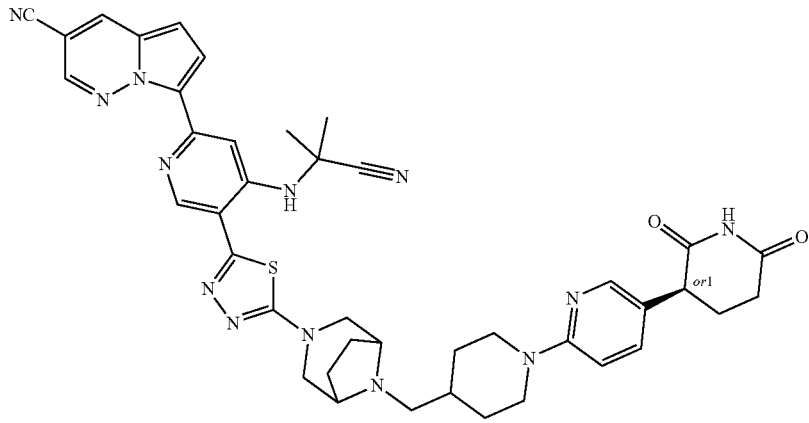 [SMILES: CC(C)(C#N)Nc1cc(-c2ccc3cc(C#N)cnn23)ncc1-c1nnc(N2CC3CCC(C2)N3CC2CCN(c3ccc([C@@H]4CCC(=O)NC4=O)cn3)CC2)s1]

7-{4-[(1-cyano-1-methylethyl)amino]-5-(5-{8-[(1-{5-[(3S)-2,6-dioxopiperidin-3-yl]pyridin-2-yl}piperidin-4-yl)methyl]-3,8-diazabicyclo[3.2.1]octan-3-yl}-1,3,4-thiadiazol-2-yl)pyridin-2-yl}pyrrolo[1,2-b]pyridazine-3-carbonitrile The title compound was synthesized from Intermediate AX and HA-32 by reductive amination using General Method B. LCMS: $C_{41}H_{43}N_{13}O_2S$ requires: 781.3, found: m/z=782.7 [M+H]$^+$. $^1$H NMR (500 MHz, DMSO) δ 10.90 (s, 1H), 9.07 (s, 1H), 8.91 (d, J=2.2 Hz, 1H), 8.75-8.68 (m, 3H), 7.96-7.90 (m, 2H), 7.18 (d, J=4.8 Hz, 1H), 4.32 (d, J=12.8 Hz, 2H), 4.26 (s, 2H), 4.01 (s, 2H), 3.92 (d, J=12.9 Hz, 2H), 3.02 (t, J=6.2 Hz, 2H), 2.72-2.65 (m, 1H), 2.27 (s, 7H), 2.04-1.96 (m, 6H), 1.94 (s, 6H), 1.35 (s, 2H).

Example 147

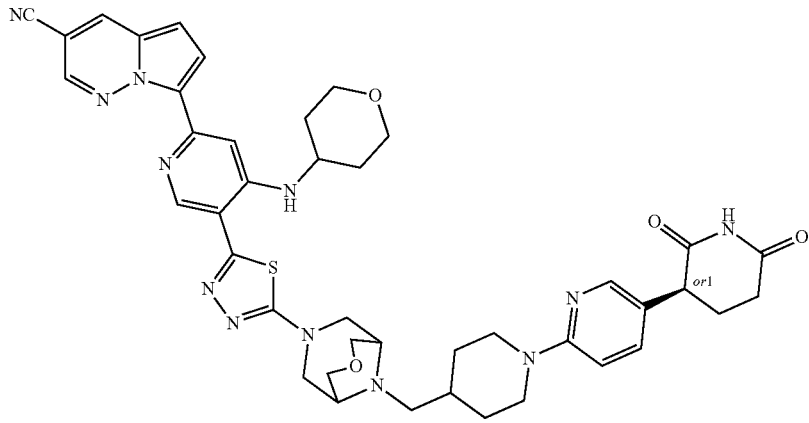 [SMILES: N#Cc1cnn2c(-c3cc(NC4CCOCC4)c(-c4nnc(N5CC6COCC(C5)N6CC5CCN(c6ccc([C@@H]7CCC(=O)NC7=O)cn6)CC5)s4)cn3)ccc2c1]

7-[5-(5-{9-[(1-{5-[(3S)-2,6-dioxopiperidin-3-yl]pyridin-2-yl}piperidin-4-yl)methyl]-3-oxa-7,9-diazabicyclo[3.3.1]nonan-7-yl}-1,3,4-thiadiazol-2-yl)-4-[(oxan-4-yl)amino]pyridin-2-yl]pyrrolo[1,2-b]pyridazine-3-carbonitrile The title compound was synthesized from Intermediate AY and HA-32 by reductive amination using General Method B. LCMS: $C_{42}H_{46}N_{12}O_4S$ requires: 814.3, found: m/z=815.8 [M+H]$^+$. $^1$H NMR (500 MHz, DMSO) δ 10.81 (s, 1H), 8.85 (d, J=2.2 Hz, 1H), 8.78 (d, J=2.2 Hz, 1H), 8.72 (d, J=6.9 Hz, 1H), 8.52 (s, 1H), 8.30 (s, 1H), 7.95 (d, J=2.5 Hz, 1H), 7.85 (d, J=4.8 Hz, 1H), 7.37 (dd, J=8.8, 2.5 Hz, 1H), 7.13 (d, J=4.8 Hz, 1H), 6.81 (d, J=8.9 Hz, 1H), 4.29 (d, J=12.6 Hz, 2H), 3.94 (dt, J=12.2, 4.0 Hz, 2H), 3.83 (s, 3H), 3.77 (dd, J=12.8, 4.4 Hz, 2H), 3.76-3.66 (m, 2H), 3.61 (t, J=10.8 Hz, 2H), 2.84 (s, 2H), 2.79 (t, J=12.4 Hz, 2H), 2.68 (dd, J=16.8, 9.7 Hz, 3H), 2.16 (dd, J=27.9, 12.8 Hz, 3H), 1.98 (d, J=14.4 Hz, 1H), 1.84 (d, J=12.6 Hz, 2H), 1.75 (s, 1H), 1.59 (td, J=10.1, 6.6 Hz, 2H), 1.14 (h, J=9.6, 8.9 Hz, 2H).

Biological Data

Biological Example 1

IRAK4 Degradation HiBiT Assay

Compound dilution series (11-point, 3.16-fold dilutions in DMSO, columns 1-11 and 12-22) at 500× the final required concentrations were prepared in Labcyte LDV 384-well plates (cat. no. LP-0200) using a Labcyte Echo 550 Liquid Handler. The 500× solutions ranged from 5 mM to 0.5 µM (final assay concentration range 10 µM to 0.1 nM). Using the Echo, the 500× solutions were stamped into white, 384-well assay plates (Corning, cat. no. 3570) at 60 nL/well. The following assay plate controls were also stamped at 60 nL/well: DMSO in wells E23-P23 (NC, Negative Control, maximum signal), 5 mM solution control compound a1 in wells A23-D23 and M24-P24 (AC, Active Control, minimum signal/background, 10 µM final assay concentration), control compound a1 dilution series in wells A23-D23 (12-point, 4-fold dilutions). C-terminal HiBiT-tagged Jurkat cells (polyclonal cell line or clone 8D5) were plated at 1×106 cells/mL, 30 µL/well (3×104 cells/well) in complete RPMI (10% FBS, 1% L-glutamine). Cells were incubated for 4 hrs at 32° C./6% $CO_2$. Compound a1 has the following structure:

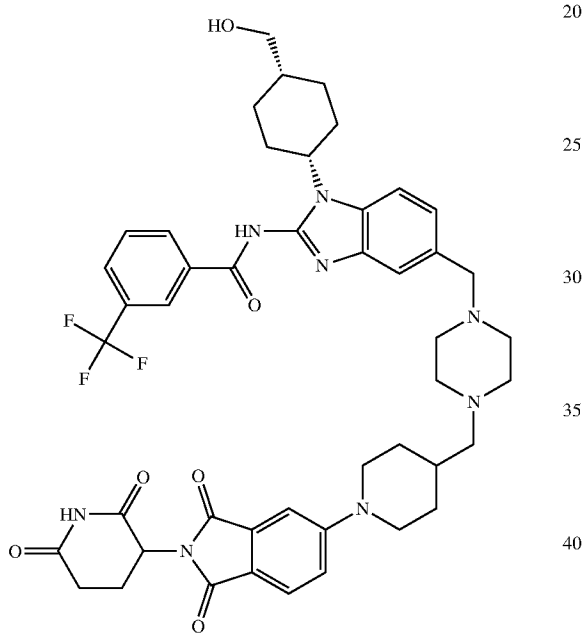

Following incubation, 30 µL of complete Nano-Glo HiBiT Lytic Detection Reagent (Nano-Glo HiBiT Lytic Buffer with 1:50 Nano-Glo HiBiT Lytic Substrate and 1:100 LgBiT Protein; Promega cat. no. N3040) was added. Cells were further incubated for 10 min at room temperature (RT). Luminescence units (LU) were read on an EnVision plate reader (Perkin Elmer, 0.1 sec per well). Percent IRAK4 remaining per sample was calculated as follows:

$$\% \ IRAK4 \ \text{remaining} = \left[ \frac{\text{sample } LU - \text{average } AC \ LU}{\text{average } NC \ LU - \text{avereage } AC \ LU} \right] \times 100$$

Using Graphpad Prism, % IRAK4 remaining values were plotted as a function of compound concentration. To determine $DC_{50}$ and $D_{max}$ values, resulting curves were fit to the Prism curve-fitting equation "log(inhibitor) vs response—Variable slope (four parameters)" (reported best fit value $IC_{50}$ used as $DC_{50}$). Table 1 summarizes the biological data of Compounds of Examples 1-137 and 142-145 obtained from the assays described herein.

TABLE 1

| EXAMPLE | DC50 (µM) | Dmax (%) |
|---|---|---|
| 1 | 0.860 | 96 |
| 2 | 0.053 | 67 |
| 3 | 0.055 | 93 |
| 4 | 0.065 | 90 |
| 5 | 0.021 | 79 |
| 6 | 0.070 | 36 |
| 7 | 0.129 | 17 |
| 8 | 0.029 | 110 |
| 9 | 0.069 | 90 |
| 10 | 0.041 | 71 |
| 11 | 0.032 | 77 |
| 12 | 0.036 | 60 |
| 13 | 0.032 | 66 |
| 14 | 0.070 | 81 |
| 15 | 0.015 | 60 |
| 16 | 0.026 | 62 |
| 17 | 0.012 | 100 |
| 18 | 0.012 | 103 |
| 19 | 0.029 | 103 |
| 20 | 0.020 | 98 |
| 21 | 0.060 | 91 |
| 22 | 0.023 | 84 |
| 23 | 0.018 | 90 |
| 24 | 0.077 | 83 |
| 25 | 0.053 | 106 |
| 26 | 0.120 | 80 |
| 27 | 0.012 | 101 |
| 28 | 0.015 | 107 |
| 29 | 0.009 | 79 |
| 30 | 0.040 | 104 |
| 31 | 0.160 | 53 |
| 32 | 0.010 | 54 |
| 33 | 0.045 | 101 |
| 34 | 0.024 | 97 |
| 35 | 0.027 | 105 |
| 36 | 0.020 | 105 |
| 37 | 0.013 | 108 |
| 38 | 0.012 | 109 |
| 39 | 0.019 | 108 |
| 40 | 0.019 | 114 |
| 41 | 1.050 | 83 |
| 42 | 0.016 | 115 |
| 43 | 0.014 | 111 |
| 44 | 0.012 | 114 |
| 45 | 0.013 | 113 |
| 46 | 0.006 | 111 |
| 47 | 0.015 | 111 |
| 48 | 0.023 | 109 |
| 49 | 0.013 | 112 |
| 50 | 0.091 | 111 |
| 51 | 0.010 | 112 |
| 52 | 0.019 | 113 |
| 53 | 0.064 | 114 |
| 54 | 0.095 | 112 |
| 55 | 0.061 | 109 |
| 56 | 0.160 | 102 |
| 57 | 0.071 | 104 |
| 58 | 0.021 | 113 |
| 59 | 0.007 | 120 |
| 60 | 0.016 | 86 |
| 61 | 0.018 | 111 |
| 62 | 0.012 | 41 |
| 63 | 0.029 | 95 |
| 64 | 0.123 | 76 |
| 65 | 0.043 | 110 |
| 66 | 0.008 | 110 |
| 67 | 0.038 | 85 |
| 68 | 0.187 | 103 |
| 69 | 1.004 | 84 |
| 70 | 0.042 | 112 |
| 71 | 0.006 | 110 |
| 72 | 0.045 | 60 |
| 73 | 0.029 | 105 |
| 74 | 0.023 | 71 |
| 75 | 0.009 | 111 |
| 76 | 0.023 | 111 |
| 77 | 0.053 | 90 |
| 78 | 0.019 | 111 |

TABLE 1-continued

| EXAMPLE | DC50 (μM) | Dmax (%) |
|---|---|---|
| 79 | 0.021 | 115 |
| 80 | 0.084 | 90 |
| 81 | 0.010 | 116 |
| 82 | 0.008 | 114 |
| 83 | 0.052 | 80 |
| 84 | 0.024 | 77 |
| 85 | 0.025 | 73 |
| 86 | 0.012 | 111 |
| 87 | 0.047 | 61 |
| 88 | 0.011 | 115 |
| 89 | 0.024 | 112 |
| 90 | 0.064 | 25 |
| 91 | 0.097 | 32 |
| 92 | 0.024 | 114 |
| 93 | 0.016 | 115 |
| 94 | 0.010 | 114 |
| 95 | 0.027 | 108 |
| 96 | 0.083 | 103 |
| 97 | 0.018 | 111 |
| 98 | 0.016 | 105 |
| 99 | 0.056 | 73 |
| 100 | 0.020 | 95 |
| 101 | 0.007 | 55 |
| 102 | 0.042 | 107 |
| 103 | 0.012 | 106 |
| 104 | 0.004 | 115 |
| 105 | 0.006 | 112 |
| 106 | 0.021 | 99 |
| 107 | 0.065 | 111 |
| 108 | 0.040 | 87 |
| 109 | 0.052 | 94 |
| 110 | 0.050 | 50 |
| 111 | 0.032 | 110 |
| 112 | 0.033 | 92 |
| 113 | 0.239 | 105 |
| 114 | 0.100 | 110 |
| 115 | 0.048 | 109 |
| 116 | 0.100 | 111 |
| 117 | 0.075 | 106 |
| 118 | 0.049 | 110 |
| 119 | 0.030 | 111 |
| 120 | 0.068 | 109 |
| 121 | 0.073 | 88 |
| 122 | 0.058 | 105 |
| 123 | 0.080 | 96 |
| 124 | 0.008 | 110 |
| 125 | 0.030 | 106 |
| 126 | 0.043 | 108 |
| 127 | 0.009 | 113 |
| 128 | 0.006 | 111 |
| 129 | 0.005 | 113 |
| 130 | 0.022 | 112 |
| 131 | 0.021 | 110 |
| 132 | 0.013 | 111 |
| 133 | 0.013 | 110 |
| 134 | 0.020 | 111 |
| 135 | 0.005 | 108 |
| 136 | 0.025 | 113 |
| 137 | 0.104 | 88 |
| 142 | 0.012 | 96 |
| 143 | 0.072 | 99 |
| 144 | 0.166 | 87 |
| 145 | 0.022 | 113 |

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A compound selected from the group consisting of:

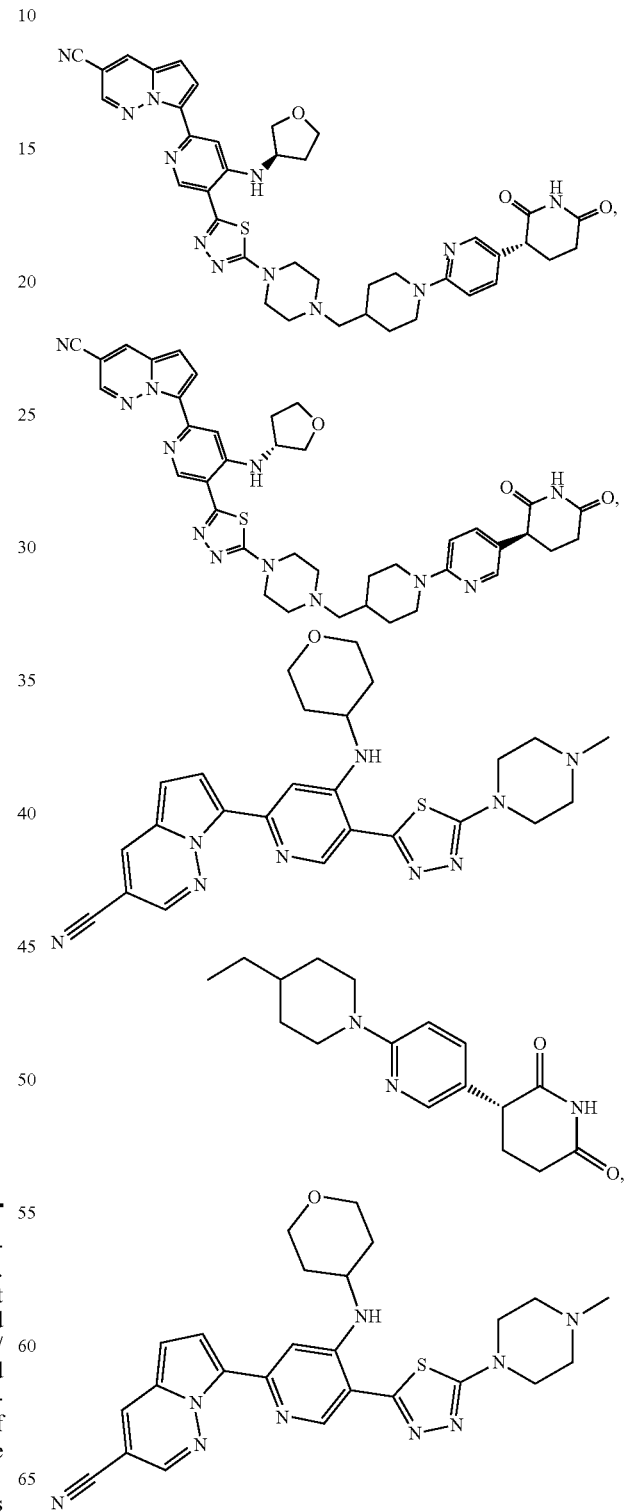

365
-continued
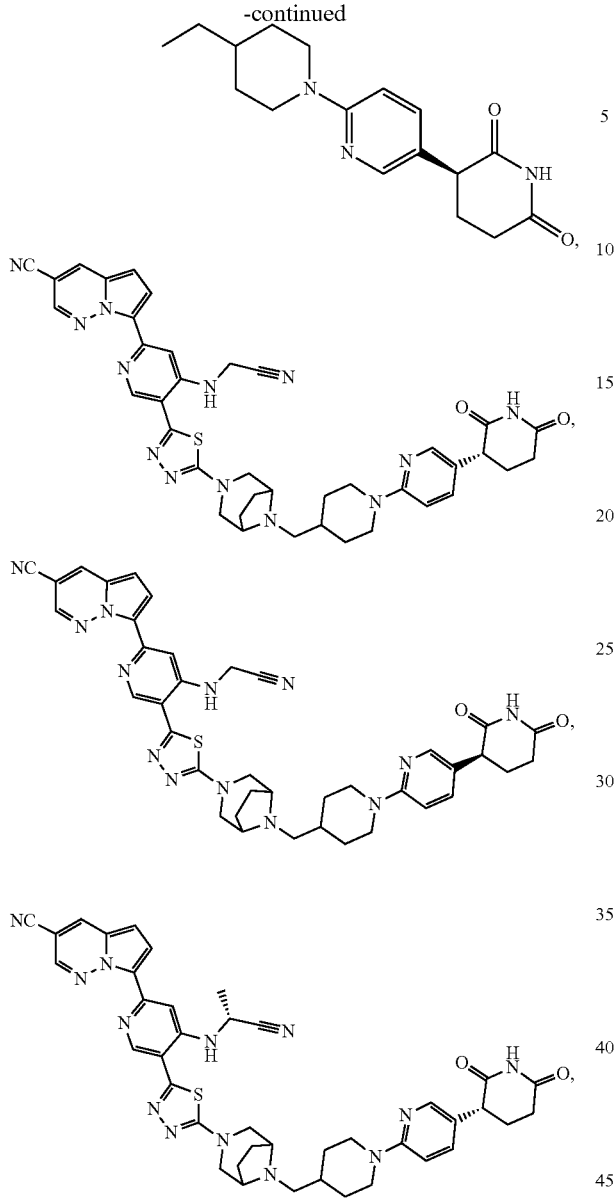
366
-continued
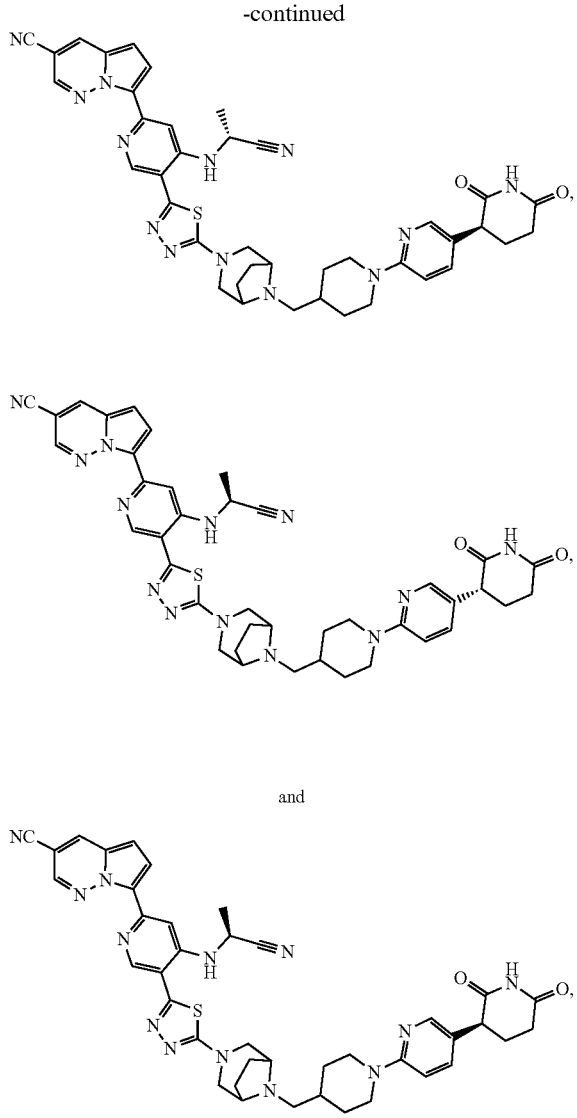
or a pharmaceutically acceptable salt thereof.
2. The compound of claim 1, wherein the compound is
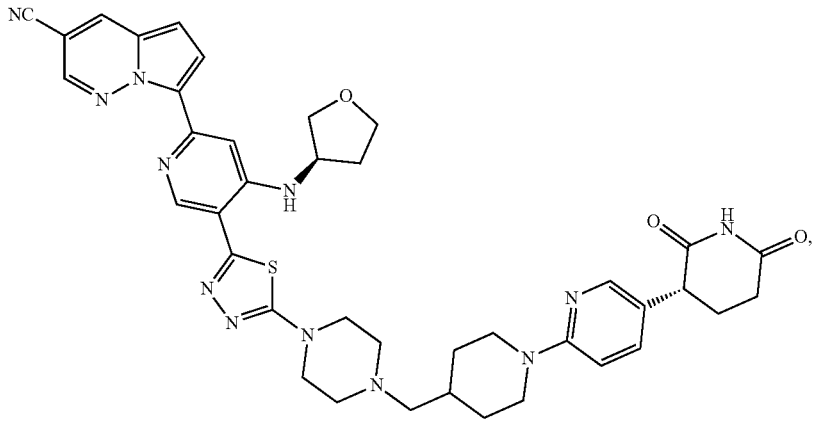 [SMILES: N#Cc1cnn2c(-c3cc(N[C@@H]4CCOC4)c(-c4nnc(N5CCN(CC6CCN(c7ccc([C@H]8CCC(=O)NC8=O)cn7)CC6)CC5)s4)cn3)ccc2c1]
or a pharmaceutically acceptable salt thereof.

3. The compound of claim 1, wherein the compound is
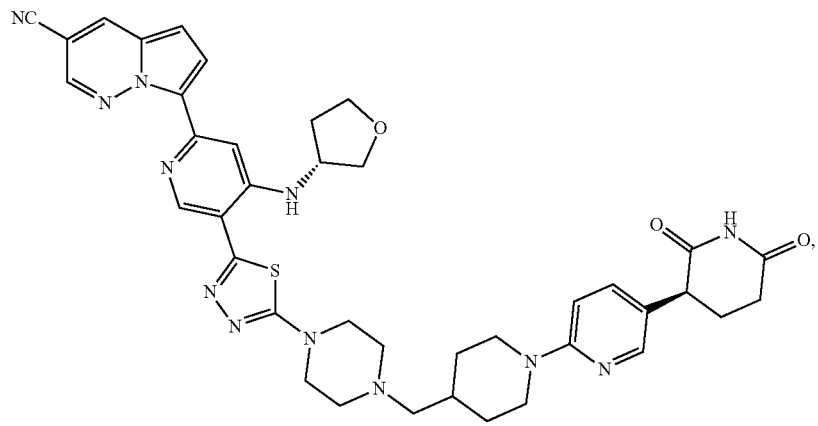 [SMILES: N#Cc1cnn2c(-c3cc(N[C@@H]4CCOC4)c(-c4nnc(N5CCN(CC6CCN(c7ccc([C@@H]8CCC(=O)NC8=O)cn7)CC6)CC5)s4)cn3)ccc2c1]
or a pharmaceutically acceptable salt thereof.
4. The compound of claim 1, wherein the compound is
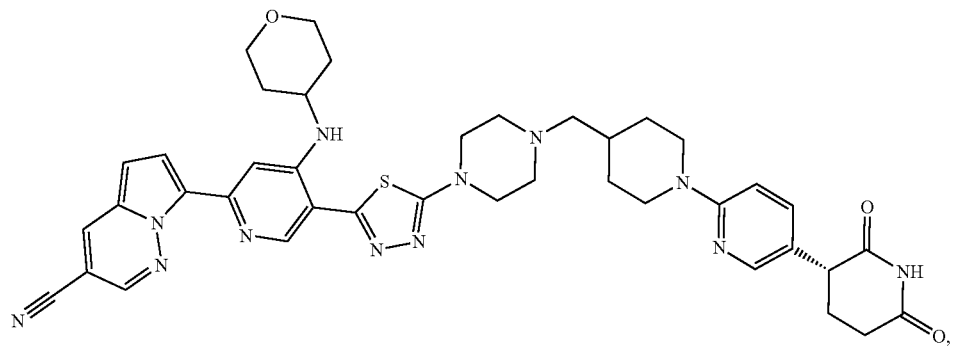 [SMILES: N#Cc1cnn2c(-c3cc(NC4CCOCC4)c(-c4nnc(N5CCN(CC6CCN(c7ccc([C@H]8CCC(=O)NC8=O)cn7)CC6)CC5)s4)cn3)ccc2c1]
or a pharmaceutically acceptable salt thereof.
5. The compound of claim 1, wherein the compound is
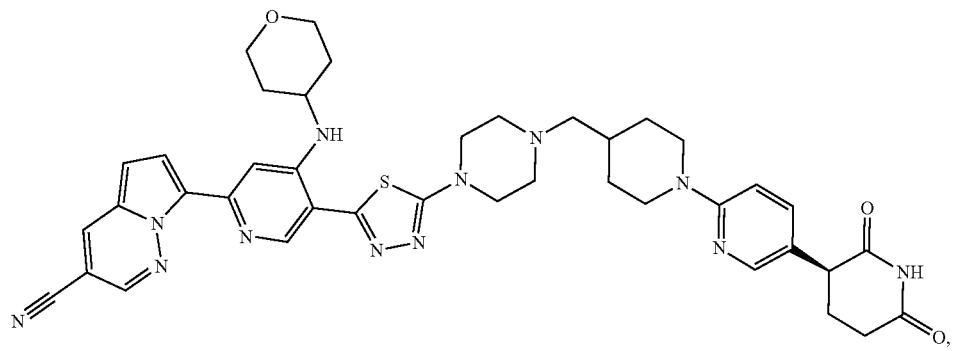 [SMILES: N#Cc1cnn2c(-c3cc(NC4CCOCC4)c(-c4nnc(N5CCN(CC6CCN(c7ccc([C@@H]8CCC(=O)NC8=O)cn7)CC6)CC5)s4)cn3)ccc2c1]
or a pharmaceutically acceptable salt thereof.

6. The compound of claim 1, wherein the compound is
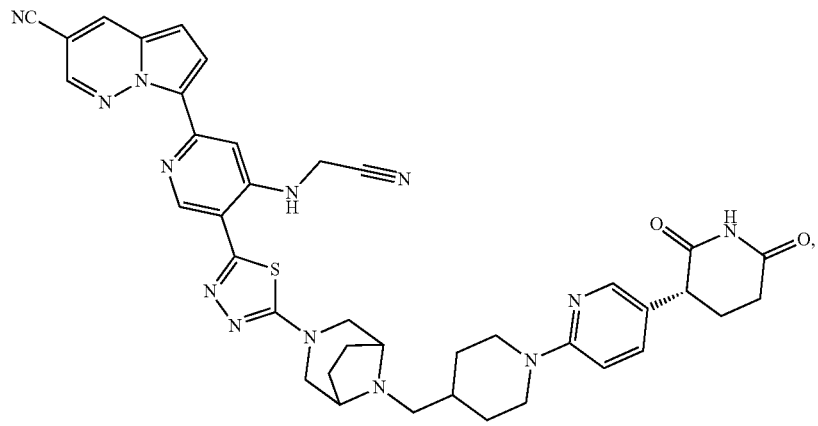 [SMILES: N#CCNc1cc(-c2ccc3cc(C#N)cnn23)ncc1-c1nnc(N2CC3CCC(C2)N3CC2CCN(c3ccc([C@H]4CCC(=O)NC4=O)cn3)CC2)s1]
or a pharmaceutically acceptable salt thereof.
7. The compound of claim 1, wherein the compound is
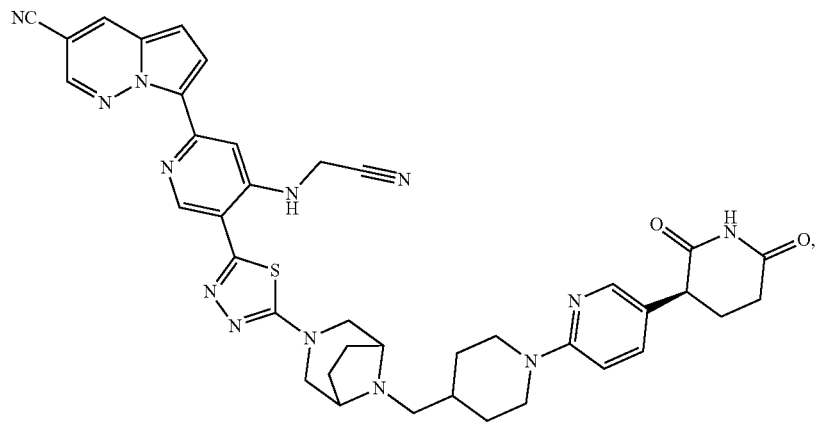 [SMILES: N#CCNc1cc(-c2ccc3cc(C#N)cnn23)ncc1-c1nnc(N2CC3CCC(C2)N3CC2CCN(c3ccc([C@@H]4CCC(=O)NC4=O)cn3)CC2)s1]
or a pharmaceutically acceptable salt thereof.
8. The compound of claim 1, wherein the compound is
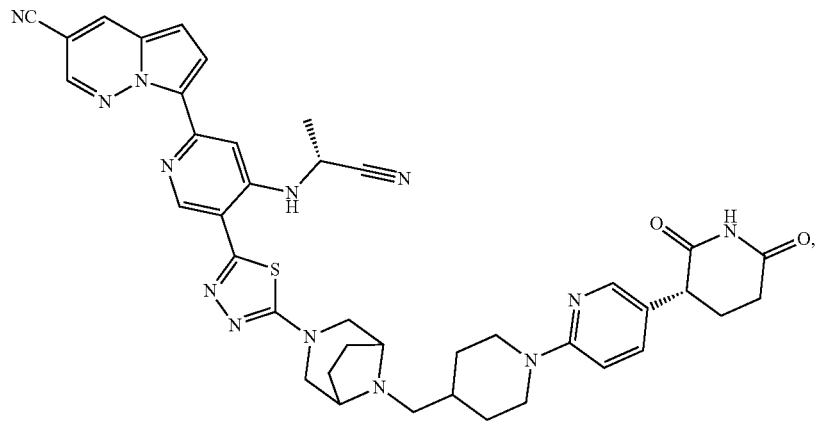 [SMILES: C[C@H](C#N)Nc1cc(-c2ccc3cc(C#N)cnn23)ncc1-c1nnc(N2CC3CCC(C2)N3CC2CCN(c3ccc([C@H]4CCC(=O)NC4=O)cn3)CC2)s1]
or a pharmaceutically acceptable salt thereof.

9. The compound of claim 1, wherein the compound is
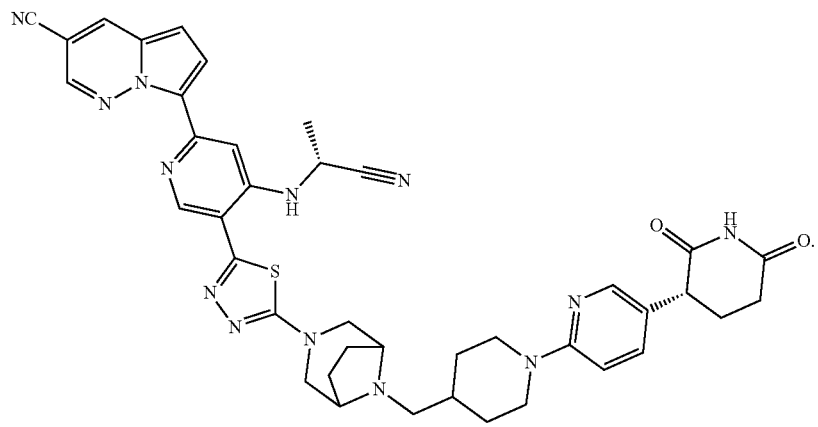 [SMILES: C[C@H](C#N)Nc1cc(-c2ccc3cc(C#N)cnn23)ncc1-c1nnc(N2CC3CCC(C2)N3CC2CCN(c3ccc([C@H]4CCC(=O)NC4=O)cn3)CC2)s1]
10. The compound of claim 1, wherein the compound is
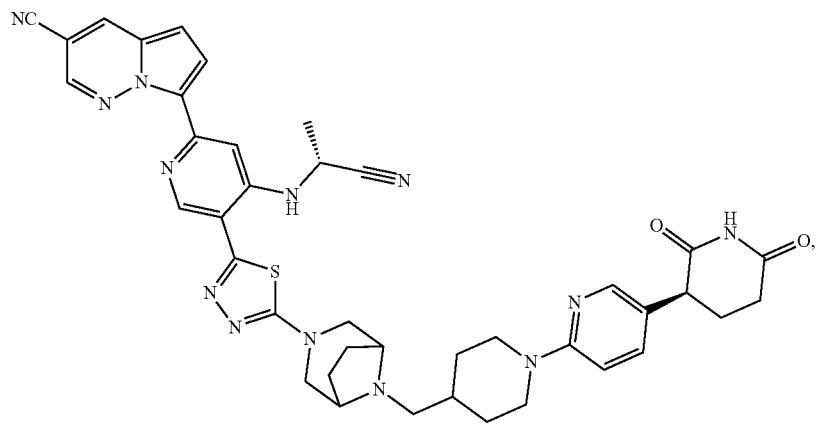 [SMILES: C[C@H](C#N)Nc1cc(-c2ccc3cc(C#N)cnn23)ncc1-c1nnc(N2CC3CCC(C2)N3CC2CCN(c3ccc([C@@H]4CCC(=O)NC4=O)cn3)CC2)s1]
or a pharmaceutically acceptable salt thereof.
11. The compound of claim 1, wherein the compound is
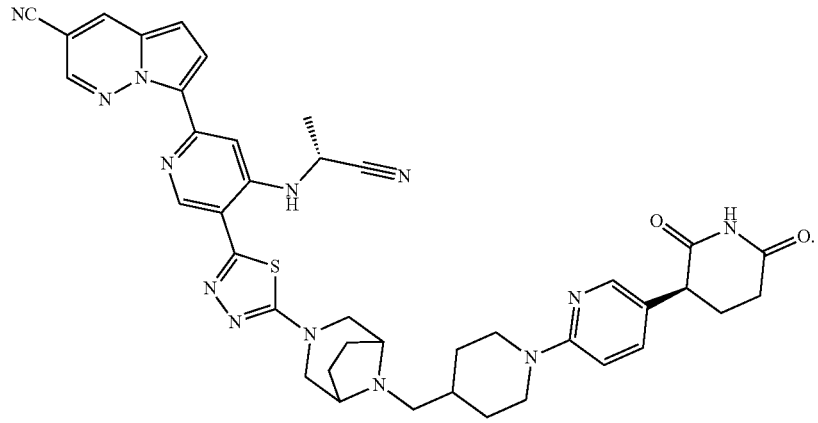

12. The compound of claim 1, wherein the compound is
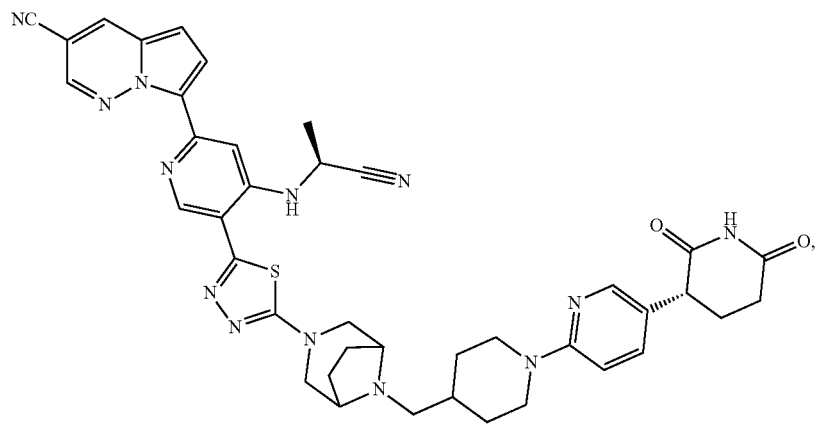 [SMILES: C[C@@H](C#N)Nc1cc(-c2ccc3cc(C#N)cnn23)ncc1-c1nnc(N2CC3CCC(C2)N3CC2CCN(c3ccc([C@H]4CCC(=O)NC4=O)cn3)CC2)s1]
or a pharmaceutically acceptable salt thereof.
13. The compound of claim 1, wherein the compound is
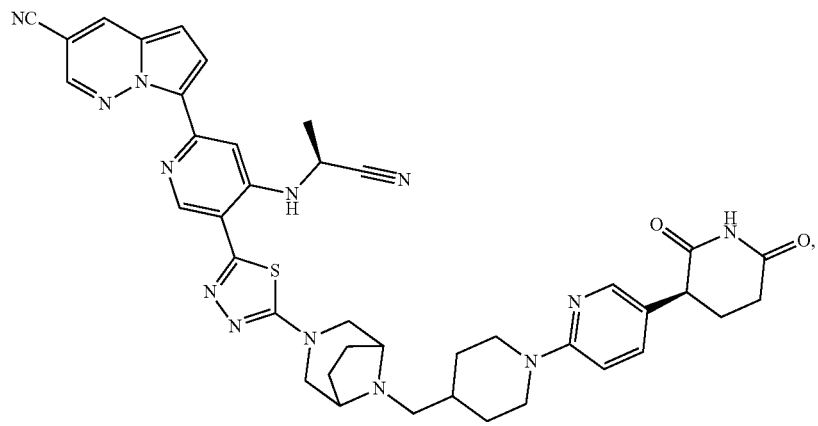 [SMILES: C[C@@H](C#N)Nc1cc(-c2ccc3cc(C#N)cnn23)ncc1-c1nnc(N2CC3CCC(C2)N3CC2CCN(c3ccc([C@@H]4CCC(=O)NC4=O)cn3)CC2)s1]
or a pharmaceutically acceptable salt thereof.
14. A pharmaceutical composition comprising a pharmaceutically acceptable carrier and a compound of claim 1, or a pharmaceutically acceptable salt thereof.
* * * * *

UNITED STATES PATENT AND TRADEMARK OFFICE
CERTIFICATE OF CORRECTION

Page 1 of 1

PATENT NO. : 11,976,071 B2
APPLICATION NO. : 17/820770
DATED : May 7, 2024
INVENTOR(S) : Wylie Palmer et al.

It is certified that error appears in the above-identified patent and that said Letters Patent is hereby corrected as shown below:

On the Title Page

Item (73), under "Assignee", Line 1, please insert:
--Nurix Therapeutics, Inc., San Francisco, CA (US)--

Signed and Sealed this
Thirteenth Day of January, 2026

John A. Squires
*Director of the United States Patent and Trademark Office*